(12) United States Patent
Sayre et al.

(10) Patent No.: US 11,946,059 B2
(45) Date of Patent: *Apr. 2, 2024

(54) IN VIVO GENERATION OF WATER-SOLUBLE CANNABINOIDS IN PLANT CELL SUSPENSION CULTURES

(71) Applicant: Trait Biosciences Inc., Los Alamos, NM (US)

(72) Inventors: Richard T. Sayre, Los Alamos, NM (US); Elton Carvalho Gonçalves, Los Alamos, NM (US); Tawanda Zidenga, White Rock, NM (US); Stephanie Willette, Santa Fe, NM (US)

(73) Assignee: TRAIT BIOSCIENCES, INC., Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/426,059

(22) Filed: May 30, 2019

(65) Prior Publication Data

US 2019/0316144 A1    Oct. 17, 2019

Related U.S. Application Data

(63) Continuation-in-part of application No. 16/110,954, filed on Aug. 23, 2018, which is a continuation-in-part of application No. PCT/US2018/041710, filed on Jul. 11, 2018, which is a continuation-in-part of application No. PCT/US2018/024409, filed on Mar. 26, 2018.

(60) Provisional application No. 62/531,123, filed on Jul. 11, 2017, provisional application No. 62/588,662, filed on Nov. 20, 2017, provisional application No. 62/621,166, filed on Jan. 24, 2018.

(51) Int. Cl.
*C12N 15/82* (2006.01)
*A61K 31/352* (2006.01)
*C12N 9/02* (2006.01)
*C12N 9/10* (2006.01)

(52) U.S. Cl.
CPC ........ *C12N 15/8257* (2013.01); *A61K 31/352* (2013.01); *C12N 9/0042* (2013.01); *C12N 9/1051* (2013.01); *C12N 15/8201* (2013.01); *C12Y 106/02004* (2013.01); *C12Y 204/01* (2013.01)

(58) Field of Classification Search
CPC .................................................. C12N 15/8257
See application file for complete search history.

(56) References Cited

U.S. PATENT DOCUMENTS

| | | | |
|---|---|---|---|
| 5,292,899 A | 3/1994 | Tius et al. | |
| 7,807,711 B2 | 10/2010 | Korthout et al. | |
| 8,410,064 B2 | 4/2013 | Radominska-Pandya et al. | |
| 8,673,368 B2 | 3/2014 | Guy et al. | |
| 8,829,043 B2 | 9/2014 | Riggs-Sauthier et al. | |
| 9,155,797 B2 | 10/2015 | Riggs-Sauthier et al. | |
| 9,205,063 B2 | 12/2015 | Guy et al. | |
| 9,394,510 B2 | 7/2016 | Peet et al. | |
| 9,512,391 B2 | 12/2016 | Peet et al. | |
| 9,546,362 B2 | 1/2017 | Page et al. | |
| 9,611,460 B2 | 4/2017 | Page et al. | |
| 9,822,384 B2 | 11/2017 | Poulos et al. | |
| 9,861,609 B2 | 1/2018 | Winnicki et al. | |
| 2006/0106212 A1 | 5/2006 | Hollingsworth et al. | |
| 2006/0174377 A1 | 8/2006 | Nakamura et al. | |
| 2010/0021967 A1 | 1/2010 | Draborg | |
| 2015/0099277 A1 | 4/2015 | Devaraj et al. | |
| 2016/0010126 A1 | 1/2016 | Poulos et al. | |
| 2016/0298151 A1 | 10/2016 | Butt et al. | |
| 2016/0355853 A1 | 12/2016 | Winnicki et al. | |
| 2017/0044552 A1 | 2/2017 | Kumar | |

FOREIGN PATENT DOCUMENTS

| | | | |
|---|---|---|---|
| CA | 2454644 A1 | 2/2004 | |
| WO | 2007005604 A2 | 1/2007 | |
| WO | 2008034648 A1 | 3/2008 | |
| WO | 2016168413 A1 | 10/2016 | |
| WO | 2017034942 A1 | 3/2017 | |
| WO | 2017053574 A1 | 3/2017 | |
| WO | WO-2017053574 A1 * | 3/2017 | ........... A61K 31/352 |

OTHER PUBLICATIONS

Wang et al (2009) Front Biol. China, 4:39-46.*
Nelson et al, Plant J. (2011) 66:194-211.*
Carvalho et al, FEMS (2017) 17:1-9.*
Tanaka et al, J. of Nat. Prod. (1993) 56:2068-2072.*
Hardman et al, BioRxiv Preprint Server for Biology (Cold Spring Harbor), p. 1-25; published online Jan. 30, 2017.*
Holland et al (British J. of Pharmacology (2007) 152:815-824.*
Morimoto et al, J. Biol. Chem. (2007) 282:20739-20751.*
Andre et al, Frontiers in Plant Sci. (2016) 7:19.*
Sirikantaramas et al, Plant Cell. Physiol. (2005) 1578-1582.*
Akhtar et al, Biocatalysis and Biotransformation (2015) 33:279-286.*
Hakkinen et al, J. of Biotechnology (2012) 157:287-294.*
Nakajima et al, Phytochemistry (2004) 65:1383-1387.*
Li et al, Euro. J. Med. Chem. (2020) 192:112-163.*
Ivanchenko, et al., "Maize ROP7 GTPase contains a unique, CaaX box-independent plasma membrane targeting signal", The Plant Journal, Jul. 12, 2000, pp. 79-90, vol. 24, Issue 1, Blackwell Science Ltd.
Norambuena, et al., "Transport of UDP-galactose in Plants: Identification and Functional Characterization of AtUTr1, an *Arabidopsis thaliana* UDP-Galactose/UDP-Glucose Transporter", The Journal of Biological Chemistry, May 31, 2002, p. 32923-32929, vol. 277, No. 36, Issue of Sep. 6, The American Society for Biochemistry and Molecular Biology, Inc.

(Continued)

Primary Examiner — Mykola V. Kovalenko
(74) Attorney, Agent, or Firm — Berg Hill Greenleaf Ruscitti LLP

(57) ABSTRACT

The present invention includes systems, methods and compositions for the in vivo bioconversion of water-soluble cannabinoids in plant cell suspension cultures.

1 Claim, 51 Drawing Sheets

Specification includes a Sequence Listing.

(56) References Cited

OTHER PUBLICATIONS

Wang et al., "Glycosyltransferases: key players involved in the modification of plant secondary metabolites", Front. Biol. China, 2009, pp. 39-46, Higher Education Press and Springer-Verlag 2008.
Nelson, et al., "A P450-centric view of plant evolution", The Plant Journal, 2011, pp. 194-211, Blackwell Publishing Ltd.
Carvalho, et al., "Designing microorganisms for heterologous biosynthesis of cannabinoids", FEMS Yeast Research, Apr. 2, 2017, pp. 1-11.
Tanaka, et al., "Cannabis, 21. Biotransformation of Cannabinol to its Glycosides by in Vitro Plant Tissue", Journal of Natural Products, Dec. 1993, pp. 2068-2072.
Martins, et al., "Catalase activity is stimulated by H202 in rich culture medium and is required for H202 resistance and adaptation in yeast", Redox Biology, 2014, pp. 308-313.
Uni Prat Accession No. P21179, *E. coli* catalase KatE, submitted on May 1, 1991, pp. 1-13.
Office Action dated Aug. 2, 2019 in U.S. Appl. No. 16/110,954, filed Aug. 23, 2018.
Madhav, Harish et al., "Functional and structural variation of uridine diphosphate glycosyltransferase (UGT) gene of Stevia rebaudiana-UGTSr involved in the synthesis of rebaudioside A", Plant Physiology and Biochemistry, vol. 63, Feb. 1, 2013 (Feb. 1, 2013), pp. 245-253, XP055111642, ISSN: 0981-9428, DOI: 10.1016/j.plaphy.2012.11.029 * p. 249, col. 1, last paragraph-p. 250, col. 1, paragraph 1, 9 pages.
Beaune, Philippe H et al., "Isolation and Sequence Determination of a CDNA Clone Related to Human Cytchrome P-450 Nifedipine Oxidase", Proceedings of the National Academy of Sciences, National Academy of Sciences, vol. 83, No. 83, Jan. 1, 1996 (Jan. 1, 1996), pp. 8064-8068, XP000907192, ISSN: 0027-8424 * figures 3,4, 5 pages.
Richman, Alex et al., "Functional genomics uncovers three glucosyltransferases involved in the synthesis of the major sweet glucosides of Stevia rebaudiana", The Plant Journal, Blackwell Scientific Publications, Oxford, GB, vol. 41, No. 1, Jan. 1, 2005 (Jan. 1, 2005), pp. 56-67, XP002686584, ISSN: 0960-7412, DOI: 10.III/J.1365-313X.2004.02275.X; 12 pages.
Haniu, Mitsuru et al., "Biochemistry (preceding paper in this issue) Structural and Functional Analysis of NADPH-Cytochrome P-450 Reductase from Human Liver: Complete Sequence of Human Enzyme and NADPH-Binding Sites* 1''", Biochemistry Biophys. J. Biochem. Soc. Trans, vol. 28, No. 21, Jan. 1, 1989 (Jan. 1, 1989), pp. 8639-8645, XP055722680, DOI: 10.1021/bi00447a054, 7 pages.
Supplemental European Search Report dated Nov. 27, 2020, 7 pages.
International Preliminary Report on Patentability dated Jan. 14, 2020, 15 pages.
Guelck, Thies et al., "Synthetic Biology of Cannabinoids and Cannabinoid Glucosides in Nicotiana benthamiana and *Saccharomyces cerevisiae*", p. 54.
Blatt-Janmaat, Kaitlyn et al., "The Biochemistry of Phytocannabinoids and Metabolic Engineering of Their Production in Heterologous Systems", International Journal of Molecular Sciences, 2021, 19 pages.
Haertl, Katja et al., "Tailoring Natural Products with Glycosyltransferases", Biotechnology of Natural Products, Technische Universität München, 2018, 45 pages.
Holland, et al., "The multidrug transporter ABCG2 (BCRP) is inhibited by plant-derived cannabinoids", British Journal of Pharmacology, Oct. 1, 2007, pp. 815-824, Nature Publishing Group.
Vanchenko, et al., "Maize ROP7 GTPase contains a unique, CaaX box-independent plasma membrane targeting signal", The Plant Journal, Jul. 12, 2000, pp. 79-90, vol. 24, Issue 1, Blackwell Science Ltd.
Marks, et al., "Identification of candidate genes affecting Δ9-tetrahydrocannabinol biosynthesis in Cannabis sativa", Journal of Experimental Botany, Jul. 6, 2009, pp. 3715-3726, vol. 60, No. 13, Advance Access.

Nagaya, et al., "The HSP Terminator of *Arabidopsis thaliana* Increases Gene Expression in Plant Cells", Plant & Cell Physiology, Dec. 15, 2009, pp. 328-332, vol. 51, Issue 2, Oxford University Press on behalf of Japanese Society of Plant Physiologists.
Norambuena, et al., "Transport of UDP-galactose in Plants: Identification and Functional Characterization of AtUTr1, an *Arabidopsis thaliana* UDP-Galactose/UDP-Glucose Transporter", The Journal of Biological Chemistry, May 31, 2002, pp. 32923-32929, vol. 277, No. 36, Issue of Sep. 6, The American Society for Biochemistry and Molecular Biology, Inc.
Onofri, et al., "Sequence heterogeneity of cannabidiolic- and tetrahydrocannabinolic acid-synthase in *Cannabis sativa* L. and its relationship with chemical phenotype", Phytochemistry, Apr. 9, 2015, pp. 57-68, vol. 116, Elsevier Ltd.
Priest, et al., "Use of the glucosyltransferase UGT71B6 to disturb abscisic acid homeostasis in *Arabidopsis thaliana*", The Plant Journal, Jan. 12, 2006, pp. 492-502, vol. 46, 2006 Blackwell Publishing Ltd.
Siritunga, et al., "Generation of cyanogen-free transgenic cassava", Planta, Mar. 18, 2003, pp. 367-373, vol. 217, Springer-Verlag.
Sparkes, et al., "Rapid, transient expression of fluorescent fusion proteins in tobacco plants and generation of stably transformed plants", Nature Protocols, Nov. 30, 2006, pp. 2019-2025, vol. 1, No. 4, Nature Publishing Group.
Taura, et al., "Purification and Characterization of Cannabidiolic-acid Synthase from *Cannabis sativa* L.: Biochemical Analysis of a Novel Enzyme that Catalyzes the Oxidocyclization of Cannabigerolic Acid to Cannabidiolic Acid", The Journal of Biological Chemistry, Apr. 26, 1996, pp. 17411-17416, vol. 271, No. 29, Issue of Jul. 19, The American Society for Biochemistry and Molecular Biology, Inc., printed in USA.
Taura, et al., "Cannabidiolic-acid synthase, the chemotype-determining enzyme in the fiber-type Cannabis sativa", FEBS Leters, May 15, 2007, pp. 2929-2934, vol. 581, Elsevier B.V.
Yoo, et al., "*Arabidopsis* mesophyll protoplasts: a versatile cell system for transient gene expression analysis", Nature Protocols, Jun. 21, 2007, pp. 1565-1572, vol. 2, No. 7, Nature Publishing Group.
Matsui, et al., "High level expression of transgenes by use of 5'-untranslated region of the *Arabidopsis thaliana* arabinogalactan-protein 21 gene in dicotyledons", Plant Biotechnology, Mar. 22, 2012, pp. 319-322, vol. 29, The Japanese Society for Plant Cell and Molecular Biology.
Murashige, et al., "A Revised Medium for Rapid Growth and Bio Assays with Tobacco Tissue Cultures", Physiologia Plantarum, Apr. 1, 1962, pp. 473-497, vol. 15.
Hardman, et al., "Cannabinoid glycosides: In vitro production of a new class of cannabinoids with improved physicochemical properties", BioRxiv Pre-Print, Jan. 30, 2017, pp. 1-37.
Mohamed, et al., "Overexpression of bacterial catalase in tomato leaf chloroplasts enhances photo-oxidative stress tolerance" Plant, Cell and Environment, 2003, pp. 2037-2046, vol. 26, Blackwell Publishing Ltd.
Akhtar, "Cannabinoids and zebrafish", Universiteit Leiden dissertation, May 22, 2013, pp. 1-179.
Hussein, "Cannabinoids production in *Cannabis sativa* L.: An in vitro approach", University Dortmund dissertation, Nov. 26, 2014, pp. 1-138.
Watanabe, et al., "Cytochrome P450 enzymes involved in the metabolism of tetrahydrocannabinols and cannabinol by human hepatic microsomes", Life Sciences, Dec. 27, 2006, pp. 1415-1419, vol. 80 (2007), Elsevier Inc.
Flores-Sanchez, et al., "Elicitation studies in cell suspension cultures of *Cannabis sativa* L.", Journal of Biotechnology, May 12, 2009, pp. 157-168, vol. 143 (2009), Elsevier B.V.
Stout, et al., "Exogenous cannabinoids as substrates, inhibitors, and inducers of human drug metabolizing enzymes: a systematic review", Drug Metabolism Reviews, 2014, pp. 86-95, vol. 46, Issue 1, Informa Healthcare USA, Inc.
Andre, et al., "*Cannabis sativa*: The Plant of the Thousand and One Molecules", Frontiers in Plant Science, Feb. 4, 2016, pp. 1-17, vol. 7, Article 19, CrossMark.

(56) References Cited

OTHER PUBLICATIONS

Mahlberg, et al., Accumulation of Cannabinoids in Glandular Trichomes of Cannabis (Cannabaceae), Journal of Industrial Hemp, Sep. 25, 2008, pp. 14-36, Taylor & Francis Group.

Sirikantaramas, et al., "Tetrahydrocannabinolic Acid Synthase, the Enzyme Controlling Marijuana Psychoactivity, is Secreted into the Storage Cavity of the Glandular Trichomes", Plant Cell Physiology, 2005, pp. 1578-1582, vol. 46, Issue 9, JSPP.

Schilmiller, et al., "Harnessing plant trichome biochemistry for the production of useful compounds", The Plant Journal, Dec. 6, 2007, pp. 702-711, vol. 54, Blackwell Publishing Ltd.

Matias-Hernandez, et al., "AaMYB1 and its orthologue AtMYB61 affect terpene metabolism and trichome development in Artemisia annua and *Arabidopsis thaliana*", The Plant Journal, Feb. 16, 2017, pp. 520-534, vol. 90, John Wiley & Sons Ltd.

Ahmad, et al., "Protein expression in Pichia pastoris: recent achievements and perspectives for heterologous protein production", Applied Microbiology Biotechnology, Apr. 18, 2014, pp. 5301-5317, vol. 98, Springer.

Cregg, et al., "Rocombinant Protein Expression in Pichia pastoris", The Journal of Molecular Biology Research, Protocols, Reviews, and Applications: Molecular Biotechnology, Sep. 2000, pp. 23-52 and cover, vol. 16, Humana Press.

Ellis, et al., "Isolation of Alcohol Oxidase and Two Other Methanol Regulatable Genes from the Yeast *Pichia pastoris*", Molecular and Cellular Biology, Jan. 23, 1985, pp. 1111-1121, vol. 5, No. 5, American Society for Microbiology.

Santos, et al., "Putting the Spotlight Back on Plant Suspension Cultures", Frontiers in Plant Science, Mar. 11, 2016, pp. 1-12, vol. 7, Article 297, CrossMark.

Nagata, et al., "Tobacco BY-2 Cell Line as the "HeLa" Cell in the Cell Biology of Higher Plants", International Review of Cytology, 1992, pp. 1-30, vol. 132, Academic Press, Inc.

Solymosi, et al., "Cannabis: A Treasure Trove or Pandora's Box?", Mini Reviews in Medicinal Chemistry, Oct. 2016, pp. 1-70 and cover, vol. 17, Bentham Science Publishers.

Von Ossowski, et al., "Nucleotide Sequence of *Escherichia coli* katE, Which Encodes Catalase HPII", Journal of Bacteriology, Jan. 1991, pp. 514-520, vol. 173, No. 2, American Society for Microbiology.

Rini, et al., "Chaper 5: Glycosyltransferases and Glycan-processing Enzymes", Essentials of Glycobiology, 2009, retrieved online on Aug. 17, 2018 from https://www.ncbi.nlm.nih.gov/books/NBK1921/, pp. 1-8, 2nd edition, Cold Spring Harbor, New York, USA.

Invitation to Pay Additional Fees And, Where Applicable, Protest Fee dated Sep. 18, 2018 in International Application No. PCT/US18/41710 filed Jul. 11, 2018.

International Search Report and Written Opinion dated Nov. 8, 2018 in International Application No. PCT/US18/41710 filed Jul. 11, 2018.

International Search Report and Written Opinion dated Oct. 22, 2018 in International Application No. PCT/US18/24409 filed Mar. 26, 2018.

GenBank accession No. AB176523.1 "Nicotiana tabacum NtGT5a mRNA for glycosyltransferase, complete cds", Mar. 11, 2009 [online]. [Retrieved on Oct. 29, 2018]. Retrieved from the internet <URL:https://www.ncbi.nlm.nih.gov/nuccore/AB176523.1?report=genbank > sequence.

Logrono, "In Vitro Cell Culture of Cannabis Sativa for the Production of Cannabinoids" Poster [online]. Universitat Autonoma de Barcelona, Bellaterra. 2014 [Retrieved on Sep. 6, 2018]. Retrieved from the Internet: <URL: https://ddd.uab.cat/pub/tfg/2014/119249/TFG_javierlidoylogrono.pdf>; 1st col. 2nd paragraph; 3rd col. cell suspension Figures 3 and 4.

Akhtar, et al., "Hydrozylation and glycosylation of Delta 9-tetrahydrocannabinol by Catharanthus roseus cell suspension culture", Biocatalysis and Biotransformation, 2015, pp. 279-286, vol. 33 (5-6), Taylor & Francis Group.

\* cited by examiner

```
CAT1    MDPYVRPSAHDSPFFTTNSGAPVWNNSSLTVGTRGPILLEDYHLLEKLANFDRERIPERVVHARGASAKGFFEVTHDITQLTSADFLRGPGVQTPVI
CAT2    MDPYKYRPASSVNSPFFTTNSGAPVWNNSSMTVGPRGPILLEDYHLVEKLANFDRERIPERVVHARGASAKGFFEVTHDISNLTCADFLRAPGVQTPVI
CAT3    MDPYKYRPASAVNAPFVTTNGAPVSNNISSLTIGERGPVLLEDYHLIEKVANFTRERIPERVVHARGISAKGFFEVTHDISNLTCADFLRAPGVQTPVI
                10        20        30        40        50        60        70        80        90       100

CAT1    VRFSTVIHERGSPETIRDPRGFAVKFYTREGNFDLVGNNFPVFFVRDGMKFPDMVHALKPNPKSHIQENWRILDFFSHPESLHMFSFLFDDIGIPQDYR
CAT2    VRFSTVIHERGSPETIRDPRGFAVKFYTREGNFDLVGNNFPVFFIRDGMKFPDMVHALKPNPKSHIQENWRILDFFSHPESLNMFTFLFDDIGTPQDIR
CAT3    VRFSTVIHERASPETRRDIRGFAVKFYTREGNFDLVGNNTPVFFIRDGIQFPDVVHALKPNPKTHIQEYWRILDYMSHLPESLIIYCWMFDDVGTPQDYR
                110       120       130       140       150       160       170       180       190       200

CAT1    HMEGAGVNTYMLYMLINKAGKAHYVKFHWKPTCGIKCLSDEEAIRVGGANHSHATKDLYDSIAAGYNPOWNLFVQVMDPAHEDKFDFPLDVTKIWPEDILPL
CAT2    HMDGSGVNTYMLINKAGKAHYVKFHWKPTCGVKSLLEEDAIRVGGTNHSHATQDLYDSIAAGNPSWLFIQIDPADEDKFDFPLDVTKIWPEDILPL
CAT3    HMEGFGVHTYTLIIAKSGKVLFVKFHWKPTCGKVLFVKFHWKPTCGKVFRMKDLHDATASGNPEWKLFIQIIDPADEDKFDFPLDVTKIWPEDILPL
                210       220       230       240       250       260       270       280       290       300

CAT1    QPVGRIVLNKNIDNFFENENEQIAFCPALVPGIHYSDDKLLQTRIFSYADSQRHRLGPNYLQLPVNAPKCAHHNNHDGFMNFMHRDEEVNYFPSRLDPV
CAT2    QPVGRIVLNKNIDNFFAENEQLAFCPAIVPGIHYSDDKLLQTRVFSYADTQRHRLGPNYLQLPVNAPKCAHHNNHEGFMNFMHRDEEVNYFPSRYDQV
CAT3    QPVGRIVLNRTIDNFNETEQLAFNPGLWPGIYYSDDKLLQCRIFAYGDTQRHRLGPNYLQLPVNAPKCAHHNNHEGFMNFMHRDEEVNYPSKEDPV
                310       320       330       340       350       360       370       380       390

CAT1    RHAEKVPTTPIVCSGNREKCFIGKENNFKQPGERYRSMDSDRQERFVKRFVEAISEPRVTHEIRSTWISYWSQADKSLGQKIA TRLWRPNF
CAT2    RHAEKVPTPAVCSGKRERCIEKENNFKEPGERYRTFPERQERFIQRWIDALSDPRITHEIRSTWISYWSQADKSLGQKIASRLNVRPSI
CAT3    RCAEKVPTFNSYIGRTKCVIKKENNFKQAGDRYRSWAPDRQDRFVKRWVETLSEPRLTHEIRGTWISYWSQADRSLGQKIASRLWRPSH
                410       420       430       440       450       460       470       480       490
```

FIG. 33

IN VIVO GENERATION OF WATER-SOLUBLE CANNABINOIDS IN PLANT CELL SUSPENSION CULTURES

CROSS REFERENCE TO RELATED APPLICATIONS

This application is a Continuation-in-Part of U.S. application Ser. No. 16/110,954, filed Aug. 23, 2018; which is a Continuation-in-Part of International Application No. PCT/US18/41710, filed Jul. 11, 2018; which claims the benefit of and priority to U.S. Provisional Application No. 62/531,123, filed Jul. 11, 2017. International Application No. PCT/US18/41710, filed Jul. 11, 2018 is a Continuation-in-Part of International Application No. PCT/US18/24409, filed Mar. 26, 2018; which claims the benefit of and priority to U.S. Provisional Application Nos. 62/588,662, filed Nov. 20, 2017 and 62/621,166, filed Jan. 24, 2018.

SEQUENCE LISTING

The instant application contains a Sequence Listing which has been submitted electronically in ASCII format and is hereby incorporated by reference in its entirety.

TECHNICAL FIELD

The field of the present invention relates generally to systems and methods for the generation of water-soluble cannabinoids in yeast, and other plant cell suspension cultures. The field of the present invention also relates generally to compositions of matter that may contain one or more water-soluble cannabinoids.

BACKGROUND

Cannabinoids are a class of specialized compounds synthesized by *Cannabis*. They are formed by condensation of terpene and phenol precursors. They include these more abundant forms: Delta-9-tetrahydrocannabinol (THC), cannabidiol (CBD), cannabichromene (CBC), and cannabigerol (CBG). Another cannabinoid, cannabinol (CBN), is formed from THC as a degradation product and can be detected in some plant strains. Typically, THC, CBD, CBC, and CBG occur together in different ratios in the various plant strains.

Cannabinoids are generally classified into two types, neutral cannabinoids and cannabinoid acids, based on whether they contain a carboxyl group or not. It is known that, in fresh plants, the concentrations of neutral cannabinoids are much lower than those of cannabinoid acids. One strain *Cannabis sativa* contains approximately 61 compounds belonging to the general class of cannabinoids. These cannabinoids are generally lipophilic, nitrogen-free, mostly phenolic compounds, and are derived biogenetically from a monoterpene and phenol, the acid cannabinoids from a monoterpene and phenol carboxylic acid, and have a C21 to base material.

Cannabinoids also find their corresponding carboxylic acids in plant products. In general, the carboxylic acids have the function of a biosynthetic precursor. For example, these compounds arise in vivo from the THC carboxylic acids by decarboxylation the tetrahydrocannabinols Δ9- and Δ8-THC and CBD from the associated cannabidiol. As generally shown in FIG. 28, THC and CBD may be derived artificially from their acidic precursor's tetrahydrocannabinolic acid (THCA) and cannabidiolic acid (CBDA) by non-enzymatic decarboxylation.

Cannabinoids are widely consumed, in a variety of forms around the world. Cannabinoid-rich preparations of *Cannabis*, either in herb (i.e. marijuana) or resin form (i.e., hash oil), are used by an estimated 2.6-5.0% of the world population (UNODC, 2012). Cannabinoid containing pharmaceutical products, either containing natural *cannabis* extracts (Sativex®) or the synthetic cannabinoids dronabinol or nabilone, are available for medical use in several countries As noted above, 4-9-tetrahydrocannabinol (also known as THC) is one of the main biologically active components in the *Cannabis* plant which has been approved by the Food and Drug Administration (FDA) for the control of nausea and vomiting associated with chemotherapy and, more recently, for appetite stimulation of AIDS patients suffering from wasting syndrome. The drug, however, shows other biological activities which lend themselves to possible therapeutic applications, such as in the treatment of glaucoma, migraine headaches, spasticity, anxiety, and as an analgesic.

Indeed, it is well documented that agents, such as cannabinoids and endocannabinoids that activate cannabinoid receptors in the body modulate appetite, and alleviate nausea, vomiting, and pain (Martin B. R. and Wiley, J. L, *Mechanism of action of cannabinoids: how it may lead to treatment of cachexia, emesis and pain*, Journal of Supportive Oncology 2: 1-10, 2004), multiple sclerosis (Pertwee, R. G., *Cannabinoids and multiple sclerosis*, Pharmacol. Ther. 95, 165-174, 2002), and epilepsy (Wallace, M. J., Blair, R. E., Falenski, K. W W., Martin, B. R., and DeLorenzo, R. J. Journal Pharmacology and Experimental Therapeutics, 307: 129-137, 2003). In addition, CB2 receptor agonists have been shown to be effective in treating pain (Clayton N., Marshall F. H., Bountra C., O'Shaughnessy C. T., 2002. CB1 and CB2 cannabinoid receptors are implicated in inflammatory pain. 96, 253-260; Malan T. P., Ibrahim M. M., Vanderah T. W., Makriyannis A., Porreca F., 2002. Inhibition of pain responses by activation of CB(2) cannabinoid receptors. Chemistry and Physics of Lipids 121, 191-200; Malan T. P., Jr., Ibrahim M. M., Deng H., Liu Q., Mata H. P., Vanderah T., Porreca F., Makriyannis A., 2001. *CB2 cannabinoid receptor-mediated peripheral antinociception.* 93, 239-245.; Quartilho A., Mata H. P., Ibrahim M. M., Vanderah T. W., Porreca F., Makriyannis A., Malan T. P., Jr., 2003. *Inhibition of inflammatory hyperalgesia by activation of peripheral CB2 cannabinoid receptors*. Anesthesiology 99, 955-960) and multiple sclerosis (Pertwee, R. G., *Cannabinoids and multiple sclerosis*, Pharmacol. Ther. 95, 165-174, 2002) in animal models.

More recently, several states have approved use of *Cannabis* and cannabinoid infused products for both recreational and medical uses. As these new medical and commercial markets have developed, there has grown a need to develop more efficient production and isolation of cannabinoid compounds. Traditional methods of cannabinoid production typically focus on extraction and purification of cannabinoids from raw harvested *Cannabis*. However, traditional cannabinoid extraction and purification methods have a number of technical and practical problems that limits its usefulness.

Limitations of Traditional Cannabinoid Production and Extraction Methods

For example, in U.S. Pat. No. 6,403,126 (Webster et al.), cannabinoids, and other related compounds are isolated from raw harvested *Cannabis* and treated with an organic solvent, typically a petroleum derived hydrocarbon, or a low molecular-weight alcohol to solubilize the cannabinoids for later isolation. This traditional method is limited in that it relies on naturally grown plant matter that may have been exposed to various toxic pesticides, herbicides and the like. In addition, such traditional extraction methods are imprecise resulting in unreliable and varied concentrations of extracted THC. In addition, many *Cannabis* strains are grown in hydroponic environments which are also not regulated and can results in the widespread contamination of such strains with chemical and other undesired compounds.

In another example, US Pat. App. No. 20160326130 (Lekhram et al.), cannabinoids, and other related compounds are isolated from raw harvested *Cannabis* using, again, a series of organic solvents to convert the cannabinoids cannabinoids into a salt, and then back to its original carboxylic acid form. Similar to Webster, this traditional method is limited in that is relies on naturally grown plant matter that may have been exposed to various toxic pesticides, herbicides and the like. In addition, the multiple organic solvents used in this traditional process must be recovered and either recycled and/or properly disposed of.

Another traditional method of cannabinoid extraction involves the generation of hash oils utilizing supercritical carbon-dioxide ($sCO_2$). Under this traditional method, again the dried plant matter is ground and subjected to a $sCO_2$ extraction environment. The primary extract being initially obtained and further separated. For example, as generally described by CA2424356 (Muller et al.) cannabinoids are extracted with the aid of $sCO_2$ under supercritical pressure and temperature conditions and by the addition of accessory solvents (modifiers) such as alcohols. Under this process, this supercritical $CO_2$ evaporates and dissolves into the cannabinoids. However, this traditional process also has certain limiting disadvantages. For example, due to the low solubility in supercritical $sCO_2$, recovery of the cannabinoids of interest is inconsistent. Additionally, any solvents used must be recycled and pumped back to the extractor, in order to minimize operating costs.

Another method utilizes butane to extract cannabinoids, in particular high concentrations of THC, from raw harvested *Cannabis*. Because butane is non-polar, this process does not extract water soluble by-products such as chlorophyll and plant alkaloids. That said, this process may take up to 48 hours and as such is limited in its ability to scale-up for maximum commercial viability. The other major drawback of traditional butane-based extraction processes is the potential dangers of using flammable solvents, as well as the need to ensure all of the butane is fully removed from the extracted cannabinoids.

Another limiting factor in the viability of these traditional methods of cannabinoid extraction methods is the inability to maintain *Cannabis* strain integrity. For example, cannabinoids used in medical and research applications, or that are subject to controlled clinical trials, are tightly regulated by various government agencies in the United States and elsewhere. These regulatory agencies require that the *Cannabis* strains remain chemically consistent over time. Unfortunately, the genetic/chemical compositions of the *Cannabis* strains change over generations such that they cannot satisfy regulatory mandates present in most clinical trials or certified for use in other pharmaceutical applications.

Several attempts have been made to address these concerns. For example, efforts have been made to produce cannabinoids in genetically engineered organisms. For example, in U.S. patent application Ser. No. 14/795,816 (Poulos, et al.) Here, the applicant claims to have generated a genetically modified strain of yeast capable of producing a cannabinoid by inserting genes that produce the appropriate enzymes for its metabolic production. However, such application is limited in its ability to produce only a single or very limited number of cannabinoid compounds. This limitation is clinically significant. Recent clinical studies have found that the use of a single isolated cannabinoid as a therapeutic agent is not as effective as treatment with the naturally-occurring "entourage" of primary and secondary cannabinoids associated with various select strains. The system in Poulos is further limited in the ability to account for toxic by-products of cannabinoid synthesis, as well as the directly toxic effects of the insoluble, and/or only lipid-soluble, cannabinoid compounds themselves.

Additional attempts have been made to chemically synthesize cannabinoids, such as THC. However, the chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*.

Efforts to generate large-scale *Cannabis* cell cultures have also raised a number of technical problems. Chief among them is the fact that cannabinoids are cytotoxic. Under natural conditions cannabinoids are generated and then stored extracellularly in small glandular structures called trichomes. Trichomes can be visualized as small hairs or other outgrowths from the epidermis of a *Cannabis* plant. As a result, in *Cannabis* cell cultures, the inability to store cannabinoids extracellularly means any accumulation of cannabinoids would be toxic to the cultured cells. Such limitations impair the ability of *Cannabis* cell cultures to be scaled-up for industrial levels of production.

Cannabinoid Biosynthesis Toxicity Limits In Vivo Production Systems

Efforts to generate *Cannabis* strains/cell cultures that produce or accumulate high-levels of cannabinoids have raised a number of technical problems. Chief among them is the fact that cannabinoid synthesis produces toxic by-products. Notably, both CBDA and THCA synthases require molecular oxygen, in conjunction with a molecule of FAD, to oxidize Cannabigerolic acid (CBGA). Specifically, as shown in FIG. 29, two electrons from the substrate are accepted by an enzyme-bound FAD, and then transferred to molecular oxygen to re-oxidize FAD. CBDA and THCA are synthesized from the ionic intermediates via stereoselective cyclization by the enzymes. The hydride ion is transferred from the reduced flavin to molecular oxygen, resulting in the formation of hydrogen peroxide and re-activation of the flavin for the next cycle. As a result, in addition to producing CBDA and THCA respectively, this reaction produces hydrogen peroxide ($H_2O_2$) which is naturally toxic to the host cell. Due to this production of a toxic hydrogen peroxide byproduct, cannabinoid synthesis generates a self-limiting feed-back loop preventing high-level production and/or accumulation of cannabinoids in in vivo systems. One way that *Cannabis* plants deal with these cellular cytotoxic effects is through the use of trichomes for Cannabinoid production and accumulations.

*Cannabis* plants deal with this toxicity by sequestering cannabinoid biosynthesis and storage extracellularly in small glandular structures called trichomes as note above. For example, THCA synthase is a water soluble enzyme that is responsible for the production of THC. For example, THC biosynthesis occurs in glandular trichomes and begins with condensation of geranyl pyrophosphate with olivetolic acid to produce cannabigerolic acid (CBGA); the reaction is catalyzed by an enzyme called geranylpyrophosphate:olivatolate geranyltransferase. CBGA then undergoes oxidative cyclization to generate tetrahydrocannabinolic acid (THCA) in the presence of THCA synthase. THCA is then transformed into THC by non-enzymatic decarboxylation. Subcellular localization studies using RT-PCR and enzymatic activity analyses demonstrate that THCA synthase is expressed in the secretory cells of glandular trichomes, and then is translocated into the secretory cavity where the end product THCA accumulates. THCA synthase present in the secretory cavity is functional, indicating that the storage cavity is the site for THCA biosynthesis and storage. In this way, the *Cannabis* is able to produce cannabinoids extracellularly and thereby avoid the cytotoxic effects of these compounds. However, as a result, the ability to access and chemically alter cannabinoids in vivo is impeded by this cellular compartmentalization.

To address these concerns, some have proposed chemically modifying cannabinoid compounds to reduce their cytotoxic effects. For example, Zipp, et al., have proposed utilizing an in vitro method to produce cannabinoid glycosides. However, this application is limited to in vitro systems only. Specifically, as noted above, cannabinoid synthase enzymes, such as THCA synthase, are water soluble proteins that are exported out of the basal trichome cells into the storage compartment where it is active and catalyzes the synthesis of THCA. Specifically, in order to effectively mediate the cellular export of such cannabinoid synthase, this enzyme contains a 28 amino acid signal peptide that directs its export out of the cell and into the extracellular trichrome where cannabinoid synthesis occurs.

The foregoing problems regarding the production, detoxification and isolation of cannabinoids may represent a long-felt need for an effective—and economical—solution to the same. While implementing elements may have been available, actual attempts to meet this need may have been lacking to some degree. This may have been due to a failure of those having ordinary skill in the art to fully appreciate or understand the nature of the problems and challenges involved.

As a result of this lack of understanding, attempts to meet these long-felt needs may have failed to effectively solve one or more of the problems or challenges here identified. These attempts may even have led away from the technical directions taken by the present inventive technology and may even result in the achievements of the present inventive technology being considered to some degree an unexpected result of the approach taken by some in the field.

As will be discussed in more detail below, the current inventive technology overcomes the limitations of traditional cannabinoid production systems while meeting the objectives of a truly effective and scalable cannabinoid production, modification and isolation system.

SUMMARY OF THE INVENTION(S)

Generally, the inventive technology relates to the field of chemical modification and isolation in yeast suspension cultures. The present inventive technology further relates to improved systems and methods for the modification and isolation of pharmaceutically active components from plant materials. In one embodiment, the inventive technology may encompass a novel system for the generation of chemically modified-cannabinoid compounds in a yeast suspension culture. The inventive technology may include systems and methods for high-efficiency chemical modification and isolation of cannabinoid compounds from yeast suspension cultures. In this embodiment, various select cannabinoid compounds may be chemically modified into soluble and non-toxic configurations.

One aim of the current inventive technology includes improved systems and methods for the modification of cannabinoids in a sterile yeast and/or plant culture system. In one embodiment, the inventive technology may include the production of a sterile yeast and/or plant cell suspension culture. The inventive technology may allow for certain transgenes to be introduced into these yeast strains and/or plant to transiently modify the chemical structure of the cannabinoid compounds. This transient modification may render the cannabinoids soluble in water. Such modifications may also alter the rate at which the cannabinoids are metabolized generating a modified cannabinoid with enhanced kinetics that may be used in certain therapeutic applications or as a prodrug. These transiently modified cannabinoids, aided by their modified chemical structure, may be allowed to accumulate at higher than native levels without having a deleterious effect on the cultured yeast and/or plant cells. Being soluble, they may also be secreted through endogenous and/or exogenous ABC or other transmembrane protein transporters into the culture medium for later harvesting and isolation. It is noted that naturally occurring cannabinoids are strong inhibitors of ABC transporters. These transiently modified cannabinoids may be harvested and isolated from the aforementioned culture systems, and then enzymatically restored to their original chemical structure. Other embodiments may allow for the regulation of cannabinoid modification and isolation. In such embodiment, discreet and known amounts of cannabinoids may be introduced into a yeast and/or plant suspension culture and transiently modified. Later, the modified cannabinoids may be extracted from the cell culture and isolated such that the quantity and relative ratios of the various cannabinoids is known and quantifiable. In this manner the isolated cannabinoid extract may be chemically consistent and as such, easily dosable for both pharmaceutical and/or recreational applications.

Additional aims of the inventive technology may include the transient modification of cannabinoid compounds to render them water-soluble in yeast cell culture systems. In a preferred embodiment, such soluble cannabinoids may have reduced cytotoxicity to yeast cells in culture and may further be actively transported out of the cell and allowed to accumulate at levels that would normally have a deleterious effect on the cell culture. Additional embodiments may include the isolation of these transiently modified cannabinoids followed by enzymatic conversion or reconstitution to their original and/or partially modified structure.

Another aim of the current invention may include the systems, methods and compositions for the generation of water-soluble cannabinoid compounds. Another aim of the current inventive technology includes the generation of various compositions of matter containing water-soluble cannabinoids. In one preferred embodiment, such compositions of matter may contain water-soluble cannabinoids generated in an in vitro and/or in vivo system.

Additional aims of the invention may include delivery systems and compositions that include water-soluble cannabinoids, preferably glycosylated and/or acetylated cannabinoids. Additional embodiments may further include methods and systems for the production of compositions that include water-soluble cannabinoids, preferably glycosylated and/or acetylated cannabinoids.

Another aim of the current invention may include systems, methods and compositions for the delivery of water-soluble cannabinoids, preferably glycosylated and/or acetylated cannabinoids as a prodrug. Included in this invention may include novel prodrug compositions.

One aim of the invention may include systems, methods and compositions for the in vivo production, modification and isolation of cannabinoid compounds from *Cannabis* plants. In particular, the invention provides systems and methods for high level in vivo biosynthesis of water-soluble cannabinoids in yeast. In one preferred embodiment, the suspension culture may include the biotransformation of one or more cannabinoids in yeast, or other plant cells into a water-soluble form.

One aim of the invention may include systems, methods and compositions for the in vivo production, modification and isolation of cannabinoid compounds from *Cannabis* plants. In particular, the invention provides systems and methods for high level in vivo biosynthesis of water-soluble cannabinoids in cell suspension cultures. In one preferred embodiment, the suspension culture may include a yeast suspension culture, a tobacco or other plant cell suspension culture or a *cannabis* plant cell suspension culture.

The current inventive technology includes systems and methods for enhanced production and/or accumulation of cannabinoids. In one embodiment, the invention may include systems and methods for enhanced production and/or accumulation of cannabinoids in an in vivo system, such as a yeast, or plant cell suspension culture.

Another aim of the current invention may include the generation of genetically modified plants cells that may further be in a suspension culture that may overexpress certain endogenous/exogenous genes that result in the overproduction and/or accumulation of cannabinoids above wild-type levels. In one preferred embodiment, such transgenic plant cell cultures may exhibit enhanced production and accumulation of cannabinoid precursor compounds, such as THCA (tetrahydrocannabinolic acid), CBCA (cannabichromenic acid), and CBDA (cannabidiolic acid). Such transgenic plant cells in culture may additionally exhibit enhanced production and localized accumulation of cannabinoids, such as THCs, CBCs and CBDs.

An additional aim of the current invention may include the generation of genetically modified plant cells in culture expressing certain endogenous/exogenous that result in the enhanced biomodification of cannabinoids. In one preferred embodiment, such cultured transgenic plant cells may exhibit enhanced modification of cannabinoids including hydroxylation, and/or acetylation, and/or glycosylation. In additional preferred embodiments, such transgenic plants may exhibit enhanced modification of cannabinoids including acetylation and glycosylation, such as an O acetylated glycoside form. For example, acetylation adds an acetyl group ($-CH_3OOH$) to a cannabinoid such that the carboxylate group is acidic and charged at neutral pH making it highly water-soluble.

Another aim of the current invention may include the generation of genetically modified yeast strains overexpressing certain endogenous/exogenous genes that result in the over-production and/or accumulation of cannabinoids above wild-type levels. In one preferred embodiment, such transgenic yeast may exhibit enhanced production and localized accumulation of cannabinoid precursor compounds, such as THCA (tetrahydrocannabinolic acid), CBCA (cannabichromenic acid), and CBDA (cannabidiolic acid). Such transgenic plants may additionally exhibit enhanced production and localized accumulation of cannabinoids, such as THCs, CBCs and CBDs.

An additional aim of the current invention may include the generation of genetically modified plants expressing certain genes that result in the modification of cannabinoids into water-soluble forms. In one preferred embodiment, such transgenic yeast may exhibit enhanced modification of cannabinoids including hydroxylation, and/or acetylation, and/ or glycosylation. In additional preferred embodiments, such transgenic plants may exhibit enhanced modification of cannabinoids including acetylation and glycosylation, such as an O acetyl glycoside form. For example, acetylation adds an acetate group ($-CH_3COOH$) to a cannabinoid such that the carboxylate group is acidic and charged at neutral pH making it highly water-soluble.

One aim of the current inventive technology may be to generate genetically modified, or transgenic plant cells in a suspension culture that overexpresses one or more transcription factors, such as myb, that enhance metabolite flux through the cannabinoid biosynthetic pathway. In one preferred embodiment, these transcription factors may include various analogues. In certain preferred embodiments, one or more of these transgenes may be operably-linked to one or more promoters.

One aim of the current inventive technology may be to generate genetically modified or transgenic *Cannabis* plant cells in a suspension culture that overexpresses one or more transcription factors, such as myb, that enhance metabolite flux through the cannabinoid biosynthetic pathway. In one preferred embodiment, these transcription factors may include various analogues. In certain preferred embodiment, one or more of these transgenes may be operably-linked to one or more promoters.

Another aim of the current inventive technology may be to generate a genetically modified or transgenic tobacco cell culture that overexpresses one or more transcription factors that enhance metabolite flux through the cannabinoid biosynthetic pathway. In one preferred embodiment, these transgenes may be operably linked to one or more promoters.

Yet, another aim of the current inventive technology may be to generate a genetically modified or transgenic plant cell that expresses an enzyme that is configured to be capable of reducing hydrogen peroxide ($H_2O_2$) levels that may be generated during cannabinoid synthesis. In one preferred embodiment, the current inventive technology may be to generate a genetically modified or transgenic tobacco and/or *Cannabis* plant cell in a suspension culture that expresses a catalase protein. In this embodiment, this catalase protein may reduce hydrogen peroxide ($H_2O_2$) levels generated during cannabinoid synthesis.

Yet, another aim of the current inventive technology may be to generate genetically modified plants, plant cells and/or yeast cells that expresses an enzyme that is configured to be capable of reducing hydrogen peroxide ($H_2O_2$) levels that may be generated during cannabinoid synthesis. In one preferred embodiment, the current inventive technology may be to generate a genetically modified or transgenic yeast cell in a suspension culture that expresses a catalase protein. In this embodiment, this catalase protein may reduce hydrogen peroxide ($H_2O_2$) levels generated during cannabinoid synthesis.

Another aim of the current invention may include the introduction of one or more compounds to facilitate the chemical decomposition of hydrogen peroxide resulting from cannabinoids biosynthesis. In one preferred embodiment, one or more chemicals, metal ions, and/or catalysts may be introduced into a growth media to detoxify hydrogen peroxide ($H_2O_2$) in both yeast and plant cell cultures. It should be noted that additional cell cultures and cell lines may be contemplated in the invention. For example, CHO cells, HeLa cells and insect cell lines, like SF-9 cells may be genetically modified as generally described herein to generate water-soluble cannabinoids.

Additional embodiments of the inventive technology may include the transient modification of cannabinoid compounds to reduce and/or eliminate their cytotoxicity in plants or plant cell culture systems. In a preferred embodiment, such transiently modified cannabinoids may be allowed to accumulate at levels that would normally have a deleterious effect on the cell. Additional embodiments may include the isolation of these transiently modified cannabinoids followed by enzymatic conversion or reconstitution to their original and/or partially modified structure.

Another aim of the invention may include the generation of a transgenic plant and or plant cell cultures that may over express endogenous genes that may be configured to modify cannabinoids. Additional aim may include the co-expression of heterologous transcription factors that may increase cannabinoid production. Another aim of the invention may include the co-expression of heterologous genes that detoxify the hydrogen peroxide byproducts generated through cannabinoid biosynthesis. Co-expression of such genes may be additive with the co-expression of genes configured to modify and/or localize cannabinoid biomodifications.

Another aim of the invention may include systems, methods and compositions for the generation of a yeast cannabinoid production system coupled with systems, methods and compositions for the reducing hydrogen peroxide toxicity resulting from cannabinoid synthesis. Another aim of the invention may include systems, methods and compositions for the generation of a yeast cannabinoid production system coupled with systems, methods and compositions for the biomodification of such yeast generated cannabinoids into functionalized as well as water-soluble forms as generally described herein.

Additional embodiments of the invention may include:

1. An in vivo method of producing water-soluble cannabinoids comprising the steps of:
   genetically modifying a tobacco cell to express:
      a nucleotide sequence encoding a heterologous cytochrome P450 operably linked to a promoter having hydroxylation or oxidation activity toward one or more cannabinoids to generate a hydroxylated cannabinoid or a cannabinoid carboxylic acid;
      a nucleotide sequence encoding a heterologous P450 oxidoreductase operably linked to a promoter that facilitates electron transfer from nicotinamide adenine dinucleotide phosphate (NADPH) to the cytochrome P450;
      wherein said tobacco cell expresses at least one endogenous glycosyltransferase protein having glycosylation activity towards one or more cannabinoids.
   establishing a suspension cell culture of said genetically modified tobacco cells;
   introducing one or more cannabinoids to said suspension cell culture of said genetically modified tobacco cells;
   chemically converting said one or more cannabinoids into one or more water soluble glycosylated cannabinoids; and
   isolating said water soluble glycosylated cannabinoids.

2. The method of embodiment 1, wherein said endogenous glycosyltransferase protein comprises an endogenous glycosyltransferase protein selected from the group consisting of: NtGT3; NtGT4; and NtGT5, and a homolog or ortholog of NtGT3, NtGT4, and NtGT5 having glycosylation activity towards one or more cannabinoids.

3. The method of embodiment 1, wherein said endogenous glycosyltransferase comprises an endogenous glycosyltransferase protein selected from the group of amino acid sequences consisting of: SEQ ID NO. 26, SEQ ID NO. 28, SEQ ID NO. 30, SEQ ID NO. 36.

4. The method of embodiment 1, further comprising the step of genetically modifying said tobacco cell to overexpress a nucleotide sequence encoding one or more endogenous glycosyltransferases having glycosylation activity towards one or more cannabinoids, wherein said nucleotide sequence is operably linked to a promoter.

5. The method of embodiment 1, wherein said nucleotide sequence encoding a heterologous cytochrome P450 is identified as SEQ ID NO. 1.

6. The method of embodiment 1, wherein said nucleotide sequence encoding a heterologous P450 oxidoreductase is identified as SEQ ID NO. 3.

7. The method of embodiment 1, further comprising the step of genetically modifying said tobacco cell to express a nucleotide sequence, operably linked to a promoter, encoding a heterologous ABC transporter that facilitates the transport of said glycosylated cannabinoids out of said genetically modified tobacco cell.

8. The method of embodiment 7, wherein said nucleotide sequence encoding a heterologous ABC transporter is selected from the group consisting of: the nucleotide sequence of SEQ ID NO. 9, and the nucleotide sequence of SEQ ID NO. 67.

9. An in vivo method for the generation of water-soluble cannabinoids comprising the steps of:
   establishing a suspension cell culture of tobacco cells that expresses at least one endogenous glycosyltransferase protein having glycosylation activity towards one or more cannabinoids;
   introducing one or more cannabinoids to said suspension cell culture of tobacco cells; and
   chemically converting said one or more cannabinoids into one or more water soluble glycosylated cannabinoids through the action of said at least one endogenous glycosyltransferase.

10. The method of embodiment 9, wherein said endogenous glycosyltransferase protein comprises an endogenous glycosyltransferase protein selected from the group consisting of: NtGT3; NtGT4; and NtGT5, and a homolog or ortholog of NtGT3, NtGT4, and NtGT5 having glycosylation activity towards one or more cannabinoids.

11. The method of embodiment 9, wherein said endogenous glycosyltransferase protein comprises an endogenous glycosyltransferase protein selected from the group of amino acid sequences consisting of: SEQ ID NO. 26, SEQ ID NO. 28, SEQ ID NO. 30, SEQ ID NO. 36.

12. The method of embodiment 9, further comprising the step of genetically modifying said tobacco cells in said suspension culture to overexpress one or more endogenous glycosyltransferase proteins.

13. The method of embodiment 12, wherein said endogenous glycosyltransferase protein comprises an endogenous glycosyltransferase protein selected from the group consisting of: NtGT3; NtGT4; and NtGT5, and a homolog or ortholog of NtGT3, NtGT4, and NtGT5 having glycosylation activity towards one or more cannabinoids.

14. The method of embodiment 9, further comprising the step of genetically modifying said tobacco cells in said suspension culture to express a heterologous ABC transporter protein to facilitate the transport of said glycosylated cannabinoids out of said tobacco cell.

15. The method of embodiment 14, wherein said multidrug ABC transporter protein is selected from the group consisting of: SEQ ID NO. 10, and SEQ ID NO. 68.

16. The method of embodiment 9, and further comprising the step of genetically modifying said tobacco cells in said suspension culture to express a heterologous cytochrome P450 protein wherein said heterologous cytochrome P450 hydroxylates said one or more cannabinoids to form a hydroxylated cannabinoid and/or oxidizes a said hydroxylated cannabinoid to form a cannabinoid carboxylic acid.

17. The method of embodiment 16, wherein said heterologous cytochrome P450 protein is identified as SEQ ID NO. 2.

18. The method of embodiment 16, further comprising the step of genetically modifying said tobacco cells in said suspension culture to express a heterologous P450 oxidoreductase protein wherein said heterologous P450 oxidoreductase protein facilitates electron transfer from a nicotinamide adenine dinucleotide phosphate (NADPH) to said cytochrome P450.

19. The method of embodiment 18, wherein said heterologous P450 oxidoreductase protein is identified as SEQ ID NO. 4.

20. A non-genetically modified in vivo method of producing water-soluble cannabinoids comprising the steps of:
    establishing a plant cell suspension cell culture from a non-cannabinoid producing plant that expresses at least one endogenous glycosyltransferase having glycosylation activity towards one or more cannabinoids;
    introducing one or more cannabinoids to said plant cell suspension culture;
    chemically converting said one or more cannabinoids into one or more water soluble glycosylated cannabinoids through the action of said at least one endogenous glycosyltransferase;
    isolating said glycosylated cannabinoids from said plant cell suspension culture.

21. The method of embodiment 20, wherein said plant cell suspension cell culture from a non-cannabinoid producing plant comprises a tobacco cell suspension culture.

22. The method of embodiment 21, wherein said endogenous glycosyltransferase comprises an endogenous glycosyltransferase selected from the group consisting of: NtGT3; NtGT4; and NtGT5, and a homolog or ortholog of NtGT3, NtGT4, and NtGT5 having glycosylation activity towards one or more cannabinoids.

23. A method of producing water-soluble cannabinoids comprising the steps of:
    genetically modifying a plant cell to express a nucleotide sequence operably linked to a promoter encoding a heterologous glycosyltransferase from a tobacco plant having glycosylation activity towards one or more cannabinoids;
    establishing a suspension cell culture of said genetically modified plant cells;
    introducing one or more cannabinoids to said suspension cell culture of said genetically modified plant cells;
    chemically converting said one or more cannabinoids into one or more water soluble glycosylated cannabinoids; and
    isolating said glycosylated cannabinoids from said plant cell suspension culture.

24. The method of embodiment 23, wherein said heterologous glycosyltransferase from a tobacco plant comprises a heterologous glycosyltransferase from a tobacco plant selected from the group consisting of: NtGT3; NtGT4; and NtGT5, and a homolog or ortholog of NtGT3, NtGT4, and NtGT5 having glycosylation activity towards one or more cannabinoids.

25. The method of embodiment 23, further comprising the step of genetically modifying said plant cells to express a nucleotide sequence encoding a heterologous ABC transporter that facilitates the transport of said glycosylated cannabinoids out of said genetically modifying plant cell, wherein said nucleotide sequence is operably linked to a promoter 26. The method of embodiment 25, wherein said nucleotide sequence encoding a heterologous ABC transporter is selected from the group consisting of: the nucleotide sequence of SEQ ID NO. 9, and the nucleotide sequence of SEQ ID NO. 67.

27. The method of embodiment 23, further comprising the step of genetically modifying said plant cells to express a heterologous cytochrome P450 protein wherein said heterologous cytochrome P450 hydroxylates said one or more cannabinoids to form a hydroxylated cannabinoid and/or oxidizes a said hydroxylated cannabinoid to form a cannabinoid carboxylic acid.

28. The method of embodiment 27, wherein said heterologous cytochrome P450 protein is identified as SEQ ID NO. 2.

29. The method of embodiment 23, further comprising the step of genetically modifying said plant cells to express a heterologous P450 oxidoreductase protein wherein said heterologous P450 oxidoreductase protein facilitates electron transfer from a nicotinamide adenine dinucleotide phosphate (NADPH) to said cytochrome P450.

30. The method of embodiment 29 wherein said heterologous P450 oxidoreductase protein is identified as SEQ ID NO. 4.

Another aim of the invention includes compositions of novel water-soluble cannabinoids and their method or manufacture. Still other aims of the current invention include additional compositions of matter that incorporate one or more water-soluble cannabinoids.

BRIEF DESCRIPTION OF THE FIGURES

The above and other aspects, features, and advantages of the present disclosure will be better understood from the following detailed descriptions taken in conjunction with the accompanying figures, all of which are given by way of illustration only, and are not limiting the presently disclosed embodiments, in which:

FIG. 33. Amino Acid sequence comparison of exemplary *Arabidopsis* catalase protein sequences. FIG. 33 also contains SEQ. ID NO. 73 which represents CAT gene 1; SEQ. ID NO. 74 which represents CAT gene 2; and SEQ. ID NO. 75 which represents CAT gene 3. Boxes 1, 2, and 3 highlight conserved amino acid sequence at the C-terminal tail of the exemplary catalase enzymes identified above.

(FIG. 50A) Demonstrates the percent loss of CBDA in solution over 7 day period at room temperature; and (FIG. 50B) Demonstrates the percent loss of 1×CBDA glycoside in solution over 7 day period at room temperature.

(FIG. 51A) Demonstrates the 1×CBD Glycoside content in solution over at day 7; and (FIG. 51B) Demonstrates the percent conversion of 1×CBDA Glycoside to 1×CBD Glycoside.

MODE(S) FOR CARRYING OUT THE INVENTION(S)

Figure 1:
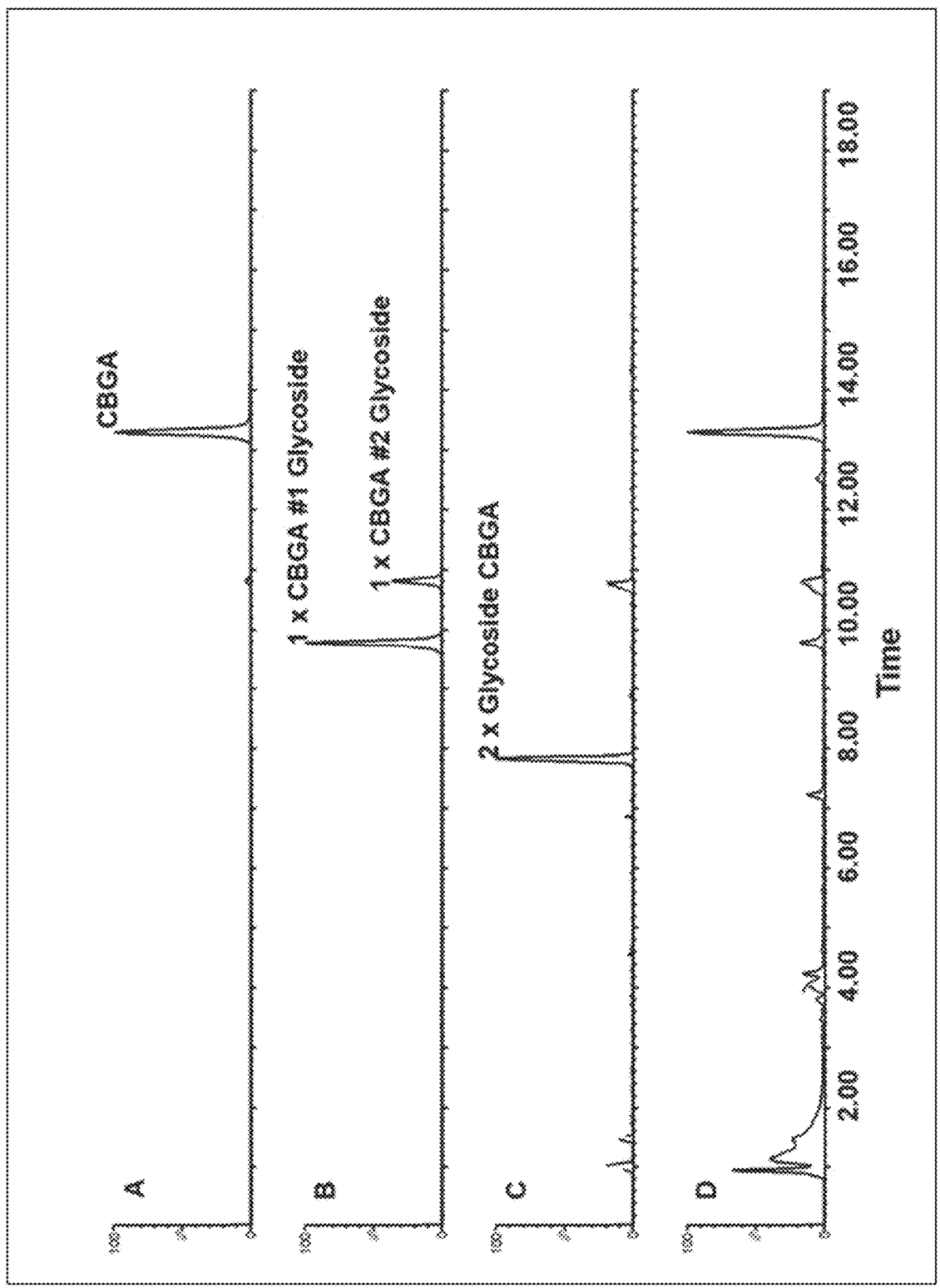
FIG. 1. Representative Chromatographic Elution profile of CBGA Glycosides found in in vitro Assays. Chromatograms A, B, and C represent respective extracted ion chromatograms for each glycoside product. Chromatogram D is representative of the total ion chromatogram. Peak Intensities are illustrated as relative abundance to most abundant peak in each respective chromatogram.
Figure 2:
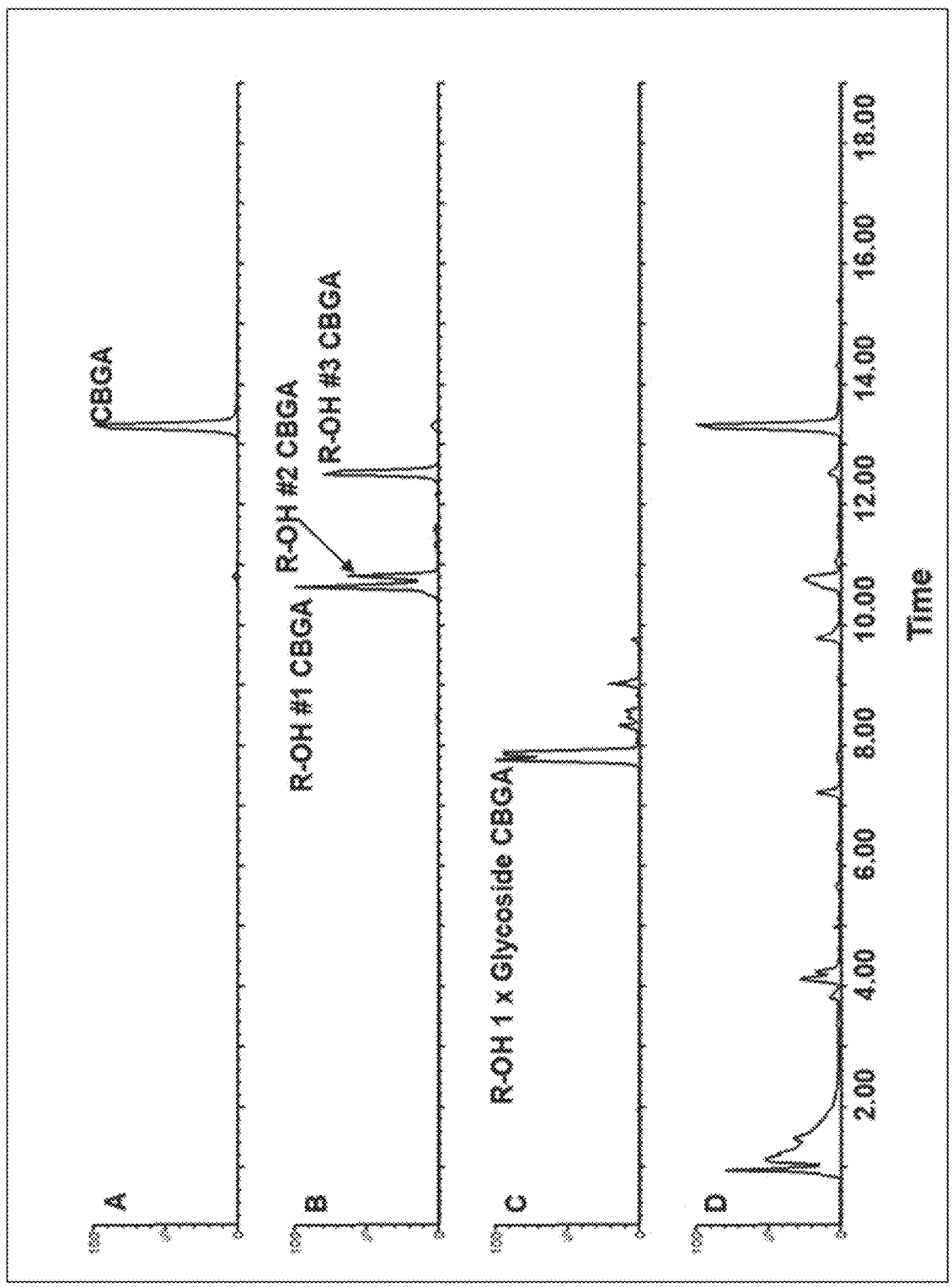
FIG. 2. Representative Chromatographic Elution profiles of Functionalized CBGA and Glycosides found in in vitro assays. Chromatograms A, B, and C represent respective extract rated ion chromatograms for each product. Chromatogram D is representative of the total ion chromatogram. Peak Intensities are illustrated as relative abundance to most abundant peak in each respective chromatogram.
Figure 3:
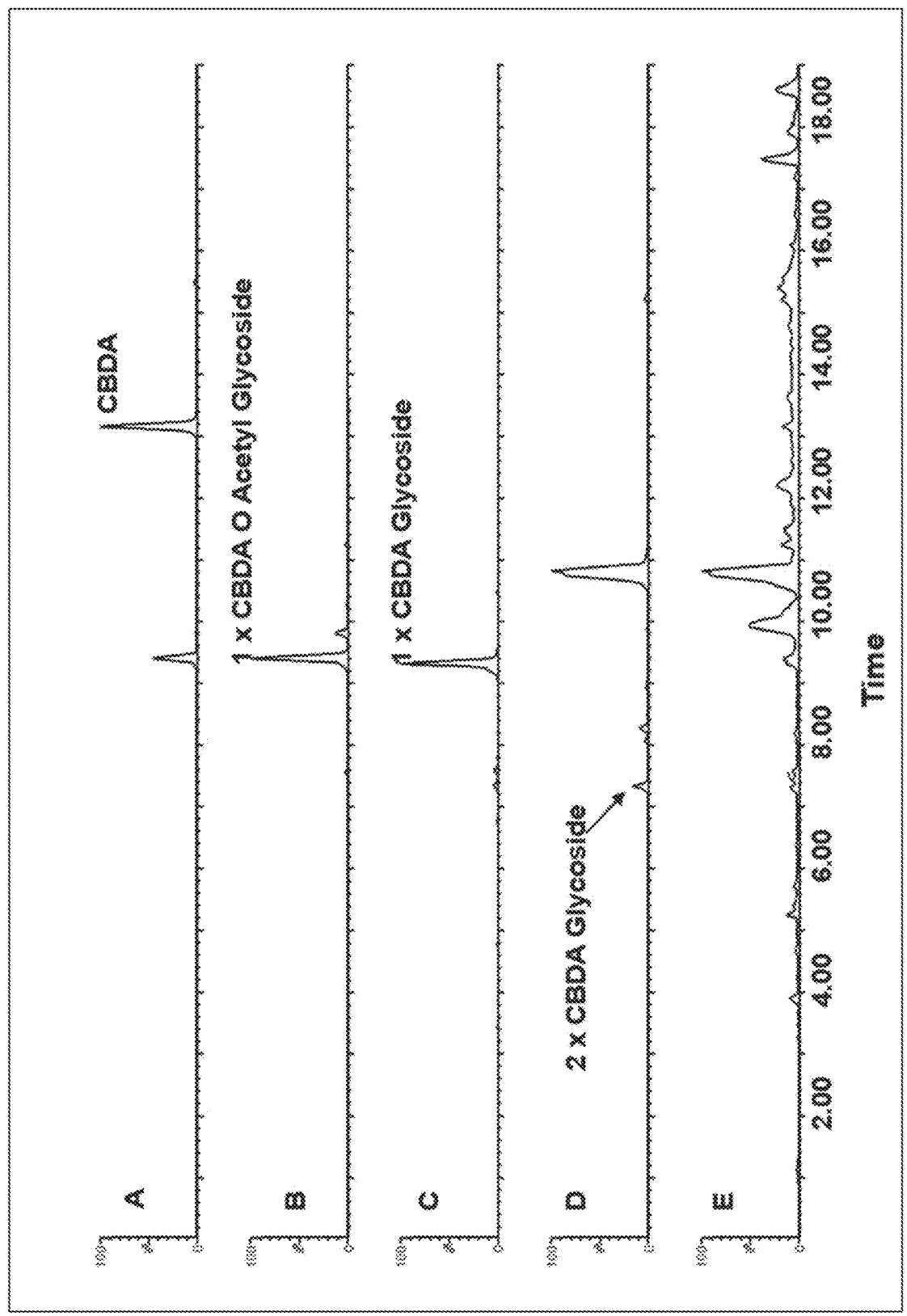
FIG. 3. Representative Chromatographic Elution profile of CBDA Glycosides profiles found in Leaf Extracts. Chromatograms A, B, C, and D represent respective extract rated ion chromatograms for each glycoside product. Chromatogram E is representative of the total ion chromatogram. Peak Intensities are illustrated as relative abundance to most abundant peak in each respective chromatogram.
Figure 4:
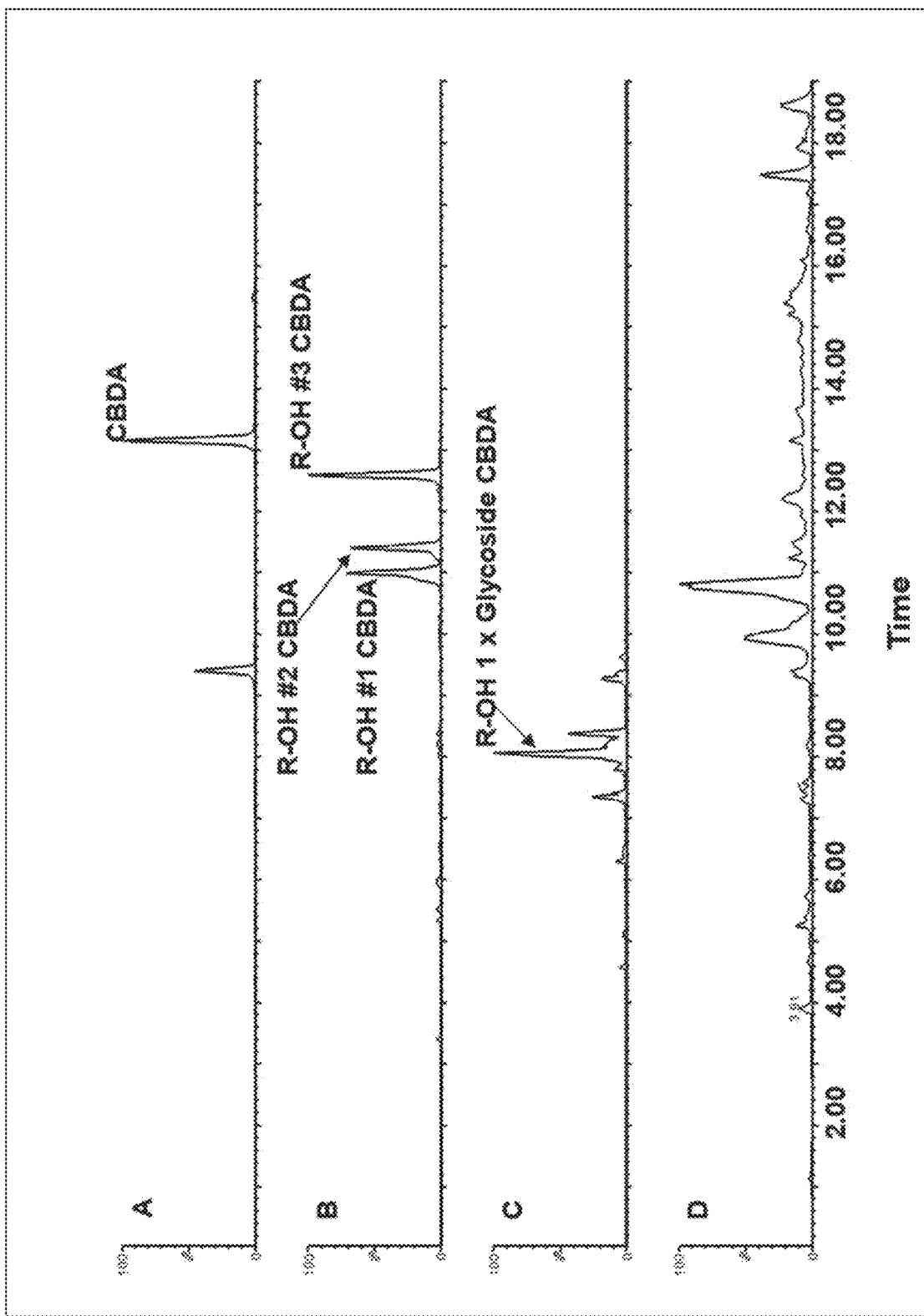
FIG. 4. Chromatographic Elution of Functionalized CBDA and Functionalized Glycosides in Leaf Extracts. Chromatograms A, B, and C represent respective extract rated ion chromatograms for each product. Chromatogram D is representative of the total ion chromatogram. Peak Intensities are illustrated as relative abundance to most abundant peak in each respective chromatogram.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The inventive technology may include systems and methods for the chemical modification of cannabinoid compounds. In one embodiment, a suspension culture of one or more yeast strains may be established. In one preferred embodiment, culture, and more preferably a suspension culture of *Saccharomyces cerevisiae* and/or *Pichia pastoris* or other suitable yeast species may be established in a fermenter or other similar apparatus. It should be noted that the use of the above identified example in this embodiment is exemplary only, as various yeast strains, mixes of strains, hybrids of different strains or clones may be used to generate a suspension culture. For example, *Pichia pastoris* or any other appropriate yeast strain, including but not limited to all strains of yeast deposited with the ATCC. (The yeast strain deposit database(s) being incorporated by reference in its entirety.) In certain cases, such fermenters may include large industrial-scale fermenters allowing for a large quantity of yeast cells to be grown. In this embodiment, it may be possible to culture a large quantity of cells from a single-strain of, for example, *P. pastoris* or *K. marxianus*, which may establish a cell culture having a consistent rate of cannabinoid modification. Such cultured growth may be continuously sustained with the continual addition of nutrient and other growth factors being added to the culture. Such features may be automated or accomplished manually.

As noted above, cannabinoid producing strains of *Cannabis*, as well as other plants may be utilized with the inventive technology. In certain preferred embodiments, *Cannabis* plant material may be harvested and undergo cannabinoid extraction through one or more of the methods generally described above. These extracted cannabinoids may be introduced into a genetically modified yeast suspension cell culture to be further modified as described below.

As noted above, accumulation of high-levels of cannabinoids may be toxic for the yeast cell. As such, the inventive technology may transiently modify the cannabinoids produced in the yeast cell culture in vivo. In one preferred embodiment, cytochrome P450's (CYP) monooxygenases may be utilized to transiently modify or functionalize the chemical structure of the cannabinoids to produce water-soluble forms. CYPs constitute a major enzyme family capable of catalyzing the oxidative biotransformation of many pharmacologically active chemical compounds and other lipophilic xenobiotics. For example, the most common reaction catalyzed by cytochromes P450 is a monooxygenase reaction, e.g., insertion of one atom of oxygen into the aliphatic position of an organic substrate (RH) while the other oxygen atom is reduced to water:

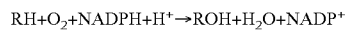

$RH+O_2+NADPH+H^+ \rightarrow ROH+H_2O+NADP^+$

Several cannabinoids, including THC, have been shown to serve as a substrate for human CYPs (CYP2C9 and CYP3A4). Similarly, CYPs have been identified that metabolize cannabidiol (CYPs 2C19, 3A4); cannabinol (CYPs 2C9, 3A4); JWH-018 (CYPs 1A2, 2C9); and AM2201 (CYPs 1A2, 2C9). For example, as shown generally below, in one exemplary system, CYP2C9 may hydroxylate a THC molecule resulting in a hydroxyl form of THC. Further oxidation of the hydroxyl form of THC by CYP2C9 may convert it into a carboxylic acid form, which loses its psychoactive capabilities rendering it an inactive metabolite.

In one embodiment, yeast cells may be transformed with artificially created genetic constructs encoding one or more CYPs. In one preferred embodiment, genes encoding one or more non-human isoforms and/or analogs, as well as possibly other CYPs that may functionalize cannabinoids may be expressed in transgenic yeast grown in a suspension culture. Additional embodiments may include genetic control elements such as promotors and/or enhancers as well as post-transcriptional regulatory elements that may also be expressed in transgenic yeast such that the presence, quantity and activity of any CYPs present in the suspension culture may be modified and/or calibrated.

In this preferred embodiment, NADPH-cytochrome P450 oxidoreductase (CPR) may be used to assist in the activity/function of one or more of the CYPs expressed within a genetically modified yeast cell. In this embodiment, CPR may serve as an electron donor to eukaryotic CYPs facilitating their enzymatic function within the transgenic yeast strain(s) described above. In one preferred embodiment, genes encoding CPR, or one or more non-human isoforms and/or analogs of CPR that may act as an electron donor to CYPs may be expressed in transgenic yeast grown in a suspension culture. Additional embodiments may include genetic control elements such as promotors and/or enhancers as well as post-transcriptional regulatory elements that may also be expressed in transgenic yeast such that the presence, quantity and activity of CPR present in the suspension culture may be modified and/or calibrated. For example, downregulation of the expression of CPR may decrease or stop the functionalization of cannabinoids by preventing the enzymatic action of the CYPs in the yeast cell.

Additional steps may be taken to further modify the functionalized cannabinoids. In a preferred embodiment, glycosylation of functionalized cannabinoids may covert to them into a water-soluble form. In an exemplary embodiment shown below, the inventive technology may utilize one or more UDP-glucuronosyltransferases (UGT) to catalyze the glucuronosylation or glucuronidation of both primary (CBD, CBN) and secondary cannabinoids (THC, JWH-018, JWH-073). In this embodiment, glucuronidation may consist of the transfer of a glucuronic acid component of uridine diphosphate glucuronic acid to a cannabinoid substrate by any of several types of UGTs as described above. Glucuronic acid is a sugar acid derived from glucose, with its sixth carbon atom oxidized to a carboxylic acid.

The conversion of a functionalized cannabinoid, in this example a carboxylic acid form of THC, to a glycosylated form of THC may generate a transiently modified cannabinoid that may be both soluble, and non-toxic to the cells in a suspension culture. These chemical modifications may allow for greater levels of cannabinoid accumulation within a yeast cell and/or in the surrounding cell culture media without the deleterious cytotoxic effects that may be seen with unmodified cannabinoids.

The inventive technology may include the generation of transgenic yeast strains having artificial genetic constructs that that may express one or more glycosyltransferases, or other enzymes capable of glycosylating functionalized cannabinoid compounds. In one preferred embodiment, artificial genetic constructs having genes encoding one or more UDP- and/or ADP-glycosyltransferases, including non-human analogues of those described above, as well as other isoforms, may be expressed in transgenic yeast cells and grown in suspension or other cell cultures. Additional embodiments may include genetic control elements such as promotors and/or enhancers as well as post-transcriptional regulatory control elements that may also be expressed in a transgenic yeast strain such that the presence, quantity and activity of any glycosyltransferases present in the suspension culture may be regulated. Additional embodiments may include artificial genetic constructs having one or more genes encoding one or more UDP- and/or ADP-glycosyltransferases having tags that may assist in the movement of the gene product to a certain portion of the cell, such as the cellular locations were cannabinoids and/or functionalized cannabinoids may be stored, and/or excreted from the cell.

In one embodiment of the inventive technology, the water-soluble, glycosylated cannabinoids, generally being referred to as transiently modified cannabinoids, may be transported into and harvested from the yeast cell culture media. In one embodiment, transiently modified cannabinoids may accumulate within the yeast cell itself. In this example, the yeast cell culture may be allowed to grow to a desired level of cell or optical density, or in other instances until a desired level of transiently modified cannabinoids have accumulated in the cultured cells and/or media. All, or a portion of the yeast cells containing the accumulated transiently modified cannabinoids may then be harvested from the culture and/or media, which in a preferred embodiment may be an industrial-scale fermenter or other apparatus suitable for the large-scale culturing of yeast or other microorganisms. The harvested yeast cells may be lysed such that the accumulated transiently modified cannabinoids may be released to the surrounding lysate. Additional steps may include treating this lysate. Examples of such treatment may include filtering, centrifugation or screening to remove extraneous cellular material as well as chemical treatments to improve later cannabinoid yields.

The transiently modified cannabinoids may be further isolated and purified. In one preferred embodiment, the yeast lysate may be processed utilizing affinity chromatography or other purification methods. In this preferred embodiment, an affinity column having a ligand configured to bind with one or more of the transiently modified cannabinoids, for example, through association with the glucuronic acid functional group, among others, may be immobilized or coupled to a solid support. The lysate may then be passed over the column such that the transiently modified cannabinoids, having specific binding affinity to the ligand become bound and immobilized. In some embodiments, non-binding and non-specific binding proteins that may have been present in the lysate may be removed. Finally, the transiently modified cannabinoids may be eluted or displaced from the affinity column by, for example, a corresponding sugar or other compound that may displace or disrupt the cannabinoid-ligand bond. The eluted transiently modified cannabinoids may be collected and further purified or processed.

In yet another separate embodiment, the now soluble transiently modified cannabinoids may be passively and/or actively excreted from the cell. In one exemplary model, an ATP-binding cassette transporter (ABC transporters) or other similar molecular structure may recognize the glucuronic acid functional group (conjugate) on the transiently modified cannabinoid and actively transport it into the surrounding media. In this embodiment, a yeast cell culture may be allowed to grow until an output parameter is reached. In one example, an output parameter may include allowing the yeast cell culture to grow until a desired cell/optical density is reached, or a desired level of transiently modified cannabinoids is reached. In this embodiment, the culture media containing the transiently modified cannabinoid may be harvested for later cannabinoid extraction. In some embodiments, this harvested media may be treated in a manner similar to the lysate generally described above. Additionally, the transiently modified cannabinoids present in the raw and/or treated media may be isolated and purified, for example, through affinity chromatography in a manner similar to that described above.

In certain embodiments, this purified cannabinoid isolate may contain a mixture of primary and secondary glycosylated cannabinoids. As noted above, such purified glycosylated cannabinoids may be water-soluble and metabolized slower than unmodified cannabinoids providing a slow-release capability that may be desirable in certain pharmaceutical applications, such as for use in tissue-specific applications or as a prodrug. In this embodiment, purified glycosylated cannabinoids may be incorporated into a variety of pharmaceutical and/or nutraceutical applications. For example, the purified glycosylated cannabinoids may be incorporated into various solid and/or liquid delivery vectors for use in pharmaceutical applications. As noted above, absent modification, these transiently modified cannabinoids no longer possess their psychoactive component, making their application in research, therapeutic and pharmaceutical applications especially advantageous. Additional therapeutic applications may include the administration of a therapeutic dose of an "entourage" of isolated and purified transiently modified cannabinoids.

The inventive technology may also include a system to convert or reconstitute transiently modified cannabinoids. In one preferred embodiment, glycosylated cannabinoids may be converted into non-glycosylated cannabinoids through their treatment with one or more generalized or specific glycosidases. In this embodiment, these glycosidase enzymes may remove a sugar moiety. Specifically, these glycosidases may remove the glucuronic acid moiety reconstituting the cannabinoid compound to a form exhibiting psychoactive activity. This reconstitution process may generate a highly purified "entourage" of primary and secondary cannabinoids. These reconstituted cannabinoid compounds may also be incorporated into various solid and/or liquid delivery vectors for use in a variety of pharmaceutical and other commercial applications. In certain embodiments, transiently modified cannabinoids may be reconstituted through incubation with one or more generalized or specific glycosidases in an in vitro system.

As noted above, cannabinoid producing strains of *Cannabis*, as well as other plants may be utilized with the inventive technology. In certain preferred embodiments, Cannabis plant material may be harvested and undergo cannabinoid extraction. These traditionally extracted cannabinoids may then be modified from their native forms through the in vitro application of one or more CYP's that may generate hydroxyl and carboxylic acid forms of these cannabinoids respectively. These functionalized cannabinoids may be further modified through the in vitro application of one or more UGTs as generally described below. In this embodiment, the new transiently modified cannabinoids may be isolated and purified through a process of affinity chromatography and then applied to various commercial and other therapeutic uses. In other embodiments, the transiently modified cannabinoids may be restored and reconstituted through the in vitro application of one or more glycosidase enzymes. These restored cannabinoids may also be applied to various commercial and other therapeutic uses.

The inventive technology includes systems and methods for high-level production of cannabinoid compounds in cell culture systems. As used herein, the term "high level" in this instance may mean higher than wild-type biosynthesis or accumulation of one or more cannabinoids in a yeast or plant cell culture. In one embodiment, a suspension or hairy root or cell suspension culture of one or more plant strains may be established. In one preferred embodiment, a suspension or hairy root or cell suspension culture of a tobacco plant may be established. It should be noted that the term strain may refer to a plant strain, as well as a cell culture, or cell line derived from a plant, such as tobacco. In another preferred embodiment, a suspension or hairy root or cell suspension culture of one or more yeast strains may be established.

Another embodiment of the inventive technology may include systems and methods for high level production of modified cannabinoid compounds. In one embodiment, a suspension or hairy root culture of one or more tobacco plant strains may be established. It should be noted that the term strain may refer to a plant strain, as well as a cell culture, or cell line derived from a tobacco plant. In one preferred embodiment, a suspension or hairy root culture of BY2 tobacco cells may be established in a fermenter or other similar apparatus. In an alternative embodiment, a suspension or hairy root culture of *Nicotiana tabacum* and/or *Nicotiana benthamiana* plant may be established in a fermenter or other similar apparatus. It should be noted that the use of *N. tabacum* and *N. benthamiana* in these embodiments is exemplary only. For example, in certain other embodiments, various *Nicotiana* strains, mixes of strains, hybrids of different strains or clones, as well as different varieties may be used to generate a cell suspension or hairy root culture.

In certain cases, such fermenters may include large industrial-scale fermenters allowing for a large quantity of tobacco cells to be cultured. In this embodiment, harvested cannabinoids may be introduced to this suspension culture, and modified as generally described herein. Similarly, such cultured growth of tobacco cells may be continuously sustained with the continual addition of nutrient and other growth factors being added to the culture. Such features may be automated or accomplished manually.

Another embodiment of the invention may include the production of genetically modified yeast and/or tobacco cells to express varying exogenous and/or endogenous genes that may modify the chemical structure of cannabinoid compounds. Such transgenic strains may be configured to produce and/or modify large quantities of cannabinoid compounds generally, as well as targeted increases in the production of specific cannabinoids such as THC, Cannabidiol (CBD) or Cannabinol (CBN) and the like.

Additional embodiments of the inventive technology may include novel systems, methods and compositions for the production and in vivo modification of cannabinoid compounds in a plant and/or yeast suspension culture system. In certain embodiments, these in vivo modifications may lead to the production of different forms of cannabinoids with special properties, e.g. water-soluble, slow-release cannabinoids or prodrugs. In one preferred embodiment, the inventive technology may include novel systems, methods and compositions for the hydroxylation, acetylation and/or glycosylation. Modified cannabinoids can be made water-soluble, for example by glycosylation.

Figure 13:
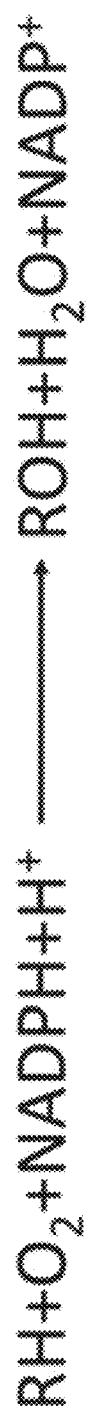
FIG. 13. Exemplary monooxygenase reaction, catalyzed by cytochromes P450.

As noted above, production and/or accumulation of high-levels of cannabinoids would be toxic for a plant cell host. As such, one embodiment of the inventive technology may include systems and methods to transiently modify cannabinoids in vivo. One aim of the current invention may include the use of cytochrome P450's (CYP) monooxygenases to transiently modify or functionalize the chemical structure of the cannabinoids. CYPs constitute a major enzyme family capable of catalyzing the oxidative biotransformation of many pharmacologically active chemical compounds and other lipophilic xenobiotics. For example, as shown in FIG. 13, the most common reaction catalyzed by cytochromes P450 is a monooxygenase reaction, e.g., insertion of one atom of oxygen into the aliphatic position of an organic substrate (RH) while the other oxygen atom is reduced to water.

Figure 30:
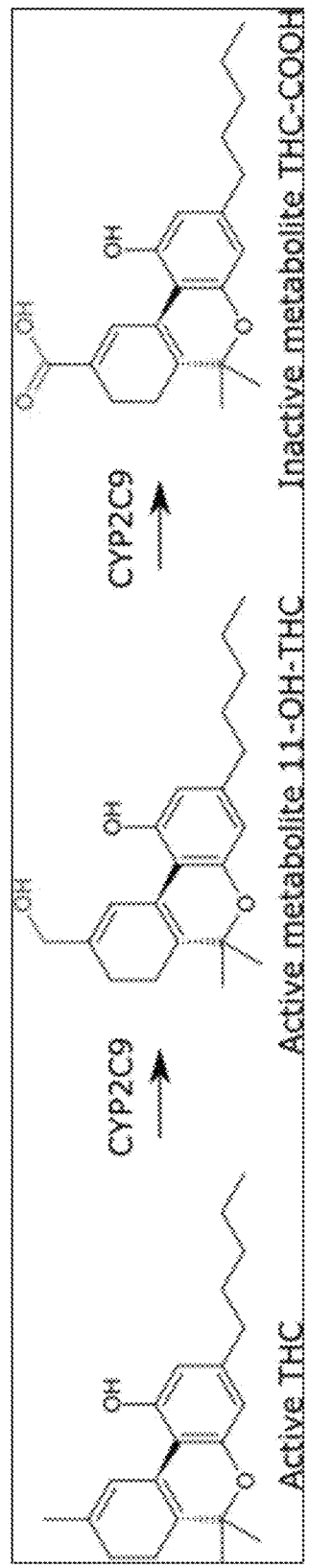
FIG. 30. Hydroxylation followed by oxidation of THC by CYP2C9/

Several cannabinoids, including THC, have been shown to serve as a substrate for human CYPs (CYP2C9 and CYP3A4). Similarly, CYPs have been identified that metabolize cannabidiol (CYPs 2C19, 3A4); cannabinol (CYPs 2C9, 3A4); JWH-018 (CYPs 1A2, 2C9); and AM2201 (CYPs 1A2, 2C9). For example, as shown generally in FIG. 30, in one exemplary system, CYP2C9 may "functionalize" or hydroxylate a THC molecule resulting in a hydroxyl-form of THC. Further oxidation of the hydroxyl form of THC by CYP2C9 may convert it into a carboxylic-acid form which loses its psychoactive capabilities, rendering it an inactive metabolite.

As such, another embodiment of the invention may include the creation of a yeast or plant cell culture that may be transformed with artificially created genetic constructs encoding one or more exogenous CYPs. In one preferred embodiment, genes encoding one or more non-human isoforms and/or analogs, as well as possibly other CYPs that may functionalize cannabinoids, may be expressed in transgenic yeast or tobacco cells. In another preferred embodiment, genes encoding one or more non-human isoforms and/or analogs, as well as possibly other CYPs that may functionalize cannabinoids, may be expressed in transgenic yeast tobacco strains grown in a suspension culture. Additional embodiments may include genetic control elements such as promotors and/or enhancers as well as post-transcriptional regulatory elements that may also be expressed such that the presence, quantity and activity of any CYPs present in the suspension culture may be modified and/or calibrated.

Another embodiment of the invention may include the creation of a tobacco or yeast cells may be transformed with artificially created genetic constructs encoding one or more exogenous CYPs. In one preferred embodiment, genes encoding one or more non-human isoforms and/or analogs, as well as possibly other CYPs that may functionalize cannabinoids introduced to a transgenic tobacco cell and/or yeast suspension culture.

Figure 31:
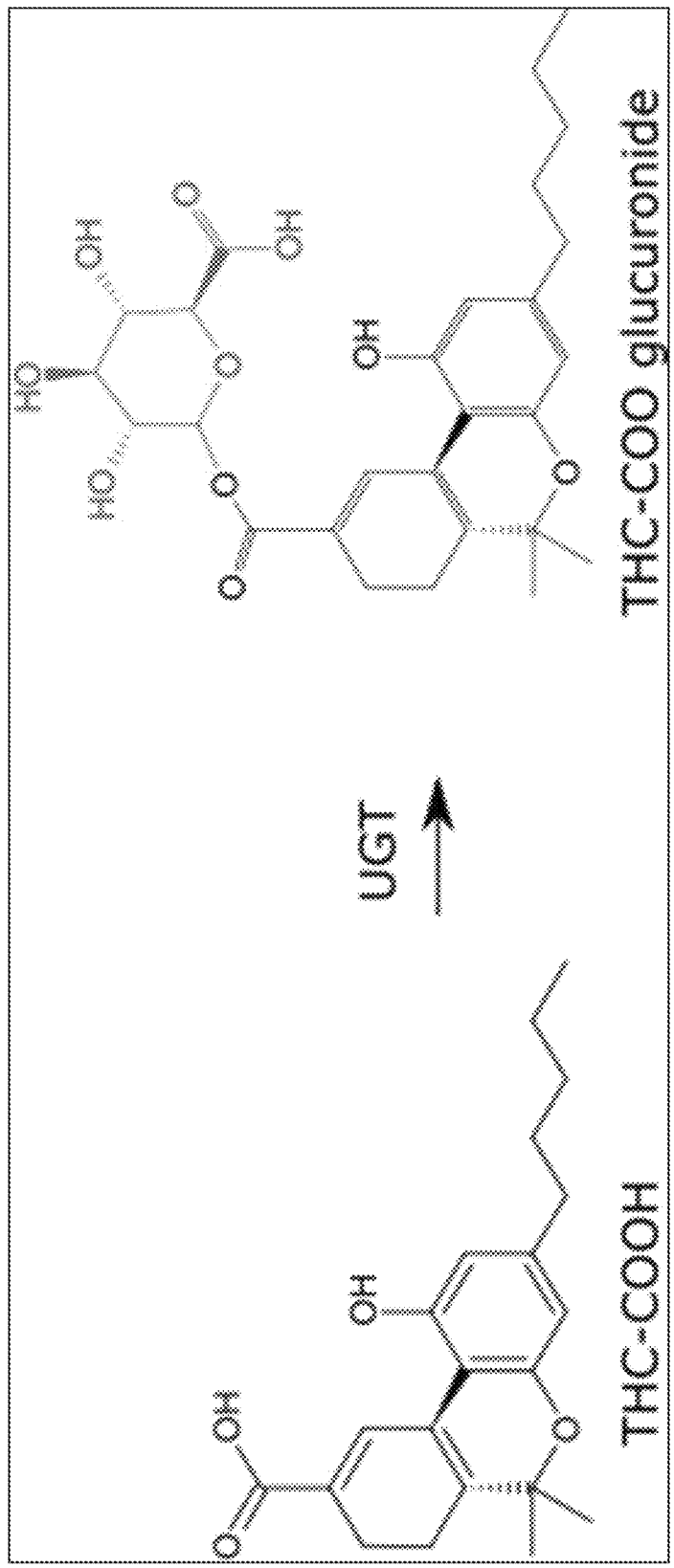
FIG. 31. Transfer of a glucuronic acid component to a cannabinoid substrate by UGT.

Another aim of the invention may be to further modify, in vivo, cannabinoids and/or already functionalized cannabinoids. In a preferred embodiment, glycosylation of cannabinoids and/or functionalized cannabinoids may covert to them into a water-soluble form. In an exemplary embodiment shown in FIG. 31, the inventive technology may utilize one or more glycosyltransferase enzymes, such as UDP-glycosyltransferase (UGT), to catalyze, in vivo the glucuronosylation or glucuronidation of cannabinoids, such as primary (CBD, CBN) and secondary cannabinoids (THC, JWH-018, JWH-073). In this embodiment, glucuronidation may consist of the transfer of a glucuronic acid component of uridine diphosphate glucuronic acid to a cannabinoid substrate by any of several types of glycosyltransferases as described herein. Glucuronic acid is a sugar acid derived from glucose, with its sixth carbon atom oxidized to a carboxylic acid.

Yet another embodiment of the current invention may include the in vivo conversion of a functionalized cannabinoid, in this example a carboxylic acid form of the cannabinoid, to a glycosylated form of cannabinoid that may be both water-soluble and non-toxic to the cell host. These chemical modifications may allow for greater levels of cannabinoid accumulation in a plant or yeast cell culture without the deleterious cytotoxic effects that would be seen with unmodified cannabinoids due to this water-solubility.

Another embodiment of the invention may include the generation of transgenic or genetically modified strains/cells of yeast and/or tobacco, having artificial genetic constructs that may express one or more genes that may increase cannabinoids solubility and/or decrease cannabinoid cytotoxicity. For example, the inventive technology may include the generation of transgenic plant and/or yeast cell lines having artificial genetic constructs that may express one or more endogenous/or exogenous glycosyltransferases or other enzymes capable of glycosylating cannabinoid compounds. For example, in one embodiment one or more exogenous glycosyltransferases from tobacco or other non-*cannabis* plants may be introduced into a *cannabis* plant or cell culture and configured to glycosylate cannabinoids in vivo.

In an additional embodiment, of the inventive technology may include the generation of artificial genetic constructs having genes encoding one or more glycosyltransferases, including non-human analogues of those described herein as well as other isoforms, that may further may be expressed in transgenic plant and/or yeast cells which may further be grown in a suspension culture. Additional embodiments may include genetic control elements such as promotors and/or enhancers as well as post-transcriptional regulatory control elements that may also be expressed in such transgenic cell systems such that the presence, quantity and activity of any glycosyltransferases present in the suspension culture may be regulated.

An additional embodiment of the invention may include artificial genetic constructs having one or more genes encoding one or more UDP- and/or ADP-glycosyltransferases having localization sequences or domains that may assist in the movement of the protein to a certain portion of the cell, such as the cellular locations were cannabinoids and/or functionalized cannabinoids may be modified, produced, stored, and/or excreted from the cell.

An additional embodiment of the invention may include artificial genetic constructs having one or more genes encoding one or more UDP- and/or ADP-glycosyltransferases being co-expressed with one or more exogenous genes that may assist in the movement of the protein to a certain portion of the cell, such as the cellular locations were cannabinoids and/or functionalized cannabinoids may be stored, and/or excreted from the cell.

One preferred embodiment of the inventive technology may include the high level in vivo production of water-soluble, glycosylated cannabinoids, generally being referred to as transiently modified cannabinoids that may be harvested from a plant and/or yeast cell culture. In one embodiment, transiently modified cannabinoids may accumulate within the cell that is part of a suspension culture. In this example, the cell culture may be allowed to grow to a desired level of cell or optical density, or in other instances until a desired level of transiently modified cannabinoids have accumulated in the cultured plant or yeast cells. Such exogenous genes may be localized, for example to the cytosol as generally described herein, and may further be co-expressed with other exogenous genes that may reduce cannabinoid biosynthesis toxicity and/or facilitate cannabinoid transport through, or out of the cell.

All or a portion of the cultured plant and/or yeast cells containing the accumulated transiently modified cannabinoids may then be harvested from the culture, which in a preferred embodiment may be an industrial-scale fermenter or other apparatus suitable for the large-scale culturing of plant cells. The harvested *Cannabis* cells may be lysed such that the accumulated transiently modified cannabinoids may be released to the surrounding lysate. Additional steps may include treating this lysate. Examples of such treatment may include filtering or screening this lysate to remove extraneous plant material as well as chemical treatments to improve later cannabinoid yields.

Another embodiment of inventive technology may include the high level in vivo generation of water-soluble, glycosylated cannabinoids, generally being referred to as transiently modified cannabinoids that may be harvested from a plant and/or yeast cell culture. In one embodiment, cannabinoids may be introduced to a non-cannabinoid producing plant and/or yeast cell culture, such as BY2 tobacco cells. In this preferred embodiment, the non-cannabinoid producing cell culture may be genetically modified to express one or more endogenous or exogenous genes that may modify the cannabinoids, for example through hydroxylation, acetylation and/or glycosylation. Such endogenous or exogenous genes may be localized, as generally described herein, and may further be co-expressed with other exogenous genes that may reduce cannabinoid biosynthesis toxicity and/or facilitate cannabinoid transport through, or out of the cell into a surrounding media.

This non-cannabinoid producing the cell culture may be allowed to grow to a desired level of cell or optical density, or in other instances until a desired level of transiently modified cannabinoids have accumulated in the cultured cells. In one embodiment, all or a portion of the BY2 and/or yeast cells containing the accumulated cannabinoids may then be harvested from the culture, which in a preferred embodiment may be an industrial-scale fermenter or other apparatus suitable for the large-scale culturing of cells. The harvested cells may be lysed such that the accumulated transiently modified cannabinoids may be released to the surrounding lysate. Additional steps may include treating this lysate. Examples of such treatment may include filtering or screening this lysate to remove extraneous material as well as chemical treatments to improve later cannabinoid yields.

Another embodiment of the inventive technology may include methods to isolate and purified transiently modified cannabinoids from a plant or suspension culture. In one preferred embodiment, a plant and/or yeast cell culture lysate may be generated and processed utilizing affinity chromatography or other purification methods. In this preferred embodiment, an affinity column having a ligand or protein receptor configured to bind with the transiently modified cannabinoids, for example through association with a glycosyl or glucuronic acid functional group among others, may be immobilized or coupled to a solid support. The lysate may then be passed over the column such that the transiently modified cannabinoids, having specific binding affinity to the ligand become bound and immobilized. In some embodiments, non-binding and non-specific binding proteins that may have been present in the lysate may be removed. Finally, the transiently modified cannabinoids may be eluted or displaced from the affinity column by, for example, a corresponding sugar or other compound that may displace or disrupt the cannabinoid-ligand bond. The eluted transiently modified cannabinoids may be collected and further purified or processed.

One embodiment of the invention may include the generation of transiently modified cannabinoids that may be passively and/or actively excreted from a cultured plant and/or yeast cell. In one exemplary model, an exogenous ATP-binding cassette transporter (ABC transporters) or other similar molecular structure may recognize the glycosyl or glucuronic acid functional group (conjugate) on the transiently modified cannabinoid and actively transport it across the cell wall/membrane and into the surrounding media. In this embodiment, the cell culture may be allowed to grow until an output parameter is reached. In one example, an output parameter may include allowing the cell culture to grow until a desired cell/optical density is reach, or a desired concentration of transiently modified cannabinoid is reached. In this embodiment, the culture media containing the transiently modified cannabinoids may be harvested for later cannabinoid extraction. In some embodiments, this harvested media may be treated in a manner similar to the lysate generally described above. Additionally, the transiently modified cannabinoids present in the raw and/or treated media may be isolated and purified, for example, through affinity chromatography in a manner similar to that described above.

In certain embodiments, this purified cannabinoid isolate may contain a mixture of primary and secondary glycosylated cannabinoids. As noted above, such purified glycosylated cannabinoids may be water-soluble and metabolized slower than unmodified cannabinoids providing a slow-release capability that may be desirable in certain pharmaceutical applications, such as for use in tissue-specific applications, or as a prodrug. As such, in one embodiment of the invention, isolated glycosylated cannabinoids may be incorporated into a variety of pharmaceutical and/or nutraceutical applications as well as other compositions of matter outline herein.

For example, the purified glycosylated cannabinoids may be incorporated into various solid and/or liquid delivery vectors for use in pharmaceutical applications. As noted above, these transiently modified cannabinoids may no longer possess their psychoactive component, making their application in research, therapeutic and pharmaceutical applications especially advantageous. For example, the treatment of children may be accomplished through administration of a therapeutic dose of isolated and purified transiently modified cannabinoids, without the undesired psychoactive effect. Additional therapeutic applications may include the harvesting and later administration of a therapeutic dose of an "entourage" of isolated and purified transiently modified cannabinoids.

Another embodiment of the invention may include a system to convert or reconstitute transiently modified cannabinoids. In one preferred embodiment, glycosylated cannabinoids may be converted into non-glycosylated cannabinoids through their treatment with one or more generalized or specific glycosidases. The use and availability of glycosidase enzymes would be recognized by those in the art without requiring undue experimentation. In this embodiment, these glycosidase enzymes may remove a sugar moiety. Specifically, these glycosidases may remove the glycosyl or glucuronic acid moiety reconstituting the cannabinoid compound to a form exhibiting psychoactive activity. This reconstitution process may generate a highly purified "entourage" of primary and secondary cannabinoids. These reconstituted cannabinoid compounds may also be incorporated into various solid and/or liquid delivery vectors for use in a variety of pharmaceutical and other commercial applications.

As noted above, in one embodiment of the invention, cannabinoid producing strains of *Cannabis*, as well as other plants may be utilized with the inventive technology. In certain preferred embodiments, in lieu of growing the target cannabinoid producing plant in a cell culture, the raw plant material may be harvested and undergo cannabinoid extraction utilizing one or more of the methods described herein. These traditionally extracted cannabinoids may then be modified from their native forms through the in vitro application of one or more CYP's that may generate hydroxyl and carboxylic acid forms of these cannabinoids respectively. These functionalized cannabinoids may be further modified through the in vitro application of one or more glycosyltransferases as generally described herein. In this embodiment, the new transiently modified cannabinoids may be isolated and purified through a process of affinity chromatography, or other extraction protocol, and then applied to various commercial and other therapeutic uses. In other embodiments, the transiently modified cannabinoids may be restored and reconstituted through the in vitro application of one or more glycosidase enzymes. These restored cannabinoids may also be applied to various commercial and other therapeutic uses.

Another embodiment of the invention may include the use of other non-cannabinoid producing plants in lieu of growing a cannabinoid producing plant in a cell culture. Here, cannabinoid may be introduced to genetically modified plants, or plant cell cultures that express one or more CYP's that may generate hydroxyl and carboxylic acid forms of these cannabinoids respectively. These functionalized cannabinoids may be further modified through the action of one or more glycosidases that may also be expressed in the non-cannabinoid producing plant or cell culture. In one preferred embodiment, a non-cannabinoid producing cell culture may include tobacco plant or tobacco cell cultures. Additional embodiments may similarly use genetically modified yeast cells grown in culture to generate biomodified cannabinoid compounds.

One embodiment of the invention may include an in vivo method of trichome-targeted cannabinoid accumulation and modification. One preferred embodiment of this in vivo system may include the creation of a recombinant protein that may allow the translocation of a CYP or glycosyltransferases to a site of extracellular cannabinoid synthesis in a whole plant. More specifically, in this preferred embodiment, one or more CYPs or glycosyltransferases may either be engineered to express all or part of the N-terminal extracellular targeting sequence as present in cannabinoid synthase protein, such as THCA synthase or CBDA synthase.

One another embodiment of the invention may include an in vivo method of high-level trichome-targeted cannabinoid biosynthesis, accumulation and/or modification. One preferred embodiment of this in vivo system may include the creation of a recombinant protein that may allow the translocation of a catalase to a site of extracellular cannabinoid synthesis in a whole plant. More specifically, in this preferred embodiment, one or more catalase enzymes may either be engineered to express all or part of the N-terminal extracellular targeting sequence as present in cannabinoid synthase protein, such as THCA synthase or CBDA synthase. In this embodiment, the catalase may be targeted to the site of cannabinoid biosynthesis allowing it to more efficiently neutralize hydrogen peroxide byproducts.

Another aim of the current invention may include the introduction of one or more compounds to facilitate the chemical decomposition of hydrogen peroxide resulting from cannabinoids biosynthesis. In one embodiment, one or more chemicals, metal ions, and/or catalysts may be introduced into a growth media to detoxify hydrogen peroxide ($H_2O_2$) in both yeast and plant cell cultures. Examples may include magnesium dioxide ($MnO_2$), permanganate ion-$MnO_4$, and silver ion ($Ag^+$), iron oxide, ($Fe_2O_3$), lead dioxide ($PbO_2$), cupric oxide (CuO), Hafnium(IV) oxide ($HfO_2$), ceric dioxide ($CeO_2$), Gadolinium trioxide ($Gd_2O_3$), Sodium Phosphate, Tribasic ($NaPO_4$), iodide ions, manganese metal, iron(III) Chloride Solution($FeCl_3$). Such chemicals, ions, and/or catalyst may be added directly, or in solution to a cell culture. The amount may be dependent on the amount of hydrogen peroxide present which may be determined through a variety of established assays. As such, determinations of the optimal amounts are within the skill of those in the art.

In this preferred embodiment, this N-terminal trichome targeting sequence or domain may generally include the first 28 amino acid residues of a generalized synthase. An exemplary trichome targeting sequence for THCA synthase is identified SEQ ID NO. 40, while trichome targeting sequence for CBDA synthase is identified SEQ ID NO. 41. This extracellular targeting sequence may be recognized by the plant cell and cause the transport of the glycosyltransferase from the cytoplasm to the plant's trichrome, and in particular the storage compartment of the plant trichrome where extracellular cannabinoid glycosylation may occur. More specifically, in this preferred embodiment, one or more glycosyltransferases, such as UDP glycosyltransferase may either be engineered to express all or part of the N-terminal extracellular targeting sequence as present in an exemplary synthase enzyme.

Another embodiment of the invention may include an in vivo method of cytosolic-targeted cannabinoid production, accumulation and/or modification. One preferred embodiment of this in vivo system may include the creation of a recombinant protein that may allow the localization of cannabinoid synthases and/or glycosyltransferases to the cytosol.

More specifically, in this preferred embodiment, one or more cannabinoid synthases may be modified to remove all or part of the N-terminal extracellular targeting sequence. An exemplary trichome targeting sequence for THCA synthase is identified SEQ ID NO. 40, while trichome targeting sequence for CBDA synthase is identified SEQ ID NO. 41. Co-expression with this cytosolic-targeted synthase with a cytosolic-targeted CYP or glycosyltransferase, may allow the localization of cannabinoid synthesis, accumulation and modification to the cytosol. Such cytosolic target enzymes may be co-expressed with catalase, ABC transporter or other genes that may reduce cannabinoid biosynthesis toxicity and or facilitate transport through or out of the cell.

Another embodiment of the invention may include the generation of an expression vector comprising this polynucleotide, namely a cannabinoid synthase N-terminal extracellular targeting sequence and glycosyltransferase genes, operably linked to a promoter. A genetically altered plant or parts thereof and its progeny comprising this polynucleotide operably linked to a promoter, wherein said plant or parts thereof and its progeny produce said chimeric protein, is yet another embodiment. For example, seeds and pollen contain this polynucleotide sequence or a homologue thereof, a genetically altered plant cell comprising this polynucleotide operably linked to a promoter such that said plant cell produces said chimeric protein. Another embodiment comprises a tissue culture comprising a plurality of the genetically altered plant cells.

Another embodiment of the invention provides for a genetically altered plant or cell expressing a chimeric or fusion protein having a cannabinoid synthase N-terminal extracellular targeting sequence (see i.e., SEQ ID: 40-41; see also SEQ ID NO. 42 for full amino acid sequence of THCA synthase) coupled with a UDP glycosyltransferase genes, operably linked to a promoter. Another embodiment provides a method for constructing a genetically altered plant or part thereof having glycosylation of cannabinoids in the extracellular storage compartment of the plant's trichrome compared to a non-genetically altered plant or part thereof, the method comprising the steps of: introducing a polynucleotide encoding the above protein into a plant or part thereof to provide a genetically altered plant or part thereof, wherein said chimeric protein comprising a first domain, a second domain, and wherein said first domain comprises a cannabinoid synthase N-terminal extracellular targeting sequence, and a second domain comprises a glycosyltransferase sequence. These domains may be separated by a third domain or linker. This linker may be any nucleotide sequence that may separate a first domain from a second domain such that the first domain and the second domain can each fold into its appropriate three-dimensional shape and retain its activity.

One preferred embodiment of the invention may include a genetically altered plant or cell expressing a cytosolic-targeted cannabinoid synthase protein having a cannabinoid synthase N-terminal extracellular targeting sequence (SEQ IDs. 40-41) inactivated or removed. In one embodiment, a cytosolic targeted THCA synthase (ctTHCAs) may be identified as SEQ ID NO. 46, while in another embodiment cytosolic targeted CBDA synthase (cytCBDAs) is identified as SEQ ID NO. 22-23). Such cytosolic-targeted cannabinoid synthase protein may be operably linked to a promoter. Another embodiment provides a method for constructing a genetically altered plant or part thereof having glycosylation of cannabinoids in the plant's cytosol compared to a non-genetically altered plant or part thereof, the method comprising the steps of: introducing a polynucleotide encoding the above protein into a plant or part thereof to provide a genetically altered plant or part thereof, wherein said a cannabinoid synthase N-terminal extracellular targeting sequence has been disrupted or removed.

Yet another embodiment of the invention may include an in vivo method of cannabinoid glycosylation in a *cannabis* cell culture. In one preferred embodiment, to facilitate glycosylation of cannabinoids in *cannabis* cell culture, which would lack an extracellular trichrome structure, a cannabinoid synthase gene may be genetically modified to remove or disrupt, for example through a directed mutation, the extra-cellular N-terminal targeting domain which may then be used to transform a *Cannabis* plant cell in a cell culture. In this embodiment, without this targeting domain the cannabinoid synthase, for example THCA or CBDA synthases, may remain within the plant cell, as opposed to being actively transported out of the cell, where it may be expressed with one or more glycosyltransferases, such as UDP glycosyltransferase in the cytoplasm.

Another embodiment of the inventive technology may include systems and methods for enhanced production and/or accumulation of cannabinoid compounds in an in vivo system. In one preferred embodiment, the invention may include the generation of a genetically modified or transgenic *Cannabis* plant that may produce and/or accumulate one or more cannabinoids at higher than wild-type levels. In one embodiment, a transgenic *Cannabis* plant may be generated to express one or more *Cannabis sativa* transcription factors that may enhance the cannabinoid metabolic pathway(s). In one preferred embodiment, a polynucleotide may be generated that encodes for one or more *Cannabis sativa* myb transcription factors genes, and/or one or more exogenous ortholog genes that enhance the metabolite flux through the cannabinoid biosynthetic pathway.

Figure 32:
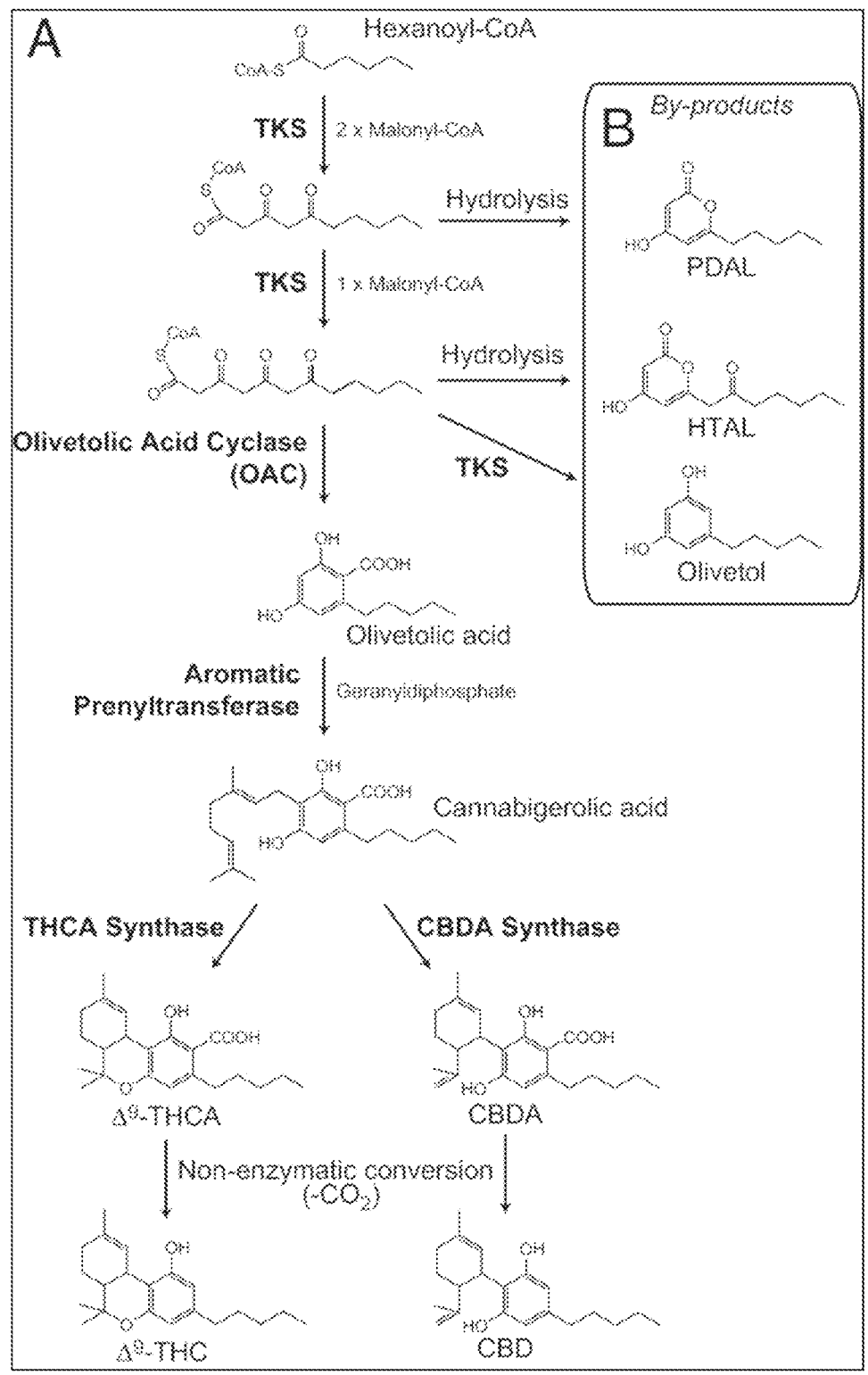
FIG. 32. Synthesis Olivetolic Acid a precursor of CBGA

In this preferred embodiment, a polynucleotide may be generated that encodes for one or more *Cannabis sativa* myb transcription factors genes, such as CAN833 and/or CAN738 that. As shown in FIG. 32, these transcriptions factors may drive the production of olivetolic acid, which is a precursor of CBGA, which in turn is a precursor in the biosynthetic pathway of THCs, CBDs and CBC. In an alternative embodiment, a polynucleotide may be generated that encodes for one or more *Cannabis sativa* myb transcription factors genes orthologs, specifically *cannabis* Myb12 (SEQ IDs. 11-12), Myb8 (SEQ ID NO. 43), AtMyb12 (SEQ ID NO.44), and/or MYB112 (SEQ ID NO. 45) that may also drive the production of olivetolic acid, which is a precursor of CBGA, which in turn is a precursor in the biosynthetic pathway of THCs, CBDs and CBC.

In one preferred embodiment, the invention may include methods of generating a polynucleotide that expresses one or more of the SEQ IDs related to enhanced cannabinoid production identified herein. In certain preferred embodiments, the proteins of the invention may be expressed using any of a number of systems, such as in whole plants, as well as plant cell and/or yeast suspension cultures. Typically, the polynucleotide that encodes the protein or component thereof is placed under the control of a promoter that is functional in the desired host cell. An extremely wide variety of promoters may be available and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

Additional embodiments of the invention may include selecting a genetically altered plant or part thereof that expresses the cannabinoid production transcription factor protein, wherein the expressed protein has increased cannabinoid biosynthesis capabilities. In certain embodiments, a polynucleotide encoding the cannabinoid production transcription factor protein is introduced via transforming said plant with an expression vector comprising said polynucleotide operably linked to a promoter. The cannabinoid production transcription factor protein may comprise a SEQ ID selected from the group consisting of SEQ ID NO: 11-2 or 43-45, or a homologue thereof.

As noted above, one embodiment of the invention may include systems and methods for general and/or localized detoxification of cannabinoid biosynthesis in an in vivo system. In one preferred embodiment, the invention may include the generation of a genetically modified or transgenic *Cannabis* or other plant that may be configured to be capable of detoxifying hydrogen peroxide by-products resulting from cannabinoid biosynthesis at higher than wild-type levels. In addition, this detoxification may be configured to be localized to the cytosol and/or trichome structure of the *Cannabis* plant where cannabinoids are actively being synthesized in a whole plant system. In this preferred embodiment of the invention, a transgenic plant, such as a *cannabis* or tobacco plant or cell, that express one or more genes that may up-regulate hydrogen peroxide detoxification. In an alternative embodiment, the invention may include the generation of a genetically modified plant cell and/or yeast cell suspension cultures that may be configured to be capable of expressing an exogenous catalase, or over expressing an endogenous catalase or both. In this example, the catalase expressed in the plant and/or yeast cell culture may act to detoxify hydrogen peroxide by-products resulting from cannabinoid biosynthesis at higher than wild-type levels. In some embodiment, the catalase expressed in a plant, and/or plant cell or yeast cell culture may be heterologous or exogenous, while in other embodiments, it may be an endogenous catalase that may be operably linked to a promoter to allow constitutive, inducible, and/or overexpression.

In one preferred embodiment, a polynucleotide may be generated that encodes for one or more endogenous and/or exogenous transcription catalase genes, and/or orthologs that catalyze the reduction of hydrogen peroxide:

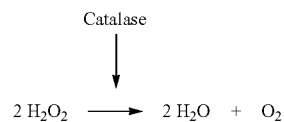

As such, in one embodiment, the invention comprises the generation of a polynucleotide encoding an exogenous catalase protein that may be expressed within a transformed plant and/or cell culture. In a preferred embodiment, a catalase enzyme configured reduce hydrogen peroxide ($H_2O_2$) generated during cannabinoid synthesis may be used to transform a *cannabis* or other plant, such as a tobacco plant. While a number of generic catalase enzymes may be included in this first domain, as merely one exemplary model, a first domain may include an exogenous catalase derived from *Arabidopsis* (SEQ ID NO. 13-14; see also FIG. 33), or *Escherichia coli* (SEQ ID NO. 15-16), or any appropriate catalase ortholog, protein fragment, or catalases with a homology between about 70%—and approximately 100% as herein defined.

Another embodiment of the current invention may include localization of the catalase enzyme to a trichome structure.

As generally outlined above, in this embodiment a trichome targeting sequence from a cannabinoid synthase may be coupled with one or more catalase enzymes in a fusion or chimera—the terms being generally interchangeable in this application. This artificial trichome-target catalase gene may be used to transform a plant having trichome structures, such as *Cannabis* or tobacco. In a preferred embodiment, a trichome-targeted catalase from *Arabidopsis thaliana* with a THCA synthase trichome targeting domain is identified as SEQ ID NO. 47, while a trichome-targeted catalase *Arabidopsis thaliana* with a CBDA synthase trichome targeting domain is identified as SEQ ID NO. 48. In another embodiment, a trichome-targeted catalase from *Escherichia coli* with a THCA synthase trichome targeting domain is identified as SEQ ID NO. 49, while a trichome-targeted catalase *Escherichia coli* with a CBDA synthase trichome targeting domain is identified as SEQ ID NO. 50.

Another embodiment of the invention comprises generating a polynucleotide of a nucleic acid sequence encoding the chimeric/fusion catalase protein. Another embodiment includes an expression vector comprising this polynucleotide operably linked to a promoter. A genetically altered plant or parts thereof and its progeny comprising this polynucleotide operably linked to a promoter, wherein said plant or parts thereof and its progeny produce said fusion protein is yet another embodiment. For example, seeds and pollen contain this polynucleotide sequence or a homologue thereof, a genetically altered plant cell comprising this polynucleotide operably linked to a promoter such that said plant cell produces said chimeric protein. Another embodiment comprises a tissue culture comprising a plurality of the genetically altered plant cells.

In a preferred embodiment, a polynucleotide encoding a trichome-targeted fusion protein may be operably linked to a promoter that may be appropriate for protein expression in a *Cannabis*, tobacco or other plant. Exemplary promotors may include, but not be limited to: a non-constitutive promotor; an inducible promotor, a tissue-preferred promotor; a tissue-specific promotor, a plant-specific promotor, or a constitutive promotor. In a preferred embodiment, one or more select genes may be operably linked to a leaf-specific gene promoter, such as Cab 1. Additional promoters and operable configurations for expression, as well as co-expression of one or more of the selected genes are generally known in the art.

Another embodiment of the invention may provide for a method for constructing a genetically altered plant or part thereof having increased resistance to hydrogen peroxide cytotoxicity generated during cannabinoid synthesis compared to a non-genetically altered plant or part thereof, the method comprising the steps of: introducing a polynucleotide encoding a fusion protein into a plant or part thereof to provide a genetically altered plant or part thereof, wherein said fusion protein comprising a catalase and a trichome-targeting sequence from a cannabinoid synthase.

Figure 34:
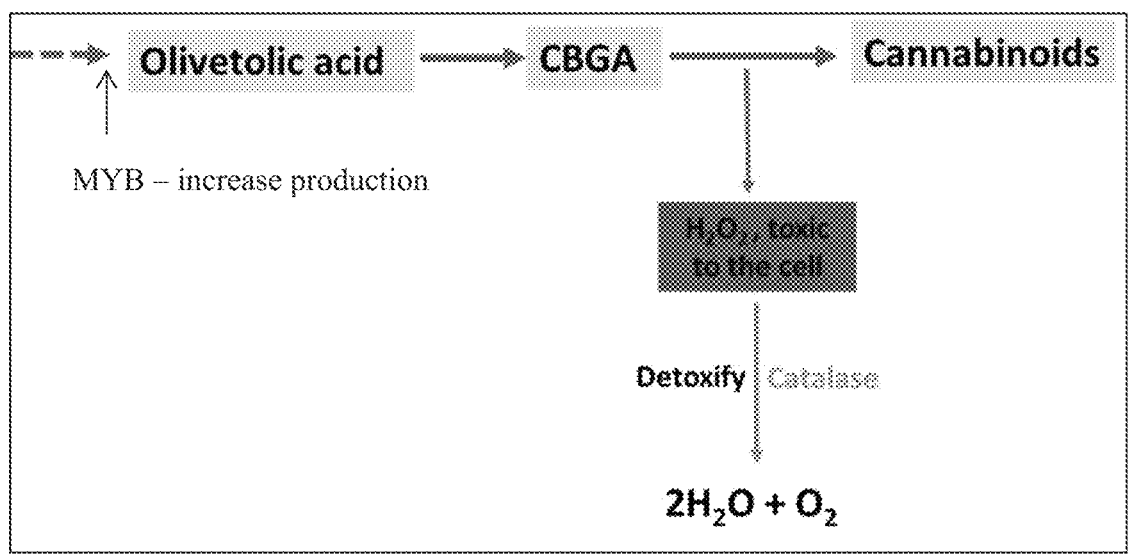
FIG. 34. Schematic diagram of increase cannabinoid production coupled with reduced oxidative damage system in one embodiment thereof.

In one embodiment, the invention may encompass a system to increase overall cannabinoid production and accumulation in trichomes while preventing potential cytotoxicity effects. As generally shown in FIG. 34, the system may include, in a preferred embodiment, creating a transgenic *Cannabis*, tobacco or other plant or suspension culture plant that overexpresses at least one Myb transcription factor to increase overall cannabinoid biosynthesis. In further preferred embodiments, this transgenic plant may co-express a catalase enzyme to reduce oxidative damage resulting from hydrogen peroxide production associated with cannabinoid synthesis reducing cell toxicity. In certain preferred embodiments, this catalase may be fused with an N-terminal synthase trichome targeting domain, for example from THCA and/or CBDA synthase, helping localize the catalase to the trichome in the case of whole plant systems, and reduce potentially toxic levels of hydrogen peroxide produced by THCA, CBCA and/or CBDA synthase activity.

Another embodiment of the invention may comprise a combination polynucleotide of a nucleic acid sequence encoding a combination of: 1) a cannabinoid production transcription factor protein, such as a myb gene; and/or a catalase protein, or any homologue thereof, which may further include a trichome targeting or localization signal. A genetically altered plant or parts thereof and its progeny comprising this combination polynucleotide operably linked to a promoter, wherein said plant or parts thereof and its progeny produce said protein is yet another embodiment. For example, seeds and pollen contain this polynucleotide sequence or a homologue thereof, a genetically altered plant cell comprising this polynucleotide operably linked to a promoter such that said plant cell produces said proteins. Another embodiment comprises a tissue culture comprising a plurality of the genetically altered plant cells.

Another embodiment of the invention may provide for a method for constructing a genetically altered plant or part thereof having: 1) increased cannabinoid production compared to a non-genetically altered plant or part thereof and/or 2) increased resistance to hydrogen peroxide cytotoxicity generated during cannabinoid synthesis compared to a non-genetically altered plant or part thereof, the method comprising the steps of: introducing a combination polynucleotide into a plant or part thereof to provide a genetically altered plant or part thereof.

Additional embodiments of the invention may include selecting a genetically altered plant or part thereof that expresses one or more of the proteins, wherein the expressed protein(s) may have: 1) increased cannabinoid production capabilities, for example through overexpression of an endogenous myb gene; and 2) catalase with/or without a trichome localization capability, or any combination thereof. In certain embodiments, a combination polynucleotide encoding the proteins is introduced via transforming said plant with an expression vector comprising said combination polynucleotide operably linked to a promoter. The cannabinoid production transcription factor protein may comprise a SEQ ID selected from the sequences identified herein, or homologues thereof. Naturally, such combinations and expression combination strategies, such identified in Tables 7-8, 10 below and elsewhere, are exemplary, as multiple combinations of the elements as herein described is included in the invention.

In one preferred embodiment, the inventive technology may include systems, methods and compositions high levels of in vivo cannabinoid hydroxylation, acetylation and/or glycosylation and/or a combination of all three. In a preferred embodiment, the in vivo cannabinoid hydroxylation, acetylation and/or glycosylation and/or a combination of all three may occur in a cannabinoid-producing plant or cell culture system. While in alternative embodiments may include a non-cannabinoid producing plant or cell culture system such as a tobacco plant, like *N. benthamiana*, or a yeast cell culture.

In one embodiment, the invention may include a cannabinoid production, accumulation and modification system. In one preferred embodiment, a plant, such as *cannabis* or tobacco, as well as a yeast cell, may be genetically modified to express one or more heterologous cytochrome P450 genes. In this preferred embodiment, a heterologous cytochrome P450 (CYP3A4) SEQ ID NO. 1 may be expressed in a cannabinoid-producing plant or cell culture system. While in alternative embodiments, a heterologous human cytochrome P450 (CYP3A4) may be expressed non-cannabinoid producing plant or cell culture system such as a tobacco plant, like *N. benthamiana* or a yeast cell, such a *P. pastoris*. In this embodiment, the overexpression of a heterologous human cytochrome P450 protein, identified as SEQ ID NO. 2, may functionalize endogenously-created cannabinoids so that they can be more efficiently glycosylated and/or acetylated in vivo, rendering them water-soluble.

In an alternative embodiment, the invention may include a cannabinoid production, accumulation and modification system. In one preferred embodiment, a plant, such as *cannabis* or tobacco, may be genetically modified to express one or more heterologous cytochrome P450 oxidoreductase genes. In this preferred embodiment, a heterologous cytochrome P450 oxidoreductase (oxred) identified as SEQ ID NO. 3, and SEQ ID NO. 72, identified as an ortholog, may be expressed in a cannabinoid-producing plant or cell culture system. While in alternative embodiments a heterologous human heterologous cytochrome P450 oxidoreductase (oxred) may be expressed non-cannabinoid producing plant or cell culture system such as a tobacco plant, like BY2 tobacco cells, or yeast cells. In this embodiment, the overexpression of a heterologous cytochrome P450 oxidoreductase (oxred) protein, identified as SEQ ID NO. 4, may functionalize endogenously-created cannabinoids so that they can be more efficiently glycosylated and/or acetylated in vivo, rendering them water-soluble.

In one preferred embodiment, a tobacco cell suspension culture may be generated using BY2 cells. Such BY2 cell may express a heterologous cytochrome P450 oxidoreductase (oxred) identified as SEQ ID NO. 3, and/or a heterologous glycosyltransferases, such as GT76G1 (SEQ ID NO. 61). Further, in this embodiment, a BY2 tobacco cell culture may also be genetically modified to express one or more multi-drug ABC transporters, such as ABCG2 (SEQ ID NO. 67). In this embodiment, one or more cannabinoids may be introduced to the genetically modified yeast cells, preferably in in a suspension culture, and may be functionalize and/or directly glycosylated prior to their active transport out of the cell into the surrounding media through the action of an ABC transporter, such as ABCG2. In still further example, a yeast cell may be genetically modified to express an alpha-factor secretion signal to further facilitate secretion of the modified cannabinoids, or cannabinoid precursors out of the yeast cell and into a surrounding media. In this system, one or multiple cannabinoids and/or cannabinoid precursors may be introduced to the yeast cell culture to be modified, for example through an cannabinoid oil or other extract.

It should be noted that in one embodiment, one or more glycosyltransferases may have an affinity for either of the hydroxy groups located at positions 2,4 on the pentylbenzoate/pentlybenzoic ring of a cannabinoid, compound, such a CBDA (2,4-dihydroxy-3-[(6R)-3-methyl-6-(prop-1-en-2-yl)cyclohex-2-en-1-yl]-6-pentylbenzoate) and/or CBGA ((E)-3-(3,7-Dimethyl-2,6-octadienyl)-2,4-dihydroxy-6-pentylbenzoic acid).

On one embodiment, one or more glycosidase inhibitors may be introduced to a plant and/or yeast cell culture as well as a whole plant where the production of glycosylated cannabinoids may be occurring. In one preferred embodiment, one or more of the following glycosidase inhibitors may be utilized: D,L-1,2-Anhydro-myo-inositol (Conduritol B Epoxide (CBE)); 6-Epicastanospermine (Castanospermine); 6-bromocyclohex-4-ene-1,2,3-triol (Bromoconduritol); (+)-1-Deoxynojirimycin (Deoxynojirimycin); 1,5-Di deoxy-1,5-imino-D-sorbitol hydrochloride (1-Deoxynojirimycin Hydrochloride); 1R,2S,3S,4R)-rel-5-Cyclohexene-1,2,3,4-tetrol (Conduritol B); (3R,4R,5R)-5-(Hydroxymethyl)-3,4-piperidinediol (2S,3S)-2,3-Dihydroxybutanedioate (Isofagomine D-Tartrate); O-(D-Glucopyranosylidene)amino N-Phenylcarbamate; and (3S,4S,5R,6R)-3, 4,5-Trihydroxy-6-(hydroxymethyl)-2-piperidinone (D-Manno-γ-lactam). Such glycosidase inhibitors are exemplary only and should not be seen as limiting on the invention in any way.

In an alternative embodiment, a heterologous cytochrome P450 gene may be expressed in a genetically modified yeast strain. For example, heterologous cytochrome P450 (CYP3A4) (SEQ ID NO. 69), and/or CYP oxidoreductase (SEQ ID NO. 71), may be introduced and expressed in to a yeast cell. In this embodiment, such genes may further be codon optimized for expression in yeast. Such a heterologous human cytochrome P450 proteins may functionalize cannabinoids introduced to the yeast cell culture so that they can be more efficiently glycosylated and/or acetylated in vivo, rendering them water-soluble. In this embodiment, such yeast cells may further express one or more heterologous glycosyltransferases, which may further be codon optimized for expression in yeast cells. In one preferred embodiment, the invention may one or more codon optimized heterologous glycosyltransferases from tobacco, including but not limited to: NtGT1 (SEQ ID NO. 51); NtGT2 (SEQ ID NO. 53); NtGT3 (SEQ ID NO. 55); NtGT4 (SEQ ID NO. 57); and NtGT5 (SEQ ID NO. 59).

In one embodiment, the invention may include a cannabinoid production, accumulation and modification system in a non-cannabinoid producing plant. In one preferred embodiment, a plant, such as tobacco, may be genetically modified to express one or more heterologous cytochrome P450 oxidoreductase genes. In this preferred embodiment, a heterologous cytochrome P450 oxidoreductase (oxred) identified as SEQ ID NO. 3 may be expressed in a cannabinoid-producing plant or cell culture system. While in alternative embodiments a heterologous cytochrome P450 oxidoreductase (oxred) may be expressed non-cannabinoid producing plant or cell culture system such as a tobacco plant, like *N. benthamiana*. In this embodiment, the overexpression of a heterologous cytochrome P450 oxidoreductase (oxred) protein, identified as SEQ ID NO. 4, may help to functionalize cannabinoids introduced to the genetically modified plant or plant cell culture system so that they can be more efficiently glycosylated and/or acetylated, in vivo, rendering them water-soluble.

In a preferred embodiment cytochrome 450 and P450 oxidoreductase are co-expressed. In another embodiment, cytochrome P450 and P450 oxidoreductase may also be expressed as a fusion protein. It should be noted that any nucleic and or amino acid expressed in this system may be expressed single or as a fusion protein, In another embodiment, the invention may include the expression of one or more exogenous or heterologous, the terms being generally interchangeable, cannabinoid synthase gene in a non-cannabinoid producing plant or plant-cell culture system. In one preferred embodiment, such a gene may include one or more of a CBG, THCA, CBDA or CBCA synthase genes. For example in one embodiment, a Cannabidiolic acid (CBDA) synthase, identified as SEQ ID NO. 5 (gene) or SEQ ID NO. 6 (protein) from *Cannabis sativa* may use expressed in a non-*cannabis*-producing plant, such as or plant cell suspension culture of *N. benthamiana*. In another preferred embodiment, a Tetrahydrocannabinolic acid (THCA) synthase, identified as SEQ ID NO. 42 (gene) from *Cannabis sativa* may use expressed in a non-*cannabis*-producing plant, such as a plant cell suspension culture of *N. benthamiana*.

In another preferred embodiment, such cannabinoid synthase genes expressed in a cannabinoid and/or non-cannabinoid plant or plant-cell suspension culture may be target or localized to certain parts of a cell. For example, in one preferred embodiment, cannabinoid production may be localized to the cytosol allowing cannabinoids to accumulate in the cytoplasm. In one exemplary embodiment, an artificially modified cannabinoids synthase protein may be generated. In this example embodiment, a CBDA synthase may have the trichome targeting sequence remove forming a cytosolic CBDA synthase (cytCBDAs) identified as SEQ ID NO. 22, (gene) or 23 (protein). Alternative embodiments would include generation of other artificial cytosol target synthase genes, such as cytosolic THCA synthase (cytTHCAs) identified as SEQ ID NO. 46 (gene).

These preferred embodiments may be particularly suited for cannabinoid cell-suspension culture cannabinoid expression systems, as such culture systems lack the trichomes present in whole plants. As such, in one preferred embodiment, a cannabinoid producing plant may be transformed to one or more of the artificial cytosolic targeted cannabinoid synthase genes lacking a trichome-targeting signal. In an alternative embodiment, such artificial cytosolic targeted cannabinoid synthase genes may be expressed in a cannabinoid producing plant suspension culture where the corresponding endogenous wild-type synthase gene has been inhibited and/or knocked out.

In one embodiment, the invention may include a cannabinoid production, accumulation and modification system that may generate water-soluble cannabinoids. In one preferred embodiment, a plant, such as *cannabis* or tobacco, may be genetically modified to express one or more heterologous glycosyltransferase genes, such as UDP glycosyltransferase. In this preferred embodiment, UDP glycosyltransferase (76G1) (SEQ ID NO. 7) (gene)/SEQ ID NO. 8 (protein) from *Stevia rebaudiana* may be expressed in cannabinoid producing plant or cell suspension culture. In a preferred embodiment, the cannabinoid producing plant or cell suspension culture may be *Cannabis*. In another embodiment, one or more glycosyltransferase from *Nicotiana tabacum* and/or a homologous glycosyltransferase from *Nicotiana benthamiana*, may be expressed in a cannabinoid-producing plant, such as *cannabis*, or may be over-expressed in an endogenous plant and/or plant cell culture system. In a preferred embodiment, a glycosyltransferase gene and/or protein may be selected from the exemplary plant, such as *Nicotiana tabacum* Such glycosyltransferase gene and/or protein may include, but not limited to: Glycosyltransferase (NtGT5a) *Nicotiana tabacum* (SEQ ID NO. 26) (Amino Acid); Glycosyltransferase (NtGT5a) *Nicotiana tabacum* (SEQ ID NO. 27) (DNA); Glycosyltransferase (NtGT5b) *Nicotiana tabacum* (SEQ ID NO. 28) (Amino Acid); Glycosyltransferase (NtGT5b) *Nicotiana tabacum* (SEQ ID NO. 29) (DNA); UDP-glycosyltransferase 73C3 (NtGT4) *Nicotiana tabacum* (SEQ ID NO. 30) (Amino Acid); UDP-glycosyltransferase 73C3 (NtGT4) *Nicotiana tabacum* (SEQ ID NO. 31) (DNA); Glycosyltransferase (NtGT1b) *Nicotiana tabacum* (SEQ ID NO. 32) (Amino Acid); Glycosyltransferase (NtGT1b) *Nicotiana tabacum* (SEQ ID NO. 33) (DNA); Glycosyltransferase (NtGT1a) *Nicotiana tabacum* (SEQ ID NO. 34) (Amino Acid); Glycosyltransferase (NtGT1a) *Nicotiana tabacum* (SEQ ID NO. 35) (DNA); Glycosyltransferase (NtGT3) *Nicotiana tabacum* (SEQ ID NO. 36) (Amino Acid); Glycosyltransferase (NtGT3) *Nicotiana tabacum* (SEQ ID NO. 37) (DNA); Glycosyltransferase (NtGT2) *Nicotiana tabacum* (SEQ ID NO. 38) (Amino Acid); and/or Glycosyltransferase (NtGT2) *Nicotiana tabacum* (SEQ ID NO. 39) (DNA). The sequences from *Nicotiana tabacum* are exemplary only as other tobacco and non-tobacco glycosyltransferase may be used.

As noted above, such glycosyltransferases may glycosylate the cannabinoids and/or functionalized cannabinoids in a plant or plant cell suspension culture as generally described here. Naturally, other glycosyltransferase genes from alternative sources may be included in the current invention.

As noted above, in one embodiment, one or more glycosyltransferases may be targeted or localized to a portion of the plant cell. For example, in this preferred embodiment, cannabinoid glycosylation may be localized to the trichome allowing cannabinoids to accumulate at higher-then wild-type levels in that structure. In one exemplary embodiment, an artificially modified glycosyltransferase may be generated. In this example embodiment, a UDP glycosyltransferase (76G1) may be fused with a trichome-targeting sequence at its N-terminal tail. This trichome targeting sequence may be recognized by the cell and cause it to be transported to the trichome. This artificial gene construct is identified as SEQ ID NO. 19 (gene), or SEQ ID NO. 20 (protein). In one embodiment, a trichome targeting sequence or domain may be derived from any number of synthases. For example, in one embodiment a THCA Synthase Trichome domain (SEQ ID NO. 40) may be coupled with a glycosyltransferase as generally described above. Moreover, in another example, a CBDA Synthase Trichome targeting domain (SEQ ID NO. 41) may be coupled with a glycosyltransferase as generally described above.

In one embodiment, the inventive technology may include the in vivo generation of one or more cannabinoid glucuronides. As also noted above, UDP-glucuronosyltransferases catalyze the transfer of the glucuronosyl group from uridine 5'-diphospho-glucuronic acid (UDP-glucuronic acid) to substrate molecules that contain oxygen, nitrogen, sulfur or carboxyl functional groups. Glucuronidation of a compound, such as a cannabinoid may modulate the bio-availability, activity, and clearance rate of a compound. As such, in one embodiment, the invention may include a cannabinoid production, accumulation and modification system that may generate water-soluble cannabinoid glucuronides. In one preferred embodiment, a plant, such as *cannabis* or tobacco, or another eukaryotic cell, such as yeast, may be genetically modified to express one or more endogenous and/or heterologous UDP-glucuronosyltransferases. Such a UDP-glucuronosyltransferases may be expressed in cannabinoid producing plant, non-cannabinoid producing plant, cell suspension culture, or yeast culture. Non-limiting examples of UDP-glucuronosyltransferases may include UGT1A1, UGT1A3, UGT1A4, UGT1A6, UGT1A7, UGT1A8, UGT1A9, UGT1A10, UGT2B4, UGT2B7, UGT2B15, and UGT2B17—there nucleotide and amino acid sequences being generally know to those of ordinary skill in the art. These UDP-glucuronosyltransferases may be a recombinant UDP-glucuronosyltransferases. In additional embodiments, a UDP-glucuronosyltransferase may be codon optimized for expression in, for example yeast. Methods of making, transforming plant cells, and expressing recombinant UDP-glucuronosyltransferases are known in the art. In a preferred embodiment, the cannabinoid producing plant or cell suspension culture may be *cannabis*. In another embodiment, one or more UDP-glucuronosyltransferases and/or a homolog/ortholog of a UDP-glucuronosyltransferase, may be expressed in a cannabinoid-producing plant, such as *cannabis*, or may be overexpressed in an endogenous plant and/or plant cell culture system or in yeast. In a preferred embodiment, a UDP-glucuronosyltransferase may be targeted or localized to a portion of the plant cell. For example, in this preferred embodiment, cannabinoid glucuronidation may be localized to the trichome allowing cannabinoids to accumulate at higher-then wild-type levels in that structure. In one exemplary embodiment, an artificially modified UDP-glucuronosyltransferase may be generated. In this embodiment, a UDP-glucuronosyltransferase may be fused with a trichome-targeting sequence at its N-terminal tail. This trichome targeting sequence may be recognized by the cell and cause it to be transported to the trichome. In one embodiment, a trichome targeting sequence or domain may be derived from any number of synthases. For example, in one embodiment a THCA Synthase trichome domain (SEQ ID NO. 40) may be coupled with a UDP-glucuronosyltransferase as generally described above. Moreover, in another example, a CBDA Synthase trichome targeting domain (SEQ ID NO. 41) may be coupled with a UDP-glucuronosyltransferase as generally described above. In another embodiment, a UDP-glucuronosyltransferase may further be targeted to the cytosol as generally described herein.

In another embodiment, invention may include an embodiment where transiently modified cannabinoids may be passively and/or actively excreted from a cell or into a cell wall. In one exemplary model, an exogenous ATP-binding cassette transporter (ABC transporters or ABCt) or other similar molecular structure may recognize the glycosyl or glucuronic acid or acetyl functional group (conjugate) on the transiently modified cannabinoid and actively transport it across the cell wall/membrane and into the surrounding media.

In one embodiment, a plant may be transformed to express a heterologous ABC transporter. In this embodiment, an ABCt may facilitate cannabinoid transport outside the cells in suspension cultures, such as a *cannabis* or tobacco cell suspension culture. In this preferred embodiment, a human multi-drug transported (ABCG2) may be expressed in a plant cell suspension culture of the same respectively. ABCG2 is a plasma membrane directed protein and may further be identified as SEQ ID NO. 9 (gene), or 10 (protein).

Generally, a trichome structure, such as in *Cannabis* or tobacco, will have very little to no substrate for a glycosyltransferase enzyme to use to effectuate glycosylation. To resolve this problem, in one embodiment, the invention may include systems, methods and compositions to increase substrates for glycosyltransferase, namely select sugars in a trichome. In one preferred embodiment, the invention may include the targeted or localization of sugar transport to the trichome. In this preferred embodiment, an exogenous or endogenous UDP-glucose/UDP-galactose transporter (UTR1) may be expressed in a trichome producing plant, such as *cannabis* or tobacco and the like. In this embodiment, the UDP-glucose/UDP-galactose transporter (UTR1) may be modified to include a plasma-membrane targeting sequence and/or domain. With this targeting domain, the UDP-glucose/UDP-galactose transporter (UTR1) may allow the artificial fusion protein to be anchored to the plasma membrane. In this configuration, sugar substrates from the cytosol may pass through the plasma membrane bound UDP-glucose/UDP-galactose transporter (PM-UTR1) into the trichome. In this embodiment, substrates for glycosyltransferase may be localized to the trichome and allowed to accumulate further allowing enhanced glycosylation of cannabinoids in the trichome. In one example, SEQ ID NO. 21 is identified as the polynucleotide gene sequence for a heterologous UDP-glucose/galactose transporter (UTR1) from *Arabidopsis thaliana* having a plasma-membrane targeting sequence replacing a tonoplast targeting sequence. The plasma membrane targeting sequence of this exemplary fusion protein may include the following sequence (see SEQ ID NO 21) TGCTCCATAATGAACTTAATGTGTGGGTC-TACCTGCGCCGCT, or a sequence having 70-99% homology with the sequence.

It should be noted that a number of combinations and permutations of the genes/proteins described herein may be co-expressed and thereby accomplish one or more of the goals of the current invention. Such combinations are exemplary of preferred embodiments only, and not limiting in any way.

In one embodiment, a gene, such as a cannabinoid synthase, or a gene fragment corresponding with, for example a signal domain may be inhibited, downregulated, disrupted, or may even be knocked-out. One of ordinary skill in the art will recognize the many processes that can accomplish this without undue experimentation. In other embodiment, a knock-out may mean overexpression of a modified endo- or exogenous gene compared to the wild-type version.

For example, in one embodiment high levels of cannabinoid glycosylation may be generated by co-expressing CYP3A4 and CYP oxidoreductase (cytochrome P450 with P450 oxidoreductase) and at least one endogenous glycosyltransferases in *N. benthamiana*. In another embodiment, one or more of the endogenous or exogenous gene may be expressed in a plant or plant cell culture with the co-expression of myb and/or a catalase. In this configuration, there exists an additive effect of over-expressing a Myb transcription factor and a catalase, one or more of which may be targeted or localized, in the synthesis of water-soluble cannabinoids (glycosylated and hydroxylated) in *Cannabis sativa*.

In certain embodiments, endocannabinoids may be functionalized and/or acetylated and/or glycosylated as generally described herein.

All sequences described herein include sequences having between 70-99% homology with the sequence identified.

The inventive technology may further include novel cannabinoid compounds as well as their in vivo generation. As demonstrated in FIGS. 36 and 37 respectively, the invention includes modified cannabinoid compounds identified as: 36B, 36C, 36D, 37A, 37B, 37C, 37D, 37E and 37F and/or a physiologically acceptable salt thereof. In one preferred embodiment, the invention may include a pharmaceutical composition as active ingredient an effective amount or dose of one or more compounds identified as 36A, 36B, 36C, 36D, 37B, 37C, 37D, 37E and 37F and/or a physiologically acceptable salt thereof, wherein the active ingredient is provided together with pharmaceutically tolerable adjuvants and/or excipients in the pharmaceutical composition. Such pharmaceutical composition may optionally be in combination with one or more further active ingredients. In one embodiment, one of the aforementioned compositions may act as a prodrug. The term "prodrug" is taken to mean compounds according to the invention which have been modified by means of, for example, sugars and which are cleaved in the organism to form the effective compounds according to the invention. The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

In the meaning of the present invention, the compound is further defined to include pharmaceutically usable derivatives, solvates, prodrugs, tautomers, enantiomers, racemates and stereoisomers thereof, including mixtures thereof in all ratios.

In one embodiment, the current invention may include systems, methods and compositions for the efficient production of cannabidiolic acid (CBDA) in yeast coupled with a system of hydrogen peroxide detoxification. In this embodiment, the inventive technology may include the generation of a genetically modified yeast cell.

In one embodiment, the inventive system may include: 1) transforming a yeast cell with a first nucleotide sequence comprising the nucleotide sequence expressing an acyl-activating enzyme and expressing a mutant prenyltransferase; and 2) transforming the yeast cell with a second nucleotide sequence comprising the nucleotide sequence expressing olivetolic synthase, expressing olivetolic acid cyclase and expressing aromatic prenyltransferase; 3) and transforming a yeast cell with a third nucleotide sequence expressing a catalase gene.

In another embodiment, the inventive system may include the step of: 1) transforming a yeast cell with a first nucleotide sequence expressing an acyl-activating enzyme and expressing a mutant prenyltransferase; 2) transforming a yeast cell with a second nucleotide sequence expressing olivetolic synthase and expressing olivetolic acid cyclase; and transforming a yeast cell with a third nucleotide sequence expressing aromatic prenyltransferase and expressing cannabidiolic acid synthase; and 3) transforming a yeast cell with a third nucleotide sequence expressing a catalase gene.

Additional embodiments of the invention may further include: 1) transforming a yeast strain with a first nucleotide sequence expressing an acyl-activating enzyme; 2) transforming the yeast strain with a second nucleotide sequence expressing a mutant prenyltransferase; 3) transforming the yeast strain with a third nucleotide sequence expressing olivetolic synthase; 4) transforming the yeast strain with a fourth nucleotide sequence expressing olivetolic acid cyclase; 5) transforming the yeast strain with a fifth nucleotide sequence expressing aromatic prenyltransferase; 6) transforming the yeast strain with a sixth nucleotide expressing cannabidiolic acid synthase; and 7) transforming the yeast strain with a sixth nucleotide expressing a catalase.

Additional embodiments of the invention may further include: 1) transforming a yeast cell with a first nucleotide sequence expressing an acyl-activating enzyme and expressing a mutant prenyltransferase; 2) transforming the yeast cell with a second nucleotide sequence expressing olivetolic synthase and expressing olivetolic acid cyclase; 3) and transforming the yeast cell with a third nucleotide sequence expressing aromatic prenyltransferase and expressing cannabidiolic acid synthase; and 7) transforming the yeast cell with a fourth nucleotide expressing a catalase.

Additional embodiments of the invention may further include: 1) transforming a yeast cell with a first nucleotide sequence expressing an acyl-activating enzyme and expressing a mutant prenyltransferase; 2) transforming the yeast cell with a second nucleotide sequence expressing olivetolic synthase and expressing olivetolic acid cyclase; 3) transforming the yeast cell with a third nucleotide sequence expressing aromatic prenyltransferase and expressing cannabidiolic acid synthase, and 7) transforming the yeast cell with a fourth nucleotide expressing a catalase.

Sequence listings for the above identified sequences can be found in specification index NOs 1 and 2 filed in application Ser. No. 15/815,651, both of which are incorporated herein by reference. In particular, the following sequences are specifically incorporated by reference: iSEQ. ID. NO. 1; iSEQ. ID. NO. 2; iSEQ. ID. NO. 4; iSEQ. ID. NO. 5; iSEQ. ID. NO. 6; iSEQ. ID. NO. 7; iSEQ. ID. NO. 8; iSEQ. ID. NO. 9; iSEQ. ID. NO. 10; iSEQ. ID. NO. 11; iSEQ. ID. NO. 12; iSEQ. ID. NO. 13; iSEQ. ID. NO. 14; iSEQ. ID. NO. 15; iSEQ. ID. NO. 16; iSEQ. ID. NO. 23; iSEQ. ID. NO. 24; iSEQ. ID. NO. 22; iSEQ. ID. NO. 25; iSEQ. ID. NO. 26; iSEQ. ID. NO. 27; and iSEQ. ID. NO. 28. (The above sequences are marked with an "i" to denote their incorporation by reference.

In one embodiment, the invention may include systems, methods and compositions for the expression of exogenous, or heterologous genes in a yeast cell that may allow the biomodification and/or secretion of cannabinoids generated in a yeast cell. Specifically, the invention may allow the generation of cannabinoids and/or cannabinoid precursors in a genetically modified yeast cell, which may further be functionalized and/or modified into a water-soluble form. This embodiment may include transforming a yeast cell to express one or more of the following: heterologous cytochrome P450, and/or a heterologous P450 oxidoreductase, and/or a glycosyltransferase and/or heterologous ABC transporter. Similar to the above example, the genes may further be codon optimized for expression in a yeast cell that is configured to produce one or more cannabinoids or cannabinoid precursors, such as those genetically modified yeast cells described in U.S. Pat. No. 9,822,384, and U.S. patent application Ser. No. 15/815,651. In this embodiment, the exogenous catalase may be capable of generating water-soluble cannabinoid in one or more of the yeast cells identified in U.S. Pat. No. 9,822,384, and U.S. patent application Ser. No. 15/815,651, both of which are hereby incorporated in their entirety.

In one embodiment, the current invention may include systems, methods and compositions for the efficient production of cannabidiolic acid (CBDA) in yeast coupled with a system of biotransformation of the cannabinoids into a water-soluble form. In this embodiment, the inventive technology may include the generation of a genetically modified yeast cell.

In one embodiment, the inventive system may include: 1) transforming a yeast cell with a first nucleotide sequence comprising the nucleotide sequence expressing an acyl-activating enzyme and expressing a mutant prenyltransferase; and 2) transforming the yeast cell with a second nucleotide sequence comprising the nucleotide sequence expressing olivetolic synthase, expressing olivetolic acid cyclase and expressing aromatic prenyltransferase.; 3) and transforming a yeast cell to express one or more of the following: heterologous cytochrome P450, and/or a heterologous P450 oxidoreductase, and/or a glycosyltransferase and/or heterologous ABC transporter, and/or a catalase. In this embodiment, the heterologous cytochrome P450, and/or a heterologous P450 oxidoreductase, and/or a glycosyltransferase and/or heterologous ABC transporter, and/or a catalase, the sequences identified herein may further be codon optimized for expression in yeast. Such codon optimization being generally within the knowledge and ability of one of ordinary skill in the art.

In another embodiment, the inventive system may include the step of: 1) transforming a yeast cell with a first nucleotide sequence expressing an acyl-activating enzyme and expressing a mutant prenyltransferase; 2) transforming a yeast cell with a second nucleotide sequence expressing olivetolic synthase and expressing olivetolic acid cyclase; and transforming a yeast cell with a third nucleotide sequence expressing aromatic prenyltransferase and expressing cannabidiolic acid synthase; 3) and transforming a yeast cell to express one or more of the following: heterologous cytochrome P450, and/or a heterologous P450 oxidoreductase, and/or a glycosyltransferase and/or heterologous ABC transporter, and/or a catalase.

Additional embodiments of the invention may further include: 1) transforming a yeast strain with a first nucleotide sequence expressing an acyl-activating enzyme; 2) transforming the yeast strain with a second nucleotide sequence expressing a mutant prenyltransferase; 3) transforming the yeast strain with a third nucleotide sequence expressing olivetolic synthase; 4) transforming the yeast strain with a fourth nucleotide sequence expressing olivetolic acid cyclase; 5) transforming the yeast strain with a fifth nucleotide sequence expressing aromatic prenyltransferase; 6) transforming the yeast strain with a sixth nucleotide expressing cannabidiolic acid synthase; and 7) and transforming a yeast cell to express one or more of the following: heterologous cytochrome P450, and/or a heterologous P450 oxidoreductase, and/or a glycosyltransferase and/or heterologous ABC transporter, and/or a catalase.

Additional embodiments of the invention may further include: 1) transforming a yeast cell with a first nucleotide sequence expressing an acyl-activating enzyme and expressing a mutant prenyltransferase; 2) transforming the yeast cell with a second nucleotide sequence expressing olivetolic synthase and expressing olivetolic acid cyclase; 3) and transforming the yeast cell with a third nucleotide sequence expressing aromatic prenyltransferase and expressing cannabidiolic acid synthase; and 7) and transforming a yeast cell to express one or more of the following: heterologous cytochrome P450, and/or a heterologous P450 oxidoreductase, and/or a glycosyltransferase and/or heterologous ABC transporter, and/or a catalase.

Additional embodiments of the invention may further include: 1) transforming a yeast cell with a first nucleotide sequence expressing an acyl-activating enzyme and expressing a mutant prenyltransferase; 2) transforming the yeast cell with a second nucleotide sequence expressing olivetolic synthase and expressing olivetolic acid cyclase; 3) transforming the yeast cell with a third nucleotide sequence expressing aromatic prenyltransferase and expressing cannabidiolic acid synthase, and 7) and transforming a yeast cell to express one or more of the following: heterologous cytochrome P450, and/or a heterologous P450 oxidoreductase, and/or a glycosyltransferase and/or heterologous ABC transporter, and/or a catalase.

Sequence listings for the above identified sequences can be found in specification index NOs 1 and 2 filed in application Ser. No. 15/815,651, both of which are incorporated herein by reference. In particular, the following sequences are specifically incorporated by reference: iSEQ. ID. NO. 1; iSEQ. ID. NO. 2; iSEQ. ID. NO. 4; iSEQ. ID. NO. 5; iSEQ. ID. NO. 6; iSEQ. ID. NO. 7; iSEQ. ID. NO. 8; iSEQ. ID. NO. 9; iSEQ. ID. NO. 10; iSEQ. ID. NO. 11; iSEQ. ID. NO. 12; iSEQ. ID. NO. 13; iSEQ. ID. NO. 14; iSEQ. ID. NO. 15; iSEQ. ID. NO. 16; iSEQ. ID. NO. 23; iSEQ. ID. NO. 24; iSEQ. ID. NO. 22; iSEQ. ID. NO. 25; iSEQ. ID. NO. 26; iSEQ. ID. NO. 27; and iSEQ. ID. NO. 28. (The above sequences are marked with an "i" to denote their incorporation by reference.

The invention may further include systems, method and compositions for the generation of water-soluble cannabinoids in a cell culture system expressing an endogenous glycosyltransferase. In this embodiment, one or more cannabinoids, such as in the form of a cannabinoid extract, may be introduced to a tobacco cell culture expressing one or more endogenous glycosyltransferase that may generate water-soluble cannabinoids. In some embodiment, a tobacco cell culture may be further genetically modified to express an endogenous glycosyltransferase which may be operably linked to a promoter. In this embodiment, such a promotor may be an inducible, constitutive or other promotor. In this preferred embodiment, such an endogenous glycosyltransferase may cause the overexpression of the protein generating a more robust cannabinoid biotransformation system.

As noted above, present invention allows the scaled production of water-soluble cannabinoids. Because of this enhanced solubility, the invention allows for the addition of such water-soluble cannabinoid to a variety of compositions without requiring oils and or emulsions that are generally required to maintain the non-modified cannabinoids in suspension. As a result, the present invention may all for the production of a variety of compositions for both the food and beverage industry, as well as pharmaceutical applications that do not required oils and emulsion suspensions and the like.

In one embodiment the invention may include aqueous compositions containing one or more water-soluble cannabinoids that may be introduced to a food or beverage. In a preferred embodiment, the invention may include an aqueous solution containing one or more dissolved water-soluble cannabinoids. In this embodiment, such water-soluble cannabinoid may include a glycosylated cannabinoid, and/or an acetylated cannabinoid, and/or a mixture of both. Here, the glycosylated cannabinoid, and/or said acetylated cannabinoid were generated in vivo as generally described herein, or in vitro. In additional embodiment, the water-soluble cannabinoid may be an isolated non-psychoactive, such as CBD and the like. Moreover, in this embodiment, the aqueous may contain one or more of the following: saline, purified water, propylene glycol, deionized water, and/or an alcohol such as ethanol as well as a pH buffer that may allow the aqueous solution to be maintained at a pH below 7.4.

Additional embodiments may include the addition an acid of base, such as formic acid, or ammonium hydroxide.

In another embodiment, the invention may include a consumable food additive having at least one water-soluble cannabinoid, such as a glycosylated and/or an acetylated cannabinoid, and/or a mixture of both, where such water-soluble cannabinoids may be generated in vivo and/or in vitro. This consumable food additive may further include one or more a food additive polysaccharides, such as dextrin and/or maltodextrin, as well as an emulsifier. Example emulisifiers may include, but not be limited to: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcel-laran, Gellan gum, psyllium, curdlan, konjac mannan, agar, and cellulose derivatives, or combinations thereof.

The consumable food additive of the invention may be a homogenous composition and may further comprising a flavoring agent. Exemplary flavoring agents may include: sucrose (sugar), glucose, fructose, sorbitol, mannitol, corn syrup, high fructose corn syrup, saccharin, aspartame, sucralose, acesulfame potassium (acesulfame-K), neotame. The consumable food additive of the invention may also contain one or more coloring agents. Exemplary coloring agents may include: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate.

The consumable food additive of the invention may also contain one or more surfactants, such as glycerol monostearate and polysorbate 80. The consumable food additive of the invention may also contain one or more preservatives. Exemplary preservatives may include ascorbic acid, citric acid, sodium benzoate, calcium propionate, sodium erythorbate, sodium nitrite, calcium sorbate, potassium sorbate, BHA, BHT, EDTA, tocopherols. The consumable food additive of the invention may also contain one or more nutrient supplements, such as: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

In one embodiment, the invention may include a consumable fluid containing at least one dissolved water-soluble cannabinoid. In one preferred embodiment, this consumable fluid may be added to a drink or beverage to infused it with the dissolved water-soluble cannabinoid generated in an in vivo system as generally herein described, or through an in vitro process, for example as identified by Zipp et al. which is incorporated herein by reference. As noted above, such water-soluble cannabinoid may include a water-soluble glycosylated cannabinoid and/or a water-soluble acetylated cannabinoid, and/or a mixture of both. The consumable fluid may include a food additive polysaccharide such as maltodextrin and/or dextrin, which may further be in an aqueous form and/or solution. For example, in one embodiment, and aqueous maltodextrin solution may include a quantity of sorbic acid and an acidifying agent to provide a food grade aqueous solution of maltodextrin having a pH of 2-4 and a sorbic acid content of 0.02-0.1% by weight.

In certain embodiments, the consumable fluid may include water, as well as an alcoholic beverage; a non-alcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water. The consumable fluid may further include at least one additional ingredients, including but not limited to: xanthan gum, cellulose gum, whey protein hydrolysate, ascorbic acid, citric acid, malic acid, sodium benzoate, sodium citrate, sugar, phosphoric acid, and water.

In one embodiment, the invention may include a consumable gel having at least one water-soluble cannabinoid and gelatin in an aqueous solution. In a preferred embodiment, the consumable gel may include a water-soluble glycosylated cannabinoid and/or a water-soluble acetylated cannabinoid, or a mixture of both, generated in an in vivo system, such as a whole plant or cell suspension culture system as generally herein described.

Additional embodiments may include a liquid composition having at least one water-soluble cannabinoid solubilized in a first quantity of water; and at least one of: xanthan gum, cellulose gum, whey protein hydrolysate, ascorbic acid, citric acid, malic acid, sodium benzoate, sodium citrate, sugar, phosphoric acid, and/or a sugar alcohol. In this embodiment, a water-soluble cannabinoid may include a glycosylated water-soluble cannabinoid, an acetylated water-soluble cannabinoid, or a mixture of both. In one preferred embodiment, the composition may further include a quantity of ethanol. Here, the amount of water-soluble cannabinoid may include: less than 10 mass % water; more than 95 mass % water; about 0.1 mg to about 1000 mg of the water-soluble cannabinoid; about 0.1 mg to about 500 mg of the water-soluble cannabinoid; about 0.1 mg to about 200 mg of the water-soluble cannabinoid; about 0.1 mg to about 100 mg of the water-soluble cannabinoid; about 0.1 mg to about 100 mg of the water-soluble cannabinoid; about 0.1 mg to about 10 mg of the water-soluble cannabinoid; about 0.5 mg to about 5 mg of the water-soluble cannabinoid; about 1 mg/kg to 5 mg/kg (body weight) in a human of the water-soluble cannabinoid.

In alternative embodiment, the composition may include at least one water-soluble cannabinoid in the range of 50 mg/L to 300 mg/L; at least one water-soluble cannabinoid in the range of 50 mg/L to 100 mg/L; at least one water-soluble cannabinoid in the range of 50 mg/L to 500 mg/L; at least one water-soluble cannabinoid over 500 mg/L; at least one water-soluble cannabinoid under 50 mg/L. Additional embodiments may include one or more of the following additional components: a flavoring agent; a coloring agent; a coloring agent; and/or caffeine.

In one embodiment, the invention may include a liquid composition having at least one water-soluble cannabinoid solubilized in said first quantity of water and a first quantity of ethanol in a liquid state. In a preferred embodiment, a first quantity of ethanol in a liquid state may be between 1% to 20% weight by volume of the liquid composition. In this embodiment, a water-soluble cannabinoid may include a glycosylated water-soluble cannabinoid, an acetylated water-soluble cannabinoid, or a mixture of both. Such water-soluble cannabinoids may be generated in an in vivo and/or in vitro system as herein identified. In a preferred embodiment, the ethanol, or ethyl alcohol component may be up to about ninety-nine point nine-five percent (99.95%) by weight and the water-soluble cannabinoid about zero point zero five percent (0.05%) by weight. In another embodiment, Examples of the preferred embodiment may include liquid ethyl alcohol compositions having one or more water-soluble cannabinoids wherein said ethyl alcohol has a proof greater than 100, and/or less than 100. Additional examples of a liquid composition containing ethyl alcohol and at least one water-soluble cannabinoid may include, beer, wine and/or distilled spirit.

Additional embodiments of the invention may include a chewing gum composition having a first quantity of at least one water-soluble cannabinoid. In a preferred embodiment, a chewing gum composition may further include a gum base comprising a buffering agent selected from the group consisting of acetates, glycinates, phosphates, carbonates, glycerophosphates, citrates, borates, and mixtures thereof. Additional components may include at least one sweetening agent; and at least one flavoring agent. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

In one embodiment, the chewing gum composition described above may include:
 0.01 to 1% by weight of at least one water-soluble cannabinoid;
 25 to 85% by weight of a gum base;
 10 to 35% by weight of at least one sweetening agent; and
 1 to 10% by weight of a flavoring agent.

Here, such flavoring agents may include: menthol flavor, *eucalyptus*, mint flavor and/or L-menthol. Sweetening agents may include one or more of the following: xylitol, sorbitol, isomalt, aspartame, sucralose, acesulfame potassium, and saccharin. Additional preferred embodiment may include a chewing gum having a pharmaceutically acceptable excipient selected from the group consisting of: fillers, disintegrants, binders, lubricants, and antioxidants. The chewing gum composition may further be non-disintegrating and also include one or more coloring and/or flavoring agents.

The invention may further include a composition for a water-soluble cannabinoid infused solution comprising essentially of: water and/or purified water, at least one water-soluble cannabinoid, and at least one flavoring agent. A water-soluble cannabinoid infused solution of the invention may further include a sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of the water-soluble cannabinoid infused solution may include, but not be limited to: sodium chloride, sodium chloride solution, glycerin, a coloring agent, and a demulcent. As to this last potential component, in certain embodiment, a demulcent may include: pectin, glycerin, honey, methylcellulose, and/or propylene glycol. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may further include a composition for a water-soluble cannabinoid infused anesthetic solution having water, or purified water, at least one water-soluble cannabinoid, and at least one oral anesthetic. In a preferred embodiment, an anesthetic may include benzocaine, and/or phenol in a quantity of between 0.1% to 15% volume by weight.

Additional embodiments may include a water-soluble cannabinoid infused anesthetic solution having a sweetener which may be selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of the water-soluble cannabinoid infused solution may include, but not be limited to: sodium chloride, sodium chloride solution, glycerin, a coloring agent a demulcent. In a preferred embodiment, a demulcent may selected from the group consisting of: pectin, glycerin, honey, methylcellulose, and propylene glycol. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may further include a composition for a hard lozenge for rapid delivery of water-soluble cannabinoids through the oral mucosa. In this embodiment, such a hard lozenge composition may include: a crystalized sugar base, and at least one water-soluble cannabinoid, wherein the hard lozenge has a moisture content between 0.1 to 2%. In this embodiment, the water-soluble cannabinoid may be added to the sugar based when it is in a liquefied form and prior to the evaporation of the majority of water content. Such a hard lozenge may further be referred to as a candy.

In a preferred embodiment, a crystalized sugar base may be formed from one or more of the following: sucrose, invert sugar, corn syrup, and isomalt or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The hard lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may include a chewable lozenge for rapid delivery of water-soluble cannabinoids through the oral mucosa. In a preferred embodiment, the compositions may include: a glycerinated gelatin base, at least one sweetener; and at least one water-soluble cannabinoid dissolved in a first quantity of water. In this embodiment, a sweetener may include sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The chewable lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

The invention may include a soft lozenge for rapid delivery of water-soluble cannabinoids through the oral mucosa. In a preferred embodiment, the compositions may include: polyethylene glycol base, at least one sweetener; and at least one water-soluble cannabinoid dissolved in a first quantity of water. In this embodiment, a sweetener may include sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The soft lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively.

In another embodiment, the invention may include a tablet or capsule consisting essentially of a water-soluble glycosylated cannabinoid and a pharmaceutically acceptable excipient. Example may include solid, semi-solid and aqueous excipients such as: maltodextrin, whey protein isolate, xanthan gum, guar gum, diglycerides, monoglycerides, carboxymethyl cellulose, glycerin, gelatin, polyethylene glycol and water-based excipients.

In a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively. Examples of such in vivo systems being generally described herein, including in plant, as well as cell culture systems including *cannabis* cell culture, tobacco cell culture and yeast cell culture systems. In one embodiment, a tablet or capsule may include an amount of water-soluble cannabinoid of 5 milligrams or less. Alternative embodiments may include an amount of water-soluble cannabinoid between 5 milligrams and 200 milligrams. Still other embodiments may include a tablet or capsule having amount of water-soluble cannabinoid that is more than 200 milligrams.

The invention may further include a method of manufacturing and packaging a cannabinoid dosage, consisting of the following steps: 1) preparing a fill solution with a desired concentration of a water-soluble cannabinoid in a liquid carrier wherein said cannabinoid solubilized in said liquid carrier; 2) encapsulating said fill solution in capsules; 3) packaging said capsules in a closed packaging system; and 4) removing atmospheric air from the capsules. In one embodiment, the step of removing of atmospheric air consists of purging the packaging system with an inert gas, such as, for example, nitrogen gas, such that said packaging system provides a room temperature stable product. In one preferred embodiment, the packaging system may include a plaster package, which may be constructed of material that minimizes exposure to moisture and air.

In one embodiment a preferred liquid carrier may include a water-based carrier, such as for example an aqueous sodium chloride solution. In a preferred embodiment, a water-soluble cannabinoid may include at least one water-soluble acetylated cannabinoid, and/or at least one water-soluble glycosylated cannabinoid, or a mixture of the two. In this embodiment, such water soluble glycosylated cannabinoid, and/or said acetylated cannabinoid may have been glycosylated and/or acetylated in vivo respectively. Examples of such in vivo systems being generally described herein, including in plant, as well as cell culture systems including *cannabis* cell culture, tobacco cell culture and yeast cell culture systems. In one embodiment, a desired cannabinoid concentration may be about 1-10% w/w, while in other embodiments it may be about 1.5-6.5% w/w. Alternative embodiments may include an amount of water-soluble cannabinoid between 5 milligrams and 200 milligrams. Still other embodiments may include a tablet or capsule having amount of water-soluble cannabinoid that is more than 200 milligrams.

The invention may include an oral pharmaceutical solution, such as a sub-lingual spray, consisting essentially of a water-soluble cannabinoid, 30-33% w/w water, about 50% w/w alcohol, 0.01% w/w butylated hydroxylanisole (BHA) or 0.1% w/w ethylenediaminetetraacetic acid (EDTA) and 5-21% w/w co-solvent, having a combined total of 100%, wherein said co-solvent is selected from the group consisting of propylene glycol, polyethylene glycol and combinations thereof, and wherein said water-soluble cannabinoid is a glycosylated cannabinoid, an acetylated cannabinoid or a mixture of the two. In an alternative embodiment, such a oral pharmaceutical solution may consist essentially of 0.1 to 5% w/w of said water-soluble cannabinoid, about 50% w/w alcohol, 5.5% w/w propylene glycol, 12% w/w polyethylene glycol and 30-33% w/w water. In a preferred composition, the alcohol component may be ethanol.

The invention may include an oral pharmaceutical solution, such as a sublingual spray, consisting essentially of about 0.1% to 1% w/w water-soluble cannabinoid, about 50% w/w alcohol, 5.5% w/w propylene glycol, 12% w/w polyethylene glycol, 30-33% w/w water, 0.01% w/w butylated hydroxyanisole, having a combined total of 100%, and wherein said water-soluble cannabinoid is a glycosylated cannabinoid, an acetylated cannabinoid or a mixture of the two wherein that were generated in vivo. In an alternative embodiment, such a oral pharmaceutical solution may consist essentially of 0.54% w/w water-soluble cannabinoid, 31.9% w/w water, 12% w/w polyethylene glycol 400, 5.5% w/w propylene glycol, 0.01% w/w butylated hydroxyanisole, 0.05% w/w sucralose, and 50% w/w alcohol, wherein the a the alcohol components may be ethanol.

The invention may include a solution for nasal and/or sublingual administration of a cannabinoid including: 1) an excipient of propylene glycol, ethanol anhydrous, or a mixture of both; and 2) a water-soluble cannabinoid which may include glycosylated cannabinoid an acetylated cannabinoid or a mixture of the two generated in vivo and/or in vitro. In a preferred embodiment, the composition may further include a topical decongestant, which may include phenylephrine hydrochloride, Oxymetazoline hydrochloride, and Xylometazoline in certain preferred embodiments. The composition may further include an antihistamine, and/or a steroid. Preferably, the steroid component is a corticosteroid selected from the group consisting of: neclomethasone dipropionate, budesonide, ciclesonide, flunisolide, fluticasone furoate, fluticasone propionate, mometasone, triamcinolone acetonide. In alternative embodiment, the solution for nasal and/or sublingual administration of a cannabinoid may further comprise at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

The invention may further include an aqueous solution for nasal and/or sublingual administration of a cannabinoid comprising: a water and/or saline solution; and a water-soluble cannabinoid which may include a glycosylated cannabinoid, an acetylated cannabinoid or a mixture of the two generated in vivo and/or in vitro. In a preferred embodiment, the composition may further include a topical decongestant, which may include phenylephrine hydrochloride, Oxymetazoline hydrochloride, and Xylometazoline in certain preferred embodiments. The composition may further include an antihistamine, and/or a steroid. Preferably, the steroid component is a corticosteroid selected from the group consisting of: neclomethasone dipropionate, budesonide, ciclesonide, flunisolide, fluticasone furoate, fluticasone propionate, mometasone, triamcinolone acetonide. In alternative embodiment, the aqueous solution may further comprise at least one of the following: benzalkonium chloride solution, benzyl alcohol, boric acid, purified water, sodium borate, polysorbate 80, phenyl ethyl alcohol, microcrystalline cellulose, carboxymethylcellulose sodium, dextrose, dipasic, sodium phosphate, edetate disodium, monobasic sodium phosphate, propylene glycol.

The invention may include a topical formulation for the transdermal delivery of water-soluble cannabinoid. In a preferred embodiment, a topical formulation for the transdermal delivery of water-soluble cannabinoid may include a water-soluble glycosylated cannabinoid, and/or water-soluble acetylated cannabinoid, or a mixture of both, and a pharmaceutically acceptable excipient. Here, a glycosylated cannabinoid and/or acetylated cannabinoid may be generated in vivo and/or in vitro. Preferably a pharmaceutically acceptable excipient may include one or more: gels, ointments, cataplasms, poultices, pastes, creams, lotions, plasters and jellies or even polyethylene glycol. Additional embodiments may further include one or more of the following components: a quantity of capsaicin; a quantity of benzocaine; a quantity of lidocaine; a quantity of camphor; a quantity of benzoin resin; a quantity of methylsalicilate; a quantity of triethanolamine salicylate; a quantity of hydrocortisone; a quantity of salicylic acid.

The invention may include a gel for transdermal administration of a water soluble-cannabinoid which may be generated in vitro and/or in vivo. In this embodiment, the mixture preferably contains from 15% to about 90% ethanol, about 10% to about 60% buffered aqueous solution or water, about 0.1 to about 25% propylene glycol, from about 0.1 to about 20% of a gelling agent, from about 0.1 to about 20% of a base, from about 0.1 to about 20% of an absorption enhancer and from about 1% to about 25% polyethylene glycol and a water-soluble cannabinoid such as a glycosylated cannabinoid, and/or acetylated cannabinoid, and/or a mixture of the two.

In another embodiment, the invention may further include a transdermal composition having a pharmaceutically effective amount of a water-soluble cannabinoid for delivery of the cannabinoid to the bloodstream of a user. This transdermal composition may include a pharmaceutically acceptable excipient and at least one water-soluble cannabinoid, such as a glycosylated cannabinoid, an acetylated cannabinoid, and a mixture of both, wherein the cannabinoid is capable of diffusing from the composition into the bloodstream of the user. In a preferred embodiment, a pharmaceutically acceptable excipient to create a transdermal dosage form selected from the group consisting of: gels, ointments, cataplasms, poultices, pastes, creams, lotions, plasters and jellies. The transdermal composition may further include one or more surfactants. In one preferred embodiment, the surfactant may include a surfactant-lecithin organogel, which may further be present in an amount of between about between about 95% and about 98% w/w. In an alternative embodiment, a surfactant-lecithin organogel comprises lecithin and PPG-2 myristyl ether propionate and/or high molecular weight polyacrylic acid polymers. The transdermal composition may further include a quantity of isopropyl myristate.

The invention may further include transdermal composition having one or more permeation enhancers to facilitate transfer of the water-soluble cannabinoid across a dermal layer. In a preferred embodiment, a permeation enhancer may include one or more of the following: propylene glycol monolaurate, diethylene glycol monoethyl ether, an oleoyl macrogolglyceride, a caprylocaproyl macrogolglyceride, and an oleyl alcohol, The invention may also include a liquid cannabinoid liniment composition consisting of water, isopropyl alcohol solution and a water-soluble cannabinoid, such as glycosylated cannabinoid, and/or said acetylated cannabinoid which may further have been generated in vivo. This liquid cannabinoid liniment composition may further include approximately 97.5% to about 99.5% by weight of 70% isopropyl alcohol solution and from about 0.5% to about 2.5% by weight of a water-soluble cannabinoid mixture.

Based on to improved solubility and other physical properties, as well as cost advantage and scalability of the invention's in vivo water-soluble production platform, the invention may include one or more commercial infusions. For example, commercially available products, such as a lip balm, soap, shampoos, lotions, creams and cosmetics may be infused with one or more water-soluble cannabinoids.

As generally described herein, the invention may include one or more plants, such as a tobacco plant and/or cell culture that may be genetically modified to produce, for example water-soluble glycosylated cannabinoids in vivo. As such, in one preferred embodiment, the invention may include a tobacco plant and or cell that contain at least one water-soluble cannabinoid. In a preferred embodiment, a tobacco plant containing a quantity of water-soluble cannabinoids may be used to generate a water-soluble cannabinoid infused tobacco product such as a cigarette, pipe tobacco, chewing tobacco, cigar, and smokeless tobacco. In one embodiment, the tobacco plant may be treated with one or more glycosidase inhibitors. In a preferred embodiment, since the cannabinoid being introduced to the tobacco plant may be controlled, the inventive tobacco plant may generate one or more selected water-cannabinoids. For example, in one embodiment, the genetically modified tobacco plant may be introduced to a single cannabinoid, such as a non-psychoactive CBD compound, while in other embodiment, the genetically modified tobacco plant may be introduced to a cannabinoid extract containing a full and/or partial entourage of cannabinoid compounds.

The invention may further include a novel composition that may be used to supplement a cigarette, or other tobacco-based product. In this embodiment, the composition may include at least one water-soluble cannabinoid dissolved in an aqueous solution. This aqueous solution may be wherein said composition may be introduced to a tobacco product, such as a cigarette and/or a tobacco leaf such that the aqueous solution may evaporate generating a cigarette and/or a tobacco leaf that contains the aforementioned water-soluble cannabinoid(s), which may further have been generated in vivo as generally described herein.

On one embodiment the invention may include one or more method of treating a medical condition in a mammal. In this embodiment, the novel method may include of administering a therapeutically effective amount of a water-soluble cannabinoid, such as an in vivo generated glycosylated cannabinoid, and/or an acetylated cannabinoid, and/or a mixture of both or a pharmaceutically acceptable salt thereof, wherein the medical condition is selected from the group consisting of: obesity, post-traumatic stress syndrome, anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, *cannabis* use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis. In a preferred embodiment, the pharmaceutical composition may be administered by a route selected from the group consisting of: transdermal, topical, oral, buccal, sublingual, intra-venous, intra-muscular, vaginal, rectal, ocular, nasal and follicular. The amount of water-soluble cannabinoids may be a therapeutically effective amount, which may be determined by the patient's age, weight, medical condition cannabinoid-delivered, route of delivery and the like. In one embodiment, a therapeutically effective amount may be 50 mg or less of a water-soluble cannabinoid. In another embodiment, a therapeutically effective amount may be 50 mg or more of a water-soluble cannabinoid.

It should be noted that for any of the above composition, unless otherwise stated, an effective amount of water-soluble cannabinoids may include amounts between: 0.01 mg to 0.1 mg; 0.01 mg to 0.5 mg; 0.01 mg to 1 mg; 0.01 mg to 5 mg; 0.01 mg to 10 mg; 0.01 mg to 25 mg; 0.01 mg to 50 mg; 0.01 mg to 75 mg; 0.01 mg to 100 mg; 0.01 mg to 125 mg; 0.01 mg to 150 mg; 0.01 mg to 175 mg; 0.01 mg to 200 mg; 0.01 mg to 225 mg; 0.01 mg to 250 mg; 0.01 mg to 275 mg; 0.01 mg to 300 mg; 0.01 mg to 225 mg; 0.01 mg to 350 mg; 0.01 mg to 375 mg; 0.01 mg to 400 mg; 0.01 mg to 425 mg; 0.01 mg to 450 mg; 0.01 mg to 475 mg; 0.01 mg to 500 mg; 0.01 mg to 525 mg; 0.01 mg to 550 mg; 0.01 mg to 575 mg; 0.01 mg to 600 mg; 0.01 mg to 625 mg; 0.01 mg to 650 mg; 0.01 mg to 675 mg; 0.01 mg to 700 mg; 0.01 mg to 725 mg; 0.01 mg to 750 mg; 0.01 mg to 775 mg; 0.01 mg to 800 mg; 0.01 mg to 825 mg; 0.01 mg to 950 mg; 0.01 mg to 875 mg; 0.01 mg to 900 mg; 0.01 mg to 925 mg; 0.01 mg to 950 mg; 0.01 mg to 975 mg; 0.01 mg to 1000 mg; 0.01 mg to 2000 mg; 0.01 mg to 3000 mg; 0.01 mg to 4000 mg; 01 mg to 5000 mg; 0.01 mg to 0.1 mg/kg.; 0.01 mg to 0.5 mg/kg; 01 mg to 1 mg/kg; 0.01 mg to 5 mg/kg; 0.01 mg to 10 mg/kg; 0.01 mg to 25 mg/kg; 0.01 mg to 50 mg/kg; 0.01 mg to 75 mg/kg; and 0.01 mg to 100 mg/kg.

The modified cannabinoids compounds of the present invention are useful for a variety of therapeutic applications. For example, the compounds are useful for treating or alleviating symptoms of diseases and disorders involving CB1 and CB2 receptors, including appetite loss, nausea and vomiting, pain, multiple sclerosis and epilepsy. For example, they may be used to treat pain (i.e. as analgesics) in a variety of applications including but not limited to pain management. In additional embodiments, such modified cannabinoids compounds may be used as an appetite suppressant. Additional embodiment may include administering the modified cannabinoids compounds.

By "treating" the present inventors mean that the compound is administered in order to alleviate symptoms of the disease or disorder being treated. Those of skill in the art will recognize that the symptoms of the disease or disorder that is treated may be completely eliminated, or may simply be lessened. Further, the compounds may be administered in combination with other drugs or treatment modalities, such as with chemotherapy or other cancer-fighting drugs.

Implementation may generally involve identifying patients suffering from the indicated disorders and administering the compounds of the present invention in an acceptable form by an appropriate route. The exact dosage to be administered may vary depending on the age, gender, weight and overall health status of the individual patient, as well as the precise etiology of the disease. However, in general, for administration in mammals (e.g. humans), dosages in the range of from about 0.01 to about 300 mg of compound per kg of body weight per 24 hr., and more preferably about 0.01 to about 100 mg of compound per kg of body weight per 24 hr., are effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.). In a preferred embodiment of the invention, the water-soluble cannabinoid analogs are provided orally or intravenously.

In particular, the phenolic esters of the invention are preferentially administered systemically in order to afford an opportunity for metabolic activation via in vivo cleavage of the ester. In addition, the water soluble compounds with azole moieties at the pentyl side chain do not require in vivo activation and may be suitable for direct administration (e.g. site specific injection).

The compounds may be administered in the pure form or in a pharmaceutically acceptable formulation including suitable elixirs, binders, and the like (generally referred to a "carriers") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the compounds of the present invention may be intermittent, bolus dose, or at a gradual or continuous, constant or controlled rate to a patient. In addition, the time of day and the number of times per day that the pharmaceutical formulation is administered may vary are and best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

Genes encoding by a combination polynucleotide and/or a homologue thereof, may be introduced into a plant, and/or plant cell using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants.

As used herein, a "cannabinoid" is a chemical compound (such as cannabinol, THC or cannabidiol) that is found in the plant species *Cannabis* among others like *Echinacea; Acmella Oleracea;* Helichrysum Umbraculigerum; Radula *Marginata* (Liverwort) and *Theobroma Cacao*, and metabolites and synthetic analogues thereof that may or may not have psychoactive properties. Cannabinoids therefore include (without limitation) compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3S,4R)-7-hydroxy-46-tetrahydrocannabinol homologs and derivatives described in U.S. Pat. No. 4,876,276, incorporated by reference; (+)-4-[4-DMH-2,6-diacetoxyphenyl]-2-carboxy-6,6-dimethylbicyclo[3.1.1]hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., J. Clin. Phannacol. 21:428S-436S, 1981, which is also incorporated by reference. Many other cannabinoids are similarly disclosed in Agurell et al., Pharmacol. Rev. 38:31-43, 1986, which is also incorporated by reference.

As claimed herein, the term "cannabinoid" may also include different modified forms of a cannabinoid such as a hydroxylated cannabinoid or cannabinoid carboxylic acid. For example, if a glycosyltransferase were to be capable of glycosylating a cannabinoid, it would include the term cannabinoid as defined elsewhere, as well as the aforementioned modified forms. It may further include multiple glycosylation moieties.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-iso-tetrahydrocannabivarin, delta-8-tetrahydrocannabinoic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol, trihydroxy-delta-9-tetrahydrocannabinol, and cannabinol. Examples of cannabinoids within the context of this disclosure include tetrahydrocannabinol and cannabidiol.

The term "endocannabinoid" refer to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

Hydroxylation is a chemical process that introduces a hydroxyl group (—OH) into an organic compound. Acetylation is a chemical reaction that adds an acetyl chemical group. Glycosylation is the coupling of a glycosyl donor, to a glycosyl acceptor forming a glycoside.

The term "prodrug" refers to a precursor of a biologically active pharmaceutical agent (drug). Prodrugs must undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative process that removes the prodrug moiety to form the biologically active pharmaceutical agent.

The term "glycosidase inhibitor" and as used in the present invention is used to mean a compound, which can inhibit glycosidase enzymes which catalyst the hydrolysis of glycosidic bonds. Techniques for determining whether a compound acts as a glycosidase inhibitor will be well known to the skilled person, but may include, for example use of substrates such as p-nitrophenyl-glycosides, where the presence of an inhibitor will reduce the release of the colored p-nitrophenol when an appropriate glycosidase is present.

As used herein, the term "homologous" with regard to a contiguous nucleic acid sequence, refers to contiguous nucleotide sequences that hybridize under appropriate conditions to the reference nucleic acid sequence. For example, homologous sequences may have from about 70%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific."

A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most cell or tissue types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone are general examples (Schena et al. (1991) Proc. Natl. Acad. Sci. USA 88:0421).

As used herein, the term "transformation" or "genetically modified" refers to the transfer of one or more nucleic acid molecule(s) into a cell. A plant is "transformed" or "genetically modified" by a nucleic acid molecule transduced into the plant when the nucleic acid molecule becomes stably replicated by the plant. As used herein, the term "transformation" or "genetically modified" encompasses all techniques by which a nucleic acid molecule can be introduced into, such as a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria.

As is known in the art, different organisms preferentially utilize different codons for generating polypeptides. Such "codon usage" preferences may be used in the design of nucleic acid molecules encoding the proteins and chimeras of the invention in order to optimize expression in a particular host cell system.

An "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 1a, infra, contains information about which nucleic acid codons encode which amino acids.

TABLE 4

Amino acid Nucleic acid codons

| Amino Acid | Nucleic Acid Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "plant" or "plant system" includes whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The invention may also include Cannabaceae and other *Cannabis* strains, such as *C. sativa* generally.

The term "expression," as used herein, or "expression of a coding sequence" (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acetylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

The term "sequence identity" or "identity," as used herein in the context of two nucleic acid or polypeptide sequences, refers to the residues in the two sequences that are the same when aligned for maximum correspondence over a specified comparison window.

The term "recombinant" when used with reference, e.g., to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed—over-expressed, under expressed or not expressed at all.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

As used herein, "heterologous" or "exogenous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

EXAMPLES

Example 1: Functionalization of Cannabinoids by Cytochrome P450s

The present inventors have demonstrated that cannabinoids can be functionalized in an in vivo plant system. Specifically, the present inventors utilized cytochrome P450 monooxygenases (CYP) to modify or functionalize the chemical structure of cannabinoids. As shown below, CYPs do this by inserting an oxygen atom into hydrophobic molecules to make them more reactive and hydrophilic. A representative reaction may include the generalized reaction in FIG. 13.

Figure 5:
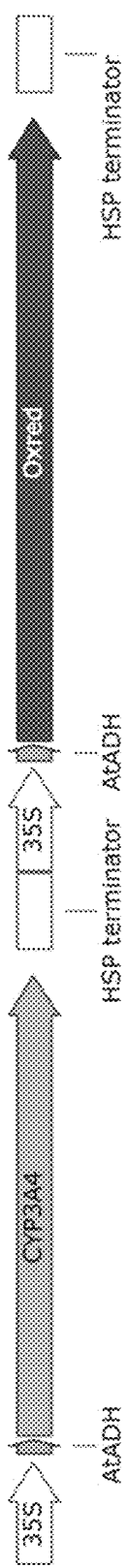
FIG. 5. Gene construct for expression of cytochrome P450 (CYP3A4) gene, (SEQ ID NO. 1), expressing the cytochrome P450 (CYP3A4) protein (SEQ ID NO. 2) and P450 oxidoreductase gene (oxred) (SEQ ID NO. 3) expressing the P450 oxidoreductase protein (SEQ ID NO. 4), in plants. Both genes were driven by the constitutive 35S promoter (35S) and featured 5' untranslated regions from Arabidopsis thaliana alcohol dehydrogenase (AtADH) as translational enhancers.

The P450 enzyme system involves several cytochrome P450 species and nonspecific cytochrome P450 oxidoreductases. As shown in FIG. 5, the present inventors used a human cytochrome P450 (CYP3A4) in a double construct with an exemplary human cytochrome P450 oxidoreductase, both expressed under the control of the constitutive CaMV 35S promoter with 5' untranslated regions to enhance translation. Protein and DNA sequences for the functionalization of cannabinoids (CYP3A4 and P450 oxidoreductase) are identified as SEQ ID NO's. 1-4. Expression was confirmed using RT-PCR utilizing the forward and reverse primers identified in Table 3 below. As noted above, the present inventors demonstrated that overexpressing of P450s generated functionalized cannabinoids which could then be glycosylated, rendering them water-soluble.

Figure 6:
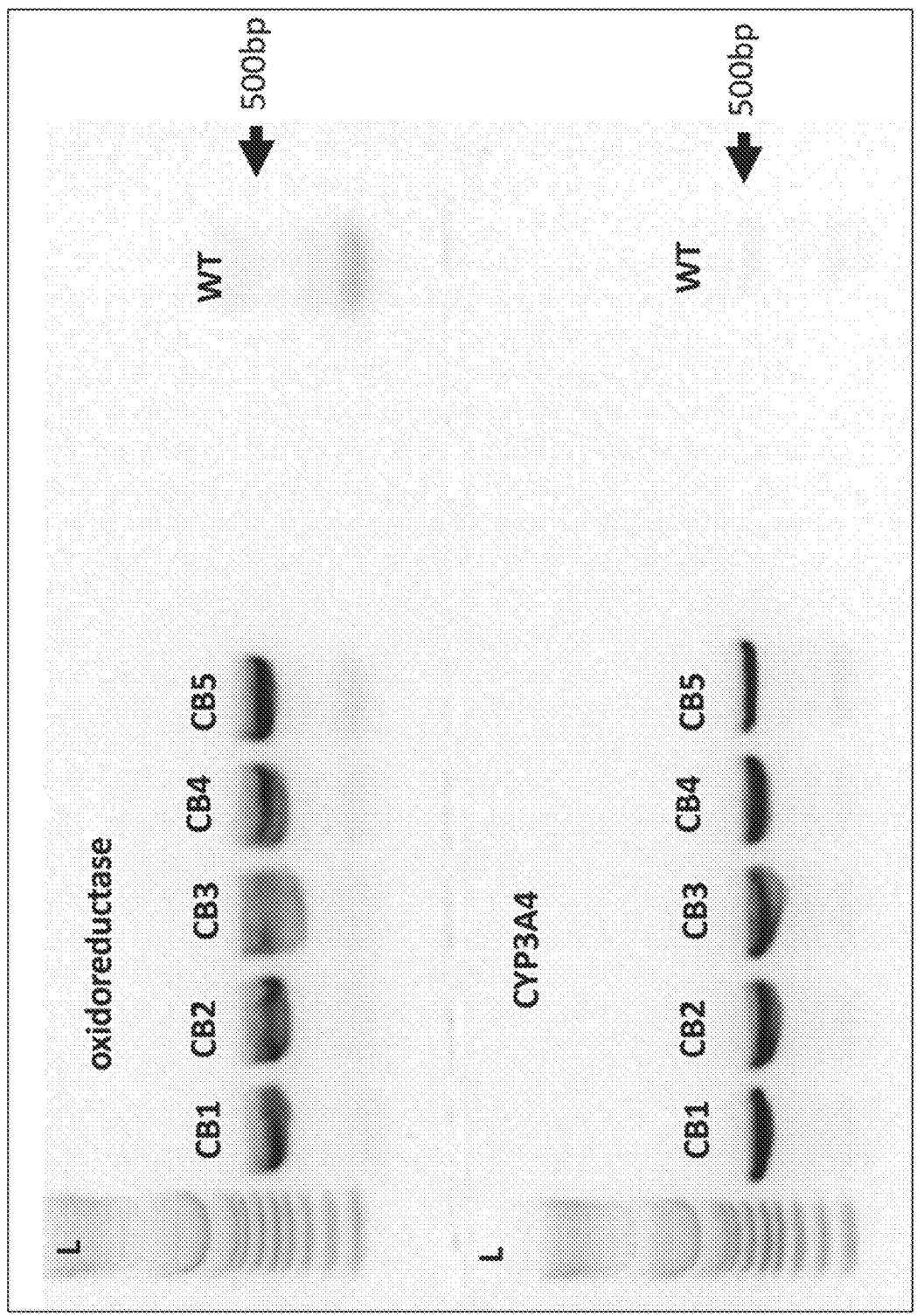
FIG. 6. Confirmation of expression of CYP3A4 and P450 oxidoreductase in tobacco leaves. CB1-CBS, biological replicates of leaves infiltrated with the CYP3A4/P450 oxidoreductase; WT=wild type tobacco leaves with no infiltration. L=1 kb plus ladder (Thermo Fisher Scientific, USA). The arrows show the expected (500 bp) band indicating expression of the transgene.

Example 2: P450 Overexpression Enhances In Vivo Hydroxylation and Glycosylation of Cannabinoids in Plant Systems The present inventors have demonstrated that overexpression enhanced in vivo hydroxylation and glycosylation of CBDA in an exemplary plant system. Specifically, as generally shown in FIG. 6, the present inventors demonstrate that infiltration of tobacco leaves with *Agrobacterium* carrying CYP3A4 and P450 oxidoreductase was accomplished as described in herein. Confirmation of expression was done using RT-PCR 2-3 days after infiltration (FIG. 6).

Figure 7:
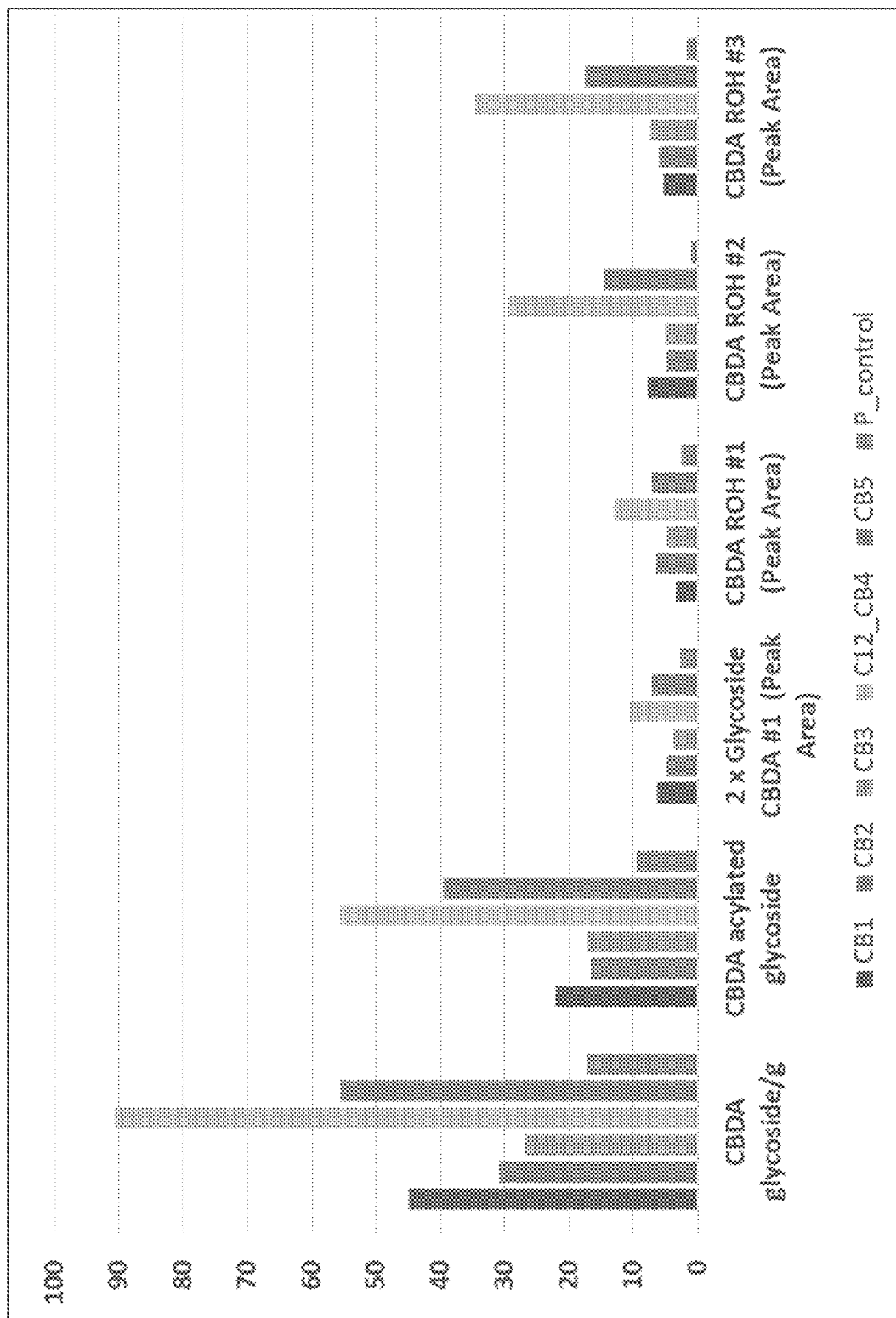
FIG. 7. Enhanced glycosylation of cannabinoids in P450-over expressing N. benthamiana plants. CB1-CB5 are biological reps overexpressing CYP3A4+P450 oxidoreductase, P control is the P19 silencing suppressor ('empty vector' control). Vertical axis shows relative amounts expressed as peak area per g fresh weight.

As generally shown in FIG. 7, the present inventors demonstrate that overexpression of the CYP3A4+P450 oxidoreductase construct and subsequent feeding of at least one cannabinoid, in this case CBDA, upon confirmation of expression resulted in in vivo glycosylation of CBDA in tobacco leaves (FIG. 7). On average, glycosylation increased 3-fold in transgenic *N. benthamiana* plants compared to the control while hydroxylation increased up to 13-fold. As such, in certain embodiment, tobacco glycosyltransferases may be utilized as key targets in the current inventive technology for glycosylation of cannabinoids.

Example 3: Identification of Modified Water-Soluble Cannabinoids by Mass Spectrometry The present inventors demonstrated the biosynthesis of modified functionalized as well as water-soluble cannabinoids in both in vitro as well as in vivo plant system. Specifically, the present inventors identified the cannabinoid biotransformations associated with the gene constructs in both in vitro assays and transient leaf expression. Through the use of accurate mass spectrometry measurements, the present inventors were able to identify and confirm the biosynthesis of modified water-soluble cannabinoids.

Specifically, as generally shown in FIGS. 1-4, the present inventors were able to identify the glycosylated water-soluble cannabinoids in the chromatographic analysis and were able to produce extracted ion chromatograms for peak integration. For example, FIG. 1 panel B, illustrates the identification of multiple constitutional cannabinoid isomers of a single glycoside moiety, while in FIG. 2 panel B, an example of multiple constitutional isomers of the cytochrome P450 oxidation are illustrated. Peak areas for each identified molecule were used for relative quantification between treatments. Based on these results we confirmed biosynthesis of modified cannabinoid molecules containing up to two glycosides moieties, O acetyl glycoside, as well as hydroxylation (R—OH) biotransformations. Summaries of those identifications are presented in FIGS. 36 and 37 for CBGA and CBDA respectively.

Tables 1 and 2 are provided below further demonstrating the production of the select modified cannabinoid molecules. Generally referring to Tables 1-2 below, the present inventors demonstrated that based on the reduced retention time in the water: acetonitrile HPLC gradient, the glycosylated and hydroxylated cannabinoids, which eluted earlier than their non-modified forms, are demonstrated to be more water soluble than their non-modified forms.

Figure 8:
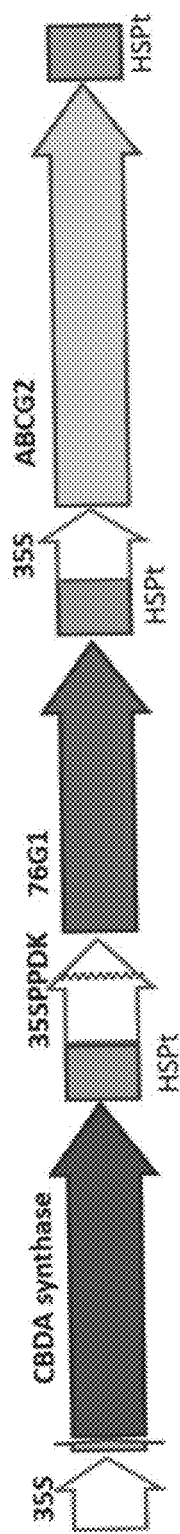
FIG. 8. Gene construct for the cytosol and suspension culture cannabinoid production system. 35S, Cauliflower mosaic 35S promoter; HSPt, HSP terminator; 35PPDK, hybrid promoter consisting of the cauliflower mosaic virus 35S enhancer fused to the maize C4PPDK basal promoter (Yoo et al. 2007); 76G1, UDP glycosyltransferase from Stevia rebaudiana; ABCG2, human multi-drug transporter.

Example 4: Generation of Heterologous Cytosolic Synthesis and Glycosylation Gene Constructs for Expressions in Tobacco Leaves and Cell Suspensions As shown in FIG. 8, the present inventors generated a triple gene construct for expression of cannabidiolic acid (CBDA) synthase in which the trichome targeting sequence had been removed, and the glycosyltransferase 76G1 from *Stevia rebaudiana*. In this construct the multi-drug ABC transporter ABCG2 was also included.

In one embodiment of the present inventive technology, the gene construct may be used to transform a plant cell that may further be configured to be cultured in a suspension culture. In one preferred embodiment, a *cannabis* cell may be transformed with the construct generally outline in FIG. 8. In this preferred embodiment, cannabinoids produced by the *cannabis* cells in the cell culture may be functionalize through the overexpression of the CYP3A4+P450 oxidoreductase as described above, and further glycosylated by the expression and action of the heterologous UDP glycosyltransferase (76G1) from *Stevia rebaudiana* referend above. Moreover, as generally outline herein, the cannabinoids may be modified so as to be functionalized and/or glycosylated, or generally water-soluble, and may then be secreted into the cell wall area, in the case of a whole plant, or the surrounding media in suspension cultures, with the aid of the ABC transporter. In one embodiment, this construct may be used for synthesis and modification of cannabinoids in cell suspension cultures, utilizing tobacco bright yellow cells or *cannabis* cells.

Figure 9:
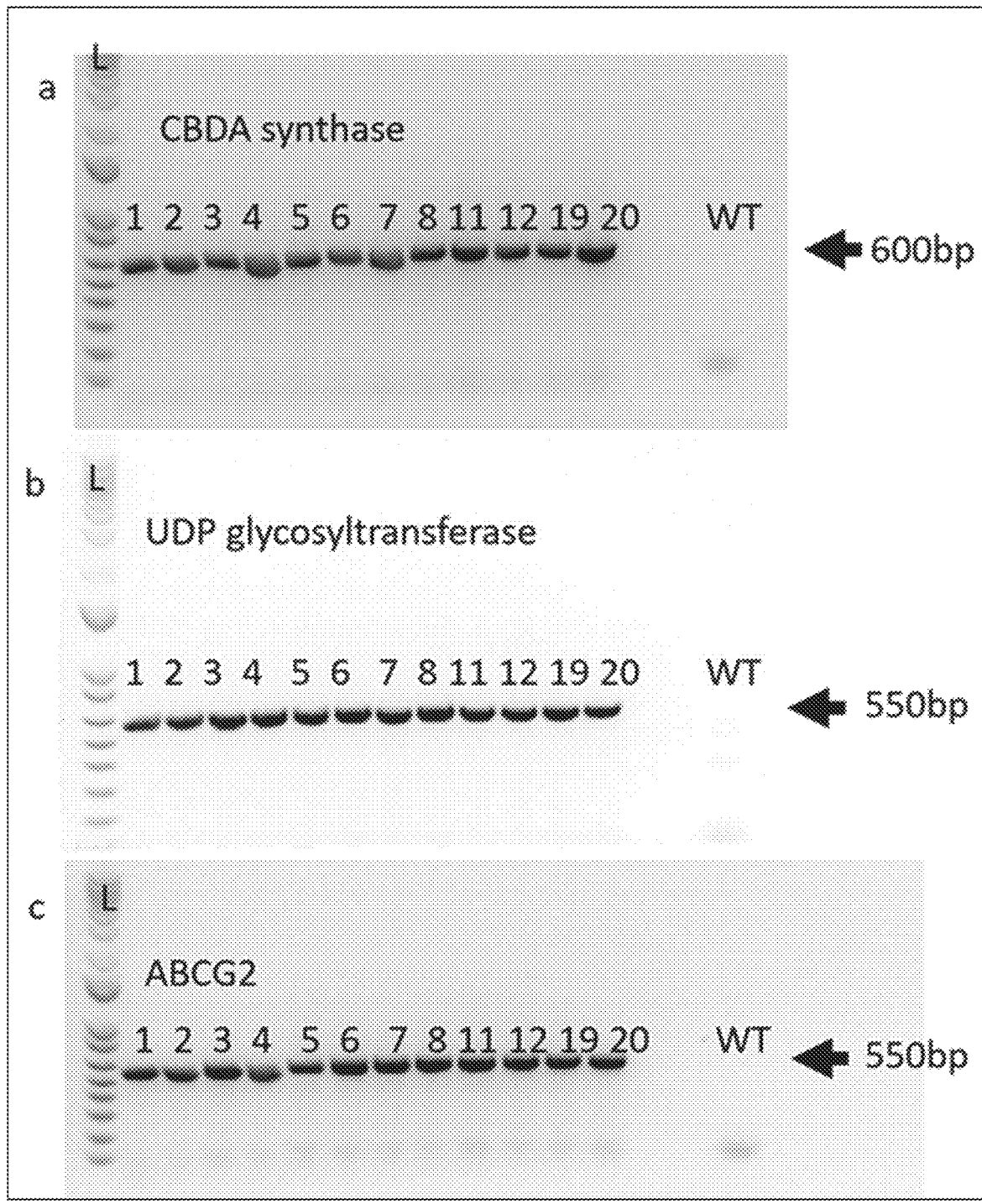
FIG. 9. Demonstrates RT-PCR confirmation of expression of CBDA synthase (a), UDP glycosyltransferase (b) and ABCG2 (c) in tobacco leaf cells. L is the 1 kb plus ladder (Thermo Fisher Scientific, USA). Numbers on the lanes represent independent transgenic lines. The arrows point to the expected band that shows expression of the transgene.

As generally shown in FIG. 9, in vivo expression of CBDA synthase, UDP glycosyltransferase 76G1 and ABCG2 was confirmed. Reverse and forward primers used in the RT-PCR reactions are provided below in Table 4 below.

The gene and protein sequence identifications for CBDA synthase are provided as SEQ ID NO's 5 and 6 respectively. It should be noted that a variety of cannabinoid synthase genes/proteins may be used with the current inventive technology, CBDA synthase being exemplary only. Indeed, it is specifically contemplated that the synthase enzyme associated with any of the cannabinoids identified herein may be incorporated into the current invention without undue experimentation. In one embodiment, one or more of such exogenous or endogenous synthase enzyme may further have the trichome targeting sequence excised, again, a step that can be readily accomplished without undue experimentation. Example may THCA synthase, CBG synthase, THCA synthase, CBDA synthase or CBCA synthase, which may in this embodiment have their trichome targeting sequence had been removed.

The gene and protein sequence identifications for glycosyltransferase 76G1 from *Stevia rebaudiana* are provided as SEQ ID NO's. 7, and 8 respectively. The gene and protein sequence identifications for the multi-drug ABC transporter ABCG2 are provided as SEQ ID NO's 9 and 10 respectively.

Figure 10:
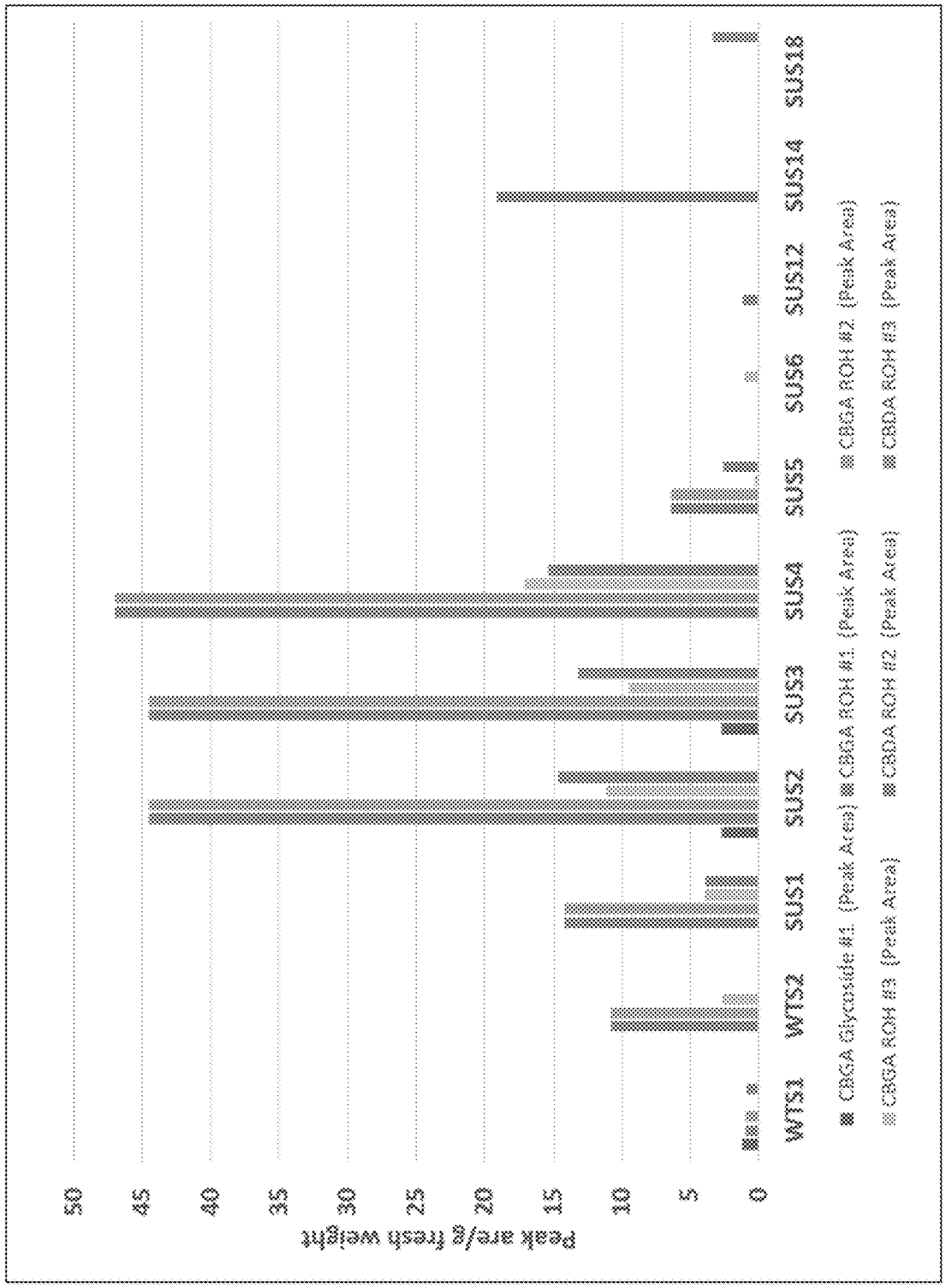
FIG. 10. Hydroxylation and glycosylation of cannabinoids in transgenic tobacco (SUS, numbered) overexpressing CBDA synthase, UDP glycosyltransferase and ABC transporter. WTS1 and 2 are wild type fed with substrate for endogenous reactions. There was some endogenous glycosylation of CBGA, as well as evidence for enhanced transgenic glycosyltransferase activity (e.g. SUS2, SUS3 and SUS4). The data has been corrected to peak area per g fresh weight.

Example 5: In Vivo Cytosolic Synthesis and Glycosylation of Cannabinoids in *N. benthamiana* Leaves and Cell Suspensions As shown in FIG. 10, the present inventors demonstrate that in plants, in this embodiment *N. benthamiana*, expressing the above referenced cytosolic construct, glycosylation of CBGA occurred as well as formation of modified or hydroxylated CBDA. The glycosylation of CBGA evidences in vivo glycosylation of cannabinoids by overexpressing a glycosyltransferase in *N. benthamiana* plants. The presence of glycosylated cannabinoids in wild type plants suggests the presence of a strong glycosyltransferase in tobacco. As such, in one embodiment, over expression of a heterologous or homologous tobacco glycosyltransferase may expressed or overexpressed resulting in the enhanced in vivo biosynthesis of water-soluble cannabinoids in whole plants, as well as in suspension cultures. For example, in one embodiment, a heterologous tobacco glycosyltransferase may be expressed in a *cannabis* plant or cell culture resulting in the in vivo biosynthesis of water-soluble cannabinoids in the *Cannabis* plant and/or a *Cannabis* suspension cultures.

Figure 27:
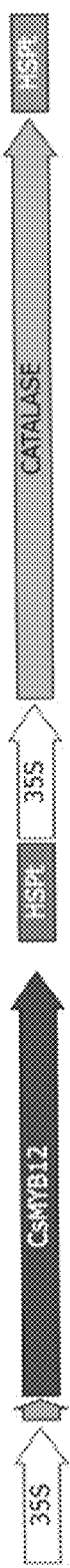
FIG. 27. Gene construct used to boost cannabinoid production and mitigate toxicity. CsMYB12, predicted *Cannabis sativa* MYB transcription factor for enhancing flavonol biosynthesis; HSPt, efficient transcription terminator from the *Arabidopsis thaliana* heat shock protein 18.2 gene; 35S, constitutive promoter from cauliflower mosaic virus; Catalase, *Arabidopsis thaliana* catalase gene.
Figure 28:
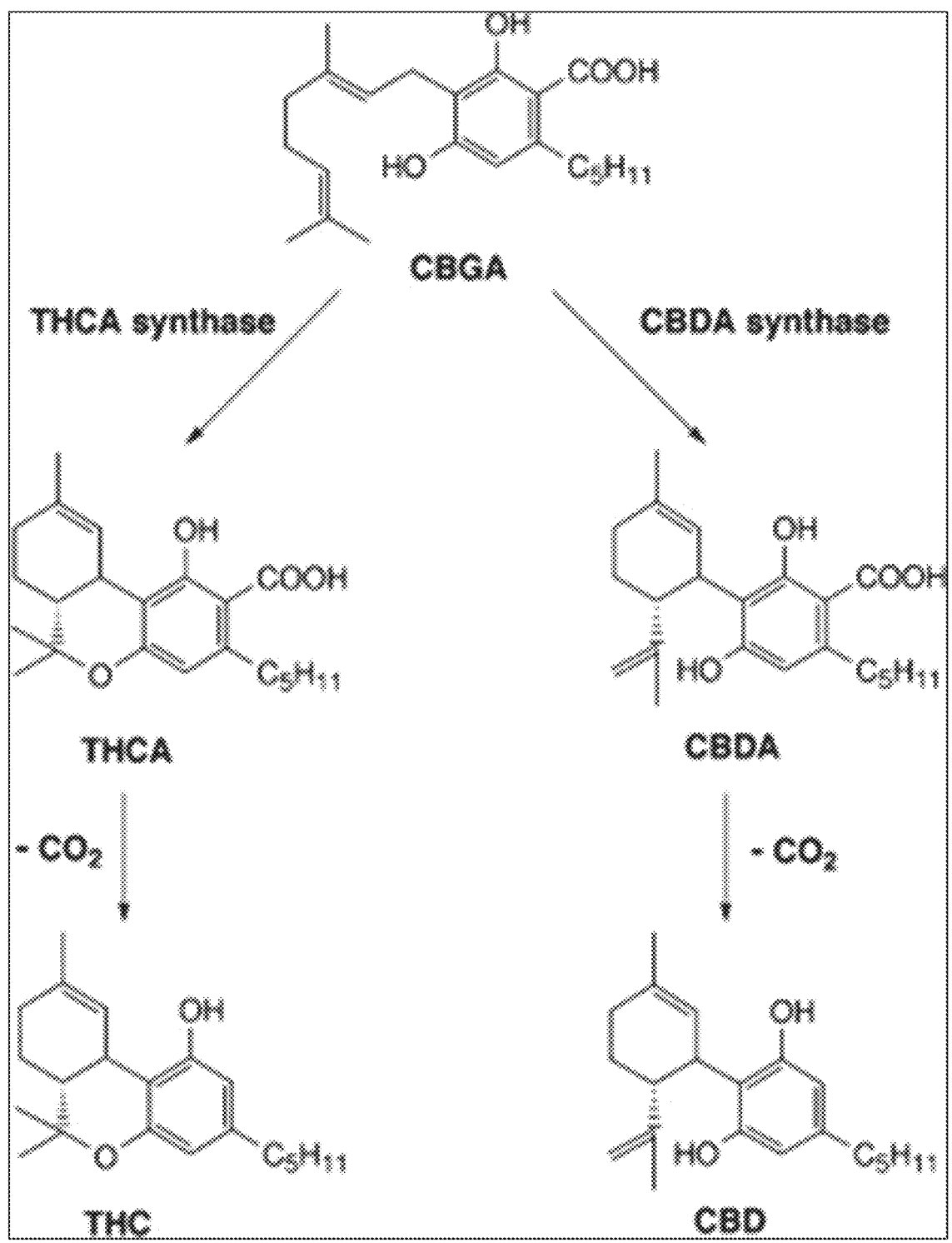
FIG. 28. Synthesis of THC and CBD from common precursor CBGA.
Figure 29:
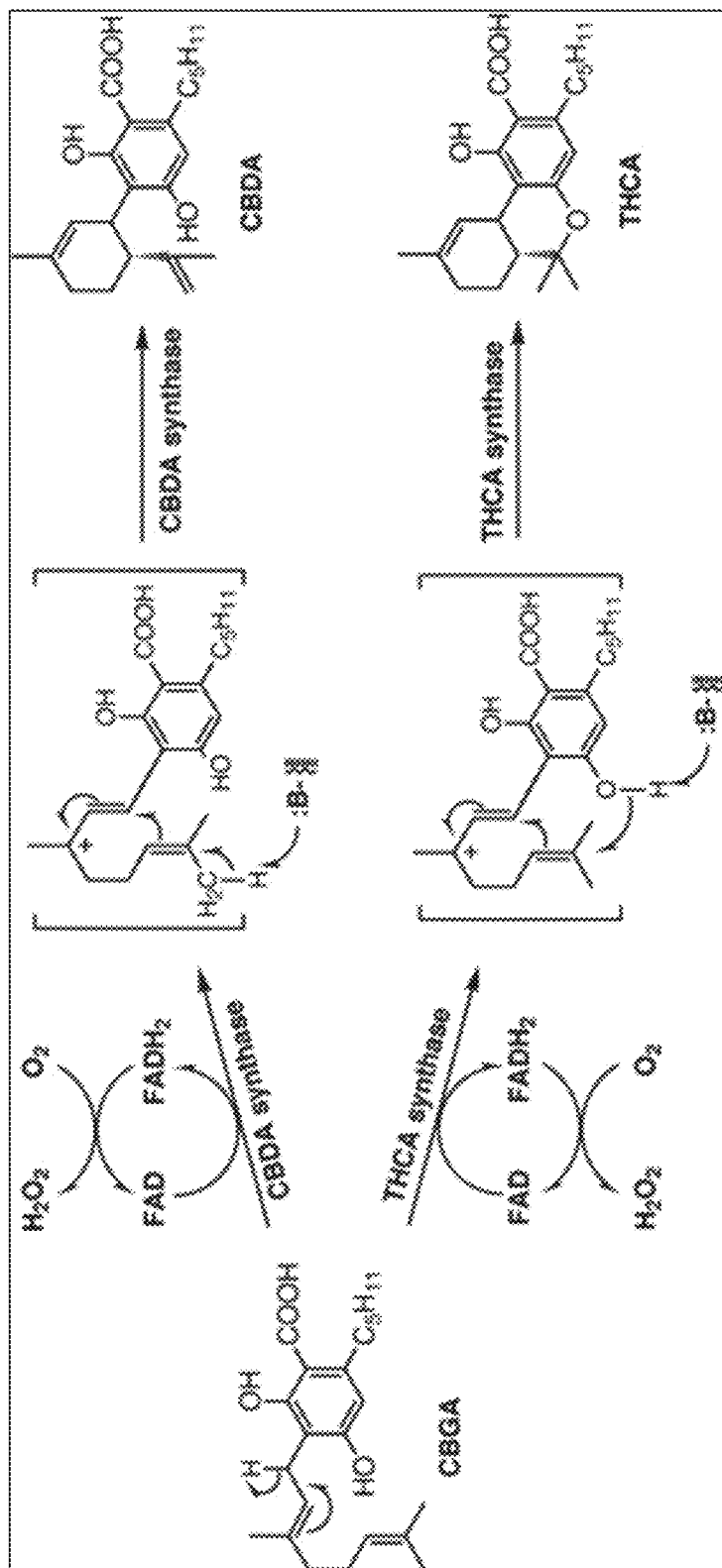
FIG. 29. Generation of hydrogen peroxide during cannabinoid biosynthesis.

Example 6: Water Soluble Cannabinoid Production Systems Utilizing MTB Transcription Factor and/or Catalase The present inventors have developed a plurality of systems for the biosynthesis and modification of cannabinoids based on cellular location using novel methods of protein targeting. As shown in Table 10, the present inventors designed such novel systems and methods to enhance production and modification (glycosylation, acetylation and functionalization) of cannabinoids as well as to mitigate toxicity resulting from cannabinoid accumulation. Certain embodiments, included the expression of a MYB transcription factor and a catalase (FIG. 27) to degrade hydrogen peroxide resulting from CBDA synthase activity. In one preferred embodiment, the present inventors used *Arabidopsis thaliana* or an *E. coli* catalase gene and a predicted *Cannabis* MYB transcription factor involved in elevating genes involved in cannabinoid biosynthesis. DNA and protein sequences for *Cannabis* predicted MYB transcription factor (SEQ ID NOs. 11-12, DNA and amino acid sequences respectively), *Arabidopsis thaliana* catalase SEQ ID NOs. 13-14, DNA and amino acid sequences respectively) and/or *E. coli* catalase (SEQ ID NO. 15-16, DNA and amino acid sequences).

Figure 11:
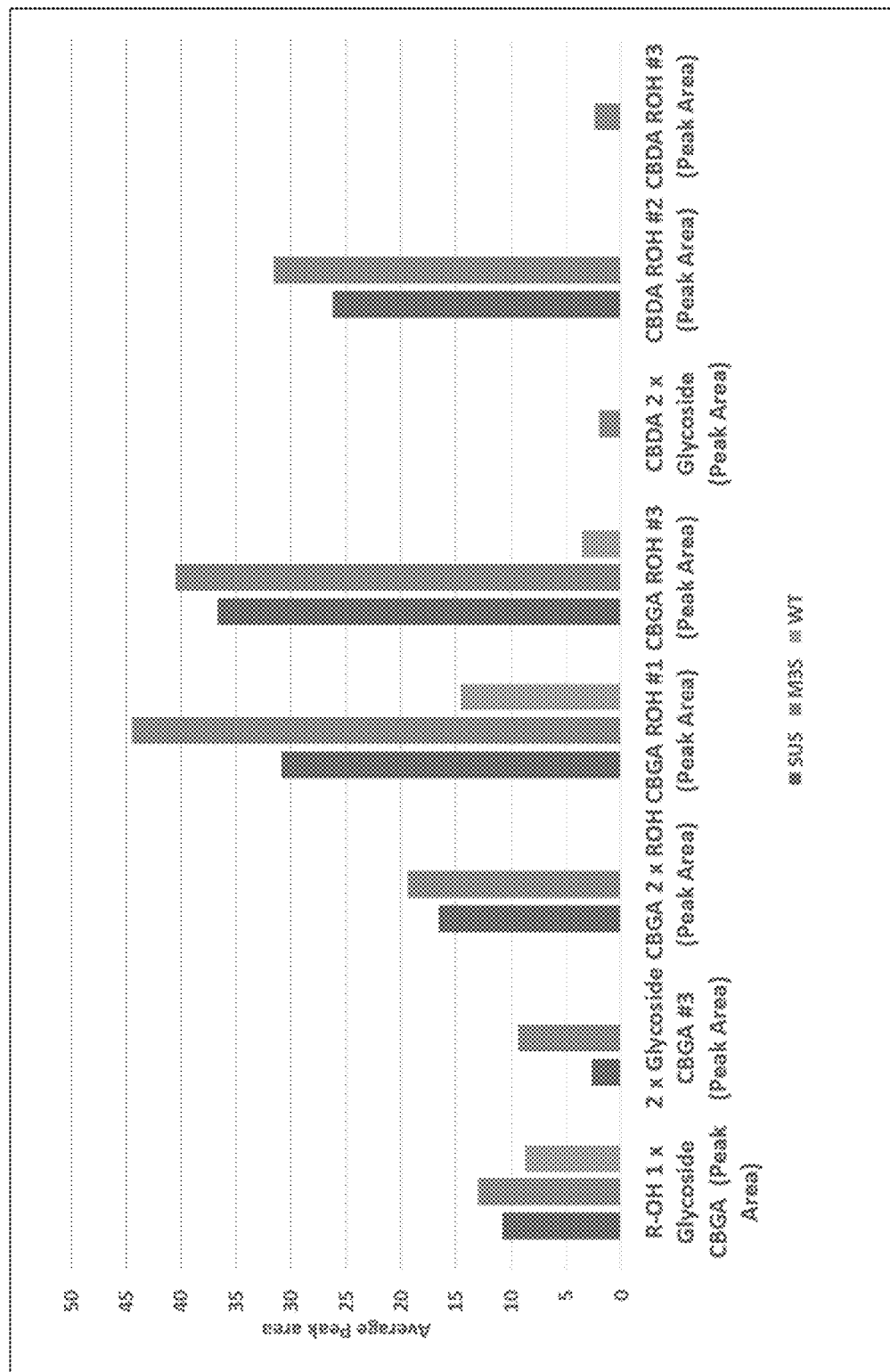
FIG. 11. Enhanced modification of cannabinoids in transgenic N. benthamiana plants co-infected with constructs for glycosylation, P450-mediated functionalization (hydroxylation) and detoxification of hydrogen peroxide by catalase. SUS=construct for overexpressing CBDA synthase, UDP glycosyltransferase and ABC transporter; M3S=construct for overexpressing CBDA synthase, UDP glycosyltransferase and ABC transporter with Cannabis MYB12-like and Arabidopsis thaliana catalase.

Example 7: Enhanced In Vivo Cytosolic Synthesis and Glycosylation of Cannabinoids in Tobacco Leaves and Cell Suspensions The present inventors have demonstrated the enhanced in vivo modification of cannabinoids in transgenic plants co-infected with constructs for glycosylation, P450-mediated functionalization (hydroxylation) and detoxification of hydrogen peroxide by catalase. As further shown in FIG. 11, functionalization and glycosylation, mainly of the substrate CBGA was observed in transgenic tobacco plants overexpressing CBDA synthase, UDP glycosyltransferase and ABC transporter but increased when overexpression of this construct was coupled with cytochrome P450, MYB transcription factor and catalase. As previously noted, overexpression of a cytochrome P450 enhanced glycosylation of cannabinoids. As such, the present inventor demonstrated the formation and glycosylation of CBDA in vivo in transiently transformed tobacco leaves fed with the precursor CBGA.

Figure 12:
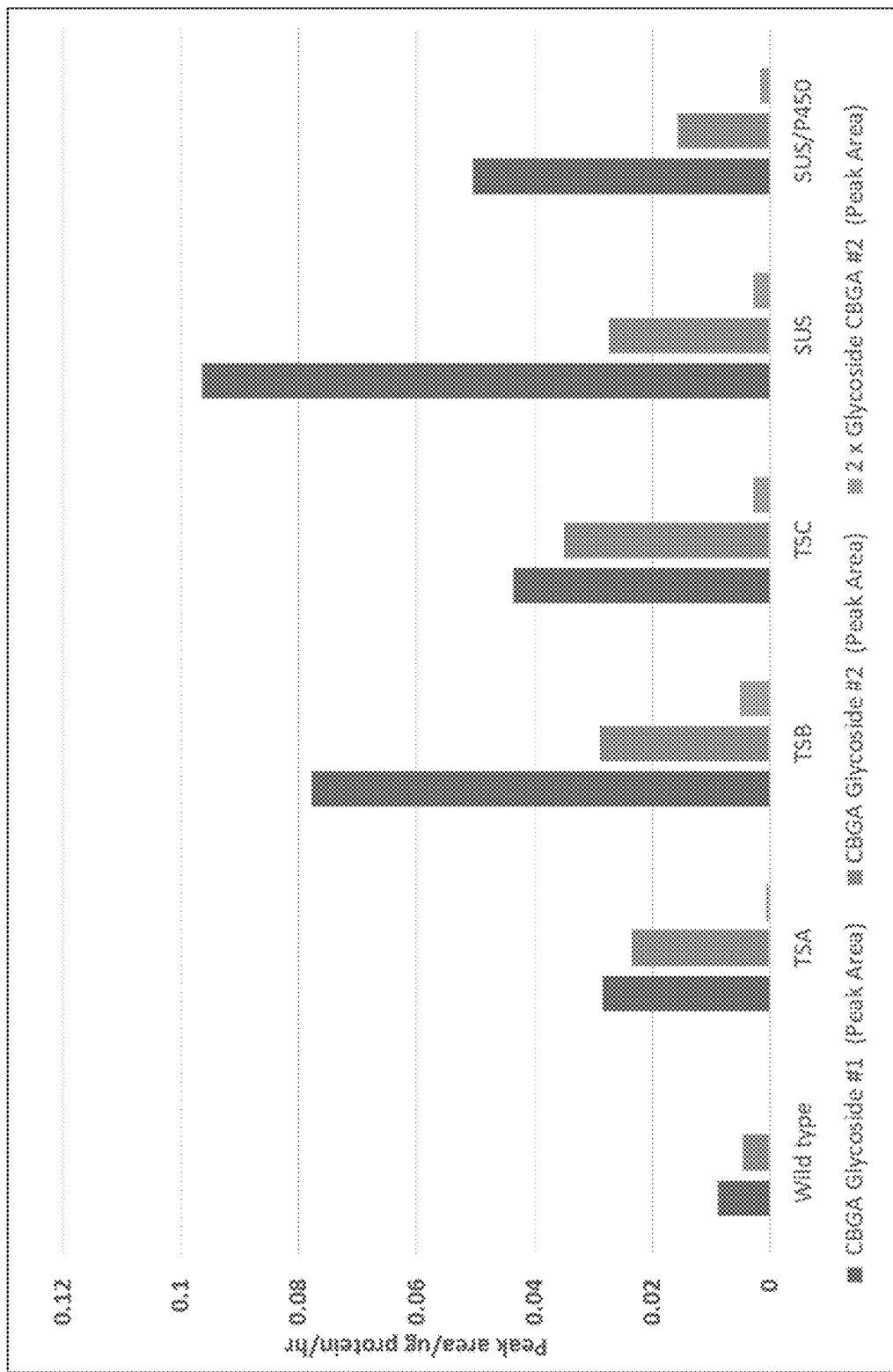
FIG. 12. Increased glycosylation activity in transgenic N. benthamiana plants (TSA, TSB, TSC, SUS, SUS/P450) overexpressing a glycosyltransferase compared to wild type in 14-hour transient expression assays.

The present inventors also compared the activities of endogenous and transgenic glycosyltransferase activities in tobacco. Specifically, as shown in FIG. 12, the present inventor performed in vitro assays of UDP glycosyltransferase and CBDA synthase. Short assays of 3 hours at 30° C. did not reveal any difference in glycosylation of CBGA between the wild type and transgenic *N. benthamiana* plants, suggesting endogenous glycosylation. In extended assays (14 hours), there was a significant difference in the detection of glycosylated CBGA in transgenic plants compared to the wild type demonstrating increased glycosylation activity in transgenic plants.

In certain embodiment, glycosyltransferases from tobacco, or other plants may be used as herein described. In one embodiment, one or more heterologous or homologous glycosyltransferases may be expressed or over expressed in a plant, such as tobacco or *Cannabis*. Gene and protein sequences for exemplary glycosyltransferases are identified below in Table 9.

Example 8: Generation of Trichome-Targeted Cannabinoid Synthesis and Glycosylation Constructs of Cannabidiolic Acid (CBDA)

Figure 14:
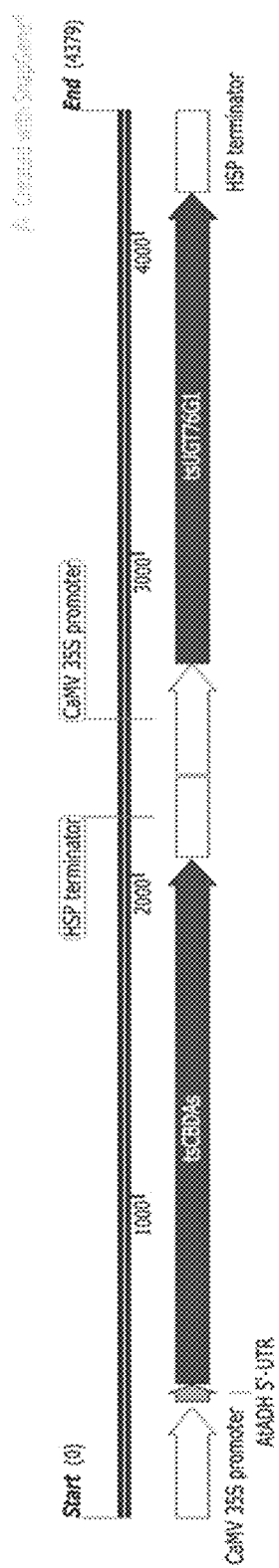
FIG. 14. Gene construct 1 for the trichome cannabinoid production system. Cauliflower mosaic 35S promoter; AtADH 5'-UTR, translation enhancer element (Matsui et al. 2012); tsCBDAs, cannabidiolic acid synthase with its original trichome target sequence; HSP terminator; tsUGT76G1, UDP glycosyltransferase from Stevia rebaudiana with CBDAs trichome target sequence.
Figure 15:
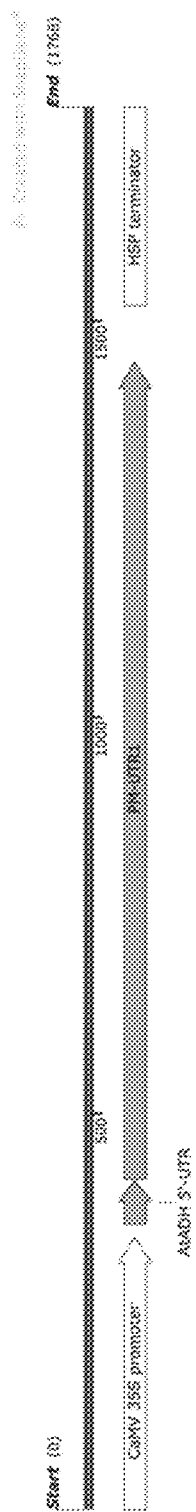
FIG. 15. Gene construct 2 for the trichome cannabinoid production system. Cauliflower mosaic 35S promoter; AtADH 5'-UTR, enhancer element; PM-UTR1, Arabidopsis thaliana UDP-glucose/galactose transporter targeted to the plasma membrane; HSP terminator.

As shown in FIGS. 14-15, the present inventors demonstrated a system of trichome-targeted synthesis and synthesis and glycosylation of cannabinoid compounds, such as CBDA.

By targeting CBDA synthase, a UDP-glucose/UDP-galactose transporter (PM-UTR1) targeted to the plasma, and a *Stevia* UDP-glycosyltransferase 76G1 (tsUGT) to the trichomes, these genes may produce and accumulate, in this case CBDA and its glycosylated derivatives (primary, secondary glycoside), as well as novel CBDA derivatives, in the trichomes.

SEQ ID NO. 17 is identified as the polynucleotide gene sequence for a CBDA synthase having a trichome targeting sequence. SEQ ID NO. 18 is identified as the corresponding protein sequence for a CBDA synthase having a trichome targeting domain.

SEQ ID NO. 19 is identified as the polynucleotide gene sequence for a trichome-targeted UDP-glycosyltransferase (76G1) coding sequence, in this instance being optimized for *Arabidopsis thaliana* expression, although other codon optimized versions fall within the scope of this invention. SEQ ID NO. 20 is identified as the corresponding protein sequence for a UDP-glycosyltransferase (76G1) having a trichome targeting domain.

SEQ ID NO. 21 is identified as the polynucleotide gene sequence for a UDP-glucose/galactose transporter (UTR1) having a plasma-membrane targeting sequence.

Example 9: Trichome-Targeted Synthesis and Glycosylation of Cannabidiolic Acid (CBDA)

Figure 16:
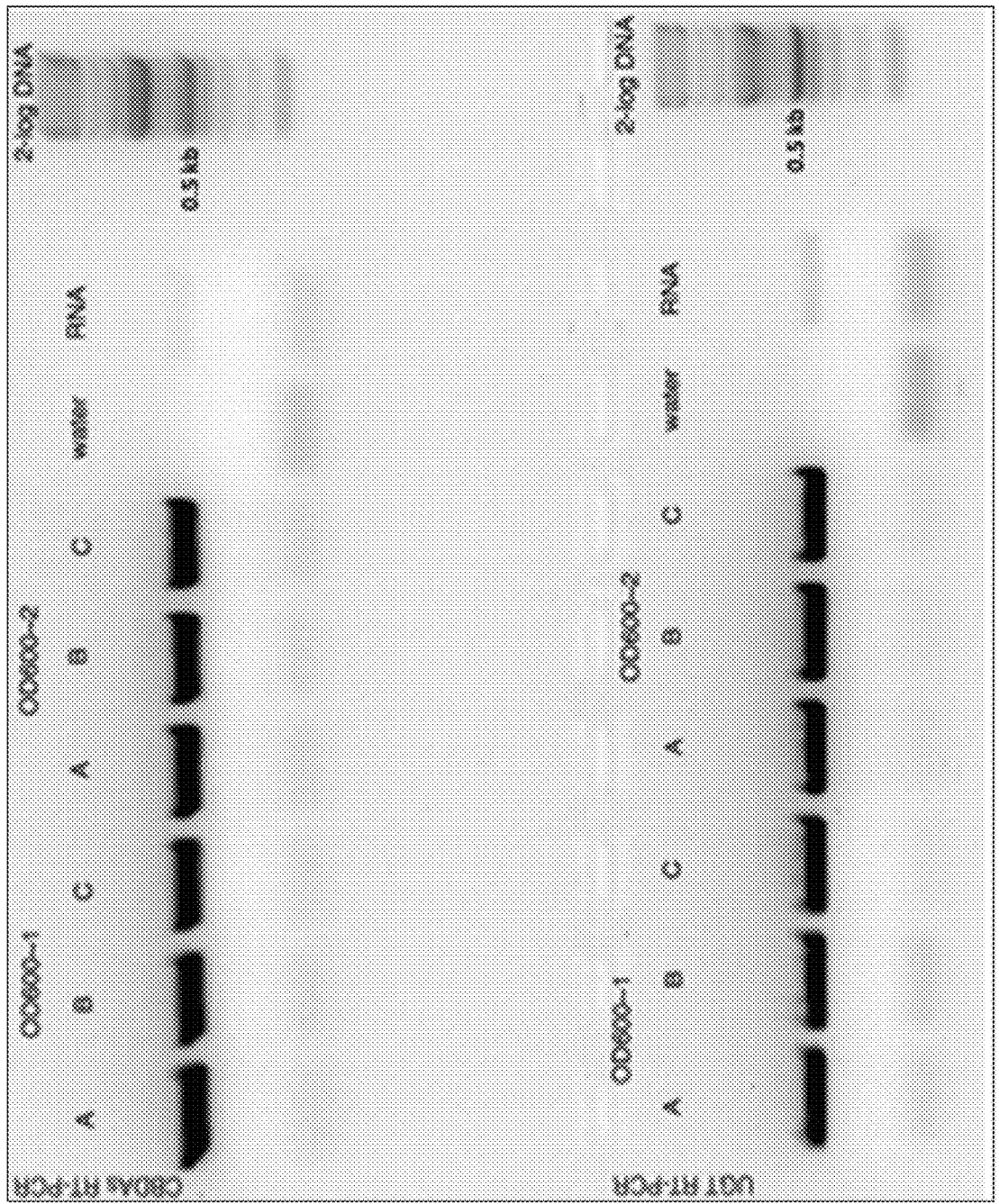
FIG. 16. Trichome-targeted CBDA synthase RT-PCR (top), Trichome-targeted UDP glycosyltransferase (76G1) UGT RT-PCR (bottom). A, B, and C are biological replicates collected after 2 DPI.
Figure 17:
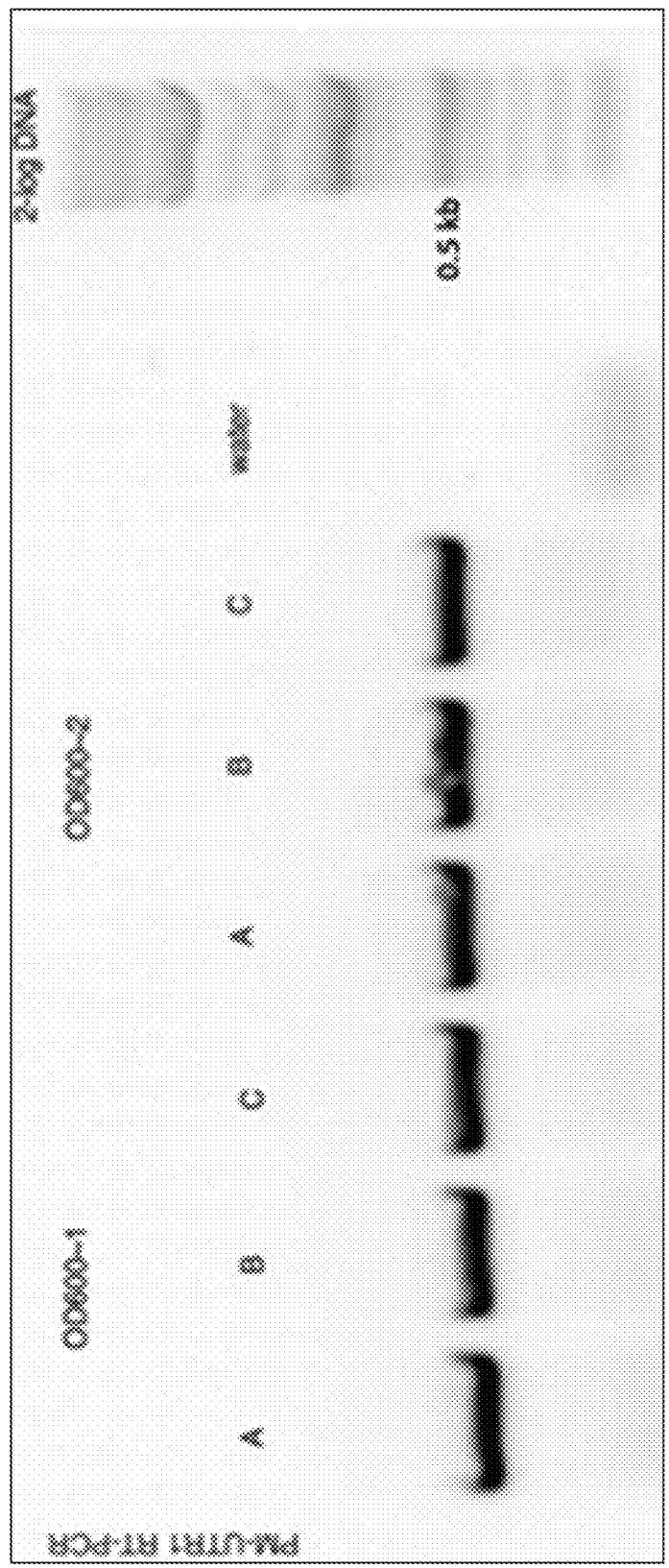
FIG. 17. PM-UTR1 RT-PCR. A, B, and C are biological replicates collected after 2 DPI.
Figure 19:
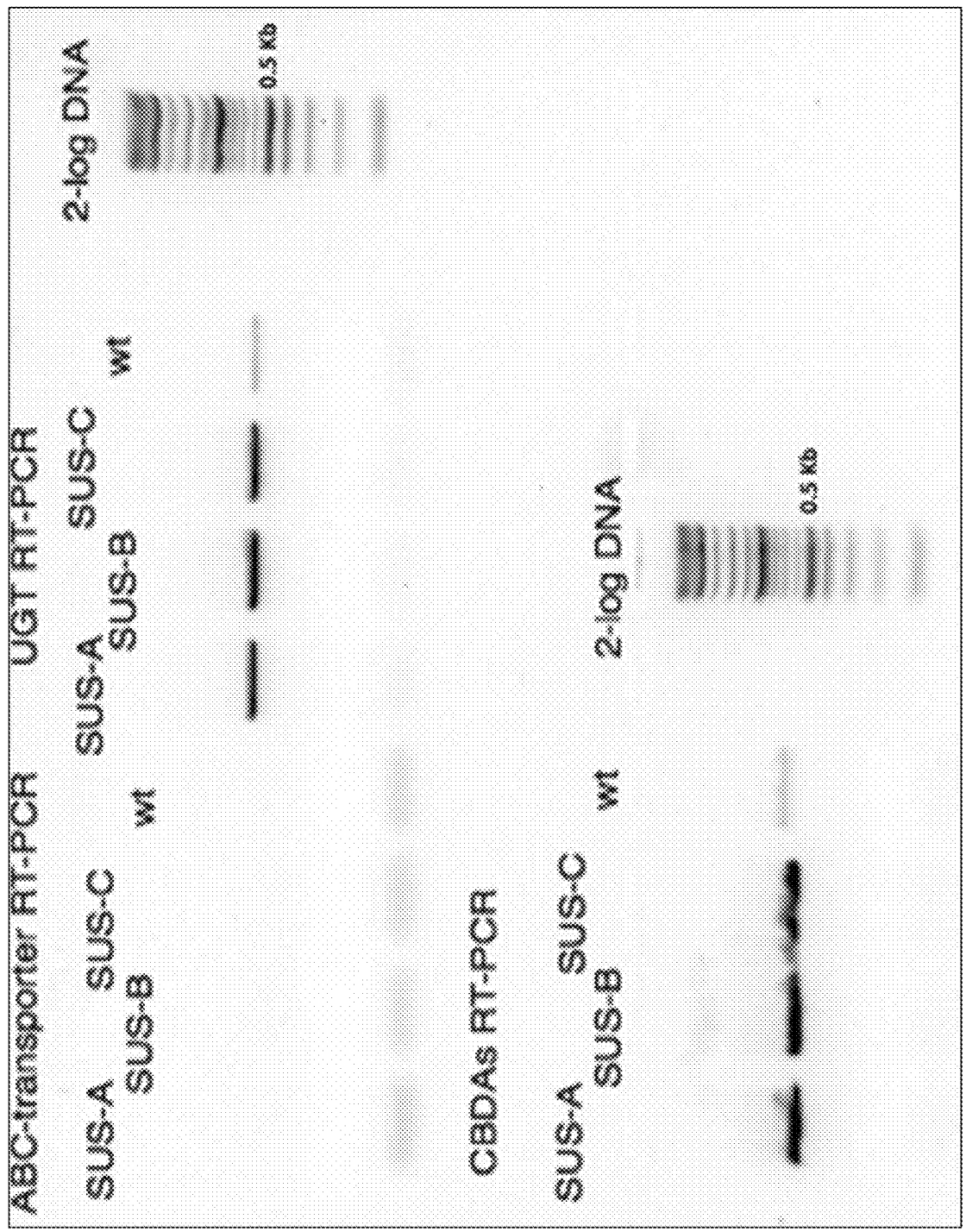
FIG. 19. SUS-A to SUS-C are biological replicates for the cell suspension (201-SUS) transformation after 1 DPI.
Figure 20:
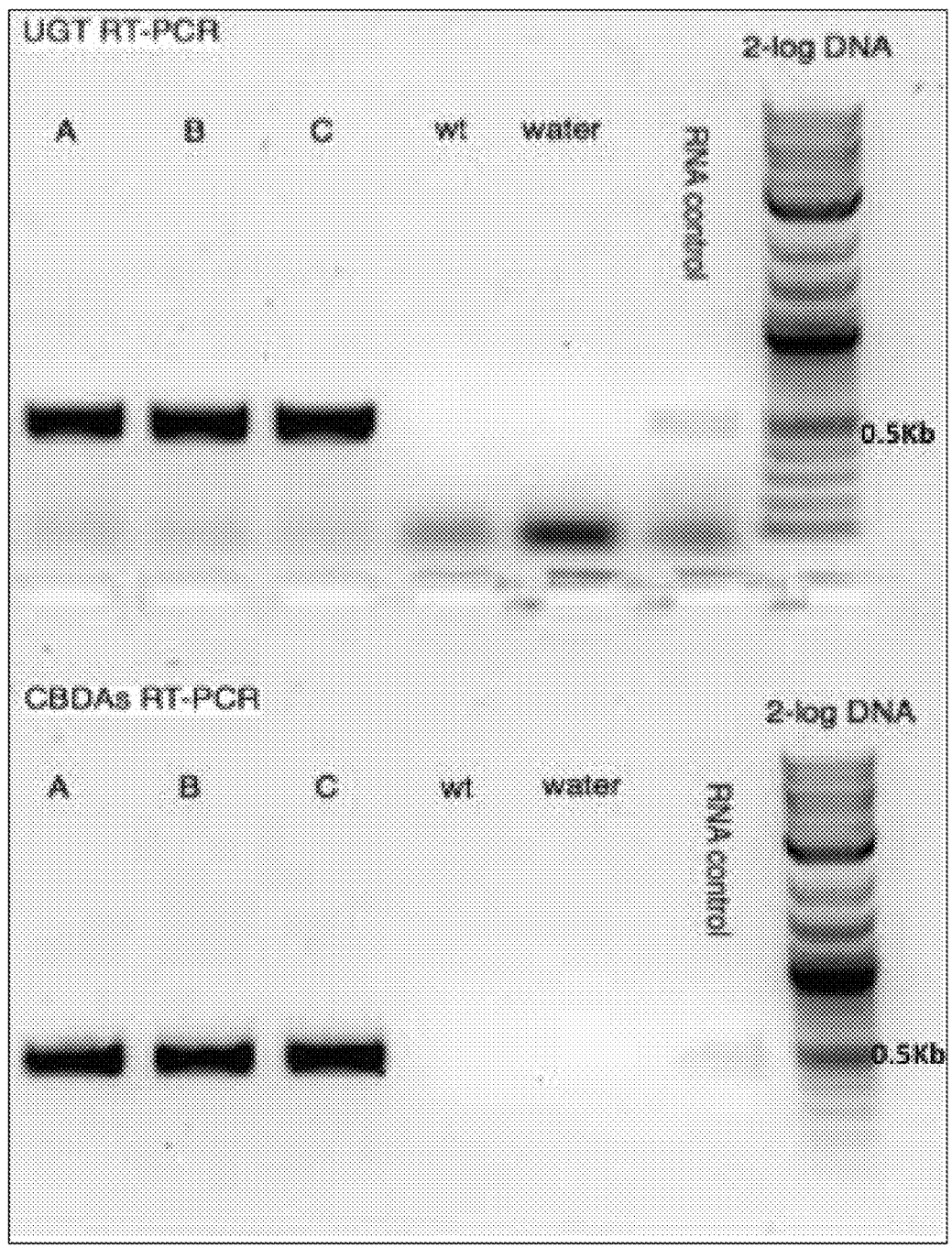
FIG. 20. cytUGT RT-PCR (top), cytCBDAs RT-PCR (bottom). A, B, and C are biological replicates for cytosolic construct infiltration after 2 DPI.

As shown in FIGS. 16-17, gene expression of CBDA synthase, tsUGT and PM-UTR1 in *N. benthamiana* infiltrated leaves was confirmed 2 DPI (Days Post Infiltration of *Agrobacterium* Ti-plasmid constructs) via RT-PCR (FIGS. 19 and 20). As expected, CBGA substrate was detected in all infiltrated leaves and wild type control (no *Agrobacterium* infiltration). CBGA primary and secondary glycosides were also detected in all infiltrated leaves and wild-type control, further demonstrating an endogenous glycosyltransferase activity acting upon CBGA. Moreover, CBGA acetylated primary glycoside was detected in all samples, including WT control, providing evidence of endogenous acetylation. CBDA was detected at marginal levels in samples infiltrated with both trichome and cell suspension constructs, but not in wild type plants.

Example 10: Cytosolic-Targeted Synthesis and Glycosylation of Cannabidiolic Acid (CBDA)

Figure 18:
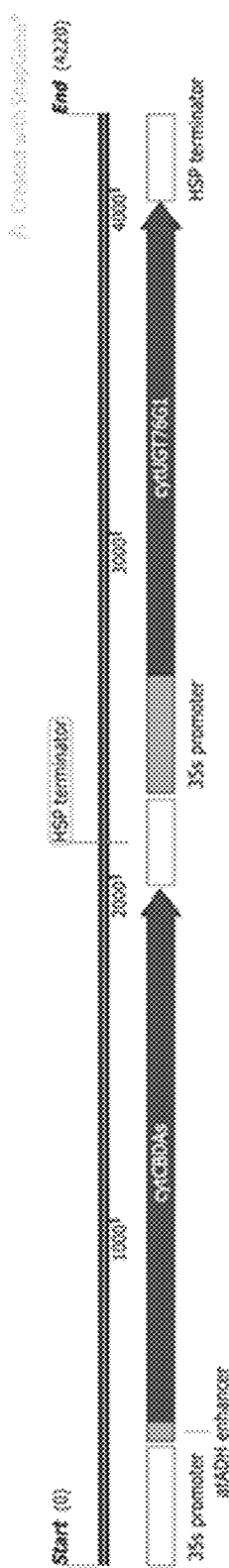
FIG. 18. Gene construct for the cytosolic cannabinoid production system. Cauliflower mosaic 35S promoter; AtADH 5'-UTR, enhancer element; cytCBDAs, cannabidiolic acid synthase with the trichome target sequence removed; HSP terminator; cytUGT76G1, UDP glycosyltransferase from Stevia rebaudiana.

The present inventors have demonstrated a system of cytosolic-targeted cannabinoid synthesis and glycosylation. By targeting or localizing, CBDA synthase (CBDAs) and UDP-glycosyltransferase 76G1 (UGT) to the cytosol, the present inventors demonstrated that plants expressing these heterologous genes produce and accumulate, in this embodiment, CBDA and its glycosylated derivatives (primary, secondary glycoside), as well as other CBDA derivatives, in the cytosol. As shown in FIG. 18, a gene expression vector for the cytosolic cannabinoid production system was generated. This construct included a cauliflower mosaic 35S promoter; AtADH 5'-UTR, enhancer element; cytCBDAs, cannabidiolic acid synthase with the trichome target sequence removed; HSP terminator; cytUGT76G1, UDP glycosyltransferase from *Stevia rebaudiana*.

SEQ ID NO. 22 is identified as the polynucleotide gene sequence for a, cannabidiolic acid synthase with the trichome target sequence removed (cytCBDAs). SEQ ID NO. 23 is identified as the corresponding protein sequence of cytCBDAs.

SEQ ID NO. 24 is identified as the polynucleotide gene sequence for a, Cytosolic-targeted UDP-glycosyltransferase (UGT76G1) coding sequence (optimized for *Arabidopsis thaliana* expression) (cytUGT76G1 or cytUTG). SEQ ID NO. 25 is identified as the corresponding protein sequence of cytUGT76G1 or cytUTG.

As an exemplary plant model, *N. benthamiana* plants were grown from seed and after 4 weeks of vegetative growth, leaves were co-infiltrated with *Agrobacterium tumefaciens* GV3101 carrying the following constructs: Cytosolic CBDAs+Cytosolic UGT in pRI201-AN or cell suspension construct, Myb/catalase in pRI201-AN, and p19 silencing suppressor in pDGB3alpha2. *Agrobacterium* density was normalized to 2 at absorbance of 600 nm using a spectrophotometer and cultures co-infiltrated in same ratio (1:1:1). After 2 and 4 days post-*Agrobacterium* infiltration (DPI), 1 mL CBGA (2.7 mM) dissolved in 0.1% Tween 20 (Sigma-Aldrich) or 0.1% Triton X-100 (Sigma-Aldrich) was infiltrated to each leaf. In a second embodiment using the cytosolic construct, 4 mM UDP-glucose was added to the CBGA media before feeding. Three biological replicates were used. RT-PCR primers are outlined in Table 5 below.

Figure 21:
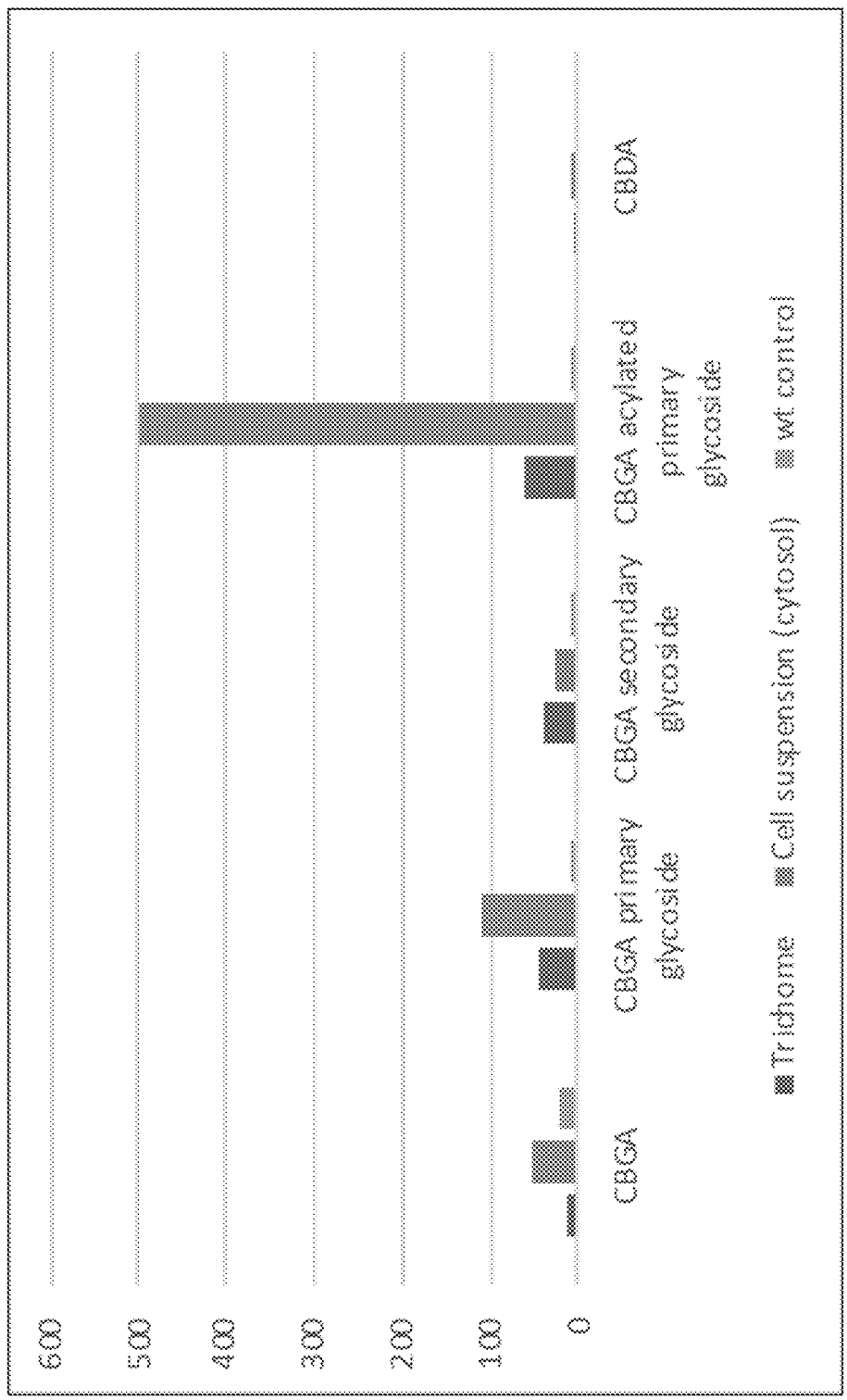
FIG. 21. Cannabinoid detection in leaves infiltrated with trichome or cell suspension constructs and fed with CBGA 2.7 mM. The color code refers to the target compartment for CBDAs and UGT76G1 protein accumulation, either trichome or cell suspension cytostol. Y-axis: CBGA and CBDA expressed as parts per million (ppm). Primary, secondary, and acetylated glycosides expressed as peak area.
Figure 22:
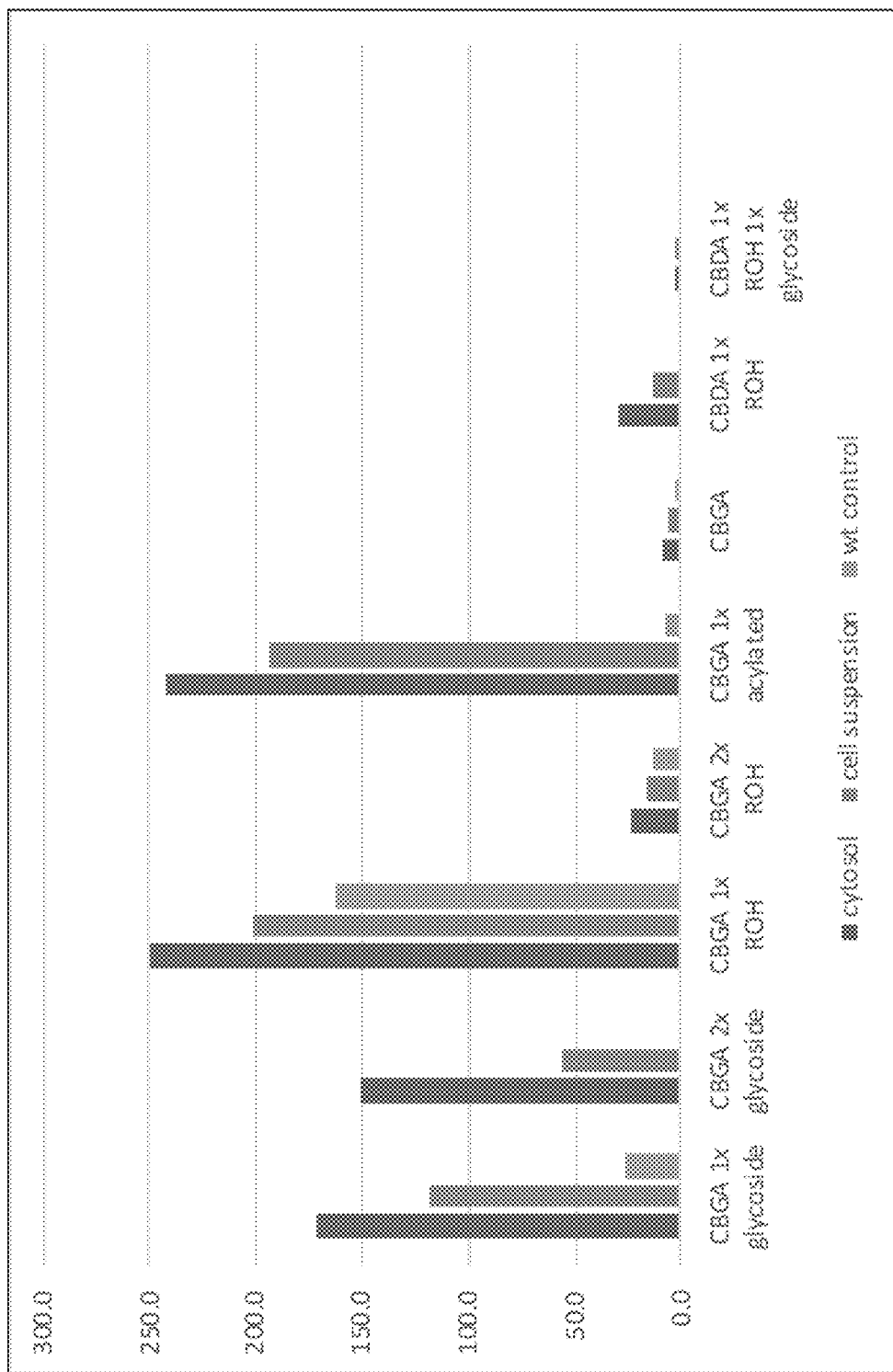
FIG. 22. Cannabinoid detection in leaves infiltrated with cytosolic or cell suspension construct and fed with CBGA 2.7 mM and UDP-glucose 4 mM. The color code refers to the target compartment for CBDAs and UGT76G1 protein accumulation. Y-axis: CBGA expressed as parts per million (ppm). All other cannabinoid derivatives expressed as peak area (no standards available).
Figure 23:
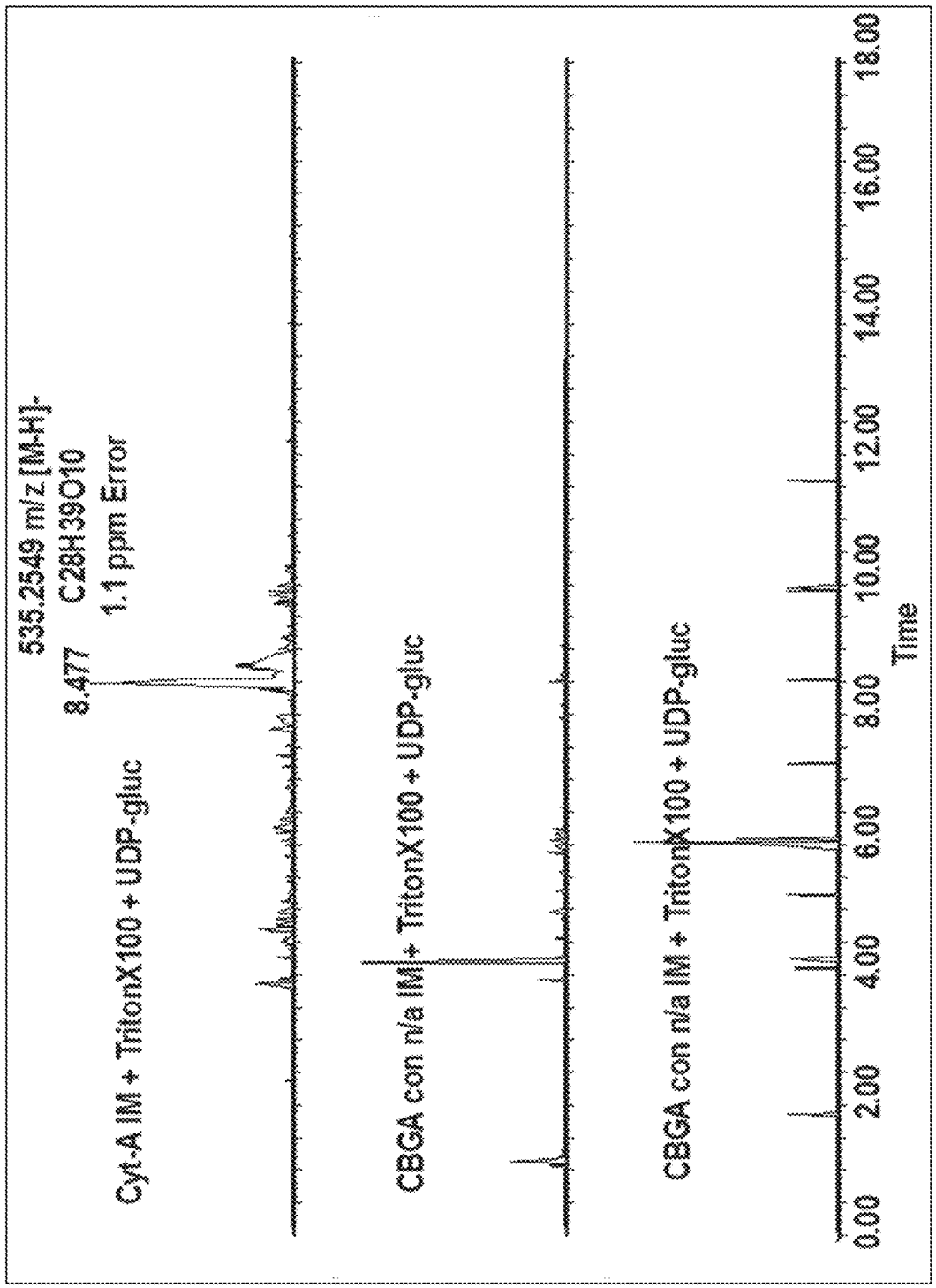
FIG. 23. Extracted Ion Chromatograms of R—OH Functionalized 1× Glycosylated CBDA Analog. (A) Chromatographic trace, ion m/z, calculated elemental composition, confirming presence of trace levels of CBDA analog (B) Absence of CBDA analog in control extract (C) Absence of CBDA analog in biological duplicate control extract.

As shown in FIGS. 19-20, gene expression of cytCBDAs and cytUGT was confirmed via RT-PCR after 1 and 2 DPI. No expression of ABC transporter (ABCt) was observed after 1 DPI in leaves infiltrated cells suspension construct. This does not impact this experiment as the role of ABCt was to facilitate cannabinoid transport outside the cells in suspension cultures. As shown in FIG. 21, CBGA and its glycosylated and acetylated derivatives were detected in concentrations higher than in the trichome construct infiltrated leaves, except for secondary glycosides. Moreover, CBDA was detected in higher concentrations (up to 34 ppm) in leaves infiltrated with the cell suspension construct, compared to the trichome construct experiments (up to 2.6 ppm). As shown in FIG. 22, when UDP-glucose 4 mM (substrate for UGT) was provided together with CBGA (substrate for CBDAs), the present inventors detected low levels of glycosylated and hydroxylated CBDA in leaves infiltrated with both the cytosolic and cell suspension construct, but not in the WT control. This result demonstrates the novel in plant synthesis, glycosylation and hydroxylation of CBDA in the surrogate plant *N. benthamiana*, as demonstrated by the Extracted Ion Chromatograms shown in FIG. 23.

Example 11: Hydroxylation and Glycosylation of Cannabinoids in *Cannabis sativa*

Figure 24:
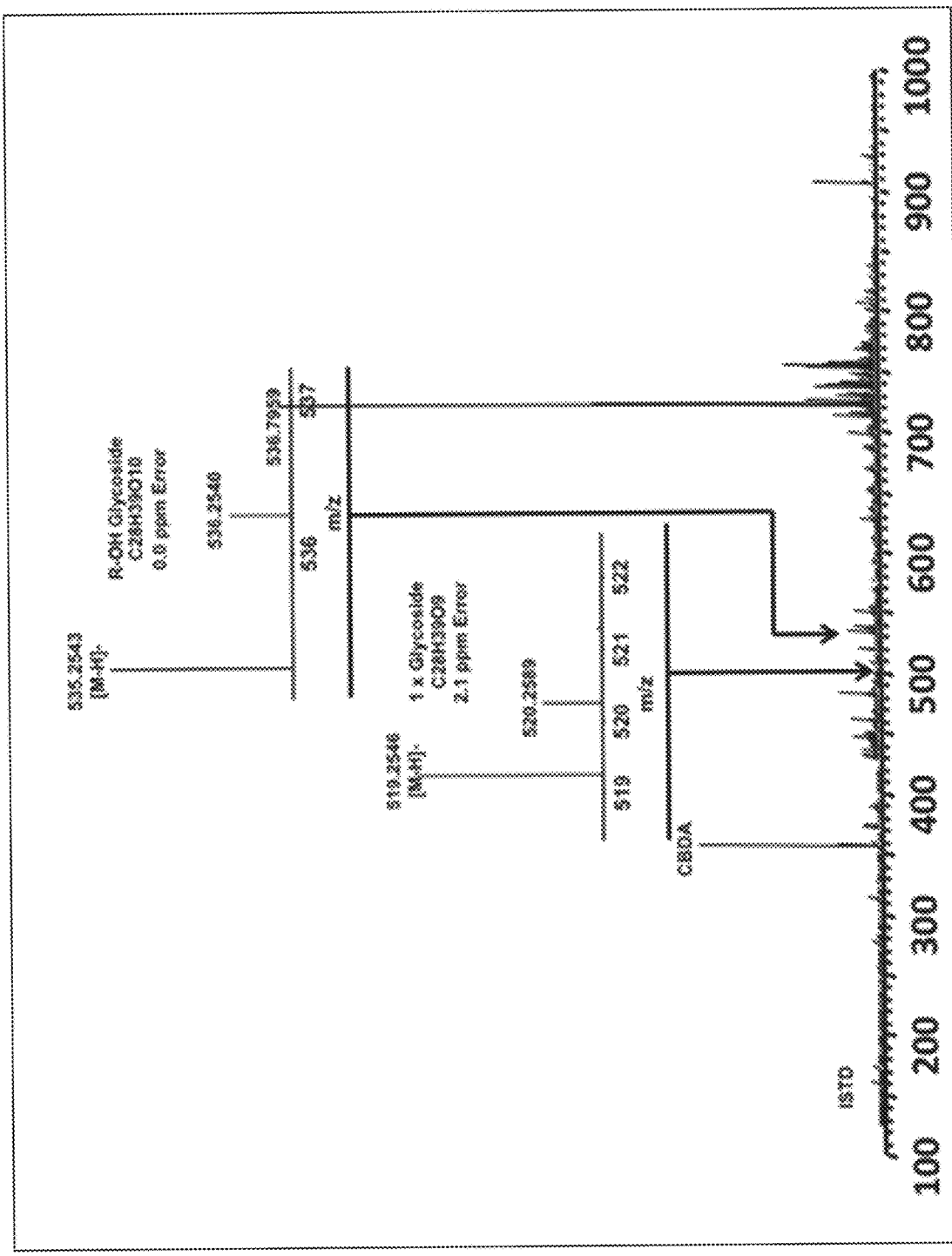
FIG. 24. Direct Infusion Mass Spectrum of Cannabis sativa extract. Spectral insets represent CBDA with a single glycosylation (519.2546 m/z), and CBDA functionalized with R—OH and a single glycosylation (535.2543 m/z). Peak Intensities are illustrated as relative abundance to most intense ion.
Figure 25:
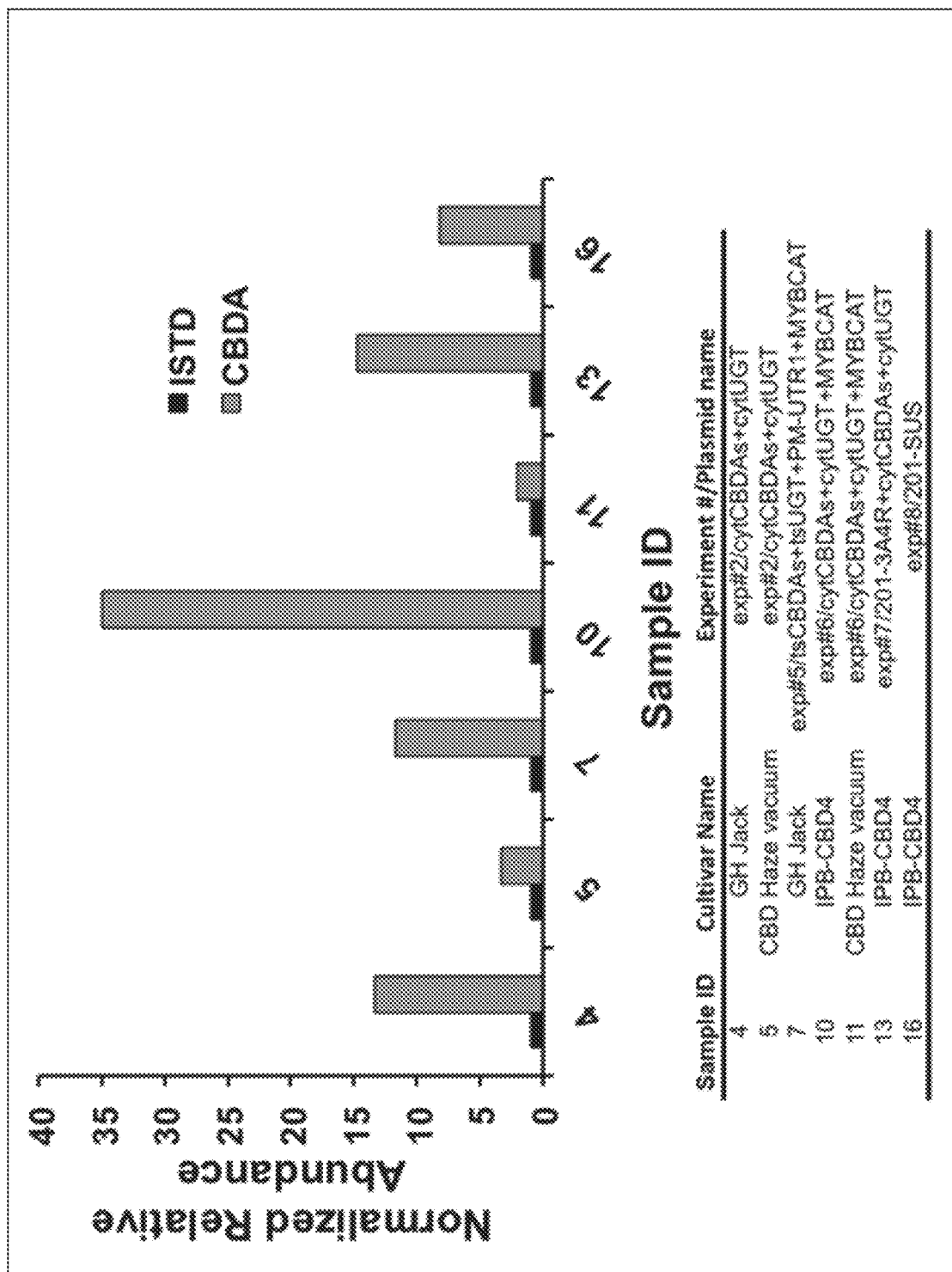
FIG. 25. Relative abundance of CBDA in extracts of various Cannabis sativa strains infiltrated with Agrobacterium cultures harboring CBDA synthase (CBDAs) and UGT plasmid combinations. Normalized relative abundance data is presented as the ion intensity of each compound divided by the ion intensity of the internal standard 7-hydroxycoumarin (20 ppm).
Figure 26:
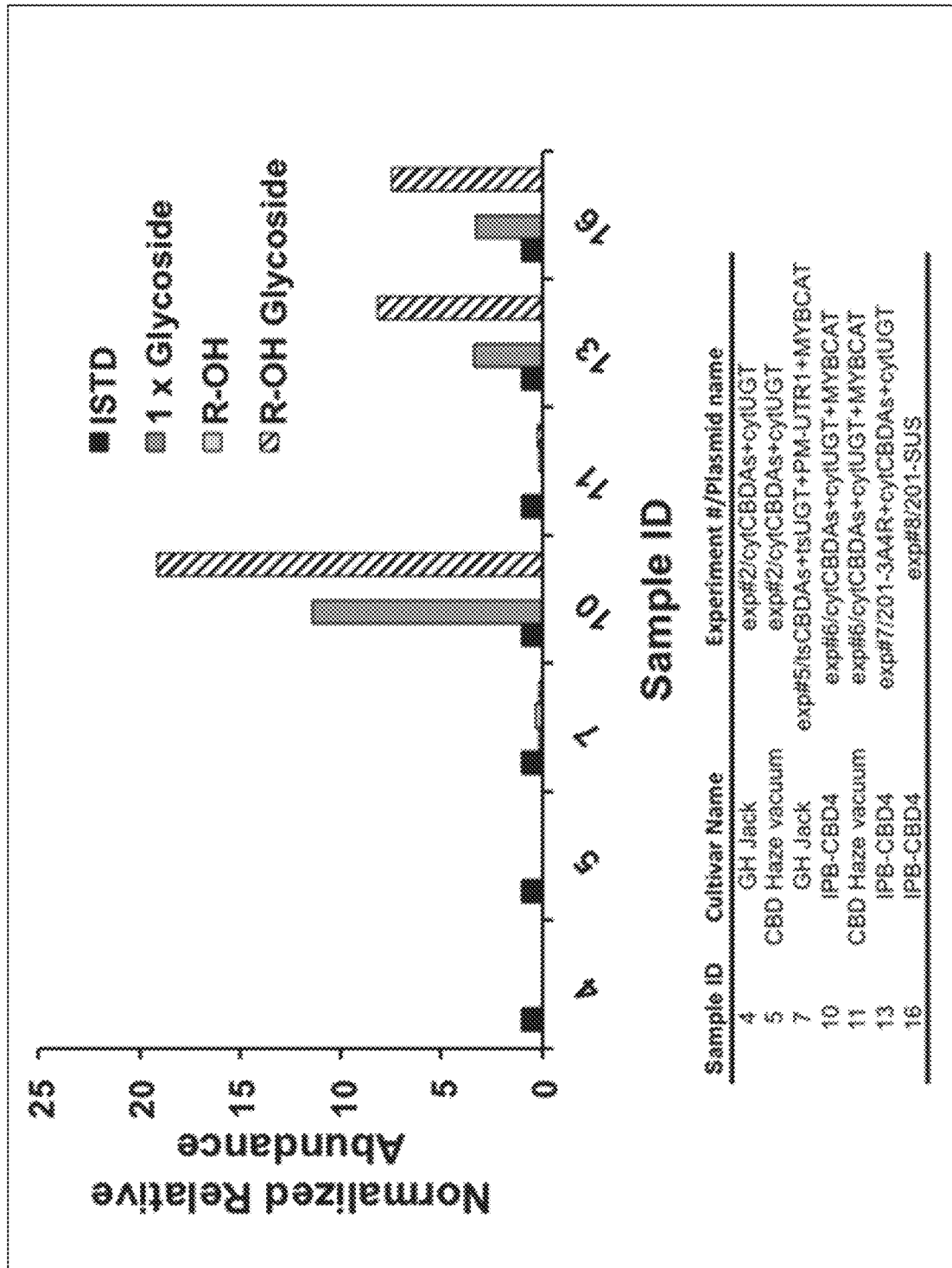
FIG. 26. Relative abundance of modified CBDA (glycosylated and/or hydroxylated) in extracts of various Cannabis sativa strains infiltrated with Agrobacterium cultures harboring CBDAs and UGT plasmid combinations. Normalized relative abundance data is presented as the ion intensity of each compound divided by the ion intensity of the internal standard 7-hydroxycoumarin (20 ppm).

The present inventors demonstrate the glycosylation and hydroxylation of cannabinoids in *Cannabis sativa*. To further confirm our findings using *N. benthamiana* as a plant model, we performed *Agrobacterium* infiltration of the same plasmid constructs described in the section above in various strains of *Cannabis sativa* (see FIG. 24 Sample IDs). As shown in FIGS. 24-26, expression of the select genetic constructs in *C. sativa*, as in *N. benthamiana*, demonstrate synthesis and accumulation of hydroxylated and/or glycosylated cannabinoids, in this case CBDA. A comparison of the results using different *Agrobacterium* genetic constructs is presented in Table 8 below.

As the present inventors have demonstrated, in one embodiment, where the cytosolic construct was con-transformed with the Myb/catalase (MYBCAT) expression vector, yielded the highest detection of CBDA and CBDA glycoside, demonstrating the role of these genes in mitigating toxicity effects due to hydrogen peroxide accumulation (catalase) and overall increase in cannabinoid synthesis (Myb transcription factor).

Example 12: Intracellular Expression of Glycosyltransferases in Yeast Cells

Four glycosyltransferases from *Nicotiana tabacum* (NtGT1, NtGT2, NtGT4, NtGT5), one from *Stevia rebaudiana* (UGT76G1), and *Escherichia coli* catalase E (Kat-E) encoding sequences were codon-optimized for expression in *Pichia pastoris*, synthesized by Genewiz, and cloned into pPink-HC or pPINK-αHC vector as described in the PichiaPink expression system manual (Invitrogen). The assembled constructs were verified by restriction enzyme digestion and DNA sequencing. Each of the constructs was used to transform the wild-type strain (strain 4).

Figure 41:
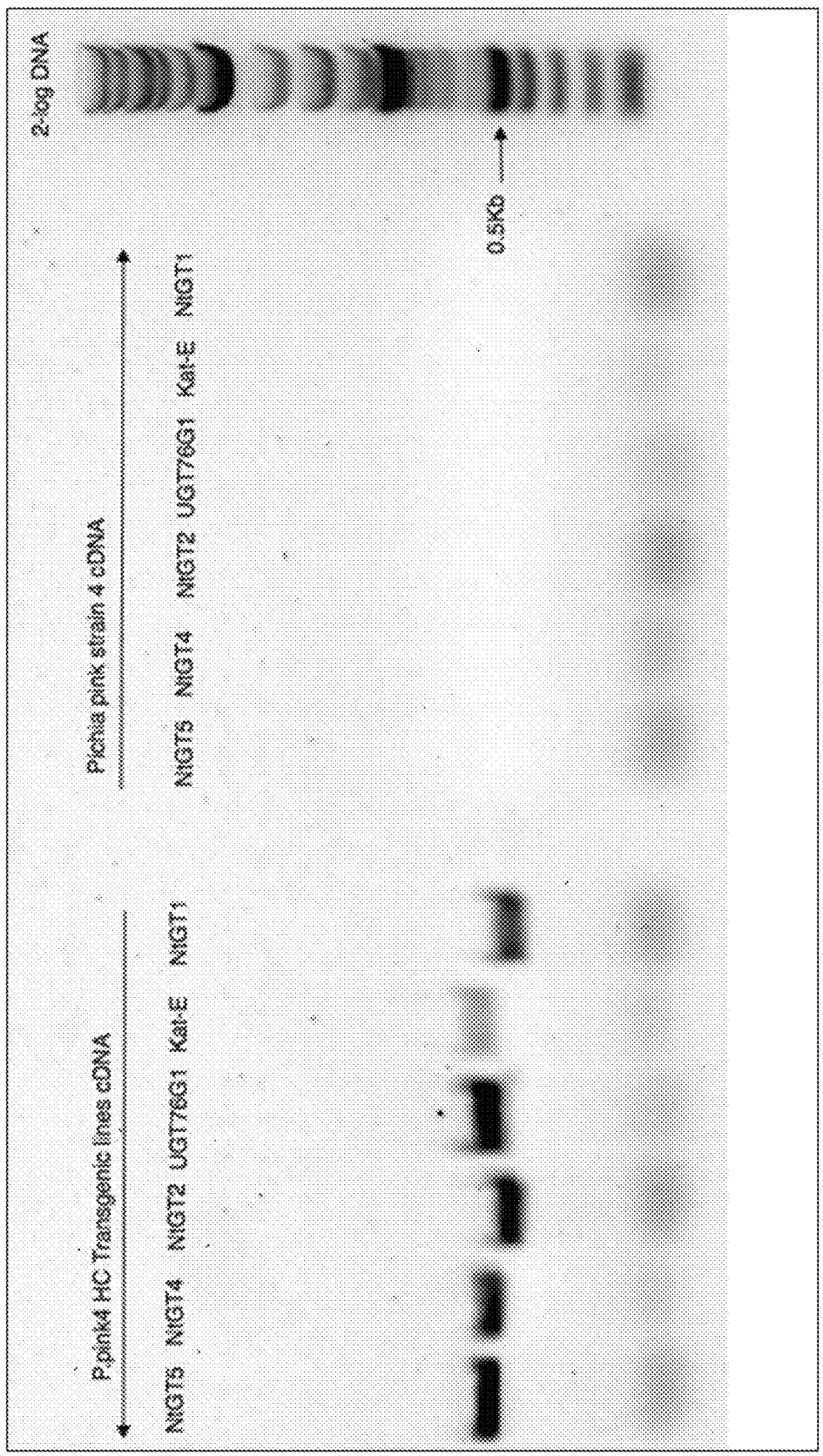
FIG. 41. Demonstration of expression of glycosyltransferases and Kat-E in *Pichia pastoris*.

Transgene expression in transgenic yeast and expression was verified by RT-PCR (FIG. 41). The list of primers used in PCR verification of transgene expression is shown in Table 13. Codon optimized DNA and corresponding amino acid sequence identities are as follows: NtGT1 (SEQ ID NO. 51, and SEQ ID NO. 52 respectively); NtGT2 (SEQ ID NO. 53, and SEQ ID NO. 54 respectively); NtGT3 (SEQ ID NO. 55, and SEQ ID NO. 56 respectively); NtGT4 (SEQ ID NO. 57, and SEQ ID NO. 58 respectively); NtGT5 (SEQ ID NO. 59, and SEQ ID NO. 60 respectively); UGT76G1 (SEQ ID NO. 61, and SEQ ID NO. 62 respectively); Kat-E (SEQ ID NO. 65, and SEQ ID NO. 66 respectively). Additional codon optimized exogenous glycosyltransferases that may be used with the current invention may include, but not be limited to: UGT73A10 (SEQ ID NO. 63, and SEQ ID NO. 64 respectively);

Example 13: Introducing CBDA to Yeast Cells in Acetonitrile

The present inventors demonstrated that after transformation of vectors into the wild type yeast strain, white colonies were selected and transferred into 250 mL flasks containing 50 mL YPG media (yeast extract, peptone, glycerol). After overnight growth (the cultures reached an $OD_{600}$~1), 100% methanol was added at 5% v/v to induce gene expression overnight. The following morning, cultures were aliquoted into 3×10 mL cultures, centrifuged and resuspended in fresh YPG media with 2.5% v/v methanol, and 50 uL of CBDA in acetonitrile (1 mg/mL, Cayman Chem) was added to a final concentration of 14 uM. After 72 hs, the samples were centrifuged down and the cell pellet and supernatant were separately frozen in liquid nitrogen and stored at −80° C. for further LC/MS analysis of cannabinoids.

Example 14: Glycosylation of CBDA by NtGT4

Figure 42:
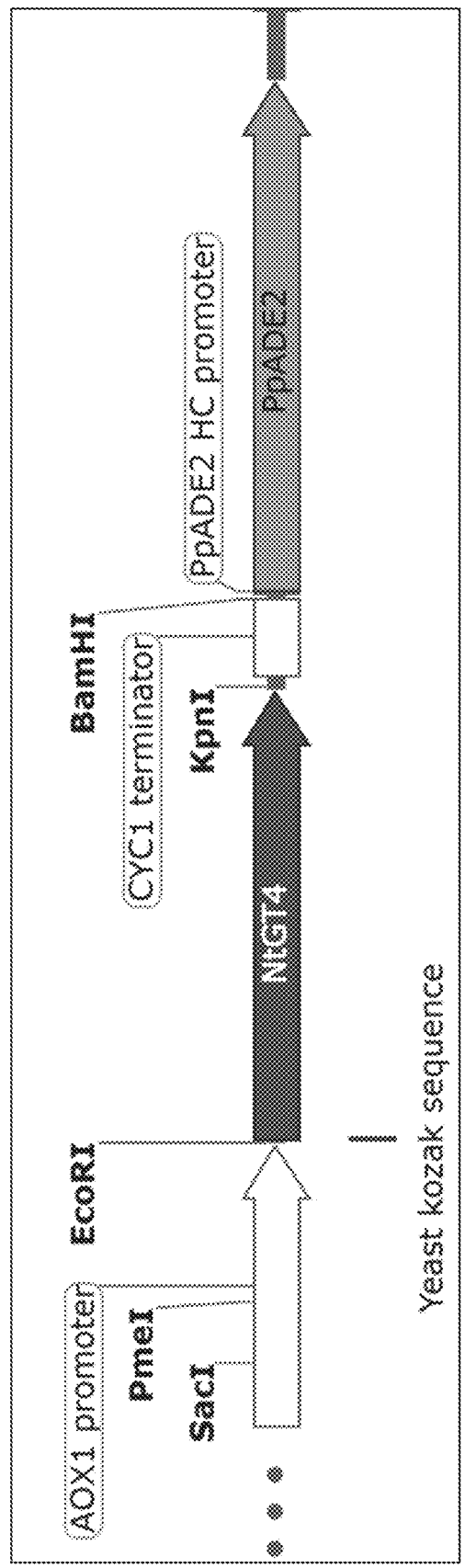
FIG. 42. Gene construct for intracellular expression of NtGT4 in *Pichia pastoris*. Expression was driven by the AOX1 promoter and terminated by the cytochrome C1 (CYC1) terminator. Other exemplary glycosyltransferases were cloned in the manner shown.

The present inventors demonstrate that intracellular expression of NtGT4 (construct outlined in FIG. 42), the UGT 73-like glycosyltransferase from *Nicotiana tabacum*, led to the highest level of glycosylation of CBDA (FIGS. 43A and B). The CBDA glycoside was detected in the pellet (FIG. 43B) as well as in the supernatant (FIG. 9A) suggesting that the yeast is secreting the product into the media, presumably by an endogenous ABC transporter. Overall, glycosylation by NtGT4 was significantly higher than by any other glycosyltransferase tested. NtGT1, NtGT2 and the *Stevia* UGT76G1 had only trace levels of CBDA glycosides that were not significantly different in yield from the untransformed wild-type strain.

Example 15: Glycosylation of CBDA by NtGT5

Figure 43:
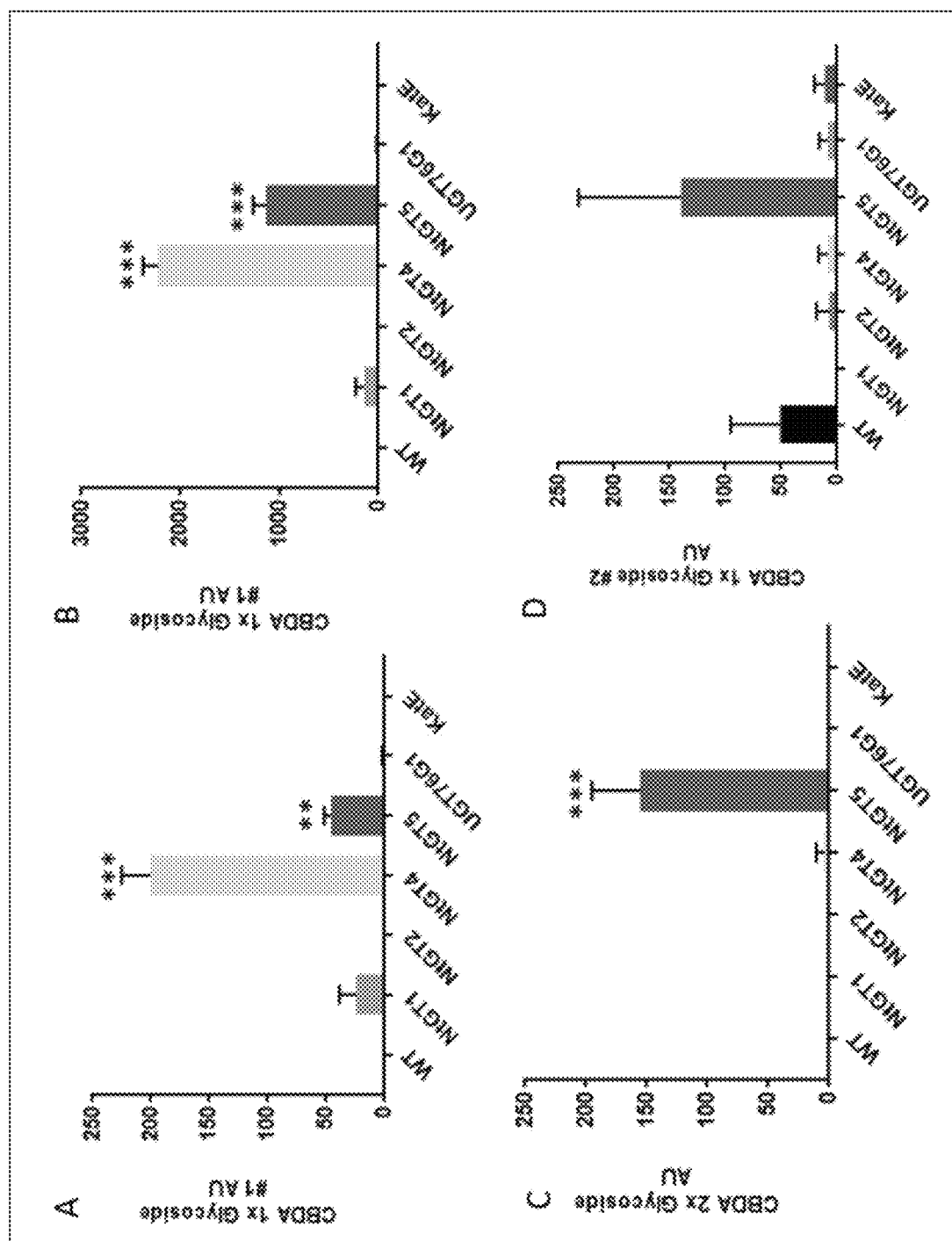
FIG. 43. Post-harvest glycosylation of CBDA in yeast. Glycosides are measured in normalized arbitrary units (AU) based on LC-MS peak area. Asterisks show significant difference (a greater number of asterisks means a lower P value) from the wild type at P=0.05. (A) CBDA 1× glycosides in NtGT1, NtGT4 and NtGT5 detected in the supernatant. (B) CBDA 1× glycosides in NtGT1, NtGT4 and NtGT5 detected in the pellet. (C) CBDA 2× glycoside (NtGT5) in the supernatant. (D) CBDA 1× glycoside on a different position mainly detected in NtGT5 transgenic lines in the pellet.
Figure 44:
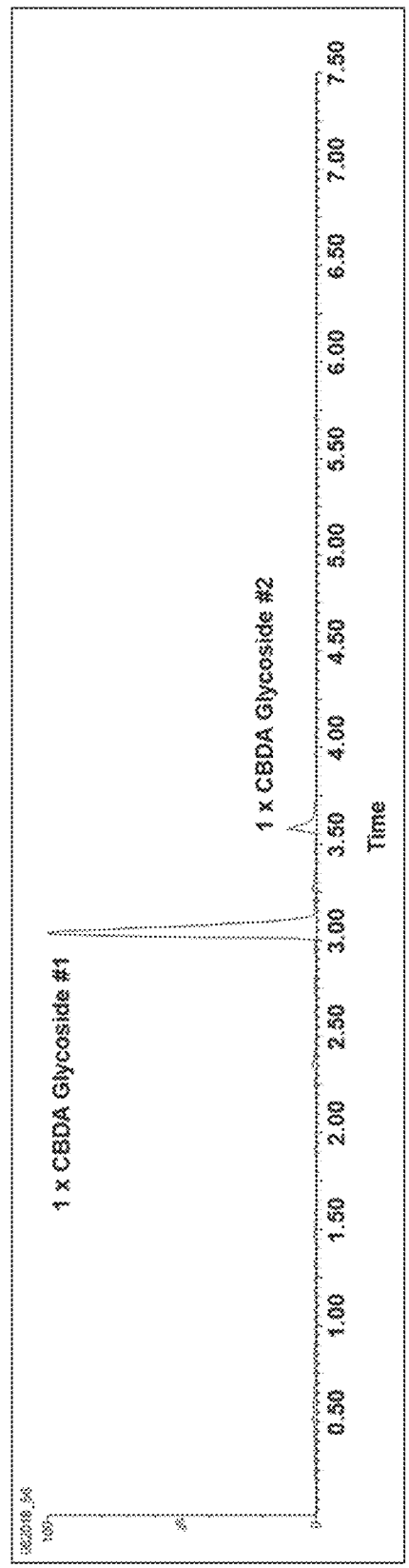
FIG. 44. Representative chromatographic elution profile of CBDA 1× glycosides found in yeast cell pellets for the intracellular expression of NtGT5. Chromatogram represents extraction ion chromatograms of the 519.259 m/z 1× glycoside ion. Peak Intensities are illustrated as relative abundance to most abundant peak in each respective chromatogram.

The present inventors demonstrate that intracellular expression of NtGT5, the 7-deoxyloganetin glycosyltransferase-like from *Nicotiana tabacum*, led to glycosylation of CBDA (FIGS. 43 and 44). The present inventors further demonstrate that NtGT5 is not only capable of catalyzing the same R—OH position as NtGT4 but preferentially glycosylates a different and less water-soluble position than NtGT4. (Generally panels B &E of FIG. 37)

Figure 45:
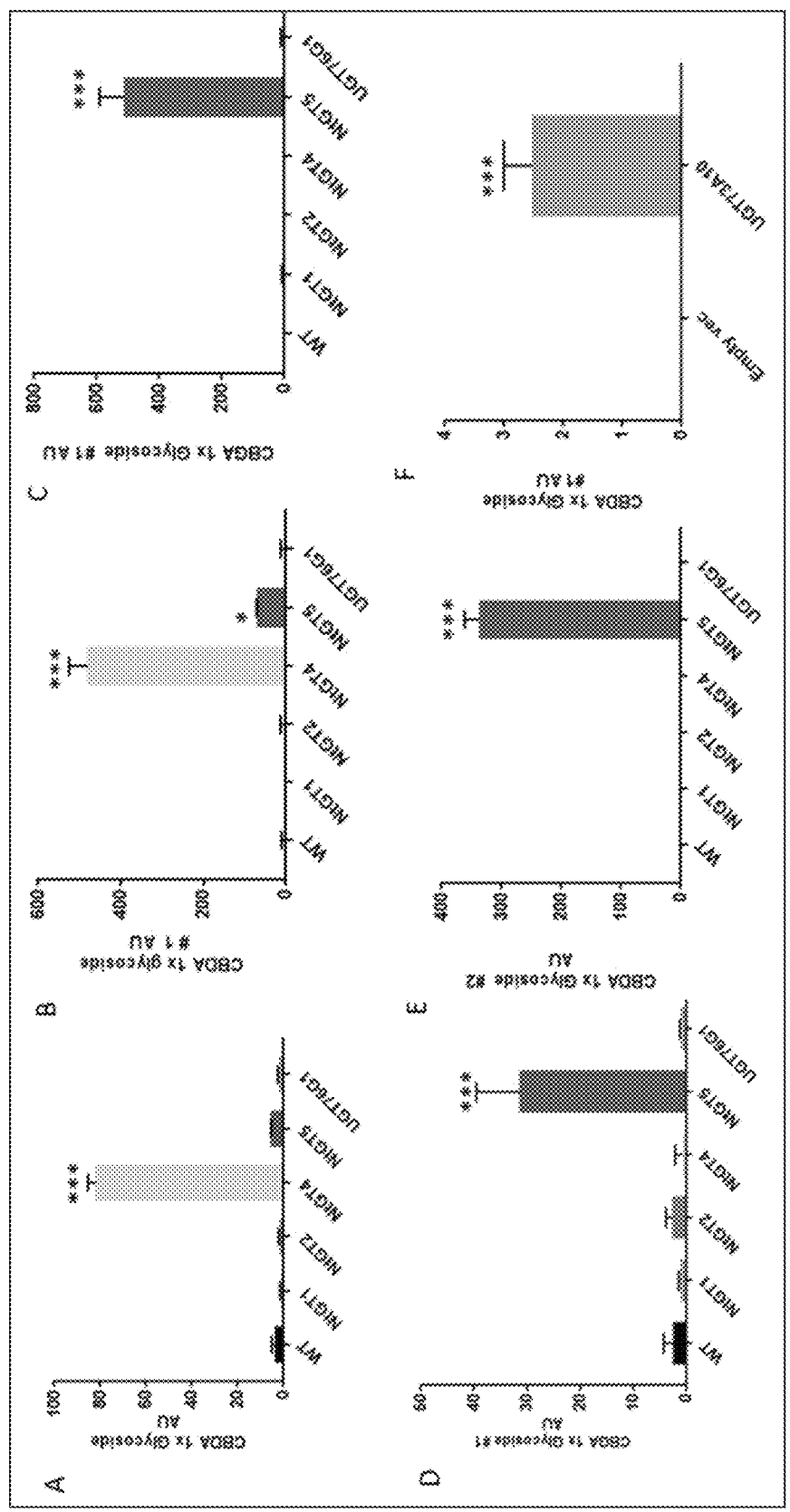
FIG. 45. Postharvest glycosylation of CBD oil in yeast. Glycosides are measured in normalized arbitrary units (AU) based on LC-MS peak area. Asterisks show significant difference (a higher number of asterisks means a lower P value) from the wild type at P=0.05. WT=wild type *Pichia pastoris* Strain 4, Empty vec=yeast transformed with the empty vector pPINK-HC.

Example 16: Introducing CBD Oil Extract to Yeast Cells 50 mL cultures of transgenic yeast were induced with methanol after 24 hours of growth in YPG and fed with 227 uM cannabidiol (CBD) in the form of a commercial diluted CBD oil (Minnerva *Canna*). After 72 hs, the samples were centrifuged down and pellet and supernatant were separately frozen in liquid nitrogen and stored at −80° C. for LC/MS analysis of cannabinoids. As in the CBDA feeding experiments, the present inventors demonstrate that NtGT4 and NtGT5 yielded the highest levels of glycosylation in different positions on CBD oil feeding experiments (FIG. 44). CBDA glycosides were detected in both supernatant (FIGS. 45A, D and F) and pellet (FIGS. 45B, C and E). Oil extract feeding allowed the present inventors to investigate glycosylation of other cannabinoids. NtGT5 glycosylated the cannabinoid precursor CBGA (FIG. 45).

Example 17: Extracellular Glycosylation of Cannabinoids

Figure 46:
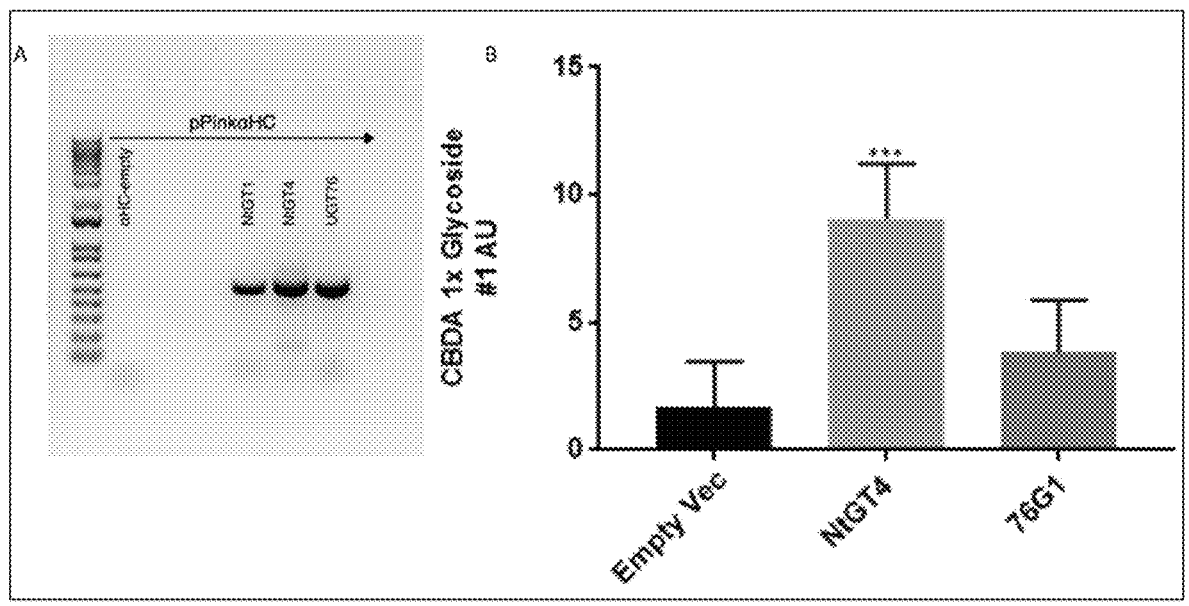
FIG. 46. (A) Confirmation of transgene expression in yeast from secretion expression constructs NtGT1, NtGT4 and UGT76G1. αHC-empty is the empty vector control. (B) CBDA glycosides in the supernatant of yeast cultures secreting recombinant glycosyltransferases into the media. Asterisks show significant difference from the wild type at P=0.05.

As described above, in one exemplary embodiment, an expression vector was used by the present inventors to secrete proteins into the media for an extracellular glycosylation of cannabinoids. Transgenic yeast lines expressing glycosyltransferases with the α-factor secretion signal (FIG. 35A) were fed CBD oil extract as previously described and analyzed for glycosylated cannabinoids. There was no glycosylation in the pellets as expected since the enzymes were secreted into the media. There was only minimal glycosylation in the supernatant (FIG. 46) in comparison with the intracellular system.

Example 18: Time Course Analysis of Intracellular Cannabinoid Glycosylation

Figure 47:
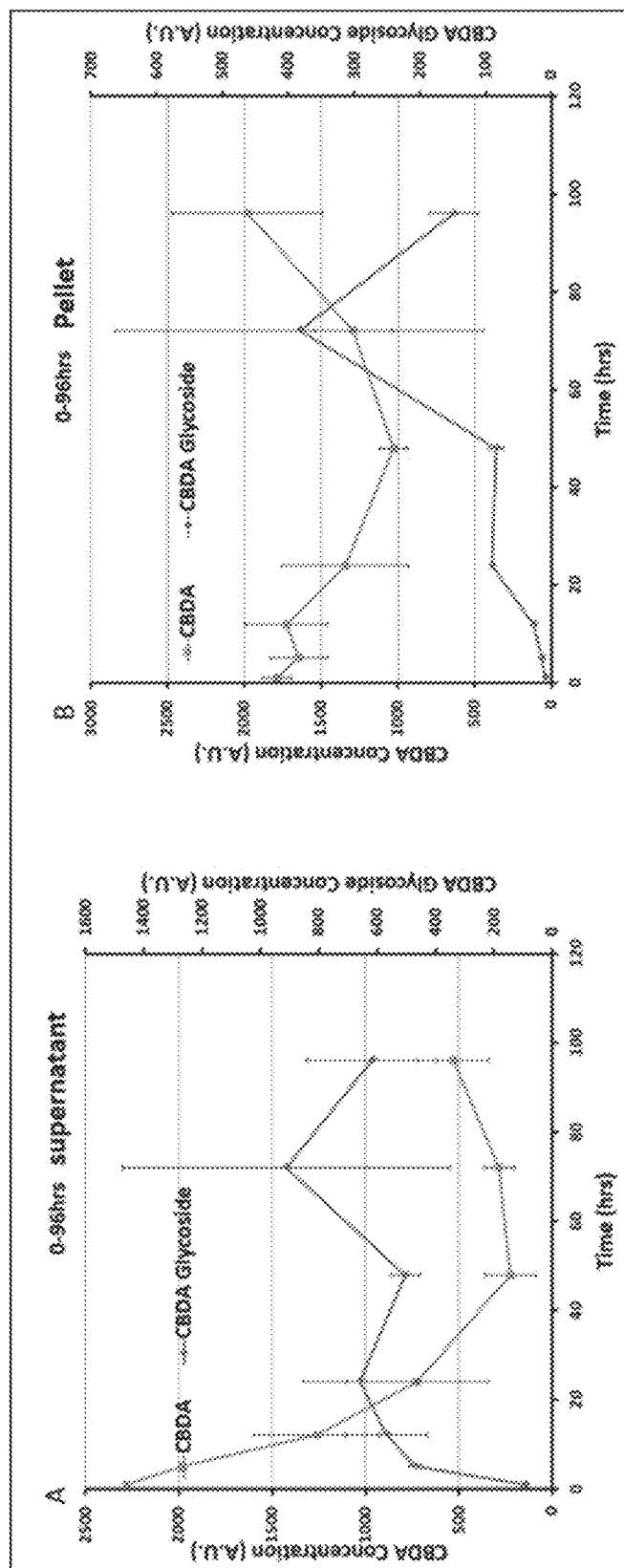
FIG. 47. Time course analysis of CBDA glycosylation in transgenic yeast. Depletion of CBDA was quantified along with accumulation of CBDA glycosides in the supernatant (A) and the pellet (B).

To determine the optimum time for cannabinoid glycosylation in yeast, the present inventors set up a time course experiment. Transgenic yeast expressing NtGT4 intracellularly were fed with CBDA (27 μM) and incubated for up to 96 hours. Samples were collected at different time points during the incubation and analyzed for the formation of CBDA glycosides (See FIG. 47). In both pellet and supernatant, a reciprocal relationship was observed by the present inventors between CBDA loss and CBDA glycoside production. For the supernatant (media), CBDA depletion was most likely due to uptake by the yeast. In the pellet, CBDA depletion can be explained by its glycosylation into CBDA glycosides. The optimal time for CBDA glycosylation was 48 hours, after which CBDA levels increased and CBDA glycosides dropped, suggesting that there is possibly an inducible and competing glycosidase activity present in the yeast that is turning over the CBDA glycoside. To prevent this glycosidase, the present inventors may introduce glycosidase inhibitors to preserve CBDA glycosides or suppress the expression of the endogenous glycosidases. In additional embodiment, the present inventors may overexpress an ABC transporter to speed up secretion of CBDA glycosides into the media. One example may include the expression of a multi-drug resistant transporter ABCG2 (SEQ ID No. 67 and SEQ ID No. 67) in tobacco. Through transcriptomics may also be employed by to identify possible candidates in yeast overexpressing glycosyltransferases.

Example 18: Glycosylation of Cannabinoids in Tobacco Bright Yellow Cells

Figure 48:
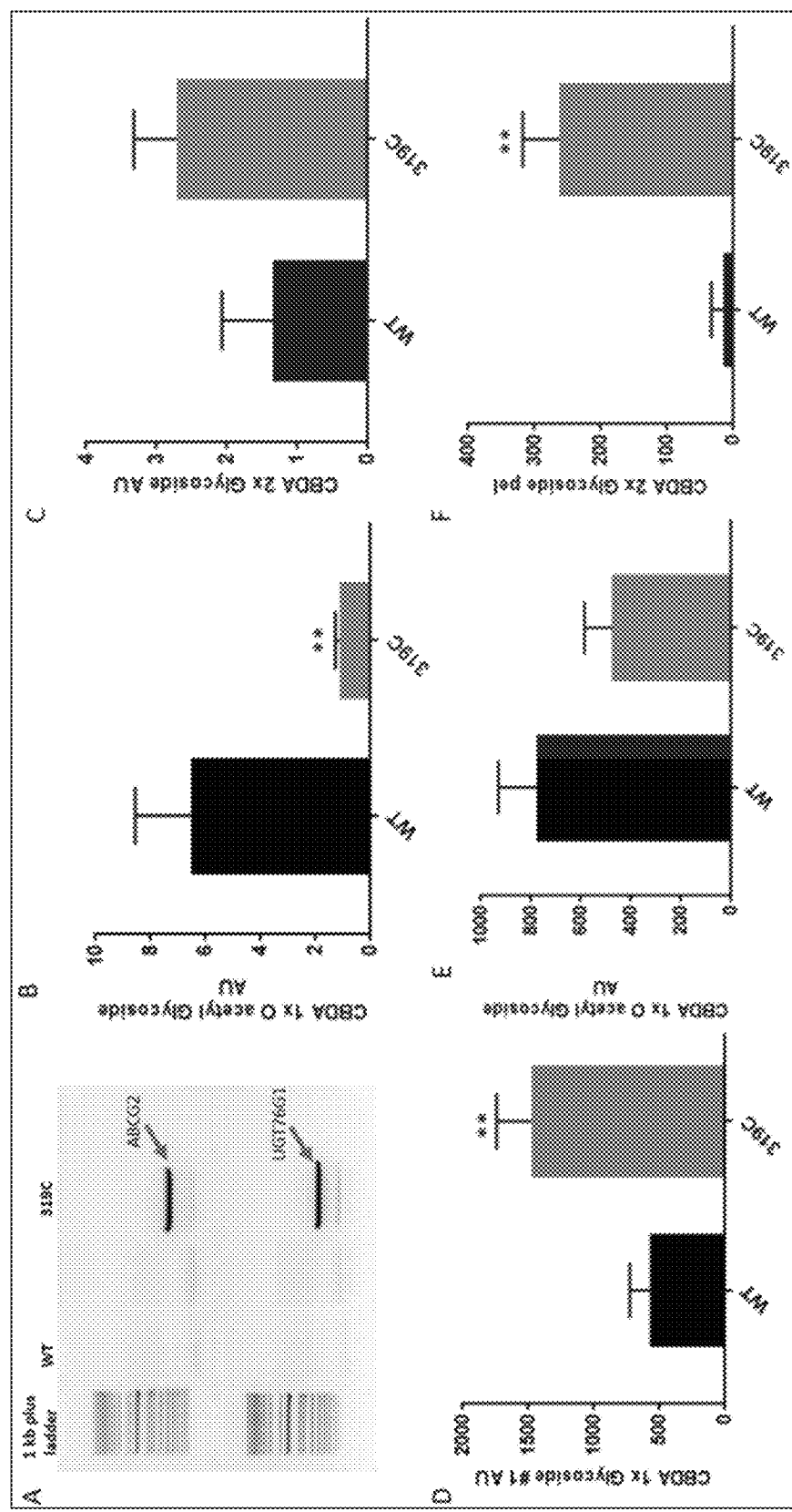
FIG. 48. Confirmation of transgene expression in BY2 cell cultures. The cell culture line 319C overexpresses the ABC transporter (ABCG2) and the glycosyltransferase UGT76G1. (B-F). Glycosylated CBDA compounds produced from wild type (WT) and transgenic (319C) BY2 cells. 319C overexpresses UGT76G1 and ABCG2. Glycosylated CBDA compounds were detected mainly in the pellet (D, E and F) and to a lesser extent in the supernatant (B and C).

Similar to yeast suspension cultures, plant cell cultures are a viable platform for the production of recombinant proteins because they can be cultivated under sterile conditions and can be scaled up in fermenters for industrial level production. One of the most widely used cell lines in plant biology is the tobacco Bright Yellow 2 (BY2) cell line developed in 1968 at the Hatano Tobacco Experimental Station, Japan Tobacco Company. BY2 cells have a doubling time of 16-24 hours, multiplying up to a 100-fold in 7 days t al., 2016), can be easily transformed by *Agrobacterium* mediated transformation and require basic plant growth media for maintenance. As described above, the prevent inventors demonstrated endogenous glycosylation in tobacco leading to the possibility of using tobacco suspension cultures as a postharvest glycosylation platform. In this embodiment, the present inventors introduced wild-type and transgenic BY2 cells expressing the *Stevia* glycosyltransferase UGT76G1 (SEQ ID NO. 61 and SEQ ID NO. 62) and the multidrug resistance transporter ABCG2 (319C) (SEQ ID NO. 67 and SEQ ID NO. 67) with 5 μM CBDA in acetonitrile and grew the cultures for 3 days. Confirmation of transgene expression in BY2 cells was done by RT-PCR with primers amplifying a region of the transgene (FIG. 48).

Figure 49:
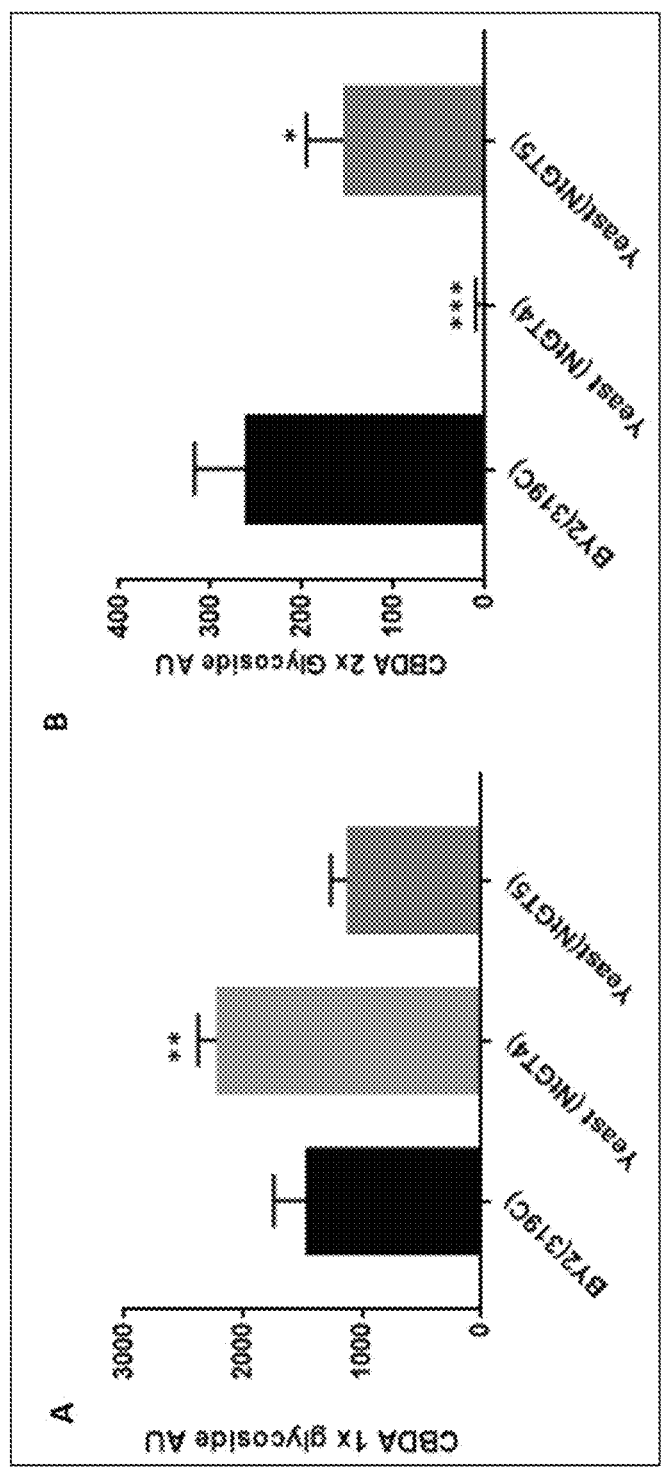
FIG. 49. Relative glycosylated cannabinoid yields for tobacco BY2 (319C) and yeast (NtGT4 and NtGT5) cell extracts, normalized to fresh weight. Asterisks show significant difference (a greater number of asterisks means a lower P value) from BY2 cell extracts at P=0.05.
Figure 50A:
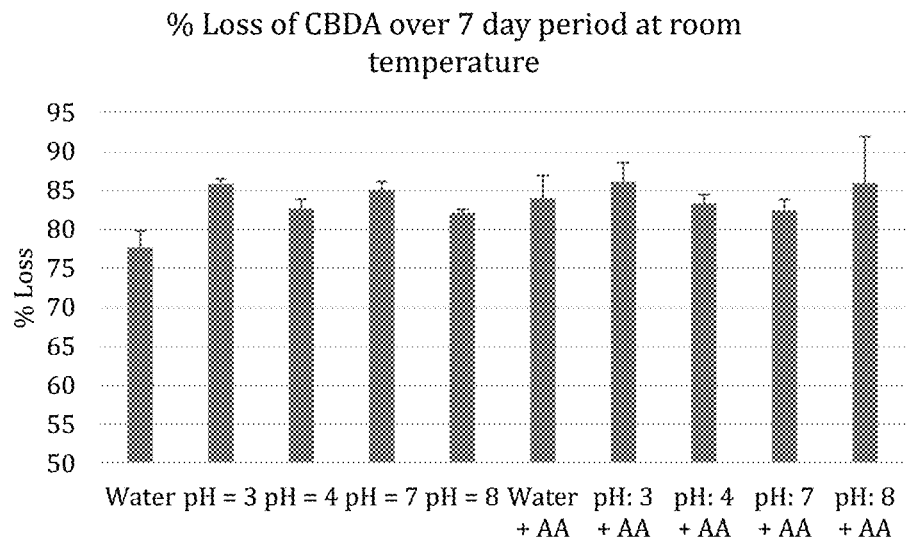
FIG. 50A-B. Solution stability analysis for cannabinoids, cannabinoid glycosides and acetylated cannabinoid glycosides.
Figure 50B:
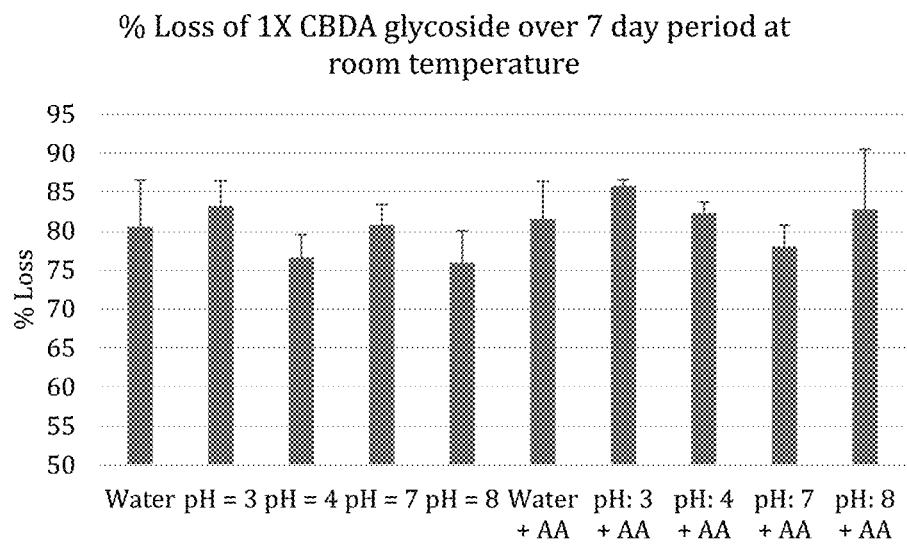
Figure 51A:
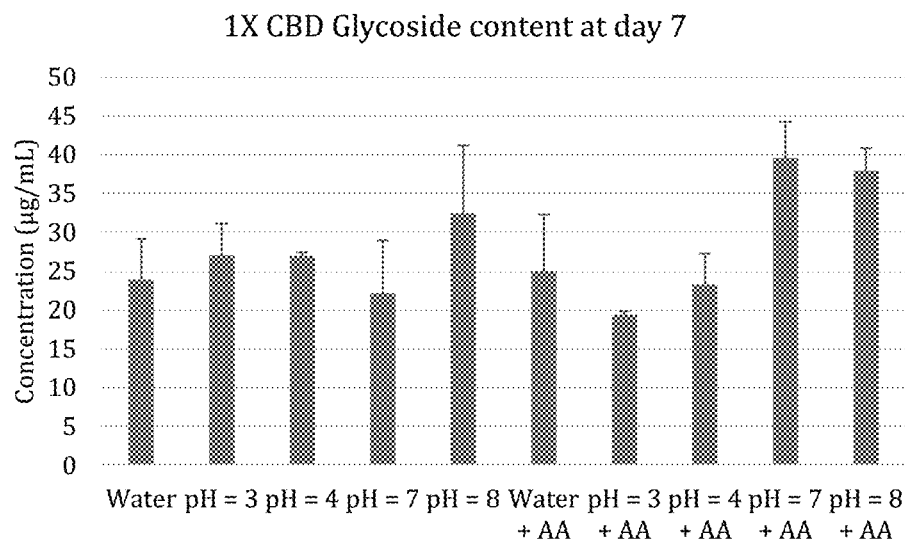
FIG. 51A-B. Solution stability analysis for cannabinoids, cannabinoid glycosides and acetylated cannabinoid glycosides at various pH ranges.
Figure 51B:
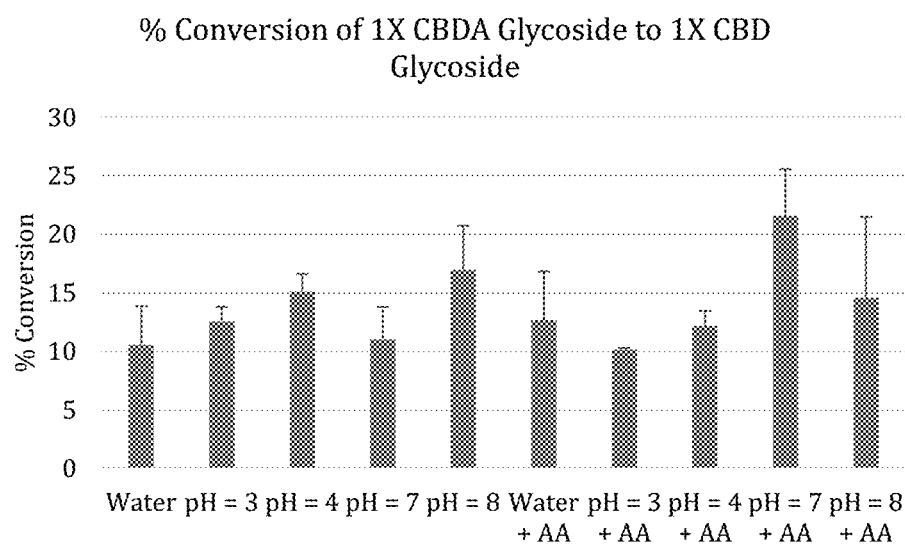

For the CBDA 1× O acetyl glycoside, glycosylation was observed in the wild type more than in transgenic lines. For all other forms of glycosylated CBDA, the transgenic line 319C had increased glycosylation compared to the wild type. The present inventors ran a comparison between glycosylation in yeast and tobacco yields, normalizing with pellet mass (FIG. 49).

Figure 38:
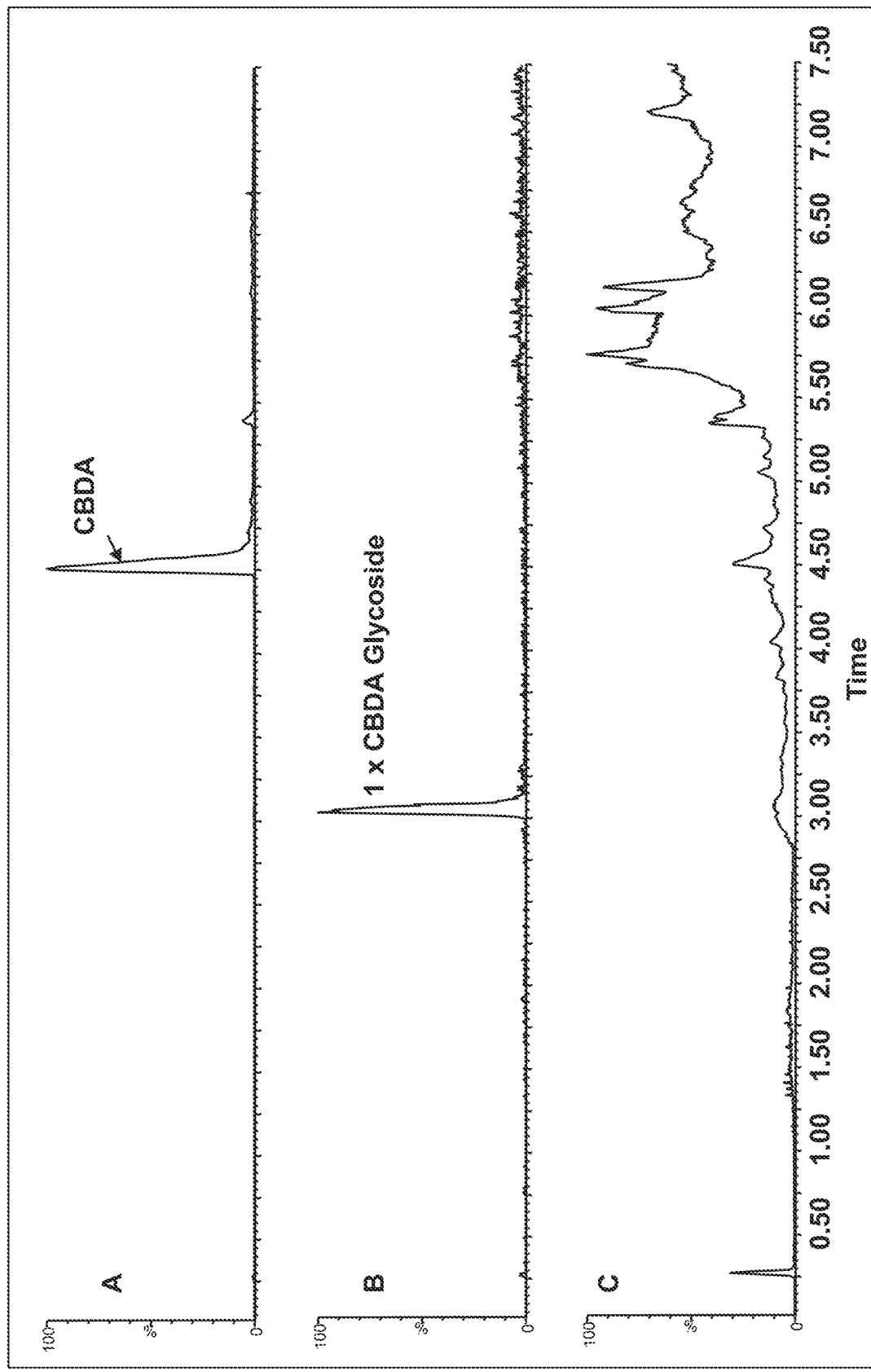
FIG. 38. Representative Chromatographic Elution Profile of CBDA Glycosides found in yeast cell extracts. Chromatograms A, and B represent respective extract rated ion chromatograms for the parent and glycoside molecules. Chromatogram C is representative of the total ion chromatogram. Peak Intensities are illustrated as relative abundance to most abundant peak in each respective chromatogram.
Figure 39:
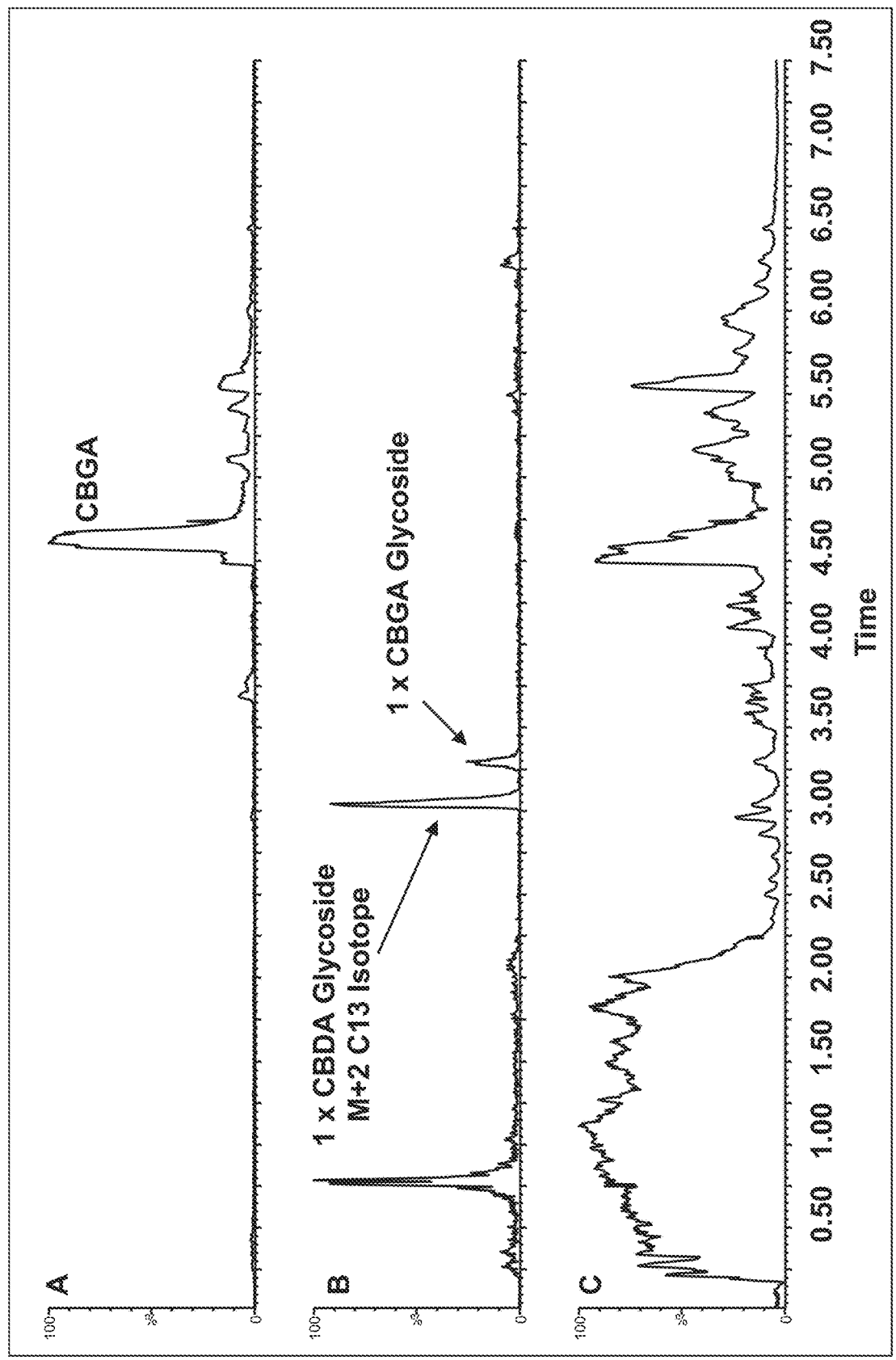
FIG. 39. Representative chromatographic elution profile of CBGA glycosides found in yeast cell supernatants. Chromatograms A, and B represent respective extract rated ion chromatograms for parent and glycoside molecules. Panel B also illustrates a 13C isotope of the CBDA glycoside also found in the same analysis. Chromatogram C is representative of the total ion chromatogram. Peak Intensities are illustrated as relative abundance to most abundant peak in each respective chromatogram.
Figure 40:
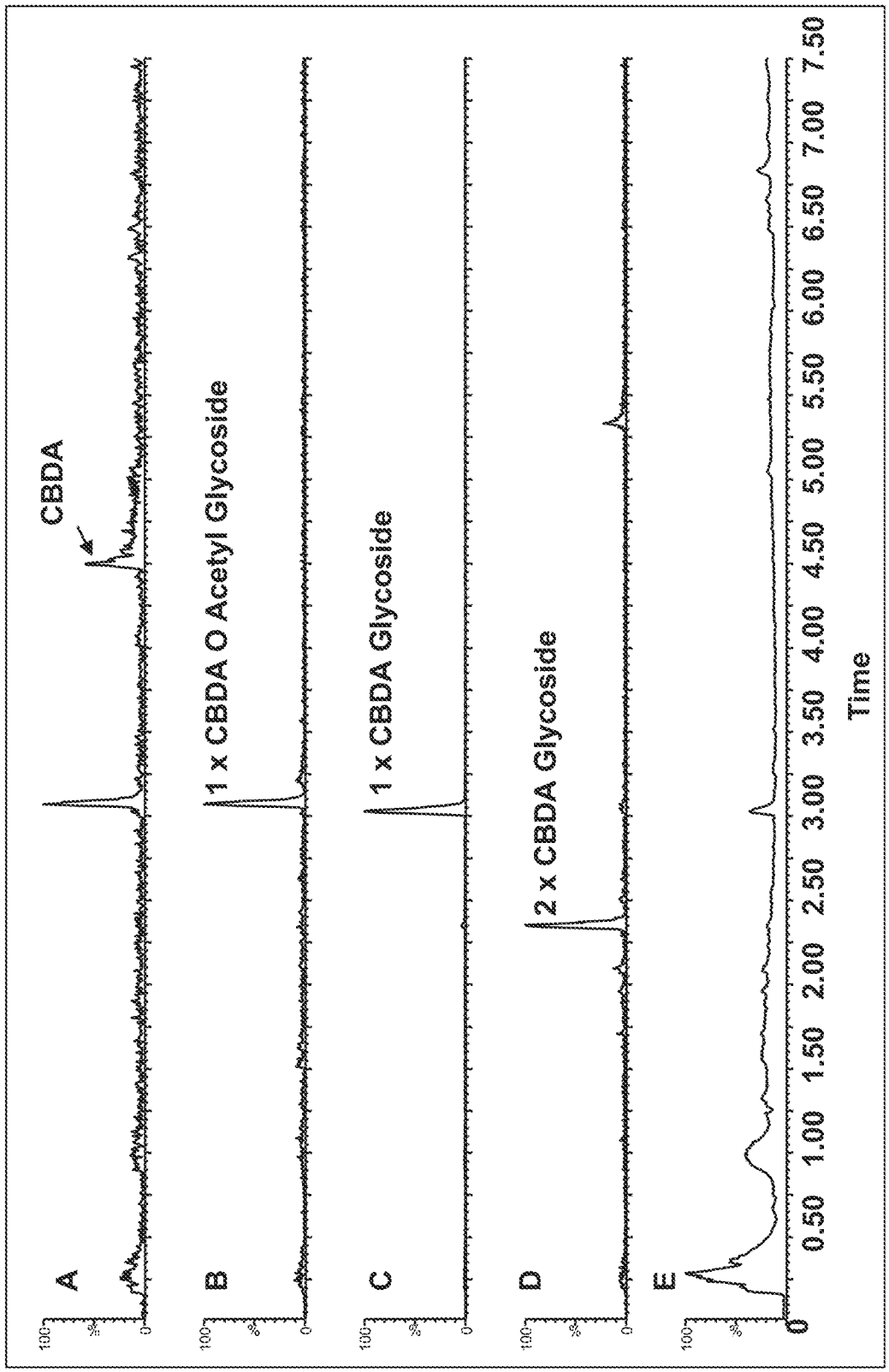
FIG. 40. Representative chromatographic elution profile of CBDA glycosides found in tobacco cell extracts. Chromatograms A, B, C, and D represent respective extract rated ion chromatograms for each glycoside product. Chromatogram E is representative of the total ion chromatogram. Peak Intensities are illustrated as relative abundance to most abundant peak in each respective chromatogram.

As demonstrated in the figures, in general, a more diverse range of glycosylated products were obtained in tobacco compared to yeast (see chromatograms in FIGS. 38, 39 and 40). The common compounds produced were the CBDA 1× glycoside and the CBDA 2× glycoside. For the 1× glycoside, glycosylation in yeast lines overexpressing NtGT4 was significantly higher than in the BY2 cells overexpressing the *Stevia* UGT76G1. However, for the 2× glycoside (predicted to be more water-soluble than 1× glycoside), BY2 cells demonstrated higher glycosylation rate than the yeast (FIG. 49B). However, in BY2 cell cultures, low amounts of CBDA glycosides (<6 arbitrary units, normalized to fresh weight) compared to yeast cells (50-200 normalized arbitrary units)

were detected in the supernatant, suggesting lower secretion in tobacco suspension cultures. In certain embodiments, co-expressing the tobacco NtGT4 and NtGT5 with an ABC transporter, such as ABCG2, under constitutive promoters in BY2 cells may increase glycosylation in tobacco and make BY2 cell cultures providing an alternative platform for production of water-soluble cannabinoids.

Additional embodiments of the current invention may include the transformation of tobacco, yeast or plant cells, such as *Cannabis*, with one or more exogenous P450 genes. In one preferred embodiment, this may include Cytochrome P450 (CYP3A4) from *Mus musculus* (SEQ ID NO. 69 and 70) as well as P450 oxidoreductase gene (CYP oxidoreductase) from *Mus musculus* (SEQ ID NO. 71 and 72). In some embodiment, the aforementioned gene may be codon optimized for expression in yeast cells.

Example 19: Acetylated Cannabinoid Glycosides Exhibit Enhanced Stability in Solution As generally described in FIGS. 50(A)-(B) and 51A-B, and Tables 14-19, the present inventors demonstrate that acetylated cannabinoid glycosides exhibit enhanced stability of the sugar moiety in solution compared to non-glycosylated cannabinoids, or cannabinoid glycosides. Due to this enhanced stability of the sugar moiety, acetylated cannabinoid glycosides exhibit both improved water solubility and/or chemical stability in solution, as well as enhanced resistance to chemical degradation into alternative cannabinoid forms over time.

In FIGS. 50(A)-(B) and 51(A)-(B), the present inventors demonstrated the loss of CBDA and 1×CBDA glycoside and the quantity of 1×CBD glycoside formed, presumably from decarboxylation of 1×CBDA glycoside over time. As also demonstrated in FIGS. 50 and 51, and Tables 14-19, the present inventors demonstrate that CBD 0-Acetyl Glycoside was not found to decrease in any sample after day 7. Rather, levels increased slightly in all treatments. The absence of any residual UGTs were cross-check and confirmed as the samples were purified by SPE, washed and eluted in 30% and 65%-100% ethanol, respectively.

Materials and Methods

Materials and Methods Example 1: Use of a Tobacco as an Exemplary Plant System for the In Vivo Functionalization and Glycosylation of Cannabinoids.

The present inventors demonstrated the in vivo functionalization and glycosylation of cannabinoids in a model plant system. Specifically, the present inventors used *N. benthamiana* (tobacco) as a model system to demonstrate in vivo functionalization and glycosylation of cannabinoids. In this embodiment, transient transformation through *Agrobacterium* infiltration was performed in *N. benthamiana*. The present inventors demonstrated expression of heterologous genes that were expressed in transformed *N. benthamiana* using a number of heterologous gene expression vectors (described below). In this exemplary embodiment, upon confirmation of expression of the heterologous genes that would functionalize and glycosylate cannabinoid molecules, the present inventors introduced to the plants select cannabinoid compounds. In this embodiment, the present inventors introduced to the transgenic *N. benthamiana* plants cannabigerolic acid (CBGA) and/or cannabidiolic acid (CBDA). The present inventors also demonstrated the in vivo functionalization and glycosylation of cannabinoids in a cell suspension culture. Specifically, the inventors used exemplary tobacco bright yellow (BY2) cells as a cell suspension system for studies of cannabinoid production, functionalization and/or glycosylation.

Materials and Methods Example 2: Transient Transformation of the Exemplary Plant Model *Nicotiana benthamiana*.

The present inventors used *Agrobacterium tumefaciens* Ti-plasmid-mediated transformation with the plant expression vector pRI201-AN (Takara Bio USA), a binary vector for high-level expression of a foreign gene in dicotyledonous plants carrying the constitutive 35S promoter and an *Arabidopsis thaliana* Alcohol dehydrogenase (AtAdh) as a translational enhancer (Matsui et al. 2012). *N. benthamiana* was transiently transformed according to the method described by Sparkes et al. 2006. Overnight cultures of *Agrobacterium* strain GV3101 were transferred to a 250 mL flask with 50 mL LB medium supplemented with 50 mg/L of Kanamycin, 50 mg/L of Gentamycin and 10 mg/L of Rifampicin and grown for 4-8 hours until the optical density at 600 nm (OD600) reached approximately between 0.75 and 1. The cells were pelleted in a centrifuge at room temperature and resuspended in 45 mL of infiltration medium containing 5 g/L D-glucose, 10 mM MES, 10 mM MgCl2 and 100 µM acetosyringone. 1 ml of the solution was used to infiltrate the leaves using a 1 mL syringe. Expression of the transgene(s) was confirmed 2-4 days after infiltration by RT-PCR. For RT-PCR analysis, 100 mg of leaf tissue were frozen in liquid nitrogen and ground in a TissueLyser (QIAGEN Inc, USA). RNA was extracted following the EZNA plant RNA extraction kit (Omega Bio-tek Inc, USA). Up to a microgram of total RNA was used to synthesize cDNA using the superscript III cDNA synthesis kit (Thermo Fisher Scientific, USA). The cDNA was used to check for the expression of transgene(s) by RT-PCR.

Materials and Methods Example 3: Introduction of Select Cannabinoid Substrate(s) to the Transgenic *N. benthamiana* Strain.

Select enzyme substrates were introduced to the transgenic or genetically modified *N. benthamiana* strain two days after *Agrobacterium* infiltration and upon confirmation of transgene expression by RT-PCR. In this example, approximately 277 µM cannabigerolic acid (CBGA) and/or cannabidiolic acid (CBDA) was dissolved in 1 mL of buffer containing 10 mM MES, 10 mM MgCl$_2$ and 0.1% Triton X100 or 0.1% Tween20 and applied to the transformed leaves either by infiltration or by dabbing with a cotton applicator. Plants were harvested after 1-4 days, weighed for fresh weight and frozen at −80° C. before conducting LC-MS analysis for the presence of modified cannabinoids.

Materials and Methods Example 4: In Vitro Assays for CBDA Synthase and Glycosyltransferase Activity.

CBDA synthase is generally active in the pH range 4-6 (Taura et al. 1996) while glycosyltransferases are typically active in the pH range 5.0 to 7.0 (Rini and Esko, 2017). Based on this difference in optimal pH for enzyme activity, the present inventors generated a single extraction buffer for a combined assay of CBDA synthase and UDP glycosyltransferase at pH 6 and 30° C. in in vitro assays (Priest et al., 2006). The present inventors ground the transformed leaf tissue in liquid nitrogen. A grinding buffer was added consisting of 50 mM MES, pH 6, 1 mM EDTA, 5 mM β-mercaptoethanol and 0.1% Triton X-100 was added at 5:1 ratio of buffer to fresh weight of plant using a mortar and pestle. The extract was filtered on ice through 2 layers of cheesecloth to remove debris and centrifuged at 21000 g for 5 minutes at 4° C. The supernatant was used in subsequent assays. Protein concentration of the supernatant was quantified by the Bradford assay, using bovine serum albumin as the standard. To start the reaction, 100-200 µg of crude total protein was used. The assay was carried out with and without UDP-glucose to check if glycosylation of cannabinoid substrate was preventing downstream reactions or transport of CBGA. Wild type plants were used as controls to separate endogenous from overexpressed UDP glycosyltransferase activity. The reaction was started by adding 100 µg of protein, and 8 mM uridine diphosphate glucose (UDPG) as the sugar-nucleotide donor to a reaction mixture consisting of approximately 277 µM CBGA, 0.1% (w/v) Triton X-100, 3 mM $MgCl_2$ and 50 mM IVIES (pH 6.0). The reaction was incubated at 30° C. for 3h or overnight for 14 hours. The reaction was terminated by freezing in liquid nitrogen and the samples were stored at −80° C. before LC-MS analysis.

Materials and Methods Example 5: Trichome-Targeted Synthesis and Glycosylation.

As an exemplary plant model, *N. benthamiana* plants were grown from seed and, after 4 weeks of vegetative growth, the leaves were co-infiltrated with *Agrobacterium tumefaciens* GV3101 carrying the following constructs: Trichome CBDAs+trichome UGT in pRI201-AN (trichome construct), PM-UTR1 in pRI201-AN, and p19 silencing suppressor in pDGB3alpha2. In a second experiment, leaves were also infiltrated with the *Agrobacterium* expressing a Ti-plasmid with the Myb/catalase genes. *Agrobacterium* density was normalized to 1 or 2 at absorbance of 600 nm using a spectrophotometer and cultures co-infiltrated in same ratio (1:1:1). After 1 and 4 days post-*Agrobacterium* infiltration (DPI), 1 mL CBGA (277 µM) dissolved in 0.1% Tween20 (Sigma-Aldrich) or 3% DMSO (Sigma-Aldrich) was infiltrated to each leaf. Three biological replicates were used. The experiment was repeated twice. After preliminary results, *Agrobacterium* densities of 2 at OD600 were selected for all following infiltration experiments. Moreover, 0.1% Tween20 was chosen over DMSO 3% due to better solubilizing CBGA substrate.

In this embodiment, leaf samples were collected at 2 DPI and immediately frozen in liquid nitrogen. RNA extraction was done using RNA plant mini-kit as described by manufacturer (Qiagen). cDNA was synthesized using RNA to cDNA Ecodry Premix as described by manufacturer (Takara). Template cDNA was normalized to 50 ng of corresponding total RNA per reaction. Annealing temperature in Celsius: 60. Extension time: 15s. 35 cycles. Q5 DNA polymerase kit used as described by manufacturer (New England Biolabs). RT-PCR primers are outlined in Table 5 below.

Materials and Methods Example 6: Transient Transformation of *Cannabis sativa*.

The present inventors performed *Agrobacterium tumefaciens*-mediated transient transformation of *Cannabis sativa*. The experimental groups consisted of young leaves of high CBD variety (~10% in dried flowers) and trichome leaves of high THC variety (~20% dried flowers).

To transform leaves of high CBD varieties, the present inventors germinated 100 seeds three times; this was done to ensure that a sufficient number of plants would be available for all 9 independent transformation events. To transform trichome leaves, the present inventors used small trichome-containing leaves of several varieties known to be high THC varieties. Experimental set up consisted of 2 different *Agrobacterium tumefaciens* strains. For transient transformation of *Agrobacterium* strain EHA 105, the present inventors grew cells in 10 ml of LB medium supplemented with 100 mg/L of Rifampicin and 50 mg/L of Kanamycin and for *Agrobacterium* strain GV3101::6000 cells were grown with 50 mg/L of Kanamycin, 25 mg/L of Gentamycin and 50 mg/L of Rifampicin. A single *Agrobacterium* colony was used for inoculation and grown overnight. Then, 1 ml of this culture was inoculated into 500 ml of aforementioned LB medium supplemented with 20 µM acetosyringone. Agrobacteria were grown to $OD_{600}$ of approximately between 1 and 1.5. The cells were pelleted in a centrifuge at room temperature and resuspended in infiltration medium containing 10 mM MES, 10 mM $MgCl_2$ and 200 µM acetosyringone to an $OD_{600}$ of 0.5.

Bacterial culture was then used for three different types of *Cannabis Sativa* transformations. In all cases, transformation was done in the form of co-transformation, mixing all relevant strains (plasmids) in equal proportion of cell numbers. First, for the present inventors infiltrated young (two weeks old) fully expended *Cannabis sativa* plants using 1 ml syringe. Prior to transformation, plants were kept under plastic cover, to ensure maximum softness of the leaves. Infiltration was performed from abaxial side, ensuring that the entire surface of the leaf is infiltrated at 12/h/12h day/night at 22° C.

Second, the present inventors vacuum infiltrated detached young (two weeks old) fully expended *Cannabis sativa* leaves. Prior to transformation, plants were kept under plastic cover, to ensure maximum softness of the leaves. Leaves were then placed on half-strength Murashige and Skoog (1962) (½ MS) agar supplemented with 61.8 mM ammonium nitrate and incubated for 5 days at 12/h/12h day/night at 22° C.

Third, trichome leaves were detached, placed into 50 ml Falcon tubes and vacuum infiltrated with aforementioned bacterial solution 2× for 10 min each. Leaves were then placed on ½ MS agar supplemented with 61.8 mM ammonium nitrate and incubated for 5 days.

All experiments were done in triplicates, with the fourth replicate done for collection of DNA/RNA and staining X-gluc for measuring the activity of beta-glucuronidase (GUS) after co-infiltration with *Agrobacterium*-containing GUS gene. In all cases, leaves were harvested after 5 days of transformation, frozen in liquid nitrogen and stored at −80° C.

Materials and Methods Example 7: Extraction of Water-Soluble Cannabinoids from *N. benthamiana*.

Fresh transformed plant material was harvested from greenhouse experiments in 15 or 50 mL polypropylene centrifuge tubes and flash frozen in liquid Na. The frozen plant material was enzymatically quenched by submersing the plant material in boiling methanol for 2 min. The methanol-quenched material was homogenised using a P-10-35 homogenizer (Kinematica, Bohemia NY). The homogenate was extracted by brief agitation in a final volume of 10 mL or 30 mL 70% methanol (v/v) respective to tube size. The resulting extracts were clarified by centrifugation at 2,500 rpm at 4° C. for 15 minutes in a Beckman J-6B floor centrifuge (Beckman Coulter, Indianapolis IN). The supernatant was transferred into a polypropylene tube and evaporated under a stream of Na at 45° C. until dried. The extracts were reconstituted in methanol containing 20 µg/mL of the internal standard 7-Hydroxyoumarin (Sigma-Aldrich, H24003). The reconstituted extracts were placed into 1.5 mL microfuge tubes and clarified in a microcentrifuge at 10,000 g for 15 min. 500 µL of the supernatant was transferred to a 2 mL auto sampler vial and kept at 4° C. until analysis. In vitro assays sample preparation: samples were syringed filtered through 0.45 µm PVDF membrane into a 2 mL auto sampler vial.

Materials and Methods Example 8: Extraction of Water-Soluble Cannabinoids from *Cannabis sativa*.

Fresh plant material was harvested from plants grown in chamber in 1.5 mL polypropylene centrifuge tubes and flash frozen in liquid Na. The frozen plant material was homogenized using pestle and mortar and enzymatically quenched by submersing the plant material in boiling 100% ethanol for 2 min. Homogenized solution was diluted to 70% ethanol. The resulting extracts were clarified by centrifugation at 2,500 rpm at 4° C. for 15 minutes in Eppendorf centrifuge (Centrifuge 5415 R). The supernatant was transferred into a polypropylene tube and concentrated three times using vacuum centrifuge (Speedvac SC110, Savant). 2 µl of 20 µg/mL of the internal standard Umbelliferone (Sigma-Aldrich, H24003) was added to 98 µl of concentrated extract and taken for analysis.

Materials and Methods Example 9: Liquid Chromatography Mass Spectrometry Used to Confirm Functionalization and Glycosylation of Cannabinoids.

The present inventor used liquid chromatography mass spectrometry to confirm functionalization and glycosylation of cannabinoids in the exemplary plant systems described herein. Specifically, mass spectrometry was performed on a quadrupole time-of-flight (QTOF) mass spectrometer (QTOF Micro, Waters, Manchester, UK) equipped with a Lockspray™ electrospray ion source coupled to a Waters Acquity UPLC system (Waters, Manchester, UK). Mass spectra were collected in the negative electrospray ionization mode (ESI−). The nebulization gas was set to 400 L/h at a temperature of 350° C., the cone gas was set to 15 L/H and the source temperature was set to 110° C. A capillary voltage and cone voltage were set to 2500 and 35 V, respectively. The MCP detector voltage was set to 2500 V. The Q-TOF micro MS acquisition rate was set to 1.0 s with a 0.1 s interscan delay. The scan range was from 100 to 1500 m/z. Data was collected in continuum mode. A lockmass solution of 50 ppm raffinose (503.1612 m/z) in 50:50 water:methanol was delivered at 20 µL/min through an auxiliary pump and acquired every 10 s during the MS acquisition. Separations were performed on a Waters HSS T3 C18 column (2.1×100 mm, particle size 1.8 µm) using a Waters ACQUITY UPLC System, equipped with an ACQUITY Binary Solvent Manager, ACQUITY Column Manager and ACQUITY Sample Manager (10 µL sample loop, partial loop injection mode, 5 µL injection volume, 4° C.). Eluents A and B were water and acetonitrile, respectively, both containing 0.1% formic acid. Elution was performed isocratically for 0.5 min at 10% eluent B and then linear gradient 100% eluent B in 14.5 min, and isocratically for 3 min at 100% eluent B. The column was re-equilibrated for 6 min. The flow rate was set to 250 µL/min and the column temperature was maintained at 30° C.

Materials and Methods Example 10: Data Processing.

Identification of individual cannabinoid analogs was performed by the present inventors, by their corresponding accurate mass shifts by Metabolynx (Waters Corp., Milford, USA). The method parameters for data processing were set as follows: retention time range 0.1-18 min, mass range 100-1500 Da, retention time tolerance 0.2 min, mass tolerance 0.05 Da, peak intensity threshold 14. Accurate mass measure of the continuum data was performed using the raffinose lock mass. Raw chromatographic data were additionally processed for extracted ion chromatogram sand peak area integration using Masslynx 4.1 (Waters Corp., Milford, USA). The select cannabinoids, CBGA and CBDA were identified and quantitated using certified reference materials (Cerilliant, Round Rock, TX). All chemical structures and physiochemical and constitutional properties were generated using ChemDoodle version 8.1.0 (IChemLabs™ Chesterfield, VA).

Materials and Methods Example 11: Yeast Cell Gene Expression System.

Figure 35:
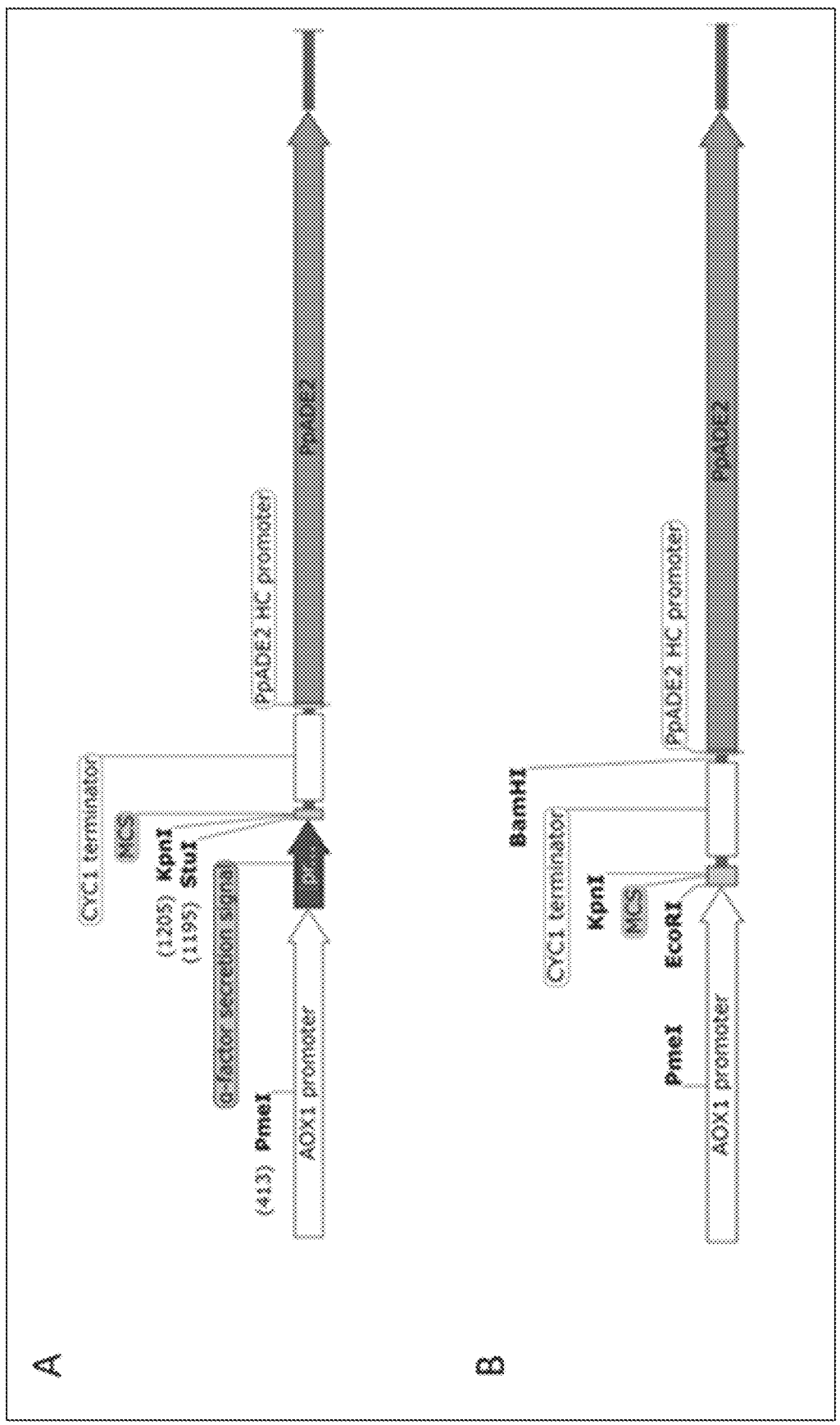
FIG. 35. Part of the pPINK-αHC (A) and pPINK-HC (B) vectors showing the α-factor secretion signal, the ADE2 gene (PpADE2) which produces phosphoribosylaminoimidazole carboxylase in *Pichia pastoris*, utilized for adenine biosynthesis and the multiple cloning site (MSC) for cloning genes of interest. All the genes were cloned in the MCS for both vectors.

The present inventors generated an exemplary yeast-cell expression system based on the methylotrophic yeast *Pichia pastoris* (Komagataella phaffii) was used in this work. The Pichiapink™ system includes protease-deficient host strains and allows both intracellular as well as secreted protein production. In addition, the use of the inducible promoter alcohol oxidase (AOX1) uncouples growth from production of desired proteins, so that cells are not stressed by the accumulation of recombinant protein during growth phase yeast strain 4 (herein referred to as wild-type, WT), a double knockout for proteases prb1, pep4 (to avoid degradation of desired protein), was the background strain in the present inventor's yeast transformations. For secretion of proteins into the media, genes of interest were cloned in frame into the vector pPINK-αHC which contains the *Saccharomyces cerevisiae* α-mating factor pre-sequence for secreted expression of recombinant proteins. For intracellular production of proteins, the vector pPINK-HC was used. Both vectors contained the ADE2 marker for selection on minimal media lacking adenine (FIG. 35). Transformation and selection of transformants was conducted according to the manufacturer's instructions (Invitrogen). Such example is non-limiting, as a variety of expression vectors may be used with the current invention.

Materials and Methods Example 12: Analysis of Yeast System Transgene Expression.

Expression analysis for introduced transgenes was carried out by RT-PCR. For yeast, 2 mL of a 2-day old culture induced by methanol was centrifuged in a microfuge tube. The pellet was ground in a TissueLyser (QIAGEN Inc, USA). RNA was extracted following the EZNA plant RNA extraction kit (Omega Bio-tek Inc, USA). Up to a microgram of total RNA was used to synthesize cDNA using the superscript III cDNA synthesis kit (Thermo Fisher Scientific, USA). The cDNA was used to check for the expression of transgenes by RT-PCR.

Materials and Methods Example 13: Transformation of Tobacco BY2 Cells for Cell Suspension Expression System.

The present inventors used *Agrobacterium* Ti-plasmid mediated transformation with the plant expression vector pRI201-AN (Takara Bio USA), a binary vector for high-level expression of a foreign gene in dicotyledonous plants carrying the constitutive 35S promoter and an *Arabidopsis* Alcohol dehydrogenase (AtAdh) as a translational enhancer. 5 mL of LB containing 50 mg/L kanamycin was inoculated with a single colony of *Agrobacterium tumefaciens* strain GV3101 carrying a binary vector for the expression of the glycosyltransferase 76G1 from *Stevia rebaudiana* (SEQ ID NO. 61 and SEQ ID NO. 62) and the multi-drug ABC transporter ABCG2 (SEQ ID NO. 67 and SEQ ID NO. 68). The *Agrobacterium* culture was grown overnight at 180 rpm and 28° C. to an OD600 of 0.6 to 0.8. For transformation, 10 ml of 3-day old BY2 cell cultures was incubated with 500u1 of the *Agrobacterium* culture and 10 µl of 100 mM acetosyringone for 48 hours in the dark at room temperature in sterile 50 mL falcon tubes. After 48 hours, the cells were washed twice in Murashige and Skoog medium supplemented with 500 mg/L carbenicillin before plating on selective media (Murashige and Skoog supplemented with 500 mg/L carbenicillin and 50 mg/L kanamycin). Calli were picked at 4 weeks and re-plated for further screening for transgene expression.

Materials and Methods Example 14: Statistical Analysis of Yeast and Tobacco Expressions systems.

All experimental treatments were carried out in triplicates. Data were analyzed using GraphPad Prism software package. Student's t-test and one-way analysis of variance (ANOVA) with Dunnett's Multiple Comparison test for comparing multiple lines with the control were used. All analyses for significant differences were performed at P≤0.05.

Materials and Methods Example 15: Yeast and/or Tobacco Cell Suspension Sample Preparation for the Analysis of Water-Soluble Cannabinoids.

Cell suspension cultures were harvested by centrifugation in 15 or 50 mL polypropylene centrifuge tubes. The supernatants were transferred to a new centrifuge tube and both the cell pellet and supernatant was flash frozen in liquid N2. Cell pellets were freeze dried and ~100 mg of material was extracted by bead milling with 250 uL volume of 0.1 mm zirconia beads in 1 mL of 70% methanol: water (v/v) containing 20 μg/mL of the internal standard 7-hydroxyoumarin (Sigma-Aldrich, H24003). The resulting extracts were clarified by centrifugation at 13,000 rcf for 10 minutes. The clarified supernatant was transferred into a 2 mL autosampler. Supernatants were concentrated by freeze drying 2-fold and spiked at 20 pg/mL of the internal standard 7-hydroxyoumarin final concentration. A 1 mL aliquot was transferred to a 2 mL autosampler.

Materials and Methods Example 16: Liquid Chromatography Mass Spectrometry for Yeast and Tobacco Suspension Culture Systems.

Mass spectrometry was performed on a quadrupole time-of-flight (QTOF) mass spectrometer (QTOF Ultima, Waters, Manchester, UK) equipped with a Lockspray™ electrospray ion source coupled to a Waters Acquity UPLC system (Waters, Manchester, UK). Mass spectra were collected in the negative electrospray ionization mode (ESI−). The nebulization gas was set to 650 L/h at a temperature of 500° C., the cone gas was set to 15 L/H and the source temperature was set to 110° C. A capillary voltage and cone voltage were set to 2500 and 35 V, respectively. The MCP detector voltage was set to 2200 V. The Q-TOF Ultima MS acquisition rate was set to 0.25 s with a 0.1 s interscan delay. The scan range was from 100 to 1500 m/z. Data was collected in continuum mode. A lockmass solution of 50 ppm raffinose (503.1612 m/z) in 50:50 water: methanol was delivered at 20 μL/min through an auxiliary pump and acquired every 10 s during the MS acquisition. Separations were performed on a Waters BEH C18 column (2.1×50 mm, particle size 1.8 μm) using a Waters ACQUITY UPLC System, equipped with an ACQUITY Binary Solvent Manager, and ACQUITY Sample Manager (20 μL sample loop, partial loop injection mode, 5 μL (Cell extracts) or 10 μL (Supernatant) injection volume, 4° C.). Eluents A and B were water and acetonitrile, respectively, both containing 0.1% formic acid. Elution was performed isocratically for 0.1 min at 8% eluent B and then linear gradient 100% eluent B in 6.0 min, and isocratically for 1 min at 100% eluent B. The column was re-equilibrated for 1.5 min. The flow rate was set to 500 μL/min and the column temperature was maintained at 40° C.

Materials and Methods Example 17: Data Processing for Individual Cannabinoid Analogs in Yeast and Tobacco Suspension Culture Systems.

Identification of individual cannabinoid analogs was performed, by their corresponding accurate mass shifts by Metabolynx (Waters Corp., Milford, USA). The method parameters for data processing were set as follows: retention time range 0.1-7.5 min, mass range 100-1500 Da, retention time tolerance 0.2 min, mass tolerance 0.05 Da, peak intensity threshold 14. Accurate mass measure of the continuum data was performed using the raffinose lock mass. Raw chromatographic data were additionally processed for extracted ion chromatogram sand peak area integration using Masslynx 4.1 (Waters Corp., Milford, USA). CBGA and CBDA were identified and quantitated using certified reference materials (Cerilliant, Round Rock, TX). All chemical structures and physiochemical and constitutional properties were generated using ChemDoodle version 8.1.0 (IChemLabs™, Chesterfield, VA).

Materials and Methods Example 18: Spectral Analysis of Water Soluble Cannabinoids Identification of Modified Cannabinoids by Mass Spectrometry.

Figure 36:
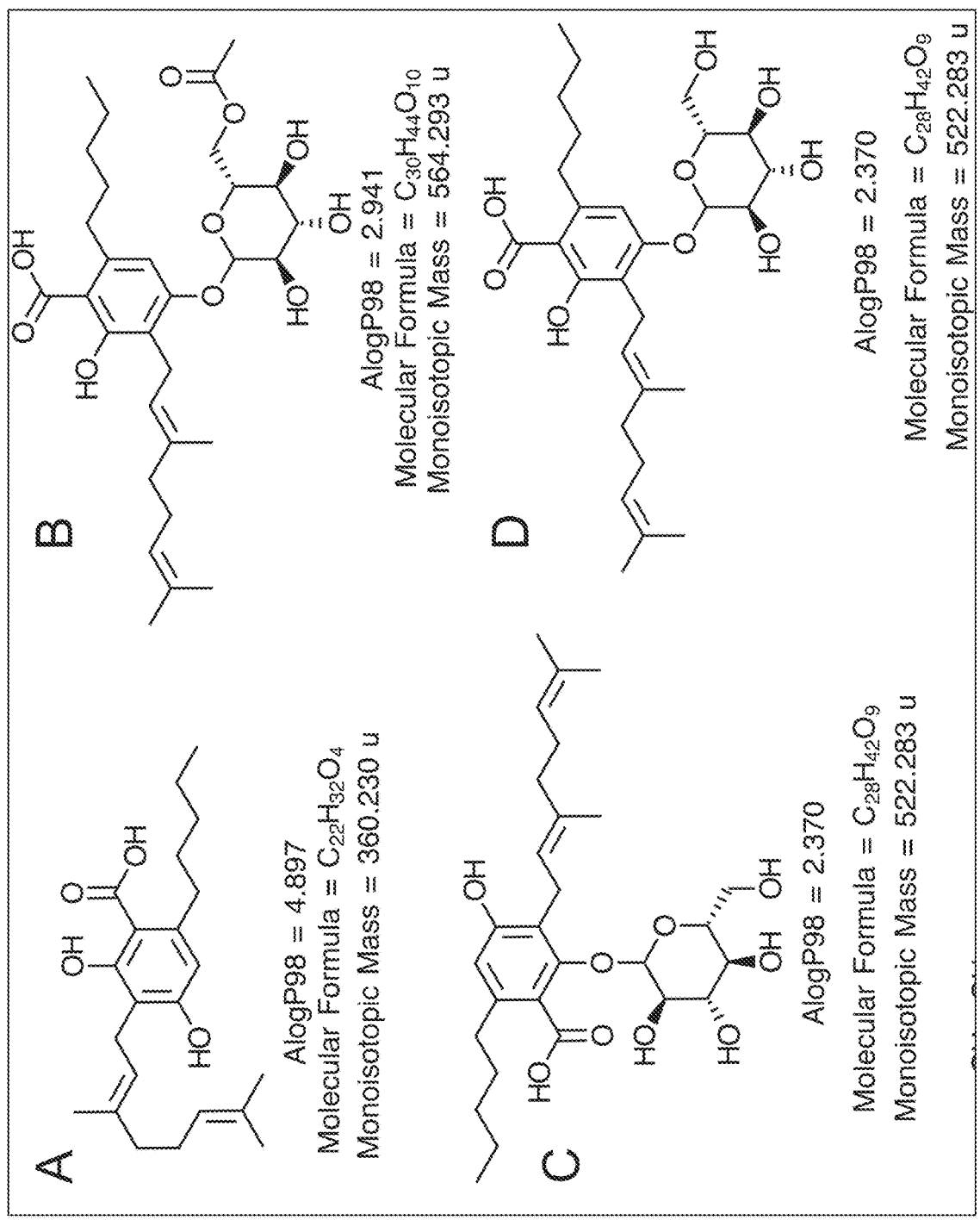
FIG. 36. CBGA Glycoside Structures with Physiochemical and Constitutional Properties. A) CBGA, B) O Acetyl Glycoside, C) 1× Glycoside, D) 1× Glycoside FIG. 37. CBDA Glycoside Structures with Physiochemical and Constitutional Properties. A) CBDA, B) 1× Glycoside, C) 2× Glycoside, D) 0 Acetyl Glycoside, E) 1× Glycoside, F) 2× Glycoside, the disaccharide moiety can also be located on the opposite R—OH of CBDA as illustrated with the single glycoside product found in panels B & E.
Figure 37:
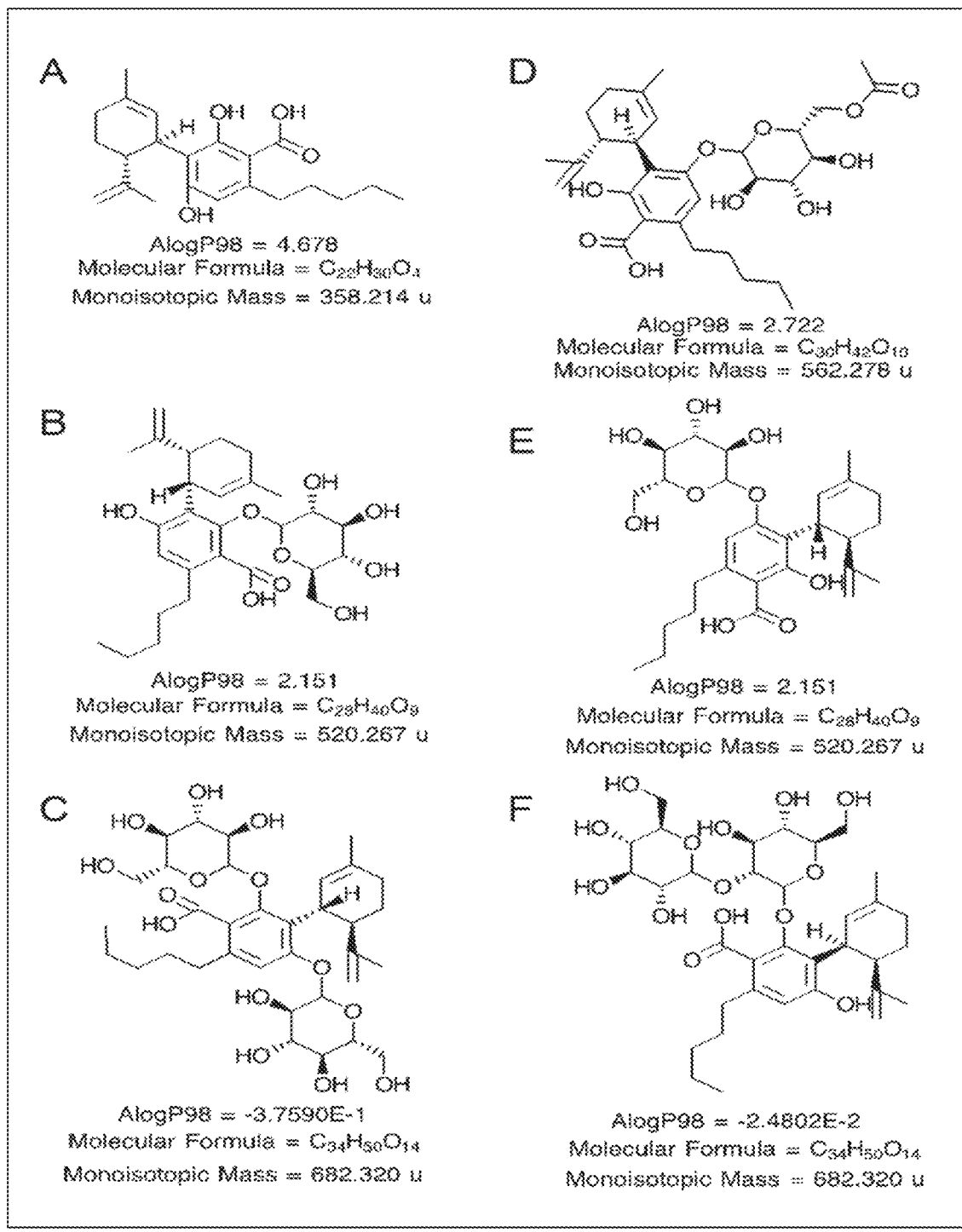

The present inventors identified the cannabinoid biotransformations associated with the gene constructs expressed in tobacco cell suspension and yeast cultures. Based on the predicted glycosylation reactions and empirical information from the chromatographic assays, we predicted the most likely glycosylation events that would occur to the parent molecules CBGA and CBDA along with their physiochemical and constitutional properties (FIGS. 36 and 37, respectively). With this information and through the use of accurate mass measurements, we were able to identify the molecules in the chromatographic analysis and produce extracted ion chromatograms for peak integration as illustrated in FIGS. 38-40. Peak areas for each identified molecule were used for relative quantification between treatments. Based on these results we identified cannabinoid molecules containing up to two glycosides moieties and an O-acetyl glycoside. Summaries of those identifications are presented in Tables 11 and 12 for exemplary cannabinoids CBGA and CBDA respectively.

Materials and Methods Example 19: Cannabinoid Stability in Solution.

The present inventors generated a stock solution of the CBD/CBDA+glycosides mixture in water which was further diluted 10× in all treatment solutions. A 10 mL starting volume was used for all treatments, and all treatments were prepared in triplicate. The initial molar concentration of each substrate was as follows: CBD: 1.85 μM; CBDA: 5.83 μM; 1×CBDA Gly: 0.40 μM; and 1×CBD 0-Acetyl Gly: 0.22 μM. Each sample was incubated at room temperature. Samples were stored in 15 mL polypropylene centrifuge tubes. All samples were shielded from light—tubes were wrapped in aluminum foil. Each sample was prepared in triplicate in the following buffers: water only; pH=3; pH=4; pH=7; pH=8; water only+10 mM ascorbic acid; pH=3+10 mM ascorbic acid; pH=4+10 mM ascorbic acid; pH=7+10 mM ascorbic acid; and pH=8+10 mM ascorbic acid.

Those skilled in the art will appreciate, or be able to ascertain using no more than routine experimentation, further features and advantages of the invention based on the above-described embodiments. Accordingly, the invention is not to be limited by what has been particularly shown and described. All publications and references are herein expressly incorporated by reference in their entirety.

TABLES

TABLE 1

CBGA Biotransformed Products

| Product | RRT to Parent | Expected m/z | Found m/z | Error (mDa) | Error (ppm) | Molecular Formula [M − H]− |
|---|---|---|---|---|---|---|
| R—OH 1 x Glycoside | 0.58 | 537.2700 | 537.2703 | −0.30 | 0.6 | C28H41O10 |
| 2 x Glycoside | 0.59 | 683.3279 | 683.3258 | 2.10 | −3.1 | C34H51O14 |
| 1 x O acetyl Glycoside | 0.73 | 563.2856 | 563.2844 | 1.20 | −2.1 | C30H43O10 |
| 1 x Glycoside #1 | 0.74 | 521.2751 | 521.2734 | 1.70 | −3.3 | C28H41O9 |
| R—OH #1 | 0.80 | 375.2171 | 375.2224 | −5.30 | 14.1 | C22H31O5 |
| 1 x Glycoside #2 | 0.81 | 521.2751 | 521.2727 | 2.40 | −4.6 | C28H41O9 |
| R—OH #2 | 0.81 | 375.2171 | 375.2237 | −6.60 | 17.6 | C22H31O5 |
| R—OH #3 | 0.94 | 375.2171 | 375.2192 | −2.10 | 5.6 | C22H31O5 |
| CBGA | 1.00 | 359.2222 | 359.2245 | −2.30 | 6.4 | C22H31O4 |

RRT Relative Retention Time to Parent Molecule
R—OH Functionalized by addition of O atom

TABLE 2

CBDA Biotransformed Products

| Product | RRT to Parent | Expected m/z | Found m/z | Error (mDa) | Error (ppm) | Molecular Formula [M − H]− |
|---|---|---|---|---|---|---|
| 2 x Glycoside | 0.56 | 681.3122 | 681.3097 | 2.50 | −3.7 | C34H49O14 |
| R—OH 1 x Glycoside | 0.61 | 535.2543 | 535.2599 | −5.60 | 10.5 | C28H39O10 |
| 1 x Glycoside | 0.71 | 519.2601 | 519.2594 | 0.70 | 1.3 | C28H39O9 |
| 1 x O acetyl Glycoside | 0.71 | 561.2700 | 561.2700 | 0.00 | 0 | C30H41O10 |
| R—OH #1 | 0.84 | 373.2015 | 373.2074 | −5.90 | 15.8 | C22H29O5 |
| R—OH #2 | 0.87 | 373.2015 | 373.2034 | −1.90 | 5.1 | C22H29O5 |
| R—OH #3 | 0.96 | 373.2015 | 373.2040 | −2.50 | −8 | C22H29O5 |
| CBDA | 1.00 | 357.2066 | 357.2122 | −5.60 | 15.7 | C22H29O4 |

RRT Relative Retention Time to Parent Molecule
R—OH Functionalized by addition of O atom'

TABLE 3

Forward and reverse primers for RT-PCR of CYP3A4 and P450 oxidoreductase. SEQ. ID NO. 76 represents the forward primer of CYP3A4; SEQ. ID NO. 77 represents the reverse primer of CYP3A4; SEQ. ID NO. 78 represents the forward primer of P450 oxidoreductase; and SEQ. ID NO. 79 represents the reverse primer of P450 oxidoreductase.

| Sequence | CYP3A4 | P450 oxidoreductase |
|---|---|---|
| Primers for RT-PCR | Forward TGCCTAATAAAGCTCCTCCTACT<br>Reverse GCTCCTGAAACAGTTCCATCTC | Forward GGAAGAGCTTTGGTTCCTATGT<br>Reverse GCTCCCAATTCAGCAACAATATC |

TABLE 4

Forward and reverse primers for CBDA synthase, UGT76G1 and ABCG2. SEQ. ID NO. 80 represents the forward primer of CBDA synthase; SEQ. ID NO. 81 represents the reverse primer of CBDA synthase; SEQ. ID NO. 82 represents the forward primer of UGT76G1; SEQ. ID NO. 83 represents the reverse primer of UGT76G1; SEQ. ID NO. 84 represents the forward primer of ABCG2; and SEQ. ID NO. 85 represents the reverse primer of ABCG2.

| Sequence | CBDA synthase | UGT76G1 | ABCG2 |
|---|---|---|---|
| Primers for RT-PCR | Forward primer:<br>ACATCACAATCACACA<br>AAACTAACAAAAG<br>Reverse primer:<br>GGCCATAGTTTCTCAT<br>CAATGG | Forward primer:<br>GATTGGAAGAACAAGCTT<br>CAGGATTTCC<br>Reverse primer:<br>CCATCCTGAATGAGTCCA<br>AAAAGCTC | Forward primer:<br>CCTTCAGGATTGTCAGGA<br>GATG<br>Reverse primer:<br>GCAGGTCCATGAAACAT<br>CAATC |

TABLE 5

Trichome-targeted CBDA synthase (CBDAs), Trichome-targeted UGT and PM-targeted UTR1. SEQ. ID NO. 86 represents the forward primer of Trichome-targeted CBDAs; SEQ. ID NO. 87 represents the reverse primer of Trichome-targeted CBDAs; SEQ. ID NO. 88 represents the forward primer of Trichome-targeted UGT; SEQ. ID NO. 89 represents the reverse primer of Trichome-targeted UGT; SEQ. ID NO. 90 represents the forward primer of Plasma membrane-targeted UTRI; and SEQ. ID NO. 91 represents the reverse primer of Plasma membrane-targeted UTRI.

| Sequence | Trichome-targeted CBDAs | Trichome-targeted UGT | Plasma membrane-targeted UTR1 |
|---|---|---|---|
| Primers for RT-PCR | Forward primer: AAAGATCAAAAGCAAGTTCTTCACTGT<br>Reverse primer: CCATGCAGTTTGGCTATGAACATCT | Forward primer: AGTGCTCAACATTCTCCTTTTGGTT<br>Reverse primer: TCTGAAGCCAACATCAACAATTCCA | Forward primer: TTGTTCCTTAAACCTCGCCTTTGAC<br>Reverse primer: TCATTATGGAGCACTCCACTCTCTG |

TABLE 6

Cytosolic-targeted CBDA synthase (cytCBDAs), Cytosolic-targeted UGT (cytUGT). SEQ. ID NO. 92 represents the forward primer of Cytosolic-targeted CBDA synthase; SEQ. ID NO. 93 represents the reverse primer of Cytosolic-targeted CBDA synthase; SEQ. ID NO. 94 represents the forward primer of Cytosolic-targeted UGT; and SEQ. ID NO. 95 represents the reverse primer of Cytosolic-targeted UGT.

| Sequence | Cytosolic-targeted CBDA synthase | Cytosolic-targeted UGT |
|---|---|---|
| Primers for RT-PCR | Forward primer: AAAGATCAAAAGCAAGTTCTTCACTGT<br>Reverse primer: ATAAACTTCTCCAAGGGTAGCTCCG | Forward primer: AGAACTGGAAGAATCCGAACTGGAA<br>Reverse primer: AAATCATCGGGACACCTTCACAAAC |

TABLE 7

Summary of results from glycosylation and functionalization experiments in *N. benthamiana* leaves.

| *Agrobacterium* Constructs | Substrate fed | CBGA (relative amount) | CBGA glycoside (relative amount) | CBGA glycoside + acetylated (relative amount) | CBDA (relative amount) | CBDA glycoside (relative amount) | CBDA Hydroxyl (relative amount) |
|---|---|---|---|---|---|---|---|
| Trichome CBDA synthase + trichome glycosyltransferase + PM-UTR1 + Myb/catalase* + P19 silencing supressor* | CBGA | + | + | + | + | ND | ND |
| Cytosolic CBDA synthase, glycosyltransferase and plasma membrane ABC transporter) + Myb/catalase + P19 silencing suppressor | CBGA | + | +++ | +++ | +++ | ND | ND |
| 201-SUS (cytosolic CBDA synthase, glycosyltransferase and plasma membrane ABC transporter) | CBGA | + | +++ | ++++ | + | + | + |
| CYP3A4 + oxidoreductase (cytochrome P450 with P450 oxidoreductase) | CBDA | ND | + | ND | +++ | +++++ | +++++ |
| Cytosolic CBDA synthase + cytosolic glycosyltransferase + Myb/catalase* + P19 silencing suppressor* | CBGA | ++++ | +++++ | +++++ | ND | ++ | ++ |
| P450/MYBcatalase/cytosolic CBDA synthase, glycosyltransferase and plasma membrane ABC transporter | CBGA | + | ++++ | + | ND | ++ | ++ |

TABLE 7-continued

Summary of results from glycosylation and functionalization experiments in *N. benthamiana* leaves.

| Agrobacterium Constructs | Substrate fed | CBGA (relative amount) | CBGA glycoside (relative amount) | CBGA glycoside + acetylated (relative amount) | CBDA (relative amount) | CBDA glycoside (relative amount) | CBDA Hydroxyl (relative amount) |
|---|---|---|---|---|---|---|---|
| No *agrobacterium* (negative control) | CBGA | + | + | + | ND | ND | ND |

*Co-infiltration with and without construct was tested in different replicates

TABLE 8

Summary of results from glycosylation and functionalization experiments in *Cannabis sativa* leaves.

| Agrobacterium Constructs | CBDA (relative amount) | CBDA glycoside (relative amount) | CBDA Hydroxyl (relative amount) |
|---|---|---|---|
| Trichome CBDA synthase + trichome glycosyltransferase + plasma membrane-targeted sugar transporter) + Myb/catalase | ++ | trace | trace |
| cytosolic CBDA synthase, cytosolic glycosyltransferase + Myb/catalase | +++ | ++++ | +++++ |
| 201-SUS (cytosolic CBDA synthase, glycosyltransferase and plasma membrane ABC transporter) | ++ | ++ | ++ |

TABLE 9

Exemplary Glycosyltransferase sequence identification

| SEQ ID NO. | Name | Organism | Type |
|---|---|---|---|
| SEQ ID NO. 26 | NtGT5a | *Nicotiana tabacum* | Amino Acid |
| SEQ ID NO. 27 | NtGT5a | *Nicotiana tabacum* | DNA |
| SEQ ID NO. 28 | NtGT5b | *Nicotiana tabacum* | Amino Acid |
| SEQ ID NO. 29 | NtGT5b | *Nicotiana tabacum* | DNA |
| SEQ ID NO. 30 | NtGT4 | *Nicotiana tabacum* | Amino Acid |
| SEQ ID NO. 31 | NtGT4 | *Nicotiana tabacum* | DNA |
| SEQ ID NO. 32 | NtGT1b | *Nicotiana tabacum* | Amino Acid |
| SEQ ID NO. 33 | NtGT1b | *Nicotiana tabacum* | DNA |
| SEQ ID NO. 34 | NtGT1a | *Nicotiana tabacum* | Amino Acid |
| SEQ ID NO. 35 | NtGT1a | *Nicotiana tabacum* | DNA |
| SEQ ID NO. 36 | NtGT3 | *Nicotiana tabacum* | Amino Acid |
| SEQ ID NO. 37 | NtGT3 | *Nicotiana tabacum* | DNA |
| SEQ ID NO. 38 | NtGT2 | *Nicotiana tabacum* | Amino Acid |
| SEQ ID NO. 39 | NtGT2 | *Nicotiana tabacum* | DNA |

TABLE 10

Cannabinoid production cellular compartmentalization models. Different shaded columns and rows correspond to different exemplary expression constructs used.

| Cannabinoid production/ accumulation system | CBDA Synthase | UDP glycosyl transferase | Cannabinoid ABC transporter | UDP glucose transporter | Myb transcription factor for cannabinoids | Catalase to degrade $H_2O_2$ from CBDA Synthase |
|---|---|---|---|---|---|---|
| Cytoplasmic accumulation | Minus trichome target sequence | Required but no targeting change | No gene required | No gene required | Express | Express |
| Trichome (low pH) synthesis | No change | Add trichome target sequence | No gene required | Target to plasma membrane | Express | Express |
| Cell suspension cultures | Minus trichome target sequence | Required but no targeting change | Target to plasma membrane (PM) | No gene required | Express | Express |

TABLE 11

CBGA Biotransformed Products

| Product | RRT to Parent | Expected m/z | Found m/z | Error (mDa) | Error (ppm) | Molecular Formula [M − H]− |
|---|---|---|---|---|---|---|
| 1 x Glycoside | 0.72 | 521.2751 | 521.2700 | −5.1 | −9.8 | C28H41O9 |
| CBGA | 1.00 | 359.2222 | 359.2190 | −3.2 | −8.9 | C22H31O4 |

RRT Relative Retention Time to Parent Molecule

TABLE 12

CBDA Biotransformed Products

| Product | RRT to Parent | Expected m/z | Found m/z | Error (mDa) | Error (ppm) | Molecular Formula [M − H]− |
|---|---|---|---|---|---|---|
| 2 x Glycoside | 0.52 | 681.3122 | 681.3076 | −4.76 | −6.8 | C34H49O14 |
| 1 x Glycoside #1 | 0.67 | 519.2594 | 519.2583 | −1.1 | −2.1 | C28H39O9 |
| 1 x O acetyl Glycoside | 0.68 | 561.2700 | 561.2653 | −4.7 | −8.4 | C30H41O10 |
| 1 x Glycoside #2 | 0.80 | 519.2594 | 519.2681 | 8.8 | 16.7 | C28H39O9 |
| CBDA | 1.00 | 357.2066 | 357.2091 | 2.5 | 7.0 | C22H29O4 |

RRT Relative Retention Time to Parent Molecule

Based on the reduced retention time in the HPLC gradient. The glycosylated cannabinoids, which eluted earlier than their non-modified forms, are demonstrated to be more water-soluble than their non-modified forms.

TABLE 13

RT-PCR primers for confirmation of gene expression in transgenic intracellular Pichia and tobacco cultures. SEQ. ID NO. 96 represents the forward primer of NtGT1; SEQ. ID NO. 97 represents the reverse primer of NtGT1; SEQ. ID NO. 98 represents the forward primer of NtGT2; SEQ. ID NO. 99 represents the reverse primer of NtGT2; SEQ. ID NO. 100 represents the forward primer of NtGT3; SEQ. ID NO. 101 represents the reverse primer of NtGT3; SEQ. ID NO. 102 represents the forward primer of NtGT4; SEQ. ID NO. 103 represents the reverse primer of NtGT4; SEQ. ID NO. 104 represents the forward primer of NtGT5; SEQ. ID NO. 105 represents the reverse primer of NtGT5; SEQ. ID NO. 106 represents the forward primer for Kat-E; SEQ. ID NO. 107 represents the reverse primer for Kat-E; SEQ. ID NO. 108 represents the forward primer of UGT76G1; SEQ. ID NO. 109 represents the reverse primer of UGT76G1; SEQ. ID NO. 110 represents the forward primer of UGT76G1 (for tobacco BY2 cells); SEQ. ID NO. 111 represents the reverse primer of UGT76G1 (for tobacco BY2 cells); SEQ. ID NO. 112 represents the forward primer of ABCG2 (for tobacco BY2 cells); and SEQ. ID NO. 113 represents the reverse primer of ABCG2 (for tobacco BY2 cells).

| Target gene | Forward primer | Reverse primer |
|---|---|---|
| NtGT1 | ATGAAAACAACAGAACTTGTCTTCA | TGAAGTTGTAGGCCTAGCATGG |
| NtGT2 | ATGGTTCAACCACACGTCTTACTGG | TTGAATACACCAGTTGGGGTCG |
| NtGT3 | ATGAAAGAGACTAAAAAAATTGAGT | CATCACGCAGATTTTGAATATGG |
| NtGT4 | ATGGCTACTCAGGTGCATAAATTGC | GGCCTTAGTTAGCTCGACACGG |
| NtGT5 | ATGGGCTCTATCGGTGCAGAACTAA | CGGGGATGAAGTCCAAGGTTGT |
| Kat-E | ATGTCTCAACATAACGAGAAAAACC | CGTAGCAAATCCCCTGATGTCT |
| UGT76G1 | ATGGAGAACAAAACCGAGACAACCG | CCTTTAGCATGGGAAAACCGGA |
| UGT76G1 (for tobacco BY2 cells) | GATTGGAAGAACAAGCTTCAGGATTTCC | CCATCCTGAATGAGTCCAAAAAGCTC |
| ABCG2 (for tobacco BY2 cells) | CCTTCAGGATTGTCAGGAGATG | GCAGGTCCATGAAACATCAATC |

TABLE 14

Day 0 time course incubation of unmodified, glycosylated, and acetylated cannabinoid glycoside compounds in solution.

| Day 0 (ug/mL) | CBD | CBDA | 1X CBDA Gly | 1X CBD O-Acetyl Gly |
|---|---|---|---|---|
| Water | 399.81 ± 111.06 | 1689.45 ± 345.00 | 230.85 ± 36.38 | 137.46 ± 35.49 |
| pH = 3 | 568.71 ± 115.90 | 2278.25 ± 279.51 | 217.58 ± 45.40 | 126.49 ± 43.90 |
| pH = 4 | 505.97 ± 5.10 | 1941.33 ± 141.84 | 179.48 ± 20.25 | 101.60 ± 31.49 |

TABLE 14-continued

Day 0 time course incubation of unmodified, glycosylated, and acetylated cannabinoid glycoside compounds in solution.

| Day 0 (ug/mL) | CBD | CBDA | 1X CBDA Gly | 1X CBD O-Acetyl Gly |
|---|---|---|---|---|
| pH = 7 | 528.04 ± 91.17 | 2098.05 ± 71.62 | 199.19 ± 24.03 | 107.55 ± 20.03 |
| pH = 8 | 513.35 ± 39.23 | 1907.82 ± 81.03 | 190.06 ± 16.22 | 108.41 ± 12.42 |
| Water + AA | 561.85 ± 86.83 | 1925.54 ± 266.50 | 198.81 ± 27.15 | 102.24 ± 12.18 |
| pH = 3 + AA | 565.75 ± 40.96 | 2099.04 ± 78.79 | 190.77 ± 3.98 | 110.44 ± 13.31 |
| pH = 4 + AA | 524.40 ± 34.95 | 1928.33 ± 22.80 | 190.28 ± 14.45 | 118.27 ± 1.16 |
| pH = 7 + AA | 500.03 ± 21.45 | 1956.80 ± 114.66 | 185.33 ± 20.89 | 108.19 ± 19.12 |
| pH = 8 + AA | 1136.36 ± 996.36 | 3072.96 ± 1630.46 | 315.93 ± 180.23 | 137.53 ± 6.71 |

TABLE 15

Day 1 time course incubation of unmodified, glycosylated, and acetylated cannabinoid glycoside compounds in solution.

| Day 1 (ug/mL) | CBD | CBDA | 1X CBDA Gly | 1X CBD Gly | 1X CBD O-Acetyl Gly |
|---|---|---|---|---|---|
| Water | 629.00 ± 383.79 | 2132.80 ± 1412.98 | 205.52 ± 198.82 | 1.20 ± 21.68 | 136.86 ± 139.68 |
| pH = 3 | 713.93 ± 41.47 | 2550.09 ± 85.93 | 299.02 ± 9.63 | 8.83 ± 1.80 | 216.46 ± 9.61 |
| pH = 4 | 380.77 ± 233.10 | 1504.66 ± 600.27 | 177.59 ± 62.72 | below LOQ | 150.94 ± 27.25 |
| pH = 7 | 880.54 ± 5.87 | 2577.70 ± 0.44 | 345.49 ± 23.25 | 15.45 ± 0.07 | 250.75 ± 6.23 |
| pH = 8 | 747.61 ± 101.87 | 2572.31 ± 140.62 | 326.74 ± 21.82 | 12.86 ± 4.15 | 221.10 ± 16.30 |
| Water + AA | 428.63 ± 198.77 | 1765.03 ± 561.85 | 246.74 ± 47.28 | 7.99 ± 4.17 | 204.63 ± 24.09 |
| pH = 3 + AA | 650.49 ± 12.10 | 2330.65 ± 45.55 | 283.54 ± 46.51 | 9.78 ± 5.27 | 223.32 ± 48.67 |
| pH = 4 + AA | 406.17 ± 210.69 | 1614.31 ± 504.29 | 230.30 ± 51.72 | 5.82 ± 3.11 | 198.56 ± 24.37 |
| pH = 7 + AA | 505.88 ± 276.58 | 1944.55 ± 741.75 | 249.00 ± 83.03 | 5.73 ± 4.70 | 185.02 ± 35.46 |
| pH = 8 + AA | 291.15 ± 78.65 | 1331.89 ± 302.72 | 195.97 ± 48.06 | 1.04 ± 4.15 | 180.83 ± 33.60 |

TABLE 16

Day 4 time course incubation of unmodified, glycosylated, and acetylated cannabinoid glycoside compounds in solution.

| Day 4 (ug/mL) | CBD | CBDA | 1X CBDA Gly | 1X CBD Gly | 1X CBD O-Acetyl Gly |
|---|---|---|---|---|---|
| Water | 432.54 ± 251.39 | 348.83 ± 126.90 | 50.55 ± 10.85 | 15.11 ± 10.77 | 160.23 ± 23.75 |
| pH = 3 | 191.94 ± 55.68 | 215.62 ± 28.65 | 35.62 ± 8.29 | 18.94 ± 4.88 | 174.88 ± 14.16 |
| pH = 4 | 278.33 ± 85.33 | 264.51 ± 58.26 | 65.29 ± 9.09 | 29.03 ± 8.17 | 225.84 ± 39.59 |
| pH = 7 | 539.55 ± 260.69 | 373.85 ± 102.13 | 51.73 ± 7.48 | 19.64 ± 3.44 | 190.05 ± 24.38 |
| pH = 8 | 560.90 ± 69.27 | 461.23 ± 80.64 | 61.23 ± 21.53 | 26.99 ± 15.29 | 174.09 ± 59.87 |
| Water + AA | 182.66 ± 25.03 | 197.39 ± 11.23 | 33.74 ± 8.21 | 17.55 ± 5.99 | 153.06 ± 28.19 |
| pH = 3 + AA | 232.39 ± 113.88 | 217.83 ± 61.23 | 31.98 ± 6.06 | 17.99 ± 4.60 | 157.19 ± 1.58 |
| pH = 4 + AA | 305.20 ± 97.35 | 267.13 ± 59.52 | 40.84 ± 3.72 | 17.02 ± 5.68 | 144.44 ± 18.85 |
| pH = 7 + AA | 398.16 ± 391.86 | 286.12 ± 150.45 | 41.31 ± 15.16 | 19.96 ± 9.83 | 176.48 ± 33.58 |
| pH = 8 + AA | 173.43 ± 17.53 | 182.43 ± 4.69 | 35.59 ± 2.84 | 15.86 ± 2.63 | 152.03 ± 5.79 |

TABLE 17

Day 5 time course incubation of unmodified, glycosylated, and acetylated cannabinoid glycoside compounds in solution.

| Day 5 (ug/mL) | CBD | CBDA | 1X CBDA Gly | 1X CBD Gly | 1X CBD O-Acetyl Gly |
|---|---|---|---|---|---|
| Water | 466.09 ± 130.53 | 232.98 ± 82.28 | 27.85 ± 10.52 | 14.60 ± 1.31 | 131.77 ± 33.91 |
| pH = 3 | 330.79 ± 138.28 | 151.00 ± 27.30 | 14.46 ± 6.76 | 18.00 ± 0.59 | 83.72 ± 35.56 |
| pH = 4 | 510.50 ± 76.06 | 166.21 ± 10.23 | 33.83 ± 4.89 | 18.26 ± 0.52 | 164.84 ± 35.61 |
| pH = 7 | 593.92 ± 6.30 | 214.85 ± 24.56 | 36.02 ± 8.21 | 17.50 ± 1.63 | 186.93 ± 5.65 |
| pH = 8 | 498.21 ± 92.88 | 324.72 ± 32.71 | 37.06 ± 3.83 | 19.73 ± 0.55 | 162.75 ± 31.35 |
| Water + AA | 448.64 ± 33.51 | 134.25 ± 11.78 | 18.19 ± 2.31 | 19.70 ± 0.80 | 146.60 ± 10.68 |
| pH = 3 + AA | 320.48 ± 92.87 | 119.25 ± 35.92 | 13.83 ± 7.04 | 19.29 ± 3.26 | 97.81 ± 29.67 |
| pH = 4 + AA | 366.65 ± 92.35 | 141.46 ± 34.95 | 17.99 ± 5.54 | 19.34 ± 1.90 | 113.89 ± 31.15 |
| pH = 7 + AA | 353.25 ± 135.11 | 160.93 ± 99.51 | 18.25 ± 14.93 | 19.05 ± 3.91 | 110.66 ± 48.12 |
| pH = 8 + AA | 287.24 ± 39.56 | 110.83 ± 6.09 | 12.07 ± 2.03 | 20.14 ± 1.73 | 92.06 ± 15.47 |

TABLE 18

Day 6 time course incubation of unmodified, glycosylated, and acetylated cannabinoid glycoside compounds in solution.

| Day 6 (ug/mL) | CBD | CBDA | 1X CBDA Gly | 1X CBD Gly | 1X CBD O-Acetyl Gly |
|---|---|---|---|---|---|
| Water | 179.13 ± 17.88 | 177.27 ± 31.31 | 24.40 ± 9.39 | 8.56 ± 7.04 | 148.36 ± 33.57 |
| pH = 3 | 607.98 ± 416.07 | 299.37 ± 129.48 | 29.72 ± 11.20 | 21.59 ± 7.97 | 175.06 ± 31.37 |
| pH = 4 | 897.52 ± 65.92 | 437.55 ± 32.34 | 47.69 ± 7.79 | 32.87 ± 8.08 | 231.03 ± 36.34 |
| pH = 7 | 1115.01 ± 169.64 | 516.99 ± 40.18 | 67.01 ± 7.94 | 46.80 ± 10.12 | 267.45 ± 30.83 |
| pH = 8 | 911.61 ± 84.17 | 492.64 ± 27.37 | 62.45 ± 1.31 | 44.10 ± 3.45 | 218.64 ± 22.05 |
| Water + AA | 957.17 ± 315.70 | 446.90 ± 93.03 | 46.98 ± 17.51 | 34.98 ± 9.28 | 200.20 ± 37.42 |
| pH = 3 + AA | 801.14 ± 230.88 | 407.88 ± 70.00 | 37.19 ± 11.66 | 27.67 ± 9.51 | 190.69 ± 36.71 |
| pH = 4 + AA | 777.26 ± 56.02 | 408.97 ± 19.32 | 41.59 ± 4.42 | 31.67 ± 4.29 | 215.72 ± 16.69 |
| pH = 7 + AA | 828.02 ± 269.38 | 448.43 ± 75.60 | 47.26 ± 13.89 | 30.43 ± 4.82 | 205.61 ± 26.64 |
| pH = 8 + AA | 847.26 ± 88.56 | 439.50 ± 16.67 | 46.68 ± 2.47 | 32.97 ± 1.31 | 217.66 ± 11.23 |

TABLE 19

Day 7 time course incubation of unmodified, glycosylated, and acetylated cannabinoid glycoside compounds in solution.

| Day 7 (ug/mL) | CBD | CBDA | 1X CBDA Gly | 1X CBD Gly | 1X CBD O-Acetyl Gly |
|---|---|---|---|---|---|
| Water | 680.13 ± 229.24 | 373.94 ± 53.04 | 43.73 ± 8.52 | 23.89 ± 5.27 | 185.62 ± 22.87 |
| pH = 3 | 563.80 ± 65.50 | 320.95 ± 26.33 | 35.76 ± 6.26 | 27.06 ± 4.05 | 195.77 ± 15.07 |
| pH = 4 | 641.86 ± 33.49 | 335.80 ± 1.93 | 41.68 ± 3.18 | 26.96 ± 0.46 | 201.23 ± 6.99 |
| pH = 7 | 544.28 ± 57.97 | 312.75 ± 23.38 | 38.14 ± 5.56 | 22.14 ± 6.83 | 187.10 ± 28.07 |
| pH = 8 | 580.54 ± 94.41 | 341.39 ± 18.75 | 45.78 ± 9.19 | 32.42 ± 8.76 | 193.61 ± 21.84 |
| Water + AA | 592.44 ± 87.97 | 303.62 ± 20.47 | 36.23 ± 7.46 | 24.99 ± 7.29 | 167.42 ± 22.79 |
| pH = 3 + AA | 464.35 ± 105.43 | 291.96 ± 59.24 | 27.10 ± 1.76 | 19.38 ± 0.46 | 147.21 ± 8.07 |
| pH = 4 + AA | 557.34 ± 60.39 | 321.77 ± 18.46 | 33.65 ± 4.13 | 23.30 ± 3.95 | 166.23 ± 17.10 |
| pH = 7 + AA | 549.93 ± 39.69 | 342.03 ± 11.62 | 40.31 ± 2.01 | 39.57 ± 4.63 | 157.89 ± 17.21 |
| pH = 8 + AA | 630.99 ± 2.44 | 367.78 ± 11.21 | 45.19 ± 2.45 | 37.93 ± 2.89 | 181.7 ± 29.53 |

PRESERVED CLAUSES

Each of the below clauses is specifically incorporated into the specification of the current application. Each of the below clauses may be amended and presented as a formal claim and further represents an independent invention. It should be noted that for each instance that a preserved clause indicates a glycosylated cannabinoid, and/or an acetylated cannabinoid, such clause should also expressly include and/or a cannabinoid glucuronide or other water-soluble cannabinoid.

1. A composition comprising:
an aqueous solution;
water-soluble cannabinoid dissolved in said aqueous solution wherein said water-soluble cannabinoid comprises a glycosylated cannabinoid, and/or an acetylated cannabinoid, and/or a mixture of both;
wherein said composition may be introduced to a food or beverage.

2. The composition of clause 1, wherein said glycosylated cannabinoid, and/or said acetylated cannabinoid were generated in vivo.

3. The composition of clause 1, wherein said glycosylated cannabinoid, and/or said acetylated cannabinoid were generated in vitro.

4. The composition of clause 1, wherein said water-soluble cannabinoid is non-psychoactive.

5. The composition of clause 1, wherein said aqueous solution comprises an aqueous solution selected from the group consisting of: saline, purified water, ethanol.

6. The composition of clause 1, wherein said aqueous solution comprises propylene glycol, deionized water, an alcohol.

7. The composition of clause 1, wherein said alcohol comprises ethanol.

8. The composition of clause 7, further comprising a buffer.

9. The composition of clause 8, wherein said buffer maintains said aqueous solution at a pH below 7.4.

10. The composition of clause 7, further comprising formic acid, or ammonium hydroxide.

11. A consumable food additive comprising at least one water-soluble glycosylated cannabinoid.

12. A consumable food additive as described in clause 11 and further comprising a food additive polysaccharide.

13. A consumable food additive as described in clause 12 wherein said food additive polysaccharide comprises dextrin and/or maltodextrin.

14. A consumable food additive as described in clause 11 and further comprising a emulsifier.

15. A consumable food additive as described in clause 14 wherein said emulsifier is selected from the group consisting of: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, *quillaia*, whey protein isolate, casein, soy protein, vegetable protein, pullulan, sodium alginate, guar gum, locust bean gum, tragacanth gum, tamarind gum, carrageenan, furcellaran, Gellan gum, *psyllium*, curdlan, konjac mannan, agar, and cellulose derivatives, or combinations thereof.

16. A consumable food additive as described in clause 11, wherein said water-soluble glycosylated cannabinoid is a non-psychoactive cannabinoid.

17. A consumable food additive as described in clause 11, wherein said water-soluble glycosylated cannabinoid is generated in vivo.

18. A consumable food additive as described in clause 11, wherein said water-soluble glycosylated cannabinoid is generated in vitro.

19. A consumable food additive as described in clause 13, wherein said consumable food additive is a homogenous composition.

20. A consumable food additive as described in clause 11, and further comprising a flavoring agent.

21. A consumable food additive as described in clause 20 wherein said flavoring agent comprises a flavoring agent selected from the group consisting of: Sucrose (sugar), glucose, fructose, sorbitol, mannitol, corn syrup, high fructose corn syrup, saccharin, aspartame, sucralose, acesulfame potassium (acesulfame-K), neotame.

22. A consumable food additive as described in clause 11, and further comprising a coloring agent.

23. A consumable food additive as described in clause 22 wherein said coloring agent comprises a coloring agent selected from the group consisting of: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate 24. A consumable food additive as described in clause 11, and further comprising a surfactant.

25. A consumable food additive as described in clause 24 wherein said surfactant comprises a surfactant selected from the group consisting of glycerol monostearate and polysorbate 80.

26. A consumable food additive as described in clause 11, and further comprising a preservative.

27. A consumable food additive as described in clause 26, wherein said preservative comprises a preservative selected from the group consisting of: ascorbic acid, citric acid, sodium benzoate, calcium propionate, sodium erythorbate, sodium nitrite, calcium sorbate, potassium sorbate, BHA, BHT, EDTA, tocopherols.

28. A consumable food additive as described in clause 11 and further comprising a nutrient supplement.

29. A consumable food additive as described in clause 28, wherein said nutrient supplement comprises a nutrient supplement selected from the group consisting of: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

30. A consumable food additive as described in clause 11 and further comprising at least one water-soluble acetylated cannabinoid.

31. A consumable food additive comprising at least one water-soluble acetylated cannabinoid.

32. A consumable food additive as described in clause 31 and further comprising a food additive polysaccharide.

33. A consumable food additive as described in clause 32 wherein said food additive polysaccharide comprises dextrin and/or maltodextrin.

34. A consumable food additive as described in clause 32 and further comprising a emulsifier.

35. A consumable food additive as described in clause 34 wherein said emulsifier is selected from the group consisting of: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, *quillaia*, whey protein isolate, casein, soy protein, vegetable protein, pullulan, sodium alginate, guar gum, locust bean gum, tragacanth gum, tamarind gum, carrageenan, furcellaran, Gellan gum, *psyllium*, curdlan, konjac mannan, agar, and cellulose derivatives, or combinations thereof.

36. A consumable food additive as described in clause 31, wherein said water-soluble acetylated cannabinoid is a non-psychoactive cannabinoid.

37. A consumable food additive as described in clause 31, wherein said water-soluble acetylated cannabinoid is generated in vivo.

38. A consumable food additive as described in clause 31, wherein said water-soluble acetylated cannabinoid is generated in vitro.

39. A consumable food additive as described in clause 31, wherein said consumable food additive is a homogenous composition.

40. A consumable food additive as described in clause 31, and further comprising a flavoring agent.

41. A consumable food additive as described in clause 40 wherein said flavoring agent comprises a flavoring agent selected from the group consisting of: Sucrose (sugar), glucose, fructose, sorbitol, mannitol, corn syrup, high fructose corn syrup, saccharin, aspartame, sucralose, acesulfame potassium (acesulfame-K), neotame.

42. A consumable food additive as described in clause 31, and further comprising a coloring agent.

43. A consumable food additive as described in clause 42 wherein said coloring agent comprises a coloring agent selected from the group consisting of: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate 44. A consumable food additive as described in clause 31, and further comprising a surfactant.

45. A consumable food additive as described in clause 44 wherein said surfactant comprises a surfactant selected from the group consisting of glycerol monostearate and polysorbate 80.

46. A consumable food additive as described in clause 31, and further comprising a preservative.

47. A consumable food additive as described in clause 46, wherein said preservative comprises a preservative selected from the group consisting of: ascorbic acid, citric acid, sodium benzoate, calcium propionate, sodium erythorbate, sodium nitrite, calcium sorbate, potassium sorbate, BHA, BHT, EDTA, tocopherols 48. A consumable food additive as described in clause 31 and further comprising a nutrient supplement.

49. A consumable food additive as described in clause 48, wherein said nutrient supplement comprises a nutrient supplement selected from the group consisting of: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

50. A consumable food additive as described in clause 31 and further comprising at least one water-soluble glycosylated cannabinoid.

51. A consumable food additive comprising a mixture of at least one water-soluble glycosylated cannabinoid and at least one water-soluble acetylated cannabinoid.

52. A consumable food additive as described in clause 51 and further comprising a food additive polysaccharide.

53. A consumable food additive as described in clause 52 wherein said food additive polysaccharide comprises dextrin and/or maltodextrin.

54. A consumable food additive as described in clause 51 and further comprising a emulsifier.

55. A consumable food additive as described in clause 54 wherein said emulsifier is selected from the group consisting of: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, *quillaia*, whey protein isolate, casein, soy protein, vegetable protein, pullulan, sodium alginate, guar gum, locust bean gum, tragacanth gum, tamarind gum, carrageenan, furcellaran, Gellan gum, *psyllium*, curdlan, konjac mannan, agar, and cellulose derivatives, or combinations thereof.

56. A consumable food additive as described in clause 51, wherein said water-soluble acetylated cannabinoid and said water-soluble glycosylated cannabinoid are non-psychoactive cannabinoids.

57. A consumable food additive as described in clause 51, wherein said water-soluble acetylated cannabinoid and said water-soluble glycosylated cannabinoid are generated in vivo.

58. A consumable food additive as described in clause 51, wherein said water-soluble acetylated cannabinoid and said water-soluble glycosylated cannabinoid are generated in vitro.

59. A consumable food additive as described in clause 51, wherein said consumable food additive is a homogenous composition.

60. A consumable food additive as described in clause 51, and further comprising a flavoring agent.

61. A consumable food additive as described in clause 60 wherein said flavoring agent comprises a flavoring agent selected from the group consisting of: Sucrose (sugar), glucose, fructose, sorbitol, mannitol, corn syrup, high fructose corn syrup, saccharin, aspartame, sucralose, acesulfame potassium (acesulfame-K), neotame.

62. A consumable food additive as described in clause 51, and further comprising a coloring agent.

63. A consumable food additive as described in clause 62 wherein said coloring agent comprises a coloring agent selected from the group consisting of: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate 64. A consumable food additive as described in clause 51, and further comprising a surfactant.

65. A consumable food additive as described in clause 64 wherein said surfactant comprises a surfactant selected from the group consisting of glycerol monostearate and polysorbate 80.

66. A consumable food additive as described in clause 51, and further comprising a preservative.

67. A consumable food additive as described in clause 66, wherein said preservative comprises a preservative selected from the group consisting of: ascorbic acid, citric acid, sodium benzoate, calcium propionate, sodium erythorbate, sodium nitrite, calcium sorbate, potassium sorbate, BHA, BHT, EDTA, tocopherols 68 A consumable food additive as described in clause 51 and further comprising a nutrient supplement.

69. A consumable food additive as described in clause 68, wherein said nutrient supplement comprises a nutrient supplement selected from the group consisting of: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

70. A consumable fluid comprising at least one water-soluble glycosylated cannabinoid.

71. A consumable fluid as described in clause 70, further comprising a food additive polysaccharide.

72. A consumable fluid as described in clause 70, wherein said food additive polysaccharide comprises maltodextrin and/or dextrin.

73. A consumable fluid as described in clause 73, wherein said maltodextrin is an aqueous maltodextrin solution.

74. A consumable fluid as described in clause 73, wherein said aqueous maltodextrin solution further comprises sorbic acid and an acidifying agent to provide a food grade aqueous solution of maltodextrin having a pH of 2-4 and a sorbic acid content of 0.02-0.1% by weight.

75. A consumable fluid as described in clause 70, wherein said consumable fluid is water.

76. A consumable fluid as described in clause 75, wherein said consumable fluid is selected from the group consisting of: an alcoholic beverage; a non-alcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water.

77. A consumable fluid as described in clause 70, wherein said water-soluble glycosylated cannabinoid is a non-psychoactive cannabinoid.

78. A consumable fluid as described in clause 70, wherein said water-soluble glycosylated cannabinoid is generated in vivo.

79 A consumable fluid as described in clause 70, wherein said water-soluble glycosylated cannabinoid is generated in vitro.

80. A consumable fluid as described in clause 70 further comprising at least one of: xanthan gum, cellulose gum, whey protein hydrolysate, ascorbic acid, citric acid, malic acid, sodium benzoate, sodium citrate, sugar, phosphoric acid, and water.

81. A consumable fluid comprising at least one water-soluble acetylated cannabinoid.

82. A consumable fluid as described in clause 81 further comprising a food additive polysaccharide.

83. A consumable fluid as described in clause 81 wherein said food additive polysaccharide comprises maltodextrin and/or dextrin.

84. A consumable fluid as described in clause 83, wherein said maltodextrin is an aqueous maltodextrin solution.

85. A consumable fluid as described in clause 84, wherein said aqueous maltodextrin solution further comprises sorbic acid and an acidifying agent to provide a food grade aqueous solution of maltodextrin having a pH of 2-4 and a sorbic acid content of 0.02-0.1% by weight.

86. A consumable fluid as described in clause 81, wherein said consumable fluid is water.

87. A consumable fluid as described in clause 81, wherein said consumable fluid is selected from the group consisting of: an alcoholic beverage; a non-alcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water.

88. A consumable fluid as described in clause 81, wherein said water-soluble acetylated cannabinoid is a non-psychoactive cannabinoid.

89. A consumable fluid as described in clause 81, wherein said water-soluble acetylated cannabinoid is generated in vivo.

90. A consumable fluid as described in clause 81, wherein said water-soluble acetylated cannabinoid is generated in vitro.

91. A consumable fluid as described in clause 81 further comprising at least one of: xanthan gum, cellulose gum, whey protein hydrolysate, ascorbic acid, citric acid, malic acid, sodium benzoate, sodium citrate, sugar, phosphoric acid, and water.

92. A consumable gel comprising at least one water-soluble glycosylated cannabinoid and gelatin in an aqueous solution.

93. A consumable gel as described in clause 92 wherein said water-soluble glycosylated cannabinoid is generated in vivo.

94. A consumable gel as described in clause 92 wherein said water-soluble glycosylated cannabinoid is generated in vitro.

95. A consumable gel comprising at least one water-soluble acetylated cannabinoid and gelatin in an aqueous solution.

96. A consumable gel as described in clause 95 wherein said water-soluble acetylated cannabinoid is generated in vivo.

97. A consumable gel as described in clause 95 wherein said water-soluble acetylated cannabinoid is generated in vitro.

98. A consumable gel comprising at least one water-soluble acetylated cannabinoid, at least one water-soluble glycosylated cannabinoid and gelatin in an aqueous solution.

99. A consumable gel as described in clause 98 wherein said water-soluble acetylated cannabinoid and said water-soluble acetylated cannabinoid are generated in vivo.

100. A consumable gel as described in clause 99 wherein said water-soluble acetylated cannabinoid and said water-soluble acetylated cannabinoid are generated in vitro.

101. A method of making a consumable fluid additive comprising the steps:
solubilizing a water-soluble glycosylated cannabinoid with a food additive polysaccharide to provide an aqueous solution containing said water-soluble glycosylated cannabinoid and said food additive polysaccharide; and
adding said water-soluble glycosylated cannabinoid and food additive polysaccharide aqueous solution to a consumable fluid. 102. The method of clause 101, wherein said food additive polysaccharide is selected from the group consisting of: maltodextrin and/or dextrin. 103. The method of clause 102, wherein said food additive polysaccharide is maltodextrin.

104. The method of clause 103, wherein said maltodextrin is an aqueous maltodextrin solution.

105. The method of clause 104, wherein said aqueous maltodextrin solution further comprises sorbic acid and an acidifying agent to provide a food grade aqueous solution of maltodextrin having a pH of 2-4 and a sorbic acid content of 0.02-0.1% by weight.

106. The method of clause 104, wherein said consumable fluid is water.

107. The method of clause 106, wherein said consumable fluid is selected from the group consisting of: an alcoholic beverage; a non-alcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water.

108. The method of clause 101, wherein said water-soluble glycosylated cannabinoid is a non-psychoactive cannabinoid.

109. The method of clause 101, wherein said water-soluble glycosylated cannabinoid is generated in vivo.

110. The method of clause 101, wherein said water-soluble glycosylated cannabinoid is generated in vitro.

110. The method of clause 101, and further comprising the step of adding a flavor to said consumable fluid.

111. The method of clause 101, further comprising the step of adding at least one of: xanthan gum, cellulose gum, whey protein hydrolysate, ascorbic acid, citric acid, malic acid, sodium benzoate, sodium citrate, sugar, phosphoric acid, and water.

112. A composition comprising:
a first quantity of water;
a water-soluble cannabinoid solubilized in said first quantity of water; and
at least one of: xanthan gum, cellulose gum, whey protein hydrolysate, ascorbic acid, citric acid, malic acid, sodium benzoate, sodium citrate, sugar, phosphoric acid, and/or a sugar alcohol.

113. The composition of clause 112, wherein said water-soluble cannabinoid comprises a glycosylated water-soluble cannabinoid, an acetylated water-soluble cannabinoid or a mixture of both.

114. The composition of clause 113, wherein said water-soluble cannabinoid is non-psychoactive.

115. The composition of clause 112, and further comprising ethanol.

116. The composition of clause 112, comprising less than 10 mass % water.

117. The composition of clause 112, comprising more than 95 mass % water.

118. The composition of clause 113, comprising about 0.1 mg to about 1000 mg of the water-soluble cannabinoid.

119. The composition of clause 113, comprising about 0.1 mg to about 500 mg of the water-soluble cannabinoid.

120. The composition of clause 113, comprising about 0.1 mg to about 200 mg of the water-soluble cannabinoid.

121. The composition of clause 113, comprising about 0.1 mg to about 100 mg of the water-soluble cannabinoid.

122. The composition of clause 113, comprising about 0.1 mg to about 100 mg of the water-soluble cannabinoid.

123. The composition of clause 113, comprising about 0.1 mg to about 10 mg of the water-soluble cannabinoid.

124. The composition of clause 113, comprising about 0.5 mg to about 5 mg of the water-soluble cannabinoid.

125. The composition of clause 113, comprising about 1 mg/kg to 5 mg/kg (body weight) in a human of the water-soluble cannabinoid.

126. The composition of clause 113, comprising water-soluble cannabinoid in the range of 50 mg/L to 300 mg/L.

127. The composition of clause 113, comprising water-soluble cannabinoid in the range of 50 mg/L to 100 mg/L.

128. The composition of clause 113, comprising water-soluble cannabinoid in the range of 50 mg/L to 500 mg/L.

129. The composition of clause 113, comprising water-soluble cannabinoid over 500 mg/L.

130. The composition of clause 113, comprising water-soluble cannabinoid under 50 mg/L.

131. The composition of clause 112, wherein the composition is homogeneous.

132. The composition of clause 112, comprising a flavoring agent.

133. The composition of clause 112, comprising a coloring agent.

134. The composition of clause 112, comprising caffeine.

135. The composition of clause 112, comprising a coloring agent.

136. A composition comprising:
   a first quantity of water;
   a water-soluble cannabinoid solubilized in said first quantity of water; and
   a first quantity of ethanol in a liquid state.

137. A composition according to clause 136 wherein said water-soluble cannabinoid is a glycosylated cannabinoid.

138. A composition according to clause 136 wherein said water-soluble cannabinoid is an acetylated cannabinoid.

139. A composition according to clause 136 wherein said water-soluble cannabinoid is a mixture of glycosylated cannabinoids and acetylated cannabinoid.

140. A composition according to clause 137 wherein said glycosylated cannabinoid is glycosylated in vivo.

141. A composition according to clause 137 wherein said glycosylated cannabinoid is glycosylated in vitro.

142. A composition according to clause 138 wherein said acetylated cannabinoid is acetylated in vivo.

143. A composition according to clause 138 wherein said acetylated cannabinoid is acetylated in vitro.

144. A composition according to clause 139 wherein said acetylated cannabinoid is acetylated in vivo and glycosylated cannabinoid is glycosylated in vivo.

145. A composition according to clause 139 wherein said acetylated cannabinoid is acetylated in vitro and glycosylated cannabinoid is glycosylated in vitro.

146. A composition according to clause 136 wherein said ethanol can be up to about ninety-nine point nine-five percent (99.95%) by weight and said water-soluble cannabinoid about zero point zero five percent (0.05%) by weight.

147. A composition according to clause 136, wherein said water-soluble cannabinoid is non-psychoactive.

148. A composition according to clause 136, wherein said ethanol is an ethyl alcohol.

149. A cannabinoid enriched alcohol composition according to clause 148, wherein said ethyl alcohol has a proof greater than 100.

150. A composition according to clause 148, wherein said ethyl alcohol has a proof less than 100.

151. A composition according to clause 148, wherein said ethyl alcohol is a spirit.

152. A composition according to clause 148, wherein said ethyl alcohol is beer, and/or wine.

153. A cannabinoid enriched alcohol composition for human consumption, said composition comprising by weight about:
   a first quantity of water;
   a water-soluble cannabinoid solubilized in said first quantity of water; and
   a first quantity of ethanol in a liquid state wherein said first quantity of ethanol is between 1% to 20% weight by volume.

154. A cannabinoid enriched alcohol composition according to clause 153 wherein said water-soluble cannabinoid is a glycosylated cannabinoid.

155. A cannabinoid enriched alcohol composition according to clause 153 wherein said water-soluble cannabinoid is an acetylated cannabinoid.

156. A cannabinoid enriched alcohol composition according to clause 153 wherein said water-soluble cannabinoid is a mixture of glycosylated cannabinoids and acetylated cannabinoid.

157. A cannabinoid enriched alcohol composition according to clause 154 wherein said glycosylated cannabinoid is glycosylated in vivo.

158. A cannabinoid enriched alcohol composition according to clause 154 wherein said glycosylated cannabinoid is glycosylated in vitro.

159. A cannabinoid enriched alcohol composition according to clause 155 wherein said acetylated cannabinoid is acetylated in vivo.

160. A cannabinoid enriched alcohol composition according to clause 155 wherein said acetylated cannabinoid is acetylated in vitro.

161. A cannabinoid enriched alcohol composition according to clause 156 wherein said acetylated cannabinoid is acetylated in vivo and glycosylated cannabinoid is glycosylated in vivo.

162. A cannabinoid enriched alcohol composition according to clause 156 wherein said acetylated cannabinoid is acetylated in vitro and glycosylated cannabinoid is glycosylated in vitro.

163. A cannabinoid enriched alcohol composition according to clause 153, wherein said water-soluble cannabinoid is non-psychoactive.

164. A cannabinoid enriched alcohol composition according to clause 153, wherein said ethanol is an ethyl alcohol.

165. A cannabinoid enriched alcohol composition according to clause 164, wherein said ethyl alcohol has a proof greater than 100.

166. A cannabinoid enriched alcohol composition according to clause 164, wherein said ethyl alcohol is beer.

167. A cannabinoid enriched alcohol composition according to clause 164, wherein said ethyl alcohol is wine.

168. A cannabinoid enriched alcohol composition according to clause 164, wherein said ethyl alcohol is a distilled spirit.

169. A chewing gum composition comprising:
a first quantity of at least one water-soluble cannabinoid;
a gum base comprising a buffering agent selected from the group consisting of acetates, glycinates, phosphates, carbonates, glycerophosphates, citrates, borates, and mixtures thereof;
at least one sweetening agent; and
at least one flavoring agent.

170. The chewing gum composition of clause 169, wherein said water-soluble cannabinoid comprises at least one water-soluble glycosylated cannabinoid.

171. The chewing gum composition of clause 169, wherein said water-soluble cannabinoid comprises at least one water-soluble acetylated cannabinoid.

172. The chewing gum composition of clause 169, wherein said water-soluble cannabinoid comprises at least one water-soluble acetylated cannabinoid, and at least one water-soluble glycosylated cannabinoid.

173. The chewing gum composition of clause 172, wherein said water soluble glycosylated cannabinoid, and/or said acetylated cannabinoid were glycosylated and acetylated in vivo respectively 174. The chewing gum composition of clause 169, comprising
0.01 to 1% by weight of said water-soluble cannabinoid;
25 to 85% by weight of said gum base;
10 to 35% by weight of said at least one sweetening agent; and
1 to 10% by weight of said flavoring agent.

175. The chewing gum composition of clause 174, wherein said flavoring agents comprise a flavoring agent selected from the group consisting of menthol flavor, *eucalyptus*, mint flavor and/or L-menthol.

176. The chewing gum composition of clause 174, wherein said sweetening agent comprises a sweetening agent selected from the group consisting of xylitol, sorbitol, isomalt, aspartame, sucralose, acesulfame potassium, and saccharin.

177. The chewing gum composition according to clause 169, wherein the chewing gum composition comprises an antioxidant.

178. The chewing gum composition according to clause 169, wherein the chewing gum composition comprises a pharmaceutically acceptable excipient selected from the group consisting of fillers, disintegrants, binders, lubricants, and antioxidants.

179. The chewing gum composition according to clause 169, wherein the chewing gum composition is non-disintegrating.

180. The chewing gum composition according to clause 169, wherein the chewing gum comprises natural flavors.

181. The chewing gum composition according to clause 169, and further comprising a coloring agent.

182. The chewing gum composition according to clause 169, and further comprising a flavoring agent.

183. The chewing gum composition according to clause 169, wherein said water-soluble cannabinoid is non-psychoactive.

184. A composition for a water-soluble cannabinoid infused solution comprising:
purified water;
at least one water-soluble cannabinoid;
at least one flavoring agent.

185. The composition of clause 1, and further comprising a sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

186. The composition of clause 184, and further comprising sodium chloride.

187. The composition of clause 184, and further comprising glycerin.

188. The composition of clause 184, and further comprising a coloring agent.

189. The composition of clause 184, and further comprising a first quantity of a demulcent.

190. The composition of clause 184, wherein said demulcent is selected from the group consisting of: pectin, glycerin, honey, methylcellulose, and propylene glycol.

191. The composition of clause 184, wherein said water-soluble cannabinoid is selected from the group consisting of: a water soluble glycosylated cannabinoid, a water soluble acetylated cannabinoid, or a mixture of both.

192. The composition of clause 191, wherein said water soluble glycosylated cannabinoid, and/or said acetylated cannabinoid were glycosylated and acetylated in vivo respectively.

193. The composition of clause 184, wherein said water-soluble cannabinoid is non-psychoactive.

194. A composition for a water-soluble cannabinoid infused anesthetic solution comprising:
purified water;
at least one water-soluble cannabinoid;
at least one oral anesthetic.

195. The composition of clause 194, and further comprising a sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

196. The composition of clause 194, and further comprising sodium chloride.

197. The composition of clause 194, and further comprising glycerin.

198. The composition of clause 194, and further comprising a coloring agent.

199. The composition of clause 194, wherein said anesthetic is selected from the group consisting of: benzocaine, and phenol.

200. The composition of clause 199, wherein said first quantity of anesthetic is between 0.1% to 15% volume by weight.

201. The composition of clause 194, and further comprising a first quantity of a demulcent.

202. The composition of clause 201, wherein said demulcent is selected from the group consisting of: pectin, glycerin, honey, methylcellulose, and propylene glycol.

203. The composition of clause 194, wherein said water-soluble cannabinoid is selected from the group consisting of: a water soluble glycosylated cannabinoid, a water soluble acetylated cannabinoid, or a mixture of both.

204. The composition of clause 203, wherein said water soluble glycosylated cannabinoid, and/or said acetylated cannabinoid were glycosylated and acetylated in vivo respectively.

205. The composition of clause 203, wherein said water soluble glycosylated cannabinoid, and/or said acetylated cannabinoid were glycosylated and acetylated in vitro respectively.

206. The composition of clause 194, wherein said water-soluble cannabinoid is non-psychoactive.

207. A composition for a hard lozenge for rapid delivery of water-soluble cannabinoids through the oral mucosa, the lozenge comprising:
 a crystalized sugar base;
 at least one water-soluble cannabinoid;
 wherein said hard lozenge has a moisture content between 0.1 to 2%.

208. The composition of clause 207, wherein said crystalized sugar base comprises a crystalized sugar base selected from the group consisting of: sucrose, invert sugar, corn syrup, and isomalt or a combination of the same.

209. The composition of clause 207, and further comprising at least one acidulant.

210. The composition of clause 209, wherein said acidulant is selected from the group consisting of: citric acid, tartaric acid, fumaric acid, and malic acid.

211. The composition of clause 209, and further comprising at least one pH adjustor.

212. The composition of clause 211, wherein said pH adjustor is selected from the group consisting of: calcium carbonate, sodium bicarbonate, and magnesium trisilicate.

213. The composition of clause 207, and further comprising at least one anesthetic.

214. The composition of clause 213, wherein said anesthetic is selected from the group consisting of: benzocaine, and phenol.

215. The composition of clause 213, wherein said first quantity of anesthetic is between 1 mg to 15 mg.

216. The composition of clause 1207, and further comprising a first quantity of menthol.

217. The composition of clause 216, wherein said first quantity of menthol is between 1 mg to 20 mg.

218. The composition of clause 207, and further comprising a first quantity of a demulcent.

219. The composition of clause 218, wherein said demulcent is selected from the group consisting of: pectin, glycerin, honey, methylcellulose, propylene glycol, and glycerine.

220. The composition of clause 218, wherein said first quantity of demulcent is between 1 mg to 10 mg.

221. The composition of clause 207, wherein said water-soluble cannabinoid is selected from the group consisting of: a water soluble glycosylated cannabinoid, an acetylated cannabinoid, or a mixture of both.

222. The composition of clause 221, wherein said water soluble glycosylated cannabinoid, and/or said acetylated cannabinoid were glycosylated and acetylated in vivo respectively.

223. The composition of clause 221, wherein said water soluble glycosylated cannabinoid, and/or said acetylated cannabinoid were glycosylated and acetylated in vitro respectively.

224. The composition of clause 221, wherein the water-soluble cannabinoid is below 50 mg.

225. The composition of clause 221, wherein the water-soluble cannabinoid is above 50 mg.

226. The composition of clause 221, wherein said water-soluble cannabinoid is non-psychoactive.

227. A chewable lozenge for rapid delivery of water-soluble cannabinoids through the oral mucosa, the lozenge comprising:
 a glycerinated gelatin base;
 at least one sweetener; and
 at least one water-soluble cannabinoid dissolved in a first quantity of water.

228. The composition of clause 227, wherein said sweetener comprises a sweetener selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

229. The composition of clause 227, and further comprising at least one acidulant.

230. The composition of clause 229, wherein said acidulant is selected from the group consisting of: citric acid, tartaric acid, fumaric acid, and malic acid.

231. The composition of clause 229, and further comprising at least one pH adjustor.

232. The composition of clause 231, wherein said pH adjustor is selected from the group consisting of: calcium carbonate, sodium bicarbonate, and magnesium trisilicate.

233. The composition of clause 227, and further comprising at least one anesthetic.

234. The composition of clause 233, wherein said anesthetic is selected from the group consisting of: benzocaine, and phenol.

235. The composition of clause 233, wherein said first quantity of anesthetic is between 1 mg to 15 mg.

236. The composition of clause 227, and further comprising a first quantity of menthol.

237. The composition of clause 236, wherein said first quantity of menthol is between 1 mg to 20 mg.

238. The composition of clause 227, and further comprising a first quantity of a demulcent.

239. The composition of clause 238, wherein said demulcent is selected from the group consisting of: pectin, glycerin, honey, methylcellulose, propylene glycol, and glycerine.

240. The composition of clause 238, wherein said first quantity of demulcent is between 1 mg to 10 mg.

241. The composition of clause 227, wherein said water-soluble cannabinoid is selected from the group consisting of: a water soluble glycosylated cannabinoid, an acetylated cannabinoid, or a mixture of both.

242. The composition of clause 241, wherein said water soluble glycosylated cannabinoid, and/or said acetylated cannabinoid were glycosylated and acetylated in vivo respectively 243. The composition of clause 241, wherein the water-soluble cannabinoid is below 50 mg.

244. The composition of clause 241, wherein the water-soluble cannabinoid is above 50 mg.

245. The composition of clause 227, wherein said water-soluble cannabinoid is non-psychoactive.

246. A soft lozenge for rapid delivery of cannabinoids through the oral mucosa, the lozenge comprising:
 a polyethylene glycol base;
 at least one sweetener; and
 at least one water-soluble cannabinoid.

247. The composition of clause 246, wherein said sweetener comprises a crystalized sugar base selected from the group consisting of: glucose, sucrose, invert sugar, corn syrup, *stevia* extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

248. The composition of clause 246, and further comprising at least one acidulant.

249. The composition of clause 248, wherein said acidulant is selected from the group consisting of: citric acid, tartaric acid, fumaric acid, and malic acid.

250. The composition of clause 248, and further comprising at least one pH adjustor.

251. The composition of clause 250, wherein said pH adjustor is selected from the group consisting of: calcium carbonate, sodium bicarbonate, and magnesium trisilicate.

252. The composition of clause 247, and further comprising at least one anesthetic.

253. The composition of clause 252, wherein said anesthetic is selected from the group consisting of: benzocaine, and phenol.

254. The composition of clause 252, wherein said first quantity of anesthetic is between 1 mg to 15 mg.

255. The composition of clause 246, and further comprising a first quantity of menthol.

256. The composition of clause 255, wherein said first quantity of menthol is between 1 mg to 20 mg.

257. The composition of clause 246, and further comprising a first quantity of a demulcent.

258. The composition of clause 257, wherein said demulcent is selected from the group consisting of: pectin, glycerin, honey, methylcellulose, propylene glycol, and glycerine.

259. The composition of clause 2258, wherein said first quantity of demulcent is between 1 mg to 10 mg.

260. The composition of clause 246, wherein said water-soluble cannabinoid is selected from the group consisting of: a water soluble glycosylated cannabinoid, an acetylated cannabinoid, or a mixture of both.

261. The composition of clause 260, wherein said water soluble glycosylated cannabinoid, and/or said acetylated cannabinoid were glycosylated and acetylated in vivo respectively.

262 The composition of clause 260, wherein the water-soluble cannabinoid is below 50 mg.

263. The composition of clause 260, wherein the water-soluble cannabinoid is above 50 mg.

264. The composition of clause 246, wherein said water-soluble cannabinoid is non-psychoactive.

265. A tablet or capsule consisting essentially of a water-soluble glycosylated cannabinoid and maltodextrin.

266. The tablet or capsule of clause 265, wherein said water-soluble glycosylated cannabinoid comprises a water-soluble glycosylated cannabinoid generated in vivo.

267. The tablet or capsule of clause 265, wherein said water-soluble glycosylated cannabinoid comprises a water-soluble glycosylated cannabinoid generated in vitro.

268. The tablet or capsule of clause 265, wherein said water-soluble glycosylated cannabinoid comprises a non-psychoactive water-soluble glycosylated cannabinoid.

269. The tablet or capsule of clause 265, wherein the amount of water-soluble glycosylated cannabinoid is 5 milligrams or less.

270. The tablet or capsule of clause 265, wherein the amount of water-soluble glycosylated cannabinoid 5 milligrams and 200 milligrams.

271. The tablet or capsule of clause 265, wherein the wherein the amount of water-soluble glycosylated cannabinoid is more than 200 milligrams.

272. A tablet or capsule consisting essentially of a water-soluble glycosylated cannabinoid and whey protein isolate.

273. The tablet or capsule of clause 272, wherein said water-soluble glycosylated cannabinoid comprises a water-soluble glycosylated cannabinoid generated in vivo.

274. The tablet or capsule of clause 272, wherein said water-soluble glycosylated cannabinoid comprises a water-soluble glycosylated cannabinoid generated in vitro.

274. The tablet or capsule of clause 272, wherein said water-soluble glycosylated cannabinoid comprises a non-psychoactive water-soluble glycosylated cannabinoid.

275. The tablet or capsule of clause 272, wherein the amount of water-soluble glycosylated cannabinoid is 5 milligrams or less.

276. The tablet or capsule of clause 272, wherein the amount of water-soluble glycosylated cannabinoid 5 milligrams and 200 milligrams.

277. The tablet or capsule of clause 272, wherein the wherein the amount of water-soluble glycosylated cannabinoid is more than 200 milligrams.

278. A tablet or capsule consisting essentially of a water-soluble glycosylated cannabinoid and xanthan gum.

279. The tablet or capsule of clause 278, wherein said water-soluble glycosylated cannabinoid comprises a water-soluble glycosylated cannabinoid generated in vivo.

280. The tablet or capsule of clause 278, wherein said water-soluble glycosylated cannabinoid comprises a water-soluble glycosylated cannabinoid generated in vitro.

281. The tablet or capsule of clause 278, wherein said water-soluble glycosylated cannabinoid comprises a non-psychoactive water-soluble glycosylated cannabinoid.

282. The tablet or capsule of clause 278, wherein the amount of water-soluble glycosylated cannabinoid is 5 milligrams or less.

283. The tablet or capsule of clause 278, wherein the amount of water-soluble glycosylated cannabinoid 5 milligrams and 200 milligrams.

284. The tablet or capsule of clause 278, wherein the wherein the amount of water-soluble glycosylated cannabinoid is more than 200 milligrams.

285. A tablet or capsule consisting essentially of a water-soluble glycosylated cannabinoid and guar gum.

286. The tablet or capsule of clause 285, wherein said water-soluble glycosylated cannabinoid comprises a water-soluble glycosylated cannabinoid generated in vivo.

287. The tablet or capsule of clause 285, wherein said water-soluble glycosylated cannabinoid comprises a water-soluble glycosylated cannabinoid generated in vitro.

288. The tablet or capsule of clause 285, wherein said water-soluble glycosylated cannabinoid comprises a non-psychoactive water-soluble glycosylated cannabinoid.

289. The tablet or capsule of clause 285, wherein the amount of water-soluble glycosylated cannabinoid is 5 milligrams or less.

290. The tablet or capsule of clause 285, wherein the amount of water-soluble glycosylated cannabinoid 5 milligrams and 200 milligrams.

291. The tablet or capsule of clause 285, wherein the wherein the amount of water-soluble glycosylated cannabinoid is more than 200 milligrams.

292. A tablet or capsule consisting essentially of water-soluble glycosylated cannabinoid and diglycerides.

293. The tablet or capsule of clause 292 wherein the diglycerides are in a mix with monoglycerides.

294. The tablet or capsule of clause 292, wherein said water-soluble glycosylated cannabinoid comprises a water-soluble glycosylated cannabinoid generated in vivo.

295. The tablet or capsule of clause 292, wherein said water-soluble glycosylated cannabinoid comprises a water-soluble glycosylated cannabinoid generated in vitro.

296. The tablet or capsule of clause 292, wherein said water-soluble glycosylated cannabinoid comprises a non-psychoactive water-soluble glycosylated cannabinoid.

297. The tablet or capsule of clause 292, wherein the amount of water-soluble glycosylated cannabinoid is 5 milligrams or less.

298. The tablet or capsule of clause 292, wherein the amount of water-soluble glycosylated cannabinoid 5 milligrams and 200 milligrams.

299. The tablet or capsule of clause 292, wherein the wherein the amount of water-soluble glycosylated cannabinoid is more than 200 milligrams.

300. A tablet or capsule consisting essentially of a water-soluble glycosylated cannabinoid and guar gum.

301. The tablet or capsule of clause 300, wherein said water-soluble glycosylated cannabinoid comprises a water-soluble glycosylated cannabinoid generated in vivo.

302. The tablet or capsule of clause 300, wherein said water-soluble glycosylated cannabinoid comprises a water-soluble glycosylated cannabinoid generated in vitro.

303. The tablet or capsule of clause 300, wherein said water-soluble glycosylated cannabinoid comprises a non-psychoactive water-soluble glycosylated cannabinoid.

304. The tablet or capsule of clause 300, wherein the amount of water-soluble glycosylated cannabinoid is 5 milligrams or less.

305. The tablet or capsule of clause 300, wherein the amount of water-soluble glycosylated cannabinoid 5 milligrams and 200 milligrams.

306. The tablet or capsule of clause 300, wherein the wherein the amount of water-soluble glycosylated cannabinoid is more than 200 milligrams.

307. A tablet or capsule consisting essentially of water-soluble glycosylated cannabinoid and carboxymethyl cellulose.

308. The tablet or capsule of clause 307, wherein said water-soluble glycosylated cannabinoid comprises a water-soluble glycosylated cannabinoid generated in vivo.

309. The tablet or capsule of clause 307, wherein said water-soluble glycosylated cannabinoid comprises a water-soluble glycosylated cannabinoid generated in vitro.

310. The tablet or capsule of clause 307, wherein said water-soluble glycosylated cannabinoid comprises a non-psychoactive water-soluble glycosylated cannabinoid.

311. The tablet or capsule of clause 307, wherein the amount of water-soluble glycosylated cannabinoid is 5 milligrams or less.

312. The tablet or capsule of clause 307, wherein the amount of water-soluble glycosylated cannabinoid 5 milligrams and 200 milligrams.

313. The tablet or capsule of clause 307, wherein the wherein the amount of water-soluble glycosylated cannabinoid is more than 200 milligrams.

314. A tablet or capsule consisting essentially a water-soluble glycosylated cannabinoid and glycerin.

315. The tablet or capsule of clause 314, wherein said water-soluble glycosylated cannabinoid comprises a water-soluble glycosylated cannabinoid generated in vivo.

316. The tablet or capsule of clause 314, wherein said water-soluble glycosylated cannabinoid comprises a water-soluble glycosylated cannabinoid generated in vitro.

317. The tablet or capsule of clause 314, wherein said water-soluble glycosylated cannabinoid comprises a non-psychoactive water-soluble glycosylated cannabinoid.

318. The tablet or capsule of clause 314, wherein the amount of water-soluble glycosylated cannabinoid is 5 milligrams or less.

319. The tablet or capsule of clause 314, wherein the amount of water-soluble glycosylated cannabinoid 5 milligrams and 200 milligrams.

320. The tablet or capsule of clause 314, wherein the wherein the amount of water-soluble glycosylated cannabinoid is more than 200 milligrams.

321. A tablet or capsule consisting essentially of a water-soluble glycosylated cannabinoid and gelatin.

322. The tablet or capsule of clause 321, wherein said water-soluble glycosylated cannabinoid comprises a water-soluble glycosylated cannabinoid generated in vivo.

323. The tablet or capsule of clause 321, wherein said water-soluble glycosylated cannabinoid comprises a water-soluble glycosylated cannabinoid generated in vitro.

324. The tablet or capsule of clause 321, wherein said water-soluble glycosylated cannabinoid comprises a non-psychoactive water-soluble glycosylated cannabinoid.

325. The tablet or capsule of clause 321, wherein the amount of water-soluble glycosylated cannabinoid is 5 milligrams or less.

326. The tablet or capsule of clause 321, wherein the amount of water-soluble glycosylated cannabinoid 5 milligrams and 200 milligrams.

327. The tablet or capsule of clause 321, wherein the wherein the amount of water-soluble glycosylated cannabinoid is more than 200 milligrams.

328. A tablet or capsule consisting essentially of water-soluble glycosylated cannabinoid and polyethylene glycol.

329. The tablet or capsule of clause 328, wherein said water-soluble glycosylated cannabinoid comprises a water-soluble glycosylated cannabinoid generated in vivo.

330. The tablet or capsule of clause 328, wherein said water-soluble glycosylated cannabinoid comprises a water-soluble glycosylated cannabinoid generated in vitro.

331. The tablet or capsule of clause 328, wherein said water-soluble glycosylated cannabinoid comprises a non-psychoactive water-soluble glycosylated cannabinoid.

332. The tablet or capsule of clause 328, wherein the amount of water-soluble glycosylated cannabinoid is 5 milligrams or less.

333. The tablet or capsule of clause 328, wherein the amount of water-soluble glycosylated cannabinoid 5 milligrams and 200 milligrams.

334. The tablet or capsule of clause 328, wherein the wherein the amount of water-soluble glycosylated cannabinoid is more than 200 milligrams.

335. A tablet or capsule consisting essentially of a water-soluble acetylated cannabinoid and maltodextrin.

336. The tablet or capsule of clause 335, wherein said water-soluble acetylated cannabinoid comprises a water-soluble acetylated cannabinoid generated in vivo.

337. The tablet or capsule of clause 335, wherein said water-soluble acetylated cannabinoid comprises a water-soluble acetylated cannabinoid generated in vitro.

338. The tablet or capsule of clause 335, wherein said water-soluble acetylated cannabinoid comprises a non-psychoactive water-soluble acetylated cannabinoid.

339. The tablet or capsule of clause 335, wherein the amount of water-soluble acetylated cannabinoid is 5 milligrams or less.

340. The tablet or capsule of clause 335, wherein the amount of water-soluble acetylated cannabinoid 5 milligrams and 200 milligrams.

340. The tablet or capsule of clause 335, wherein the wherein the amount of water-soluble acetylated cannabinoid is more than 200 milligrams.

341. A tablet or capsule consisting essentially of a water-soluble acetylated cannabinoid and whey protein isolate.

342. The tablet or capsule of clause 341, wherein said water-soluble acetylated cannabinoid comprises a water-soluble acetylated cannabinoid generated in vivo.

343. The tablet or capsule of clause 341, wherein said water-soluble acetylated cannabinoid comprises a water-soluble acetylated cannabinoid generated in vitro.

344. The tablet or capsule of clause 341, wherein said water-soluble acetylated cannabinoid comprises a non-psychoactive water-soluble acetylated cannabinoid.

345. The tablet or capsule of clause 341, wherein the amount of water-soluble acetylated cannabinoid is 5 milligrams or less.

346. The tablet or capsule of clause 341, wherein the amount of water-soluble acetylated cannabinoid 5 milligrams and 200 milligrams.

347. The tablet or capsule of clause 341, wherein the wherein the amount of water-soluble acetylated cannabinoid is more than 200 milligrams.

348. A tablet or capsule consisting essentially of a water-soluble acetylated cannabinoid and xanthan gum.

349. The tablet or capsule of clause 348, wherein said water-soluble acetylated cannabinoid comprises a water-soluble acetylated cannabinoid generated in vivo.

350. The tablet or capsule of clause 348, wherein said water-soluble acetylated cannabinoid comprises a water-soluble acetylated cannabinoid generated in vitro.

351. The tablet or capsule of clause 348, wherein said water-soluble acetylated cannabinoid.

352. The tablet or capsule of clause 348, wherein the amount of water-soluble acetylated cannabinoid is 5 milligrams or less.

353. The tablet or capsule of clause 348, wherein the amount of water-soluble acetylated cannabinoid 5 milligrams and 200 milligrams.

354. The tablet or capsule of clause 348, wherein the wherein the amount of water-soluble acetylated cannabinoid is more than 200 milligrams.

355. A tablet or capsule consisting essentially of a water-soluble acetylated cannabinoid and guar gum.

356. The tablet or capsule of clause 355, wherein said water-soluble acetylated cannabinoid comprises a water-soluble acetylated cannabinoid generated in vivo.

357. The tablet or capsule of clause 355, wherein said water-soluble acetylated cannabinoid comprises a water-soluble acetylated cannabinoid generated in vitro.

358. The tablet or capsule of clause 355, wherein said water-soluble acetylated cannabinoid comprises a non-psychoactive water-soluble acetylated cannabinoid.

359. The tablet or capsule of clause 355, wherein the amount of water-soluble acetylated cannabinoid is 5 milligrams or less.

360. The tablet or capsule of clause 355, wherein the amount of water-soluble acetylated cannabinoid 5 milligrams and 200 milligrams.

361. The tablet or capsule of clause 355, wherein the wherein the amount of water-soluble acetylated cannabinoid is more than 200 milligrams.

362. A tablet or capsule consisting essentially of water-soluble acetylated cannabinoid and diglycerides.

363. The tablet or capsule of clause 362 wherein the diglycerides are in a mix with monoglycerides.

364. The tablet or capsule of clause 362, wherein said water-soluble acetylated cannabinoid comprises a water-soluble acetylated cannabinoid generated in vivo.

365. The tablet or capsule of clause 362, wherein said water-soluble acetylated cannabinoid comprises a water-soluble acetylated cannabinoid generated in vitro.

366. The tablet or capsule of clause 362, wherein said water-soluble acetylated cannabinoid.

367. The tablet or capsule of clause 362, wherein the amount of water-soluble acetylated cannabinoid is 5 milligrams or less.

368. The tablet or capsule of clause 362, wherein the amount of water-soluble acetylated cannabinoid 5 milligrams and 200 milligrams.

369. The tablet or capsule of clause 362, wherein the wherein the amount of water-soluble acetylated cannabinoid is more than 200 milligrams.

370. A tablet or capsule consisting essentially of a water-soluble acetylated cannabinoid and guar gum.

371. The tablet or capsule of clause 370, wherein said water-soluble acetylated cannabinoid comprises a water-soluble acetylated cannabinoid generated in vivo.

372. The tablet or capsule of clause 370, wherein said water-soluble acetylated cannabinoid comprises a water-soluble acetylated cannabinoid generated in vitro.

373. The tablet or capsule of clause 370, wherein said water-soluble acetylated cannabinoid comprises a non-psychoactive water-soluble acetylated cannabinoid.

374. The tablet or capsule of clause 370, wherein the amount of water-soluble acetylated cannabinoid is 5 milligrams or less.

375. The tablet or capsule of clause 370, wherein the amount of water-soluble acetylated cannabinoid 5 milligrams and 200 milligrams.

376. The tablet or capsule of clause 370, wherein the wherein the amount of water-soluble acetylated cannabinoid is more than 200 milligrams.

377. A tablet or capsule consisting essentially of a water-soluble acetylated cannabinoid and carboxymethyl cellulose.

378. The tablet or capsule of clause 377, wherein said water-soluble acetylated cannabinoid comprises a water-soluble acetylated cannabinoid generated in vivo.

379. The tablet or capsule of clause 377, wherein said water-soluble acetylated cannabinoid comprises a water-soluble acetylated cannabinoid generated in vitro.

380. The tablet or capsule of clause 377, wherein said water-soluble acetylated cannabinoid comprises a non-psychoactive water-soluble acetylated cannabinoid.

390. The tablet or capsule of clause 377, wherein the amount of water-soluble acetylated cannabinoid is 5 milligrams or less.

391. The tablet or capsule of clause 377, wherein the amount of water-soluble acetylated cannabinoid 5 milligrams and 200 milligrams.

392. The tablet or capsule of clause 377, wherein the wherein the amount of water-soluble acetylated cannabinoid is more than 200 milligrams.

393. A tablet or capsule consisting essentially a water-soluble acetylated cannabinoid and glycerin.

394. The tablet or capsule of clause 393, wherein said water-soluble acetylated cannabinoid comprises a water-soluble acetylated cannabinoid generated in vivo.

395. The tablet or capsule of clause 393, wherein said water-soluble acetylated cannabinoid comprises a water-soluble acetylated cannabinoid generated in vitro.

396. The tablet or capsule of clause 393, wherein said water-soluble acetylated cannabinoid comprises a non-psychoactive water-soluble acetylated cannabinoid.

397. The tablet or capsule of clause 393, wherein the amount of water-soluble acetylated cannabinoid is 5 milligrams or less.

398. The tablet or capsule of clause 393, wherein the amount of water-soluble acetylated cannabinoid 5 milligrams and 200 milligrams.

399. The tablet or capsule of clause 393, wherein the wherein the amount of water-soluble acetylated cannabinoid is more than 200 milligrams.

400. A tablet or capsule consisting essentially of a water-soluble acetylated cannabinoid and gelatin.

401. The tablet or capsule of clause 400, wherein said water-soluble acetylated cannabinoid comprises a water-soluble acetylated cannabinoid generated in vivo.

402. The tablet or capsule of clause 400, wherein said water-soluble acetylated cannabinoid comprises a water-soluble acetylated cannabinoid generated in vitro.

403. The tablet or capsule of clause 400, wherein said water-soluble acetylated cannabinoid comprises a non-psychoactive water-soluble acetylated cannabinoid.

404. The tablet or capsule of clause 400, wherein the amount of water-soluble acetylated cannabinoid is 5 milligrams or less.

405. The tablet or capsule of clause 400, wherein the amount of water-soluble acetylated cannabinoid 5 milligrams and 200 milligrams.

406. The tablet or capsule of clause 400, wherein the wherein the amount of water-soluble acetylated cannabinoid is more than 200 milligrams.

407. A tablet or capsule consisting essentially of a water-soluble acetylated cannabinoid and polyethylene glycol.

408. The tablet or capsule of clause 407, wherein said water-soluble acetylated cannabinoid comprises a water-soluble acetylated cannabinoid generated in vivo.

409. The tablet or capsule of clause 407, wherein said water-soluble acetylated cannabinoid comprises a water-soluble acetylated cannabinoid generated in vitro.

410. The tablet or capsule of clause 407, wherein said water-soluble acetylated cannabinoid comprises a non-psychoactive water-soluble acetylated cannabinoid.

411. The tablet or capsule of clause 407, wherein the amount of water-soluble acetylated cannabinoid is 5 milligrams or less.

412. The tablet or capsule of clause 407, wherein the amount of water-soluble acetylated cannabinoid is between 5 milligrams and 200 milligrams.

413. The tablet or capsule of clause 407, wherein the wherein the amount of water-soluble acetylated cannabinoid is more than 200 milligrams.

414. A tablet or capsule consisting essentially of a water-soluble acetylated cannabinoid and a water-soluble glycosylated cannabinoid and a water-soluble glycosylated cannabinoid and maltodextrin.

415. The tablet or capsule of clause 414, wherein said water-soluble acetylated cannabinoid comprises a water-soluble acetylated cannabinoid and a water-soluble glycosylated cannabinoid and a water-soluble glycosylated cannabinoid generated in vivo.

416. The tablet or capsule of clause 414, wherein said water-soluble acetylated cannabinoid comprises a water-soluble acetylated cannabinoid and a water-soluble glycosylated cannabinoid and a water-soluble glycosylated cannabinoid generated in vitro.

417. The tablet or capsule of clause 414, wherein said water-soluble acetylated cannabinoid comprises a non-psychoactive water-soluble acetylated cannabinoid.

418. The tablet or capsule of clause 414, wherein the amount of water-soluble acetylated cannabinoid is 5 milligrams or less.

419. The tablet or capsule of clause 414, wherein the amount of water-soluble acetylated cannabinoid 5 milligrams and 200 milligrams.

420. The tablet or capsule of clause 414, wherein the wherein the amount of water-soluble acetylated cannabinoid is more than 200 milligrams.

421. A tablet or capsule consisting essentially of a water-soluble acetylated cannabinoid and a water-soluble glycosylated cannabinoid and a water-soluble glycosylated cannabinoid and whey protein isolate.

422. The tablet or capsule of clause 421, wherein said water-soluble acetylated cannabinoid comprises a water-soluble acetylated cannabinoid and a water-soluble glycosylated cannabinoid and a water-soluble glycosylated cannabinoid generated in vivo.

423. The tablet or capsule of clause 421, wherein said water-soluble acetylated cannabinoid comprises a water-soluble acetylated cannabinoid and a water-soluble glycosylated cannabinoid and a water-soluble glycosylated cannabinoid generated in vitro.

424. The tablet or capsule of clause 421, wherein said water-soluble acetylated cannabinoid comprises a non-psychoactive water-soluble acetylated cannabinoid.

425. The tablet or capsule of clause 421, wherein the amount of water-soluble acetylated cannabinoid is 5 milligrams or less.

426. The tablet or capsule of clause 421, wherein the amount of water-soluble acetylated cannabinoid 5 milligrams and 200 milligrams.

427. The tablet or capsule of clause 421, wherein the wherein the amount of water-soluble acetylated cannabinoid is more than 200 milligrams.

428. A tablet or capsule consisting essentially of a water-soluble acetylated cannabinoid and a water-soluble glycosylated cannabinoid and a water-soluble glycosylated cannabinoid and xanthan gum.

429. The tablet or capsule of clause 428, wherein said water-soluble acetylated cannabinoid comprises a water-soluble acetylated cannabinoid and a water-soluble glycosylated cannabinoid and a water-soluble glycosylated cannabinoid generated in vivo.

430. The tablet or capsule of clause 428, wherein said water-soluble acetylated cannabinoid comprises a water-soluble acetylated cannabinoid and a water-soluble glycosylated cannabinoid and a water-soluble glycosylated cannabinoid generated in vitro.

431. The tablet or capsule of clause 428, wherein said water-soluble acetylated cannabinoid 432. The tablet or capsule of clause 428, wherein the amount of water-soluble acetylated cannabinoid is 5 milligrams or less.

433. The tablet or capsule of clause 428, wherein the amount of water-soluble acetylated cannabinoid 5 milligrams and 200 milligrams.

432. The tablet or capsule of clause 428, wherein the wherein the amount of water-soluble acetylated cannabinoid is more than 200 milligrams.

433. A tablet or capsule consisting essentially of a water-soluble acetylated cannabinoid and a water-soluble glycosylated cannabinoid and a water-soluble glycosylated cannabinoid and guar gum.

434. The tablet or capsule of clause 433, wherein said water-soluble acetylated cannabinoid comprises a water-soluble acetylated cannabinoid and a water-soluble glycosylated cannabinoid and a water-soluble glycosylated cannabinoid generated in vivo.

435. The tablet or capsule of clause 433, wherein said water-soluble acetylated cannabinoid comprises a water-soluble acetylated cannabinoid and a water-soluble glycosylated cannabinoid and a water-soluble glycosylated cannabinoid generated in vitro.

436. The tablet or capsule of clause 433, wherein said water-soluble acetylated cannabinoid comprises a non-psychoactive water-soluble acetylated cannabinoid.

437. The tablet or capsule of clause 433, wherein the amount of water-soluble acetylated cannabinoid is 5 milligrams or less.

438. The tablet or capsule of clause 433, wherein the amount of water-soluble acetylated cannabinoid 5 milligrams and 200 milligrams.

439. The tablet or capsule of clause 433, wherein the wherein the amount of water-soluble acetylated cannabinoid is more than 200 milligrams.

440. A tablet or capsule consisting essentially of a water-soluble acetylated cannabinoid and a water-soluble glycosylated cannabinoid and a water-soluble glycosylated cannabinoid and diglycerides.

441. The tablet or capsule of clause 440 wherein the diglycerides are in a mix with monoglycerides.

442. The tablet or capsule of clause 440, wherein said water-soluble cannabinoid comprises a water-soluble acetylated cannabinoid and a water-soluble glycosylated cannabinoid and a water-soluble glycosylated cannabinoid generated in vivo.

443. The tablet or capsule of clause 440, wherein said water-soluble cannabinoid comprises a water-soluble acetylated cannabinoid and a water-soluble glycosylated cannabinoid and a water-soluble glycosylated cannabinoid generated in vitro.

444. The tablet or capsule of clause 440, wherein said water-soluble acetylated cannabinoid comprises a non-psychoactive water-soluble acetylated cannabinoid.

445. The tablet or capsule of clause 440, wherein the amount of water-soluble acetylated cannabinoid is 5 milligrams or less.

446. The tablet or capsule of clause 440, wherein the amount of water-soluble acetylated cannabinoid 5 milligrams and 200 milligrams.

447. The tablet or capsule of clause 440, wherein the wherein the amount of a water-soluble acetylated cannabinoid and a water-soluble glycosylated cannabinoid is more than 200 milligrams.

448. A tablet or capsule consisting essentially of a water-soluble acetylated cannabinoid and a water-soluble glycosylated cannabinoid and guar gum.

449. The tablet or capsule of clause 448, wherein said a water-soluble acetylated cannabinoid and a water-soluble glycosylated cannabinoid comprises a water-soluble acetylated cannabinoid and a water-soluble glycosylated cannabinoid generated in vivo.

450. The tablet or capsule of clause 448, wherein said a water-soluble acetylated cannabinoid and a water-soluble glycosylated cannabinoid comprises a water-soluble acetylated cannabinoid and a water-soluble glycosylated cannabinoid generated in vitro.

451. The tablet or capsule of clause 448, wherein said a water-soluble acetylated cannabinoid and a water-soluble glycosylated cannabinoid comprises a non-psychoactive a water-soluble acetylated cannabinoid and a water-soluble glycosylated cannabinoid.

452. The tablet or capsule of clause 448, wherein the amount of a water-soluble acetylated cannabinoid and a water-soluble glycosylated cannabinoid is 5 milligrams or less.

453. The tablet or capsule of clause 448, wherein the amount of a water-soluble acetylated cannabinoid and a water-soluble glycosylated cannabinoid 5 milligrams and 200 milligrams.

454. The tablet or capsule of clause 448, wherein the wherein the amount of a water-soluble acetylated cannabinoid and a water-soluble glycosylated cannabinoid is more than 200 milligrams.

455. A tablet or capsule consisting essentially of comprises a water-soluble acetylated cannabinoid and a water-soluble glycosylated cannabinoid and a water-soluble glycosylated cannabinoid and carboxymethyl cellulose.

456. The tablet or capsule of clause 455, wherein said a water-soluble acetylated cannabinoid and a water-soluble glycosylated cannabinoid comprises a water-soluble acetylated cannabinoid and a water-soluble glycosylated cannabinoid generated in vivo.

457. The tablet or capsule of clause 455, wherein said a water-soluble acetylated cannabinoid and a water-soluble glycosylated cannabinoid comprises a water-soluble acetylated cannabinoid and a water-soluble glycosylated cannabinoid generated in vitro.

458. The tablet or capsule of clause 455, wherein said a water-soluble acetylated cannabinoid and a water-soluble glycosylated cannabinoid comprises a non-psychoactive a water-soluble acetylated cannabinoid and a water-soluble glycosylated cannabinoid.

459. The tablet or capsule of clause 455, wherein the amount of a water-soluble acetylated cannabinoid and a water-soluble glycosylated cannabinoid is 5 milligrams or less.

460. The tablet or capsule of clause 455, wherein the amount of a water-soluble acetylated cannabinoid and a water-soluble glycosylated cannabinoid 5 milligrams and 200 milligrams.

461. The tablet or capsule of clause 455, wherein the wherein the amount of a water-soluble acetylated cannabinoid and a water-soluble glycosylated cannabinoid is more than 200 milligrams.

462. A tablet or capsule consisting essentially a water-soluble acetylated cannabinoid and a water-soluble glycosylated cannabinoid and glycerin.

463. The tablet or capsule of clause 462, wherein said a water-soluble acetylated cannabinoid and a water-soluble glycosylated cannabinoid comprises a water-soluble acetylated cannabinoid and a water-soluble glycosylated cannabinoid generated in vivo.

464. The tablet or capsule of clause 462, wherein said a water-soluble acetylated cannabinoid and a water-soluble glycosylated cannabinoid comprises a water-soluble acetylated cannabinoid and a water-soluble glycosylated cannabinoid generated in vitro.

465. The tablet or capsule of clause 462, wherein said a water-soluble acetylated cannabinoid and a water-soluble glycosylated cannabinoid comprises a non-psychoactive a water-soluble acetylated cannabinoid and a water-soluble glycosylated cannabinoid.

466. The tablet or capsule of clause 462, wherein the amount of a water-soluble acetylated cannabinoid and a water-soluble glycosylated cannabinoid is 5 milligrams or less.

467. The tablet or capsule of clause 462, wherein the amount of a water-soluble acetylated cannabinoid and a water-soluble glycosylated cannabinoid 5 milligrams and 200 milligrams.

468. The tablet or capsule of clause 462, wherein the wherein the amount of a water-soluble acetylated cannabinoid and a water-soluble glycosylated cannabinoid is more than 200 milligrams.

462. A tablet or capsule consisting essentially of a water-soluble acetylated cannabinoid and a water-soluble glycosylated cannabinoid and a water-soluble glycosylated cannabinoid and gelatin.

470. The tablet or capsule of clause 462, wherein said a water-soluble acetylated cannabinoid and a water-soluble glycosylated cannabinoid comprises a water-soluble acetylated cannabinoid and a water-soluble glycosylated cannabinoid generated in vivo.

471. The tablet or capsule of clause 462, wherein said a water-soluble acetylated cannabinoid and a water-soluble glycosylated cannabinoid comprises a water-soluble acetylated cannabinoid and a water-soluble glycosylated cannabinoid generated in vitro.

472. The tablet or capsule of clause 462, wherein said a water-soluble acetylated cannabinoid and a water-soluble glycosylated cannabinoid comprises a non-psychoactive a water-soluble acetylated cannabinoid and a water-soluble glycosylated cannabinoid.

473. The tablet or capsule of clause 462, wherein the amount of a water-soluble acetylated cannabinoid and a water-soluble glycosylated cannabinoid is 5 milligrams or less.

474. The tablet or capsule of clause 462, wherein the amount of a water-soluble acetylated cannabinoid and a water-soluble glycosylated cannabinoid 5 milligrams and 200 milligrams.

475. The tablet or capsule of clause 462, wherein the wherein the amount of a water-soluble acetylated cannabinoid and a water-soluble glycosylated cannabinoid is more than 200 milligrams.

476. A tablet or capsule consisting essentially of a water-soluble acetylated cannabinoid and a water-soluble glycosylated cannabinoid and a water-soluble glycosylated cannabinoid and polyethylene glycol.

477. The tablet or capsule of clause 476, wherein said a water-soluble acetylated cannabinoid and a water-soluble glycosylated cannabinoid comprises a water-soluble acetylated cannabinoid and a water-soluble glycosylated cannabinoid generated in vivo.

478. The tablet or capsule of clause 476, wherein said a water-soluble acetylated cannabinoid and a water-soluble glycosylated cannabinoid comprises a water-soluble acetylated cannabinoid and a water-soluble glycosylated cannabinoid generated in vitro.

479. The tablet or capsule of clause 476, wherein said a water-soluble acetylated cannabinoid and a water-soluble glycosylated cannabinoid comprises a non-psychoactive a water-soluble acetylated cannabinoid and a water-soluble glycosylated cannabinoid.

480. The tablet or capsule of clause 476, wherein the amount of a water-soluble acetylated cannabinoid and a water-soluble glycosylated cannabinoid is 5 milligrams or less.

481. The tablet or capsule of clause 476, wherein the amount of a water-soluble acetylated cannabinoid and a water-soluble glycosylated cannabinoid is between 5 milligrams and 200 milligrams.

482. The tablet or capsule of clause 476, wherein the wherein the amount of a water-soluble acetylated cannabinoid and a water-soluble glycosylated cannabinoid is more than 200 milligrams.

483. A method of manufacturing and packaging a cannabinoid dosage, consisting of the following steps:
preparing a fill solution with a desired concentration of a water-soluble cannabinoid in a liquid carrier wherein said cannabinoid solubilized in said liquid carrier;
encapsulating said fill solution in capsules;
packaging said capsules in a closed packaging system; and
removing atmospheric air from the capsules, wherein the removing of atmospheric air consists solely of purging said packaging system with an inert gas, and wherein said packaging system provides a room temperature stable product.

484. The method of clause 483, wherein the packaging system is a blister package.

485. The method of clause 484 wherein the blister package is constructed of material that minimizes exposure to moisture and air.

486. The method of clause 483, wherein the cannabinoid is a glycosylated cannabinoid, a acetylated cannabinoid or a mixture of the two.

487. The method of clause 486, wherein said glycosylated cannabinoid and/or said acetylated cannabinoid are generated in vivo.

488. The method of clause 486, wherein said glycosylated cannabinoid and/or said acetylated cannabinoid are generated in vitro.

489. The method of clause 483, wherein the liquid carrier is water-based carrier.

490. The method of clause 487, wherein the water-based carrier is an aqueous sodium chloride solution.

491. The method of clause 483, wherein the capsules are soft gelatin capsules.

492. The method of clause 483, wherein the inert gas is nitrogen.

493. The method of clause 483, wherein the desired cannabinoid concentration is about 1-10% w/w.

494. The method of clause 493 wherein the desired concentration is about 1.5-6.5% w/w.

495. An oral pharmaceutical solution consisting essentially of a water-soluble cannabinoid, 30-33% w/w water, about 50% w/w alcohol, 0.01% w/w butylated hydroxylanisole (BHA) or 0.1% w/w ethylenediaminetetraacetic acid (EDTA) and 5-21% w/w co-solvent, having a combined total of 100%, wherein said co-solvent is selected from the group consisting of propylene glycol, polyethylene glycol and combinations thereof, and wherein said water-soluble cannabinoid is a glycosylated cannabinoid, an acetylated cannabinoid or a mixture of the two.

496. The oral pharmaceutical solution of clause 495 consisting essentially of 0.1 to 5% w/w of said water-soluble cannabinoid, about 50% w/w alcohol, 5.5% w/w propylene glycol, 12% w/w polyethylene glycol and 30-33% w/w water.

497. The oral pharmaceutical solution of clause 496, wherein said alcohol is ethanol.

498. An oral pharmaceutical solution consisting essentially of about 0.1% to 1% w/w water-soluble cannabinoid, about 50% w/w alcohol, 5.5% w/w propylene glycol, 12% w/w polyethylene glycol, 30-33% w/w water, 0.01% w/w butylated hydroxyanisole, having a combined total of 100%, and wherein said water-soluble cannabinoid is a glycosylated cannabinoid, an acetylated cannabinoid or a mixture of the two wherein that were generated in vivo.

499. The oral pharmaceutical solution of clause 498 in sublingual spray form.

500. An oral pharmaceutical solution comprising 0.54% w/w water-soluble cannabinoid, 31.9% w/w water, 12% w/w polyethylene glycol 400, 5.5% w/w propylene glycol, 0.01% w/w butylated hydroxyanisole, 0.05% w/w sucralose, and 50% w/w alcohol.

501. An solution for nasal and/or sublingual administration of a composition comprising:
  an excipient of propylene glycol, ethanol anhydrous, or a mixture of both;
  a water-soluble glycosylated cannabinoid;

502. The solution of clause 501, wherein said glycosylated cannabinoid is generated in vivo.

503. The solution of clause 501, wherein said glycosylated cannabinoid is generated in vitro.

504. The solution of clause 501, wherein said glycosylated cannabinoid is non-psychoactive.

505. The aqueous solution of clause 501, and further comprising a topical decongestant.

506. The aqueous solution of clause 505, wherein said topical decongestant is selected from the group consisting of: phenylephrine hydrochloride, Oxymetazoline hydrochloride, and Xylometazoline.

507. The aqueous solution of clause 501, and further comprising an antihistamine.

508. The aqueous solution of clause 501, and further comprising a steroid.

509. The aqueous solution of clause 509, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

510. The aqueous solution of clause 501, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

511. An solution for nasal and/or sublingual administration of a composition comprising:
  an excipient of propylene glycol, ethanol anhydrous or a mixture of both; and
  an water-soluble acetylated cannabinoid.

512. The solution of clause 511, wherein said acetylated cannabinoid is generated in vivo.

513. The solution of clause 511, wherein said acetylated cannabinoid is generated in vitro.

514. The solution of clause 511, wherein said acetylated cannabinoid is non-psychoactive.

515. The aqueous solution of clause 511, and further comprising a topical decongestant.

516. The aqueous solution of clause 515, wherein said topical decongestant is selected from the group consisting of: phenylephrine hydrochloride, Oxymetazoline hydrochloride, and Xylometazoline.

517. The aqueous solution of clause 511, and further comprising an antihistamine.

518. The aqueous solution of clause 511, and further comprising a steroid.

519. The aqueous solution of clause 518, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

520. The aqueous solution of clause 519, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

521. A solution for nasal and/or sublingual administration of a composition comprising:
  an excipient of propylene glycol, ethanol anhydrous or a mixture of both; and
  a water-soluble glycosylated cannabinoid and an water-soluble acetylated cannabinoid.

522. The solution of clause 521, wherein said acetylated cannabinoid and said glycosylated cannabinoid is generated in vivo.

523. The solution of clause 521, wherein said acetylated cannabinoid and said glycosylated cannabinoid is generated in vitro.

524. The solution of clause 521, wherein said acetylated cannabinoid and said glycosylated cannabinoid are non-psychoactive.

525. The aqueous solution of clause 521, and further comprising a topical decongestant.

526. The aqueous solution of clause 525, wherein said topical decongestant is selected from the group consisting of: phenylephrine hydrochloride, Oxymetazoline hydrochloride, and Xylometazoline.

527. The aqueous solution of clause 521, and further comprising an antihistamine.

528. The aqueous solution of clause 521, and further comprising a steroid.

529. The aqueous solution of clause 528, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

530. The aqueous solution of clause 529, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

531. An aqueous solution for nasal and/or sublingual administration of a compositions comprising:
  a saline solution; and
  a water-soluble glycosylated cannabinoid.

532. The aqueous solution of clause 531, wherein said glycosylated cannabinoid is generated in vivo.

533. The aqueous solution of clause 531, wherein said glycosylated cannabinoid is generated in vitro.

534. The aqueous solution of clause 531, wherein said glycosylated cannabinoid is non-psychoactive.

535. The aqueous solution of clause aqueous 531, and further comprising a topical decongestant.

536. The aqueous solution of clause 535, wherein said topical decongestant is selected from the group consisting of: phenylephrine hydrochloride, Oxymetazoline hydrochloride, and Xylometazoline.

537. The aqueous solution of clause 531, and further comprising an antihistamine.

538. The aqueous solution of clause 531, and further comprising a steroid.

539. The aqueous solution of clause 539, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

540. The aqueous solution of clause 531, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

541. An aqueous solution for nasal and/or sublingual administration of a composition comprising:
a saline solution; and
a water-soluble acetylated cannabinoid.

542. The aqueous solution of clause 541, wherein said acetylated cannabinoid is generated in vivo.

543. The aqueous solution of clause 541, wherein said acetylated cannabinoid is generated in vitro.

544. The aqueous solution of clause 541, wherein said acetylated cannabinoid is non-psychoactive.

545. The aqueous solution of clause 541, and further comprising a topical decongestant.

546. The aqueous solution of clause 545, wherein said topical decongestant is selected from the group consisting of: phenylephrine hydrochloride, Oxymetazoline hydrochloride, and Xylometazoline.

547. The aqueous solution of clause 546, and further comprising an antihistamine.

548. The aqueous solution of clause 545, and further comprising a steroid.

549. The aqueous solution of clause 548, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

550. The aqueous solution of clause 549, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

551. An aqueous solution for nasal and/or sublingual administration of a composition comprising:
a saline solution; and
a water-soluble acetylated cannabinoid and a water-soluble glycosylated cannabinoid.

552. The aqueous solution of clause 551, wherein said acetylated cannabinoid and said glycosylated cannabinoid is generated in vivo.

553. The aqueous solution of clause 551, wherein said acetylated cannabinoid and said glycosylated cannabinoid is generated in vitro.

554. The aqueous solution of clause 551, wherein said acetylated cannabinoid and said glycosylated cannabinoid are non-psychoactive.

555. The aqueous solution of clause 551, and further comprising a topical decongestant.

556. The aqueous solution of clause 555, wherein said topical decongestant is selected from the group consisting of: phenylephrine hydrochloride, Oxymetazoline hydrochloride, and Xylometazoline.

557. The aqueous solution of clause 551, and further comprising an antihistamine.

558. The aqueous solution of clause 551, and further comprising a steroid.

559. The aqueous solution of clause 557, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

560. The aqueous solution of clause 551, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

561. An aqueous solution for nasal and/or sublingual administration of a compositions comprising:
purified water; and
a water-soluble glycosylated cannabinoid.

562. The aqueous solution of clause 561, wherein said glycosylated cannabinoid is generated in vivo.

563. The aqueous solution of clause 561, wherein said glycosylated cannabinoid is generated in vitro.

564. The solution of clause 561, wherein said glycosylated cannabinoid is non-psychoactive.

565. The aqueous solution of clause 561, and further comprising a topical decongestant.

566. The aqueous solution of clause 565, wherein said topical decongestant is selected from the group consisting of: phenylephrine hydrochloride, Oxymetazoline hydrochloride, and Xylometazoline.

567. The aqueous solution of clause 561, and further comprising an antihistamine.

568. The aqueous solution of clause 561, and further comprising a steroid.

569. The aqueous solution of clause 568, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

570. The aqueous solution of clause 561, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

571. An aqueous solution for nasal and/or sublingual administration of a composition comprising:
purified water; and
a water-soluble acetylated cannabinoid.

572. The aqueous solution of clause 571, wherein said acetylated cannabinoid is generated in vivo.

573. The aqueous solution of clause 571, wherein said acetylated cannabinoid is generated in vitro.

574. The solution of clause 571, wherein said acetylated cannabinoid is non-psychoactive.

575. The aqueous solution of clause 571, and further comprising a topical decongestant.

576. The aqueous solution of clause 575, wherein said topical decongestant is selected from the group consisting of: phenylephrine hydrochloride, Oxymetazoline hydrochloride, and Xylometazoline.

577. The aqueous solution of clause 571, and further comprising an antihistamine.

578. The aqueous solution of clause 571, and further comprising a steroid.

579. The aqueous solution of clause 578, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

580. The aqueous solution of clause 579, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

581. An aqueous solution for nasal and/or sublingual administration of a composition comprising:
purified water; and
a water-soluble acetylated cannabinoid and a water-soluble glycosylated cannabinoid.

582. The aqueous solution of clause 581, wherein said acetylated cannabinoid and said glycosylated cannabinoid is generated in vivo.

583. The aqueous solution of clause 581, wherein said acetylated cannabinoid and said glycosylated cannabinoid is generated in vitro.

584. The aqueous solution of clause 581, wherein said acetylated cannabinoid and said glycosylated cannabinoid are non-psychoactive.

585. The aqueous solution of clause 581, and further comprising a topical decongestant.

586. The aqueous solution of clause 585, wherein said topical decongestant is selected from the group consisting of: phenylephrine hydrochloride, Oxymetazoline hydrochloride, and Xylometazoline.

587. The aqueous solution of clause 581, and further comprising an antihistamine.

588. The aqueous solution of clause 581, and further comprising a steroid.

589. The aqueous solution of clause 588, wherein said steroid is a corticosteroid selected from the group consisting of: neclomethasone dipropionate, budesonide, ciclesonide, flunisolide, fluticasone furoate, fluticasone propionate, mometasone, triamcinolone acetonide.

590. The aqueous solution of clause 581, the solution further comprising at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, propylene glycol.

591. A topical formulation consisting of a water-soluble glycosylated cannabinoid, and/or water-soluble acetylated cannabinoid, or a mixture of both, and a pharmaceutically acceptable excipient.

592. The topical formulation according to clause 591, and further comprising a quantity of capsaicin.

593. The topical formulation according to clause 591, and further comprising a quantity of benzocaine.

594. The topical formulation according to clause 591, and further comprising a quantity of lidocaine.

595. The topical formulation according to clause 591, and further comprising a quantity of camphor.

596. The topical formulation according to clause 591, and further comprising a quantity of benzoin resin.

597. The topical formulation according to clause 591, and further comprising a quantity of methyl salicilate.

598. The topical formulation according to clause 591, and further comprising a quantity of triethanolamine salicylate.

599. The topical formulation according to clause 591, and further comprising a quantity of hydrocortisone.

600. The topical formulation according to clause 591, and further comprising a quantity of salicylic acid.

601. The topical formulation according to clause 591, and further comprising a wherein the pharmaceutically acceptable excipient is selected from the group consisting of: gels, ointments, cataplasms, poultices, pastes, creams, lotions, plasters and jellies 602. The topical formulation according to clause 591, and further comprising a polyethylene glycol.

603. A gel for transdermal administration, the mixture preferably contains from 15% to about 90% ethanol, from about 10% to about 60% buffered aqueous solution or water, from about 0.1 to about 25% propylene glycol, from about 0.1 to about 20% of a gelling agent, from about 0.1 to about 20% of a base, from about 0.1 to about 20% of an absorption enhancer and from about 1% to about 25% polyethylene glycol and a water-soluble cannabinoid.

604. The gel of clause 603, wherein said water-soluble cannabinoid comprises a water-soluble glycosylated cannabinoid, and/or water-soluble acetylated cannabinoid, or a mixture of both 605. The gel of clause 604, wherein said glycosylated cannabinoid, and/or said acetylated cannabinoid were generated in vivo.

606. The gel of clause 604, wherein said glycosylated cannabinoid, and/or said acetylated cannabinoid were generated in vitro.

607. A formulation comprising the following volumetric amounts: (i) from about 15% to about 90% ethanol, (ii) a glycol selected from the group consisting of (a) propylene glycol from about 0.1% to about 25%, (b) polyethylene glycol from about 1 to about 30%, and (c) a combination of (a) and (b), (iii) from about 0.1 to about 20% of a gelling agent, (iv) from about 0.1 to about 20% of a base and (v) from about 0.1 to about 20% of an absorption enhancer, and a water-soluble cannabinoid, said formulation being suitable for transdermal administration.

608. The formulation of clause 607, wherein said water-soluble cannabinoid comprises a water-soluble glycosylated cannabinoid, and/or water-soluble acetylated cannabinoid, or a mixture of both.

609. The formulation of clause 608, wherein said glycosylated cannabinoid, and/or said acetylated cannabinoid were generated in vivo.

610. The formulation of clause 608, wherein said glycosylated cannabinoid, and/or said acetylated cannabinoid were generated in vitro.

611. A transdermal composition comprising a pharmaceutically effective amount of a water-soluble cannabinoid for delivery of the cannabinoid to the bloodstream of a user, said composition comprising:
a pharmaceutically acceptable excipient;
at least one water-soluble cannabinoid;
wherein the cannabinoid is capable of diffusing from the composition into the bloodstream of the user.

612. The composition of clause 611, wherein the water-soluble cannabinoid is selected from the group consisting of: a glycosylated cannabinoid, an acetylated cannabinoid, and a mixture of both.

613. The composition of clause 612, wherein said glycosylated cannabinoid, and/or said acetylated cannabinoid were generated in vivo.

614. The composition of clause 611, wherein the transdermal composition further comprises one or more pharmaceutically acceptable excipients to create a transdermal dosage form selected from the group consisting of: gels, ointments, cataplasms, poultices, pastes, creams, lotions, plasters and jellies.

615. The composition of clause 611, and further comprising a surfactant.

616. The composition of clause 611, wherein the surfactant is a surfactant-lecithin organogel.

617. The composition of clause 611, wherein the surfactant-lecithin organogel is present in an amount of between about between about 95% and about 98% w/w.

618. The composition of clause 611, wherein the surfactant-lecithin organogel comprises lecithin and PPG-2 myristyl ether propionate.

619. The composition of clause 611, wherein the surfactant-lecithin organogel comprises a surfactant comprising high molecular weight polyacrylic acid polymers.

622. The composition of clause 611, wherein the composition further comprises isopropyl myristate.

623. The composition of clause 611, wherein the water-soluble cannabinoid is non-psychoactive.

624. The composition of clause 611, wherein the pharmaceutically acceptable excipients is selected from the group consisting of: gels, ointments, cataplasms, poultices, pastes, creams, lotions, plasters and jellies 625. A transdermal composition comprising a pharmaceutically effective amount of a water-soluble cannabinoid for delivery of the cannabinoid to the bloodstream of a user, said composition comprising:
a permeation enhancer;
at least one water-soluble cannabinoid;
wherein the cannabinoid is capable of diffusing from the composition into the bloodstream of the user.

626. The composition of clause 625, wherein the water-soluble cannabinoid is selected from the group consisting of: a glycosylated cannabinoid, an acetylated cannabinoid, and a mixture of both.

627. The composition of clause 626, wherein said glycosylated cannabinoid, and/or said acetylated cannabinoid were generated in vivo.

628. The composition of clause 625, wherein the permeation enhancer is selected from the group consisting of: propylene glycol monolaurate, diethylene glycol monoethyl ether, an oleoyl macrogolglyceride, a caprylocaproyl macrogolglyceride, and an oleyl alcohol.

629. The composition of clause 625, herein the transdermal composition further comprises one or more pharmaceutically acceptable excipients to create a transdermal dosage form selected from the group consisting of: gels, ointments, cataplasms, poultices, pastes, creams, lotions, plasters and jellies.

630. A liquid cannabinoid liniment composition consisting of water, isopropyl alcohol solution and a water-soluble cannabinoid.

631. The composition of clause 630, wherein said water-soluble cannabinoid is selected from the group consisting of: a glycosylated cannabinoid, an acetylated cannabinoid, and a mixture of both.

632. The composition of clause 632, wherein said glycosylated cannabinoid, and/or said acetylated cannabinoid were generated in vivo.

633. The composition of clause 630, consisting of from about 97.5% to about 99.5% by weight of 70% isopropyl alcohol solution and from about 0.5% to about 2.5% by weight of a cannabinoid mixture 634. A commercially available topical creme composition infused with a glycosylated cannabinoid, an acetylated cannabinoid, and a mixture of both.

635. The composition of clause 634, wherein said glycosylated cannabinoid, and/or said acetylated cannabinoid were generated in vivo.

636. A commercially available lip balm composition supplemented with a water-soluble cannabinoid wherein said comprises a glycosylated cannabinoid, and/or an acetylated cannabinoid, and/or a mixture of both.

637. The composition of clause 636, wherein said glycosylated cannabinoid, and/or said acetylated cannabinoid were generated in vivo.

638. A commercially available cosmetic composition supplemented with a water-soluble cannabinoid wherein said comprises a glycosylated cannabinoid, and/or an acetylated cannabinoid, and/or a mixture of both.

639. The composition of clause 638, wherein said glycosylated cannabinoid, and/or said acetylated cannabinoid were generated in vivo.

640. A tobacco plant containing at least one water-soluble cannabinoids.

641. The tobacco plant in clause 640, wherein said water-soluble cannabinoid comprises a glycosylated cannabinoid, and/or an acetylated cannabinoid, and/or a mixture of both.

642. The tobacco plant of clause 641, wherein said glycosylated cannabinoid, and/or said acetylated cannabinoid were generated in vivo.

643. The tobacco plant of clause 641, wherein said glycosylated cannabinoid, and/or said acetylated cannabinoid were generated in vitro.

644. The tobacco plant of clause 640, wherein said water-soluble cannabinoid is non-psychoactive.

645. The tobacco plant of clause 640, wherein said tobacco plant is used to generate a water-soluble cannabinoid infused tobacco product.

646. The tobacco plant of clause 645, wherein said cannabinoid infused tobacco product is a cigarette, pipe tobacco, chewing tobacco, cigar, smokeless tobacco.

646. A composition comprising:
an aqueous solution;
water-soluble cannabinoid dissolved in said aqueous solution wherein said water-soluble cannabinoid comprises a glycosylated cannabinoid, and/or an acetylated cannabinoid, and/or a mixture of both;
wherein said composition may be introduced to a cigarette and/or a tobacco leaf such that said aqueous solution may evaporate generating a cigarette and/or a tobacco leaf that contains said water-soluble cannabinoid.

647. The composition of clause 646, wherein said glycosylated cannabinoid, and/or said acetylated cannabinoid were generated in vivo.

648. The composition of clause 646, wherein said glycosylated cannabinoid, and/or said acetylated cannabinoid were generated in vivo.

649. The composition of clause 646, wherein said water-soluble cannabinoid is non-psychoactive.

650. The composition of clause 646, wherein said aqueous solution comprises purified water.

651. A method of treating a medical condition in a mammal comprising the step of administering a therapeutically effective amount of a glycosylated cannabinoid, and/or an acetylated cannabinoid, and/or a mixture of both or a pharmaceutically acceptable salt thereof, wherein the medical condition is selected from the group consisting of:

obesity, post-traumatic stress syndrome, anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, *cannabis* use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis.

652. The method of clause 651 wherein the compound is administered by a route selected from the group consisting of: transdermal, topical, oral, buccal, sublingual, intra-venous, intra-muscular, vaginal, rectal, ocular, nasal and follicular. 653. The method of clause 652, wherein said glycosylated cannabinoid, and/or an acetylated cannabinoid, and/or a mixture of both are glycosylated cannabinoid, and/or acetylated in vivo.

REFERENCES

The following references are hereby incorporated in their entirety by reference:

[1] I von Ossowski, M R Mulvey, P A Leco, A Borys and P C Loewen, *J Bacteriol.* 1991, 173(2):514.
[2] Behera, A., Behera, A., Mishra, S. C., Swain, S. K., & Author, C. (2003). Cannabinoid glycosides: In vitro production of a new class of cannabinoids with improved physicochemical properties. *Proc. Intl. Soc. Mag. Reson. Med* (Vol. 14).
[3] Holland, M. L., Lau, D. T. T., Allen, J. D., & Arnold, J. C. (2009). The multidrug transporter ABCG2 (BCRP) is inhibited by plant-derived cannabinoids. *British Journal of Pharmacology*, 152(5), 815-824.
[4] Ivanchenco. M., Vejlupkova. Z., Quatrano. R. S., Fowler. J. E. (2000) Maize ROP7 GTPase contains a unique, CaaX box-independent plasma membrane targeting signal. *The Plant Journal*, (24)1, 79-90.
[5] James M. Rini and Jeffrey D. Esko. Glycosyltransferases and Glycan-Processing Enzymes. In: Essentials of Glycobiology [Internet]. 3rd edition.
[6] Marks, M. D., Tian, L., Wenger, J. P., Omburo, S. N., Soto-Fuentes, W., He, J., . . . Dixon, R. A. (2009). Identification of candidate genes affecting 49-tetrahydrocannabinol biosynthesis in *Cannabis sativa*. *Journal of Experimental Botany*, 60(13), 3715-3726.
[7] Nagaya, S., Kawamura, K., Shinmyo, A., & Kato, K. (2010). The HSP terminator of *Arabidopsis thaliana* increases gene expression in plant cells. *Plant and Cell Physiology*, 51(2), 328-332.
[8] Norambuena, L., Marchant, L., Berninsone, P., Hirschberg, C. B., Silva, H., & Orellana, A. (2002). Transport of UDP-galactose in plants. Identification and functional characterization of AtUTr1, an *Arabidopsis thaliana* UDP-galactose/UDP-glucose transporter. *Journal of Biological Chemistry*, 277(36), 32923-32929.
[9] Onofri, C., De Meijer, E. P. M., & Mandolino, G. (2015). Sequence heterogeneity of cannabidiolic- and tetrahydrocannabinolic acid-synthase in *Cannabis sativa* L. and its relationship with chemical phenotype. *Phytochemistry*, 116(1), 57-68.
[9] Priest, D. M., Ambrose, S. J., Vaistij, F. E., Elias, L., Higgins, G. S., Ross, A. R. S., . . . Bowles, D. J. (2006). Use of the glucosyltransferase UGT71B6 to disturb abscisic acid homeostasis in *Arabidopsis thaliana*. *Plant Journal*, 46(3), 492-502.
[10] Siritunga, D., and Sayre, R. T. (2003). Generation of cyanogen-free transgenic cassava. Planta 217, 367-373.
[11] Sparkes, I. A., Runions, J., Kearns, A., & Hawes, C. (2006). Rapid, transient expression of fluorescent fusion proteins in tobacco plants and generation of stably transformed plants. *Nature Protocols*, 1(4), 2019-2025.
[13] Taura, F., Morimoto, S., & Shoyama, Y. (1996). Purification and characterization of cannabidiolic-acid synthase from *Cannabis sativa* L. Biochemical analysis of a novel enzyme that catalyzes the oxidocyclization of. *Journal of Biological Chemistry*, 27/(29), 17411-17416.
[14] Taura, F., Sirikantaramas, S., Shoyama Y, Yoshikai K, Shoyama Y, Morimoto S. (2007) Cannabidiolic-acid synthase, the chemotype-determining enzyme in the fiber-type *Cannabis sativa*. *Febbs letters*, 581(16), 2929-34. DOI:10.1016/j.febslet.2007.05.043
[15] Yoo, S. D., Cho, Y. H., & Sheen, J. (2007). *Arabidopsis* mesophyll protoplasts: A versatile cell system for transient gene expression analysis. *Nature Protocols*, 2(7), 1565-1572.
[16] Matsui, T., Matsuura, H., Sawada, K., Takita, E., Kinjo, S., Takenami, S., . . . Kato, K. (2012). High level expression of transgenes by use of 5'-untranslated region of the *Arabidopsis thaliana* arabinogalactan-protein 21 gene in dicotyledons. *Plant Biotechnology*, 29(3), 319-322.
[17] Murashige, T., and Skoog, F. (1962). A revised medium for rapid growth and bioassays with tobacco tissue culture. Physiol. Plant. 15, 473-497.
[18] Zipp, et al., Cannabinoid glycosides: In vitro production of a new class of cannabinoids with improved physicochemical properties. bioRxiv preprint doi: Mohamed, E. A., T. Iwaki, I. Munir, M. Tamoi, S. Shigeoka, and A. Wadano. 2003. Overexpression of bacterial catalase in tomato leaf chloroplasts enhances photo-oxidative stress tolerance. Plant Cell Environ. 26:2037-2046.
[20] Akhtar, M. T., 2013, Doctoral Thesis, Leiden University. Cannabinoids and zebrafish. 2013-05-22.
[21] Sayed Farag. Cannabinoids production in *Cannabis sativa* L.: An in vitro approach. Thesis January 2014.
[21] K, Watanabe, et al., Cytochrome P450 enzymes involved in the metabolism of tetrahydrocannabinols and cannabinol by human hepatic microsomes. Life Sciences. Volume 80, Issue 15, 20 Mar. 2007, Pages 1415-1419
[22] Flores-Sanchez I J. et al., Elicitation studies in cell suspension cultures of *Cannabis sativa* L. J Biotechnol. 2009 Aug. 20; 143(2):157-68.
[23] Stephen M. Stout & Nina M. Cimino (2013) Exogenous cannabinoids as substrates, inhibitors, and inducers of human drug metabolizing enzymes: a systematic review, Drug Metabolism Reviews, 46:1, 86-95
[24] Andre C M, Hausman J-F, Guerriero G. *Cannabis sativa*: The Plant of the Thousand and One Molecules. Frontiers in Plant Science. 2016; 7:19.

[25] Mahlberg Pl. et al., Accumulation of Cannabinoids in Glandular Trichomes of *Cannabis* (Cannabaceae). Journal of Industrial Hemp 9(1):15-36 June 2004 with 273 Reads

[25] Katalin S., et al., Mini Rev Med Chem. 2017; 17(13): 1223-1291.

[26] Sirikantaramas S., et al., Tetrahydrocannabinolic Acid Synthase, the Enzyme Controlling Marijuana Psychoactivity, is Secreted into the Storage Cavity of the Glandular Trichomes. Plant and Cell Physiology, Volume 46, Issue 9, 1 Sep. 2005, Pages 1578-1582.

[26] Schilmiller A L, Last R L, Pichersky E (2008) Harnessing plant trichome biochemistry for the production of useful compounds. Plant Journal 54: 702-711.

[27] Matias-Hernandez, L. et al. AaMYB1 and its orthologue AtMYB61 affect terpene metabolism and trichome development in *Artemisia annua* and *Arabidopsis thaliana*. Plant I

[28] Ahmad, M., Hirz, M., Pichler, H., & Schwab, H. (2014). Protein expression in *Pichia pastoris*: Recent achievements and perspectives for heterologous protein production. *Applied Microbiology and Biotechnology*, 98(12), 5301-5317.

[29] Cregg, J. M., Cereghino, J. L., Shi, J., & Higgins, D. R. (2000). Recombinant Protein Expression in *Pichia pastoris*. Molecular Biotechnology, 16(1), 23-52.

[30] Ellis, S. B., Brust, P. F., Koutz, P. J., Waters, A. N. N. F., Harpold, M. M., Gingeras, T. R., & Al, E. E. T. (1985). Isolation of Alcohol Oxidase and Two Other Methanol Regulatable Genes from the Yeast *Pichia pastoris*, 5(5), 1111-1121.

[31] antos, R. B., Abranches, R., Fischer, R., Sack, M., & Holland, T. (2016). Putting the Spotlight Back on Plant Suspension Cultures. *Frontiers in Plant Science*, 7(March), 1-12.

[32] Nagata, T., Nemoto, Y., and Hasezawa, S. (1992). Tobacco BY-2 cell line as the "HeLa" cell in the cell biology of higher plants. Int. Rev. Cytol. 132, 1-30.

SEQUENCE LISTINGS

As noted above, the instant application contains a full Sequence Listing which has been submitted electronically in ASCII format and is hereby incorporated by reference in its entirety. The following sequences are further provided herewith and are hereby incorporated into the specification in their entirety:

```
DNA
Cytochrome P450 (CYP3A4)
Human
                                              SEQ ID NO. 1
ATGGCTTTGATTCCTGATTTGGCTATGGAAACTAGATTGTTGTTGGCTGTTTCATTGGTTTTGT

TGTATTTGTATGGAACTCATTCACATGGATTGTTTAAAAAATTGGGAATTCCTGGACCTACTCC

TTTGCCTTTTTTGGGAAATATTTTGTCATATCATAAAGGATTTTGCATGTTTGATATGGAATGC

CATAAAAATATGGAAAGTTTGGGGATTTTATGATGGACAACAACCTGTTTTGGCTATTACTG

ATCCTGATATGATTAAAACTGTTTTGGTTAAAGAATGCTATTCAGTTTTTACTAATAGAAGACC

TTTTGGACCTGTTGGATTTATGAAATCAGCTATTTCAATTGCTGAAGATGAAGAATGGAAAAGA

TTGAGATCATTGTTGTCACCTACTTTTACTTCAGGAAAATTGAAAGAAATGGTTCCTATTATTG

CTCAATATGGAGATGTTTTGGTTAGAAATTTGAGAAGAGAAGCTGAAACTGGAAAACCTGTTAC

TTTGAAAGATGTTTTTGGAGCTTATTCAATGGATGTTATTACTTCAACTTCATTTGGAGTTAAT

ATTGATTCATTGAATAATCCTCAAGATCCTTTTGTTGAAAATACTAAAAAATTGTTGAGATTTG

ATTTTTTGGATCCTTTTTTTTGTCAATTACTGTTTTTCCTTTTTTGATTCCTATTTTGGAAGT

TTTGAATATTTGCGTTTTTCCTAGAGAAGTTACTAATTTTTTGAGAAAATCAGTTAAAAGAATG

AAAGAATCAAGATTGGAAGATACTCAAAAACATAGAGTTGATTTTTTGCAATTGATGATTGATT

CACAAAATTCAAAAGAAACTGAATCACATAAAGCTTTGTCAGATTTGGAATTGGTTGCTCAATC

AATTATTTTATTTTTGCTGGATGCGAAACTACTTCATCAGTTTTGTCATTTATTATGTATGAA

TTGGCTACTCATCCTGATGTTCAACAAAAATTGCAAGAAGAAATTGATGCTGTTTTGCCTAATA

AAGCTCCTCCTACTTATGATACTGTTTTGCAAATGGAATATTTGGATATGGTTGTTAATGAAAC

TTTGAGATTGTTTCCTATTGCTATGAGATTGGAAAGAGTTTGCAAAAAAGATGTTGAAATTAAT

GGAATGTTATTCCTAAAGGAGTTGTTGTTATGATTCCTTCATATGCTTTGCATAGAGATCCTA

AATATTGGACTGAACCTGAAAAATTTTTGCCTGAAAGATTTTCAAAAAAAAATAAAGATAATAT

TGATCCTTATATTTATACTCCTTTTGGATCAGGACCTAGAAATTGCATTGGAATGAGATTTGCT

TTGATGAATATGAAATTGGCTTTGATTAGAGTTTTGCAAAATTTTTCATTTAAACCTTGCAAAG

AAACTCAAATTCCTTTGAAATTGTCATTGGGAGGATTGTTGCAACCTGAAAAACCTGTTGTTTT

GAAAGTTGAATCAAGAGATGGAACTGTTTCAGGAGCT
```

-continued

Amino Acid
Cytochrome P450 (CYP3A4)
Human

SEQ ID NO. 2

MALIPDLAMETRLLLAVSLVLLYLYGTHSHGLFKKLGIPGPTPLPFLGNILSYHKGFCMFDMEC

HKKYGKVWGFYDGQQPVLAITDPDMIKTVLVKECYSVFTNRRPFGPVGFMKSAISIAEDEEWKR

LRSLLSPTFTSGKLKEMVPIIAQYGDVLVRNLRREAETGKPVTLKDVFGAYSMDVITSTSFGVN

IDSLNNPQDPFVENTKKLLRFDFLDPFFLSITVFPFLIPILEVLNICVFPREVTNFLRKSVKRM

KESRLEDTQKHRVDFLQLMIDSQNSKETESHKALSDLELVAQSIIFIFAGCETTSSVLSFIMYE

LATHPDVQQKLQEEIDAVLPNKAPPTYDTVLQMEYLDMVVNETLRLFPIAMRLERVCKKDVEIN

GMFIPKGVVVMIPSYALHRDPKYWTEPEKFLPERFSKKNKDNIDPYIYTPFGSGPRNCIGMRFA

LMNMKLALIRVLQNFSFKPCKETQIPLKLSLGGLLQPEKPVVLKVESRDGTVSGA

DNA
P450 oxidoreductase gene (oxred)
Human

SEQ ID NO. 3

ATGATTAATATGGGAGATTCACATGTTGATACTTCATCAACTGTTTCAGAAGCTGTTGCTGAAG

AAGTTTCATTGTTTTCAATGACTGATATGATTTTGTTTTCATTGATTGTTGGATTGTTGACTTA

TTGGTTTTTGTTTAGAAAAAAAAAGAAGAAGTTCCTGAATTTACTAAAATTCAAACTTTGACT

TCATCAGTTAGAGAATCATCATTTGTTGAAAAAATGAAAAAAACTGGAAGAAATATTATTGTTT

TTTATGGATCACAAACTGGAACTGCTGAAGAATTTGCTAATAGATTGTCAAAAGATGCTCATAG

ATATGGAATGAGAGGAATGTCAGCTGATCCTGAAGAATATGATTTGGCTGATTTGTCATCATTG

CCTGAAATTGATAATGCTTTGGTTGTTTTTGCATGGCTACTTATGGAGAAGGAGATCCTACTG

ATAATGCTCAAGATTTTTATGATTGGTTGCAAGAAACTGATGTTGATTTGTCAGGAGTTAAATT

TGCTGTTTTTGGATTGGGAAATAAAACTTATGAACATTTTAATGCTATGGGAAAATATGTTGAT

AAAAGATTGGAACAATTGGGAGCTCAAAGAATTTTTGAATTGGGATTGGGAGATGATGATGGAA

ATTTGGAAGAAGATTTTATTACTTGGAGAGAACAATTTTGGTTGGCTGTTTGCGAACATTTTGG

AGTTGAAGCTACTGGAGAAGAATCATCAATTAGACAATATGAATTGGTTGTTCATACTGATATT

GATGCTGCTAAAGTTTATATGGGAGAAATGGGAAGATTGAAATCATATGAAAATCAAAAACCTC

CTTTTGATGCTAAAAATCCTTTTTTGGCTGCTGTTACTACTAATAGAAAATTGAATCAAGGAAC

TGAAAGACATTTGATGCATTTGGAATTGGATATTTCAGATTCAAAAATTAGATATGAATCAGGA

GATCATGTTGCTGTTTATCCTGCTAATGATTCAGCTTTGGTTAATCAATTGGGAAAAATTTTGG

GAGCTGATTTGGATGTTGTTATGTCATTGAATAATTTGGATGAAGAATCAAATAAAAAACATCC

TTTTCCTTGCCCTACTTCATATAGAACTGCTTTGACTTATTATTTGGATATTACTAATCCTCCT

AGAACTAATGTTTTGTATGAATTGGCTCAATATGCTTCAGAACCTTCAGAACAAGAATTGTTGA

GAAAAATGGCTTCATCATCAGGAGAAGGAAAAGAATTGTATTTGTCATGGGTTGTTGAAGCTAG

AAGACATATTTTGGCTATTTTGCAAGATTGCCCTTCATTGAGACCTCCTATTGATCATTTGTGC

GAATTGTTGCCTAGATTGCAAGCTAGATATTATTCAATTGCTTCATCATCAAAAGTTCATCCTA

ATTCAGTTCATATTTGCGCTGTTGTTGTTGAATATGAAACTAAAGCTGGAAGAATTAATAAAGG

AGTTGCTACTAATTGGTTGAGAGCTAAAGAACCTGTTGGAGAAAATGGAGGAAGAGCTTTGGTT

CCTATGTTTGTTAGAAAATCACAATTTAGATTGCCTTTTAAAGCTACTACTCCTGTTATTATGG

TTGGACCTGGAACTGGAGTTGCTCCTTTTATTGGATTTATTCAAGAAAGAGCTTGGTTGAGACA

ACAAGGAAAAGAAGTTGGAGAAACTTTGTTGTATTATGGATGCAGAAGATCAGATGAAGATTAT

TTGTATAGAGAAGAATTGGCTCAATTTCATAGAGATGGAGCTTTGACTCAATTGAATGTTGCTT

-continued

```
TTTCAAGAGAACAATCACATAAAGTTTATGTTCAACATTTGTTGAAACAAGATAGAGAACATTT

GTGGAAATTGATTGAAGGAGGAGCTCATATTTATGTTTGCGGAGATGCTAGAAATATGGCTAGA

GATGTTCAAAATACTTTTTATGATATTGTTGCTGAATTGGGAGCTATGGAACATGCTCAAGCTG

TTGATTATATTAAAAAATTGATGACTAAAGGAAGATATTCATTGGATGTTTGGTCA
```

```
Amino Acid
P450 oxidoreductase
Human
                                                           SEQ ID NO. 4
MINMGDSHVDTSSTVSEAVAEEVSLFSMTDMILFSLIVGLLTYWFLFRKKKEEVPEFTKIQTLT

SSVRESSFVEKMKKTGRNIIVFYGSQTGTAEEFANRLSKDAHRYGMRGMSADPEEYDLADLSSL

PEIDNALVVFCMATYGEGDPTDNAQDFYDWLQETDVDLSGVKFAVFGLGNKTYEHFNAMGKYVD

KRLEQLGAQRIFELGLGDDDGNLEEDFITWREQFWLAVCEHFGVEATGEESSIRQYELVVHTDI

DAAKVYMGEMGRLKSYENQKPPFDAKNPFLAAVTTNRKLNQGTERHLMHLELDISDSKIRYESG

DHVAVYPANDSALVNQLGKILGADLDVVMSLNNLDEESNKKHPFPCPTSYRTALTYYLDITNPP

RTNVLYELAQYASEPSEQELLRKMASSSGEGKELYLSWVVEARRHILAILQDCPSLRPPIDHLC

ELLPRLQARYYSIASSSKVHPNSVHICAVVVEYETKAGRINKGVATNWLRAKEPVGENGGRALV

PMFVRKSQFRLPFKATTPVIMVGPGTGVAPFIGFIQERAWLRQQGKEVGETLLYYGCRRSDEDY

LYREELAQFHRDGALTQLNVAFSREQSHKVYVQHLLKQDREHLWKLIEGGAHIYVCGDARNMAR

DVQNTFYDIVAELGAMEHAQAVDYIKKLMTKGRYSLDVWS
```

```
DNA
cannabidiolic acid (CBDA) synthase
Cannabis sativa
                                                           SEQ ID NO. 5
ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAGAT

CATGGAGATACATGAGCTTGTCAAGTTAGTTAACAAATGGCAAAATATTGCTTACAAGTATGAC

AAAGATTTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT

TGCTTGATAGATCCGCTGGGCAGAACGGTGCTTTCAAGATTAAGTTAGACTACGTTAAGAAACC

AATTCCAGAATCTGTATTTGTCCAAATTTTGGAAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAAGCAAGAAGATAA

CGAAAAGCATCTAAACTGGATTAGAAATATTTATAACTTCATGACTCCTTATGTGTCCAAAAAT
```

-continued

```
TCAAGATTGGCATATCTCAATTATAGAGACCTTGATATAGGAATAAATGATCCCAAGAATCCAA

ATAATTACACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCAA

CCACGGCATCGTCATTAA
```

Amino Acid
Cannabidiolic acid (CBDA) synthase
*Cannabis sativa*

SEQ ID NO. 6

```
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

SRLAYLNYRDLDIGINDPKNPNNYTQARIWGEKYFGKNFDRLVKVKTLVDPNNFFRNEQSIPPQ

PRHRH
```

DNA
UDP glycosyltransferase 76G1
*Stevia rebaudiana*

SEQ ID NO. 7

```
ATGGAAAATAAAACTGAAACTACTGTTAGAAGAAGAAGAAGAATTATTTTGTTTCCTGTTCCTT

TTCAAGGACATATTAATCCTATTTTGCAATTGGCTAATGTTTTGTATTCAAAAGGATTTTCAAT

TACTATTTTTCATACTAATTTTAATAAACCTAAAACTTCAAATTATCCTCATTTTACTTTTAGA

TTTATTTTGGATAATGATCCTCAAGATGAAAGAATTTCAAATTTGCCTACTCATGGACCTTTGG

CTGGAATGAGAATTCCTATTATTAATGAACATGGAGCTGATGAATTGAGAAGAGAATTGGAATT

GTTGATGTTGGCTTCAGAAGAAGATGAAGAAGTTTCATGCTTGATTACTGATGCTTTGTGGTAT

TTTGCTCAATCAGTTGCTGATTCATTGAATTTGAGAAGATTGGTTTTGATGACTTCATCATTGT

TTAATTTTCATGCTCATGTTTCATTGCCTCAATTTGATGAATTGGGATATTTGGATCCTGATGA

TAAAACTAGATTGGAAGAACAAGCTTCAGGATTTCCTATGTTGAAAGTTAAAGATATTAAATCA

GCTTATTCAAATTGGCAAATTTTGAAAGAAATTTTGGGAAAAATGATTAAACAAACTAGAGCTT

CATCAGGAGTTATTTGGAATTCATTTAAAGAATTGGAAGAATCAGAATTGGAAACTGTTATTAG

AGAAATTCCTGCTCCTTCATTTTTGATTCCTTTGCCTAAACATTTGACTGCTTCATCATCATCA

TTGTTGGATCATGATAGAACTGTTTTTCAATGGTTGGATCAACAACCTCCTTCATCAGTTTTGT

ATGTTTCATTTGGATCAACTTCAGAAGTTGATGAAAAAGATTTTTTGGAAATTGCTAGAGGATT

GGTTGATTCAAAACAATCATTTTTGTGGGTTGTTAGACCTGGATTTGTTAAAGGATCAACTTGG

GTTGAACCTTTGCCTGATGGATTTTTGGGAGAAAGAGGAAGAATTGTTAAATGGGTTCCTCAAC

AAGAAGTTTTGGCTCATGGAGCTATTGGAGCTTTTTGGACTCATTCAGGATGGAATTCAACTTT

GGAATCAGTTTGCGAAGGAGTTCCTATGATTTTTTCAGATTTTGGATTGGATCAACCTTTGAAT

GCTAGATATATGTCAGATGTTTTGAAAGTTGGAGTTTATTGGAAAATGGATGGGAAAGAGGAG

AAATTGCTAATGCTATTAGAAGAGTTATGGTTGATGAAGAAGGAGAATATATTAGACAAAATGC

TAGAGTTTTGAAACAAAAAGCTGATGTTTCATTGATGAAAGGAGGATCATCATATGAATCATTG

GAATCATTGGTTTCATATATTTCATCATTG
```

-continued

Amino Acid
UPD glycosyltransferase 76G1
Stevia rebaudiana

SEQ ID NO. 8

MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTRASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL

DNA
ABC transporter ABCG2
Human

SEQ ID NO. 9

ATGTCATCATCAAATGTTGAAGTTTTTATTCCTGTTTCACAAGGAAATACTAATGGATTTCCTG

CTACTGCTTCAAATGATTTGAAAGCTTTTACTGAAGGAGCTGTTTTGTCATTTCATAATATTTG

CTATAGAGTTAAATTGAAATCAGGATTTTTGCCTTGCAGAAAACCTGTTGAAAAAGAAATTTTG

TCAAATATTAATGGAATTATGAAACCTGGATTGAATGCTATTTTGGGACCTACTGGAGGAGGAA

AATCATCATTGTTGGATGTTTTGGCTGCTAGAAAAGATCCTTCAGGATTGTCAGGAGATGTTTT

GATTAATGGAGCTCCTAGACCTGCTAATTTTAAATGCAATTCAGGATATGTTGTTCAAGATGAT

GTTGTTATGGGAACTTTGACTGTTAGAGAAAATTTGCAATTTTCAGCTGCTTTGAGATTGGCTA

CTACTATGACTAATCATGAAAAAAATGAAAGAATTAATAGAGTTATTCAAGAATTGGGATTGGA

TAAAGTTGCTGATTCAAAAGTTGGAACTCAATTTATTAGAGGAGTTTCAGGAGGAGAAAGAAAA

AGAACTTCAATTGGAATGGAATTGATTACTGATCCTTCAATTTTGTTTTTGGATGAACCTACTA

CTGGATTGGATTCATCAACTGCTAATGCTGTTTTGTTGTTGAAAAGAATGTCAAAACAAGG

AAGAACTATTATTTTTTCAATTCATCAACCTAGATATTCAATTTTTAAATTGTTTGATTCATTG

ACTTTGTTGGCTTCAGGAAGATTGATGTTTCATGGACCTGCTCAAGAAGCTTTGGGATATTTTG

AATCAGCTGGATATCATTGCGAAGCTTATAATAATCCTGCTGATTTTTTTTGGATATTATTAA

TGGAGATTCAACTGCTGTTGCTTTGAATAGAGAAGAAGATTTTAAAGCTACTGAAATTATTGAA

CCTTCAAAACAAGATAAACCTTTGATTGAAAAATTGGCTGAAATTTATGTTAATTCATCATTTT

ATAAAGAAACTAAAGCTGAATTGCATCAATTGTCAGGAGGAGAAAAAAAAAAAAAAATTACTGT

TTTTAAAGAAATTTCATATACTACTTCATTTTGCCATCAATTGAGATGGGTTTCAAAAAGATCA

TTTAAAAATTTGTTGGGAAATCCTCAAGCTTCAATTGCTCAAATTATTGTTACTGTTGTTTTGG

GATTGGTTATTGGAGCTATTTATTTTGGATTGAAAAATGATTCAACTGGAATTCAAAATAGAGC

TGGAGTTTTGTTTTTTTTGACTACTAATCAATGCTTTTCATCAGTTTCAGCTGTTGAATTGTTT

GTTGTTGAAAAAAAATTGTTTATTCATGAATATATTTCAGGATATTATAGAGTTTCATCATATT

TTTTGGGAAAATTGTTGTCAGATTTGTTGCCTATGAGAATGTTGCCTTCAATTATTTTTACTTG

CATTGTTTATTTTATGTTGGGATTGAAAGCTAAAGCTGATGCTTTTTTTGTTATGATGTTTACT

TTGATGATGGTTGCTTATTCAGCTTCATCAATGGCTTTGGCTATTGCTGCTGGACAATCAGTTG

TTTCAGTTGCTACTTTGTTGATGACTATTTGCTTTGTTTTTATGATGATTTTTTCAGGATTGTT

GGTTAATTTGACTACTATTGCTTCATGGTTGTCATGGTTGCAATATTTTTCAATTCCTAGATAT

GGATTTACTGCTTTGCAACATAATGAATTTTTGGGACAAAATTTTTGCCCTGGATTGAATGCTA

CTGGAAATAATCCTTGCAATTATGCTACTTGCACTGGAGAAGAATATTTGGTTAAACAAGGAAT

-continued

```
TGATTTGTCACCTTGGGGATTGTGGAAAAATCATGTTGCTTTGGCTTGCATGATTGTTATTTTT

TTGACTATTGCTTATTTGAAATTGTTGTTTTTGAAAAAATATTCA
```

Amino Acid
ABC transporter ABCG2
Human

SEQ ID NO. 10

```
MSSSNVEVFIPVSQGNTNGFPATASNDLKAFTEGAVLSFHNICYRVKLKSGFLPCRKPVEKEIL

SNINGIMKPGLNAILGPTGGGKSSLLDVLAARKDPSGLSGDVLINGAPRPANFKCNSGYVVQDD

VVMGTLTVRENLQFSAALRLATTMTNHEKNERINRVIQELGLDKVADSKVGTQFIRGVSGGERK

RTSIGMELITDPSILFLDEPTTGLDSSTANAVLLLLKRMSKQGRTIIFSIHQPRYSIFKLFDSL

TLLASGRLMFHGPAQEALGYFESAGYHCEAYNNPADFFLDIINGDSTAVALNREEDFKATEIIE

PSKQDKPLIEKLAEIYVNSSFYKETKAELHQLSGGEKKKKITVFKEISYTTSFCHQLRWVSKRS

FKNLLGNPQASIAQIIVTVVLGLVIGAIYFGLKNDSTGIQNRAGVLFFLTTNQCFSSVSAVELF

VVEKKLFIHEYISGYYRVSSYFLGKLLSDLLPMRMLPSIIFTCIVYFMLGLKAKADAFFVMMFT

LMMVAYSASSMALAIAAGQSVVSVATLLMTICFVFMMIFSGLLVNLTTIASWLSWLQYFSIPRY

GFTALQHNEFLGQNFCPGLNATGNNPCNYATCTGEEYLVKQGIDLSPWGLWKNHVALACMIVIF

LTIAYLKLLFLKKYS
```

DNA
MYB12-like
*Cannabis*

SEQ ID NO. 11

```
ATGAAGAAGAACAAATCAACTAGTAATAATAAGAACAACAACAGTAATAATATCATCAAAAACG

ACATCGTATCATCATCATCATCAACAACAACAACATCATCAACAACTACAGCAACATCATCATT

TCATAATGAGAAAGTTACTGTCAGTACTGATCATATTATTAATCTTGATGATAAGCAGAAACGA

CAATTATGTCGTTGTCGTTTAGAAAAAGAAGAAGAAGAAGAAGGAAGTGGTGGTTGTGGTGAGA

CAGTAGTAATGATGCTAGGGTCAGTATCTCCTGCTGCTGCTACTGCTGCTGCAGCTGGGGGCTC

ATCAAGTTGTGATGAAGACATGTTGGGTGGTCATGATCAACTGTTGTTGTTGTTGTTCTGAG

AAAAAAACGACAGAAATTTCATCAGTGGTGAACTTTAATAATAATAATAATAATAATAAGGAAA

ATGGTGACGAAGTTTCAGGACCGTACGATTATCATCATCATAAAGAAGAGGAAGAAGAAGAAGA

AGAAGATGAAGCATCTGCATCAGTAGCAGCTGTTGATGAAGGGATGTTGTTGTGCTTTGATGAC

ATAATAGATAGCCACTTGCTAAATCCAAATGAGGTTTTGACTTTAAGAGAAGATAGCCATAATG

AAGGTGGGGCAGCTGATCAGATTGACAAGACTACTTGTAATAATACTACTATTACTACTAATGA

TGATTATAACAATAACTTGATGATGTTGAGCTGCAATAATAACGAGATTATGTTATTAGTGAT

GATCATGATGATCAGTACTGGATAGACGACGTCGTTGGAGTTGACTTTTGGAGTTGGGAGAGTT

CGACTACTACTGTTATTACCCAAGAACAAGAACAAGAACAAGATCAAGTTCAAGAACAGAAGAA

TATGTGGGATAATGAGAAAGAGAAACTGTTGTCTTTGCTATGGGATAATAGTGATAACAGCAGC

AGTTGGGAGTTACAAGATAAAAGCAATAATAATAATAATAATAATGTTCCTAACAAATGTCAAG

AGATTACCTCTGATAAAGAAAATGCTATGGTTGCATGGCTTCTCTCCTGA
```

Amino Acid
MYB12
*Cannabis*

SEQ ID NO. 12

```
MKKNKSTSNNKNNNSNNIIKNDIVSSSSSTTTTSSTTTATSSFHNEKVTVSTDHIINLDDKQKR

QLCRCRLEKEEEEGSGGCGETVVMMLGSVSPAAATAAAAGGSSSCDEDMLGGHDQLLLLCCSE

KKTTEISSVVNFNNNNNNNKENGDEVSGPYDYHHHKEEEEEEEEDEASASVAAVDEGMLLCFDD

IIDSHLLNPNEVLTLREDSHNEGGAADQIDKTTCNNTTITTNDDYNNNLMMLSCNNNGDYVISD
```

-continued

```
DHDDQYWIDDVVGVDFWSWESSTTTVITQEQEQEQDQVQEQKNMWDNEKEKLLSLLWDNSDNSS

SWELQDKSNNNNNNNVPNKCQEITSDKENAMVAWLLS

DNA
Catalase
Arabidopsis thaliana
                                                    SEQ ID NO. 13
ATGGATCCTTATAAATATAGACCTGCTTCATCATATAATTCACCTTTTTTTACTACTAATTCAG

GAGCTCCTGTTTGGAATAATAATTCATCAATGACTGTTGGACCTAGAGGATTGATTTTGTTGGA

AGATTATCATTTGGTTGAAAAATTGGCTAATTTTGATAGAGAAAGAATTCCTGAAAGAGTTGTT

CATGCTAGAGGAGCTTCAGCTAAAGGATTTTTTGAAGTTACTCATGATATTTCAAATTTGACTT

GCGCTGATTTTTTGAGAGCTCCTGGAGTTCAAACTCCTGTTATTGTTAGATTTTCAACTGTTAT

TCATGCTAGAGGATCACCTGAAACTTTGAGAGATCCTAGAGGATTTGCTGTTAAATTTTATACT

AGAGAAGGAAATTTTGATTTGGTTGGAAATAATTTTCCTGTTTTTTTTATTAGAGATGGAATGA

AATTTCCTGATATTGTTCATGCTTTGAAACCTAATCCTAAATCACATATTCAAGAAAATTGGAG

AATTTTGGATTTTTTTTCACATCATCCTGAATCATTGAATATGTTTACTTTTTTGTTTGATGAT

ATTGGAATTCCTCAAGATTATAGACATATGGATGGATCAGGAGTTAATACTTATATGTTGATTA

ATAAAGCTGGAAAAGCTCATTATGTTAAATTTCATTGGAAACCTACTTGCGGAGTTAAATCATT

GTTGGAAGAAGATGCTATTAGATTGGGAGGAACTAATCATTCACATGCTACTCAAGATTTGTAT

GATTCAATTGCTGCTGGAAATTATCCTGAATGGAAATTGTTTATTCAAATTATTGATCCTGCTG

ATGAAGATAAATTTGATTTTGATCCTTTGGATGTTACTAAAACTTGGCCTGAAGATATTTTGCC

TTTGCAACCTGTTGGAAGAATGGTTTTGAATAAAAATATTGATAATTTTTTTGCTGAAAATGAA

CAATTGGCTTTTTGCCCTGCTATTATTGTTCCTGGAATTCATTATTCAGATGATAAATTGTTGC

AAACTAGAGTTTTTTCATATGCTGATACTCAAAGACATAGATTGGGACCTAATTATTTGCAATT

GCCTGTTAATGCTCCTAAATGCGCTCATCATAATAATCATCATGAAGGATTTATGAATTTTATG

CATAGAGATGAAGAAGTTAATTATTTTCCTTCAAGATATGATCAAGTTAGACATGCTGAAAAAT

ATCCTACTCCTCCTGCTGTTTGCTCAGGAAAAAGAGAAAGATGCATTATTGAAAAGAAAATAA

TTTTAAAGAACCTGGAGAAAGATATAGAACTTTTACTCCTGAAAGACAAGAAAGATTTATTCAA

AGATGGATTGATGCTTTGTCAGATCCTAGAATTACTCATGAAATTAGATCAATTTGGATTTCAT

ATTGGTCACAAGCTGATAAATCATTGGGACAAAAATTGGCTTCAAGATTGAATGTTAGACCTTC

AATT

Amino Acid
Catalase
Arabidopsis thaliana
                                                    SEQ ID NO. 14
MDPYKYRPASSYNSPFFTTNSGAPVWNNNSSMTVGPRGLILLEDYHLVEKLANFDRERIPERVV

HARGASAKGFFEVTHDISNLTCADFLRAPGVQTPVIVRFSTVIHARGSPETLRDPRGFAVKFYT

REGNFDLVGNNFPVFFIRDGMKFPDIVHALKPNPKSHIQENWRILDFFSHHPESLNMFTFLFDD

IGIPQDYRHMDGSGVNTYMLINKAGKAHYVKFHWKPTCGVKSLLEEDAIRLGGTNHSHATQDLY

DSIAAGNYPEWKLFIQIIDPADEDKFDFDPLDVTKTWPEDILPLQPVGRMVLNKNIDNFFAENE

QLAFCPAIIVPGIHYSDDKLLQTRVFSYADTQRHRLGPNYLQLPVNAPKCAHHNNHHEGFMNFM

HRDEEVNYFPSRYDQVRHAEKYPTPPAVCSGKRERCIIEKENNFKEPGERYRTFTPERQERFIQ

RWIDALSDPRITHEIRSIWISYWSQADKSLGQKLASRLNVRPSI
```

DNA
Catalase HPII (KatE)
*Escherichia coli*

SEQ ID NO. 15

```
ATGTCGCAACATAACGAAAAGAACCCACATCAGCACCAGTCACCACTACACGATTCCAGCGAAG
CGAAACCGGGGATGGACTCACTGGCACCTGAGGACGGCTCTCATCGTCCAGCGGCTGAACCAAC
ACCGCCAGGTGCACAACCTACCGCCCCAGGGAGCCTGAAAGCCCCTGATACGCGTAACGAAAAA
CTTAATTCTCTGGAAGACGTACGCAAAGGCAGTGAAAATTATGCGCTGACCACTAATCAGGGCG
TGCGCATCGCCGACGATCAAAACTCACTGCGTGCCGGTAGCCGTGGTCCAACGCTGCTGGAAGA
TTTTATTCTGCGCGAGAAAATCACCCACTTTGACCATGAGCGCATTCCGGAACGTATTGTTCAT
GCACGCGGATCAGCCGCTCACGGTTATTTCCAGCCATATAAAAGCTTAAGCGATATTACCAAAG
CGGATTTCCTCTCAGATCCGAACAAAATCACCCCAGTATTTGTACGTTTCTCTACCGTTCAGGG
TGGTGCTGGCTCTGCTGATACCGTGCGTGATATCCGTGGCTTTGCCACCAAGTTCTATACCGAA
GAGGGTATTTTTGACCTCGTTGGCAATAACACGCCAATCTTCTTTATCCAGGATGCGCATAAAT
TCCCCGATTTTGTTCATGCGGTAAAACCAGAACCGCACTGGGCAATTCCACAAGGGCAAAGTGC
CCACGATACTTTCTGGGATTATGTTTCTCTGCAACCTGAAACTCTGCACAACGTGATGTGGGCG
ATGTCGGATCGCGGCATCCCCCGCAGTTACCGCACCATGGAAGGCTTCGGTATTCACACCTTCC
GCCTGATTAATGCCGAAGGGAAGGCAACGTTTGTACGTTTCCACTGGAAACCACTGGCAGGTAA
AGCCTCACTCGTTTGGGATGAAGCACAAAAACTCACCGGACGTGACCCGGACTTCCACCGCCGC
GAGTTGTGGGAAGCCATTGAAGCAGGCGATTTTCCGGAATACGAACTGGGCTTCCAGTTGATTC
CTGAAGAAGATGAATTCAAGTTCGACTTCGATCTTCTCGATCCAACCAAACTTATCCCGGAAGA
ACTGGTGCCCGTTCAGCGTGTCGGCAAAATGGTGCTCAATCGCAACCCGGATAACTTCTTTGCT
GAAAACGAACAGGCGGCTTTCCATCCTGGGCATATCGTGCCGGGACTGGACTTCACCAACGATC
CGCTGTTGCAGGGACGTTTGTTCTCCTATACCGATACACAAATCAGTCGTCTTGGTGGGCCGAA
TTTCCATGAGATTCCGATTAACCGTCCGACCTGCCCTTACCATAATTTCCAGCGTGACGGCATG
CATCGCATGGGGATCGACACTAACCCGGCGAATTACGAACCGAACTCGATTAACGATAACTGGC
CGCGCGAAACACCGCCGGGGCCGAAACGCGGCGGTTTTGAATCATACCAGGAGCGCGTGGAAGG
CAATAAAGTTCGCGAGCGCAGCCCATCGTTTGGCGAATATTATTCCCATCCGCGTCTGTTCTGG
CTAAGTCAGACGCCATTTGAGCAGCGCCATATTGTCGATGGTTTCAGTTTTGAGTTAAGCAAAG
TCGTTCGTCCGTATATTCGTGAGCGCGTTGTTGACCAGCTGGCGCATATTGATCTCACTCTGGC
CCAGGCGGTGGCGAAAAATCTCGGTATCGAACTGACTGACGACCAGCTGAATATCACCCCACCT
CCGGACGTCAACGGTCTGAAAAAGGATCCATCCTTAAGTTTGTACGCCATTCCTGACGGTGATG
TGAAAGGTCGCGTGGTAGCGATTTTACTTAATGATGAAGTGAGATCGGCAGACCTTCTGGCCAT
TCTCAAGGCGCTGAAGGCCAAAGGCGTTCATGCCAAACTGCTCTACTCCCGAATGGGTGAAGTG
ACTGCGGATGACGGTACGGTGTTGCCTATAGCCGCTACCTTTGCCGGTGCACCTTCGCTGACGG
TCGATGCGGTCATTGTCCCTTGCGGCAATATCGCGGATATCGCTGACAACGGCGATGCCAACTA
CTACCTGATGGAAGCCTACAAACACCTTAAACCGATTGCGCTGGCGGGTGACGCGCGCAAGTTT
AAAGCAACAATCAAGATCGCTGACCAGGGTGAAGAAGGGATTGTGGAAGCTGACAGCGCTGACG
GTAGTTTTATGGATGAACTGCTAACGCTGATGGCAGCACACCGCGTGTGGTCACGCATTCCTAA
GATTGACAAAATTCCTGCCTGA
```

-continued

Amino Acid
Catalase HPII (KatE)
*Escherichia coli*
SEQ ID NO. 16

MSQHNEKNPHQHQSPLHDSSEAKPGMDSLAPEDGSHRPAAEPTPPGAQPTAPGSLKAPDTRNEK

LNSLEDVRKGSENYALTTNQGVRIADDQNSLRAGSRGPTLLEDFILREKITHFDHERIPERIVH

ARGSAAHGYFQPYKSLSDITKADFLSDPNKITPVFVRFSTVQGGAGSADTVRDIRGFATKFYTE

EGIFDLVGNNTPIFFIQDAHKFPDFVHAVKPEPHWAIPQGQSAHDTFWDYVSLQPETLHNVMWA

MSDRGIPRSYRTMEGFGIHTFRLINAEGKATFVRFHWKPLAGKASLVWDEAQKLTGRDPDFHRR

ELWEAIEAGDFPEYELGFQLIPEEDEFKFDFDLLDPTKLIPEELVPVQRVGKMVLNRNPDNFFA

ENEQAAFHPGHIVPGLDFTNDPLLQGRLFSYTDTQISRLGGPNFHEIPINRPTCPYHNFQRDGM

HRMGIDTNPANYEPNSINDNWPRETPPGPKRGGFESYQERVEGNKVRERSPSFGEYYSHPRLFW

LSQTPFEQRHIVDGFSFELSKVVRPYIRERVVDQLAHIDLTLAQAVAKNLGIELTDDQLNITPP

PDVNGLKKDPSLSLYAIPDGDVKGRVVAILLNDEVRSADLLAILKALKAKGVHAKLLYSRMGEV

TADDGTVLPIAATFAGAPSLTVDAVIVPCGNIADIADNGDANYYLMEAYKHLKPIALAGDARKF

KATIKIADQGEEGIVEADSADGSFMDELLTLMAAHRVWSRIPKIDKIPA

DNA
Trichome-targeted CBDA synthase
*Cannabis*
SEQ ID NO. 17

ATGAAGTGCTCAACATTCTCCTTTTGGTTTGTTTGCAAGATAATATTTTTCTTTTTCTCATTCA

ATATCCAAACTTCCATTGCTAATCCTCGAGAAAACTTCCTTAAATGCTTCTCGCAATATATTCC

CAATAATGCAACAAATCTAAAACTCGTATACACTCAAAACAACCCATTGTATATGTCTGTCCTA

AATTCGACAATACACAATCTTAGATTCACCTCTGACACAACCCCAAAACCACTTGTTATCGTCA

CTCCTTCACATGTCTCTCATATCCAAGGCACTATTCTATGCTCCAAGAAAGTTGGCTTGCAGAT

TCGAACTCGAAGTGGTGGTCATGATTCTGAGGGCATGTCCTACATATCTCAAGTCCCATTTGTT

ATAGTAGACTTGAGAAACATGCGTTCAATCAAAATAGATGTTCATAGCCAAACTGCATGGGTTG

AAGCCGGAGCTACCCTTGGAGAAGTTTATTATTGGGTTAATGAGAAAAATGAGAATCTTAGTTT

GGCGGCTGGGTATTGCCCTACTGTTTGCGCAGGTGGACACTTTGGTGGAGGAGGCTATGGACCA

TTGATGAGAAACTATGGCCTCGCGGCTGATAATATCATTGATGCACACTTAGTCAACGTTCATG

GAAAAGTGCTAGATCGAAAATCTATGGGGGAAGATCTCTTTTGGGCTTTACGTGGTGGTGGAGC

AGAAAGCTTCGGAATCATTGTAGCATGGAAAATTAGACTGGTTGCTGTCCCAAAGTCTACTATG

TTTAGTGTTAAAAAGATCATGGAGATACATGAGCTTGTCAAGTTAGTTAACAAATGGCAAATA

TTGCTTACAAGTATGACAAAGATTTATTACTCATGACTCACTTCATAACTAGGAACATTACAGA

TAATCAAGGGAAGAATAAGACAGCAATACACACTTACTTCTCTTCAGTTTTCCTTGGTGGAGTG

GATAGTCTAGTCGACTTGATGAACAAGAGTTTTCCTGAGTTGGGTATTAAAAAAACGGATTGCA

GACAATTGAGCTGGATTGATACTATCATCTTCTATAGTGGTGTTGTAAATTACGACACTGATAA

TTTTAACAAGGAAATTTTGCTTGATAGATCCGCTGGGCAGAACGGTGCTTTCAAGATTAAGTTA

GACTACGTTAAGAAACCAATTCCAGAATCTGTATTTGTCCAAATTTTGGAAAAATTATATGAAG

AAGATATAGGAGCTGGGATGTATGCGTTGTACCCTTACGGTGGTATAATGGATGAGATTTCAGA

ATCAGCAATTCCATTCCCTCATCGAGCTGGAATCTTGTATGAGTTATGGTACATATGTAGTTGG

GAGAAGCAAGAAGATAACGAAAAGCATCTAAACTGGATTAGAAATATTTATAACTTCATGACTC

CTTATGTGTCCAAAAATCCAAGATTGGCATATCTCAATTATAGAGACCTTGATATAGGAATAAA

TGATCCCAAGAATCCAAATAATTACACACAAGCACGTATTTGGGGTGAGAAGTATTTTGGTAAA

-continued

```
AATTTTGACAGGCTAGTAAAAGTGAAAACCCTGGTTGATCCCAATAACTTTTTTAGAAACGAAC

AAAGCATCCCACCTCTACCACGGCATCGTCATTAA
```

Amino Acid
Trichome-targeted CBDA synthase
*Cannabis*

SEQ ID NO. 18

```
MKCSTFSFWFVCKIIFFFFSFNIQTSIANPRENFLKCFSQYIPNNATNLKLVYTQNNPLYMSVL

NSTIHNLRFTSDTTPKPLVIVTPSHVSHIQGTILCSKKVGLQIRTRSGGHDSEGMSYISQVPFV

IVDLRNMRSIKIDVHSQTAWVEAGATLGEVYYWVNEKNENLSLAAGYCPTVCAGGHFGGGGYGP

LMRNYGLAADNIIDAHLVNVHGKVLDRKSMGEDLFWALRGGGAESFGIIVAWKIRLVAVPKSTM

FSVKKIMEIHELVKLVNKWQNIAYKYDKDLLLMTHFITRNITDNQGKNKTAIHTYFSSVFLGGV

DSLVDLMNKSFPELGIKKTDCRQLSWIDTIIFYSGVVNYDTDNFNKEILLDRSAGQNGAFKIKL

DYVKKPIPESVFVQILEKLYEEDIGAGMYALYPYGGIMDEISESAIPFPHRAGILYELWYICSW

EKQEDNEKHLNWIRNIYNFMTPYVSKNPRLAYLNYRDLDIGINDPKNPNNYTQARIWGEKYFGK

NFDRLVKVKTLVDPNNFFRNEQSIPPLPRHRH
```

DNA
Trichome-targeted UDP glycosyltransferase 76G1
*Stevia rebaudiana*

SEQ ID NO. 19

```
ATGAAGTGCTCAACATTCTCCTTTTGGTTTGTTTGCAAGATAATATTTTCTTTTTCTCATTCA

ATATCCAAACTTCCATTGCTAATCCTCGAGAAAATAAAACTGAAACTACTGTTAGAAGAAGAAG

AAGAATTATTTTGTTTCCTGTTCCTTTTCAAGGACATATTAATCCTATTTTGCAATTGGCTAAT

GTTTTGTATTCAAAAGGATTTTCAATTACTATTTTTCATACTAATTTTAATAAACCTAAAACTT

CAAATTATCCTCATTTTACTTTTAGATTTATTTTGGATAATGATCCTCAAGATGAAAGAATTTC

AAATTTGCCTACTCATGGACCTTTGGCTGGAATGAGAATTCCTATTATTAATGAACATGGAGCT

GATGAATTGAGAAGAGAATTGGAATTGTTGATGTTGGCTTCAGAAGAAGATGAAGAAGTTTCAT

GCTTGATTACTGATGCTTTGTGGTATTTTGCTCAATCAGTTGCTGATTCATTGAATTTGAGAAG

ATTGGTTTTGATGACTTCATCATTGTTTAATTTTCATGCTCATGTTTCATTGCCTCAATTTGAT

GAATTGGGATATTTGGATCCTGATGATAAAACTAGATTGGAAGAACAAGCTTCAGGATTTCCTA

TGTTGAAAGTTAAAGATATTAAATCAGCTTATTCAAATTGGCAAATTTTGAAAGAAATTTTGGG

AAAAATGATTAAACAAACTAGAGCTTCATCAGGAGTTATTTGGAATTCATTTAAAGAATTGGAA

GAATCAGAATTGGAAACTGTTATTAGAGAAATTCCTGCTCCTTCATTTTTGATTCCTTTGCCTA

AACATTTGACTGCTTCATCATCATCATTGTTGGATCATGATAGAACTGTTTTTCAATGGTTGGA

TCAACAACCTCCTTCATCAGTTTTGTATGTTTCATTTGGATCAACTTCAGAAGTTGATGAAAAA

GATTTTTTGGAAATTGCTAGAGGATTGGTTGATTCAAAACAATCATTTTTGTGGGTTGTTAGAC

CTGGATTTGTTAAAGGATCAACTTGGGTTGAACCTTTGCCTGATGGATTTTTGGGAGAAAGAGG

AAGAATTGTTAAATGGGTTCCTCAACAAGAAGTTTTGGCTCATGGAGCTATTGGAGCTTTTTGG

ACTCATTCAGGATGAATTCAACTTTGGAATCAGTTTGCGAAGGAGTTCCTATGATTTTTTCAG

ATTTTGGATTGGATCAACCTTTGAATGCTAGATATATGTCAGATGTTTTGAAAGTTGGAGTTTA

TTTGGAAAATGGATGGGAAAGAGGAGAAATTGCTAATGCTATTAGAAGAGTTATGGTTGATGAA

GAAGGAGAATATATTAGACAAAATGCTAGAGTTTTGAAACAAAAAGCTGATGTTTCATTGATGA

AAGGAGGATCATCATATGAATCATTGGAATCATTGGTTTCATATATTTCATCATTGTAA
```

-continued

Amino Acid
Trichome-targeted UDP glycosyltransferase 76G1
*Stevia rebaudiana*

SEQ ID NO. 20

MKCSTFSFWFVCKIIFFFFSFNIQTSIANPRENKTETTVRRRRRIILFPVPFQGHINPILQLAN

VLYSKGFSITIFHTNFNKPKTSNYPHFTFRFILDNDPQDERISNLPTHGPLAGMRIPIINEHGA

DELRRELELLMLASEEDEEVSCLITDALWYFAQSVADSLNLRRLVLMTSSLFNFHAHVSLPQFD

ELGYLDPDDKTRLEEQASGFPMLKVKDIKSAYSNWQILKEILGKMIKQTRASSGVIWNSFKELE

ESELETVIREIPAPSFLIPLPKHLTASSSSLLDHDRTVFQWLDQQPPSSVLYVSFGSTSEVDEK

DFLEIARGLVDSKQSFLWVVRPGFVKGSTWVEPLPDGFLGERGRIVKWVPQQEVLAHGAIGAFW

THSGWNSTLESVCEGVPMIFSDFGLDQPLNARYMSDVLKVGVYLENGWERGEIANAIRRVMVDE

EGEYIRQNARVLKQKADVSLMKGGSSYESLESLVSYISSL

DNA
PM-UTR1
*Arabidopsis thaliana*

SEQ ID NO. 21

ATGGAGGTCCATGGCTCCGGATTCCGTCGAATTCTGTTGTTGGCGTTGTGTATCTCCGGGATCT

GGTCCGCCTACATCTACCAAGGCGTTCTTCAAGAGACTCTGTCCACGAAGAGATTTGGTCCAGA

TGAGAAGAGGTTCGAGCATCTTGCATTCTTGAACTTAGCTCAAAGTGTAGTCTGCTTGATCTGG

TCTTATATAATGATCAAGCTCTGGTCAAATGCTGGTAACGGTGGAGCACCATGGTGGACGTATT

GGAGTGCAGGCATTACTAATACAATTGGTCCTGCCATGGGAATTGAAGCCTTGAAGTATATCAG

TTATCCAGCTCAGGTTTTGGCAAAATCGTCAAAAATGATTCCAGTTATGCTAATGGGAACTTTA

GTTTACGGAATAAGATACACTTTCCCTGAATACATGTGCACCTTTCTTGTCGCTGGAGGAGTAT

CCATCTTTGCTCTTCTTAAGACAAGCTCTAAGACAATTAGCAAGCTAGCACATCCAAATGCTCC

CCTCGGTTACGCACTTTGTTCCTTAAACCTCGCCTTTGACGGATTCACAAATGCCACACAAGAC

TCCATTGCCTCAAGGTACCCAAAAACCGAAGCGTGGGACATAATGCTGGGAATGAACTTATGGG

GCACAATATACAACATTATCTACATGTTTGGCTTGCCACAAGGGATGGATTCGAAGCAATTCAG

TTCTGTAAGCTACACCCGGAAGCGGCATGGGACATTCTAAAGTATTGTATATGCGGTGCCGTGG

GACAAAACTTCATCTTCATGACAATAAGTAACTTCGGGTCACTAGCTAACACGACCATAACCAC

GACCAGGAAGTTTGTTAGCATTGTTGTATCATCAGTAATGAGCGGAAATCCATTGTCGTTGAAG

CAATGGGGATGTGTTTCGATGGTCTTTGGTGGTTTGGCATATCAAATTTATCTTAAATGGAAGA

AATTGCAGAGAGTGGAGTGCTCCATAATGAACTTAATGTGTGGGTCTACCTGCGCCGCTTGA

DNA
Cytostolic CBDA synthase (cytCBDAs)
*Cannabis sativa*

SEQ ID NO. 22

ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAAGAT

-continued

```
CATGGAGATACATGAGCTTGTCAAGTTAGTTAACAAATGGCAAATATTGCTTACAAGTATGAC

AAAGATTTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT

TGCTTGATAGATCCGCTGGGCAGAACGGTGCTTTCAAGATTAAGTTAGACTACGTTAAGAAACC

AATTCCAGAATCTGTATTTGTCCAAATTTTGGAAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAGAAGCAAGAAGATAA

CGAAAAGCATCTAAACTGGATTAGAAATATTTATAACTTCATGACTCCTTATGTGTCCAAAAAT

CCAAGATTGGCATATCTCAATTATAGAGACCTTGATATAGGAATAAATGATCCCAAGAATCCAA

ATAATTACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCTA

CCACGGCATCGTCATTAA
```

Amino Acid
Cytostolic CBDA synthase (cytCBDAs)
*Cannabis sativa*
SEQ ID NO. 23

```
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

PRLAYLNYRDLDIGINDPKNPNNYTQARIWGEKYFGKNFDRLVKVKTLVDPNNFFRNEQSIPPL

PRHRH
```

DNA
Cytostolic-targeted UDP glycosyltransferase 76G1 (cytUTG)
*Stevia rebaudiana*
SEQ ID NO. 24

```
ATGGAAAATAAAACCGAAACCACCGTCCGCCGTCGTCGCCGTATCATTCTGTTCCCGGTCCCGT

TCCAGGGCCACATCAACCCGATTCTGCAACTGGCGAACGTGCTGTATTCGAAAGGTTTCAGCAT

CACCATCTTCCATACGAACTTCAACAAGCCGAAGACCAGCAATTACCCGCACTTTACGTTCCGT

TTTATTCTGGATAACGACCCGCAGGATGAACGCATCTCTAATCTGCCGACCCACGGCCCGCTGG

CGGGTATGCGTATTCCGATTATCAACGAACACGGCGCAGATGAACTGCGTCGCGAACTGGAACT

GCTGATGCTGGCCAGCGAAGAAGATGAAGAAGTTTCTTGCCTGATCACCGACGCACTGTGGTAT

TTTGCCCAGTCTGTTGCAGATAGTCTGAACCTGCGTCGCCTGGTCCTGATGACCAGCAGCCTGT

TCAATTTTCATGCCCACGTTAGTCTGCCGCAGTTCGATGAACTGGGTTATCTGGACCCCGGATGA

CAAAACCCGCCTGGAAGAACAGGCGAGCGGCTTTCCGATGCTGAAAGTCAAGGATATTAAGTCA

GCGTACTCGAACTGGCAGATTCTGAAAGAAATCCTGGGTAAAATGATTAAGCAAACCAAAGCAA

GTTCCGGCGTCATCTGGAATAGTTTCAAGAACTGGAAGAATCCGAACTGGAAACGGTGATTCG

TGAAATCCCGGCTCCGAGTTTTCTGATTCCGCTGCCGAAGCATCTGACCGCGAGCAGCAGCAGC

CTGCTGGATCACGACCGCACGGTGTTTCAGTGGCTGGATCAGCAACCGCCGAGTTCCGTGCTGT
```

-continued

```
ATGTTAGCTTCGGTAGTACCTCGGAAGTGGATGAAAAGGACTTTCTGGAAATCGCTCGTGGCCT

GGTTGATAGCAAACAATCTTTCCTGTGGGTGGTTCGCCCGGGTTTTGTGAAGGGCTCTACGTGG

GTTGAACCGCTGCCGGACGGCTTCCTGGGTGAACGTGGCCGCATTGTCAAATGGGTGCCGCAGC

AAGAAGTGCTGGCGCATGGCGCGATTGGCGCGTTTTGGACCCACTCCGGTTGGAACTCAACGCT

GGAATCGGTTTGTGAAGGTGTCCCGATGATTTTCTCAGATTTTGGCCTGGACCAGCCGCTGAAT

GCACGTTATATGTCGGATGTTCTGAAAGTCGGTGTGTACCTGGAAAACGGTTGGGAACGCGGCG

AAATTGCGAATGCCATCCGTCGCGTTATGGTCGATGAAGAAGGCGAATACATTCGTCAGAATGC

TCGCGTCCTGAAACAAAAGGCGGACGTGAGCCTGATGAAAGGCGGTTCATCGTATGAAAGTCTG

GAATCCCTGGTTTCATACATCAGCTCTCTGTAA
```

Amino Acid
Cytostolic-targeted UDP glycosyltransferase 76G1 (cytUTG)
*Stevia rebaudiana*
SEQ ID NO. 25
```
MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTKASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL
```

Amino Acid
Glycosyltransferase (NtGT5a)
*Nicotiana tabacum*
SEQ ID NO. 26
```
MGSIGAELTKPHAVCIPYPAQGHINPMLKLAKILHHKGFHITFVNTEFNHRRLLKSRGPDSLKG

LSSFRFETIPDGLPPCEADATQDIPSLCESTTNTCLAPFRDLLAKLNDTNTSNVPPVSCIVSDG

VMSFTLAAAQELGVPEVLFWTTSACGFLGYMHYCKVIEKGYAPLKDASDLTNGYLETTLDFIPG

MKDVRLRDLPSFLRTTNPDEFMIKFVLQETERARKASAIILNTFETLEAEVLESLRNLLPPVYP

IGPLHFLVKHVDDENLKGLRSSLWKEEPECIQWLDTKEPNSVVYVNFGSITVMTPNQLIEFAWG

LANSQQTFLWIIRPDIVSGDASILPPEFVEETKNRGMLASWCSQEEVLSHPAIVGFLTHSGWNS

TLESISSGVPMICWPFFAEQQTNCWFSVTKWDVGMEIDSDVKRDEVESLVRELMVGGKGKKMKK

KAMEWKELAEASAKEHSGSSYVNIEKLVNDILLSSKH
```

DNA
Glycosyltransferase (NtGT5a)
*Nicotiana tabacum*
SEQ ID NO. 27
```
ATGGGTTCCATTGGTGCTGAATTAACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACCGACGTCTCCTTAAATCTCGTGGCCCTGATTCTCTCAAGGGT

CTTTCTTCTTTCCGTTTTGAGACCATTCCTGATGGACTTCCGCCATGTGAGGCAGATGCCACAC

AAGATATACCTTCTTTGTGTGAATCTACAACCAATACTTGCTTGGCTCCTTTTAGGGATCTTCT

TGCGAAACTCAATGATACTAACACATCTAACGTGCCACCCGTTTCGTGCATCGTCTCGGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTACTGCAAGGTTATTGAAAAAGGATATGCTCC

ACTTAAAGATGCGAGTGACTTGACAAATGGATACCTAGAGACAACATTGGATTTTATACCAGGC

ATGAAAGACGTACGTTTAAGGGATCTTCCAAGTTTCTTGAGAACTACAAATCCAGATGAATTCA
```

-continued

```
TGATCAAATTTGTCCTCCAAGAAACAGAGAGAGCAAGAAAGGCTTCTGCAATTATCCTCAACAC

ATTTGAAACACTAGAGGCTGAAGTTCTTGAATCGCTCCGAAATCTTCTTCCTCCAGTCTACCCC

ATAGGGCCCTTGCATTTTCTAGTGAAACATGTTGATGATGAGAATTTGAAGGGACTTAGATCCA

GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAGCTTATTGAGTTTGCTTGGGGA

CTTGCAAACAGCCAGCAAACATTCTTATGGATCATAAGACCTGATATTGTTTCAGGTGATGCAT

CGATTCTTCCACCCGAATTCGTGGAAGAAACGAAGAACAGAGGTATGCTTGCTAGTTGGTGTTC

ACAAGAAGAAGTACTTAGTCACCCTGCAATAGTAGGATTCTTGACTCACAGTGGATGGAATTCG

ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACAGTGATGTGAAGAG

AGATGAAGTGGAAAGCCTTGTAAGGGAATTGATGGTTGGGGAAAAGGCAAAAGATGAAGAAA

AAGGCAATGGAATGGAAGGAATTGGCTGAAGCATCTGCTAAAGAACATTCAGGGTCATCTTATG

TGAACATTGAAAAGTTGGTCAATGATATTCTTCTTTCATCCAAACATTAA
```

Amino Acid
Glycosyltransferase (NtGT5b)
*Nicotiana tabacum*
SEQ ID NO. 28

```
MGSIGAEFTKPHAVCIPYPAQGHINPMLKLAKILHHKGFHITFVNTEFNHRRLLKSRGPDSLKG

LSSFRFETIPDGLPPCDADATQDIPSLCESTTNTCLGPFRDLLAKLNDTNTSNVPPVSCIISDG

VMSFTLAAAQELGVPEVLFWTTSACGFLGYMHYYKVIEKGYAPLKDASDLTNGYLETTLDFIPC

MKDVRLRDLPSFLRTTNPDEFMIKFVLQETERARKASAIILNTYETLEAEVLESLRNLLPPVYP

IGPLHFLVKHVDDENLKGLRSSLWKEEPECIQWLDTKEPNSVVYVNFGSITVMTPNQLIEFAWG

LANSQQSFLWIIRPDIVSGDASILPPEFVEETKKRGMLASWCSQEEVLSHPAIGGFLTHSGWNS

TLESISSGVPMICWPFFAEQQTNCWFSVTKWDVGMEIDCDVKRDEVESLVRELMVGGKGKKMKK

KAMEWKELAEASAKEHSGSSYVNIEKVVNDILLSSKH
```

DNA
Glycosyltransferase (NtGT5b)
*Nicotiana tabacum*
SEQ ID NO. 29

```
ATGGGTTCCATTGGTGCTGAATTTACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACAGACGTCTGCTTAAATCTCGTGGCCCTGATTCTCTCAAGGGT

CTTTCTTCTTTCCGTTTTGAGACAATTCCTGATGGACTTCCGCCATGTGATGCAGATGCCACAC

AAGATATACCTTCTTTGTGTGAATCTACAACCAATACTTGCTTGGGTCCTTTTAGGGATCTTCT

TGCGAAACTCAATGATACTAACACATCTAACGTGCCACCCGTTTCGTGCATCATCTCAGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTATTACAAGGTTATTGAAAAAGGATACGCTCC

ACTTAAAGATGCGAGTGACTTGACAAATGGATACCTAGAGACAACATTGGATTTTATACCATGC

ATGAAAGACGTACGTTAAGGGATCTTCCAAGTTTCTTGAGAACTACAAATCCAGATGAATTCA

TGATCAAATTTGTCCTCCAAGAAACAGAGAGAGCAAGAAAGGCTTCTGCAATTATCCTCAACAC

ATATGAAACACTAGAGGCTGAAGTTCTTGAATCGCTCCGAAATCTTCTTCCTCCAGTCTACCCC

ATTGGGCCCTTGCATTTTCTAGTGAAACATGTTGATGATGAGAATTTGAAGGGACTTAGATCCA

GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAACTTATTGAATTTGCTTGGGGA
```

-continued

```
CTTGCAAACAGCCAACAATCATTCTTATGGATCATAAGACCTGATATTGTTTCAGGTGATGCAT

CGATTCTTCCCCCCGAATTCGTGGAAGAAACGAAGAAGAGAGGTATGCTTGCTAGTTGGTGTTC

ACAAGAAGAAGTACTTAGTCACCCTGCAATAGGAGGATTCTTGACTCACAGTGGATGGAATTCG

ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACTGTGATGTGAAGAG

GGATGAAGTGGAAAGCCTTGTAAGGGAATTGATGGTTGGGGGAAAAGGCAAAAAGATGAAGAAA

AAGGCAATGGAATGGAAGGAATTGGCTGAAGCATCTGCTAAAGAACATTCAGGGTCATCTTATG

TGAACATTGAGAAGGTGGTCAATGATATTCTTCTTTCGTCCAAACATTAA
```

Amino Acid
UDP-glycosyltransferase 73C3 (NtGT4)
*Nicotiana tabacum*
SEQ ID NO. 30

```
MATQVHKLHFILFPLMAPGHMIPMIDIAKLLANRGVITTIITTPVNANRFSSTITRAIKSGLRI

QILTLKFPSVEVGLPEGCENIDMLPSLDLASKFFAAISMLKQQVENLLEGINPSPSCVISDMGF

PWTTQIAQNFNIPRIVFHGTCCFSLLCSYKILSSNILENITSDSEYFVVPDLPDRVELTKAQVS

GSTKNTTSVSSSVLKEVTEQIRLAEESSYGVIVNSFEELEQVYEKEYRKARGKKVWCVGPVSLC

NKEIEDLVTRGNKTAIDNQDCLKWLDNFETESVVYASLGSLSRLTLLQMVELGLGLEESNRPFV

WVLGGGDKLNDLEKWILENGFEQRIKERGVLIRGWAPQVLILSHPAIGGVLTHCGWNSTLEGIS

AGLPMVTWPLFAEQFCNEKLVVQVLKIGVSLGVKVPVKWGDEENVGVLVKKDDVKKALDKLMDE

GEEGQVRRTKAKELGELAKKAFGEGGSSYVNLTSLIEDIIEQQNHKEK
```

DNA
UDP-glycosyltransferase 73C3 (NtGT4)
*Nicotiana tabacum*
SEQ ID NO. 31

```
ATGGCAACTCAAGTGCACAAACTTCATTTCATACTATTCCCTTTAATGGCTCCAGGCCACATGA

TTCCTATGATAGACATAGCTAAACTTCTAGCAAATCGCGGTGTCATTACCACTATCATCACCAC

TCCAGTAAACGCCAATCGTTTCAGTTCAACAATTACTCGTGCCATAAAATCCGGTCTAAGAATC

CAAATTCTTACACTCAAATTTCCAAGTGTAGAAGTAGGATTACCAGAAGGTTGCGAAAATATTG

ACATGCTTCCTTCTCTTGACTTGGCTTCAAAGTTTTTTGCTGCAATTAGTATGCTGAAACAACA

AGTTGAAAATCTCTTAGAAGGAATAAATCCAAGTCCAAGTTGTGTTATTTCAGATATGGGATTT

CCTTGGACTACTCAAATTGCACAAAATTTTAATATCCCAAGAATTGTTTTTCATGGTACTTGTT

GTTTCTCACTTTTATGTTCCTATAAAATACTTTCCTCCAACATTCTTGAAAATATAACCTCAGA

TTCAGAGTATTTTGTTGTTCCTGATTTACCCGATAGAGTTGAACTAACGAAAGCTCAGGTTTCA

GGATCGACGAAAAATACTACTTCTGTTAGTTCTTCTGTATTGAAAGAAGTTACTGAGCAAATCA

GATTAGCCGAGGAATCATCATATGGTGTAATTGTTAATAGTTTTGAGGAGTTGGAGCAAGTGTA

TGAGAAAGAATATAGGAAAGCTAGAGGGAAAAAAGTTTGGTGTGTTGGTCCTGTTTCTTTGTGT

AATAAGGAAATTGAAGATTTGGTTACAAGGGGTAATAAAACTGCAATTGATAATCAAGATTGCT

TGAAATGGTTAGATAATTTTGAAACAGAATCTGTGGTTTATGCAAGTCTTGGAAGTTTATCTCG

TTTGACATTATTGCAAATGGTGGAACTTGGTCTTGGTTTAGAAGAGTCAAATAGGCCTTTTGTA

TGGGTATTAGGAGGAGGTGATAAATTAAATGATTTAGAGAAATGGATTCTTGAGAATGGATTTG

AGCAAAGAATTAAAGAAAGAGGAGTTTTGATTAGAGGATGGGCTCCTCAAGTGCTTATACTTTC

ACACCCTGCAATTGGTGGAGTATTGACTCATTGCGGATGGAATTCTACATTGGAAGGTATTTCA

GCAGGATTACCAATGGTAACATGGCCACTATTTGCTGAGCAATTTTGCAATGAGAAGTTAGTAG

TCCAAGTGCTAAAAATTGGAGTGAGCCTAGGTGTGAAGGTGCCTGTCAAATGGGAGATGAGGA

AAATGTTGGAGTTTTGGTAAAAAAGGATGATGTTAAGAAAGCATTAGACAAACTAATGGATGAA
```

```
GGAGAAGAAGGACAAGTAAGAAGAACAAAAGCAAAAGAGTTAGGAGAATTGGCTAAAAAGGCAT

TTGGAGAAGGTGGTTCTTCTTATGTTAACTTAACATCTCTGATTGAAGACATCATTGAGCAACA

AAATCACAAGGAAAAATAG
```

```
Amino Acid
Glycosyltransferase (NtGT1b)
Nicotiana tabacum
                                                          SEQ ID NO. 32
MKTAELVFIPAPGMGHLVPTVEVAKQLVDRHEQLSITVLIMTIPLETNIPSYTKSLSSDYSSRI

TLLPLSQPETSVTMSSFNAINFFEYISSYKGRVKDAVSETSFSSSNSVKLAGFVIDMFCTAMID

VANEFGIPSYVFYTSSAAMLGLQLHFQSLSIECSPKVHNYVEPESEVLISTYMNPVPVKCLPGI

ILVNDESSTMFVNHARRFRETKGIMVNTFTELESHALKALSDDEKIPPIYPVGPILNLENGNED

HNQEYDAIMKWLDEKPNSSVVFLCFGSKGSFEEDQVKEIANALESSGYHFLWSLRRPPPKDKLQ

FPSEFENPEEVLPEGFFQRTKGRGKVIGWAPQLAILSHPSVGGFVSHCGWNSTLESVRSGVPIA

TWPLYAEQQSNAFQLVKDLGMAVEIKMDYREDFNTRNPPLVKAEEIEDGIRKLMDSENKIRAKV

TEMKDKSRAALLEGGSSYVALGHFVETVMKN
```

```
DNA
Glycosyltransferase (NtGT1b)
Nicotiana tabacum
                                                          SEQ ID NO. 33
ATGAAGACAGCAGAGTTAGTATTCATTCCTGCTCCTGGGATGGGTCACCTTGTACCAACTGTGG

AGGTGGCAAAGCAACTAGTCGACAGACACGAGCAGCTTTCGATCACAGTTCTAATCATGACAAT

TCCTTTGGAAACAAATATTCCATCATATACTAAATCACTGTCCTCAGACTACAGTTCTCGTATA

ACGCTGCTTCCACTCTCTCAACCTGAGACCCTCTGTTACTATGAGCAGTTTTAATGCCATCAATT

TTTTTGAGTACATCTCCAGCTACAAGGGTCGTGTCAAAGATGCTGTTAGTGAAACCTCCTTTAG

TTCGTCAAATTCTGTGAAACTTGCAGGATTTGTAATAGACATGTTCTGCACTGCGATGATTGAT

GTAGCGAACGAGTTTGGAATCCCAAGTTATGTGTTCTACACTTCTAGTGCAGCTATGCTTGGAC

TACAACTGCATTTTCAAAGTCTTAGCATTGAATGCAGTCCGAAAGTTCATAACTACGTTGAACC

TGAATCAGAAGTTCTGATCTCAACTTACATGAATCCGGTTCCAGTCAAATGTTTGCCCGGAATT

ATACTAGTAAATGATGAAAGTAGCACCATGTTTGTCAATCATGCACGAAGATTCAGGGAGACGA

AAGGAATTATGGTGAACACGTTCACTGAGCTTGAATCACACGCTTTGAAAGCCCTTTCCGATGA

TGAAAAAATCCCACCAATCTACCCAGTTGGACCTATACTTAACCTTGAAAATGGGAATGAAGAT

CACAATCAAGAATATGATGCGATTATGAAGTGGCTTGACGAGAAGCCTAATTCATCAGTGGTGT

TCTTATGCTTTGGAAGCAAGGGGTCTTTCGAAGAAGATCAGGTGAAGGAAATAGCAAATGCTCT

AGAGAGCAGTGGCTACCACTTCTTGTGGTCGCTAAGGCGACCGCCACCAAAAGACAAGCTACAA

TTCCCAAGCGAATTCGAGAATCCAGAGGAAGTCTTACCAGAGGGATTCTTTCAAAGGACTAAAG

GAAGAGGAAAGGTGATAGGATGGGCACCCCAGTTGGCTATTTTGTCTCATCCTTCAGTAGGAGG

ATTCGTGTCGCATTGTGGGTGGAATTCAACTCTGGAGAGCGTTCGAAGTGGAGTGCCGATAGCA

ACATGGCCATTGTATGCAGAGCAACAGAGCAATGCATTTCAACTGGTGAAGGATTTGGGTATGG

CAGTAGAGATTAAGATGGATTACAGGGAAGATTTTAATACGAGAAATCCACCACTGGTTAAAGC

TGAGGAGATAGAAGATGGAATTAGGAAGCTGATGGATTCAGAGAATAAAATCAGGGCTAAGGTG

ACGGAGATGAAGGACAAAAGTAGAGCAGCACTGCTGGAGGGCGGATCATCATATGTAGCTCTTG

GGCATTTTGTTGAGACTGTCATGAAAAACTAG
```

-continued

Amino Acid
Glycosyltransferase (NtGT1a)
*Nicotiana tabacum*
SEQ ID NO. 34

MKTTELVFIPAPGMGHLVPTVEVAKQLVDRDEQLSITVLIMTLPLETNIPSYTKSLSSDYSSRI

TLLQLSQPETSVSMSSFNAINFFEYISSYKDRVKDAVNETFSSSSSVKLKGFVIDMFCTAMIDV

ANEFGIPSYVFYTSNAAMLGLQLHFQSLSIEYSPKVHNYLDPESEVAISTYINPIPVKCLPGII

LDNDKSGTMFVNHARRFRETKGIMVNTFAELESHALKALSDDEKIPPIYPVGPILNLGDGNEDH

NQEYDMIMKWLDEQPHSSVVFLCFGSKGSFEEDQVKEIANALERSGNRFLWSLRRPPPKDTLQF

PSEFENPEEVLPVGFFQRTKGRGKVIGWAPQLAILSHPAVGGFVSHCGWNSTLESVRSGVPIAT

WPLYAEQQSNAFQLVKDLGMAVEIKMDYREDFNKTNPPLVKAEEIEDGIRKLMDSENKIRAKVM

EMKDKSRAALLEGGSSYVALGHFVETVMKN

DNA
Glycosyltransferase (NtGT1a)
*Nicotiana tabacum*
SEQ ID NO. 35

ATGAAGACAACAGAGTTAGTATTCATTCCTGCTCCTGGCATGGGTCACCTTGTACCCACTGTGG

AGGTGGCAAAGCAACTAGTCGACAGAGACGAACAGCTTTCAATCACAGTTCTCATCATGACGCT

TCCTTTGGAAACAAATATTCCATCATATACTAAATCACTGTCCTCAGACTACAGTTCTCGTATA

ACGCTGCTTCAACTTTCTCAACCTGAGACCTCTGTTAGTATGAGCAGTTTTAATGCCATCAATT

TTTTTGAGTACATCTCCAGCTACAAGGATCGTGTCAAAGATGCTGTTAATGAAACCTTTAGTTC

GTCAAGTTCTGTGAAACTCAAAGGATTTGTAATAGACATGTTCTGCACTGCGATGATTGATGTG

GCGAACGAGTTTGGAATCCCAAGTTATGTCTTCTACACTTCTAATGCAGCTATGCTTGGACTCC

AACTCCATTTTCAAAGTCTTAGTATTGAATACAGTCCGAAAGTTCATAATTACCTAGACCCTGA

ATCAGAAGTAGCGATCTCAACTTACATTAATCCGATTCCAGTCAAATGTTTGCCCGGGATTATA

CTAGACAATGATAAAAGTGGCACCATGTTCGTCAATCATGCACGAAGATTCAGG

GAGACGAAAGGAATTATGGTGAACACATTCGCTGAGCTTGAATCACACGCTTTGAAAGCCCTTT

CCGATGATGAGAAAATCCCACCAATCTACCCAGTTGGGCCTATACTTAACCTTGGAGATGGGAA

TGAAGATCACAATCAAGAATATGATATGATTATGAAGTGGCTCGACGAGCAGCCTCATTCATCA

GTGGTGTTCCTATGCTTTGGAAGCAAGGGATCTTTCGAAGAAGATCAAGTGAAGGAAATAGCAA

ATGCTCTAGAGAGAAGTGGTAACCGGTTCTTGTGGTCGCTAAGACGACCGCCACCAAAAGACAC

GCTACAATTCCCAAGCGAATTCGAGAATCCAGAGGAAGTCTTGCCGGTGGGATTCTTTCAAAGG

ACTAAAGGAAGAGGAAAGGTGATAGGATGGGCACCCCAGTTGGCTATTTTGTCTCATCCTGCAG

TAGGAGGATTCGTGTCGCATTGTGGGTGGAATTCAACTTTGGAGAGTGTTCGTAGTGGAGTACC

GATAGCAACATGGCCATTGTATGCAGAGCAACAGAGCAATGCATTTCAACTGGTGAAGGATTTG

GGGATGGCAGTGGAGATTAAGATGGATTACAGGGAAGATTTTAATAAGACAAATCCACCACTGG

TTAAAGCTGAGGAGATAGAAGATGGAATTAGGAAGCTGATGGATTCAGAGAATAAAATCAGGGC

TAAGGTGATGGAGATGAAGGACAAAAGTAGAGCAGCGTTATTAGAAGGCGGATCATCATATGTA

GCTCTCGGGCATTTTGTTGAGACTGTCATGAAAAACTAA

Amino Acid
Glycosyltransferase (NtGT3)
*Nicotiana tabacum*
SEQ ID NO. 36

MKETKKIELVFIPSPGIGHLVSTVEMAKLLIAREEQLSITVLIIQWPNDKKLDSYIQSVANFSS

RLKFIRLPQDDSIMQLLKSNIFTTFIASHKPAVRDAVADILKSESNNTLAGIVIDLFCTSMIDV

ANEFELPTYVFYTSGAATLGLHYHIQNLRDEFNKDITKYKDEPEEKLSIATYLNPFPAKCLPSV

ALDKEGGSTMFLDLAKRFRETKGIMINTFLELESYALNSLSRDKNLPPIYPVGPVLNLNNVEGD

-continued

NLGSSDQNTMKWLDDQPASSVVFLCFGSGGSFEKHQVKEIAYALESSGCRFLWSLRRPPTEDAR

FPSNYENLEEILPEGFLERTKGIGKVIGWAPQLAILSHKSTGGFVSHCGWNSTLESTYFGVPIA

TWPMYAEQQANAFQLVKDLRMGVEIKMDYRKDMKVMGKEVIVKAEEIEKAIREIMDSESEIRVK

VKEMKEKSRAAQMEGGSSYTSIGGFIQIIMENSQ

DNA
Glycosyltransferase (NtGT3)
*Nicotiana tabacum*
SEQ ID NO. 37

ATGAAAGAAACCAAGAAAATAGAGTTAGTCTTCATTCCTTCACCAGGAATTGGCCATTTAGTAT

CCACAGTTGAAATGGCAAAGCTTCTTATAGCTAGAGAAGAGCAGCTATCTATCACAGTCCTCAT

CATCCAATGGCCTAACGACAAGAAGCTCGATTCTTATATCCAATCAGTCGCCAATTTCAGCTCG

CGTTTGAAATTCATTCGACTCCCTCAGGATGATTCCATTATGCAGCTACTCAAAAGCAACATTT

TCACCACGTTTATTGCCAGTCATAAGCCTGCAGTTAGAGATGCTGTTGCTGATATTCTCAAGTC

AGAATCAATAATACGCTAGCAGGTATTGTTATCGACTTGTTCTGCACCTCAATGATAGACGTG

GCCAATGAGTTCGAGCTACCAACCTATGTTTTCTACACGTCTGGTGCAGCAACCCTTGGTCTTC

ATTATCATATACAGAATCTCAGGGATGAATTTAACAAAGATATTACCAAGTACAAAGACGAACC

TGAAGAAAAACTCTCTATAGCAACATATCTCAATCCATTTCCAGCAAAATGTTTGCCGTCTGTA

GCCTTAGACAAAGAAGGTGGTTCAACAATGTTTCTTGATCTCGCAAAAAGGTTTCGAGAAACCA

AAGGTATTATGATAAACACATTTCTAGAGCTCGAATCCTATGCATTAAACTCGCTCTCACGAGA

CAAGAATCTTCCACCTATATACCCTGTCGGACCAGTATTGAACCTTAACAATGTTGAAGGTGAC

AACTTAGGTTCATCTGACCAGAATACTATGAAATGGTTAGATGATCAGCCCGCTTCATCTGTAG

TGTTCCTTTGTTTTGGTAGTGGTGGAAGCTTTGAAAAACATCAAGTTAAGGAAATAGCCTATGC

TCTGGAGAGCAGTGGGTGTCGGTTTTTGTGGTCGTTAAGGCGACCACCAACCGAAGATGCAAGA

TTTCCAAGCAACTATGAAAATCTTGAAGAAATTTTGCCAGAAGGATTCTTGGAAAGAACAAAAG

GGATTGGAAAAGTGATAGGATGGGCACCTCAGTTGGCGATTTTGTCACATAAATCGACGGGGGG

ATTTGTGTCGCACTGTGGATGGAATTCGACTTTGGAAAGTACATATTTTGGAGTGCCAATAGCA

ACCTGGCCAATGTACGCGGAGCAACAAGCGAATGCATTTCAATTGGTTAAGGATTTGAGAATGG

GAGTTGAGATTAAGATGGATTATAGGAAGGATATGAAAGTGATGGGCAAAGAAGTTATAGTGAA

AGCTGAGGAGATTGAGAAAGCAATAAGAGAAATTATGGATTCCGAGAGTGAAATTCGGGTGAAG

GTGAAAGAGATGAAGGAGAAGAGCAGAGCAGCACAAATGGAAGGTGGCTCTTCTTACACTTCTA

TTGGAGGTTTCATCCAAATTATCATGGAGAATTCTCAATAA

Amino Acid
Glycosyltransferase (NtGT2)
*Nicotiana tabacum*
SEQ ID NO. 38

MVQPHVLLVTFPAQGHINPCLQFAKRLIRMGIEVTFATSVFAHRRMAKTTTSTLSKGLNFAAFS

DGYDDGFKADEHDSQHYMSEIKSRGSKTLKDIILKSSDEGRPVTSLVYSLLLPWAAKVAREFHI

PCALLWIQPATVLDIYYYYFNGYEDAIKGSTNDPNWCIQLPRLPLLKSQDLPSFLLSSSNEEKY

SFALPTFKEQLDTLDVEENPKVLVNTFDALEPKELKAIEKYNLIGIGPLIPSTFLDGKDPLDSS

FGGDLFQKSNDYIEWLNSKANSSVVYISFGSLLNLSKNQKEEIAKGLIEIKKPFLWVIRDQENG

KGDEKEEKLSCMMELEKQGKIVPWCSQLEVLTHPSIGCFVSHCGWNSTLESLSSGVSVVAFPHW

TDQGTNAKLIEDVWKTGVRLKKNEDGVVESEEIKRCIEMVMDGGEKGEEMRRNAQKWKELAREA

VKEGGSSEMNLKAFVQEVGKGC

-continued

DNA
Glycosyltransferase (NtGT2)
*Nicotiana tabacum*

SEQ ID NO. 39

ATGGTGCAACCCCATGTCCTCTTGGTGACTTTTCCAGCACAAGGCCATATTAATCCATGTCTCC

AATTTGCCAAGAGGCTAATTAGAATGGGCATTGAGGTAACTTTTGCCACGAGCGTTTTCGCCCA

TCGTCGTATGGCAAAAACTACGACTTCCACTCTATCCAAGGGCTTAAATTTTGCGGCATTCTCT

GATGGGTACGACGATGGTTTCAAGGCCGATGAGCATGATTCTCAACATTACATGTCGGAGATAA

AAAGTCGCGGTTCTAAAACCCTAAAAGATATCATTTTGAAGAGCTCAGACGAGGGACGTCCTGT

GACATCCCTCGTCTATTCTCTTTTGCTTCCATGGGCTGCAAAGGTAGCGCGTGAATTTCACATA

CCGTGCGCGTTACTATGGATTCAACCAGCAACTGTGCTAGACATATATTATTATTACTTCAATG

GCTATGAGGATGCCATAAAAGGTAGCACCAATGATCCAAATTGGTGTATTCAATTGCCTAGGCT

TCCACTACTAAAAAGCCAAGATCTTCCTTCTTTTTTACTTTCTTCTAGTAATGAAGAAAAATAT

AGCTTTGCTCTACCAACATTTAAAGAGCAACTTGACACATTAGATGTTGAAGAAAATCCTAAAG

TACTTGTGAACACATTTGATGCATTAGAGCCAAAGGAACTCAAAGCTATTGAAAAGTACAATTT

AATTGGGATTGGACCATTGATTCCTTCAACATTTTTGGACGGAAAAGACCCTTTGGATTCTTCC

TTTGGTGGTGATCTTTTTCAAAAGTCTAATGACTATATTGAATGGTTGAACTCAAAGGCTAACT

CATCTGTGGTTTATATCTCATTTGGGAGTCTCTTGAATTTGTCAAAAAATCAAAAGGAGGAGAT

TGCAAAAGGGTTGATAGAGATTAAAAAAGCCATTCTTGTGGGTAATAAGGATCAAGAAAATGGT

AAGGGAGATGAAAAAGAAGAGAAATTAAGTTGTATGATGGAGTTGGAAAAGCAAGGGAAAATAG

TACCATGGTGTTCACAACTTGAAGTCTTAACACATCCATCTATAGGATGTTTCGTGTCACATTG

TGGATGGAATTCGACTCTGGAAAGTTTATCGTCAGGCGTGTCAGTAGTGGCATTTCCTCATTGG

ACGGATCAAGGGACAAATGCTAAACTAATTGAAGATGTTTGGAAGACAGGTGTAAGGTTGAAAA

AGAATGAAGATGGTGTGGTTGAGAGTGAAGAGATAAAAAGGTGCATAGAAATGGTAATGGATGG

TGGAGAGAAAGGAGAAGAAATGAGAAGAAATGCTCAAAAATGGAAAGAATTGGCAAGGGAAGCT

GTAAAAGAAGGCGGATCTTCGGAAATGAATCTAAAAGCTTTTGTTCAAGAAGTTGGCAAAGGTT

GCTGA

Amino Acid
THCA Synthase Trichome targeting domain
*Cannabis*

SEQ ID NO. 40

MNCSAFSFWFVCKIIFFFLSFHIQISIA

Amino Acid
CBDA Synthase Trichome targeting domain
*Cannabis*

SEQ ID NO. 41

MKCSTFSFWFVCKIIFFFFSFNIQTSIA

Amino Acid
THCA Synthase
*Cannabis*

SEQ ID NO. 42

MNCSAFSFWFVCKIIFFFLSFHIQISIANPRENFLKCFSKHIPNNVANPKLVYTQHDQLYMSIL

NSTIQNLRFISDTTPKPLVIVTPSNNSHIQATILCSKKVGLQIRTRSGGHDAEGMSYISQVPFV

VVDLRNMHSIKIDVHSQTAWVEAGATLGEVYYWINEKNENLSFPGGYCPTVGVGGHFSGGGYGA

LMRNYGLAADNIIDAHLVNVDGKVLDRKSMGEDLFWAIRGGGGENFGIIAAWKIKLVDVPSKST

IFSVKKNMEIHGLVKLFNKWQNIAYKYDKDLVLMTHFITKNITDNHGKNKTTVHGYFSSIFHGG

VDSLVDLMNKSFPELGIKKTDCKEFSWIDTTIFYSGVVNFNTANFKKEILLDRSAGKKTAFS1K

LDYVKKPIPETAMVKILEKLYEEDVGAGMYVLYPYGGIMEEISESAIPFPHRAGIMYELWYTAS

WEKQEDNEKHINWVRSVYNFTTPYVSQNPRLAYLNYRDLDLGKTNHASPNNYTQARIWGEKYFG

KNFNRLVKVKTKVDPNNFFRNEQSIPPLPPHHH

Amino Acid
MYB8-orthologue for CAN738
*Humulus lupulus*
SEQ ID NO. 43

MGRAPCCEKVGLKKGRWTSEEDEILTKYIQSNGEGCWRSLPKNAGLLRCGKSCRLRWINYLRAD

LKRGNISSEEEDIIIKLHSTLGNRWSLIASHLPGRTDNEIKNYWNSHLSRKIHTFRRCNNTTTH

HHHLPNLVTVTKVNLPIPKRKGGRTSRLAMKKNKSSTSNQNSSVIKNDVGSSSSTTTTSVHQRT

TTTTPTMDDQQKRQLSRCRLEEKEDQDGASTGTVVMMLGQAAAVGSSCDEDMLGHDQLSFLCCS

EEKTTENSMTNLKENGDHEVSGPYDYDHRYEKETSVDEGMLLCFNDIIDSNLLNPNEVLTLSEE

SLNLGGALMDTTTSTTTNNNNYSLSYNNNGDCVISDDHDQYWLDDVVGVDFWSWESSTTVTQEQ

EQEQEQEQEQEQEQEQEHHHQQDQKKNTWDNEKEKMLALLWDSDNSNWELQDNNNYHKCQEI

TSDKENAMVAWLLS

Amino Acid
atMYB12-orthologue for CAN739
*Arabidopsis thaliana*
SEQ ID NO. 44

MGRAPCCEKVGIKRGRWTAEEDQILSNYIQSNGEGSWRSLPKNAGLKRCGKSCRLRWINYLRSD

LKRGNITPEEEELVVKLHSTLGNRWSLIAGHLPGRTDNEIKNYWNSHLSRKLHNFIRKPSISQD

VSAVIMTNASSAPPPPQAKRRLGRTSRSAMKPKIHRTKTRKTKKTSAPPEPNADVAGADKEALM

VESSGAEAELGRPCDYYGDDCNKNLMSINGDNGVLTFDDDIIDLLLDESDPGHLYTNTTCGGDG

ELHNIRDSEGARGFSDTWNQGNLDCLLQSCPSVESFLNYDHQVNDASTDEFIDWDCVWQEGSDN

NLWHEKENPDSMVSWLLDGDDEATIGNSNCENFGEPLDHDDESALVAWLLS

Amino Acid
MYB112-orthologue for CAN833
*Arabidopsis thaliana*
SEQ ID NO. 45

MNISRTEFANCKTLINHKEEVEEVEKKMEIEIRRGPWTVEEDMKLVSYISLHGEGRWNSLSRSA

GLNRTGKSCRLRWLNYLRPDIRRGDISLQEQFIILELHSRWGNRWSKIAQHLPGRTDNEIKNYW

RTRVQKHAKLLKCDVNSKQFKDTIKHLWMPRLIERIAATQSVQFTSNHYSPENSSVATATSSTS

SSEAVRSSFYGGDQVEFGTLDHMTNGGYWFNGGDTFETLCSFDELNKWLIQ

Amino Acid
Cytosolic targeted THCA Synthase (ctTHCAs)
*Cannabis*
SEQ ID NO. 46

NPRENFLKCFSKHIPNNVANPKLVYTQHDQLYMSILNSTIQNLRFISDTTPKPLVIVTPSNNSH

IQATILCSKKVGLQIRTRSGGHDAEGMSYISQVPFVVVDLRNMHSIKIDVHSQTAWVEAGATLG

EVYYWINEKNENLSFPGGYCPTVGVGGHFSGGGYGALMRNYGLAADNIIDAHLVNVDGKVLDRK

SMGEDLFWAIRGGGGENFGIIAAWKIKLVDVPSKSTIFSVKKNMEIHGLVKLFNKWQNIAYKYD

KDLVLMTHFITKNITDNHGKNKTTVHGYFSSIFHGGVDSLVDLMNKSFPELGIKKTDCKEFSWI

DTTIFYSGVVNFNTANFKKEILLDRSAGKKTAFSIKLDYVKKPIPETAMVKILEKLYEEDVGAG

MYVLYPYGGIMEEISESAIPFPHRAGIMYELWYTASWEKQEDNEKHINWVRSVYNFTTPYVSQN

PRLAYLNYRDLDLGKTNHASPNNYTQARIWGEKYFGKNFNRLVKVKTKVDPNNFFRNEQSIPPL

PPHHH

-continued

Amino Acid
Trichome targeted Catalase with THCA Synthase Trichome targeting
domain
*Arabidopsis thaliana*
SEQ ID NO. 47

MNCSAFSFWFVCKIIFFFLSFHIQISIAMDPYKYRPASSYNSPFFTTNSGAPVWNNNSSMTVGP

RGLILLEDYHLVEKLANFDRERIPERVVHARGASAKGFFEVTHDISNLTCADFLRAPGVQTPVI

VRFSTVIHARGSPETLRDPRGFAVKFYTREGNFDLVGNNFPVFFIRDGMKFPDIVHALKPNPKS

HIQENWRILDFFSHHPESLNMFTFLFDDIGIPQDYRHMDGSGVNTYMLINKAGKAHYVKFHWKP

TCGVKSLLEEDAIRLGGTNHSHATQDLYDSIAAGNYPEWKLFIQIIDPADEDKFDFDPLDVTKT

WPEDILPLQPVGRMVLNKNIDNFFAENEQLAFCPAIIVPGIHYSDDKLLQTRVFSYADTQRHRL

GPNYLQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQKLAS

RLNVRPSI

Amino Acid
Trichome targeted Catalase with CBDA Synthase Trichome targeting
domain
*Arabidopsis thaliana*
SEQ ID NO. 48

MKCSTFSFWFVCKIIFFFFSFNIQTSIAMDPYKYRPASSYNSPFFTTNSGAPVWNNNSSMTVGP

RGLILLEDYHLVEKLANFDRERIPERVVHARGASAKGFFEVTHDISNLTCADFLRAPGVQTPVI

VRFSTVIHARGSPETLRDPRGFAVKFYTREGNFDLVGNNFPVFFIRDGMKFPDIVHALKPNPKS

HIQENWRILDFFSHHPESLNMFTFLFDDIGIPQDYRHMDGSGVNTYMLINKAGKAHYVKFHWKP

TCGVKSLLEEDAIRLGGTNHSHATQDLYDSIAAGNYPEWKLFIQIIDPADEDKFDFDPLDVTKT

WPEDILPLQPVGRMVLNKNIDNFFAENEQLAFCPAIIVPGIHYSDDKLLQTRVFSYADTQRHRL

GPNYLQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQKLAS

RLNVRPSI

Amino Acid
Catalase HPII (KatE) with THCA Synthase Trichome targeting domain
*Escherichia coli*
SEQ ID NO. 49

MNCSAFSFWFVCKIIFFFLSFHIQISIAMSQHNEKNPHQHQSPLHDSSEAKPGMDSLAPEDGSH

RPAAEPTPPGAQPTAPGSLKAPDTRNEKLNSLEDVRKGSENYALTTNQGVRIADDQNSLRAGSR

GPTLLEDFILREKITHFDHERIPERIVHARGSAAHGYFQPYKSLSDITKADFLSDPNKITPVFV

RFSTVQGGAGSADTVRDIRGFATKFYTEEGIFDLVGNNTPIFFIQDAHKFPDFVHAVKPEPHWA

IPQGQSAHDTFWDYVSLQPETLHNVMWAMSDRGIPRSYRTMEGFGIHTFRLINAEGKATFVRFH

WKPLAGKASLVWDEAQKLTGRDPDFHRRELWEAIEAGDFPEYELGFQLIPEEDEFKFDFDLLDP

TKLIPEELVPVQRVGKMVLNRNPDNFFAENEQAAFHPGHIVPGLDFTNDPLLQGRLFSYTDTQI

SRLGGPNFHEIPINRPTCPYHNFQRDGMHRMGIDTNPANYEPNSINDNWPRETPPGPKRGGFES

YQERVEGNKVRERSPSFGEYYSHPRLFWLSQTPFEQRHIVDGFSFELSKVVRPYIRERVVDQLA

HIDLTLAQAVAKNLGIELTDDQLNITPPPDVNGLKKDPSLSLYAIPDGDVKGRVVAILLNDEVR

SADLLAILKALKAKGVHAKLLYSRMGEVTADDGTVLPIAATFAGAPSLTVDAVIVPCGNIADIA

DNGDANYYLMEAYKHLKPIALAGDARKFKATIKIADQGEEGIVEADSADGSFMDELLTLMAAHR

VWSRIPKIDKIPA

-continued

Amino Acid
Catalase HPII (KatE) with CBDA Synthase Trichome targeting domain
*Escherichia coli*

SEQ ID NO. 50

MKCSTFSFWFVCKIIFFFFSFNIQTSIAMSQHNEKNPHQHSPLHDSSEAKPGMDSLAPEDGSH

RPAAEPTPPGAQPTAPGSLKAPDTRNEKLNSLEDVRKGSENYALTTNQGVRIADDQNSLRAGSR

GPTLLEDFILREKITHFDHERIPERIVHARGSAAHGYFQPYKSLSDITKADFLSDPNKITPVFV

RFSTVQGGAGSADTVRDIRGFATKFYTEEGIFDLVGNNTPIFFIQDAHKFPDFVHAVKPEPHWA

IPQGQSAHDTFWDYVSLQPETLHNVMWAMSDRGIPRSYRTMEGFGIHTFRLINAEGKATFVRFH

WKPLAGKASLVWDEAQKLTGRDPDFHRRELWEAIEAGDFPEYELGFQLIPEEDEFKFDFDLLDP

TKLIPEELVPVQRVGKMVLNRNPDNFFAENEQAAFHPGHIVPGLDFTNDPLLQGRLFSYTDTQI

SRLGGPNFHEIPINRPTCPYHNFQRDGMHRMGIDTNPANYEPNSINDNWPRETPPGPKRGGFES

YQERVEGNKVRERSPSFGEYYSHPRLFWLSQTPFEQRHIVDGFSFELSKVVRPYIRERVVDQLA

HIDLTLAQAVAKNLGIELTDDQLNITPPPDVNGLKKDPSLSLYAIPDGDVKGRVVAILLNDEVR

SADLLAILKALKAKGVHAKLLYSRMGEVTADDGTVLPIAATFAGAPSLTVDAVIVPCGNIADIA

DNGDANYYLMEAYKHLKPIALAGDARKFKATIKIADQGEEGIVEADSADGSFMDELLTLMAAHR

VWSRIPKIDKIPA

DNA
Glycosyltransferase (NtGT1b-codon optimized for yeast expression)
*Nicotiana tabacum*

SEQ ID NO. 51

ATGAAAACAACAGAACTTGTCTTCATACCCGCCCCCGGTATGGGTCACCTTGTACCCACAGTCG

AAGTCGCCAAACAACTAGTTGATAGAGACGAACAGTTGTCTATTACCGTCTTGATAATGACGTT

ACCCCTGGAGACTAATATCCCAAGTTACACCAAGAGTTTGTCCTCTGACTATTCATCCCGTATC

ACGTTGTTACAACTAAGTCAACCTGAGACGAGTGTCTCAATGAGTAGTTTTAACGCCATAAACT

TCTTCGAATACATTAGTTCCTATAAGGATCGTGTTAAAGATGCCGTAAACGAGACATTCTCCTC

TTCATCCTCCGTCAAACTTAAAGGATTTGTAATCGACATGTTTTGCACGGCAATGATAGACGTG

GCCAACGAGTTCGGTATTCCATCTTATGTATTCTACACGTCCAACGCTGCCATGCTAGGCCTAC

AACTTCACTTCCAATCCTTGTCCATCGAATATTCACCTAAGGTTCATAATTATTTAGACCCTGA

ATCTGAGGTAGCTATATCAACGTACATTAACCCAATACCAGTAAAATGCTTACCCGGTATAATT

CTTGACAATGATAAGAGTGGCACTATGTTCGTAAACCATGCCAGGAGATTCCGTGAAACAAAGG

GTATAATGGTAAATACTTTTGCAGAATTAGAAAGTCACGCCCTAAAGGCACTTAGTGACGATGA

GAAAATTCCTCCAATCTATCCCGTCGGACCCATTCTAAACTTGGGTGATGGTAATGAGGATCAT

AACCAAGAGTACGACATGATAATGAAATGGCTGGATGAACAACCACACAGTTCAGTGGTTTTCC

TGTGCTTCGGTTCCAAAGGTTCATTTGAAGAAGACCAGGTTAAAGAGATAGCAAATGCTTTAGA

GAGATCAGGCAATAGGTTCCTGTGGAGTTTAAGACGTCCCCCTCCCAAGGATACTCTTCAATTC

CCTTCCGAATTTGAAAACCCCGAGGAAGTGCTACCTGTAGGATTTTTTCAAAGAACCAAAGGCA

GAGGAAAAGTCATCGGATGGGCACCACAGCTTGCAATTCTATCTCACCCTGCCGTCGGTGGATT

CGTTTCCCACTGCGGCTGGAATAGTACTTTGGAATCAGTTAGATCAGGTGTACCCATAGCAACA

TGGCCTCTTTATGCAGAGCAGCAGTCCAATGCATTTCAATTGGTCAAGGATCTAGGTATGGCCG

TCGAAATTAAAATGGATTACCGTGAGGACTTTAACAAGACTAATCCTCCATTGGTAAAGGCAGA

GGAAATAGAAGACGGCATTAGGAAGTTGATGGACTCCGAGAATAAGATTAGGGCAAAGGTGATG

GAAATGAAAGATAAGTCCAGAGCTGCATTACTGGAAGGAGGATCCTCCTATGTTGCACTGGGTC

ACTTCGTGGAGACCGTAATGAAGAACTAA

Amino Acid
Glycosyltransferase (NtGT1b-generated from codon optimized
sequence for yeast expression)
Nicotiana tabacum
SEQ ID NO. 52

MKTTELVFIPAPGMGHLVPTVEVAKQLVDRDEQLSITVLIMTLPLETNIPSYTKSLSSDYSSRI

TLLQLSQPETSVSMSSFNAINFFEYISSYKDRVKDAVNETFSSSSSVKLKGFVIDMFCTAMIDV

ANEFGIPSYVFYTSNAAMLGLQLHFQSLSIEYSPKVHNYLDPESEVAISTYINPIPVKCLPGII

LDNDKSGTMFVNHARRFRETKGIMVNTFAELESHALKALSDDEKIPPIYPVGPILNLGDGNEDH

NQEYDMIMKWLDEQPHSSVVFLCFGSKGSFEEDQVKEIANALERSGNRFLWSLRRPPPKDTLQF

PSEFENPEEVLPVGFFQRTKGRGKVIGWAPQLAILSHPAVGGFVSHCGWNSTLESVRSGVPIAT

WPLYAEQQSNAFQLVKDLGMAVEIKMDYREDFNKTNPPLVKAEEIEDGIRKLMDSENKIRAKVM

EMKDKSRAALLEGGSSYVALGHFVETVMKN

DNA
Glycosyltransferase (NtGT2-codon optimized for yeast expression)
Nicotiana tabacum
SEQ ID NO. 53

ATGGTTCAACCACACGTCTTACTGGTTACTTTTCCAGCACAAGGCCATATCAACCCTTGCCTAC

AATTCGCCAAAAGACTAATAAGGATGGGCATCGAAGTAACTTTTGCCACGAGTGTATTCGCACA

TAGGCGTATGGCTAAAACTACGACATCAACTTTGTCCAAAGGACTAAACTTCGCCGCCTTCAGT

GATGGCTATGACGATGGATTCAAAGCCGACGAACATGACAGTCAACACTACATGAGTGAAATAA

AGTCCCGTGGATCTAAAACACTTAAGGATATTATACTTAAATCCTCCGATGAGGGAAGACCCGT

TACCTCTTTAGTTTATTCACTGTTACTGCCCTGGGCTGCAAAAGTCGCCAGAGAGTTTCATATT

CCTTGCGCTTTATTGTGGATCCAACCAGCTACGGTATTAGACATCTACTATTACTACTTCAATG

GATACGAGGATGCAATAAAGGGATCAACAAACGACCCCAACTGGTGTATTCAACTGCCTAGACT

TCCTCTATTAAAAAGTCAGGACTTACCTAGTTTTTTACTGTCATCCAGTAACGAAGAAAAATAT

TCATTCGCTTTACCCACCTTCAAAGAGCAGCTTGACACTTTGGATGTTGAAGAGAACCCCAAGG

TTTTGGTCAATACTTTTGACGCTTTGGAGCCAAAAGAGCTAAAGGCTATTGAAAAATATAACCT

TATCGGCATAGGACCTTTAATCCCCTCTACTTTCTTAGATGGCAAAGACCCTCTAGATTCAAGT

TTCGGAGGTGATTTGTTTCAAAAGAGTAACGATTATATCGAGTGGCTAAATAGTAAAGCCAACT

CCAGTGTGGTCTACATTTCTTTCGGAAGTCTTCTGAATTTATCAAAAAACCAAAAGGAAGAGAT

CGCAAAAGGACTGATAGAGATAAAAAAACCTTTCTTATGGGTGATCAGAGACCAGGAAAACGGT

AAAGGCGATGAGAAGGAGGAAAAACTGTCCTGTATGATGGAGCTAGAGAAACAAGGAAAAATCG

TTCCCTGGTGTTCACAGTTAGAAGTGTTAACCCATCCATCCATAGGTTGCTTCGTATCACATTG

TGGTTGGAATAGTACACTTGAAAGTCTTTCATCAGGCGTCTCTGTCGTCGCATTCCCCCACTGG

ACGGACCAGGGCACAAACGCCAAACTGATCGAAGATGTATGGAAGACGGGCGTCAGGCTAAAAA

AAAATGAGGATGGCGTGGTAGAGAGTGAAGAGATAAAGCGTTGCATAGAAATGGTCATGGATGG

CGGTGAAAAGGGAGAGGAAATGAGGCGTAACGCACAAAAGTGGAAGGAACTAGCCCGTGAAGCA

GTGAAAGAAGGAGGTTCTAGTGAGATGAATTTAAAAGCTTTCGTGCAGGAAGTTGGAAAAGGCT

GCTGA

Amino Acid
Glycosyltransferase (NtGT2-generated from codon optimized
sequence for yeast expression)
Nicotiana tabacum
SEQ ID NO. 54

MVQPHVLLVTFPAQGHINPCLQFAKRLIRMGIEVTFATSVFAHRRMAKTTTSTLSKGLNFAAFS

DGYDDGFKADEHDSQHYMSEIKSRGSKTLKDIILKSSDEGRPVTSLVYSLLLPWAAKVAREFHI

PCALLWIQPATVLDIYYYYFNGYEDAIKGSTNDPNWCIQLPRLPLLKSQDLPSFLLSSSNEEKY

-continued

SFALPTFKEQLDTLDVEENPKVLVNTFDALEPKELKAIEKYNLIGIGPLIPSTFLDGKDPLDSS

FGGDLFQKSNDYIEWLNSKANSSVVYISFGSLLNLSKNQKEEIAKGLIEIKKPFLWVIRDQENG

KGDEKEEKLSCMMELEKQGKIVPWCSQLEVLTHPSIGCFVSHCGWNSTLESLSSGVSVVAFPHW

TDQGTNAKLIEDVWKTGVRLKKNEDGVVESEEIKRCIEMVMDGGEKGEEMRRNAQKWKELAREA

VKEGGSSEMNLKAFVQEVGKGC

DNA
Glycosyltransferase (NtGT3-codon optimized for yeast expression)
Nicotiana tabacum
SEQ ID NO. 55

ATGAAAGAGACTAAAAAAATTGAGTTAGTTTTTATCCCCAGTCCTGGTATAGGACACTTAGTCT

CAACTGTGGAGATGGCCAAACTGTTGATAGCCCGTGAAGAGCAACTTTCTATTACTGTCCTGAT

TATACAATGGCCTAATGATAAAAAGCTAGACAGTTATATCCAGTCCGTCGCAAACTTTAGTTCT

AGACTGAAGTTTATACGTCTGCCCCAAGATGACTCAATCATGCAACTTTTGAAATCAAACATTT

TCACGACATTCATCGCCTCTCACAAGCCAGCTGTAAGAGACGCCGTTGCTGACATACTAAAGAG

TGAAAGTAATAACACATTGGCAGGCATTGTAATCGATCTTTTCTGCACATCCATGATCGATGTA

GCCAATGAGTTTGAGCTGCCTACTTATGTGTTTTACACTAGTGGCGCAGCCACGTTGGGTCTGC

ACTACCATATTCAAAATCTGCGTGATGAGTTTAATAAAGACATTACCAAATATAAGGATGAGCC

AGAAGAAAAATTAAGTATAGCCACGTACCTTAACCCATTCCCTGCTAAGTGTCTACCCTCCGTG

GCATTGGATAAGGAAGGAGGATCAACGATGTTCCTAGACTTAGCTAAGAGGTTCAGGGAGACCA

AAGGCATAATGATTAACACTTTTCTTGAGCTGGAATCATACGCTCTAAACTCATTGTCTAGAGA

TAAAAACTTGCCCCCTATATACCCTGTAGGCCCTGTTTTGAACTTGAACAACGTTGAGGGTGAT

AACTTGGGCTCTAGTGATCAAAATACCATGAAATGGCTGGACGACCAGCCAGCTTCTTCCGTTG

TGTTCCTATGTTTTGGCTCAGGAGGAAGTTTCGAAAAACACCAAGTCAAAGAAATAGCTTATGC

CTTAGAATCTTCCGGATGCAGGTTCTTGTGGAGTTTGCGTAGACCCCCCACGGAAGATGCTAGG

TTCCCTTCTAATTACGAAAACTTAGAGGAAATTTTACCAGAGGGATTCTGGAAAGAACGAAAG

GCATTGGTAAGGTCATTGGATGGGCCCCACAGTTAGCAATCTTGTCTCACAAGTCCACAGGAGG

ATTCGTGTCTCATTGCGGATGGAACTCTACCCTTGAAAGTACCTATTTCGGCGTTCCTATTGCT

ACTTGGCCAATGTATGCTGAACAACAGGCCAACGCTTTTCAACTTGTTAAAGATTTGAGGATGG

GTGTTGAGATCAAAATGGATTATAGGAAGGATATGAAGGTAATGGGCAAGGAGGTTATCGTTAA

GGCAGAAGAAATTGAAAAGGCCATAAGGGAAATCATGGACTCAGAATCAGAAATCAGGGTCAAG

GTCAAAGAGATGAAGGAGAAAAGTCGTGCAGCCCAAATGGAAGGAGGATCATCATATACCTCTA

TCGGCGGCTTCATTCAAATAATCATGGAGAACTCACAGTAA

Amino Acid
Glycosyltransferase (NtGT3-generated from codon optimized sequence
for yeast expression)
Nicotiana tabacum
SEQ ID NO. 56

MKETKKIELVFIPSPGIGHLVSTVEMAKLLIAREEQLSITVLIIQWPNDKKLDSYIQSVANFSS

RLKFIRLPQDDSIMQLLKSNIFTTFIASHKPAVRDAVADILKSESNNTLAGIVIDLFCTSMIDV

ANEFELPTYVFYTSGAATLGLHYHIQNLRDEFNKDITKYKDEPEEKLSIATYLNPFPAKCLPSV

ALDKEGGSTMFLDLAKRFRETKGIMINTFLELESYALNSLSRDKNLPPIYPVGPVLNLNNVEGD

NLGSSDQNTMKWLDDQPASSVVFLCFGSGGSFEKHQVKEIAYALESSGCRFLWSLRRPPTEDAR

FPSNYENLEEILPEGFLERTKGIGKVIGWAPQLAILSHKSTGGFVSHCGWNSTLESTYFGVPIA

TWPMYAEQQANAFQLVKDLRMGVEIKMDYRKDMKVMGKEVIVKAEEIEKAIREIMDSESEIRVK

VKEMKEKSRAAQMEGGSSYTSIGGFIQIIMENSQ

DNA
UDP-glycosyltransferase 73C3 (NtGT4-codon optimized for yeast expression)
*Nicotiana tabacum*

SEQ ID NO. 57

ATGGCTACTCAGGTGCATAAATTGCATTTCATTCTGTTCCCACTGATGGCTCCCGGTCACATGA

TCCCTATGATAGACATCGCAAAACTATTGGCTAACCGTGGCGTGATAACTACCATAATAACTAC

GCCCGTTAACGCCAATCGTTTTTCCTCTACGATCACTAGGGCCATTAAATCAGGCCTAAGAATC

CAGATTTTAACCTTAAAATTCCCATCAGTTGAGGTAGGCCTGCCTGAAGGATGTGAAAACATCG

ACATGTTGCCATCTTTGGACTTAGCCTCTAAATTCTTTGCTGCTATTTCTATGCTTAAACAACA

AGTGGAGAACTTGCTAGAGGGTATTAACCCTAGTCCCTCATGCGTTATTTCTGACATGGGCTTC

CCATGGACGACACAGATCGCTCAAAATTTCAATATTCCTCGTATCGTATTTCATGGCACGTGTT

GCTTTTCTCTTCTTTGTTCTTACAAAATCCTGTCATCCAATATCTTAGAGAACATTACTAGTGA

CTCAGAGTATTTTGTCGTGCCAGATCTGCCAGACCGTGTCGAGCTAACTAAGGCCCAAGTCTCT

GGATCTACAAAGAATACTACATCAGTAAGTAGTTCAGTACTGAAGGAGGTTACAGAGCAGATCA

GGCTTGCAGAGGAATCATCCTACGGTGTGATAGTTAATTCCTTCGAAGAACTGGAACAGGTGTA

TGAAAAGAGTACAGAAAAGCCAGGGGCAAAAAGGTCTGGTGCGTGGGTCCTGTCTCTTTGTGC

AACAAGGAGATTGAAGATCTTGTTACTAGAGGAAACAAAACCGCTATAGACAATCAGGATTGTC

TTAAGTGGTTAGACAACTTCGAGACTGAATCCGTCGTCTATGCAAGTTTAGGCTCACTAAGTAG

GCTTACGTTACTGCAAATGGTTGAGCTGGGATTGGGACTGGAGGAGAGTAATAGGCCATTTGTA

TGGGTTCTGGGAGGAGGAGACAAACTAAATGATCTTGAGAAATGGATATTGGAGAATGGCTTTG

AACAGCGTATAAAGGAGAGAGGTGTCCTGATACGTGGCTGGGCACCTCAAGTATTGATTTTAAG

TCACCCCGCAATTGGAGGAGTTTTAACGCATTGTGGATGGAACTCTACATTAGAGGGCATTTCA

GCCGGACTACCCATGGTCACCTGGCCACTATTTGCCGAACAGTTCTGTAACGAAAAATTAGTAG

TGCAGGTTCTTAAAATCGGTGTCTCACTTGGAGTGAAGGTCCCTGTTAAGTGGGGTGACGAAGA

GAACGTAGGTGTCTTAGTGAAAAAGGATGACGTTAAAAAAGCACTGGATAAGCTAATGGATGAG

GGTGAGGAGGGCCAGGTTAGGAGGACCAAAGCCAAAGAGCTTGGTGAGTTAGCTAAAAAAGCCT

TTGGAGAGGGCGGATCATCCTACGTGAACCTAACGTCCCTAATTGAAGATATAATCGAGCAGCA

GAACCATAAGGAGAAGTAG

Amino Acid
UDP-glycosyltransferase 73C3 (NtGT4-generated from codon optimized sequence for yeast expression)
*Nicotiana tabacum*

SEQ ID NO. 58

MATQVHKLHFILFPLMAPGHMIPMIDIAKLLANRGVITTIITTPVNANRFSSTITRAIKSGLRI

QILTLKFPSVEVGLPEGCENIDMLPSLDLASKFFAAISMLKQQVENLLEGINPSPSCVISDMGF

PWTTQIAQNFNIPRIVFHGTCCFSLLCSYKILSSNILENITSDSEYFVVPDLPDRVELTKAQVS

GSTKNTTSVSSSVLKEVTEQIRLAEESSYGVIVNSFEELEQVYEKEYRKARGKKVWCVGPVSLC

NKEIEDLVTRGNKTAIDNQDCLKWLDNFETESVVYASLGSLSRLTLLQMVELGLGLEESNRPFV

WVLGGGDKLNDLEKWILENGFEQRIKERGVLIRGWAPQVLILSHPAIGGVLTHCGWNSTLEGIS

AGLPMVTWPLFAEQFCNEKLVVQVLKIGVSLGVKVPVKWGDEENVGVLVKKDDVKKALDKLMDE

GEEGQVRRTKAKELGELAKKAFGEGGSSYVNLTSLIEDIIEQQNHKEK

-continued

DNA
Glycosyltransferase (NtGT5-codon optimized for yeast expression)
*Nicotiana tabacum*
SEQ ID NO. 59

ATGGGCTCTATCGGTGCAGAACTAACCAAGCCACACGCCGTATGCATTCCCTATCCCGCCCAGG

GACACATAAATCCTATGCTGAAGTTAGCTAAGATACTGCATCACAAGGGCTTCCATATAACCTT

CGTAAATACGGAATTTAATCACAGGCGTCTGCTGAAGTCCAGAGGTCCTGACTCCCTGAAAGGT

CTTTCAAGTTTCAGGTTCGAGACGATACCTGACGGACTGCCCCCATGCGAAGCTGACGCTACAC

AGGACATTCCTTCACTGTGTGAATCCACGACTAATACATGTCTAGCTCCTTTTAGAGACCTACT

TGCTAAGCTAAATGATACGAATACTTCTAACGTCCCTCCCGTAAGTTGTATTGTCAGTGACGGA

GTGATGTCATTTACCCTTGCAGCTGCACAGGAACTGGGTGTCCCAGAGGTTTTATTTTGGACTA

CATCTGCTTGTGGATTCTTAGGTTACATGCACTATTGCAAAGTCATTGAAAAAGGATATGCTCC

ATTAAAAGACGCATCAGACCTGACGAATGGCTATCTTGAGACAACCTTGGACTTCATCCCCGGC

ATGAAGGACGTCAGGCTGAGAGACTTACCTTCCTTTCTTAGGACCACCAATCCAGACGAATTTA

TGATTAAGTTTGTACTACAGGAAACTGAGCGTGCTCGTAAGGCCAGTGCCATAATACTTAATAC

CTTTGAAACCTTAGAGGCAGAGGTATTAGAATCATTAAGGAACCTTCTACCCCCGTCTATCCA

ATCGGCCCCTTGCATTTCCTTGTCAAACACGTAGACGATGAGAACCTAAAAGGTCTACGTTCCT

CACTTTGGAAGGAGGAACCTGAATGTATTCAATGGTTAGACACCAAAGAACCTAACTCTGTCGT

GTACGTGAATTTCGGATCCATTACTGTGATGACTCCCAATCAATTAATAGAGTTCGCTTGGGGA

CTGGCAAACTCTCAACAGACCTTCCTTTGGATCATAAGGCCTGACATCGTAAGTGGTGATGCTT

CCATATTACCTCCCGAGTTTGTTGAGGAGACTAAGAACAGAGGCATGCTTGCCTCCTGGTGCTC

TCAGGAGGAGGTACTATCCCATCCCGCAATAGTGGGATTTTTGACGCACTCTGGTTGGAACTCA

ACTTTAGAATCAATTTCTAGTGGCGTCCCCATGATCTGTTGGCCTTTCTTTGCTGAGCAGCAAA

CGAACTGCTGGTTTTCAGTGACGAAGTGGGACGTTGGAATGGAAATTGATTCAGATGTGAAGAG

AGATGAAGTAGAGAGTTTAGTAAGAGAGTTAATGGTGGGTGGTAAAGGCAAGAAGATGAAGAAG

AAGGCAATGGAGTGGAAGGAACTGGCCGAGGCTTCAGCAAAAGAACACTCTGGCTCCTCTTACG

TCAATATCGAGAAGTTGGTTAACGATATATTACTATCTAGTAAGCACTAA

Amino Acid
Glycosyltransferase (NtGT5-generated from codon optimized sequence
for yeast expression)
*Nicotiana tabacum*
SEQ ID NO. 60

MGSIGAELTKPHAVCIPYPAQGHINPMLKLAKILHHKGFHITFVNTEFNHRRLLKSRGPDSLKG

LSSFRFETIPDGLPPCEADATQDIPSLCESTTNTCLAPFRDLLAKLNDTNTSNVPPVSCIVSDG

VMSFTLAAAQELGVPEVLFWTTSACGFLGYMHYCKVIEKGYAPLKDASDLTNGYLETTLDFIPG

MKDVRLRDLPSFLRTTNPDEFMIKFVLQETERARKASAIILNTFETLEAEVLESLRNLLPPVYP

IGPLHFLVKHVDDENLKGLRSSLWKEEPECIQWLDTKEPNSVVYVNFGSITVMTPNQLIEFAWG

LANSQQTFLWIIRPDIVSGDASILPPEFVEETKNRGMLASWCSQEEVLSHPAIVGFLTHSGWNS

TLESISSGVPMICWPFFAEQQTNCWFSVTKWDVGMEIDSDVKRDEVESLVRELMVGGKGKKMKK

KAMEWKELAEASAKEHSGSSYVNIEKLVNDILLSSKH

DNA
UDP glycosyltransferase 76G1 (UGT76G1-codon optimized for yeast
expression)
*Stevia rebaudiana*
SEQ ID NO. 61

ATGGAGAACAAAACCGAGACAACCGTTAGGCGTAGACGTAGGATAATATTGTTTCCCGTGCCCT

TTCAAGGCCATATAAACCCAATCCTGCAGCTAGCCAACGTATTGTACTCAAAGGGCTTCAGTAT

AACGATCTTCCACACCAACTTTAATAAGCCAAAAACGTCTAATTATCCACACTTCACATTTAGA

-continued

```
TTTATACTTGATAACGACCCACAGGATGAAAGAATATCAAACTTGCCCACGCACGGCCCACTAG

CCGGAATGAGAATACCAATAATCAATGAGCATGGCGCCGACGAGTTGCGTAGAGAGCTGGAATT

GTTGATGCTAGCCAGTGAGGAAGACGAAGAGGTGTCCTGCTTAATAACGGATGCACTTTGGTAT

TTTGCTCAATCTGTGGCCGACTCCCTTAACCTGAGGCGTCTTGTCCTTATGACCTCCAGTCTAT

TCAACTTTCATGCCCATGTCTCATTGCCCCAATTTGATGAGCTTGGCTATTTGGATCCTGATGA

CAAAACTAGGCTGGAGGAACAGGCTTCCGGTTTTCCCATGCTAAAGGTTAAGGACATCAAATCC

GCCTACTCAAACTGGCAGATCCTTAAGGAAATTCTTGGCAAAATGATCAAACAGACGAGGGCAT

CCAGTGGCGTCATCTGGAACTCCTTTAAGGAACTTGAAGAATCAGAACTTGAAACAGTAATCAG

AGAAATACCTGCCCCAAGTTTCTTGATCCCTCTACCTAAGCACCTTACGGCTTCTAGTTCTTCT

TTGTTGGACCACGATCGTACTGTCTTTCAATGGTTAGATCAGCAACCCCCCTCATCAGTGCTAT

ATGTGTCATTCGGTAGTACATCAGAAGTGGACGAAAAGGATTTCCTTGAGATAGCCCGTGGATT

GGTGGACTCTAAACAGTCCTTTTTATGGGTTGTGAGACCTGGATTTGTAAAGGGATCCACGTGG

GTCGAACCCTTGCCCGATGGTTTCCTGGGTGAAAGAGGAAGGATAGTGAAGTGGGTCCCTCAGC

AAGAGGTACTGGCCCATGGTGCTATAGGTGCTTTCTGGACCCACTCCGGCTGGAATAGTACACT

AGAATCCGTTTGCGAGGGTGTCCCTATGATTTTTTCTGATTTTGGTTTAGATCAACCCCTGAAT

GCTAGGTACATGTCAGACGTCCTTAAAGTCGGCGTCTACCTAGAAAATGGCTGGGAGAGGGGTG

AGATAGCAAACGCTATCAGACGTGTTATGGTAGACGAAGAGGGAGAGTACATAAGGCAAAACGC

CAGGGTCCTGAAACAAAAAGCCGATGTGTCCTTGATGAAGGGCGGCTCTTCATACGAAAGTCTA

GAAAGTCTTGTTTCTTATATTTCCTCACTATAA
```

Amino Acid
UDP glycosyltransferase 76G1 (UGT76G1-generated from codon
optimized sequence for yeast expression)
*Stevia rebaudiana*
                                                    SEQ ID NO. 62
```
MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTRASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL
```

DNA
glycosyltransferase (UGT73A10)
*Lycium barbarum*
                                                    SEQ ID NO. 63
```
ATGGGTCAATTGCATTTTTTTTGTTTCCAATGATGGCTCAAGGTCATATGATTCCAACTTTGG

ATATGGCTAAGTTGATTGCTTCTAGAGGTGTTAAGGCTACTATTATTACTACTCCATTGAACGA

ATCTGTTTTTTCTAAGGCTATTCAAAGAAACAAGCAATTGGGTATTGAAATTGAAATTGAAATT

AGATTGATTAAGTTTCCAGCTTTGGAAAACGATTTGCCAGAAGATTGTGAAAGATTGGATTTGA

TTCCAACTGAAGCTCATTTGCCAAACTTTTTTAAGGCTGCTGCTATGATGCAAGAACCATTGGA

ACAATTGATTCAAGAATGTAGACCAGATTGTTTGGTTTCTGATATGTTTTTGCCATGGACTACT

GATACTGCTGCTAAGTTTAACATTCCAAGAATTGTTTTTCATGGTACTAACTACTTTGCTTTGT

GTGTTGGTGATTCTATGAGAAGAAACAAGCCATTTAAGAACGTTTCTTCTGATTCTGAAACTTT

TGTTGTTCCAAACTTGCCACATGAAATTAAGTTGACTAGAACTCAAGTTTCTCCATTTGAACAA
```

-continued

TCTGATGAAGAATCTGTTATGTCTAGAGTTTTGAAGGAAGTTAGAGAATCTGATTTGAAGTCTT

ACGGTGTTATTTTTAACTCTTTTTACGAATTGGAACCAGATTACGTTGAACATTACACTAAGGT

TATGGGTAGAAAGTCTTGGGCTATTGGTCCATTGTCTTTGTGTAACAGAGATGTTGAAGATAAG

GCTGAAAGAGGTAAGAAGTCTTCTATTGATAAGCATGAATGTTTGGAATGGTTGGATTCTAAGA

AGCCATCTTCTATTGTTTACGTTTGTTTTGGTTCTGTTGCTAACTTTACTGTTACTCAAATGAG

AGAATTGGCTTTGGGTTTGGAAGCTTCTGGTTTGGATTTTATTTGGGCTGTTAGAGCTGATAAC

GAAGATTGGTTGCCAGAAGGTTTTGAAGAAAGAACTAAGGAAAAGGGTTTGATTATTAGAGGTT

GGGCTCCACAAGTTTTGATTTTGGATCATGAATCTGTTGGTGCTTTTGTTACTCATTGTGGTTG

GAACTCTACTTTGGAAGGTATTTCTGCTGGTGTTCCAATGGTTACTTGGCCAGTTTTTGCTGAA

CAATTTTTTAACGAAAAGTTGGTTACTCAAGTTATGAGAACTGGTGCTGGTGTTGGTTCTGTTC

AATGGAAGAGATCTGCTTCTGAAGGTGTTGAAAAGGAAGCTATTGCTAAGGCTATTAAGAGAGT

TATGGTTTCTGAAGAAGCTGAAGGTTTTAGAAACAGAGCTAGAGCTTACAAGGAAATGGCTAGA

CAAGCTATTGAAGAAGGTGGTTCTTCTTACACTGGTTTGACTACTTTGTTGGAAGATATTTCTT

CTTACGAATCTTTGTCTTCTGATTAA

Amino Acid
Glycosyltransferase (UGT73A10)
Lycium barbarum
SEQ ID NO. 64
MGQLHFFLFPMMAQGHMIPTLDMAKLIASRGVKATIITTPLNESVFSKAIQRNKQLGIEIEIEI

RLIKFPALENDLPEDCERLDLIPTEAHLPNFFKAAAMMQEPLEQLIQECRPDCLVSDMFLPWTT

DTAAKFNIPRIVFHGTNYFALCVGDSMRRNKPFKNVSSDSETFVVPNLPHEIKLTRTQVSPFEQ

SDEESVMSRVLKEVRESDLKSYGVIFNSFYELEPDYVEHYTKVMGRKSWAIGPLSLCNRDVEDK

AERGKKSSIDKHECLEWLDSKKPSSIVYVCFGSVANFTVTQMRELALGLEASGLDFIWAVRADN

EDWLPEGFEERTKEKGLIIRGWAPQVLILDHESVGAFVTHCGWNSTLEGISAGVPMVTWPVFAE

QFFNEKLVTQVMRTGAGVGSVQWKRSASEGVEKEAIAKAIKRVMVSEEAEGFRNRARAYKEMAR

QAIEEGGSSYTGLTTLLEDISSYESLSSD

DNA
Catalase HPII (KatE-codon optimized for yeast expression)
Escherichia coli
SEQ ID NO. 65
ATGTCTCAACATAACGAGAAAAACCCACATCAGCATCAATCACCACTACATGACTCCTCTGAAG

CAAAGCCAGGAATGGACTCCCTGGCTCCTGAAGATGGCTCTCACCGTCCCGCTGCCGAACCTAC

GCCACCCGGCGCACAGCCAACTGCCCCCGGTTCCCTAAAGGCCCCTGACACAAGAAATGAAAAG

TTAAATTCTCTTGAAGACGTGCGTAAAGGCAGTGAAAATTACGCTCTTACCACTAATCAAGGCG

TAAGGATAGCTGACGACCAAAACTCCCTGCGTGCTGGCTCTAGAGGCCCTACCCTTCTTGAGGA

TTTTATCCTTCGTGAAAAGATTACTCACTTCGATCACGAAAGGATTCCTGAGAGGATCGTCCAT

GCTAGAGGTTCTGCTGCTCACGGTTATTTTCAGCCCTATAAATCCCTTTCCGACATAACGAAGG

CAGATTTTTGAGTGATCCTAATAAAATAACGCCTGTATTTGTTAGATTTTCTACTGTCCAAGG

TGGTGCTGGATCAGCTGACACTGTTAGAGACATCAGGGGATTTGCTACGAAGTTTTACACTGAA

GAGGGCATCTTCGACTTGGTTGGTAATAATACACCAATATTCTTTATCCAAGACGCACACAAAT

TCCCAGACTTTGTGCATGCTGTCAAACCCGAGCCACATTGGGCTATTCCACAGGGCCAGTCTGC

CCATGACACGTTCTGGGATTACGTTTCTCTGCAACCTGAGACGCTGCACAACGTTATGTGGGCA

ATGTCAGATCGTGGAATACCTAGATCTTACAGGACAATGGAAGGCTTTGGCATACATACTTTCA

GGTTAATAAATGCCGAAGGAAAGGCCACATTCGTCAGGTTTCATTGGAAGCCCTTAGCAGGTAA

-continued

```
GGCCTCTCTAGTATGGGACGAAGCTCAAAAACTTACTGGTAGAGATCCAGACTTTCATAGGCGT

GAATTGTGGGAAGCAATCGAAGCCGGCGACTTTCCTGAGTATGAGCTGGGCTTCCAGTTGATCC

CAGAAGAGGACGAATTTAAATTTGATTTCGACTTACTTGATCCAACGAAACTGATTCCCGAGGA

GTTGGTCCCTGTCCAACGTGTCGGTAAAATGGTGTTGAACAGGAACCCTGACAATTTCTTTGCA

GAAAACGAACAAGCCGCCTTCCATCCAGGCCATATAGTACCAGGCTTAGACTTCACTAATGACC

CACTGCTGCAAGGTAGACTGTTTAGTTACACTGATACACAGATATCCAGACTAGGTGGTCCAAA

CTTCCATGAAATCCCCATCAACAGGCCCACGTGCCCCTATCACAATTTCCAGCGTGATGGCATG

CATAGAATGGGTATTGACACGAATCCCGCTAATTATGAGCCAAACTCTATAAACGATAACTGGC

CTAGAGAGACGCCACCAGGCCCTAAGCGTGGTGGTTTTGAATCCTATCAAGAGCGTGTCGAAGG

TAATAAAGTAAGGGAGAGATCACCCTCTTTCGGCGAATATTATAGTCATCCCCGTTTGTTTTGG

TTATCACAGACGCCTTTCGAACAACGTCACATAGTTGATGGATTCTCTTTTGAGCTTTCAAAAG

TGGTTCGTCCCTATATCAGGGAAAGGGTTGTCGACCAGCTTGCCCATATTGATTTAACACTTGC

ACAAGCTGTTGCCAAAAACCTAGGAATAGAGCTGACAGACGATCAACTAAATATCACCCCACCT

CCTGATGTCAACGGCTTAAAGAAGGATCCATCTTTAAGTCTATACGCAATTCCCGACGGTGATG

TTAAAGGTAGAGTGGTAGCAATTTTGCTAAACGATGAAGTGCGTAGTGCTGACCTACTAGCCAT

CTTAAAGGCCTTGAAAGCAAAGGGAGTGCACGCAAAGTTACTGTACAGTCGTATGGGAGAGGTT

ACTGCTGACGACGGTACGGTACTACCTATCGCCGCAACATTTGCCGGAGCCCCAAGTTTGACAG

TCGATGCCGTTATCGTACCTTGTGGTAATATCGCCGATATTGCCGACAACGGAGACGCTAATTA

CTACTTAATGGAGGCCTATAAGCACTTGAAGCCCATAGCACTGGCTGGAGACGCTCGTAAATTT

AAGGCTACTATCAAGATTGCAGATCAGGGCGAGGAGGGTATTGTTGAGGCAGACAGTGCAGATG

GATCTTTCATGGATGAGCTTCTAACACTAATGGCAGCACATAGAGTATGGTCTCGTATCCCCAA

GATCGACAAAATCCCTGCGTAA
```

Amino Acid
Catalase HPII (KatE-generated from codon optimized sequence for yeast expression)
Escherichia coli

SEQ ID NO. 66

```
MSQHNEKNPHQHQSPLHDSSEAKPGMDSLAPEDGSHRPAAEPTPPGAQPTAPGSLKAPDTRNEK

LNSLEDVRKGSENYALTTNQGVRIADDQNSLRAGSRGPTLLEDFILREKITHFDHERIPERIVH

ARGSAAHGYFQPYKSLSDITKADFLSDPNKITPVFVRFSTVQGGAGSADTVRDIRGFATKFYTE

EGIFDLVGNNTPIFFIQDAHKFPDFVHAVKPEPHWAIPQGQSAHDTFWDYVSLQPETLHNVMWA

MSDRGIPRSYRTMEGFGIHTFRLINAEGKATFVRFHWKPLAGKASLVWDEAQKLTGRDPDFHRR

ELWEAIEAGDFPEYELGFQLIPEEDEFKFDFDLLDPTKLIPEELVPVQRVGKMVLNRNPDNFFA

ENEQAAFHPGHIVPGLDFTNDPLLQGRLFSYTDTQISRLGGPNFHEIPINRPTCPYHNFQRDGM

HRMGIDTNPANYEPNSINDNWPRETPPGPKRGGFESYQERVEGNKVRERSPSFGEYYSHPRLFW

LSQTPFEQRHIVDGFSFELSKVVRPYIRERVVDQLAHIDLTLAQAVAKNLGIELTDDQLNITPP

PDVNGLKKDPSLSLYAIPDGDVKGRVVAILLNDEVRSADLLAILKALKAKGVHAKLLYSRMGEV

TADDGTVLPIAATFAGAPSLTVDAVIVPCGNIADIADNGDANYYLMEAYKHLKPIALAGDARKF

KATIKIADQGEEGIVEADSADGSFMDELLTLMAAHRVWSRIPKIDKIPA
```

DNA
ABC transporter ABCG2
Mus musculus

SEQ ID NO. 67

```
ATGTCTTCTTCTAACGATCATGTTTTGGTTCCAATGTCTCAAAGAAACAACAACGGTTTGCCAA

GAATGAACTCTAGAGCTGTTAGAACTTTGGCTGAAGGTGATGTTTTGTCTTTTCATCATATTAC
```

-continued

```
TTACAGAGTTAAGGTTAAGTCTGGTTTTTTGGTTAGAAAGACTGTTGAAAAGGAAATTTTGTCT
GATATTAACGGTATTATGAAGCCAGGTTTGAACGCTATTTTGGGTCCAACTGGTGGTGGTAAGT
CTTCTTTGTTGGATGTTTTGGCTGCTAGAAAGGATCCAAAGGGTTTGTCTGGTGATGTTTTGAT
TAACGGTGCTCCACAACCAGCTCATTTTAAGTGTTGTTCTGGTTACGTTGTTCAAGATGATGTT
GTTATGGGTACTTTGACTGTTAGAGAAAACTTGCAATTTTCTGCTGCTTTGAGATTGCCAACTA
CTATGAAGAACCATGAAAAGAACGAAAGAATTAACACTATTATTAAGGAATTGGGTTTGGAAAA
GGTTGCTGATTCTAAGGTTGGTACTCAATTTATTAGAGGTATTTCTGGTGGTGAAAGAAAGAGA
ACTTCTATTGGTATGGAATTGATTACTGATCCATCTATTTTGTTTTTGGATGAACCAACTACTG
GTTTGGATTCTTCTACTGCTAACGCTGTTTTGTTGTTGTTGAAGAGAATGTCTAAGCAAGGTAG
AACTATTATTTTTTCTATTCATCAACCAAGATACTCTATTTTTAAGTTGTTTGATTCTTTGACT
TTGTTGGCTTCTGGTAAGTTGGTTTTTCATGGTCCAGCTCAAAAGGCTTTGGAATACTTTGCTT
CTGCTGGTTACCATTGTGAACCATACAACAACCCAGCTGATTTTTTTTGGATGTTATTAACGG
TGATTCTTCTGCTGTTATGTTGAACAGAGAAGAACAAGATAACGAAGCTAACAAGACTGAAGAA
CCATCTAAGGGTGAAAAGCCAGTTATTGAAAACTTGTCTGAATTTTACATTAACTCTGCTATTT
ACGGTGAAACTAAGGCTGAATTGGATCAATTGCCAGGTGCTCAAGAAAAGAAGGGTACTTCTGC
TTTTAAGGAACCAGTTTACGTTACTTCTTTTTGTCATCAATTGAGATGGATTGCTAGAAGATCT
TTTAAGAACTTGTTGGGTAACCCACAAGCTTCTGTTGCTCAATTGATTGTTACTGTTATTTTGG
GTTTGATTATTGGTGCTATTTACTTTGATTTGAAGTACGATGCTGCTGGTATGCAAAACAGAGC
TGGTGTTTTGTTTTTTTTGACTACTAACCAATGTTTTCTTCTGTTTCTGCTGTTGAATTGTTT
GTTGTTGAAAAGAAGTTGTTTATTCATGAATACATTTCTGGTTACTACAGAGTTTCTTCTTACT
TTTTTGGTAAGGTTATGTCTGATTTGTTGCCAATGAGATTTTTGCCATCTGTTATTTTTACTTG
TATTTTGTACTTTATGTTGGGTTTGAAGAAGACTGTTGATGCTTTTTTTATTATGATGTTTACT
TTGATTATGGTTGCTTACACTGCTTCTTCTATGGCTTTGGCTATTGCTACTGGTCAATCTGTTG
TTTCTGTTGCTACTTTGTTGATGACTATTGCTTTTGTTTTTATGATGTTGTTTTCTGGTTTGTT
GGTTAACTTGAGAACTATTGGTCCATGGTTGTCTTGGTTGCAATACTTTTCTATTCCAAGATAC
GGTTTTACTGCTTTGCAATACAACGAATTTTTGGGTCAAGAATTTGTCCAGGTTTTAACGTTA
CTGATAACTCTACTTGTGTTAACTCTTACGCTATTTGTACTGGTAACGAATACTTGATTAACCA
AGGTATTGAATTGTCTCCATGGGGTTTGTGGAAGAACCATGTTGCTTTGGCTTGTATGATTATT
ATTTTTTTGACTATTGCTTACTTGAAGTTGTTGTTTTTGAAGAAGTACTCTTAA
```

Amino Acid  
ABC transporter ABCG2  
*Mus musculus*  
SEQ ID NO. 68

```
MSSSNDHVLVPMSQRNNNGLPRMNSRAVRTLAEGDVLSFHHITYRVKVKSGFLVRKTVEKEILS
DINGIMKPGLNAILGPTGGGKSSLLDVLAARKDPKGLSGDVLINGAPQPAHFKCCSGYVVQDDV
VMGTLTVRENLQFSAALRLPTTMKNHEKNERINTIIKELGLEKVADSKVGTQFIRGISGGERKR
TSIGMELITDPSILFLDEPTTGLDSSTANAVLLLLKRMSKQGRTIIFSIHQPRYSIFKLFDSLT
LLASGKLVFHGPAQKALEYFASAGYHCEPYNNPADFFLDVINGDSSAVMLNREEQDNEANKTEE
PSKGEKPVIENLSEFYINSAIYGETKAELDQLPGAQEKKGTSAFKEPVYVTSFCHQLRWIARRS
FKNLLGNPQASVAQLIVTVILGLIIGAIYFDLKYDAAGMQNRAGVLFFLTTNQCFSSVSAVELF
VVEKKLFIHEYISGYYRVSSYFFGKVMSDLLPMRFLPSVIFTCILYFMLGLKKTVDAFFIMMFT
LIMVAYTASSMALAIATGQSVVSVATLLMTIAFVFMMLFSGLLVNLRTIGPWLSWLQYFSIPRY
```

-continued

GFTALQYNEFLGQEFCPGFNVTDNSTCVNSYAICTGNEYLINQGIELSPWGLWKNHVALACMII

IFLTIAYLKLLFLKKYS

DNA
Cytochrome P450 (CYP3A4)
*Mus musculus*

SEQ ID NO. 69

ATGAACTTGTTTTCTGCTTTGTCTTTGGATACTTTGGTTTTGTTGGCTATTATTTTGGTTTTGT

TGTACAGATACGGTACTAGAACTCATGGTTTGTTTAAGAAGCAAGGTATTCCAGGTCCAAAGCC

ATTGCCATTTTTGGGTACTGTTTTGAACTACTACACTGGTATTTGGAAGTTTGATATGGAATGT

TACGAAAAGTACGGTAAGACTTGGGGTTTGTTTGATGGTCAAACTCCATTGTTGGTTATTACTG

ATCCAGAAACTATTAAGAACGTTTTGGTTAAGGATTGTTTGTCTGTTTTTACTAACAGAAGAGA

ATTTGGTCCAGTTGGTATTATGTCTAAGGCTATTTCTATTTCTAAGGATGAAGAATGGAAGAGA

TACAGAGCTTTGTTGTCTCCAACTTTTACTTCTGGTAGATTGAAGGAAATGTTTCCAGTTATTG

AACAATACGGTGATATTTTGGTTAAGTACTTGAGACAAGAAGCTGAAAAGGGTATGCCAGTTGC

TATGAAGGATGTTTTGGGTGCTTACTCTATGGATGTTATTACTTCTACTTCTTTTGGTGTTAAC

GTTGATTCTTTGAACAACCCAGAAGATCCATTTGTTGAAGAAGCTAAGAAGTTTTTGAGAGTTG

ATTTTTTTGATCCATTGTTGTTTCTGTTGTTTTGTTTCCATTGTTGACTCCAGTTTACGAAAT

GTTGAACATTTGTATGTTTCCAAACGATTCTATTGAATTTTTTAAGAAGTTTGTTGATAGAATG

CAAGAATCTAGATTGGATTCTAACCAAAAGCATAGAGTTGATTTTTTGCAATTGATGATGAACT

CTCATAACAACTCTAAGGATAAGGATTCTCATAAGGCTTTTTCTAACATGGAAATTACTGTTCA

ATCTATTATTTTTATTTCTGCTGGTTACGAAACTACTTCTTCTACTTTGTCTTTTACTTTGTAC

TGTTTGGCTACTCATCCAGATATTCAAAAGAAGTTGCAAGCTGAAATTGATAAGGCTTTGCCAA

ACAAGGCTACTCCAACTTGTGATACTGTTATGGAAATGGAATACTTGGATATGGTTTTGAACGA

AACTTTGAGATTGTACCCAATTGTTACTAGATTGGAAAGAGTTTGTAAGAAGGATGTTGAATTG

AACGGTGTTTACATTCCAAAGGGTTCTATGGTTATGATTCCATCTTACGCTTTGCATCATGATC

CACAACATTGGCCAGATCCAGAAGAATTTCAACCAGAAAGATTTTCTAAGGAAAACAAGGGTTC

TATTGATCCATACGTTTACTTGCCATTTGGTATTGGTCCAAGAAACTGTATTGGTATGAGATTT

GCTTTGATGAACATGAAGTTGGCTGTTACTAAGGTTTTGCAAAACTTTTCTTTTCAACCATGTC

AAGAAACTCAAATTCCATTGAAGTTGTCTAGACAAGGTATTTTGCAACCAGAAAAGCCAATTGT

TTTGAAGGTTGTTCCAAGAGATGCTGTTATTACTGGTGCTTAA

Amino Acid
Cytochrome P450 (CYP3A4)
*Mus musculus*

SEQ ID NO. 70

MNLFSALSLDTLVLLAIILVLLYRYGTRTHGLFKKQGIPGPKPLPFLGTVLNYYTGIWKFDMEC

YEKYGKTWGLFDGQTPLLVITDPETIKNVLVKDCLSVFTNRREFGPVGIMSKAISISKDEEWKR

YRALLSPTFTSGRLKEMFPVIEQYGDILVKYLRQEAEKGMPVAMKDVLGAYSMDVITSTSFGVN

VDSLNNPEDPFVEEAKKFLRVDFFDPLLFSVVLFPLLTPVYEMLNICMFPNDSIEFFKKFVDRM

QESRLDSNQKHRVDFLQLMMNSHNNSKDKDSHKAFSNMEITVQSIIFISAGYETTSSTLSFTLY

CLATHPDIQKKLQAEIDKALPNKATPTCDTVMEMEYLDMVLNETLRLYPIVTRLERVCKKDVEL

NGVYIPKGSMVMIPSYALHHDPQHWPDPEEFQPERFSKENKGSIDPYVYLPFGIGPRNCIGMRF

ALMNMKLAVTKVLQNFSFQPCQETQIPLKLSRQGILQPEKPIVLKVVPRDAVITGA

-continued

```
DNA
P450 oxidoreductase gene (CYP oxidoreductase)
Mus musculus
                                                         SEQ ID NO. 71
ATGGGTGATTCTCATGAAGATACTTCTGCTACTGTTCCAGAAGCTGTTGCTGAAGAAGTTTCTT

TGTTTTCTACTACTGATATTGTTTTGTTTTCTTTGATTGTTGGTGTTTTGACTTACTGGTTTAT

TTTTAAGAAGAAGAAGGAAGAAATTCCAGAATTTTCTAAGATTCAAACTACTGCTCCACCAGTT

AAGGAATCTTCTTTTGTTGAAAAGATGAAGAAGACTGGTAGAAACATTATTGTTTTTTACGGTT

CTCAAACTGGTACTGCTGAAGAATTTGCTAACAGATTGTCTAAGGATGCTCATAGATACGGTAT

GAGAGGTATGTCTGCTGATCCAGAAGAATACGATTTGGCTGATTTGTCTTCTTTGCCAGAAATT

GATAAGTCTTTGGTTGTTTTTTGTATGGCTACTTACGGTGAAGGTGATCCAACTGATAACGCTC

AAGATTTTTACGATTGGTTGCAAGAAACTGATGTTGATTTGACTGGTGTTAAGTTTGCTGTTTT

TGGTTTGGGTAACAAGACTTACGAACATTTTAACGCTATGGGTAAGTACGTTGATCAAGATTG

GAACAATTGGGTGCTCAAAGAATTTTTGAATTGGGTTTGGGTGATGATGATGGTAACTTGGAAG

AAGATTTTATTACTTGGAGAGAACAATTTTGGCCAGCTGTTTGTGAATTTTTTGGTGTTGAAGC

TACTGGTGAAGAATCTTCTATTAGACAATACGAATTGGTTGTTCATGAAGATATGGATACTGCT

AAGGTTTACACTGGTGAAATGGGTAGATTGAAGTCTTACGAAAACCAAAAGCCACCATTTGATG

CTAAGAACCCATTTTTGGCTGCTGTTACTACTAACAGAAAGTTGAACCAAGGTACTGAAAGACA

TTTGATGCATTTGGAATTGGATATTTCTGATTCTAAGATTAGATACGAATCTGGTGATCATGTT

GCTGTTTACCCAGCTAACGATTCTACTTTGGTTAACCAAATTGGTGAAATTTTGGGTGCTGATT

TGGATGTTATTATGTCTTTGAACAACTTGGATGAAGAATCTAACAAGAAGCATCCATTTCCATG

TCCAACTACTTACAGAACTGCTTTGACTTACTACTTGGATATTACTAACCCACCAAGAACTAAC

GTTTTGTACGAATTGGCTCAATACGCTTCTGAACCATCTGAACAAGAACATTTGCATAAGATGG

CTTCTTCTTCTGGTGAAGGTAAGGAATTGTACTTGTCTTGGGTTGTTGAAGCTAGAAGACATAT

TTTGGCTATTTTGCAAGATTACCCATCTTTGAGACCACCAATTGATCATTTGTGTGAATTGTTG

CCAAGATTGCAAGCTAGATACTACTCTATTGCTTCTTCTTCTAAGGTTCATCCAAACTCTGTTC

ATATTTGTGCTGTTGCTGTTGAATACGAAGCTAAGTCTGGTAGAGTTAACAAGGGTGTTGCTAC

TTCTTGGTTGAGAACTAAGGAACCAGCTGGTGAAAACGGTAGAAGAGCTTTGGTTCCAATGTTT

GTTAGAAAGTCTCAATTTAGATTGCCATTTAAGCCAACTACTCCAGTTATTATGGTTGGTCCAG

GTACTGGTGTTGCTCCATTTATGGGTTTTATTCAAGAAAGAGCTTGGTTGAGAGAACAAGGTAA

GGAAGTTGGTGAAACTTTGTTGTACTACGGTTGTAGAAGATCTGATGAAGATTACTTGTACAGA

GAAGAATTGGCTAGATTTCATAAGGATGGTGCTTTGACTCAATTGAACGTTGCTTTTTCTAGAG

AACAAGCTCATAAGGTTTACGTTCAACATTTGTTGAAGAGATAAGGAACATTTGTGGAAGTT

GATTCATGAAGGTGGTGCTCATATTTACGTTTGTGGTGATGCTAGAAACATGGCTAAGGATGTT

CAAAACACTTTTTACGATATTGTTGCTGAATTTGGTCCAATGGAACATACTCAAGCTGTTGATT

ACGTTAAGAAGTTGATGACTAAGGGTAGATACTCTTTGGATGTTTGGTCTTAA

Amino Acid
P450 oxidoreductase (CYP oxidoreductase)
Mus musculus
                                                         SEQ ID NO. 72
MGDSHEDTSATVPEAVAEEVSLFSTTDIVLFSLIVGVLTYWFIFKKKKEEIPEFSKIQTTAPPV

KESSFVEKMKKTGRNIIVFYGSQTGTAEEFANRLSKDAHRYGMRGMSADPEEYDLADLSSLPEI

DKSLVVFCMATYGEGDPTDNAQDFYDWLQETDVDLTGVKFAVFGLGNKTYEHFNAMGKYVDQRL

EQLGAQRIFELGLGDDDGNLEEDFITWREQFWPAVCEFFGVEATGEESSIRQYELVVHEDMDTA

KVYTGEMGRLKSYENQKPPFDAKNPFLAAVTTNRKLNQGTERHLMHLELDISDSKIRYESGDHV
```

```
AVYPANDSTLVNQIGEILGADLDVIMSLNNLDEESNKKHPFPCPTTYRTALTYYLDITNPPRTN

VLYELAQYASEPSEQEHLHKMASSSGEGKELYLSWVVEARRHILAILQDYPSLRPPIDHLCELL

PRLQARYYSIASSSKVHPNSVHICAVAVEYEAKSGRVNKGVATSWLRTKEPAGENGRRALVPMF

VRKSQFRLPFKPTTPVIMVGPGTGVAPFMGFIQERAWLREQGKEVGETLLYYGCRRSDEDYLYR

EELARFHKDGALTQLNVAFSREQAHKVYVQHLLKRDKEHLWKLIHEGGAHIYVCGDARNMAKDV

QNTFYDIVAEFGPMEHTQAVDYVKKLMTKGRYSLDVWS
```

Amino Acid
Catalase 1
*Arabidopsis thaliana*
SEQ ID NO. 73

```
MDPYRVRPSSAHDSPFFTTNSGAPVWNNNSSLTVGTRGPILLEDYHLLEKLANFDRERIP

ERVVHARGASAKGFFEVTHDITQLTSADFLRGPGVQTPVIVRFSTVIHERGSPETLRDPR

GFAVKFYTREGNFDLVGNNFPVFFVRDGMKFPDMVHALKPNPKSHIQENWRILDFFSHHP

ESLHMFSFLFDDLGIPQDYRHMEGAGVNTYMLINKAGKAHYVKFHWKPTCGIKCLSDEEA

IRVGGANHSHATKDLYDSIAAGNYPQWNLFVQVMDPAHEDKFDFDPLDVTKIWPEDILPL

QPVGRLVLNKNIDNFFNENEQIAFCPALVVPGIHYSDDKLLQTRIFSYADSQRHRLGPNY

LQLPVNAPKCAHHNNHHDGFMNFMHRDEEVNYFPSRLDPVRHAEKYPTTPIVCSGNREKC

FIGKENNFKQPGERYRSWDSDRQERFVKRFVEALSEPRVTHEIRSIWISYWSQADKSLGQ

KLATRLNVRPNF
```

Amino Acid
Catalase 2
*Arabidopsis thaliana*
SEQ ID NO. 74

```
MDPYKYRPASSYNSPFFTTNSGAPVWNNNSSMTVGPRGPILLEDYHLVEKLANFDRERIP

ERVVHARGASAKGFFEVTHDISNLTCADFLRAPGVQTPVIVRFSTVIHERGSPETLRDPR

GFAVKFYTREGNFDLVGNNFPVFFIRDGMKFPDMVHALKPNPKSHIQENWRILDFFSHHP

ESLNMFTFLFDDIGIPQDYRHMDGSGVNTYMLINKAGKAHYVKFHWKPTCGVKSLLEEDA

IRVGGTNHSHATQDLYDSIAAGNYPEWKLFIQIIDPADEDKFDFDPLDVTKTWPEDILPL

QPVGRMVLNKNIDNFFAENEQLAFCPAIIVPGIHYSDDKLLQTRVFSYADTQRHRLGPNY

LQLPVNAPKCAHHNNHHEGFMNFMHRDEEVNYFPSRYDQVRHAEKYPTPPAVCSGKRERC

IIEKENNFKEPGERYRTFTPERQERFIQRWIDALSDPRITHEIRSIWISYWSQADKSLGQ

KLASRLNVRPSI
```

Amino Acid
Catalase 3
*Arabidopsis thaliana*
SEQ ID NO. 75

```
MDPYKYRPSSAYNAPFYTTNGGAPVSNNISSLTIGERGPVLLEDYHLIEKVANFTRERIP

ERVVHARGISAKGFFEVTHDISNLTCADFLRAPGVQTPVIVRFSTVVHERASPETMRDIR

GFAVKFYTREGNFDLVGNNTPVFFIRDGIQFPDVVHALKPNPKTNIQEYWRILDYMSHLP

ESLLTWCWMFDDVGIPQDYRHMEGFGVHTYTLIAKSGKVLFVKFHWKPTCGIKNLTDEEA

KVVGGANHSHATKDLHDAIASGNYPEWKLFIQTMDPADEDKFDFDPLDVTKIWPEDILPL

QPVGRLVLNRTIDNFFNETEQLAFNPGLVVPGIYYSDDKLLQCRIFAYGDTQRHRLGPNY

LQLPVNAPKCAHHNNHHEGFMNFMHRDEEINYYPSKFDPVRCAEKVPTPTNSYTGIRTKC

VIKKENNFKQAGDRYRSWAPDRQDRFVKRWVEILSEPRLTHEIRGIWISYWSQADRSLGQ

KLASRLNVRPSI
```

-continued

```
DNA
forward primer of CYP3A4
Artificial
                                          SEQ ID NO. 76
TGCCTAATAAAGCTCCTCCTACT DNA
reverse primer of CYP3A4
Artificial
                                          SEQ ID NO. 77
GCTCCTGAAACAGTTCCATCTC DNA
forward primer of P450 oxidoreductase
Artificial
                                          SEQ ID NO. 78
GGAAGAGCTTTGGTTCCTATGT DNA
reverse primer of P450 oxidoreductase
Artificial
                                          SEQ ID NO. 79
GCTCCCAATTCAGCAACAATATC DNA
forward primer of CBDA synthase
Artificial
                                          SEQ ID NO. 80
ACATCACAATCACACAAAACTAACAAAAG DNA
reverse primer of CBDA synthase
Artificial
                                          SEQ ID NO. 81
GGCCATAGTTTCTCATCAATGG DNA
forward primer of UGT76G1
Artificial
                                          SEQ ID NO. 82
GATTGGAAGAACAAGCTTCAGGATTTCC DNA
reverse primer of UGT76G1
Artificial
                                          SEQ ID NO. 83
CCATCCTGAATGAGTCCAAAAAGCTC DNA
forward primer of ABCG2
Artificial
                                          SEQ ID NO. 84
CCTTCAGGATTGTCAGGAGATG DNA
reverse primer of ABCG2
Artificial
                                          SEQ ID NO. 85
GCAGGTCCATGAAACATCAATC DNA
forward primer of Trichome-targeted CBDAs
Artificial
                                          SEQ ID NO. 86
AAAGATCAAAAGCAAGTTCTTCACTGT DNA
reverse primer of Trichome-targeted CBDAs
Artificial
                                          SEQ ID NO. 87
CCATGCAGTTTGGCTATGAACATCT DNA
forward primer of Trichome-targeted UGT
Artificial
                                          SEQ ID NO. 88
AGTGCTCAACATTCTCCTTTTGGTT
```

-continued

DNA
reverse primer of Trichome-targeted UGT
Artificial

SEQ ID NO. 89

TCTGAAGCCAACATCAACAATTCCA

DNA
forward primer of Plasma membrane-targeted UTR1
Artificial

SEQ ID NO. 90

TTGTTCCTTAAACCTCGCCTTTGAC

DNA
reverse primer of Plasma membrane-targeted UTR1
Artificial

SEQ ID NO. 91

TCATTATGGAGCACTCCACTCTCTG

DNA
forward primer of Cytosolic-targeted CBDA synthase
Artificial

SEQ ID NO. 92

AAAGATCAAAAGCAAGTTCTTCACTGT

DNA
reverse primer of Cytosolic-targeted CBDA synthase
Artificial

SEQ ID NO. 93

ATAAACTTCTCCAAGGGTAGCTCCG

DNA
forward primer of Cytosolic-targeted UGT
Artificial

SEQ ID NO. 94

AGAACTGGAAGAATCCGAACTGGAA

DNA
reverse primer of Cytosolic-targeted UGT
Artificial

SEQ ID NO. 95

AAATCATCGGGACACCTTCACAAAC

DNA
Forward primer of NtGT1
Artificial

SEQ. ID NO. 96

ATGAAAACAACAGAACTTGTCTTCA

DNA
Reverse primer of NtGT1
Artificial

SEQ. ID NO. 97

TGAAGTTGTAGGCCTAGCATGG

DNA
Forward primer of NtGT2
Artificial

SEQ. ID NO. 98

ATGGTTCAACCACACGTCTTACTGG

DNA
Reverse primer of NtGT2
Artificial

SEQ. ID NO. 99

TTGAATACACCAGTTGGGGTCG

DNA
Forward primer of NtGT3
Artificial

SEQ. ID NO. 100

ATGAAAGAGACTAAAAAATTGAGT

DNA
Reverse primer of NtGT3
Artificial

SEQ. ID NO. 101

CATCACGCAGATTTTGAATATGG

```
DNA
Forward primer of NtGT4
Artificial
                                            SEQ. ID NO. 102
ATGGCTACTCAGGTGCATAAATTGC DNA
Reverse primer of NtGT4
Artificial
                                            SEQ. ID NO. 103
GGCCTTAGTTAGCTCGACACGG DNA
Forward primer of NtGT5
Artificial
                                            SEQ. ID NO. 104
ATGGGCTCTATCGGTGCAGAACTAA DNA
Reverse primer of NtGT5
Artificial
                                            SEQ. ID NO. 105
CGGGGATGAAGTCCAAGGTTGT DNA
Forward primer of Kat-E
Artificial
                                            SEQ. ID NO. 106
ATGTCTCAACATAACGAGAAAAACC DNA
Reverse primer of Kat-E
Artificial
                                            SEQ. ID NO. 107
CGTAGCAAATCCCCTGATGTCT DNA
Forward primer of UGT76G1
Artificial
                                            SEQ. ID NO. 108
ATGGAGAACAAAACCGAGACAACCG DNA
Reverse primer of UGT76G1
Artificial
                                            SEQ. ID NO. 109
CCTTTAGCATGGGAAAACCGGA DNA
Forward primer of UGT76G1 (for tobacco BY2 cells)
Artificial
                                            SEQ. ID NO. 110
GATTGGAAGAACAAGCTTCAGGATTTCC DNA
Reverse primer of UGT76G1 (for tobacco BY2 cells)
Artificial
                                            SEQ. ID NO. 111
CCATCCTGAATGAGTCCAAAAAGCTC DNA
Forward primer of ABCG2 (for tobacco BY2 cells)
Artificial
                                            SEQ. ID NO. 112
CCTTCAGGATTGTCAGGAGATG DNA
Reverse primer of ABCG2 (for tobacco BY2 cells)
Artificial
                                            SEQ. ID NO. 113
GCAGGTCCATGAAACATCAATC
```

What is claimed is:

1. A method of glycosylating a cannabinoid, comprising the steps of:
   (a) establishing a tobacco cell suspension culture of *Nicotiana tabacum* or *Nicotiana benthamiana* cells;
   (b) introducing into said tobacco cell suspension culture a cannabinoid, wherein the cannabinoid is cannabidiol (CBD) or cannabidiolic acid (CBDA);
   (c) incubating said cannabinoid in said tobacco cell suspension culture, thereby glycosylating the cannabinoid;
   (d) isolating a cannabinoid glycoside from said tobacco cell suspension culture, wherein the cannabinoid glycoside is a CBD-glycoside or a CBDA-glycoside.

* * * * *

SEQUENCE LISTING

<160> NUMBER OF SEQ ID NOS: 113

<210> SEQ ID NO 1
<211> LENGTH: 1509
<212> TYPE: DNA
<213> ORGANISM: Homo sapien

<400> SEQUENCE: 1

| | | | | | |
|---|---|---|---|---|---|
| atggctttga | ttcctgattt | ggctatggaa | actagattgt | tgttggctgt | ttcattggtt | 60 |
| ttgttgtatt | tgtatggaac | tcattcacat | ggattgttta | aaaaattggg | aattcctgga | 120 |
| cctactcctt | tgccttttt | gggaaatatt | ttgtcatatc | ataaaggatt | ttgcatgttt | 180 |
| gatatggaat | gccataaaaa | atatggaaaa | gtttggggat | tttatgatgg | acaacaacct | 240 |
| gttttggcta | ttactgatcc | tgatatgatt | aaaactgttt | tggttaaaga | atgctattca | 300 |
| gtttttacta | atagaagacc | ttttggacct | gttggattta | tgaaatcagc | tatttcaatt | 360 |
| gctgaagatg | aagaatggaa | aagattgaga | tcattgttgt | cacctacttt | tacttcagga | 420 |
| aaattgaaag | aaatggttcc | tattattgct | caatatggag | atgttttggt | tagaaatttg | 480 |
| agaagagaag | ctgaaactgg | aaaacctgtt | actttgaaag | atgttttttgg | agcttattca | 540 |
| atggatgtta | ttacttcaac | ttcatttgga | gttaatattg | attcattgaa | taatcctcaa | 600 |
| gatccttttg | ttgaaaatac | taaaaaattg | ttgagatttg | attttttgga | tcctttttt | 660 |
| ttgtcaatta | ctgtttttcc | tttttgatt | cctatttgg | aagttttgaa | tatttgcgtt | 720 |
| tttcctagag | aagttactaa | tttttgaga | aaatcagtta | aaagaatgaa | agaatcaaga | 780 |
| ttggaagata | ctcaaaaaca | tagagttgat | tttttgcaat | tgatgattga | ttcacaaaat | 840 |
| tcaaaagaaa | ctgaatcaca | taaagctttg | tcagatttgg | aattggttgc | tcaatcaatt | 900 |
| atttttattt | tgctggatg | cgaaactact | tcatcagttt | tgtcatttat | tatgtatgaa | 960 |
| ttggctactc | atcctgatgt | tcaacaaaaa | ttgcaagaag | aaattgatgc | tgttttgcct | 1020 |
| aataaagctc | ctcctactta | tgatactgtt | ttgcaaatgg | aatatttgga | tatggttgtt | 1080 |
| aatgaaactt | tgagattgtt | tcctattgct | atgagattgg | aaagagtttg | caaaaaagat | 1140 |
| gttgaaatta | atggaatgtt | tattcctaaa | ggagttgttg | ttatgattcc | ttcatatgct | 1200 |
| ttgcatagag | atcctaaata | ttggactgaa | cctgaaaaat | ttttgcctga | aagattttca | 1260 |
| aaaaaaata | aagataatat | tgatccttat | atttatactc | cttttggatc | aggacctaga | 1320 |
| aattgcattg | gaatgagatt | tgctttgatg | aatatgaaat | tggctttgat | tagagttttg | 1380 |
| caaaatttt | catttaaacc | ttgcaaagaa | actcaaattc | ctttgaaatt | gtcattggga | 1440 |
| ggattgttgc | aacctgaaaa | acctgttgtt | ttgaaagttg | aatcaagaga | tggaactgtt | 1500 |
| tcaggagct | | | | | | 1509 |

<210> SEQ ID NO 2
<211> LENGTH: 503
<212> TYPE: PRT
<213> ORGANISM: Homo sapien

<400> SEQUENCE: 2

Met Ala Leu Ile Pro Asp Leu Ala Met Glu Thr Arg Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

-continued

```
Asn Ile Leu Ser Tyr His Lys Gly Phe Cys Met Phe Asp Met Glu Cys
 50                  55                  60

His Lys Lys Tyr Gly Lys Val Trp Gly Phe Tyr Asp Gly Gln Gln Pro
 65                  70                  75                  80

Val Leu Ala Ile Thr Asp Pro Asp Met Ile Lys Thr Val Leu Val Lys
                 85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Trp Lys Arg
            115                 120                 125

Leu Arg Ser Leu Leu Ser Pro Thr Phe Thr Ser Gly Lys Leu Lys Glu
130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
            195                 200                 205

Lys Leu Leu Arg Phe Asp Phe Leu Asp Pro Phe Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
            260                 265                 270

Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
290                 295                 300

Ala Gly Cys Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
            355                 360                 365

Ile Ala Met Arg Leu Glu Arg Val Cys Lys Lys Asp Val Glu Ile Asn
370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
450                 455                 460

Phe Lys Pro Cys Lys Glu Thr Gln Ile Pro Leu Lys Leu Ser Leu Gly
```

```
                465                 470                 475                 480
            Gly Leu Leu Gln Pro Glu Lys Pro Val Val Leu Lys Val Glu Ser Arg
                            485                 490                 495
            Asp Gly Thr Val Ser Gly Ala
                        500

<210> SEQ ID NO 3
<211> LENGTH: 2040
<212> TYPE: DNA
<213> ORGANISM: Homo sapien

<400> SEQUENCE: 3
atgattaata tgggagattc acatgttgat acttcatcaa ctgtttcaga agctgttgct      60
gaagaagttt cattgttttc aatgactgat atgattttgt tttcattgat tgttggattg     120
ttgacttatt ggttttttgtt tagaaaaaaa aagaagaag ttcctgaatt tactaaaatt     180
caaactttga cttcatcagt tagagaatca tcatttgttg aaaaaatgaa aaaaactgga     240
agaaatatta ttgtttttta tggatcacaa actggaactg ctgaagaatt tgctaataga     300
ttgtcaaaag atgctcatag atatggaatg agaggaatgt cagctgatcc tgaagaatat     360
gatttggctg atttgtcatc attgcctgaa attgataatg ctttggttgt ttttttgcatg    420 gctacttatg gagaaggaga tcctactgat aatgctcaag atttttatga ttggttgcaa     480
gaaactgatg ttgatttgtc aggagttaaa tttgctgttt ttggattggg aaataaaact     540
tatgaacatt ttaatgctat gggaaaatat gttgataaaa gattggaaca attgggagct     600
caaagaattt tgaattggg attgggagat gatgatggaa atttggaaga gatttttatt      660
acttggagag aacaattttg gttggctgtt tgcgaacatt ttggagttga agctactgga     720
gaagaatcat caattagaca atatgaattg gttgttcata ctgatattga tgctgctaaa     780
gtttatatgg gagaaatggg aagattgaaa tcatatgaaa atcaaaaacc tccttttgat     840
gctaaaaatc cttttttggc tgctgttact actaatagaa aattgaatca aggaactgaa     900
agacatttga tgcatttgga attggatatt tcagattcaa aaattagata tgaatcagga     960
gatcatgttg ctgtttatcc tgctaatgat tcagctttgg ttaatcaatt gggaaaaatt    1020
ttgggagctg atttggatgt tgttatgtca ttgaataatt tggatgaaga atcaaataaa    1080
aaacatcctt ttccttgccc tacttcatat agaactgctt tgacttatta tttggatatt    1140
actaatcctc ctagaactaa tgttttgtat gaattggctc aatatgcttc agaaccttca    1200
gaacaagaat tgttgagaaa aatggcttca tcatcaggag aaggaaaaga attgtatttg    1260 tcatggggttg ttgaagctag aagacatatt ttggctattt tgcaagattg cccttcattg    1320
agacctccta ttgatcattt tgtgcgaattg ttgcctagat tgcaagctag atattattca    1380
attgcttcat catcaaaagt tcatcctaat tcagttcata tttgcgctgt tgttgttgaa    1440
tatgaaacta agctggaag aattaataaa ggagttgcta ctaattggtt gagagctaaa    1500
gaacctgttg gagaaaatgg aggaagagct ttggttccta tgtttgttag aaaatcacaa    1560
tttagattgc ttttaaagc tactactcct gttattatgg ttggacctgg aactggagtt    1620 gctccttttta ttgatttat tcaagaaaga gcttggttga caacaaggg aaaagaagtt    1680 ggagaaactt tgttgtatta tggatgcaga agatcagatg aagattattt gtatagagaa    1740
gaattggctc aatttcatag agatggagct ttgactcaat tgaatgttgc ttttttcaaga    1800 gaacaatcac ataaagttta tgttcaacat ttgttgaaac aagatagaga acatttgtgg    1860
aaattgattg aaggaggagc tcatatttat gtttgcggag atgctagaaa tatggctaga    1920
```

```
gatgttcaaa atacttttta tgatattgtt gctgaattgg gagctatgga acatgctcaa    1980
gctgttgatt atattaaaaa attgatgact aaaggaagat attcattgga tgtttggtca    2040
```

<210> SEQ ID NO 4
<211> LENGTH: 680
<212> TYPE: PRT
<213> ORGANISM: Homo sapien

<400> SEQUENCE: 4

```
Met Ile Asn Met Gly Asp Ser His Val Asp Thr Ser Ser Thr Val Ser
1               5                   10                  15

Glu Ala Val Ala Glu Glu Val Ser Leu Phe Ser Met Thr Asp Met Ile
                20                  25                  30

Leu Phe Ser Leu Ile Val Gly Leu Leu Thr Tyr Trp Phe Leu Phe Arg
            35                  40                  45

Lys Lys Lys Glu Glu Val Pro Glu Phe Thr Lys Ile Gln Thr Leu Thr
        50                  55                  60

Ser Ser Val Arg Glu Ser Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
            100                 105                 110

Met Ser Ala Asp Pro Glu Glu Tyr Asp Leu Ala Asp Leu Ser Ser Leu
        115                 120                 125

Pro Glu Ile Asp Asn Ala Leu Val Val Phe Cys Met Ala Thr Tyr Gly
130                 135                 140

Glu Gly Asp Pro Thr Asp Asn Ala Gln Asp Phe Tyr Asp Trp Leu Gln
145                 150                 155                 160

Glu Thr Asp Val Asp Leu Ser Gly Val Lys Phe Ala Val Phe Gly Leu
                165                 170                 175

Gly Asn Lys Thr Tyr Glu His Phe Asn Ala Met Gly Lys Tyr Val Asp
            180                 185                 190

Lys Arg Leu Glu Gln Leu Gly Ala Gln Arg Ile Phe Glu Leu Gly Leu
        195                 200                 205

Gly Asp Asp Asp Gly Asn Leu Glu Glu Asp Phe Ile Thr Trp Arg Glu
210                 215                 220

Gln Phe Trp Leu Ala Val Cys Glu His Phe Gly Val Glu Ala Thr Gly
225                 230                 235                 240

Glu Glu Ser Ser Ile Arg Gln Tyr Glu Leu Val Val His Thr Asp Ile
                245                 250                 255

Asp Ala Ala Lys Val Tyr Met Gly Glu Met Gly Arg Leu Lys Ser Tyr
            260                 265                 270

Glu Asn Gln Lys Pro Pro Phe Asp Ala Lys Asn Pro Phe Leu Ala Ala
        275                 280                 285

Val Thr Thr Asn Arg Lys Leu Asn Gln Gly Thr Glu Arg His Leu Met
290                 295                 300

His Leu Glu Leu Asp Ile Ser Asp Ser Lys Ile Arg Tyr Glu Ser Gly
305                 310                 315                 320

Asp His Val Ala Val Tyr Pro Ala Asn Asp Ser Ala Leu Val Asn Gln
                325                 330                 335

Leu Gly Lys Ile Leu Gly Ala Asp Leu Asp Val Val Met Ser Leu Asn
            340                 345                 350
```

```
Asn Leu Asp Glu Glu Ser Asn Lys Lys His Pro Phe Pro Cys Pro Thr
            355                 360                 365

Ser Tyr Arg Thr Ala Leu Thr Tyr Tyr Leu Asp Ile Thr Asn Pro Pro
    370                 375                 380

Arg Thr Asn Val Leu Tyr Glu Leu Ala Gln Tyr Ala Ser Glu Pro Ser
385                 390                 395                 400

Glu Gln Glu Leu Leu Arg Lys Met Ala Ser Ser Gly Glu Gly Lys
                405                 410                 415

Glu Leu Tyr Leu Ser Trp Val Val Glu Ala Arg Arg His Ile Leu Ala
                420                 425                 430

Ile Leu Gln Asp Cys Pro Ser Leu Arg Pro Pro Ile Asp His Leu Cys
                435                 440                 445

Glu Leu Leu Pro Arg Leu Gln Ala Arg Tyr Tyr Ser Ile Ala Ser Ser
450                 455                 460

Ser Lys Val His Pro Asn Ser Val His Ile Cys Ala Val Val Val Glu
465                 470                 475                 480

Tyr Glu Thr Lys Ala Gly Arg Ile Asn Lys Gly Val Ala Thr Asn Trp
                485                 490                 495

Leu Arg Ala Lys Glu Pro Val Gly Glu Asn Gly Gly Arg Ala Leu Val
                500                 505                 510

Pro Met Phe Val Arg Lys Ser Gln Phe Arg Leu Pro Phe Lys Ala Thr
                515                 520                 525

Thr Pro Val Ile Met Val Gly Pro Gly Thr Gly Val Ala Pro Phe Ile
                530                 535                 540

Gly Phe Ile Gln Glu Arg Ala Trp Leu Arg Gln Gln Gly Lys Glu Val
545                 550                 555                 560

Gly Glu Thr Leu Leu Tyr Tyr Gly Cys Arg Arg Ser Asp Glu Asp Tyr
                565                 570                 575

Leu Tyr Arg Glu Glu Leu Ala Gln Phe His Arg Asp Gly Ala Leu Thr
                580                 585                 590

Gln Leu Asn Val Ala Phe Ser Arg Glu Gln Ser His Lys Val Tyr Val
                595                 600                 605

Gln His Leu Leu Lys Gln Asp Arg Glu His Leu Trp Lys Leu Ile Glu
610                 615                 620

Gly Gly Ala His Ile Tyr Val Cys Gly Asp Ala Arg Asn Met Ala Arg
625                 630                 635                 640

Asp Val Gln Asn Thr Phe Tyr Asp Ile Val Ala Glu Leu Gly Ala Met
                645                 650                 655

Glu His Ala Gln Ala Val Asp Tyr Ile Lys Lys Leu Met Thr Lys Gly
                660                 665                 670

Arg Tyr Ser Leu Asp Val Trp Ser
            675                 680

<210> SEQ ID NO 5
<211> LENGTH: 1554
<212> TYPE: DNA
<213> ORGANISM: Cannabis sativa

<400> SEQUENCE: 5
atgaatcctc gagaaaactt ccttaaatgc ttctcgcaat atattcccaa taatgcaaca      60
aatctaaaac tcgtatacac tcaaaacaac ccattgtata tgtctgtcct aaattcgaca     120
atacacaatc ttagattcac ctctgacaca accccaaaac cacttgttat cgtcactcct     180
tcacatgtct ctcatatcca aggcactatt ctatgctcca agaaagttgg cttgcagatt     240
```

```
cgaactcgaa gtggtggtca tgattctgag ggcatgtcct acatatctca agtcccattt     300
gttatagtag acttgagaaa catgcgttca atcaaaatag atgttcatag ccaaactgca     360
tgggttgaag ccggagctac ccttggagaa gtttattatt gggttaatga gaaaaatgag     420
aatcttagtt tggcggctgg gtattgccct actgtttgcg caggtggaca ctttggtgga     480
ggaggctatg gaccattgat gagaaactat ggcctcgcgg ctgataatat cattgatgca     540
cacttagtca acgttcatgg aaaagtgcta gatcgaaaat ctatggggga agatctcttt     600
tgggctttac gtggtggtgg agcagaaagc ttcggaatca ttgtagcatg gaaaattaga     660
ctggttgctg tcccaaagtc tactatgttt agtgttaaaa agatcatgga gatacatgag     720
cttgtcaagt tagttaacaa atggcaaaat attgcttaca agtatgacaa agatttatta     780
ctcatgactc acttcataac taggaacatt acagataatc aagggaagaa taagacagca     840
atacacactt acttctcttc agttttcctt ggtggagtgg atagtctagt cgacttgatg     900
aacaagagtt ttcctgagtt gggtattaaa aaaacggatt gcagacaatt gagctggatt     960
gatactatca tcttctatag tggtgttgta aattacgaca ctgataattt taacaaggaa    1020
atttgtcttg atagatccgc tgggcagaac ggtgcttttca agattaagtt agactacgtt    1080
aagaaaccaa ttccagaatc tgtatttgtc caaattttgg aaaaattata tgaagaagat    1140
ataggagctg ggatgtatgc gttgtaccct tacggtggta taatggatga gatttcagaa    1200
tcagcaattc cattccctca tcgagctgga atcttgtatg agttatggta catatgtagt    1260
tgggagaagc aagaagataa cgaaaagcat ctaaactgga ttagaaatat ttataacttc    1320
atgactcctt atgtgtccaa aaattcaaga ttggcatatc tcaattatag agaccttgat    1380
ataggaataa atgatcccaa gaatccaaat aattacacac aagcacgtat ttgggggtgag    1440 aagtattttg gtaaaaattt tgacaggcta gtaaagtga aaaccctggt tgatcccaat    1500 aacttttttta gaaacgaaca aagcatccca cctcaaccac ggcatcgtca ttaa         1554
```

<210> SEQ ID NO 6
<211> LENGTH: 517
<212> TYPE: PRT
<213> ORGANISM: Cannabis sativa

<400> SEQUENCE: 6

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140
```

Ala Ala Gly Tyr Cys Pro Thr Val Cys Ala Gly His Phe Gly
145                 150                 155                 160

Gly Gly Tyr Gly Pro Leu Met Arg Asn Tyr Gly Leu Ala Ala Asp Asn
            165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
        210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
            245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
            325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365

Phe Val Gln Ile Leu Glu Lys Leu Tyr Glu Glu Asp Ile Gly Ala Gly
        370                 375                 380

Met Tyr Ala Leu Tyr Pro Tyr Gly Gly Ile Met Asp Glu Ile Ser Glu
385                 390                 395                 400

Ser Ala Ile Pro Phe Pro His Arg Ala Gly Ile Leu Tyr Glu Leu Trp
            405                 410                 415

Tyr Ile Cys Ser Trp Glu Lys Gln Glu Asp Asn Glu Lys His Leu Asn
            420                 425                 430

Trp Ile Arg Asn Ile Tyr Asn Phe Met Thr Pro Tyr Val Ser Lys Asn
        435                 440                 445

Ser Arg Leu Ala Tyr Leu Asn Tyr Arg Asp Leu Asp Ile Gly Ile Asn
    450                 455                 460

Asp Pro Lys Asn Pro Asn Asn Tyr Thr Gln Ala Arg Ile Trp Gly Glu
465                 470                 475                 480

Lys Tyr Phe Gly Lys Asn Phe Asp Arg Leu Val Lys Val Lys Thr Leu
            485                 490                 495

Val Asp Pro Asn Asn Phe Phe Arg Asn Glu Gln Ser Ile Pro Pro Gln
            500                 505                 510

Pro Arg His Arg His
        515

<210> SEQ ID NO 7
<211> LENGTH: 1374
<212> TYPE: DNA
<213> ORGANISM: Stevia rebaudiana

<400> SEQUENCE: 7

```
atggaaaata aaactgaaac tactgttaga agaagaagaa gaattatttt gtttcctgtt      60
ccttttcaag gacatattaa tcctattttg caattggcta atgttttgta ttcaaaagga     120
ttttcaatta ctattttca tactaatttt aataaaccta aacttcaaa ttatcctcat     180 tttacttta gatttatttt ggataatgat cctcaagatg aaagaatttc aaatttgcct     240
actcatggac ctttggctgg aatgagaatt cctattatta tgaacatgg agctgatgaa     300 ttgagaagag aattggaatt gttgatgttg gcttcagaag aagatgaaga agtttcatgc     360
ttgattactg atgctttgtg gtattttgct caatcagttg ctgattcatt gaatttgaga     420
agattggttt tgatgacttc atcattgttt aattttcatg ctcatgtttc attgcctcaa     480
tttgatgaat tgggatattt ggatcctgat gataaaacta gattggaaga caagcttca     540 ggatttccta tgttgaaagt taagatatt aaatcagctt attcaaattg caaattttg     600 aaagaaattt tgggaaaaat gattaaacaa actagagctt catcaggagt tatttggaat     660
tcatttaaag aattggaaga atcagaattg gaaactgtta ttagagaaat tcctgctcct     720 tcattttga ttcctttgcc taaacatttg actgcttcat catcatcatt gttggatcat     780
gatagaactg ttttttcaatg gttggatcaa caacctcctt catcagtttt gtatgtttca     840
tttggatcaa cttcagaagt tgatgaaaaa gatttttgg aaattgctag aggattggtt     900
gattcaaaac aatcattttt gtgggttgtt agacctggat tgttaaagg atcaacttgg     960 gttgaacctt tgcctgatgg attttttgga gaaagaggaa gaattgttaa atgggttcct    1020
caacaagaag ttttggctca tggagctatt ggagcttttt ggactcattc aggatggaat    1080
tcaactttgg aatcagtttg cgaaggagtt cctatgattt tttcagattt tggattggat    1140
caacctttga atgctagata tgtcagatg gttttgaaag ttggagttta tttgaaaat    1200 ggatgggaaa gaggagaaat tgctaatgct attagaagag ttatggttga tgaagaagga    1260
gaatatatta gacaaaatgc tagagttttg aaacaaaaag ctgatgtttc attgatgaaa    1320
ggaggatcat catatgaatc attggaatca ttggtttcat atatttcatc attg          1374
```

<210> SEQ ID NO 8
<211> LENGTH: 458
<212> TYPE: PRT
<213> ORGANISM: Stevia rebaudiana

<400> SEQUENCE: 8

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125
```

```
Phe Ala Gln Ser Val Ala Asp Ser Leu Asn Leu Arg Arg Leu Val Leu
    130                 135                 140
Met Thr Ser Ser Leu Phe Asn Phe His Ala His Val Ser Leu Pro Gln
145                 150                 155                 160
Phe Asp Glu Leu Gly Tyr Leu Asp Pro Asp Lys Thr Arg Leu Glu
                165                 170                 175
Glu Gln Ala Ser Gly Phe Pro Met Leu Lys Val Lys Asp Ile Lys Ser
                180                 185                 190
Ala Tyr Ser Asn Trp Gln Ile Leu Lys Glu Ile Leu Gly Lys Met Ile
                195                 200                 205
Lys Gln Thr Arg Ala Ser Ser Gly Val Ile Trp Asn Ser Phe Lys Glu
    210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
                245                 250                 255
Leu Leu Asp His Asp Arg Thr Val Phe Gln Trp Leu Asp Gln Gln Pro
            260                 265                 270
Pro Ser Ser Val Leu Tyr Val Ser Phe Gly Ser Thr Ser Glu Val Asp
    275                 280                 285
Glu Lys Asp Phe Leu Glu Ile Ala Arg Gly Leu Val Asp Ser Lys Gln
290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                325                 330                 335
Lys Trp Val Pro Gln Gln Glu Val Leu Ala His Gly Ala Ile Gly Ala
            340                 345                 350
Phe Trp Thr His Ser Gly Trp Asn Ser Thr Leu Glu Ser Val Cys Glu
        355                 360                 365
Gly Val Pro Met Ile Phe Ser Asp Phe Gly Leu Asp Gln Pro Leu Asn
    370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                405                 410                 415
Asp Glu Glu Gly Glu Tyr Ile Arg Gln Asn Ala Arg Val Leu Lys Gln
                420                 425                 430
Lys Ala Asp Val Ser Leu Met Lys Gly Gly Ser Ser Tyr Glu Ser Leu
            435                 440                 445
Glu Ser Leu Val Ser Tyr Ile Ser Ser Leu
    450                 455

<210> SEQ ID NO 9
<211> LENGTH: 1965
<212> TYPE: DNA
<213> ORGANISM: Homo sapien

<400> SEQUENCE: 9
atgtcatcat caaatgttga agttttatt cctgtttcac aaggaaatac taatggattt      60
cctgctactg cttcaaatga tttgaaagct tttactgaag gagctgtttt gtcatttcat    120
aatatttgct atagagttaa attgaaatca ggattttgc cttgcagaaa acctgttgaa    180
aaagaaattt tgtcaaatat taatggaatt atgaaacctg gattgaatgc tattttggga    240
```

```
cctactggag gaggaaaatc atcattgttg gatgttttgg ctgctagaaa agatccttca    300
ggattgtcag gagatgtttt gattaatgga gctcctagac ctgctaattt taaatgcaat    360
tcaggatatg ttgttcaaga tgatgttgtt atgggaactt tgactgttag agaaaatttg    420
caattttcag ctgctttgag attggctact actatgacta atcatgaaaa aaatgaaaga    480
attaatagag ttattcaaga attgggattg gataaagttg ctgattcaaa agttggaact    540
caatttatta gaggagtttc aggaggagaa agaaaaagaa cttcaattgg aatgaaattg    600
attactgatc cttcaatttt gttttggat gaacctacta ctggattgga ttcatcaact    660
gctaatgctg ttttgttgtt gttgaaaaga atgtcaaaac aaggaagaac tattattttt    720
tcaattcatc aacctagata ttcaattttt aaattgtttg attcattgac tttgttggct    780
tcaggaagat tgatgtttca tggacctgct caagaagctt tgggatattt tgaatcagct    840
ggatatcatt gcgaagctta taataatcct gctgatttt ttttggatat tattaatgga    900
gattcaactg ctgttgcttt gaatagagaa gaagatttta agctactga aattattgaa    960
ccttcaaaac aagataaacc tttgattgaa aaattggctg aaatttatgt taattcatca   1020
ttttataaag aaactaaagc tgaattgcat caattgtcag gaggagaaaa aaaaaaaaaa   1080
attactgttt ttaaagaaat ttcatatact acttcatttt gccatcaatt gagatgggtt   1140
tcaaaaagat catttaaaaa tttgttggga atcctcaag cttcaattgc tcaaattatt   1200
gttactgttg ttttgggatt ggttattgga gctatttatt ttggattgaa aaatgattca   1260
actggaattc aaaatagagc tggagttttg tttttttga ctactaatca atgcttttca   1320
tcagtttcag ctgttgaatt gtttgttgtt gaaaaaaaat tgtttattca tgaatatatt   1380
tcaggatatt atagagtttc atcatatttt ttgggaaaat tgttgtcaga tttgttgcct   1440
atgagaatgt tgccttcaat tattttact tgcattgttt attttatgtt gggattgaaa   1500
gctaaagctg atgcttttt tgttatgatg tttactttga tgatggttgc ttattcagct   1560
tcatcaatgg ctttggctat tgctgctgga caatcagttg tttcagttgc tactttgttg   1620
atgactattt gctttgtttt tatgatgatt tttcaggat tgttggttaa tttgactact   1680
attgcttcat ggttgtcatg gttgcaatat ttttcaattc ctagatatgg atttactgct   1740
ttgcaacata tgaatttttt gggacaaaat ttttgccctg gattgaatgc tactggaaat   1800
aatccttgca attatgctac ttgcactgga gaagaatatt tggttaaaca aggaattgat   1860
ttgtcacctt ggggattgtg gaaaaatcat gttgctttgg cttgcatgat tgttattttt   1920
ttgactattg cttatttgaa attgttgttt ttgaaaaaat attca                   1965
```

<210> SEQ ID NO 10
<211> LENGTH: 655
<212> TYPE: PRT
<213> ORGANISM: Homo sapien

<400> SEQUENCE: 10

```
Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
```

```
                65                  70                  75                  80
        Pro Thr Gly Gly Gly Lys Ser Ser Leu Leu Asp Val Leu Ala Ala Arg
                         85                  90                  95

Lys Asp Pro Ser Gly Leu Ser Gly Asp Val Leu Ile Asn Gly Ala Pro
                        100                 105                 110

Arg Pro Ala Asn Phe Lys Cys Asn Ser Gly Tyr Val Gln Asp Asp
                        115                 120                 125

Val Val Met Gly Thr Leu Thr Val Arg Glu Asn Leu Gln Phe Ser Ala
                        130                 135                 140

Ala Leu Arg Leu Ala Thr Thr Met Thr Asn His Glu Lys Asn Glu Arg
        145                 150                 155                 160

Ile Asn Arg Val Ile Gln Glu Leu Gly Leu Asp Lys Val Ala Asp Ser
                        165                 170                 175

Lys Val Gly Thr Gln Phe Ile Arg Gly Val Ser Gly Glu Arg Lys
                        180                 185                 190

Arg Thr Ser Ile Gly Met Glu Leu Ile Thr Asp Pro Ser Ile Leu Phe
                        195                 200                 205

Leu Asp Glu Pro Thr Thr Gly Leu Asp Ser Ser Thr Ala Asn Ala Val
                        210                 215                 220

Leu Leu Leu Leu Lys Arg Met Ser Lys Gln Gly Arg Thr Ile Ile Phe
        225                 230                 235                 240

Ser Ile His Gln Pro Arg Tyr Ser Ile Phe Lys Leu Phe Asp Ser Leu
                        245                 250                 255

Thr Leu Leu Ala Ser Gly Arg Leu Met Phe His Gly Pro Ala Gln Glu
                        260                 265                 270

Ala Leu Gly Tyr Phe Glu Ser Ala Gly Tyr His Cys Glu Ala Tyr Asn
                        275                 280                 285

Asn Pro Ala Asp Phe Phe Leu Asp Ile Ile Asn Gly Asp Ser Thr Ala
                        290                 295                 300

Val Ala Leu Asn Arg Glu Glu Asp Phe Lys Ala Thr Glu Ile Ile Glu
        305                 310                 315                 320

Pro Ser Lys Gln Asp Lys Pro Leu Ile Glu Lys Leu Ala Glu Ile Tyr
                        325                 330                 335

Val Asn Ser Ser Phe Tyr Lys Glu Thr Lys Ala Glu Leu His Gln Leu
                        340                 345                 350

Ser Gly Gly Glu Lys Lys Lys Ile Thr Val Phe Lys Glu Ile Ser
                        355                 360                 365

Tyr Thr Thr Ser Phe Cys His Gln Leu Arg Trp Val Ser Lys Arg Ser
                        370                 375                 380

Phe Lys Asn Leu Leu Gly Asn Pro Gln Ala Ser Ile Ala Gln Ile Ile
        385                 390                 395                 400

Val Thr Val Val Leu Gly Leu Val Ile Gly Ala Ile Tyr Phe Gly Leu
                        405                 410                 415

Lys Asn Asp Ser Thr Gly Ile Gln Asn Arg Ala Gly Val Leu Phe Phe
                        420                 425                 430

Leu Thr Thr Asn Gln Cys Phe Ser Ser Val Ser Ala Val Glu Leu Phe
                        435                 440                 445

Val Val Glu Lys Lys Leu Phe Ile His Glu Tyr Ile Ser Gly Tyr Tyr
        450                 455                 460

Arg Val Ser Ser Tyr Phe Leu Gly Lys Leu Leu Ser Asp Leu Leu Pro
        465                 470                 475                 480

Met Arg Met Leu Pro Ser Ile Ile Phe Thr Cys Ile Val Tyr Phe Met
                        485                 490                 495
```

```
Leu Gly Leu Lys Ala Lys Ala Asp Ala Phe Val Met Met Phe Thr
            500                 505                 510
Leu Met Met Val Ala Tyr Ser Ala Ser Ser Met Ala Leu Ala Ile Ala
            515                 520                 525
Ala Gly Gln Ser Val Val Ser Val Ala Thr Leu Leu Met Thr Ile Cys
            530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
                565                 570                 575
Gly Phe Thr Ala Leu Gln His Asn Glu Phe Leu Gly Gln Asn Phe Cys
                580                 585                 590
Pro Gly Leu Asn Ala Thr Gly Asn Asn Pro Cys Asn Tyr Ala Thr Cys
                595                 600                 605
Thr Gly Glu Glu Tyr Leu Val Lys Gln Gly Ile Asp Leu Ser Pro Trp
            610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
                645                 650                 655

<210> SEQ ID NO 11
<211> LENGTH: 1074
<212> TYPE: DNA
<213> ORGANISM: Cannabis

<400> SEQUENCE: 11
atgaagaaga acaaatcaac tagtaataat aagaacaaca acagtaataa tatcatcaaa      60
aacgacatcg tatcatcatc atcatcaaca acaacaacat catcaacaac tacagcaaca     120
tcatcatttc ataatgagaa agttactgtc agtactgatc atattattaa tcttgatgat     180
aagcagaaac gacaattatg tcgttgtcgt ttagaaaaag aagaagaaga agaaggaagt     240
ggtggttgtg gtgagacagt agtaatgatg ctagggtcag tatctcctgc tgctgctact     300
gctgctgcag ctgggggctc atcaagttgt gatgaagaca tgttgggtgg tcatgatcaa     360
ctgttgttgt tgtgttgttc tgagaaaaaa acgacagaaa tttcatcagt ggtgaacttt     420
aataataata ataataataa taggaaaat ggtgacgaag tttcaggacc gtacgattat     480
catcatcata agaagaggag agaagaagaa gaagaagatg aagcatctgc atcagtagca     540
gctgttgatg aagggatgtt gttgtgccttt gatgacataa tagatagcca cttgctaaat     600
ccaaatgagg ttttgacttt aagagaagat agccataatg aaggtggggc agctgatcag     660
attgacaaga ctacttgtaa taatactact attactacta atgatgatta taacaataac     720
ttgatgatgt tgagctgcaa taataacgga gattatgtta ttagtgatga tcatgatgat     780
cagtactgga tagacgacgt cgttggagtt gacttttgga gttgggagag ttcgactact     840
actgttatta cccaagaaca agaacaagaa caagatcaag ttcaagaaca gaagaatatg     900
tgggataatg agaaagagaa actgttgtct ttgctatggg ataatagtga taacagcagc     960
agttgggagt tacaagataa aagcaataat aataataata ataatgttcc taacaaatgt    1020
caagagatta cctctgataa agaaaatgct atggttgcat ggcttctctc ctga         1074

<210> SEQ ID NO 12
<211> LENGTH: 357
<212> TYPE: PRT
```

<213> ORGANISM: Cannabis

<400> SEQUENCE: 12

Met Lys Lys Asn Lys Ser Thr Ser Asn Asn Lys Asn Asn Ser Asn
1               5                   10                  15

Asn Ile Ile Lys Asn Asp Ile Val Ser Ser Ser Ser Thr Thr Thr
            20                  25                  30

Thr Ser Ser Thr Thr Thr Ala Thr Ser Ser Phe His Asn Glu Lys Val
        35                  40                  45

Thr Val Ser Thr Asp His Ile Ile Asn Leu Asp Asp Lys Gln Lys Arg
    50                  55                  60

Gln Leu Cys Arg Cys Arg Leu Glu Lys Glu Glu Glu Glu Gly Ser
65                  70                  75                  80

Gly Gly Cys Gly Glu Thr Val Val Met Met Leu Gly Ser Val Ser Pro
                85                  90                  95

Ala Ala Ala Thr Ala Ala Ala Gly Gly Ser Ser Ser Cys Asp Glu
            100                 105                 110

Asp Met Leu Gly Gly His Asp Gln Leu Leu Leu Cys Cys Ser Glu
            115                 120                 125

Lys Lys Thr Thr Glu Ile Ser Ser Val Val Asn Phe Asn Asn Asn Asn
    130                 135                 140

Asn Asn Asn Lys Glu Asn Gly Asp Glu Val Ser Gly Pro Tyr Asp Tyr
145                 150                 155                 160

His His His Lys Glu Glu Glu Glu Glu Glu Asp Glu Ala Ser
                165                 170                 175

Ala Ser Val Ala Ala Val Asp Glu Gly Met Leu Leu Cys Phe Asp Asp
            180                 185                 190

Ile Ile Asp Ser His Leu Leu Asn Pro Asn Glu Val Leu Thr Leu Arg
            195                 200                 205

Glu Asp Ser His Asn Glu Gly Gly Ala Ala Asp Gln Ile Asp Lys Thr
    210                 215                 220

Thr Cys Asn Asn Thr Thr Ile Thr Thr Asn Asp Asp Tyr Asn Asn Asn
225                 230                 235                 240

Leu Met Met Leu Ser Cys Asn Asn Gly Asp Tyr Val Ile Ser Asp
            245                 250                 255

Asp His Asp Asp Gln Tyr Trp Ile Asp Asp Val Val Gly Val Asp Phe
            260                 265                 270

Trp Ser Trp Glu Ser Ser Thr Thr Thr Val Ile Thr Gln Glu Gln Glu
            275                 280                 285

Gln Glu Gln Asp Gln Val Gln Glu Gln Lys Asn Met Trp Asp Asn Glu
    290                 295                 300

Lys Glu Lys Leu Leu Ser Leu Leu Trp Asp Asn Ser Asp Asn Ser Ser
305                 310                 315                 320

Ser Trp Glu Leu Gln Asp Lys Ser Asn Asn Asn Asn Asn Asn Val
            325                 330                 335

Pro Asn Lys Cys Gln Glu Ile Thr Ser Asp Lys Glu Asn Ala Met Val
            340                 345                 350

Ala Trp Leu Leu Ser
        355

<210> SEQ ID NO 13
<211> LENGTH: 1476
<212> TYPE: DNA
<213> ORGANISM: Arabidopsis thaliana

<400> SEQUENCE: 13

```
atggatcctt ataaatatag acctgcttca tcatataatt cacctttttt tactactaat      60
tcaggagctc ctgtttggaa taataattca tcaatgactg ttggacctag aggattgatt     120
ttgttggaag attatcattt ggttgaaaaa ttggctaatt ttgatagaga agaattcct      180
gaaagagttg ttcatgctag aggagcttca gctaaaggat tttttgaagt tactcatgat     240
atttcaaatt tgacttgcgc tgatttttg agagctcctg gagttcaaac tcctgttatt     300
gttagatttt caactgttat tcatgctaga ggatcacctg aaactttgag agatcctaga     360
ggatttgctg ttaaatttta tactagagaa ggaaattttg atttggttgg aaataatttt     420
cctgttttt ttattagaga tggaatgaaa tttcctgata ttgttcatgc tttgaaacct      480
aatcctaaat cacatattca agaaaattgg agaattttgg atttttttc acatcatcct     540
gaatcattga atatgtttac tttttgttt gatgatattg aattcctca agattataga     600
catatggatg gatcaggagt taatacttat atgttgatta ataaagctgg aaaagctcat     660
tatgttaaat tcattggaa acctacttgc ggagttaaat cattgttgga agaagatgct     720
attagattgg gaggaactaa tcattcacat gctactcaag atttgtatga ttcaattgct     780
gctgaaaatt atcctgaatg gaaattgttt attcaaatta ttgatcctgc tgatgaagat     840
aaatttgatt ttgatccttt ggatgttact aaaacttggc ctgaagatat tttgcctttg     900
caacctgttg gaagaatggt tttgaataaa aatattgata ttttttttgc tgaaaatgaa     960
caattggctt tttgccctgc tattattgtt cctggaattc attattcaga tgataaattg    1020
ttgcaaacta gagtttttc atatgctgat actcaaagac atagattggg acctaattat    1080
ttgcaattgc ctgttaatgc tcctaaatgc gctcatcata taatcatca tgaaggattt    1140
atgaattta tgcatagaga tgaagaagtt aattattttc cttcaagata tgatcaagtt    1200
agacatgctg aaaaatatcc tactcctcct gctgtttgct caggaaaaag agaaagatgc    1260
attattgaaa agaaaataa ttttaaagaa cctggagaaa gatatagaac ttttactcct    1320
gaaagacaag aaagatttat tcaaagatgg attgatgctt tgtcagatcc tagaattact    1380
catgaaatta gatcaatttg gattttcatat tggtcacaag ctgataaatc attgggacaa    1440
aaattggctt caagattgaa tgttagacct tcaatt                              1476
```

<210> SEQ ID NO 14
<211> LENGTH: 492
<212> TYPE: PRT
<213> ORGANISM: Arabidopsis thaliana

<400> SEQUENCE: 14

```
Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Asn Ser Ser Met
            20                  25                  30

Thr Val Gly Pro Arg Gly Leu Ile Leu Leu Glu Asp Tyr His Leu Val
        35                  40                  45

Glu Lys Leu Ala Asn Phe Asp Arg Glu Arg Ile Pro Glu Arg Val Val
    50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Ala Arg Gly Ser
```

```
                100               105                110
Pro Glu Thr Leu Arg Asp Pro Arg Gly Phe Ala Val Lys Phe Tyr Thr
                115                120                125
Arg Glu Gly Asn Phe Asp Leu Val Gly Asn Asn Phe Pro Val Phe Phe
            130                135                140
Ile Arg Asp Gly Met Lys Phe Pro Asp Ile Val His Ala Leu Lys Pro
145                150                155                160
Asn Pro Lys Ser His Ile Gln Glu Asn Trp Arg Ile Leu Asp Phe Phe
                165                170                175
Ser His His Pro Glu Ser Leu Asn Met Phe Thr Phe Leu Phe Asp Asp
            180                185                190
Ile Gly Ile Pro Gln Asp Tyr Arg His Met Asp Gly Ser Gly Val Asn
            195                200                205
Thr Tyr Met Leu Ile Asn Lys Ala Gly Lys Ala His Tyr Val Lys Phe
        210                215                220
His Trp Lys Pro Thr Cys Gly Val Lys Ser Leu Leu Glu Glu Asp Ala
225                230                235                240
Ile Arg Leu Gly Gly Thr Asn His Ser His Ala Thr Gln Asp Leu Tyr
                245                250                255
Asp Ser Ile Ala Ala Gly Asn Tyr Pro Glu Trp Lys Leu Phe Ile Gln
            260                265                270
Ile Ile Asp Pro Ala Asp Glu Asp Lys Phe Asp Phe Asp Pro Leu Asp
        275                280                285
Val Thr Lys Thr Trp Pro Glu Asp Ile Leu Pro Leu Gln Pro Val Gly
        290                295                300
Arg Met Val Leu Asn Lys Asn Ile Asp Asn Phe Ala Glu Asn Glu
305                310                315                320
Gln Leu Ala Phe Cys Pro Ala Ile Ile Val Pro Gly Ile His Tyr Ser
                325                330                335
Asp Asp Lys Leu Leu Gln Thr Arg Val Phe Ser Tyr Ala Asp Thr Gln
                340                345                350
Arg His Arg Leu Gly Pro Asn Tyr Leu Gln Leu Pro Val Asn Ala Pro
            355                360                365
Lys Cys Ala His His Asn Asn His His Glu Gly Phe Met Asn Phe Met
        370                375                380
His Arg Asp Glu Glu Val Asn Tyr Phe Pro Ser Arg Tyr Asp Gln Val
385                390                395                400
Arg His Ala Glu Lys Tyr Pro Thr Pro Pro Ala Val Cys Ser Gly Lys
                405                410                415
Arg Glu Arg Cys Ile Ile Glu Lys Glu Asn Asn Phe Lys Glu Pro Gly
            420                425                430
Glu Arg Tyr Arg Thr Phe Thr Pro Glu Arg Gln Glu Arg Phe Ile Gln
        435                440                445
Arg Trp Ile Asp Ala Leu Ser Asp Pro Arg Ile Thr His Glu Ile Arg
450                455                460
Ser Ile Trp Ile Ser Tyr Trp Ser Gln Ala Asp Lys Ser Leu Gly Gln
465                470                475                480
Lys Leu Ala Ser Arg Leu Asn Val Arg Pro Ser Ile
                485                490

<210> SEQ ID NO 15
<211> LENGTH: 2262
<212> TYPE: DNA
<213> ORGANISM: Escherichia coli
```

<400> SEQUENCE: 15

```
atgtcgcaac ataacgaaaa gaacccacat cagcaccagt caccactaca cgattccagc         60
gaagcgaaac cggggatgga ctcactggca cctgaggacg gctctcatcg tccagcggct        120
gaaccaacac cgccaggtgc acaacctacc gccccaggga gcctgaaagc ccctgatacg        180
cgtaacgaaa aacttaattc tctggaagac gtacgcaaag gcagtgaaaa ttatgcgctg        240
accactaatc agggcgtgcg catcgccgac gatcaaaact cactgcgtgc cggtagccgt        300
ggtccaacgc tgctggaaga ttttattctg cgcgagaaaa tcacccactt tgaccatgag        360
cgcattccgg aacgtattgt tcatgcacgc ggatcagccg ctcacggtta tttccagcca        420
tataaaagct taagcgatat taccaaagcg gatttcctct cagatccgaa caaaatcacc        480
ccagtatttg tacgtttctc taccgttcag ggtggtgctg gctctgctga taccgtgcgt        540
gatatccgtg gctttgccac caagttctat accgaagagg gtattttga cctcgttggc        600
aataacacgc caatcttctt tatccaggat gcgcataaat tccccgattt tgttcatgcg        660
gtaaaaccag aaccgcactg ggcaattcca caagggcaaa gtgcccacga tactttctgg        720
gattatgttt ctctgcaacc tgaaactctg cacaacgtga tgtgggcgat gtcggatcgc        780
ggcatccccc gcagttaccg caccatggaa ggcttcggta ttcacacctt ccgcctgatt        840
aatgccgaag gaaggcaac gtttgtacgt ttccactgga accactggca ggtaaagcc         900
tcactcgttt gggatgaagc acaaaaactc accggacgtg acccggactt ccaccgccgc        960
gagttgtggg aagccattga agcaggcgat tttccggaat acgaactggg cttccagttg       1020
attcctgaag aagatgaatt caagttcgac ttcgatcttc tcgatccaac caaacttatc       1080
ccggaagaac tggtgcccgt tcagcgtgtc ggcaaaatgg tgctcaatcg caacccggat       1140
aacttctttg ctgaaaacga acaggcggct ttccatcctg ggcatatcgt gccgggactg       1200
gacttcacca cgatccgct gttgcaggga cgtttgttct cctataccga tacacaaatc        1260
agtcgtcttg gtgggccgaa tttccatgag attccgatta accgtccgac ctgcccttac       1320
cataatttcc agcgtgacgg catgcatcgc atggggatcg acactaaccc ggcgaattac       1380
gaaccgaact cgattaacga taactggccg cgcgaaacac cgccggggcc gaaacgcggc       1440
ggttttgaat cataccagga gcgcgtggaa ggcaataaag ttcgcgagcg cagcccatcg       1500
tttggcgaat attattccca tccgcgtctg ttctggctaa gtcagacgcc atttgagcag       1560
cgccatattg tcgatggttt cagttttgag ttaagcaaag tcgttcgtcc gtatattcgt       1620
gagcgcgttg ttgaccagct ggcgcatatt gatctcactc tggcccaggc ggtggcgaaa       1680
aatctcggta tcgaactgac tgacgaccag ctgaatatca ccccacctcc ggacgtcaac       1740
ggtctgaaaa aggatccatc cttaagtttg tacgccattc tgacggtga tgtgaaaggt        1800
cgcgtggtag cgattttact taatgatgaa gtgagatcgg cagaccttct ggccattctc       1860
aaggcgctga aggccaaagg cgttcatgcc aaactgctct actcccgaat gggtgaagtg       1920
actgcggatg acggtacggt gttgcctata gccgctacct ttgccggtgc accttcgctg       1980
acggtcgatg cggtcattgt cccttgcggc aatatcgcgg atatcgctga acggcgat        2040
gccaactact acctgatgga agcctacaaa caccttaaac cgattgcgct ggcgggtgac       2100
gcgcgcaagt ttaaagcaac aatcaagatc gctgaccagg gtgaagaagg gattgtggaa       2160
gctgacagcg ctgacggtag ttttatggat gaactgctaa cgctgatggc agcacaccgc       2220
gtgtggtcac gcattcctaa gattgacaaa attcctgcct ga                         2262
```

<210> SEQ ID NO 16
<211> LENGTH: 753
<212> TYPE: PRT
<213> ORGANISM: Escherichia coli

<400> SEQUENCE: 16

```
Met Ser Gln His Asn Glu Lys Asn Pro His Gln His Gln Ser Pro Leu
 1               5                  10                  15
His Asp Ser Ser Glu Ala Lys Pro Gly Met Asp Ser Leu Ala Pro Glu
            20                  25                  30
Asp Gly Ser His Arg Pro Ala Ala Glu Pro Thr Pro Pro Gly Ala Gln
        35                  40                  45
Pro Thr Ala Pro Gly Ser Leu Lys Ala Pro Asp Thr Arg Asn Glu Lys
    50                  55                  60
Leu Asn Ser Leu Glu Asp Val Arg Lys Gly Ser Glu Asn Tyr Ala Leu
65                  70                  75                  80
Thr Thr Asn Gln Gly Val Arg Ile Ala Asp Asp Gln Asn Ser Leu Arg
                85                  90                  95
Ala Gly Ser Arg Gly Pro Thr Leu Leu Glu Asp Phe Ile Leu Arg Glu
            100                 105                 110
Lys Ile Thr His Phe Asp His Glu Arg Ile Pro Glu Arg Ile Val His
        115                 120                 125
Ala Arg Gly Ser Ala Ala His Gly Tyr Phe Gln Pro Tyr Lys Ser Leu
    130                 135                 140
Ser Asp Ile Thr Lys Ala Asp Phe Leu Ser Asp Pro Asn Lys Ile Thr
145                 150                 155                 160
Pro Val Phe Val Arg Phe Ser Thr Val Gln Gly Ala Gly Ser Ala
                165                 170                 175
Asp Thr Val Arg Asp Ile Arg Gly Phe Ala Thr Lys Phe Tyr Thr Glu
            180                 185                 190
Glu Gly Ile Phe Asp Leu Val Gly Asn Asn Thr Pro Ile Phe Phe Ile
        195                 200                 205
Gln Asp Ala His Lys Phe Pro Asp Phe Val His Ala Val Lys Pro Glu
    210                 215                 220
Pro His Trp Ala Ile Pro Gln Gly Gln Ser Ala His Asp Thr Phe Trp
225                 230                 235                 240
Asp Tyr Val Ser Leu Gln Pro Glu Thr Leu His Asn Val Met Trp Ala
                245                 250                 255
Met Ser Asp Arg Gly Ile Pro Arg Ser Tyr Arg Thr Met Glu Gly Phe
            260                 265                 270
Gly Ile His Thr Phe Arg Leu Ile Asn Ala Glu Gly Lys Ala Thr Phe
        275                 280                 285
Val Arg Phe His Trp Lys Pro Leu Ala Gly Lys Ala Ser Leu Val Trp
    290                 295                 300
Asp Glu Ala Gln Lys Leu Thr Gly Arg Asp Pro Asp Phe His Arg Arg
305                 310                 315                 320
Glu Leu Trp Glu Ala Ile Glu Ala Gly Asp Phe Pro Glu Tyr Glu Leu
                325                 330                 335
Gly Phe Gln Leu Ile Pro Glu Glu Asp Glu Phe Lys Phe Asp Phe Asp
            340                 345                 350
Leu Leu Asp Pro Thr Lys Leu Ile Pro Glu Glu Leu Val Pro Val Gln
        355                 360                 365
Arg Val Gly Lys Met Val Leu Asn Arg Asn Pro Asp Asn Phe Phe Ala
    370                 375                 380
```

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
            405                 410                 415

Asp Thr Gln Ile Ser Arg Leu Gly Gly Pro Asn Phe His Glu Ile Pro
        420                 425                 430

Ile Asn Arg Pro Thr Cys Pro Tyr His Asn Phe Gln Arg Asp Gly Met
    435                 440                 445

His Arg Met Gly Ile Asp Thr Asn Pro Ala Asn Tyr Glu Pro Asn Ser
450                 455                 460

Ile Asn Asp Asn Trp Pro Arg Glu Thr Pro Gly Pro Lys Arg Gly
465                 470                 475                 480

Gly Phe Glu Ser Tyr Gln Glu Arg Val Glu Gly Asn Lys Val Arg Glu
            485                 490                 495

Arg Ser Pro Ser Phe Gly Glu Tyr Tyr Ser His Pro Arg Leu Phe Trp
        500                 505                 510

Leu Ser Gln Thr Pro Phe Glu Gln Arg His Ile Val Asp Gly Phe Ser
    515                 520                 525

Phe Glu Leu Ser Lys Val Val Arg Pro Tyr Ile Arg Glu Arg Val Val
530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
            565                 570                 575

Pro Asp Val Asn Gly Leu Lys Lys Asp Pro Ser Leu Ser Leu Tyr Ala
        580                 585                 590

Ile Pro Asp Gly Asp Val Lys Gly Arg Val Val Ala Ile Leu Leu Asn
    595                 600                 605

Asp Glu Val Arg Ser Ala Asp Leu Leu Ala Ile Leu Lys Ala Leu Lys
610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
            645                 650                 655

Ala Pro Ser Leu Thr Val Asp Ala Val Ile Val Pro Cys Gly Asn Ile
        660                 665                 670

Ala Asp Ile Ala Asp Asn Gly Asp Ala Asn Tyr Tyr Leu Met Glu Ala
    675                 680                 685

Tyr Lys His Leu Lys Pro Ile Ala Leu Ala Gly Asp Ala Arg Lys Phe
690                 695                 700

Lys Ala Thr Ile Lys Ile Ala Asp Gln Gly Glu Glu Gly Ile Val Glu
705                 710                 715                 720

Ala Asp Ser Ala Asp Gly Ser Phe Met Asp Glu Leu Leu Thr Leu Met
            725                 730                 735

Ala Ala His Arg Val Trp Ser Arg Ile Pro Lys Ile Asp Lys Ile Pro
        740                 745                 750

Ala

<210> SEQ ID NO 17
<211> LENGTH: 1635
<212> TYPE: DNA
<213> ORGANISM: Cannabis

<400> SEQUENCE: 17

```
atgaagtgct caacattctc cttttggttt gtttgcaaga taatatttt cttttctca     60
ttcaatatcc aaacttccat tgctaatcct cgagaaaact tccttaaatg cttctcgcaa   120
tatattccca ataatgcaac aaatctaaaa ctcgtataca ctcaaaacaa cccattgtat   180
atgtctgtcc taaattcgac aatacacaat cttagattca cctctgacac aaccccaaaa   240
ccacttgtta tcgtcactcc ttcacatgtc tctcatatcc aaggcactat tctatgctcc   300
aagaaagttg gcttgcagat tcgaactcga agtggtggtc atgattctga gggcatgtcc   360
tacatatctc aagtcccatt tgttatagta gacttgagaa acatgcgttc aatcaaaata   420
gatgttcata gccaaactgc atgggttgaa gccggagcta cccttggaga agtttattat   480
tgggttaatg agaaaaatga gaatcttagt ttggcggctg gtattgccc tactgtttgc    540
gcaggtggac actttggtgg aggaggctat ggaccattga tgagaaacta tggcctcgcg   600
gctgataata tcattgatgc acacttagtc aacgttcatg gaaaagtgct agatcgaaaa   660
tctatggggg aagatctctt tgggcttta cgtggtggtg gagcagaaag cttcggaatc    720
attgtagcat ggaaaattag actggttgct gtcccaaagt ctactatgtt tagtgttaaa   780
aagatcatgg agatacatga gcttgtcaag ttagttaaca aatggcaaaa tattgcttac   840
aagtatgaca agatttatt actcatgact cacttcataa ctaggaacat tacagataat    900
caagggaaga ataagacagc aatacacact tacttctctt cagttttcct tggtggagtg   960
gatagtctag tcgacttgat gaacaagagt tttcctgagt tgggtattaa aaaaacggat  1020
tgcagacaat tgagctggat tgatactatc atcttctata gtggtgttgt aaattacgac  1080
actgataatt ttaacaagga aattttgctt gatagatccg ctgggcagaa cggtgctttc  1140
aagattaagt tagactacgt taagaaacca attccagaat ctgtatttgt ccaaattttg  1200
gaaaaattat atgaagaaga tataggagct gggatgtatg cgttgtaccc ttacggtggt  1260
ataatggatg agatttcaga atcagcaatt ccattccctc atcgagctgg aatcttgtat  1320
gagttatggt acatatgtag ttgggagaag caagaagata acgaaaagca tctaaactgg  1380
attagaaata tttataactt catgactcct tatgtgtcca aaaatccaag attggcatat  1440
ctcaattata gagaccttga tataggaata aatgatccca agaatccaaa taattacaca  1500
caagcacgta tttggggtga gaagtatttt ggtaaaaatt ttgacaggct agtaaaagtg  1560
aaacccctgg ttgatcccaa taactttttt agaaacgaac aaagcatccc acctctacca  1620
cggcatcgtc attaa                                                    1635
```

<210> SEQ ID NO 18
<211> LENGTH: 544
<212> TYPE: PRT
<213> ORGANISM: Cannabis

<400> SEQUENCE: 18

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80
```

```
Pro Leu Val Ile Val Thr Pro Ser His Val Ser His Ile Gln Gly Thr
                    85                  90                  95

Ile Leu Cys Ser Lys Lys Val Gly Leu Gln Ile Arg Thr Arg Ser Gly
                100                 105                 110

Gly His Asp Ser Glu Gly Met Ser Tyr Ile Ser Gln Val Pro Phe Val
            115                 120                 125

Ile Val Asp Leu Arg Asn Met Arg Ser Ile Lys Ile Asp Val His Ser
        130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Tyr Gly Pro
                180                 185                 190

Leu Met Arg Asn Tyr Gly Leu Ala Ala Asp Asn Ile Ile Asp Ala His
            195                 200                 205

Leu Val Asn Val His Gly Lys Val Leu Asp Arg Lys Ser Met Gly Glu
        210                 215                 220

Asp Leu Phe Trp Ala Leu Arg Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
                260                 265                 270

Asn Lys Trp Gln Asn Ile Ala Tyr Lys Tyr Asp Lys Asp Leu Leu Leu
            275                 280                 285

Met Thr His Phe Ile Thr Arg Asn Ile Thr Asp Asn Gln Gly Lys Asn
        290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Phe
                340                 345                 350

Tyr Ser Gly Val Val Asn Tyr Asp Thr Asp Asn Phe Asn Lys Glu Ile
            355                 360                 365

Leu Leu Asp Arg Ser Ala Gly Gln Asn Gly Ala Phe Lys Ile Lys Leu
        370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
                420                 425                 430

Pro His Arg Ala Gly Ile Leu Tyr Glu Leu Trp Tyr Ile Cys Ser Trp
            435                 440                 445

Glu Lys Gln Glu Asp Asn Glu Lys His Leu Asn Trp Ile Arg Asn Ile
        450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495
```

Asn Asn Tyr Thr Gln Ala Arg Ile Trp Gly Glu Lys Tyr Phe Gly Lys
                500                 505                 510

Asn Phe Asp Arg Leu Val Lys Val Lys Thr Leu Val Asp Pro Asn Asn
            515                 520                 525

Phe Phe Arg Asn Glu Gln Ser Ile Pro Pro Leu Pro Arg His Arg His
        530                 535                 540

<210> SEQ ID NO 19
<211> LENGTH: 1467
<212> TYPE: DNA
<213> ORGANISM: Stevia rebaudiana

<400> SEQUENCE: 19

| | |
|---|---:|
| atgaagtgct caacattctc cttttggttt gtttgcaaga taatattttt cttttctca | 60 |
| ttcaatatcc aaacttccat tgctaatcct cgagaaaata aaactgaaac tactgttaga | 120 |
| agaagaagaa gaattatttt gtttcctgtt ccttttcaag gacatattaa tcctattttg | 180 |
| caattggcta atgttttgta ttcaaaagga ttttcaatta ctattttca tactaatttt | 240 |
| aataaaccta aaacttcaaa ttatcctcat tttacttta gatttatttt ggataatgat | 300 |
| cctcaagatg aaagaatttc aaatttgcct actcatggac ctttggctgg aatgagaatt | 360 |
| cctattatta tgaacatgg agctgatgaa ttgagaagag aattggaatt gttgatgttg | 420 |
| gcttcagaag aagatgaaga agtttcatgc ttgattactg atgctttgtg gtattttgct | 480 |
| caatcagttg ctgattcatt gaatttgaga agattggttt tgatgacttc atcattgttt | 540 |
| aattttcatg ctcatgtttc attgcctcaa tttgatgaat tgggatattt ggatcctgat | 600 |
| gataaaacta gattggaaga acaagcttca ggatttccta tgttgaaagt taagatatt | 660 |
| aaatcagctt attcaaattg gcaaattttg aaagaaattt tgggaaaaat gattaaacaa | 720 |
| actagagctt catcaggagt tatttggaat tcatttaaag aattggaaga atcagaattg | 780 |
| gaaactgtta ttagagaaat tcctgctcct tcatttttga ttcctttgcc taaacatttg | 840 |
| actgcttcat catcatcatt gttggatcat gatagaactg ttttcaatg gttggatcaa | 900 |
| caacctcctt catcagtttt gtatgtttca tttggatcaa cttcagaagt tgatgaaaaa | 960 |
| gattttttgg aaattgctag aggattggtt gattcaaaac aatcattttt gtgggttgtt | 1020 |
| agacctggat tgttaaagg atcaactgg gttgaacctt tgcctgatgg attttgga | 1080 |
| gaaagaggaa gaattgttaa atgggttcct caacaagaag ttttggctca tggagctatt | 1140 |
| ggagcttttt ggactcattc aggatggaat tcaactttgg aatcagtttg cgaaggagtt | 1200 |
| cctatgattt tttcagattt tggattggat caaccttga atgctagata tatgtcagat | 1260 |
| gttttgaaag ttggagttta tttggaaaat ggatgggaaa gaggagaaat tgctaatgct | 1320 |
| attagaagag ttatggttga tgaagaagga gaatatatta caaaatgc tagagttttg | 1380 |
| aaacaaaaag ctgatgtttc attgatgaaa ggaggatcat catatgaatc attggaatca | 1440 |
| ttggtttcat atatttcatc attgtaa | 1467 |

<210> SEQ ID NO 20
<211> LENGTH: 488
<212> TYPE: PRT
<213> ORGANISM: Stevia rebaudiana

<400> SEQUENCE: 20

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu

```
            20                  25                  30
Asn Lys Thr Glu Thr Thr Val Arg Arg Arg Arg Ile Ile Leu Phe
         35                  40                  45
Pro Val Pro Phe Gln Gly His Ile Asn Pro Ile Leu Gln Leu Ala Asn
 50                  55                  60
Val Leu Tyr Ser Lys Gly Phe Ser Ile Thr Ile Phe His Thr Asn Phe
 65                  70                  75                  80
Asn Lys Pro Lys Thr Ser Asn Tyr Pro His Phe Thr Phe Arg Phe Ile
                 85                  90                  95
Leu Asp Asn Asp Pro Gln Asp Glu Arg Ile Ser Asn Leu Pro Thr His
                100                 105                 110
Gly Pro Leu Ala Gly Met Arg Ile Pro Ile Ile Asn Glu His Gly Ala
        115                 120                 125
Asp Glu Leu Arg Arg Glu Leu Glu Leu Leu Met Leu Ala Ser Glu Glu
        130                 135                 140
Asp Glu Glu Val Ser Cys Leu Ile Thr Asp Ala Leu Trp Tyr Phe Ala
145                 150                 155                 160
Gln Ser Val Ala Asp Ser Leu Asn Leu Arg Arg Leu Val Leu Met Thr
                165                 170                 175
Ser Ser Leu Phe Asn Phe His Ala His Val Ser Leu Pro Gln Phe Asp
                180                 185                 190
Glu Leu Gly Tyr Leu Asp Pro Asp Asp Lys Thr Arg Leu Glu Glu Gln
        195                 200                 205
Ala Ser Gly Phe Pro Met Leu Lys Val Lys Asp Ile Lys Ser Ala Tyr
        210                 215                 220
Ser Asn Trp Gln Ile Leu Lys Glu Ile Leu Gly Lys Met Ile Lys Gln
225                 230                 235                 240
Thr Arg Ala Ser Ser Gly Val Ile Trp Asn Ser Phe Lys Glu Leu Glu
                245                 250                 255
Glu Ser Glu Leu Glu Thr Val Ile Arg Glu Ile Pro Ala Pro Ser Phe
                260                 265                 270
Leu Ile Pro Leu Pro Lys His Leu Thr Ala Ser Ser Ser Ser Leu Leu
        275                 280                 285
Asp His Asp Arg Thr Val Phe Gln Trp Leu Asp Gln Gln Pro Pro Ser
        290                 295                 300
Ser Val Leu Tyr Val Ser Phe Gly Ser Thr Ser Glu Val Asp Glu Lys
305                 310                 315                 320
Asp Phe Leu Glu Ile Ala Arg Gly Leu Val Asp Ser Lys Gln Ser Phe
                325                 330                 335
Leu Trp Val Val Arg Pro Gly Phe Val Lys Gly Ser Thr Trp Val Glu
                340                 345                 350
Pro Leu Pro Asp Gly Phe Leu Gly Glu Arg Gly Arg Ile Val Lys Trp
        355                 360                 365
Val Pro Gln Gln Glu Val Leu Ala His Gly Ala Ile Gly Ala Phe Trp
        370                 375                 380
Thr His Ser Gly Trp Asn Ser Thr Leu Glu Ser Val Cys Glu Gly Val
385                 390                 395                 400
Pro Met Ile Phe Ser Asp Phe Gly Leu Asp Gln Pro Leu Asn Ala Arg
                405                 410                 415
Tyr Met Ser Asp Val Leu Lys Val Gly Val Tyr Leu Glu Asn Gly Trp
                420                 425                 430
Glu Arg Gly Glu Ile Ala Asn Ala Ile Arg Arg Val Met Val Asp Glu
        435                 440                 445
```

```
Glu Gly Glu Tyr Ile Arg Gln Asn Ala Arg Val Leu Lys Gln Lys Ala
    450                 455                 460

Asp Val Ser Leu Met Lys Gly Gly Ser Ser Tyr Glu Ser Leu Glu Ser
465                 470                 475                 480

Leu Val Ser Tyr Ile Ser Ser Leu
            485

<210> SEQ ID NO 21
<211> LENGTH: 1022
<212> TYPE: DNA
<213> ORGANISM: Arabidopsis thaliana

<400> SEQUENCE: 21
atggaggtcc atggctccgg attccgtcga attctgttgt tggcgttgtg tatctccggg      60
atctggtccg cctacatcta ccaaggcgtt cttcaagaga ctctgtccac gaagagattt     120
ggtccagatg agaagaggtt cgagcatctt gcattcttga acttagctca aagtgtagtc     180
tgcttgatct ggtcttatat aatgatcaag ctctggtcaa atgctggtaa cggtggagca     240
ccatggtgga cgtattggag tgcaggcatt actaatacaa ttggtcctgc catgggaatt     300
gaagccttga gtatatcag ttatccagct caggttttgg caaaatcgtc aaaaatgatt     360
ccagttatgc taatgggaac tttagtttac ggaataagat acactttccc tgaatacatg     420 tgcaccttc ttgtcgctgg aggagtatcc atctttgctc ttcttaagac aagctctaag     480
acaattagca agctagcaca tccaaatgct cccctcggtt acgcactttg ttccttaaac     540
ctcgcctttg acggattcac aaatgccaca caagactcca ttgcctcaag gtacccaaaa     600
accgaagcgt gggacataat gctgggaatg aacttatggg cacaatata caacattatc     660 tacatgtttg gcttgccaca agggatggat tcgaagcaat tcagttctgt aagctacacc     720
cggaagcggc atgggacatt ctaaagtatt gtatatgcgg tgccgtggga caaaacttca     780
tcttcatgac aataagtaac ttcgggtcac tagctaacac gaccataacc acgaccagga     840
agtttgttag cattgttgta tcatcagtaa tgagcggaaa tccattgtcg ttgaagcaat     900
ggggatgtgt ttcgatggtc tttggtggtt tggcatatca aatttatctt aaatggaaga     960
aattgcagag agtggagtgc tccataatga acttaatgtg tgggtctacc tgcgccgctt    1020
ga                                                                   1022

<210> SEQ ID NO 22
<211> LENGTH: 1554
<212> TYPE: DNA
<213> ORGANISM: Cannabis sativa

<400> SEQUENCE: 22
atgaatcctc gagaaaactt ccttaaatgc ttctcgcaat atattcccaa taatgcaaca      60
aatctaaaac tcgtatacac tcaaaacaac ccattgtata tgtctgtcct aaattcgaca     120
atacacaatc ttagattcac ctctgacaca accccaaaac cacttgttat cgtcactcct     180
tcacatgtct ctcatatcca aggcactatt ctatgctcca agaaagttgg cttgcagatt     240
cgaactcgaa gtggtggtca tgattctgag ggcatgtcct acatatctca agtcccattt     300
gttatagtag acttgagaaa catgcgttca atcaaaatag atgttcatag ccaaactgca     360
tgggttgaag ccggagctac ccttggagaa gtttattatt gggttaatga gaaaaatgag     420
aatcttagtt tggcggctgg gtattgccct actgtttgcg caggtggaca ctttggtgga     480
ggaggctatg gaccattgat gagaaactat ggcctcgcgg ctgataatat cattgatgca     540
```

```
cacttagtca acgttcatgg aaaagtgcta gatcgaaaat ctatggggga agatctcttt     600
tgggctttac gtggtggtgg agcagaaagc ttcggaatca ttgtagcatg gaaaattaga     660
ctggttgctg tcccaaagtc tactatgttt agtgttaaaa agatcatgga gatacatgag     720
cttgtcaagt tagttaacaa atggcaaaat attgcttaca agtatgacaa agatttatta     780
ctcatgactc acttcataac taggaacatt acagataatc aagggaagaa taagacagca     840
atacacactt acttctcttc agttttcctt ggtggagtgg atagtctagt cgacttgatg     900
aacaagagtt ttcctgagtt gggtattaaa aaaacggatt gcagacaatt gagctggatt     960
gatactatca tcttctatag tggtgttgta aattacgaca ctgataattt taacaaggaa    1020
attttgcttg atagatccgc tgggcagaac ggtgctttca agattaagtt agactacgtt    1080
aagaaaccaa ttccagaatc tgtatttgtc caaattttgg aaaaattata tgaagaagat    1140
ataggagctg ggatgtatgc gttgtaccct tacggtggta atggatgaga ttttcagaa     1200
tcagcaattc cattccctca tcgagctgga atcttgtatg agttatggta catatgtagt    1260
tgggagaagc aagaagataa cgaaaagcat ctaaactgga ttagaaatat ttataacttc    1320
atgactcctt atgtgtccaa aaatccaaga ttggcatatc tcaattatag agaccttgat    1380
ataggaataa atgatcccaa gaatccaaat aattacacac aagcacgtat ttgggggtgag   1440
aagtattttg gtaaaaattt tgacaggcta gtaaaagtga aaaccctggt tgatcccaat    1500
aacttttta gaaacgaaca aagcatccca cctctaccac ggcatcgtca ttaa           1554
```

<210> SEQ ID NO 23
<211> LENGTH: 517
<212> TYPE: PRT
<213> ORGANISM: Cannabis sativa

<400> SEQUENCE: 23

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190
```

-continued

```
Lys Ser Met Gly Glu Asp Leu Phe Trp Ala Leu Arg Gly Gly Ala
            195                 200                 205
Glu Ser Phe Gly Ile Ile Val Ala Trp Lys Ile Arg Leu Val Ala Val
        210                 215                 220
Pro Lys Ser Thr Met Phe Ser Val Lys Lys Ile Met Glu Ile His Glu
225                 230                 235                 240
Leu Val Lys Leu Val Asn Lys Trp Gln Asn Ile Ala Tyr Lys Tyr Asp
                245                 250                 255
Lys Asp Leu Leu Met Thr His Phe Ile Thr Arg Asn Ile Thr Asp
            260                 265                 270
Asn Gln Gly Lys Asn Lys Thr Ala Ile His Thr Tyr Phe Ser Ser Val
        275                 280                 285
Phe Leu Gly Gly Val Asp Ser Leu Val Asp Leu Met Asn Lys Ser Phe
    290                 295                 300
Pro Glu Leu Gly Ile Lys Lys Thr Asp Cys Arg Gln Leu Ser Trp Ile
305                 310                 315                 320
Asp Thr Ile Ile Phe Tyr Ser Gly Val Val Asn Tyr Asp Thr Asp Asn
                325                 330                 335
Phe Asn Lys Glu Ile Leu Leu Asp Arg Ser Ala Gly Gln Asn Gly Ala
            340                 345                 350
Phe Lys Ile Lys Leu Asp Tyr Val Lys Lys Pro Ile Pro Glu Ser Val
        355                 360                 365
Phe Val Gln Ile Leu Glu Lys Leu Tyr Glu Glu Asp Ile Gly Ala Gly
    370                 375                 380
Met Tyr Ala Leu Tyr Pro Tyr Gly Gly Ile Met Asp Glu Ile Ser Glu
385                 390                 395                 400
Ser Ala Ile Pro Phe Pro His Arg Ala Gly Ile Leu Tyr Glu Leu Trp
                405                 410                 415
Tyr Ile Cys Ser Trp Glu Lys Gln Glu Asp Asn Glu Lys His Leu Asn
            420                 425                 430
Trp Ile Arg Asn Ile Tyr Asn Phe Met Thr Pro Tyr Val Ser Lys Asn
        435                 440                 445
Pro Arg Leu Ala Tyr Leu Asn Tyr Arg Asp Leu Asp Ile Gly Ile Asn
    450                 455                 460
Asp Pro Lys Asn Pro Asn Asn Tyr Thr Gln Ala Arg Ile Trp Gly Glu
465                 470                 475                 480
Lys Tyr Phe Gly Lys Asn Phe Asp Arg Leu Val Lys Val Lys Thr Leu
                485                 490                 495
Val Asp Pro Asn Asn Phe Phe Arg Asn Glu Gln Ser Ile Pro Pro Leu
            500                 505                 510
Pro Arg His Arg His
        515
```

<210> SEQ ID NO 24
<211> LENGTH: 1377
<212> TYPE: DNA
<213> ORGANISM: Stevia rebaudiana

<400> SEQUENCE: 24

```
atggaaaata aaaccgaaac caccgtccgc cgtcgtcgcc gtatcattct gttcccggtc      60
ccgttccagg gccacatcaa cccgattctg caactggcga acgtgctgta ttcgaaaggt     120
ttcagcatca ccatcttcca tacgaacttc aacaagccga agaccagcaa ttacccgcac     180
tttacgttcc gttttattct ggataacgac ccgcaggatg aacgcatctc taatctgccg     240
```

| | | |
|---|---|---|
| acccacggcc cgctggcggg tatgcgtatt ccgattatca acgaacacgg cgcagatgaa | 300 |
| ctgcgtcgcg aactggaact gctgatgctg gccagcgaag aagatgaaga agtttcttgc | 360 |
| ctgatcaccg acgcactgtg gtattttgcc cagtctgttg cagatagtct gaacctgcgt | 420 |
| cgcctggtcc tgatgaccag cagcctgttc aattttcatg cccacgttag tctgccgcag | 480 |
| ttcgatgaac tgggttatct ggacccggat gacaaaaccc gcctggaaga acaggcgagc | 540 |
| ggctttccga tgctgaaagt caaggatatt aagtcagcgt actcgaactg gcagattctg | 600 |
| aaagaaatcc tgggtaaaat gattaagcaa accaaagcaa gttccggcgt catctggaat | 660 |
| agtttcaaag aactggaaga atccgaactg gaaacggtga ttcgtgaaat cccggctccg | 720 |
| agttttctga ttccgctgcc gaagcatctg accgcgagca gcagcagcct gctggatcac | 780 |
| gaccgcacgg tgtttcagtg gctggatcag caaccgccga gttccgtgct gtatgttagc | 840 |
| ttcggtagta cctcggaagt ggatgaaaag gactttctgg aaatcgctcg tggcctggtt | 900 |
| gatagcaaac aatctttcct gtgggtggtt cgcccgggtt ttgtgaaggg ctctacgtgg | 960 |
| gttgaaccgc tgccggacgg cttcctgggt gaacgtggcc gcattgtcaa atgggtgccg | 1020 |
| cagcaagaag tgctggcgca tggcgcgatt ggcgcgtttt ggacccactc cggttggaac | 1080 |
| tcaacgctgg aatcggtttg tgaaggtgtc ccgatgattt tctcagattt tggcctggac | 1140 |
| cagccgctga atgcacgtta tatgtcggat gttctgaaag tcggtgtgta cctggaaaac | 1200 |
| ggttgggaac gcggcgaaat tgcgaatgcc atccgtcgcg ttatggtcga tgaagaaggc | 1260 |
| gaatacattc gtcagaatgc tcgcgtcctg aaacaaaagg cggacgtgag cctgatgaaa | 1320 |
| ggcggttcat cgtatgaaag tctggaatcc ctggtttcat acatcagctc tctgtaa | 1377 |

<210> SEQ ID NO 25
<211> LENGTH: 458
<212> TYPE: PRT
<213> ORGANISM: Stevia rebaudiana

<400> SEQUENCE: 25

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175
```

```
Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 26
<211> LENGTH: 485
<212> TYPE: PRT
<213> ORGANISM: Nicotiana tabacum

<400> SEQUENCE: 26

Met Gly Ser Ile Gly Ala Glu Leu Thr Lys Pro His Ala Val Cys Ile
1               5                   10                  15

Pro Tyr Pro Ala Gln Gly His Ile Asn Pro Met Leu Lys Leu Ala Lys
                20                  25                  30

Ile Leu His His Lys Gly Phe His Ile Thr Phe Val Asn Thr Glu Phe
            35                  40                  45

Asn His Arg Arg Leu Leu Lys Ser Arg Gly Pro Asp Ser Leu Lys Gly
        50                  55                  60

Leu Ser Ser Phe Arg Phe Glu Thr Ile Pro Asp Gly Leu Pro Pro Cys
65                  70                  75                  80

Glu Ala Asp Ala Thr Gln Asp Ile Pro Ser Leu Cys Glu Ser Thr Thr
                85                  90                  95
```

Asn Thr Cys Leu Ala Pro Phe Arg Asp Leu Leu Ala Lys Leu Asn Asp
            100                 105                 110

Thr Asn Thr Ser Asn Val Pro Pro Val Ser Cys Ile Val Ser Asp Gly
        115                 120                 125

Val Met Ser Phe Thr Leu Ala Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Cys Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Gly
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Phe Glu Thr Leu Glu
225                 230                 235                 240

Ala Glu Val Leu Glu Ser Leu Arg Asn Leu Leu Pro Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Pro Glu Cys Ile Gln
        275                 280                 285

Trp Leu Asp Thr Lys Glu Pro Asn Ser Val Val Tyr Val Asn Phe Gly
    290                 295                 300

Ser Ile Thr Val Met Thr Pro Asn Gln Leu Ile Glu Phe Ala Trp Gly
305                 310                 315                 320

Leu Ala Asn Ser Gln Gln Thr Phe Leu Trp Ile Ile Arg Pro Asp Ile
                325                 330                 335

Val Ser Gly Asp Ala Ser Ile Leu Pro Pro Glu Phe Val Glu Glu Thr
            340                 345                 350

Lys Asn Arg Gly Met Leu Ala Ser Trp Cys Ser Gln Glu Glu Val Leu
        355                 360                 365

Ser His Pro Ala Ile Val Gly Phe Leu Thr His Ser Gly Trp Asn Ser
    370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
                405                 410                 415

Val Gly Met Glu Ile Asp Ser Asp Val Lys Arg Asp Glu Val Glu Ser
            420                 425                 430

Leu Val Arg Glu Leu Met Val Gly Gly Lys Gly Lys Met Lys Lys
        435                 440                 445

Lys Ala Met Glu Trp Lys Glu Leu Ala Glu Ala Ser Ala Lys Glu His
    450                 455                 460

Ser Gly Ser Ser Tyr Val Asn Ile Glu Lys Leu Val Asn Asp Ile Leu
465                 470                 475                 480

Leu Ser Ser Lys His
                485

<210> SEQ ID NO 27
<211> LENGTH: 1458

<212> TYPE: DNA
<213> ORGANISM: Nicotiana tabacum

<400> SEQUENCE: 27

```
atgggttcca ttggtgctga attaacaaag ccacatgcag tttgcatacc atatcccgcc      60
caaggccata ttaaccccat gttaaagcta gccaaaatcc ttcatcacaa aggctttcac     120
atcacttttg tcaatactga atttaaccac cgacgtctcc ttaaatctcg tggccctgat     180
tctctcaagg gtctttcttc tttccgtttt gagaccattc ctgatggact tccgccatgt     240
gaggcagatg ccacacaaga tataccttct tgtgtgaat ctacaaccaa tacttgcttg      300
gctccttta gggatcttct tgcgaaactc aatgataca acacatctaa cgtgccaccc        360
gtttcgtgca tcgtctcgga tggtgtcatg agcttcacct tagccgctgc acaagaattg     420
ggagtccctg aagttctgtt ttggaccact agtgcttgtg gtttcttagg ttacatgcat     480
tactgcaagg ttattgaaaa aggatatgct ccacttaaag atgcgagtga cttgacaaat     540
ggatacctag acaacatt ggattttata ccaggcatga aagacgtacg tttaagggat        600
cttccaagtt tcttgagaac tacaaatcca gatgaattca tgatcaaatt tgtcctccaa     660
gaaacagaga gagcaagaaa ggcttctgca attatcctca acacatttga aacactagag     720
gctgaagttc ttgaatcgct ccgaaatctt cttcctccag tctaccccat agggcccttg     780
cattttctag tgaaacatgt tgatgatgag aatttgaagg gacttagatc cagcctttgg    840
aaagaggaac cagagtgtat acaatggctt gataccaaag aaccaaattc tgttgtttat     900
gttaactttg gaagcattac tgttatgact cctaatcagc ttattgagtt tgcttgggga     960
cttgcaaaca gccagcaaac attcttatgg atcataagac ctgatattgt ttcaggtgat    1020
gcatcgattc ttccacccga attcgtggaa gaaacgaaga acagaggtat gcttgctagt    1080
tggtgttcac aagaagaagt acttagtcac cctgcaatag taggattctt gactcacagt    1140
ggatggaatt cgacactcga agtataagc agtggggtgc ctatgatttg ctggccattt     1200
ttcgctgaac agcaaacaaa ttgttggttt tccgtcacta atgggatgt tggaatggag      1260
attgacagtg atgtgaagag agatgaagtg gaaagccttg taaggaatt gatggttggg     1320
ggaaaaggca aaaagatgaa gaaaaaggca atggaatgga aggaattggc tgaagcatct    1380
gctaaagaac attcagggtc atcttatgtg aacattgaaa agttggtcaa tgatattctt    1440
ctttcatcca aacattaa                                                   1458
```

<210> SEQ ID NO 28
<211> LENGTH: 485
<212> TYPE: PRT
<213> ORGANISM: Nicotiana tabacum

<400> SEQUENCE: 28

```
Met Gly Ser Ile Gly Ala Glu Phe Thr Lys Pro His Ala Val Cys Ile
1               5                   10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Leu Lys Ser Arg Gly Pro Asp Ser Leu Lys Gly
    50                  55                  60

Leu Ser Ser Phe Arg Phe Glu Thr Ile Pro Asp Gly Leu Pro Pro Cys
65                  70                  75                  80

Asp Ala Asp Ala Thr Gln Asp Ile Pro Ser Leu Cys Glu Ser Thr Thr
```

```
            85                  90                  95
Asn Thr Cys Leu Gly Pro Phe Arg Asp Leu Leu Ala Lys Leu Asn Asp
            100                 105                 110

Thr Asn Thr Ser Asn Val Pro Pro Val Ser Cys Ile Ile Ser Asp Gly
            115                 120                 125

Val Met Ser Phe Thr Leu Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Tyr Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Cys
            180                 185                 190

Met Lys Asp Val Arg Leu Arg Asp Leu Pro Ser Phe Leu Arg Thr Thr
            195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Tyr Glu Thr Leu Glu
225                 230                 235                 240

Ala Glu Val Leu Glu Ser Leu Arg Asn Leu Leu Pro Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Pro Glu Cys Ile Gln
            275                 280                 285

Trp Leu Asp Thr Lys Glu Pro Asn Ser Val Val Tyr Val Asn Phe Gly
    290                 295                 300

Ser Ile Thr Val Met Thr Pro Asn Gln Leu Ile Glu Phe Ala Trp Gly
305                 310                 315                 320

Leu Ala Asn Ser Gln Gln Ser Phe Leu Trp Ile Ile Arg Pro Asp Ile
                325                 330                 335

Val Ser Gly Asp Ala Ser Ile Leu Pro Pro Glu Phe Val Glu Glu Thr
            340                 345                 350

Lys Lys Arg Gly Met Leu Ala Ser Trp Cys Ser Gln Glu Glu Val Leu
            355                 360                 365

Ser His Pro Ala Ile Gly Gly Phe Leu Thr His Ser Gly Trp Asn Ser
    370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
                405                 410                 415

Val Gly Met Glu Ile Asp Cys Asp Val Lys Arg Asp Glu Val Glu Ser
            420                 425                 430

Leu Val Arg Glu Leu Met Val Gly Gly Lys Gly Lys Lys Met Lys Lys
            435                 440                 445

Lys Ala Met Glu Trp Lys Glu Leu Ala Glu Ala Ser Ala Lys Glu His
    450                 455                 460

Ser Gly Ser Ser Tyr Val Asn Ile Glu Lys Val Val Asn Asp Ile Leu
465                 470                 475                 480

Leu Ser Ser Lys His
            485

<210> SEQ ID NO 29
```

<211> LENGTH: 1458
<212> TYPE: DNA
<213> ORGANISM: Nicotiana tabacum

<400> SEQUENCE: 29

| | | | | | |
|---|---|---|---|---|---|
| atgggttcca | ttggtgctga | atttacaaag | ccacatgcag | tttgcatacc | atatcccgcc | 60 |
| caaggccata | ttaaccccat | gttaaagcta | gccaaaatcc | ttcatcacaa | aggctttcac | 120 |
| atcacttttg | tcaatactga | atttaaccac | agacgtctgc | ttaaatctcg | tggccctgat | 180 |
| tctctcaagg | gtctttcttc | tttccgtttt | gagacaattc | ctgatggact | tccgccatgt | 240 |
| gatgcagatg | ccacacaaga | tataccttct | tgtgtgaat | ctacaaccaa | tacttgcttg | 300 |
| ggtccttta | gggatcttct | tgcgaaactc | aatgatacta | acacatctaa | cgtgccaccc | 360 |
| gtttcgtgca | tcatctcaga | tggtgtcatg | agcttcacct | tagccgctgc | acaagaattg | 420 |
| ggagtccctg | aagttctgtt | ttggaccact | agtgcttgtg | gtttcttagg | ttacatgcat | 480 |
| tattacaagg | ttattgaaaa | aggatacgct | ccacttaaag | atgcgagtga | cttgacaaat | 540 |
| ggatacctag | agacaacatt | ggattttata | ccatgcatga | agacgtacg | tttaagggat | 600 |
| cttccaagtt | tcttgagaac | tacaaatcca | gatgaattca | tgatcaaatt | tgtcctccaa | 660 |
| gaaacagaga | gagcaagaaa | ggcttctgca | attatcctca | acacatatga | aacactagag | 720 |
| gctgaagttc | ttgaatcgct | ccgaaatctt | cttcctccag | tctacccat | tgggcccttg | 780 |
| cattttctag | tgaaacatgt | tgatgatgag | aatttgaagg | gacttagatc | cagccttgg | 840 |
| aaagaggaac | cagagtgtat | acaatggctt | gataccaaag | aaccaaattc | tgttgtttat | 900 |
| gttaactttg | gaagcattac | tgttatgact | cctaatcaac | ttattgaatt | tgcttgggga | 960 |
| cttgcaaaca | gccaacaatc | attcttatgg | atcataagac | ctgatattgt | ttcaggtgat | 1020 |
| gcatcgattc | ttccccccga | attcgtggaa | gaaacgaaga | agagaggtat | gcttgctagt | 1080 |
| tggtgttcac | aagaagaagt | acttagtcac | cctgcaatag | gaggattctt | gactcacagt | 1140 |
| ggatggaatt | cgacactcga | aagtataagc | agtggggtgc | ctatgatttg | ctggccatt | 1200 |
| ttcgctgaac | agcaaacaaa | ttgttggttt | tccgtcacta | aatgggatgt | tggaatggag | 1260 |
| attgactgtg | atgtgaagag | ggatgaagtg | gaaagccttg | taagggaatt | gatggttggg | 1320 |
| ggaaaaggca | aaaagatgaa | gaaaaaggca | atggaatgga | aggaattggc | tgaagcatct | 1380 |
| gctaaagaac | attcagggtc | atcttatgtg | aacattgaga | aggtggtcaa | tgatattctt | 1440 |
| ctttcgtcca | aacattaa | | | | | 1458 |

<210> SEQ ID NO 30
<211> LENGTH: 496
<212> TYPE: PRT
<213> ORGANISM: Nicotiana tabacum

<400> SEQUENCE: 30

Met Ala Thr Gln Val His Lys Leu His Phe Ile Leu Phe Pro Leu Met
1               5                   10                  15

Ala Pro Gly His Met Ile Pro Met Ile Asp Ile Ala Lys Leu Leu Ala
            20                  25                  30

Asn Arg Gly Val Ile Thr Thr Ile Ile Thr Thr Pro Val Asn Ala Asn
        35                  40                  45

Arg Phe Ser Ser Thr Ile Thr Arg Ala Ile Lys Ser Gly Leu Arg Ile
    50                  55                  60

Gln Ile Leu Thr Leu Lys Phe Pro Ser Val Glu Val Gly Leu Pro Glu
65                  70                  75                  80

-continued

```
Gly Cys Glu Asn Ile Asp Met Leu Pro Ser Leu Asp Leu Ala Ser Lys
                85                  90                  95

Phe Phe Ala Ala Ile Ser Met Leu Lys Gln Gln Val Glu Asn Leu Leu
            100                 105                 110

Glu Gly Ile Asn Pro Ser Pro Ser Cys Val Ile Ser Asp Met Gly Phe
        115                 120                 125

Pro Trp Thr Thr Gln Ile Ala Gln Asn Phe Asn Ile Pro Arg Ile Val
    130                 135                 140

Phe His Gly Thr Cys Cys Phe Ser Leu Leu Cys Ser Tyr Lys Ile Leu
145                 150                 155                 160

Ser Ser Asn Ile Leu Glu Asn Ile Thr Ser Asp Ser Glu Tyr Phe Val
                165                 170                 175

Val Pro Asp Leu Pro Asp Arg Val Glu Leu Thr Lys Ala Gln Val Ser
            180                 185                 190

Gly Ser Thr Lys Asn Thr Thr Ser Val Ser Ser Ser Val Leu Lys Glu
        195                 200                 205

Val Thr Glu Gln Ile Arg Leu Ala Glu Glu Ser Ser Tyr Gly Val Ile
    210                 215                 220

Val Asn Ser Phe Glu Glu Leu Glu Gln Val Tyr Glu Lys Glu Tyr Arg
225                 230                 235                 240

Lys Ala Arg Gly Lys Lys Val Trp Cys Val Gly Pro Val Ser Leu Cys
                245                 250                 255

Asn Lys Glu Ile Glu Asp Leu Val Thr Arg Gly Asn Lys Thr Ala Ile
            260                 265                 270

Asp Asn Gln Asp Cys Leu Lys Trp Leu Asp Asn Phe Glu Thr Glu Ser
        275                 280                 285

Val Val Tyr Ala Ser Leu Gly Ser Leu Ser Arg Leu Thr Leu Leu Gln
    290                 295                 300

Met Val Glu Leu Gly Leu Gly Leu Glu Glu Ser Asn Arg Pro Phe Val
305                 310                 315                 320

Trp Val Leu Gly Gly Asp Lys Leu Asn Asp Leu Glu Lys Trp Ile
                325                 330                 335

Leu Glu Asn Gly Phe Glu Gln Arg Ile Lys Glu Arg Gly Val Leu Ile
            340                 345                 350

Arg Gly Trp Ala Pro Gln Val Leu Ile Leu Ser His Pro Ala Ile Gly
        355                 360                 365

Gly Val Leu Thr His Cys Gly Trp Asn Ser Thr Leu Glu Gly Ile Ser
    370                 375                 380

Ala Gly Leu Pro Met Val Thr Trp Pro Leu Phe Ala Glu Gln Phe Cys
385                 390                 395                 400

Asn Glu Lys Leu Val Val Gln Val Leu Lys Ile Gly Val Ser Leu Gly
                405                 410                 415

Val Lys Val Pro Val Lys Trp Gly Asp Glu Glu Asn Val Gly Val Leu
            420                 425                 430

Val Lys Lys Asp Asp Val Lys Lys Ala Leu Asp Lys Leu Met Asp Glu
        435                 440                 445

Gly Glu Glu Gly Gln Val Arg Arg Thr Lys Ala Lys Glu Leu Gly Glu
    450                 455                 460

Leu Ala Lys Lys Ala Phe Gly Glu Gly Ser Ser Tyr Val Asn Leu
465                 470                 475                 480

Thr Ser Leu Ile Glu Asp Ile Ile Glu Gln Gln Asn His Lys Glu Lys
                485                 490                 495
```

<210> SEQ ID NO 31
<211> LENGTH: 1491
<212> TYPE: DNA
<213> ORGANISM: Nicotiana tabacum

<400> SEQUENCE: 31

| | | | | | |
|---|---|---|---|---|---|
| atggcaactc | aagtgcacaa | acttcatttc | atactattcc | ctttaatggc | tccaggccac | 60 |
| atgattccta | tgatagacat | agctaaactt | ctagcaaatc | gcggtgtcat | taccactatc | 120 |
| atcaccactc | cagtaaacgc | caatcgtttc | agttcaacaa | ttactcgtgc | cataaaatcc | 180 |
| ggtctaagaa | tccaaattct | tacactcaaa | tttccaagtg | tagaagtagg | attaccagaa | 240 |
| ggttgcgaaa | atattgacat | gcttccttct | cttgacttgg | cttcaaagtt | ttttgctgca | 300 |
| attagtatgc | tgaaacaaca | agttgaaaat | ctcttagaag | gaataaatcc | aagtccaagt | 360 |
| tgtgttattt | cagatatggg | atttccttgg | actactcaaa | ttgcacaaaa | ttttaatatc | 420 |
| ccaagaattg | tttttcatgg | tacttgttgt | ttctcacttt | tatgttccta | taaaatactt | 480 |
| tcctccaaca | ttcttgaaaa | tataacctca | gattcagagt | attttgttgt | tcctgattta | 540 |
| cccgatagag | ttgaactaac | gaaagctcag | gtttcaggat | cgacgaaaaa | tactacttct | 600 |
| gttagttctt | ctgtattgaa | agaagttact | gagcaaatca | gattagccga | ggaatcatca | 660 |
| tatggtgtaa | ttgttaatag | ttttgaggag | ttggagcaag | tgtatgagaa | agaatatagg | 720 |
| aaagctagag | ggaaaaaagt | ttggtgtgtt | ggtcctgttt | ctttgtgtaa | taggaaaatt | 780 |
| gaagatttgg | ttacaagggg | taataaaact | gcaattgata | tcaagattg | cttgaaatgg | 840 |
| ttagataatt | ttgaaacaga | atctgtggtt | tatgcaagtc | ttggaagttt | atctcgtttg | 900 |
| acattattgc | aaatggtgga | acttggtctt | ggtttagaag | agtcaaatag | gccttttgta | 960 |
| tgggtattag | gaggaggtga | taaattaaat | gatttagaga | aatggattct | tgagaatgga | 1020 |
| tttgagcaaa | gaattaaaga | aagaggagtt | ttgattagag | gatgggctcc | tcaagtgctt | 1080 |
| atactttcac | accctgcaat | tggtggagta | ttgactcatt | gcggatggaa | ttctacattg | 1140 |
| gaaggtattt | cagcaggatt | accaatggta | acatggccac | tatttgctga | gcaattttgc | 1200 |
| aatgagaagt | tagtagtcca | agtgctaaaa | attggagtga | gcctaggtgt | gaaggtgcct | 1260 |
| gtcaaatggg | gagatgagga | aaatgttgga | gttttggtaa | aaaaggatga | tgttaagaaa | 1320 |
| gcattagaca | aactaatgga | tgaaggagaa | gaaggacaag | taagaagaac | aaaagcaaaa | 1380 |
| gagttaggag | aattggctaa | aaaggcattt | ggagaaggtg | gttcttctta | tgttaactta | 1440 |
| acatctctga | ttgaagacat | cattgagcaa | caaaatcaca | aggaaaaata | g | 1491 |

<210> SEQ ID NO 32
<211> LENGTH: 479
<212> TYPE: PRT
<213> ORGANISM: Nicotiana tabacum

<400> SEQUENCE: 32

Met Lys Thr Ala Glu Leu Val Phe Ile Pro Ala Pro Gly Met Gly His
1               5                   10                  15

Leu Val Pro Thr Val Glu Val Ala Lys Gln Leu Val Asp Arg His Glu
            20                  25                  30

Gln Leu Ser Ile Thr Val Leu Ile Met Thr Ile Pro Leu Glu Thr Asn
        35                  40                  45

Ile Pro Ser Tyr Thr Lys Ser Leu Ser Ser Asp Tyr Ser Ser Arg Ile
    50                  55                  60

Thr Leu Leu Pro Leu Ser Gln Pro Glu Thr Ser Val Thr Met Ser Ser
65                  70                  75                  80

Phe Asn Ala Ile Asn Phe Phe Glu Tyr Ile Ser Ser Tyr Lys Gly Arg
                85                  90                  95

Val Lys Asp Ala Val Ser Glu Thr Ser Phe Ser Ser Asn Ser Val
            100                 105                 110

Lys Leu Ala Gly Phe Val Ile Asp Met Phe Cys Thr Ala Met Ile Asp
        115                 120                 125

Val Ala Asn Glu Phe Gly Ile Pro Ser Tyr Val Phe Tyr Thr Ser Ser
        130                 135                 140

Ala Ala Met Leu Gly Leu Gln Leu His Phe Gln Ser Leu Ser Ile Glu
145                 150                 155                 160

Cys Ser Pro Lys Val His Asn Tyr Val Glu Pro Glu Ser Glu Val Leu
                165                 170                 175

Ile Ser Thr Tyr Met Asn Pro Val Pro Val Lys Cys Leu Pro Gly Ile
            180                 185                 190

Ile Leu Val Asn Asp Glu Ser Ser Thr Met Phe Val Asn His Ala Arg
        195                 200                 205

Arg Phe Arg Glu Thr Lys Gly Ile Met Val Asn Thr Phe Thr Glu Leu
    210                 215                 220

Glu Ser His Ala Leu Lys Ala Leu Ser Asp Asp Glu Lys Ile Pro Pro
225                 230                 235                 240

Ile Tyr Pro Val Gly Pro Ile Leu Asn Leu Glu Asn Gly Asn Glu Asp
                245                 250                 255

His Asn Gln Glu Tyr Asp Ala Ile Met Lys Trp Leu Asp Glu Lys Pro
            260                 265                 270

Asn Ser Ser Val Val Phe Leu Cys Phe Gly Ser Lys Gly Ser Phe Glu
        275                 280                 285

Glu Asp Gln Val Lys Glu Ile Ala Asn Ala Leu Glu Ser Ser Gly Tyr
    290                 295                 300

His Phe Leu Trp Ser Leu Arg Arg Pro Pro Lys Asp Lys Leu Gln
305                 310                 315                 320

Phe Pro Ser Glu Phe Glu Asn Pro Glu Glu Val Leu Pro Glu Gly Phe
                325                 330                 335

Phe Gln Arg Thr Lys Gly Arg Gly Lys Val Ile Gly Trp Ala Pro Gln
            340                 345                 350

Leu Ala Ile Leu Ser His Pro Ser Val Gly Gly Phe Val Ser His Cys
        355                 360                 365

Gly Trp Asn Ser Thr Leu Glu Ser Val Arg Ser Gly Val Pro Ile Ala
    370                 375                 380

Thr Trp Pro Leu Tyr Ala Glu Gln Gln Ser Asn Ala Phe Gln Leu Val
385                 390                 395                 400

Lys Asp Leu Gly Met Ala Val Glu Ile Lys Met Asp Tyr Arg Glu Asp
                405                 410                 415

Phe Asn Thr Arg Asn Pro Pro Leu Val Lys Ala Glu Glu Ile Glu Asp
            420                 425                 430

Gly Ile Arg Lys Leu Met Asp Ser Glu Asn Lys Ile Arg Ala Lys Val
        435                 440                 445

Thr Glu Met Lys Asp Lys Ser Arg Ala Ala Leu Leu Glu Gly Gly Ser
    450                 455                 460

Ser Tyr Val Ala Leu Gly His Phe Val Glu Thr Val Met Lys Asn
465                 470                 475

<210> SEQ ID NO 33
<211> LENGTH: 1440

<212> TYPE: DNA
<213> ORGANISM: Nicotiana tabacum

<400> SEQUENCE: 33

```
atgaagacag cagagttagt attcattcct gctcctggga tgggtcacct tgtaccaact      60
gtggaggtgg caaagcaact agtcgacaga cacgagcagc tttcgatcac agttctaatc     120
atgacaattc ctttggaaac aaatattcca tcatatacta atcactgtc ctcagactac      180
agttctcgta taacgctgct ccactctct caacctgaga cctctgttac tatgagcagt      240
tttaatgcca tcaattttt tgagtacatc tccagctaca agggtcgtgt caaagatgct      300
gttagtgaaa cctcctttag ttcgtcaaat tctgtgaaac ttgcaggatt tgtaatagac     360
atgttctgca ctgcgatgat tgatgtagcg aacgagtttg aatcccaag ttatgtgttc      420
tacacttcta gtgcagctat gcttggacta caactgcatt tcaaagtct tagcattgaa      480
tgcagtccga aagttcataa ctacgttgaa cctgaatcag aagttctgat ctcaacttac     540
atgaatccgg ttccagtcaa atgtttgccc ggaattatac tagtaaatga tgaaagtagc     600
accatgtttg tcaatcatgc acgaagattc agggagacga aggaattat ggtgaacacg      660
ttcactgagc ttgaatcaca cgctttgaaa gccctttccg atgatgaaaa atcccacca      720
atctacccag ttggacctat acttaacctt gaaaatggga tgaagatca caatcaagaa      780
tatgatgcga ttatgaagtg gcttgacgag aagcctaatt catcagtggt gttcttatgc     840
tttggaagca aggggtcttt cgaagaagat caggtgaagg aaatagcaaa tgctctagag     900
agcagtggct accacttctt gtggtcgcta aggcgaccgc caccaaaaga caagctacaa     960
ttcccaagcg aattcgagaa tccagaggaa gtcttaccag agggattctt tcaaaggact    1020
aaaggaagag gaaaggtgat aggatgggca ccccagttgg ctatttgtc tcatccttca    1080
gtaggaggat tcgtgtcgca ttgtgggtgg aattcaactc tggagagcgt tcgaagtgga    1140
gtgccgatag caacatggcc attgtatgca gagcaacaga gcaatgcatt tcaactggtg    1200
aaggatttgg gtatggcagt agagattaag atggattaca gggaagattt taatacgaga    1260
aatccaccac tggttaaagc tgaggagata aagatggaa ttaggaagct gatggattca     1320
gagaataaaa tcagggctaa ggtgacggag atgaaggaca aaagtagagc agcactgctg    1380
gagggcggat catcatatgt agctcttggg catttgttg agactgtcat gaaaaactag    1440
```

<210> SEQ ID NO 34
<211> LENGTH: 478
<212> TYPE: PRT
<213> ORGANISM: Nicotiana tabacum

<400> SEQUENCE: 34

```
Met Lys Thr Thr Glu Leu Val Phe Ile Pro Ala Pro Gly Met Gly His
1               5                   10                  15

Leu Val Pro Thr Val Glu Val Ala Lys Gln Leu Val Asp Arg Asp Glu
            20                  25                  30

Gln Leu Ser Ile Thr Val Leu Ile Met Thr Leu Pro Leu Glu Thr Asn
        35                  40                  45

Ile Pro Ser Tyr Thr Lys Ser Leu Ser Ser Asp Tyr Ser Ser Arg Ile
    50                  55                  60

Thr Leu Leu Gln Leu Ser Gln Pro Glu Thr Ser Val Ser Met Ser Ser
65                  70                  75                  80

Phe Asn Ala Ile Asn Phe Phe Glu Tyr Ile Ser Ser Tyr Lys Asp Arg
                85                  90                  95
```

Val Lys Asp Ala Val Asn Glu Thr Phe Ser Ser Ser Ser Val Lys
            100                 105                 110

Leu Lys Gly Phe Val Ile Asp Met Phe Cys Thr Ala Met Ile Asp Val
        115                 120                 125

Ala Asn Glu Phe Gly Ile Pro Ser Tyr Val Phe Tyr Thr Ser Asn Ala
130                 135                 140

Ala Met Leu Gly Leu Gln Leu His Phe Gln Ser Leu Ser Ile Glu Tyr
145                 150                 155                 160

Ser Pro Lys Val His Asn Tyr Leu Asp Pro Glu Ser Glu Val Ala Ile
                165                 170                 175

Ser Thr Tyr Ile Asn Pro Ile Pro Val Lys Cys Leu Pro Gly Ile Ile
            180                 185                 190

Leu Asp Asn Asp Lys Ser Gly Thr Met Phe Val Asn His Ala Arg Arg
        195                 200                 205

Phe Arg Glu Thr Lys Gly Ile Met Val Asn Thr Phe Ala Glu Leu Glu
210                 215                 220

Ser His Ala Leu Lys Ala Leu Ser Asp Asp Glu Lys Ile Pro Pro Ile
225                 230                 235                 240

Tyr Pro Val Gly Pro Ile Leu Asn Leu Gly Asp Gly Asn Glu Asp His
                245                 250                 255

Asn Gln Glu Tyr Asp Met Ile Met Lys Trp Leu Asp Glu Gln Pro His
            260                 265                 270

Ser Ser Val Val Phe Leu Cys Phe Gly Ser Lys Gly Ser Phe Glu Glu
        275                 280                 285

Asp Gln Val Lys Glu Ile Ala Asn Ala Leu Glu Arg Ser Gly Asn Arg
290                 295                 300

Phe Leu Trp Ser Leu Arg Arg Pro Pro Lys Asp Thr Leu Gln Phe
305                 310                 315                 320

Pro Ser Glu Phe Glu Asn Pro Glu Glu Val Leu Pro Val Gly Phe Phe
                325                 330                 335

Gln Arg Thr Lys Gly Arg Gly Lys Val Ile Gly Trp Ala Pro Gln Leu
            340                 345                 350

Ala Ile Leu Ser His Pro Ala Val Gly Gly Phe Val Ser His Cys Gly
        355                 360                 365

Trp Asn Ser Thr Leu Glu Ser Val Arg Ser Gly Val Pro Ile Ala Thr
370                 375                 380

Trp Pro Leu Tyr Ala Glu Gln Gln Ser Asn Ala Phe Gln Leu Val Lys
385                 390                 395                 400

Asp Leu Gly Met Ala Val Glu Ile Lys Met Asp Tyr Arg Glu Asp Phe
                405                 410                 415

Asn Lys Thr Asn Pro Pro Leu Val Lys Ala Glu Glu Ile Glu Asp Gly
            420                 425                 430

Ile Arg Lys Leu Met Asp Ser Glu Asn Lys Ile Arg Ala Lys Val Met
        435                 440                 445

Glu Met Lys Asp Lys Ser Arg Ala Ala Leu Leu Glu Gly Gly Ser Ser
450                 455                 460

Tyr Val Ala Leu Gly His Phe Val Glu Thr Val Met Lys Asn
465                 470                 475

<210> SEQ ID NO 35
<211> LENGTH: 1437
<212> TYPE: DNA
<213> ORGANISM: Nicotiana tabacum

<400> SEQUENCE: 35

```
atgaagacaa cagagttagt attcattcct gctcctggca tgggtcacct tgtacccact      60
gtggaggtgg caaagcaact agtcgacaga gacgaacagc tttcaatcac agttctcatc     120
atgacgcttc ctttggaaac aaatattcca tcatatacta aatcactgtc ctcagactac     180
agttctcgta taacgctgct tcaactttct caacctgaga cctctgttag tatgagcagt     240
tttaatgcca tcattttttt tgagtacatc tccagctaca aggatcgtgt caaagatgct     300
gttaatgaaa cctttagttc gtcaagttct gtgaaactca aaggatttgt aatagacatg     360
ttctgcactg cgatgattga tgtggcgaac gagtttggaa tcccaagtta tgtcttctac     420
acttctaatg cagctatgct tggactccaa ctccattttc aaagtcttag tattgaatac     480
agtccgaaag ttcataatta cctagaccct gaatcagaag tagcgatctc aacttacatt     540
aatccgattc cagtcaaatg tttgcccggg attatactag acaatgataa agtggcacc      600
atgttcgtca atcatgcacg aagattcagg gagacgaaag gaattatggt gaacacattc     660
gctgagcttg aatcacacgc tttgaaagcc ctttccgatg atgagaaaat cccaccaatc     720
tacccagttg ggcctatact taaccttgga gatgggaatg aagatcacaa tcaagaatat     780
gatatgatta tgaagtggct cgacgagcag cctcattcat cagtggtgtt cctatgcttt     840
ggaagcaagg gatctttcga agaagatcaa gtgaaggaaa tagcaaatgc tctagagaga     900
agtggtaacc ggttcttgtg gtcgctaaga cgaccgccac caaaagacac gctacaattc     960
ccaagcgaat tcgagaatcc agaggaagtc ttgccggtgg gattctttca aaggactaaa    1020
ggaagaggaa aggtgatagg atgggcaccc cagttggcta ttttgtctca tcctgcagta    1080
ggaggattcg tgtcgcattg tgggtggaat tcaacttttgg agagtgttcg tagtggagta    1140
ccgatagcaa catggccatt gtatgcagag caacagagca atgcatttca actggtgaag    1200
gatttgggga tggcagtgga gattaagatg gattacaggg aagattttaa taagacaaat    1260
ccaccactgg ttaaagctga ggagataaa gatggaatta ggaagctgat ggattcagag    1320
aataaaatca gggctaaggt gatggagatg aaggacaaaa gtagagcagc gttattagaa    1380
ggcggatcat catatgtagc tctcgggcat tttgttgaga ctgtcatgaa aaactaa      1437
```

<210> SEQ ID NO 36
<211> LENGTH: 482
<212> TYPE: PRT
<213> ORGANISM: Nicotiana tabacum

<400> SEQUENCE: 36

Met Lys Glu Thr Lys Lys Ile Glu Leu Val Phe Ile Pro Ser Pro Gly
1               5                   10                  15

Ile Gly His Leu Val Ser Thr Val Glu Met Ala Lys Leu Leu Ile Ala
            20                  25                  30

Arg Glu Glu Gln Leu Ser Ile Thr Val Leu Ile Ile Gln Trp Pro Asn
        35                  40                  45

Asp Lys Lys Leu Asp Ser Tyr Ile Gln Ser Val Ala Asn Phe Ser Ser
    50                  55                  60

Arg Leu Lys Phe Ile Arg Leu Pro Gln Asp Asp Ser Ile Met Gln Leu
65                  70                  75                  80

Leu Lys Ser Asn Ile Phe Thr Thr Phe Ile Ala Ser His Lys Pro Ala
                85                  90                  95

Val Arg Asp Ala Val Ala Asp Ile Leu Lys Ser Glu Ser Asn Asn Thr
            100                 105                 110

Leu Ala Gly Ile Val Ile Asp Leu Phe Cys Thr Ser Met Ile Asp Val

```
                115                 120                 125
Ala Asn Glu Phe Glu Leu Pro Thr Tyr Val Phe Tyr Thr Ser Gly Ala
130                 135                 140

Ala Thr Leu Gly Leu His Tyr His Ile Gln Asn Leu Arg Asp Glu Phe
145                 150                 155                 160

Asn Lys Asp Ile Thr Lys Tyr Lys Asp Glu Pro Glu Lys Leu Ser
                165                 170                 175

Ile Ala Thr Tyr Leu Asn Pro Phe Pro Ala Lys Cys Leu Pro Ser Val
                180                 185                 190

Ala Leu Asp Lys Glu Gly Gly Ser Thr Met Phe Leu Asp Leu Ala Lys
                195                 200                 205

Arg Phe Arg Glu Thr Lys Gly Ile Met Ile Asn Thr Phe Leu Glu Leu
                210                 215                 220

Glu Ser Tyr Ala Leu Asn Ser Leu Ser Arg Asp Lys Asn Leu Pro Pro
225                 230                 235                 240

Ile Tyr Pro Val Gly Pro Val Leu Asn Leu Asn Asn Val Glu Gly Asp
                245                 250                 255

Asn Leu Gly Ser Ser Asp Gln Asn Thr Met Lys Trp Leu Asp Asp Gln
                260                 265                 270

Pro Ala Ser Ser Val Val Phe Leu Cys Phe Gly Ser Gly Gly Ser Phe
                275                 280                 285

Glu Lys His Gln Val Lys Glu Ile Ala Tyr Ala Leu Glu Ser Ser Gly
                290                 295                 300

Cys Arg Phe Leu Trp Ser Leu Arg Arg Pro Thr Glu Asp Ala Arg
305                 310                 315                 320

Phe Pro Ser Asn Tyr Glu Asn Leu Glu Glu Ile Leu Pro Glu Gly Phe
                325                 330                 335

Leu Glu Arg Thr Lys Gly Ile Gly Lys Val Ile Gly Trp Ala Pro Gln
                340                 345                 350

Leu Ala Ile Leu Ser His Lys Ser Thr Gly Gly Phe Val Ser His Cys
                355                 360                 365

Gly Trp Asn Ser Thr Leu Glu Ser Thr Tyr Phe Gly Val Pro Ile Ala
                370                 375                 380

Thr Trp Pro Met Tyr Ala Glu Gln Gln Ala Asn Ala Phe Gln Leu Val
385                 390                 395                 400

Lys Asp Leu Arg Met Gly Val Glu Ile Lys Met Asp Tyr Arg Lys Asp
                405                 410                 415

Met Lys Val Met Gly Lys Glu Val Ile Val Lys Ala Glu Glu Ile Glu
                420                 425                 430

Lys Ala Ile Arg Glu Ile Met Asp Ser Glu Ser Glu Ile Arg Val Lys
                435                 440                 445

Val Lys Glu Met Lys Glu Lys Ser Arg Ala Ala Gln Met Glu Gly Gly
                450                 455                 460

Ser Ser Tyr Thr Ser Ile Gly Gly Phe Ile Gln Ile Ile Met Glu Asn
465                 470                 475                 480

Ser Gln

<210> SEQ ID NO 37
<211> LENGTH: 1449
<212> TYPE: DNA
<213> ORGANISM: Nicotiana tabacum

<400> SEQUENCE: 37
atgaaagaaa ccaagaaaat agagttagtc ttcattcctt caccaggaat tggccattta     60
```

```
gtatccacag ttgaaatggc aaagcttctt atagctagag aagagcagct atctatcaca    120
gtcctcatca tccaatggcc taacgacaag aagctcgatt cttatatcca atcagtcgcc    180
aatttcagct cgcgtttgaa attcattcga ctccctcagg atgattccat tatgcagcta    240
ctcaaaagca acattttcac cacgtttatt gccagtcata agcctgcagt tagagatgct    300
gttgctgata ttctcaagtc agaatcaaat aatacgctag caggtattgt tatcgacttg    360
ttctgcacct caatgataga cgtggccaat gagttcgagc taccaaccta tgttttctac    420
acgtctggtg cagcaaccct tggtcttcat tatcatatac agaatctcag ggatgaattt    480
aacaaagata ttaccaagta caaagacgaa cctgaagaaa aactctctat agcaacatat    540
ctcaatccat ttccagcaaa atgtttgccg tctgtagcct tagacaaaga aggtggttca    600
acaatgtttc ttgatctcgc aaaaaggttt cgagaaacca aagtattat  gataaacaca    660 tttctagagc tcgaatccta tgcattaaac tcgctctcac gagacaagaa tcttccacct    720
atataccctg tcggaccagt attgaacctt aacaatgttg aaggtgacaa cttaggttca    780
tctgaccaga atactatgaa atggttagat gatcagcccg cttcatctgt agtgttcctt    840
tgttttggta gtggtggaag ctttgaaaaa catcaagtta aggaaatagc ctatgctctg    900
gagagcagtg ggtgtcggtt tttgtggtcg ttaaggcgac caccaaccga agatgcaaga    960
tttccaagca actatgaaaa tcttgaagaa attttgccag aaggattctt ggaaagaaca   1020
aaagggattg gaaaagtgat aggatgggca cctcagttgg cgattttgtc acataaatcg   1080
acggggggat ttgtgtcgca ctgtggatgg aattcgactt tggaaagtac atattttgga   1140
gtgccaatag caacctggcc aatgtacgcg gagcaacaag cgaatgcatt tcaattggtt   1200
aaggatttga gaatgggagt tgagattaag atggattata ggaaggatat gaaagtgatg   1260
ggcaaagaag ttatagtgaa agctgaggag attgagaaag caataagaga aattatggat   1320
tccgagagtg aaattcgggt gaaggtgaaa gagatgaagg agaagagcag agcagcacaa   1380
atggaaggtg gctcttctta cacttctatt ggaggtttca tccaaattat catggagaat   1440
tctcaataa                                                            1449
```

<210> SEQ ID NO 38
<211> LENGTH: 470
<212> TYPE: PRT
<213> ORGANISM: Nicotiana tabacum

<400> SEQUENCE: 38

Met Val Gln Pro His Val Leu Leu Val Thr Phe Pro Ala Gln Gly His
1               5                  10                  15

Ile Asn Pro Cys Leu Gln Phe Ala Lys Arg Leu Ile Arg Met Gly Ile
            20                  25                  30

Glu Val Thr Phe Ala Thr Ser Val Phe Ala His Arg Arg Met Ala Lys
        35                  40                  45

Thr Thr Thr Ser Thr Leu Ser Lys Gly Leu Asn Phe Ala Ala Phe Ser
    50                  55                  60

Asp Gly Tyr Asp Asp Gly Phe Lys Ala Asp Glu His Asp Ser Gln His
65                  70                  75                  80

Tyr Met Ser Glu Ile Lys Ser Arg Gly Ser Lys Thr Leu Lys Asp Ile
                85                  90                  95

Ile Leu Lys Ser Ser Asp Glu Gly Arg Pro Val Thr Ser Leu Val Tyr
            100                 105                 110

Ser Leu Leu Leu Pro Trp Ala Ala Lys Val Ala Arg Glu Phe His Ile

```
            115                 120                 125
Pro Cys Ala Leu Leu Trp Ile Gln Pro Ala Thr Val Leu Asp Ile Tyr
    130                 135                 140

Tyr Tyr Tyr Phe Asn Gly Tyr Glu Asp Ala Ile Lys Gly Ser Thr Asn
145                 150                 155                 160

Asp Pro Asn Trp Cys Ile Gln Leu Pro Arg Leu Pro Leu Leu Lys Ser
                165                 170                 175

Gln Asp Leu Pro Ser Phe Leu Leu Ser Ser Ser Asn Glu Glu Lys Tyr
            180                 185                 190

Ser Phe Ala Leu Pro Thr Phe Lys Glu Gln Leu Asp Thr Leu Asp Val
        195                 200                 205

Glu Glu Asn Pro Lys Val Leu Val Asn Thr Phe Asp Ala Leu Glu Pro
    210                 215                 220

Lys Glu Leu Lys Ala Ile Glu Lys Tyr Asn Leu Ile Gly Ile Gly Pro
225                 230                 235                 240

Leu Ile Pro Ser Thr Phe Leu Asp Gly Lys Asp Pro Leu Asp Ser Ser
                245                 250                 255

Phe Gly Gly Asp Leu Phe Gln Lys Ser Asn Asp Tyr Ile Glu Trp Leu
            260                 265                 270

Asn Ser Lys Ala Asn Ser Ser Val Val Tyr Ile Ser Phe Gly Ser Leu
        275                 280                 285

Leu Asn Leu Ser Lys Asn Gln Lys Glu Ile Ala Lys Gly Leu Ile
    290                 295                 300

Glu Ile Lys Lys Pro Phe Leu Trp Val Ile Arg Asp Gln Glu Asn Gly
305                 310                 315                 320

Lys Gly Asp Glu Lys Glu Lys Leu Ser Cys Met Met Glu Leu Glu
                325                 330                 335

Lys Gln Gly Lys Ile Val Pro Trp Cys Ser Gln Leu Glu Val Leu Thr
            340                 345                 350

His Pro Ser Ile Gly Cys Phe Val Ser His Cys Gly Trp Asn Ser Thr
        355                 360                 365

Leu Glu Ser Leu Ser Ser Gly Val Ser Val Ala Phe Pro His Trp
    370                 375                 380

Thr Asp Gln Gly Thr Asn Ala Lys Leu Ile Glu Asp Val Trp Lys Thr
385                 390                 395                 400

Gly Val Arg Leu Lys Lys Asn Glu Asp Gly Val Val Glu Ser Glu Glu
                405                 410                 415

Ile Lys Arg Cys Ile Glu Met Val Met Asp Gly Gly Glu Lys Gly Glu
            420                 425                 430

Glu Met Arg Arg Asn Ala Gln Lys Trp Lys Glu Leu Ala Arg Glu Ala
        435                 440                 445

Val Lys Glu Gly Gly Ser Ser Glu Met Asn Leu Lys Ala Phe Val Gln
    450                 455                 460

Glu Val Gly Lys Gly Cys
465                 470

<210> SEQ ID NO 39
<211> LENGTH: 1413
<212> TYPE: DNA
<213> ORGANISM: Nicotiana tabacum

<400> SEQUENCE: 39
atggtgcaac ccatgtcct cttggtgact tttccagcac aaggccatat taatccatgt     60
ctccaatttg ccaagaggct aattagaatg ggcattgagg taactttgc cacgagcgtt    120
```

-continued

```
ttcgcccatc gtcgtatggc aaaaactacg acttccactc tatccaaggg cttaaatttt    180
gcggcattct ctgatgggta cgacgatggt ttcaaggccg atgagcatga ttctcaacat    240
tacatgtcgg agataaaaag tcgcggttct aaaaccctaa agatatcat tttgaagagc     300 tcagacgagg gacgtcctgt gacatccctc gtctattctc ttttgcttcc atgggctgca    360
aaggtagcgc gtgaatttca cataccgtgc gcgttactat ggattcaacc agcaactgtg    420
ctagacatat attattatta cttcaatggc tatgaggatg ccataaaagg tagcaccaat    480
gatccaaatt ggtgtattca attgcctagg cttccactac taaaaagcca agatcttcct    540
tcttttttac tttcttctag taatgaagaa aaatatagct ttgctctacc aacatttaaa    600
gagcaacttg acacattaga tgttgaagaa atcctaaag tacttgtgaa cacatttgat     660
gcattagagc caaaggaact caaagctatt gaaaagtaca atttaattgg gattggacca    720
ttgattcctt caacattttt ggacggaaaa gaccctttgg attcttcctt tggtggtgat    780 cttttttcaaa agtctaatga ctatattgaa tggttgaact caaaggctaa ctcatctgtg    840
gtttatatct catttgggag tctcttgaat ttgtcaaaaa atcaaaagga ggagattgca    900
aaagggttga tagagattaa aaagccattc ttgtgggtaa taagagatca agaaaatggt    960
aagggagatg aaaaagaaga gaaattaagt tgtatgatgg agttggaaaa gcaagggaaa   1020
atagtaccat ggtgttcaca acttgaagtc ttaacacatc catctatagg atgtttcgtg   1080
tcacattgtg gatggaattc gactctggaa agtttatcgt caggcgtgtc agtagtggca   1140
tttcctcatt ggacggatca agggacaaat gctaaactaa ttgaagatgt ttggaagaca   1200
ggtgtaaggt tgaaaagaa tgaagatggt gtggttgaga gtgaagagat aaaaaggtgc   1260
atagaaatgg taatgatgg tggagagaaa ggagaagaaa tgaagaaa tgctcaaaaa      1320 tggaaagaat tggcaaggga agctgtaaaa gaaggcggat cttcggaaat gaatctaaaa   1380
gcttttgttc aagaagttgg caaaggttgc tga                                1413
```

<210> SEQ ID NO 40
<211> LENGTH: 28
<212> TYPE: PRT
<213> ORGANISM: Cannabis

<400> SEQUENCE: 40

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala
            20                  25

<210> SEQ ID NO 41
<211> LENGTH: 28
<212> TYPE: PRT
<213> ORGANISM: Cannabis

<400> SEQUENCE: 41

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala
            20                  25

<210> SEQ ID NO 42
<211> LENGTH: 545
<212> TYPE: PRT
<213> ORGANISM: Cannabis

<400> SEQUENCE: 42

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
                405                 410                 415
```

```
Tyr Pro Tyr Gly Gly Ile Met Glu Glu Ile Ser Glu Ser Ala Ile Pro
            420                 425                 430

Phe Pro His Arg Ala Gly Ile Met Tyr Glu Leu Trp Tyr Thr Ala Ser
            435                 440                 445

Trp Glu Lys Gln Glu Asp Asn Glu Lys His Ile Asn Trp Val Arg Ser
            450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
            485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asn
            515                 520                 525

Asn Phe Phe Arg Asn Glu Gln Ser Ile Pro Pro Leu Pro Pro His His
            530                 535                 540

His
545

<210> SEQ ID NO 43
<211> LENGTH: 462
<212> TYPE: PRT
<213> ORGANISM: Humulus lupulus

<400> SEQUENCE: 43

Met Gly Arg Ala Pro Cys Cys Glu Lys Val Gly Leu Lys Lys Gly Arg
1               5                   10                  15

Trp Thr Ser Glu Glu Asp Glu Ile Leu Thr Lys Tyr Ile Gln Ser Asn
            20                  25                  30

Gly Glu Gly Cys Trp Arg Ser Leu Pro Lys Asn Ala Gly Leu Leu Arg
            35                  40                  45

Cys Gly Lys Ser Cys Arg Leu Arg Trp Ile Asn Tyr Leu Arg Ala Asp
        50                  55                  60

Leu Lys Arg Gly Asn Ile Ser Ser Glu Glu Asp Ile Ile Ile Lys
65                  70                  75                  80

Leu His Ser Thr Leu Gly Asn Arg Trp Ser Leu Ile Ala Ser His Leu
            85                  90                  95

Pro Gly Arg Thr Asp Asn Glu Ile Lys Asn Tyr Trp Asn Ser His Leu
            100                 105                 110

Ser Arg Lys Ile His Thr Phe Arg Arg Cys Asn Asn Thr Thr Thr His
            115                 120                 125

His His His Leu Pro Asn Leu Val Thr Val Thr Lys Val Asn Leu Pro
        130                 135                 140

Ile Pro Lys Arg Lys Gly Gly Arg Thr Ser Arg Leu Ala Met Lys Lys
145                 150                 155                 160

Asn Lys Ser Ser Thr Ser Asn Gln Asn Ser Ser Val Ile Lys Asn Asp
            165                 170                 175

Val Gly Ser Ser Ser Ser Thr Thr Thr Thr Ser Val His Gln Arg Thr
            180                 185                 190

Thr Thr Thr Thr Pro Thr Met Asp Asp Gln Gln Lys Arg Gln Leu Ser
            195                 200                 205

Arg Cys Arg Leu Glu Glu Lys Glu Asp Gln Asp Gly Ala Ser Thr Gly
        210                 215                 220

Thr Val Val Met Met Leu Gly Gln Ala Ala Ala Val Gly Ser Ser Cys
```

```
                    225                 230                 235                 240

Asp Glu Asp Met Leu Gly His Asp Gln Leu Ser Phe Leu Cys Cys Ser
                245                 250                 255

Glu Glu Lys Thr Thr Glu Asn Ser Met Thr Asn Leu Lys Glu Asn Gly
            260                 265                 270

Asp His Glu Val Ser Gly Pro Tyr Asp Tyr Asp His Arg Tyr Glu Lys
            275                 280                 285

Glu Thr Ser Val Asp Glu Gly Met Leu Leu Cys Phe Asn Asp Ile Ile
            290                 295                 300

Asp Ser Asn Leu Leu Asn Pro Asn Glu Val Leu Thr Leu Ser Glu Glu
305                 310                 315                 320

Ser Leu Asn Leu Gly Gly Ala Leu Met Asp Thr Thr Ser Thr Thr
                325                 330                 335

Thr Asn Asn Asn Asn Tyr Ser Leu Ser Tyr Asn Asn Gly Asp Cys
                340                 345                 350

Val Ile Ser Asp Asp His Asp Gln Tyr Trp Leu Asp Asp Val Val Gly
            355                 360                 365

Val Asp Phe Trp Ser Trp Glu Ser Ser Thr Thr Val Thr Gln Glu Gln
        370                 375                 380

Glu Gln Glu Gln Glu Gln Glu Gln Gln Glu Gln Glu Gln Glu Gln
385                 390                 395                 400

Glu Gln Glu His His His Gln Gln Asp Gln Lys Lys Asn Thr Trp Asp
                405                 410                 415

Asn Glu Lys Glu Lys Met Leu Ala Leu Leu Trp Asp Ser Asp Asn Ser
                420                 425                 430

Asn Trp Glu Leu Gln Asp Asn Asn Tyr His Lys Cys Gln Glu Ile
            435                 440                 445

Thr Ser Asp Lys Glu Asn Ala Met Val Ala Trp Leu Leu Ser
            450                 455                 460

<210> SEQ ID NO 44
<211> LENGTH: 371
<212> TYPE: PRT
<213> ORGANISM: Arabidopsis thaliana

<400> SEQUENCE: 44

Met Gly Arg Ala Pro Cys Cys Glu Lys Val Gly Ile Lys Arg Gly Arg
1               5                   10                  15

Trp Thr Ala Glu Glu Asp Gln Ile Leu Ser Asn Tyr Ile Gln Ser Asn
                20                  25                  30

Gly Glu Gly Ser Trp Arg Ser Leu Pro Lys Asn Ala Gly Leu Lys Arg
            35                  40                  45

Cys Gly Lys Ser Cys Arg Leu Arg Trp Ile Asn Tyr Leu Arg Ser Asp
        50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
                85                  90                  95

Pro Gly Arg Thr Asp Asn Glu Ile Lys Asn Tyr Trp Asn Ser His Leu
            100                 105                 110

Ser Arg Lys Leu His Asn Phe Ile Arg Lys Pro Ser Ile Ser Gln Asp
        115                 120                 125

Val Ser Ala Val Ile Met Thr Asn Ala Ser Ser Ala Pro Pro Pro
            130                 135                 140
```

```
Gln Ala Lys Arg Arg Leu Gly Arg Thr Ser Arg Ser Ala Met Lys Pro
145                 150                 155                 160

Lys Ile His Arg Thr Lys Thr Arg Lys Thr Lys Lys Thr Ser Ala Pro
                165                 170                 175

Pro Glu Pro Asn Ala Asp Val Ala Gly Ala Asp Lys Glu Ala Leu Met
            180                 185                 190

Val Glu Ser Ser Gly Ala Glu Ala Glu Leu Gly Arg Pro Cys Asp Tyr
        195                 200                 205

Tyr Gly Asp Asp Cys Asn Lys Asn Leu Met Ser Ile Asn Gly Asp Asn
            210                 215                 220

Gly Val Leu Thr Phe Asp Asp Ile Ile Asp Leu Leu Leu Asp Glu
225                 230                 235                 240

Ser Asp Pro Gly His Leu Tyr Thr Asn Thr Thr Cys Gly Gly Asp Gly
                245                 250                 255

Glu Leu His Asn Ile Arg Asp Ser Glu Gly Ala Arg Gly Phe Ser Asp
            260                 265                 270

Thr Trp Asn Gln Gly Asn Leu Asp Cys Leu Leu Gln Ser Cys Pro Ser
            275                 280                 285

Val Glu Ser Phe Leu Asn Tyr Asp His Gln Val Asn Asp Ala Ser Thr
290                 295                 300

Asp Glu Phe Ile Asp Trp Asp Cys Val Trp Gln Gly Ser Asp Asn
305                 310                 315                 320

Asn Leu Trp His Glu Lys Glu Asn Pro Asp Ser Met Val Ser Trp Leu
                325                 330                 335

Leu Asp Gly Asp Asp Glu Ala Thr Ile Gly Asn Ser Asn Cys Glu Asn
            340                 345                 350

Phe Gly Glu Pro Leu Asp His Asp Asp Glu Ser Ala Leu Val Ala Trp
            355                 360                 365

Leu Leu Ser
370

<210> SEQ ID NO 45
<211> LENGTH: 243
<212> TYPE: PRT
<213> ORGANISM: Arabidopsis thaliana

<400> SEQUENCE: 45

Met Asn Ile Ser Arg Thr Glu Phe Ala Asn Cys Lys Thr Leu Ile Asn
1               5                   10                  15

His Lys Glu Glu Val Glu Glu Val Glu Lys Lys Met Glu Ile Glu Ile
                20                  25                  30

Arg Arg Gly Pro Trp Thr Val Glu Glu Asp Met Lys Leu Val Ser Tyr
            35                  40                  45

Ile Ser Leu His Gly Glu Gly Arg Trp Asn Ser Leu Ser Arg Ser Ala
        50                  55                  60

Gly Leu Asn Arg Thr Gly Lys Ser Cys Arg Leu Arg Trp Leu Asn Tyr
65                  70                  75                  80

Leu Arg Pro Asp Ile Arg Arg Gly Asp Ile Ser Leu Gln Glu Gln Phe
                85                  90                  95

Ile Ile Leu Glu Leu His Ser Arg Trp Gly Asn Arg Trp Ser Lys Ile
            100                 105                 110

Ala Gln His Leu Pro Gly Arg Thr Asp Asn Glu Ile Lys Asn Tyr Trp
        115                 120                 125

Arg Thr Arg Val Gln Lys His Ala Lys Leu Leu Lys Cys Asp Val Asn
130                 135                 140
```

```
Ser Lys Gln Phe Lys Asp Thr Ile Lys His Leu Trp Met Pro Arg Leu
145                 150                 155                 160

Ile Glu Arg Ile Ala Ala Thr Gln Ser Val Gln Phe Thr Ser Asn His
                165                 170                 175

Tyr Ser Pro Glu Asn Ser Ser Val Ala Thr Ala Thr Ser Ser Thr Ser
            180                 185                 190

Ser Ser Glu Ala Val Arg Ser Ser Phe Tyr Gly Gly Asp Gln Val Glu
        195                 200                 205

Phe Gly Thr Leu Asp His Met Thr Asn Gly Gly Tyr Trp Phe Asn Gly
    210                 215                 220

Gly Asp Thr Phe Glu Thr Leu Cys Ser Phe Asp Glu Leu Asn Lys Trp
225                 230                 235                 240

Leu Ile Gln

<210> SEQ ID NO 46
<211> LENGTH: 517
<212> TYPE: PRT
<213> ORGANISM: Cannabis

<400> SEQUENCE: 46

Asn Pro Arg Glu Asn Phe Leu Lys Cys Phe Ser Lys His Ile Pro Asn
1               5                   10                  15

Asn Val Ala Asn Pro Lys Leu Val Tyr Thr Gln His Asp Gln Leu Tyr
            20                  25                  30

Met Ser Ile Leu Asn Ser Thr Ile Gln Asn Leu Arg Phe Ile Ser Asp
        35                  40                  45

Thr Thr Pro Lys Pro Leu Val Ile Val Thr Pro Ser Asn Asn Ser His
    50                  55                  60

Ile Gln Ala Thr Ile Leu Cys Ser Lys Lys Val Gly Leu Gln Ile Arg
65                  70                  75                  80

Thr Arg Ser Gly Gly His Asp Ala Glu Gly Met Ser Tyr Ile Ser Gln
                85                  90                  95

Val Pro Phe Val Val Val Asp Leu Arg Asn Met His Ser Ile Lys Ile
            100                 105                 110

Asp Val His Ser Gln Thr Ala Trp Val Glu Ala Gly Ala Thr Leu Gly
        115                 120                 125

Glu Val Tyr Tyr Trp Ile Asn Glu Lys Asn Glu Asn Leu Ser Phe Pro
    130                 135                 140

Gly Gly Tyr Cys Pro Thr Val Gly Val Gly Gly His Phe Ser Gly Gly
145                 150                 155                 160

Gly Tyr Gly Ala Leu Met Arg Asn Tyr Gly Leu Ala Ala Asp Asn Ile
                165                 170                 175

Ile Asp Ala His Leu Val Asn Val Asp Gly Lys Val Leu Asp Arg Lys
            180                 185                 190

Ser Met Gly Glu Asp Leu Phe Trp Ala Ile Arg Gly Gly Gly Gly Glu
        195                 200                 205

Asn Phe Gly Ile Ile Ala Ala Trp Lys Ile Lys Leu Val Asp Val Pro
    210                 215                 220

Ser Lys Ser Thr Ile Phe Ser Val Lys Lys Asn Met Glu Ile His Gly
225                 230                 235                 240

Leu Val Lys Leu Phe Asn Lys Trp Gln Asn Ile Ala Tyr Lys Tyr Asp
                245                 250                 255

Lys Asp Leu Val Leu Met Thr His Phe Ile Thr Lys Asn Ile Thr Asp
            260                 265                 270
```

-continued

```
Asn His Gly Lys Asn Lys Thr Thr Val His Gly Tyr Phe Ser Ser Ile
        275                 280                 285

Phe His Gly Gly Val Asp Ser Leu Val Asp Leu Met Asn Lys Ser Phe
        290                 295                 300

Pro Glu Leu Gly Ile Lys Lys Thr Asp Cys Lys Glu Phe Ser Trp Ile
305                 310                 315                 320

Asp Thr Thr Ile Phe Tyr Ser Gly Val Val Asn Phe Asn Thr Ala Asn
                    325                 330                 335

Phe Lys Lys Glu Ile Leu Leu Asp Arg Ser Ala Gly Lys Lys Thr Ala
                340                 345                 350

Phe Ser Ile Lys Leu Asp Tyr Val Lys Pro Ile Pro Glu Thr Ala
                355                 360                 365

Met Val Lys Ile Leu Glu Lys Leu Tyr Glu Glu Asp Val Gly Ala Gly
        370                 375                 380

Met Tyr Val Leu Tyr Pro Tyr Gly Gly Ile Met Glu Glu Ile Ser Glu
385                 390                 395                 400

Ser Ala Ile Pro Phe Pro His Arg Ala Gly Ile Met Tyr Glu Leu Trp
                    405                 410                 415

Tyr Thr Ala Ser Trp Glu Lys Gln Glu Asp Asn Glu Lys His Ile Asn
                420                 425                 430

Trp Val Arg Ser Val Tyr Asn Phe Thr Thr Pro Tyr Val Ser Gln Asn
                435                 440                 445

Pro Arg Leu Ala Tyr Leu Asn Tyr Arg Asp Leu Asp Leu Gly Lys Thr
        450                 455                 460

Asn His Ala Ser Pro Asn Asn Tyr Thr Gln Ala Arg Ile Trp Gly Glu
465                 470                 475                 480

Lys Tyr Phe Gly Lys Asn Phe Asn Arg Leu Val Lys Val Lys Thr Lys
                    485                 490                 495

Val Asp Pro Asn Asn Phe Phe Arg Asn Glu Gln Ser Ile Pro Pro Leu
                500                 505                 510

Pro Pro His His His
        515

<210> SEQ ID NO 47
<211> LENGTH: 520
<212> TYPE: PRT
<213> ORGANISM: Arabidopsis thaliana

<400> SEQUENCE: 47

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Met Asp Pro Tyr
                20                  25                  30

Lys Tyr Arg Pro Ala Ser Ser Tyr Asn Ser Pro Phe Phe Thr Thr Asn
            35                  40                  45

Ser Gly Ala Pro Val Trp Asn Asn Ser Ser Met Thr Val Gly Pro
        50                  55                  60

Arg Gly Leu Ile Leu Leu Glu Asp Tyr His Leu Val Glu Lys Leu Ala
65                  70                  75                  80

Asn Phe Asp Arg Glu Arg Ile Pro Glu Arg Val Val His Ala Arg Gly
                    85                  90                  95

Ala Ser Ala Lys Gly Phe Phe Glu Val Thr His Asp Ile Ser Asn Leu
                100                 105                 110

Thr Cys Ala Asp Phe Leu Arg Ala Pro Gly Val Gln Thr Pro Val Ile
```

```
            115                 120                 125
Val Arg Phe Ser Thr Val Ile His Ala Arg Gly Ser Pro Glu Thr Leu
130                 135                 140

Arg Asp Pro Arg Gly Phe Ala Val Lys Phe Tyr Thr Arg Glu Gly Asn
145                 150                 155                 160

Phe Asp Leu Val Gly Asn Asn Phe Pro Val Phe Ile Arg Asp Gly
                165                 170                 175

Met Lys Phe Pro Asp Ile Val His Ala Leu Lys Pro Asn Pro Lys Ser
                180                 185                 190

His Ile Gln Glu Asn Trp Arg Ile Leu Asp Phe Phe Ser His His Pro
            195                 200                 205

Glu Ser Leu Asn Met Phe Thr Phe Leu Phe Asp Ile Gly Ile Pro
210                 215                 220

Gln Asp Tyr Arg His Met Asp Gly Ser Gly Val Asn Thr Tyr Met Leu
225                 230                 235                 240

Ile Asn Lys Ala Gly Lys Ala His Tyr Val Lys Phe His Trp Lys Pro
                245                 250                 255

Thr Cys Gly Val Lys Ser Leu Leu Glu Glu Asp Ala Ile Arg Leu Gly
                260                 265                 270

Gly Thr Asn His Ser His Ala Thr Gln Asp Leu Tyr Asp Ser Ile Ala
            275                 280                 285

Ala Gly Asn Tyr Pro Glu Trp Lys Leu Phe Ile Gln Ile Ile Asp Pro
290                 295                 300

Ala Asp Glu Asp Lys Phe Asp Phe Asp Pro Leu Asp Val Thr Lys Thr
305                 310                 315                 320

Trp Pro Glu Asp Ile Leu Pro Leu Gln Pro Val Gly Arg Met Val Leu
                325                 330                 335

Asn Lys Asn Ile Asp Asn Phe Phe Ala Glu Asn Glu Gln Leu Ala Phe
                340                 345                 350

Cys Pro Ala Ile Ile Val Pro Gly Ile His Tyr Ser Asp Asp Lys Leu
            355                 360                 365

Leu Gln Thr Arg Val Phe Ser Tyr Ala Asp Thr Gln Arg His Arg Leu
370                 375                 380

Gly Pro Asn Tyr Leu Gln Leu Pro Val Asn Ala Pro Lys Cys Ala His
385                 390                 395                 400

His Asn Asn His His Glu Gly Phe Met Asn Phe Met His Arg Asp Glu
                405                 410                 415

Glu Val Asn Tyr Phe Pro Ser Arg Tyr Asp Gln Val Arg His Ala Glu
                420                 425                 430

Lys Tyr Pro Thr Pro Pro Ala Val Cys Ser Gly Lys Arg Glu Arg Cys
            435                 440                 445

Ile Ile Glu Lys Glu Asn Asn Phe Lys Glu Pro Gly Glu Arg Tyr Arg
            450                 455                 460

Thr Phe Thr Pro Glu Arg Gln Glu Arg Phe Ile Gln Arg Trp Ile Asp
465                 470                 475                 480

Ala Leu Ser Asp Pro Arg Ile Thr His Glu Ile Arg Ser Ile Trp Ile
                485                 490                 495

Ser Tyr Trp Ser Gln Ala Asp Lys Ser Leu Gly Gln Lys Leu Ala Ser
                500                 505                 510

Arg Leu Asn Val Arg Pro Ser Ile
            515                 520

<210> SEQ ID NO 48
```

```
<211> LENGTH: 520
<212> TYPE: PRT
<213> ORGANISM: Arabidopsis thaliana

<400> SEQUENCE: 48

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Met Asp Pro Tyr
                20                  25                  30

Lys Tyr Arg Pro Ala Ser Ser Tyr Asn Ser Pro Phe Phe Thr Thr Asn
            35                  40                  45

Ser Gly Ala Pro Val Trp Asn Asn Ser Ser Met Thr Val Gly Pro
    50                  55                  60

Arg Gly Leu Ile Leu Leu Glu Asp Tyr His Leu Val Glu Lys Leu Ala
65                  70                  75                  80

Asn Phe Asp Arg Glu Arg Ile Pro Glu Arg Val Val His Ala Arg Gly
                85                  90                  95

Ala Ser Ala Lys Gly Phe Phe Glu Val Thr His Asp Ile Ser Asn Leu
            100                 105                 110

Thr Cys Ala Asp Phe Leu Arg Ala Pro Gly Val Gln Thr Pro Val Ile
        115                 120                 125

Val Arg Phe Ser Thr Val Ile His Ala Arg Gly Ser Pro Glu Thr Leu
    130                 135                 140

Arg Asp Pro Arg Gly Phe Ala Val Lys Phe Tyr Thr Arg Glu Gly Asn
145                 150                 155                 160

Phe Asp Leu Val Gly Asn Asn Phe Pro Val Phe Phe Ile Arg Asp Gly
                165                 170                 175

Met Lys Phe Pro Asp Ile Val His Ala Leu Lys Pro Asn Pro Lys Ser
            180                 185                 190

His Ile Gln Glu Asn Trp Arg Ile Leu Asp Phe Phe Ser His His Pro
        195                 200                 205

Glu Ser Leu Asn Met Phe Thr Phe Leu Phe Asp Asp Ile Gly Ile Pro
    210                 215                 220

Gln Asp Tyr Arg His Met Asp Gly Ser Gly Val Asn Thr Tyr Met Leu
225                 230                 235                 240

Ile Asn Lys Ala Gly Lys Ala His Tyr Val Lys Phe His Trp Lys Pro
                245                 250                 255

Thr Cys Gly Val Lys Ser Leu Leu Glu Glu Asp Ala Ile Arg Leu Gly
            260                 265                 270

Gly Thr Asn His Ser His Ala Thr Gln Asp Leu Tyr Asp Ser Ile Ala
        275                 280                 285

Ala Gly Asn Tyr Pro Glu Trp Lys Leu Phe Ile Gln Ile Asp Pro
    290                 295                 300

Ala Asp Glu Asp Lys Phe Asp Phe Asp Pro Leu Asp Val Thr Lys Thr
305                 310                 315                 320

Trp Pro Glu Asp Ile Leu Pro Leu Gln Pro Val Gly Arg Met Val Leu
                325                 330                 335

Asn Lys Asn Ile Asp Asn Phe Phe Ala Glu Asn Glu Gln Leu Ala Phe
            340                 345                 350

Cys Pro Ala Ile Ile Val Pro Gly Ile His Tyr Ser Asp Asp Lys Leu
        355                 360                 365

Leu Gln Thr Arg Val Phe Ser Tyr Ala Asp Thr Gln Arg His Arg Leu
    370                 375                 380

Gly Pro Asn Tyr Leu Gln Leu Pro Val Asn Ala Pro Lys Cys Ala His
```

```
                    385                 390                 395                 400

His Asn Asn His His Glu Gly Phe Met Asn Phe Met His Arg Asp Glu
                405                 410                 415

Glu Val Asn Tyr Phe Pro Ser Arg Tyr Asp Gln Val Arg His Ala Glu
                420                 425                 430

Lys Tyr Pro Thr Pro Ala Val Cys Ser Gly Lys Arg Glu Arg Cys
                435                 440                 445

Ile Ile Glu Lys Glu Asn Asn Phe Lys Glu Pro Gly Glu Arg Tyr Arg
                450                 455                 460

Thr Phe Thr Pro Glu Arg Gln Glu Arg Phe Ile Gln Arg Trp Ile Asp
465                 470                 475                 480

Ala Leu Ser Asp Pro Arg Ile Thr His Glu Ile Arg Ser Ile Trp Ile
                485                 490                 495

Ser Tyr Trp Ser Gln Ala Asp Lys Ser Leu Gly Gln Lys Leu Ala Ser
                500                 505                 510

Arg Leu Asn Val Arg Pro Ser Ile
                515                 520

<210> SEQ ID NO 49
<211> LENGTH: 781
<212> TYPE: PRT
<213> ORGANISM: Escherichia coli

<400> SEQUENCE: 49

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Met Ser Gln His
                20                  25                  30

Asn Glu Lys Asn Pro His Gln His Gln Ser Pro Leu His Asp Ser Ser
                35                  40                  45

Glu Ala Lys Pro Gly Met Asp Ser Leu Ala Pro Glu Asp Gly Ser His
                50                  55                  60

Arg Pro Ala Ala Glu Pro Thr Pro Pro Gly Ala Gln Pro Thr Ala Pro
65                  70                  75                  80

Gly Ser Leu Lys Ala Pro Asp Thr Arg Asn Glu Lys Leu Asn Ser Leu
                85                  90                  95

Glu Asp Val Arg Lys Gly Ser Glu Asn Tyr Ala Leu Thr Thr Asn Gln
                100                 105                 110

Gly Val Arg Ile Ala Asp Asp Gln Asn Ser Leu Arg Ala Gly Ser Arg
                115                 120                 125

Gly Pro Thr Leu Leu Glu Asp Phe Ile Leu Arg Glu Lys Ile Thr His
                130                 135                 140

Phe Asp His Glu Arg Ile Pro Glu Arg Ile Val His Ala Arg Gly Ser
145                 150                 155                 160

Ala Ala His Gly Tyr Phe Gln Pro Tyr Lys Ser Leu Ser Asp Ile Thr
                165                 170                 175

Lys Ala Asp Phe Leu Ser Asp Pro Asn Lys Ile Thr Pro Val Phe Val
                180                 185                 190

Arg Phe Ser Thr Val Gln Gly Gly Ala Gly Ser Ala Asp Thr Val Arg
                195                 200                 205

Asp Ile Arg Gly Phe Ala Thr Lys Phe Tyr Thr Glu Glu Gly Ile Phe
                210                 215                 220

Asp Leu Val Gly Asn Asn Thr Pro Ile Phe Phe Ile Gln Asp Ala His
225                 230                 235                 240
```

```
Lys Phe Pro Asp Phe Val His Ala Val Lys Pro Glu Pro His Trp Ala
            245                 250                 255
Ile Pro Gln Gly Gln Ser Ala His Asp Thr Phe Trp Asp Tyr Val Ser
            260                 265                 270
Leu Gln Pro Glu Thr Leu His Asn Val Met Trp Ala Met Ser Asp Arg
            275                 280                 285
Gly Ile Pro Arg Ser Tyr Arg Thr Met Glu Gly Phe Gly Ile His Thr
            290                 295                 300
Phe Arg Leu Ile Asn Ala Glu Gly Lys Ala Thr Phe Val Arg Phe His
305                 310                 315                 320
Trp Lys Pro Leu Ala Gly Lys Ala Ser Leu Val Trp Asp Glu Ala Gln
            325                 330                 335
Lys Leu Thr Gly Arg Asp Pro Asp Phe His Arg Arg Glu Leu Trp Glu
            340                 345                 350
Ala Ile Glu Ala Gly Asp Phe Pro Glu Tyr Glu Leu Gly Phe Gln Leu
            355                 360                 365
Ile Pro Glu Glu Asp Glu Phe Lys Phe Asp Phe Asp Leu Leu Asp Pro
            370                 375                 380
Thr Lys Leu Ile Pro Glu Glu Leu Val Pro Val Gln Arg Val Gly Lys
385                 390                 395                 400
Met Val Leu Asn Arg Asn Pro Asp Asn Phe Phe Ala Glu Asn Glu Gln
            405                 410                 415
Ala Ala Phe His Pro Gly His Ile Val Pro Gly Leu Asp Phe Thr Asn
            420                 425                 430
Asp Pro Leu Leu Gln Gly Arg Leu Phe Ser Tyr Thr Asp Thr Gln Ile
            435                 440                 445
Ser Arg Leu Gly Gly Pro Asn Phe His Glu Ile Pro Ile Asn Arg Pro
            450                 455                 460
Thr Cys Pro Tyr His Asn Phe Gln Arg Asp Gly Met His Arg Met Gly
465                 470                 475                 480
Ile Asp Thr Asn Pro Ala Asn Tyr Glu Pro Asn Ser Ile Asn Asp Asn
            485                 490                 495
Trp Pro Arg Glu Thr Pro Gly Pro Lys Arg Gly Gly Phe Glu Ser
            500                 505                 510
Tyr Gln Glu Arg Val Glu Gly Asn Lys Val Arg Glu Arg Ser Pro Ser
            515                 520                 525
Phe Gly Glu Tyr Tyr Ser His Pro Arg Leu Phe Trp Leu Ser Gln Thr
            530                 535                 540
Pro Phe Glu Gln Arg His Ile Val Asp Gly Phe Ser Phe Glu Leu Ser
545                 550                 555                 560
Lys Val Val Arg Pro Tyr Ile Arg Glu Arg Val Val Asp Gln Leu Ala
            565                 570                 575
His Ile Asp Leu Thr Leu Ala Gln Ala Val Ala Lys Asn Leu Gly Ile
            580                 585                 590
Glu Leu Thr Asp Asp Gln Leu Asn Ile Thr Pro Pro Asp Val Asn
            595                 600                 605
Gly Leu Lys Lys Asp Pro Ser Leu Ser Leu Tyr Ala Ile Pro Asp Gly
            610                 615                 620
Asp Val Lys Gly Arg Val Val Ala Ile Leu Asn Asp Glu Val Arg
625                 630                 635                 640
Ser Ala Asp Leu Leu Ala Ile Leu Lys Ala Leu Lys Ala Lys Gly Val
            645                 650                 655
His Ala Lys Leu Leu Tyr Ser Arg Met Gly Glu Val Thr Ala Asp Asp
```

```
                    660                 665                 670
Gly Thr Val Leu Pro Ile Ala Ala Thr Phe Ala Gly Ala Pro Ser Leu
                675                 680                 685

Thr Val Asp Ala Val Ile Val Pro Cys Gly Asn Ile Ala Asp Ile Ala
            690                 695                 700

Asp Asn Gly Asp Ala Asn Tyr Tyr Leu Met Glu Ala Tyr Lys His Leu
705                 710                 715                 720

Lys Pro Ile Ala Leu Ala Gly Asp Ala Arg Lys Phe Lys Ala Thr Ile
                725                 730                 735

Lys Ile Ala Asp Gln Gly Glu Glu Gly Ile Val Glu Ala Asp Ser Ala
            740                 745                 750

Asp Gly Ser Phe Met Asp Glu Leu Leu Thr Leu Met Ala Ala His Arg
                755                 760                 765

Val Trp Ser Arg Ile Pro Lys Ile Asp Lys Ile Pro Ala
            770                 775                 780

<210> SEQ ID NO 50
<211> LENGTH: 781
<212> TYPE: PRT
<213> ORGANISM: Escherichia coli

<400> SEQUENCE: 50

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Met Ser Gln His
                20                  25                  30

Asn Glu Lys Asn Pro His Gln His Gln Ser Pro Leu His Asp Ser Ser
            35                  40                  45

Glu Ala Lys Pro Gly Met Asp Ser Leu Ala Pro Glu Asp Gly Ser His
50                  55                  60

Arg Pro Ala Ala Glu Pro Thr Pro Gly Ala Gln Pro Thr Ala Pro
65                  70                  75                  80

Gly Ser Leu Lys Ala Pro Asp Thr Arg Asn Glu Lys Leu Asn Ser Leu
                85                  90                  95

Glu Asp Val Arg Lys Gly Ser Glu Asn Tyr Ala Leu Thr Thr Asn Gln
            100                 105                 110

Gly Val Arg Ile Ala Asp Asp Gln Asn Ser Leu Arg Ala Gly Ser Arg
        115                 120                 125

Gly Pro Thr Leu Leu Glu Asp Phe Ile Leu Arg Glu Lys Ile Thr His
130                 135                 140

Phe Asp His Glu Arg Ile Pro Glu Arg Ile Val His Ala Arg Gly Ser
145                 150                 155                 160

Ala Ala His Gly Tyr Phe Gln Pro Tyr Lys Ser Leu Ser Asp Ile Thr
                165                 170                 175

Lys Ala Asp Phe Leu Ser Asp Pro Asn Lys Ile Thr Pro Val Phe Val
            180                 185                 190

Arg Phe Ser Thr Val Gln Gly Gly Ala Gly Ser Ala Asp Thr Val Arg
        195                 200                 205

Asp Ile Arg Gly Phe Ala Thr Lys Phe Tyr Thr Glu Glu Gly Ile Phe
    210                 215                 220

Asp Leu Val Gly Asn Asn Thr Pro Ile Phe Phe Ile Gln Asp Ala His
225                 230                 235                 240

Lys Phe Pro Asp Phe Val His Ala Val Lys Pro Glu Pro His Trp Ala
                245                 250                 255
```

Ile Pro Gln Gly Gln Ser Ala His Asp Thr Phe Trp Asp Tyr Val Ser
            260                 265                 270

Leu Gln Pro Glu Thr Leu His Asn Val Met Trp Ala Met Ser Asp Arg
        275                 280                 285

Gly Ile Pro Arg Ser Tyr Arg Thr Met Glu Gly Phe Gly Ile His Thr
    290                 295                 300

Phe Arg Leu Ile Asn Ala Glu Gly Lys Ala Thr Phe Val Arg Phe His
305                 310                 315                 320

Trp Lys Pro Leu Ala Gly Lys Ala Ser Leu Val Trp Asp Glu Ala Gln
                325                 330                 335

Lys Leu Thr Gly Arg Asp Pro Asp Phe His Arg Arg Glu Leu Trp Glu
            340                 345                 350

Ala Ile Glu Ala Gly Asp Phe Pro Glu Tyr Glu Leu Gly Phe Gln Leu
        355                 360                 365

Ile Pro Glu Glu Asp Glu Phe Lys Phe Asp Phe Asp Leu Leu Asp Pro
    370                 375                 380

Thr Lys Leu Ile Pro Glu Glu Leu Val Pro Val Gln Arg Val Gly Lys
385                 390                 395                 400

Met Val Leu Asn Arg Asn Pro Asp Asn Phe Phe Ala Glu Asn Glu Gln
                405                 410                 415

Ala Ala Phe His Pro Gly His Ile Val Pro Gly Leu Asp Phe Thr Asn
            420                 425                 430

Asp Pro Leu Leu Gln Gly Arg Leu Phe Ser Tyr Thr Asp Thr Gln Ile
        435                 440                 445

Ser Arg Leu Gly Gly Pro Asn Phe His Glu Ile Pro Ile Asn Arg Pro
    450                 455                 460

Thr Cys Pro Tyr His Asn Phe Gln Arg Asp Gly Met His Arg Met Gly
465                 470                 475                 480

Ile Asp Thr Asn Pro Ala Asn Tyr Glu Pro Asn Ser Ile Asn Asp Asn
                485                 490                 495

Trp Pro Arg Glu Thr Pro Pro Gly Pro Lys Arg Gly Gly Phe Glu Ser
            500                 505                 510

Tyr Gln Glu Arg Val Glu Gly Asn Lys Val Arg Glu Arg Ser Pro Ser
        515                 520                 525

Phe Gly Glu Tyr Tyr Ser His Pro Arg Leu Phe Trp Leu Ser Gln Thr
    530                 535                 540

Pro Phe Glu Gln Arg His Ile Val Asp Gly Phe Ser Phe Glu Leu Ser
545                 550                 555                 560

Lys Val Val Arg Pro Tyr Ile Arg Glu Arg Val Val Asp Gln Leu Ala
                565                 570                 575

His Ile Asp Leu Thr Leu Ala Gln Ala Val Ala Lys Asn Leu Gly Ile
            580                 585                 590

Glu Leu Thr Asp Asp Gln Leu Asn Ile Thr Pro Pro Asp Val Asn
        595                 600                 605

Gly Leu Lys Lys Asp Pro Ser Leu Ser Leu Tyr Ala Ile Pro Asp Gly
    610                 615                 620

Asp Val Lys Gly Arg Val Val Ala Ile Leu Asn Asp Glu Val Arg
625                 630                 635                 640

Ser Ala Asp Leu Leu Ala Ile Leu Lys Ala Leu Lys Ala Lys Gly Val
                645                 650                 655

His Ala Lys Leu Leu Tyr Ser Arg Met Gly Glu Val Thr Ala Asp Asp
            660                 665                 670

Gly Thr Val Leu Pro Ile Ala Ala Thr Phe Ala Gly Ala Pro Ser Leu

|  | 675 |  |  | 680 |  |  |  | 685 |  |  |
|---|---|---|---|---|---|---|---|---|---|---|

Thr Val Asp Ala Val Ile Val Pro Cys Gly Asn Ile Ala Asp Ile Ala
         690                   695                   700

Asp Asn Gly Asp Ala Asn Tyr Tyr Leu Met Glu Ala Tyr Lys His Leu
705                  710                   715                   720

Lys Pro Ile Ala Leu Ala Gly Asp Ala Arg Lys Phe Lys Ala Thr Ile
                 725                   730                   735

Lys Ile Ala Asp Gln Gly Glu Glu Gly Ile Val Glu Asp Ser Ala
        740                  745                  750

Asp Gly Ser Phe Met Asp Glu Leu Leu Thr Leu Met Ala Ala His Arg
             755                   760                 765

Val Trp Ser Arg Ile Pro Lys Ile Asp Lys Ile Pro Ala
        770                  775                  780

<210> SEQ ID NO 51
<211> LENGTH: 1437
<212> TYPE: DNA
<213> ORGANISM: Nicotiana tabacum

<400> SEQUENCE: 51

| | | | | |
|---|---|---|---|---|
| atgaaaacaa | cagaacttgt | cttcataccc | gcccccggta | tgggtcacct | tgtacccaca | 60 |
| gtcgaagtcg | ccaaacaact | agttgataga | gacgaacagt | tgtctattac | cgtcttgata | 120 |
| atgacgttac | ccctggagac | taatatccca | agttacacca | agagtttgtc | ctctgactat | 180 |
| tcatcccgta | tcacgttgtt | acaactaagt | caacctgaga | cgagtgtctc | aatgagtagt | 240 |
| tttaacgcca | taaacttctt | cgaatacatt | agttcctata | aggatcgtgt | taaagatgcc | 300 |
| gtaaacgaga | cattctcctc | ttcatcctcc | gtcaaactta | aggatttgt | aatcgacatg | 360 |
| ttttgcacgg | caatgataga | cgtggccaac | gagttcggta | ttccatctta | tgtattctac | 420 |
| acgtccaacg | ctgccatgct | aggcctacaa | cttcacttcc | aatccttgtc | catcgaatat | 480 |
| tcacctaagg | ttcataatta | tttagaccct | gaatctgagg | tagctatatc | aacgtacatt | 540 |
| aacccaatac | cagtaaaatg | cttacccggt | ataattcttg | acaatgataa | gagtggcact | 600 |
| atgttcgtaa | accatgccag | agattccgt | gaaacaaagg | gtataatggt | aaatactttt | 660 |
| gcagaattag | aaagtcacgc | cctaaaggca | cttagtgacg | atgagaaaat | tcctccaatc | 720 |
| tatcccgtcg | gacccattct | aaacttgggt | gatggtaatg | aggatcataa | ccaagagtac | 780 |
| gacatgataa | tgaaatggct | ggatgaacaa | ccacacagtt | cagtggtttt | cctgtgcttc | 840 |
| ggttccaaag | ttcatttga | agaagaccag | gttaaagaga | tagcaaatgc | tttagagaga | 900 |
| tcaggcaata | ggttcctgtg | agtttaaga | cgtccccctc | ccaaggatac | tcttcaattc | 960 |
| ccttccgaat | ttgaaaaccc | cgaggaagtg | ctacctgtag | attttttca | agaaccaaa | 1020 |
| ggcagaggaa | aagtcatcgg | atgggcacca | cagcttgcaa | ttctatctca | ccctgccgtc | 1080 |
| ggtggattcg | tttcccactg | cggctggaat | agtactttgg | aatcagttag | atcaggtgta | 1140 |
| cccatagcaa | catggcctct | ttatgcagag | cagcagtcca | atgcatttca | attggtcaag | 1200 |
| gatctaggta | tggccgtcga | aattaaaatg | gattaccgtg | aggactttaa | caagactaat | 1260 |
| cctccattgg | taaggcaga | ggaaatgaa | gacggcatta | gaagttgat | ggactccgag | 1320 |
| aataagatta | gggcaaaggt | gatggaaatg | aaagataagt | ccagagctgc | attactggaa | 1380 |
| ggaggatcct | cctatgttgc | actgggtcac | ttcgtggaga | ccgtaatgaa | gaactaa | 1437 |

<210> SEQ ID NO 52
<211> LENGTH: 478

```
<212> TYPE: PRT
<213> ORGANISM: Nicotiana tabacum

<400> SEQUENCE: 52

Met Lys Thr Thr Glu Leu Val Phe Ile Pro Ala Pro Gly Met Gly His
1               5                   10                  15

Leu Val Pro Thr Val Glu Val Ala Lys Gln Leu Val Asp Arg Asp Glu
            20                  25                  30

Gln Leu Ser Ile Thr Val Leu Ile Met Thr Leu Pro Leu Glu Thr Asn
        35                  40                  45

Ile Pro Ser Tyr Thr Lys Ser Leu Ser Ser Asp Tyr Ser Ser Arg Ile
    50                  55                  60

Thr Leu Leu Gln Leu Ser Gln Pro Glu Thr Ser Val Ser Met Ser Ser
65                  70                  75                  80

Phe Asn Ala Ile Asn Phe Phe Glu Tyr Ile Ser Ser Tyr Lys Asp Arg
                85                  90                  95

Val Lys Asp Ala Val Asn Glu Thr Phe Ser Ser Ser Ser Ser Val Lys
            100                 105                 110

Leu Lys Gly Phe Val Ile Asp Met Phe Cys Thr Ala Met Ile Asp Val
        115                 120                 125

Ala Asn Glu Phe Gly Ile Pro Ser Tyr Val Phe Tyr Thr Ser Asn Ala
    130                 135                 140

Ala Met Leu Gly Leu Gln Leu His Phe Gln Ser Leu Ser Ile Glu Tyr
145                 150                 155                 160

Ser Pro Lys Val His Asn Tyr Leu Asp Pro Glu Ser Glu Val Ala Ile
                165                 170                 175

Ser Thr Tyr Ile Asn Pro Ile Pro Val Lys Cys Leu Pro Gly Ile Ile
            180                 185                 190

Leu Asp Asn Asp Lys Ser Gly Thr Met Phe Val Asn His Ala Arg Arg
        195                 200                 205

Phe Arg Glu Thr Lys Gly Ile Met Val Asn Thr Phe Ala Glu Leu Glu
    210                 215                 220

Ser His Ala Leu Lys Ala Leu Ser Asp Asp Glu Lys Ile Pro Pro Ile
225                 230                 235                 240

Tyr Pro Val Gly Pro Ile Leu Asn Leu Gly Asp Gly Asn Glu Asp His
                245                 250                 255

Asn Gln Glu Tyr Asp Met Ile Met Lys Trp Leu Asp Gly Gln Pro His
            260                 265                 270

Ser Ser Val Val Phe Leu Cys Phe Gly Ser Lys Gly Ser Phe Glu Glu
        275                 280                 285

Asp Gln Val Lys Glu Ile Ala Asn Ala Leu Glu Arg Ser Gly Asn Arg
    290                 295                 300

Phe Leu Trp Ser Leu Arg Arg Pro Pro Lys Asp Thr Leu Gln Phe
305                 310                 315                 320

Pro Ser Glu Phe Glu Asn Pro Glu Glu Val Leu Pro Val Gly Phe Phe
                325                 330                 335

Gln Arg Thr Lys Gly Arg Gly Lys Val Ile Gly Trp Ala Pro Gln Leu
            340                 345                 350

Ala Ile Leu Ser His Pro Ala Val Gly Gly Phe Val Ser His Cys Gly
        355                 360                 365

Trp Asn Ser Thr Leu Glu Ser Val Arg Ser Gly Val Pro Ile Ala Thr
    370                 375                 380

Trp Pro Leu Tyr Ala Glu Gln Gln Ser Asn Ala Phe Gln Leu Val Lys
385                 390                 395                 400
```

Asp Leu Gly Met Ala Val Glu Ile Lys Met Asp Tyr Arg Glu Asp Phe
            405                 410                 415

Asn Lys Thr Asn Pro Pro Leu Val Lys Ala Glu Ile Glu Asp Gly
        420                 425                 430

Ile Arg Lys Leu Met Asp Ser Glu Asn Lys Ile Arg Ala Lys Val Met
        435                 440                 445

Glu Met Lys Asp Lys Ser Arg Ala Ala Leu Leu Glu Gly Gly Ser Ser
    450                 455                 460

Tyr Val Ala Leu Gly His Phe Val Glu Thr Val Met Lys Asn
465                 470                 475

<210> SEQ ID NO 53
<211> LENGTH: 1413
<212> TYPE: DNA
<213> ORGANISM: Nicotiana tabacum

<400> SEQUENCE: 53

| | | | | | |
|---|---|---|---|---|---|
| atggttcaac | cacacgtctt | actggttact | tttccagcac | aaggccatat | caacccttgc | 60 |
| ctacaattcg | ccaaaagact | aataaggatg | ggcatcgaag | taacttttgc | cacgagtgta | 120 |
| ttcgcacata | ggcgtatggc | taaaactacg | acatcaactt | tgtccaaagg | actaaacttc | 180 |
| gccgccttca | gtgatggcta | tgacgatgga | ttcaaagccg | acgaacatga | cagtcaacac | 240 |
| tacatgagtg | aaataaagtc | ccgtggatct | aaaacactta | aggatattat | acttaaatcc | 300 |
| tccgatgagg | aagacccgt | acctctttta | gtttattcac | tgttactgcc | ctgggctgca | 360 |
| aaagtcgcca | gagagtttca | tattccttgc | gctttattgt | ggatccaacc | agctacggta | 420 |
| ttagacatct | actattacta | cttcaatgga | tacgaggatg | caataaaggg | atcaacaaac | 480 |
| gaccccaact | ggtgtattca | actgcctaga | cttcctctat | aaaaagtca | ggacttacct | 540 |
| agttttttac | tgtcatccag | taacgaagaa | aaatattcat | tcgctttacc | caccttcaaa | 600 |
| gagcagcttg | acactttgga | tgttgaagag | aaccccaagg | ttttggtcaa | tacttttgac | 660 |
| gctttggagc | caaaagagct | aaaggctatt | gaaaaatata | accttatcgg | cataggacct | 720 |
| ttaatcccct | ctactttctt | agatggcaaa | gaccctctag | attcaagttt | cggaggtgat | 780 |
| ttgtttcaaa | agagtaacga | ttatatcgag | tggctaaata | gtaaagccaa | ctccagtgtg | 840 |
| gtctacattt | ctttcggaag | tcttctgaat | ttatcaaaaa | accaaaagga | agagatcgca | 900 |
| aaaggactga | tagagataaa | aaaacctttc | ttatgggtga | tcagagacca | ggaaaacggt | 960 |
| aaaggcgatg | agaaggagga | aaaactgtcc | tgtatgatgg | agctagagaa | caaggaaaa | 1020 |
| atcgttccct | ggtgttcaca | gttagaagtg | ttaacccatc | catccatagg | ttgcttcgta | 1080 |
| tcacattgtg | gttggaatag | tacacttgaa | agtctttcat | caggcgtctc | tgtcgtcgca | 1140 |
| ttcccccact | ggacggacca | gggcacaaac | gccaaactga | tcgaagatgt | atggaagacg | 1200 |
| ggcgtcaggc | taaaaaaaaa | tgaggatggc | gtggtagaga | gtgaagagat | aaagcgttgc | 1260 |
| atagaaatgg | tcatggatgg | cggtgaaaag | ggagaggaaa | tgaggcgtaa | cgcacaaaag | 1320 |
| tggaaggaac | tagcccgtga | agcagtgaaa | gaaggaggtt | ctagtgagat | gaatttaaaa | 1380 |
| gctttcgtgc | aggaagttgg | aaaaggctgc | tga | | | 1413 |

<210> SEQ ID NO 54
<211> LENGTH: 470
<212> TYPE: PRT
<213> ORGANISM: Nicotiana tabacum

<400> SEQUENCE: 54

-continued

```
Met Val Gln Pro His Val Leu Leu Val Thr Phe Pro Ala Gln Gly His
1               5                   10                  15

Ile Asn Pro Cys Leu Gln Phe Ala Lys Arg Leu Ile Arg Met Gly Ile
                20                  25                  30

Glu Val Thr Phe Ala Thr Ser Val Phe Ala His Arg Arg Met Ala Lys
            35                  40                  45

Thr Thr Thr Ser Thr Leu Ser Lys Gly Leu Asn Phe Ala Ala Phe Ser
        50                  55                  60

Asp Gly Tyr Asp Gly Phe Lys Ala Asp Glu His Asp Ser Gln His
65                  70                  75                  80

Tyr Met Ser Glu Ile Lys Ser Arg Gly Ser Lys Thr Leu Lys Asp Ile
                85                  90                  95

Ile Leu Lys Ser Ser Asp Glu Gly Arg Pro Val Thr Ser Leu Val Tyr
                100                 105                 110

Ser Leu Leu Leu Pro Trp Ala Ala Lys Val Ala Arg Glu Phe His Ile
            115                 120                 125

Pro Cys Ala Leu Leu Trp Ile Gln Pro Ala Thr Val Leu Asp Ile Tyr
        130                 135                 140

Tyr Tyr Tyr Phe Asn Gly Tyr Glu Asp Ala Ile Lys Gly Ser Thr Asn
145                 150                 155                 160

Asp Pro Asn Trp Cys Ile Gln Leu Pro Arg Leu Pro Leu Leu Lys Ser
                165                 170                 175

Gln Asp Leu Pro Ser Phe Leu Leu Ser Ser Asn Glu Glu Lys Tyr
                180                 185                 190

Ser Phe Ala Leu Pro Thr Phe Lys Glu Gln Leu Asp Thr Leu Asp Val
            195                 200                 205

Glu Glu Asn Pro Lys Val Leu Val Asn Thr Phe Asp Ala Leu Glu Pro
210                 215                 220

Lys Glu Leu Lys Ala Ile Glu Lys Tyr Asn Leu Ile Gly Ile Gly Pro
225                 230                 235                 240

Leu Ile Pro Ser Thr Phe Leu Asp Gly Lys Asp Pro Leu Asp Ser Ser
                245                 250                 255

Phe Gly Gly Asp Leu Phe Gln Lys Ser Asn Asp Tyr Ile Glu Trp Leu
            260                 265                 270

Asn Ser Lys Ala Asn Ser Ser Val Val Tyr Ile Ser Phe Gly Ser Leu
        275                 280                 285

Leu Asn Leu Ser Lys Asn Gln Lys Glu Glu Ile Ala Lys Gly Leu Ile
    290                 295                 300

Glu Ile Lys Lys Pro Phe Leu Trp Val Ile Arg Asp Gln Glu Asn Gly
305                 310                 315                 320

Lys Gly Asp Glu Lys Glu Glu Lys Leu Ser Cys Met Met Glu Leu Glu
                325                 330                 335

Lys Gln Gly Lys Ile Val Pro Trp Cys Ser Gln Leu Glu Val Leu Thr
            340                 345                 350

His Pro Ser Ile Gly Cys Phe Val Ser His Cys Gly Trp Asn Ser Thr
        355                 360                 365

Leu Glu Ser Leu Ser Ser Gly Val Ser Val Ala Phe Pro His Trp
    370                 375                 380

Thr Asp Gln Gly Thr Asn Ala Lys Leu Ile Glu Asp Val Trp Lys Thr
385                 390                 395                 400

Gly Val Arg Leu Lys Lys Asn Glu Asp Gly Val Val Glu Ser Glu Glu
                405                 410                 415
```

Ile Lys Arg Cys Ile Glu Met Val Met Asp Gly Glu Lys Gly Glu
            420                 425                 430

Glu Met Arg Arg Asn Ala Gln Lys Trp Lys Glu Leu Ala Arg Glu Ala
        435                 440                 445

Val Lys Glu Gly Gly Ser Ser Glu Met Asn Leu Lys Ala Phe Val Gln
450                 455                 460

Glu Val Gly Lys Gly Cys
465                 470

<210> SEQ ID NO 55
<211> LENGTH: 1449
<212> TYPE: DNA
<213> ORGANISM: Nicotiana tabacum

<400> SEQUENCE: 55

| | |
|---|---|
| atgaaagaga ctaaaaaaat tgagttagtt tttatcccca gtcctggtat aggacactta | 60 |
| gtctcaactg tggagatggc caaactgttg atagcccgtg aagagcaact ttctattact | 120 |
| gtcctgatta caatggcc taatgataaa aagctagaca gttatatcca gtccgtcgca | 180 |
| aactttagtt ctagactgaa gtttatacgt ctgccccaag atgactcaat catgcaactt | 240 |
| ttgaaatcaa acattttcac gacattcatc gcctctcaca agccagctgt aagagacgcc | 300 |
| gttgctgaca tactaaagag tgaaagtaat aacacattgg caggcattgt aatcgatctt | 360 |
| ttctgcacat ccatgatcga tgtagccaat gagtttgagc tgcctactta tgtgttttac | 420 |
| actagtggcg cagccacgtt gggtctgcac taccatattc aaaatctgcg tgatgagttt | 480 |
| aataaagaca ttaccaaata taaggatgag ccagaagaaa aattaagtat agccacgtac | 540 |
| cttaacccat ccctgctaa gtgtctaccc tccgtggcat ggataagga aggaggatca | 600 |
| acgatgttcc tagacttagc taagaggttc agggagacca aagcataat gattaacact | 660 |
| tttcttgagc tggaatcata cgctctaaac tcattgtcta gagataaaaa cttgcccct | 720 |
| atataccctg taggccctgt tttgaacttg aacaacgttg agggtgataa cttgggctct | 780 |
| agtgatcaaa ataccatgaa atggctggac gaccagccag cttcttccgt tgtgttccta | 840 |
| tgttttggct caggaggaag tttcgaaaaa caccaagtca agaaatagc ttatgcctta | 900 |
| gaatcttccg gatgcaggtt cttgtggagt ttgcgtagac cccccacgga agatgctagg | 960 |
| ttcccttcta attacgaaaa cttagaggaa attttaccag agggatttct ggaaagaacg | 1020 |
| aaaggcattg gtaaggtcat ggatgggcc ccacagttag caatcttgtc tcacaagtcc | 1080 |
| acaggaggat tcgtgtctca ttgcggatgg aactctaccc ttgaaagtac ctatttcggc | 1140 |
| gttcctattg ctacttggcc aatgtatgct gaacaacagg ccaacgcttt tcaacttgtt | 1200 |
| aaagatttga ggatgggtgt tgagatcaaa atggattata ggaaggatat gaaggtaatg | 1260 |
| ggcaaggagg ttatcgttaa ggcagaagaa attgaaaagg ccataaggga aatcatggac | 1320 |
| tcagaatcag aaatcagggt caaggtcaaa gagatgaagg agaaaagtcg tgcagcccaa | 1380 |
| atggaaggag gatcatcata ccctctatc ggcggcttca ttcaaataat catggagaac | 1440 |
| tcacagtaa | 1449 |

<210> SEQ ID NO 56
<211> LENGTH: 482
<212> TYPE: PRT
<213> ORGANISM: Nicotiana tabacum

<400> SEQUENCE: 56

Met Lys Glu Thr Lys Lys Ile Glu Leu Val Phe Ile Pro Ser Pro Gly

-continued

```
1               5               10              15
Ile Gly His Leu Val Ser Thr Val Glu Met Ala Lys Leu Leu Ile Ala
                20              25              30

Arg Glu Glu Gln Leu Ser Ile Thr Val Leu Ile Ile Gln Trp Pro Asn
                35              40              45

Asp Lys Lys Leu Asp Ser Tyr Ile Gln Ser Val Ala Asn Phe Ser Ser
                50              55              60

Arg Leu Lys Phe Ile Arg Leu Pro Gln Asp Asp Ser Ile Met Gln Leu
65              70              75              80

Leu Lys Ser Asn Ile Phe Thr Thr Phe Ile Ala Ser His Lys Pro Ala
                85              90              95

Val Arg Asp Ala Val Ala Asp Ile Leu Lys Ser Glu Ser Asn Asn Thr
                100             105             110

Leu Ala Gly Ile Val Ile Asp Leu Phe Cys Thr Ser Met Ile Asp Val
                115             120             125

Ala Asn Glu Phe Glu Leu Pro Thr Tyr Val Phe Tyr Thr Ser Gly Ala
                130             135             140

Ala Thr Leu Gly Leu His Tyr His Ile Gln Asn Leu Arg Asp Glu Phe
145             150             155             160

Asn Lys Asp Ile Thr Lys Tyr Lys Asp Glu Pro Glu Glu Lys Leu Ser
                165             170             175

Ile Ala Thr Tyr Leu Asn Pro Phe Pro Ala Lys Cys Leu Pro Ser Val
                180             185             190

Ala Leu Asp Lys Glu Gly Gly Ser Thr Met Phe Leu Asp Leu Ala Lys
                195             200             205

Arg Phe Arg Glu Thr Lys Gly Ile Met Ile Asn Thr Phe Leu Glu Leu
210             215             220

Glu Ser Tyr Ala Leu Asn Ser Leu Ser Arg Asp Lys Asn Leu Pro Pro
225             230             235             240

Ile Tyr Pro Val Gly Pro Val Leu Asn Leu Asn Asn Val Glu Gly Asp
                245             250             255

Asn Leu Gly Ser Ser Asp Gln Asn Thr Met Lys Trp Leu Asp Asp Gln
                260             265             270

Pro Ala Ser Ser Val Val Phe Leu Cys Phe Gly Ser Gly Gly Ser Phe
                275             280             285

Glu Lys His Gln Val Lys Glu Ile Ala Tyr Ala Leu Glu Ser Ser Gly
                290             295             300

Cys Arg Phe Leu Trp Ser Leu Arg Arg Pro Thr Glu Asp Ala Arg
305             310             315             320

Phe Pro Ser Asn Tyr Glu Asn Leu Glu Glu Ile Leu Pro Glu Gly Phe
                325             330             335

Leu Glu Arg Thr Lys Gly Ile Gly Lys Val Ile Gly Trp Ala Pro Gln
                340             345             350

Leu Ala Ile Leu Ser His Lys Ser Thr Gly Gly Phe Val Ser His Cys
                355             360             365

Gly Trp Asn Ser Thr Leu Glu Ser Thr Tyr Phe Gly Val Pro Ile Ala
                370             375             380

Thr Trp Pro Met Tyr Ala Glu Gln Gln Ala Asn Ala Phe Gln Leu Val
385             390             395             400

Lys Asp Leu Arg Met Gly Val Glu Ile Lys Met Asp Tyr Arg Lys Asp
                405             410             415

Met Lys Val Met Gly Lys Glu Val Ile Val Lys Ala Glu Glu Ile Glu
                420             425             430
```

Lys Ala Ile Arg Glu Ile Met Asp Ser Glu Ser Glu Ile Arg Val Lys
       435                 440                 445

Val Lys Glu Met Lys Glu Lys Ser Arg Ala Ala Gln Met Glu Gly Gly
   450                 455                 460

Ser Ser Tyr Thr Ser Ile Gly Gly Phe Ile Gln Ile Ile Met Glu Asn
465                 470                 475                 480

Ser Gln

<210> SEQ ID NO 57
<211> LENGTH: 1491
<212> TYPE: DNA
<213> ORGANISM: Nicotiana tabacum

<400> SEQUENCE: 57

| | | | | | |
|---|---|---|---|---|---|
| atggctactc | aggtgcataa | attgcatttc | attctgttcc | cactgatggc | tcccggtcac | 60 |
| atgatcccta | tgatagacat | cgcaaaacta | ttggctaacc | gtggcgtgat | aactaccata | 120 |
| ataactacgc | ccgttaacgc | caatcgtttt | tcctctacga | tcactagggc | cattaaatca | 180 |
| ggcctaagaa | tccagatttt | aaccttaaaa | ttcccatcag | ttgaggtagg | cctgcctgaa | 240 |
| ggatgtgaaa | acatcgacat | gttgccatct | ttggacttag | cctctaaatt | ctttgctgct | 300 |
| atttctatgc | ttaaacaaca | agtggagaac | ttgctagagg | gtattaaccc | tagtccctca | 360 |
| tgcgttattt | ctgacatggg | cttcccatgg | acgacacaga | tcgctcaaaa | tttcaatatt | 420 |
| cctcgtatcg | tatttcatgg | cacgtgttgc | ttttctcttc | tttgttctta | caaaatcctg | 480 |
| tcatccaata | tcttagagaa | cattactagt | gactcagagt | attttgtcgt | gccagatctg | 540 |
| ccagaccgtg | tcgagctaac | taaggcccaa | gtctctggat | ctacaaagaa | tactacatca | 600 |
| gtaagtagtt | cagtactgaa | ggaggttaca | gagcagatca | ggcttgcaga | ggaatcatcc | 660 |
| tacggtgtga | tagttaattc | cttcgaagaa | ctggaacagg | tgtatgaaaa | agagtacaga | 720 |
| aaagccaggg | gcaaaaaggt | ctggtgcgtg | ggtcctgtct | ctttgtgcaa | caggagatt | 780 |
| gaagatcttg | ttactagagg | aaacaaaacc | gctatagaca | atcaggattg | tcttaagtgg | 840 |
| ttagacaact | tcgagactga | atccgtcgtc | tatgcaagtt | taggctcact | aagtaggctt | 900 |
| acgttactgc | aaatggttga | gctgggattg | gactggagg | agagtaatag | gccatttgta | 960 |
| tgggttctgg | gaggaggaga | caaactaaat | gatcttgaga | aatggatatt | ggagaatggc | 1020 |
| tttgaacagc | gtataaagga | gagaggtgtc | ctgatacgtg | gctgggcacc | tcaagtattg | 1080 |
| attttaagtc | accccgcaat | tggaggagtt | ttaacgcatt | gtggatggaa | ctctacatta | 1140 |
| gagggcattt | cagccggact | acccatggtc | acctggccac | tatttgccga | acagttctgt | 1200 |
| aacgaaaaat | tagtagtgca | ggttcttaaa | atcggtgtct | cacttggagt | gaaggtccct | 1260 |
| gttaagtggg | gtgacgaaga | aacgtaggt | gtcttagtga | aaaaggatga | cgttaaaaaa | 1320 |
| gcactggata | gctaatgga | tgagggtgag | gagggccagg | ttaggaggac | caaagccaaa | 1380 |
| gagcttggtg | agttagctaa | aaaagccttt | ggagagggcg | gatcatccta | cgtgaaccta | 1440 |
| acgtccctaa | ttgaagatat | aatcgagcag | cagaaccata | aggagaagta | g | 1491 |

<210> SEQ ID NO 58
<211> LENGTH: 496
<212> TYPE: PRT
<213> ORGANISM: Nicotiana tabacum

<400> SEQUENCE: 58

Met Ala Thr Gln Val His Lys Leu His Phe Ile Leu Phe Pro Leu Met

-continued

```
1               5                   10                  15
Ala Pro Gly His Met Ile Pro Met Ile Asp Ile Ala Lys Leu Leu Ala
                20                  25                  30

Asn Arg Gly Val Ile Thr Thr Ile Thr Thr Pro Val Asn Ala Asn
                35                  40                  45

Arg Phe Ser Ser Thr Ile Thr Arg Ala Ile Lys Ser Gly Leu Arg Ile
        50                  55                  60

Gln Ile Leu Thr Leu Lys Phe Pro Ser Val Glu Val Gly Leu Pro Glu
65                      70                  75                  80

Gly Cys Glu Asn Ile Asp Met Leu Pro Ser Leu Asp Leu Ala Ser Lys
                    85                  90                  95

Phe Phe Ala Ala Ile Ser Met Leu Lys Gln Gln Val Glu Asn Leu Leu
                100                 105                 110

Glu Gly Ile Asn Pro Ser Pro Ser Cys Val Ile Ser Asp Met Gly Phe
                115                 120                 125

Pro Trp Thr Thr Gln Ile Ala Gln Asn Phe Asn Ile Pro Arg Ile Val
        130                 135                 140

Phe His Gly Thr Cys Cys Phe Ser Leu Leu Cys Ser Tyr Lys Ile Leu
145                 150                 155                 160

Ser Ser Asn Ile Leu Glu Asn Ile Thr Ser Asp Ser Glu Tyr Phe Val
                165                 170                 175

Val Pro Asp Leu Pro Asp Arg Val Glu Leu Thr Lys Ala Gln Val Ser
                180                 185                 190

Gly Ser Thr Lys Asn Thr Thr Ser Val Ser Ser Ser Val Leu Lys Glu
        195                 200                 205

Val Thr Glu Gln Ile Arg Leu Ala Glu Glu Ser Ser Tyr Gly Val Ile
        210                 215                 220

Val Asn Ser Phe Glu Glu Leu Glu Gln Val Tyr Glu Lys Glu Tyr Arg
225                 230                 235                 240

Lys Ala Arg Gly Lys Lys Val Trp Cys Val Gly Pro Val Ser Leu Cys
                245                 250                 255

Asn Lys Glu Ile Glu Asp Leu Val Thr Arg Gly Asn Lys Thr Ala Ile
                260                 265                 270

Asp Asn Gln Asp Cys Leu Lys Trp Leu Asp Asn Phe Glu Thr Glu Ser
            275                 280                 285

Val Val Tyr Ala Ser Leu Gly Ser Leu Ser Arg Leu Thr Leu Leu Gln
        290                 295                 300

Met Val Glu Leu Gly Leu Gly Leu Glu Glu Ser Asn Arg Pro Phe Val
305                 310                 315                 320

Trp Val Leu Gly Gly Gly Asp Lys Leu Asn Asp Leu Glu Lys Trp Ile
                325                 330                 335

Leu Glu Asn Gly Phe Glu Gln Arg Ile Lys Glu Arg Gly Val Leu Ile
            340                 345                 350

Arg Gly Trp Ala Pro Gln Val Leu Ile Leu Ser His Pro Ala Ile Gly
        355                 360                 365

Gly Val Leu Thr His Cys Gly Trp Asn Ser Thr Leu Glu Gly Ile Ser
        370                 375                 380

Ala Gly Leu Pro Met Val Thr Trp Pro Leu Phe Ala Glu Gln Phe Cys
385                 390                 395                 400

Asn Glu Lys Leu Val Val Gln Val Leu Lys Ile Gly Val Ser Leu Gly
                405                 410                 415

Val Lys Val Pro Val Lys Trp Gly Asp Glu Glu Asn Val Gly Val Leu
                420                 425                 430
```

Val Lys Lys Asp Asp Val Lys Lys Ala Leu Asp Lys Leu Met Asp Glu
        435                 440                 445

Gly Glu Glu Gly Gln Val Arg Arg Thr Lys Ala Lys Glu Leu Gly Glu
    450                 455                 460

Leu Ala Lys Lys Ala Phe Gly Glu Gly Gly Ser Ser Tyr Val Asn Leu
465                 470                 475                 480

Thr Ser Leu Ile Glu Asp Ile Ile Glu Gln Gln Asn His Lys Glu Lys
            485                 490                 495

<210> SEQ ID NO 59
<211> LENGTH: 1458
<212> TYPE: DNA
<213> ORGANISM: Nicotiana tabacum

<400> SEQUENCE: 59

| | | |
|---|---|---|
| atgggctcta tcggtgcaga actaaccaag ccacacgccg tatgcattcc ctatcccgcc | 60 |
| cagggacaca taaatcctat gctgaagtta gctaagatac tgcatcacaa gggcttccat | 120 |
| ataaccttcg taaatacgga atttaatcac aggcgtctgc tgaagtccag aggtcctgac | 180 |
| tccctgaaag gtcttcaag tttcaggttc gagacgatac ctgacggact gcccccatgc | 240 |
| gaagctgacg ctacacagga cattccttca ctgtgtgaat ccacgactaa tacatgtcta | 300 |
| gctccttta gagacctact tgctaagcta aatgatacga atacttctaa cgtccctccc | 360 |
| gtaagttgta ttgtcagtga cggagtgatg tcatttaccc ttgcagctgc acaggaactg | 420 |
| ggtgtcccag aggttttatt ttggactaca tctgcttgtg gattcttagg ttacatgcac | 480 |
| tattgcaaag tcattgaaaa aggatatgct ccattaaaag acgcatcaga cctgacgaat | 540 |
| ggctatcttg agacaacctt ggacttcatc cccggcatga aggacgtcag gctgagagac | 600 |
| ttaccttcct ttcttaggac caccaatcca gacgaattta tgattaagtt tgtactacag | 660 |
| gaaactgagc gtgctcgtaa ggccagtgcc ataatactta ataccttga aaccttagag | 720 |
| gcagaggtat tagaatcatt aaggaaccttt ctaccccccg tctatccaat cggccccttg | 780 |
| catttccttg tcaaacacgt agacgatgag aacctaaaag gtctacgttc ctcacttttgg | 840 |
| aaggaggaac ctgaatgtat tcaatggtta gacaccaaag aacctaactc tgtcgtgtac | 900 |
| gtgaatttcg gatccattac tgtgatgact cccaatcaat taatagagtt cgcttgggga | 960 |
| ctggcaaaact ctcaacagac cttcctttgg atcataaggc ctgacatcgt aagtggtgat | 1020 |
| gcttccatat tacctcccga gtttgttgag gagactaaga acagaggcat gcttgcctcc | 1080 |
| tggtgctctc aggaggaggt actatcccat cccgcaatag tgggattttt gacgcactct | 1140 |
| ggttggaact caactttaga atcaatttct agtggcgtcc ccatgatctg ttggccttc | 1200 |
| tttgctgagc agcaaacgaa ctgctggttt tcagtgacga agtgggacgt tggaatggaa | 1260 |
| attgattcag atgtgaagag agatgaagta gagagtttag taagagagtt aatggtgggt | 1320 |
| ggtaaaggca agaagatgaa gaagaaggca atggagtgga aggaactggc cgaggcttca | 1380 |
| gcaaaagaac actctggctc ctcttacgtc aatatcgaga agttggttaa cgatatatta | 1440 |
| ctatctagta agcactaa | 1458 |

<210> SEQ ID NO 60
<211> LENGTH: 485
<212> TYPE: PRT
<213> ORGANISM: Nicotiana tabacum

<400> SEQUENCE: 60

```
Met Gly Ser Ile Gly Ala Glu Leu Thr Lys Pro His Ala Val Cys Ile
1               5                   10                  15

Pro Tyr Pro Ala Gln Gly His Ile Asn Pro Met Leu Lys Leu Ala Lys
                20                  25                  30

Ile Leu His His Lys Gly Phe His Ile Thr Phe Val Asn Thr Glu Phe
            35                  40                  45

Asn His Arg Arg Leu Leu Lys Ser Arg Gly Pro Asp Ser Leu Lys Gly
        50                  55                  60

Leu Ser Ser Phe Arg Phe Glu Thr Ile Pro Asp Gly Leu Pro Pro Cys
65                  70                  75                  80

Glu Ala Asp Ala Thr Gln Asp Ile Pro Ser Leu Cys Glu Ser Thr Thr
                85                  90                  95

Asn Thr Cys Leu Ala Pro Phe Arg Asp Leu Leu Ala Lys Leu Asn Asp
            100                 105                 110

Thr Asn Thr Ser Asn Val Pro Pro Val Ser Cys Ile Ser Asp Gly
        115                 120                 125

Val Met Ser Phe Thr Leu Ala Ala Ala Gln Glu Leu Gly Val Pro Glu
        130                 135                 140

Val Leu Phe Trp Thr Thr Ser Ala Cys Gly Phe Leu Gly Tyr Met His
145                 150                 155                 160

Tyr Cys Lys Val Ile Glu Lys Gly Tyr Ala Pro Leu Lys Asp Ala Ser
            165                 170                 175

Asp Leu Thr Asn Gly Tyr Leu Glu Thr Thr Leu Asp Phe Ile Pro Gly
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
        210                 215                 220

Ala Arg Lys Ala Ser Ala Ile Ile Leu Asn Thr Phe Glu Thr Leu Glu
225                 230                 235                 240

Ala Glu Val Leu Glu Ser Leu Arg Asn Leu Leu Pro Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Pro Glu Cys Ile Gln
        275                 280                 285

Trp Leu Asp Thr Lys Glu Pro Asn Ser Val Val Tyr Val Asn Phe Gly
        290                 295                 300

Ser Ile Thr Val Met Thr Pro Asn Gln Leu Ile Glu Phe Ala Trp Gly
305                 310                 315                 320

Leu Ala Asn Ser Gln Gln Thr Phe Leu Trp Ile Ile Arg Pro Asp Ile
            325                 330                 335

Val Ser Gly Asp Ala Ser Ile Leu Pro Pro Glu Phe Val Glu Glu Thr
            340                 345                 350

Lys Asn Arg Gly Met Leu Ala Ser Trp Cys Ser Gln Glu Glu Val Leu
        355                 360                 365

Ser His Pro Ala Ile Val Gly Phe Leu Thr His Ser Gly Trp Asn Ser
    370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
                405                 410                 415

Val Gly Met Glu Ile Asp Ser Asp Val Lys Arg Asp Glu Val Glu Ser
```

```
              420              425              430
Leu Val Arg Glu Leu Met Val Gly Gly Lys Gly Lys Lys Met Lys Lys
            435                  440                  445

Lys Ala Met Glu Trp Lys Glu Leu Ala Glu Ala Ser Ala Lys Glu His
            450                  455                  460

Ser Gly Ser Ser Tyr Val Asn Ile Glu Lys Leu Val Asn Asp Ile Leu
465                 470                  475                  480

Leu Ser Ser Lys His
                485

<210> SEQ ID NO 61
<211> LENGTH: 1377
<212> TYPE: DNA
<213> ORGANISM: Stevia rebaudiana

<400> SEQUENCE: 61
atggagaaca aaaccgagac aaccgttagg cgtagacgta ggataatatt gtttcccgtg      60 cccttttcaag gccatataaa cccaatcctg cagctagcca acgtattgta ctcaaagggc    120
ttcagtataa cgatcttcca caccaacttt aataagccaa aaacgtctaa ttatccacac    180
ttcacattta gatttatact tgataacgac ccacaggatg aaagaatatc aaacttgccc    240
acgcacggcc cactagccgg aatgagaata ccaataatca tgagcatggc gccgacgag     300 ttgcgtagag agctggaatt gttgatgcta gccagtgagg aagacgaaga ggtgtcctgc    360
ttaataacgg atgcactttg gtattttgct caatctgtgg ccgactccct taacctgagg    420
cgtcttgtcc ttatgacctc cagtctattc aactttcatg cccatgtctc attgccccaa    480
tttgatgagc ttggctattt ggatcctgat gacaaaacta gctggagga acaggcttcc     540 ggttttccca tgctaaaggt taaggacatc aaatccgcct actcaaactg gcagatcctt    600
aaggaaattc ttggcaaaat gatcaaacag acgagggcat ccagtggcgt catctggaac    660
tcctttaagg aacttgaaga atcagaactt gaaacagtaa tcagagaaat acctgcccca    720
agtttcttga tccctctacc taagcacctt acggcttcta gttcttcttt gttggaccac    780
gatcgtactg tctttcaatg gttagatcag caaccccccct catcagtgct atatgtgtca    840
ttcggtagta catcagaagt ggacgaaaag gatttccttg agatagcccg tggattggtg    900
gactctaaac agtcctttt atgggttgtg agacctggat tgtaaaggg atccacgtgg     960 gtcgaaccct tgcccgatgg tttcctgggt gaaagaggaa ggatagtgaa gtgggtccct   1020
cagcaagagg tactgcccca tggtgctata ggtgctttct ggaccactc cggctggaat    1080 agtacactag aatccgtttg cgagggtgtc cctatgattt tttctgattt tggtttagat    1140 caaccccctga atgctaggta catgtcagac gtccttaaag tcggcgtcta cctagaaaat    1200
ggctgggaga ggggtgagat agcaaacgct atcagacgtg ttatggtaga cgaagaggga    1260
gagtacataa gcaaaacgc cagggtcctg aaacaaaaag ccgatgtgtc cttgatgaag    1320
ggcggctctt catacgaaag tctagaaagt cttgtttctt atatttcctc actataa      1377

<210> SEQ ID NO 62
<211> LENGTH: 458
<212> TYPE: PRT
<213> ORGANISM: Stevia rebaudiana

<400> SEQUENCE: 62

Met Glu Asn Lys Thr Glu Thr Thr Val Arg Arg Arg Arg Ile Ile
1               5                   10                  15
```

-continued

```
Leu Phe Pro Val Pro Phe Gln Gly His Ile Asn Pro Ile Gln Leu
             20                  25                  30
Ala Asn Val Leu Tyr Ser Lys Gly Phe Ser Ile Thr Ile Phe His Thr
             35                  40                  45
Asn Phe Asn Lys Pro Lys Thr Ser Asn Tyr Pro His Phe Thr Phe Arg
50                       55                  60
Phe Ile Leu Asp Asn Asp Pro Gln Asp Glu Arg Ile Ser Asn Leu Pro
65                       70                  75                  80
Thr His Gly Pro Leu Ala Gly Met Arg Ile Pro Ile Ile Asn Glu His
                    85                  90                       95
Gly Ala Asp Glu Leu Arg Arg Glu Leu Glu Leu Leu Met Leu Ala Ser
                    100                 105                 110
Glu Glu Asp Glu Glu Val Ser Cys Leu Ile Thr Asp Ala Leu Trp Tyr
                    115                 120                 125
Phe Ala Gln Ser Val Ala Asp Ser Leu Asn Leu Arg Arg Leu Val Leu
             130                 135                 140
Met Thr Ser Ser Leu Phe Asn Phe His Ala His Val Ser Leu Pro Gln
145                 150                 155                 160
Phe Asp Glu Leu Gly Tyr Leu Asp Pro Asp Asp Lys Thr Arg Leu Glu
                    165                 170                 175
Glu Gln Ala Ser Gly Phe Pro Met Leu Lys Val Lys Asp Ile Lys Ser
                    180                 185                 190
Ala Tyr Ser Asn Trp Gln Ile Leu Lys Glu Ile Leu Gly Lys Met Ile
                    195                 200                 205
Lys Gln Thr Arg Ala Ser Ser Gly Val Ile Trp Asn Ser Phe Lys Glu
             210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
                    245                 250                 255
Leu Leu Asp His Asp Arg Thr Val Phe Gln Trp Leu Asp Gln Gln Pro
                    260                 265                 270
Pro Ser Ser Val Leu Tyr Val Ser Phe Gly Ser Thr Ser Glu Val Asp
             275                 280                 285
Glu Lys Asp Phe Leu Glu Ile Ala Arg Gly Leu Val Asp Ser Lys Gln
290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                    325                 330                 335
Lys Trp Val Pro Gln Gln Glu Val Leu Ala His Gly Ala Ile Gly Ala
             340                 345                 350
Phe Trp Thr His Ser Gly Trp Asn Ser Thr Leu Glu Ser Val Cys Glu
             355                 360                 365
Gly Val Pro Met Ile Phe Ser Asp Phe Gly Leu Asp Gln Pro Leu Asn
             370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                    405                 410                 415
Asp Glu Glu Gly Glu Tyr Ile Arg Gln Asn Ala Arg Val Leu Lys Gln
                    420                 425                 430
Lys Ala Asp Val Ser Leu Met Lys Gly Gly Ser Ser Tyr Glu Ser Leu
```

```
                435                 440                 445
Glu Ser Leu Val Ser Tyr Ile Ser Ser Leu
    450                 455

<210> SEQ ID NO 63
<211> LENGTH: 1434
<212> TYPE: DNA
<213> ORGANISM: Lycium barbarum

<400> SEQUENCE: 63
atgggtcaat tgcattttt  tttgtttcca atgatggctc aaggtcatat gattccaact     60
ttggatatgg ctaagttgat tgcttctaga ggtgttaagg ctactattat tactactcca    120
ttgaacgaat ctgttttttc taaggctatt caaagaaaca agcaattggg tattgaaatt    180
gaaattgaaa ttagattgat taagtttcca gctttggaaa acgatttgcc agaagattgt    240
gaaagattgg atttgattcc aactgaagct catttgccaa acttttttaa ggctgctgct    300
atgatgcaag aaccattgga acaattgatt caagaatgta gaccagattg tttggtttct    360
gatatgtttt tgccatggac tactgatact gctgctaagt ttaacattcc aagaattgtt    420
tttcatggta ctaactactt tgctttgtgt gttggtgatt ctatgagaag aaacaagcca    480
tttaagaacg tttcttctga ttctgaaact tttgttgttc aaacttgcc  acatgaaatt    540 aagttgacta gaactcaagt ttctccattt gaacaatctg atgaagaatc tgttatgtct    600
agagttttga aggaagttag agaatctgat tgaagtctt  acggtgttat ttttaactct    660
ttttacgaat ggaaccaga  ttacgttgaa cattacacta aggttatggg tagaaagtct    720
tgggctattg gtccattgtc tttgtgtaac agagatgttg aagataaggc tgaaagaggt    780
aagaagtctt ctattgataa gcatgaatgt tggaatggt  tggattctaa gaagccatct    840
tctattgttt acgtttgttt tggttctgtt gctaacttta ctgttactca aatgagagaa    900 ttggcttttgg gttggaagc  ttctggtttg gattttattt gggctgttag agctgataac    960
gaagattggt tgccagaagg ttttgaagaa agaactaagg aaaagggttt gattattaga   1020
ggttgggctc cacaagtttt gattttggat catgaatctg ttggtgcttt tgttactcat   1080
tgtggttgga actctacttt ggaaggtatt tctgctggtg ttccaatggt tacttggcca   1140 gttttttgctg aacaattttt taacgaaaag ttggttactc aagttatgag aactggtgct   1200
ggtgttggtt ctgttcaatg gaagagatct gcttctgaag gtgttgaaaa ggaagctatt   1260
gctaaggcta ttaagagagt tatggtttct gaagaagctg aaggttttag aaacagagct   1320
agagcttaca aggaaatggc tagacaagct attgaagaag tggttcttc  ttacactggt   1380 ttgactactt tgttggaaga tatttcttct tacgaatctt gtcttctga  ttaa         1434

<210> SEQ ID NO 64
<211> LENGTH: 477
<212> TYPE: PRT
<213> ORGANISM: Lycium barbarum

<400> SEQUENCE: 64

Met Gly Gln Leu His Phe Phe Leu Phe Pro Met Met Ala Gln Gly His
1               5                   10                  15

Met Ile Pro Thr Leu Asp Met Ala Lys Leu Ile Ala Ser Arg Gly Val
            20                  25                  30

Lys Ala Thr Ile Ile Thr Thr Pro Leu Asn Glu Ser Val Phe Ser Lys
        35                  40                  45

Ala Ile Gln Arg Asn Lys Gln Leu Gly Ile Glu Ile Glu Ile Glu Ile
```

-continued

```
            50                  55                  60
Arg Leu Ile Lys Phe Pro Ala Leu Glu Asn Asp Leu Pro Glu Asp Cys
 65                  70                  75                  80

Glu Arg Leu Asp Leu Ile Pro Thr Glu Ala His Leu Pro Asn Phe Phe
                 85                  90                  95

Lys Ala Ala Ala Met Met Gln Glu Pro Leu Glu Gln Leu Ile Gln Glu
                100                 105                 110

Cys Arg Pro Asp Cys Leu Val Ser Asp Met Phe Leu Pro Trp Thr Thr
            115                 120                 125

Asp Thr Ala Ala Lys Phe Asn Ile Pro Arg Ile Val Phe His Gly Thr
        130                 135                 140

Asn Tyr Phe Ala Leu Cys Val Gly Asp Ser Met Arg Arg Asn Lys Pro
145                 150                 155                 160

Phe Lys Asn Val Ser Ser Asp Ser Glu Thr Phe Val Val Pro Asn Leu
                165                 170                 175

Pro His Glu Ile Lys Leu Thr Arg Thr Gln Val Ser Pro Phe Glu Gln
            180                 185                 190

Ser Asp Glu Glu Ser Val Met Ser Arg Val Leu Lys Glu Val Arg Glu
        195                 200                 205

Ser Asp Leu Lys Ser Tyr Gly Val Ile Phe Asn Ser Phe Tyr Glu Leu
210                 215                 220

Glu Pro Asp Tyr Val Glu His Tyr Thr Lys Val Met Gly Arg Lys Ser
225                 230                 235                 240

Trp Ala Ile Gly Pro Leu Ser Leu Cys Asn Arg Asp Val Glu Asp Lys
                245                 250                 255

Ala Glu Arg Gly Lys Lys Ser Ser Ile Asp Lys His Glu Cys Leu Glu
            260                 265                 270

Trp Leu Asp Ser Lys Lys Pro Ser Ser Ile Val Tyr Val Cys Phe Gly
        275                 280                 285

Ser Val Ala Asn Phe Thr Val Thr Gln Met Arg Glu Leu Ala Leu Gly
        290                 295                 300

Leu Glu Ala Ser Gly Leu Asp Phe Ile Trp Ala Val Arg Ala Asp Asn
305                 310                 315                 320

Glu Asp Trp Leu Pro Glu Gly Phe Glu Glu Arg Thr Lys Glu Lys Gly
                325                 330                 335

Leu Ile Ile Arg Gly Trp Ala Pro Gln Val Leu Ile Leu Asp His Glu
            340                 345                 350

Ser Val Gly Ala Phe Val Thr His Cys Gly Trp Asn Ser Thr Leu Glu
        355                 360                 365

Gly Ile Ser Ala Gly Val Pro Met Val Thr Trp Pro Val Phe Ala Glu
370                 375                 380

Gln Phe Phe Asn Glu Lys Leu Val Thr Gln Val Met Arg Thr Gly Ala
385                 390                 395                 400

Gly Val Gly Ser Val Gln Trp Lys Arg Ser Ala Ser Glu Gly Val Glu
                405                 410                 415

Lys Glu Ala Ile Ala Lys Ala Ile Lys Arg Val Met Val Ser Glu Glu
            420                 425                 430

Ala Glu Gly Phe Arg Asn Arg Ala Arg Ala Tyr Lys Glu Met Ala Arg
        435                 440                 445

Gln Ala Ile Glu Glu Gly Gly Ser Ser Tyr Thr Gly Leu Thr Thr Leu
        450                 455                 460

Leu Glu Asp Ile Ser Ser Tyr Glu Ser Leu Ser Ser Asp
465                 470                 475
```

<210> SEQ ID NO 65
<211> LENGTH: 2262
<212> TYPE: DNA
<213> ORGANISM: Escherichia coli

<400> SEQUENCE: 65

| | | | | | | |
|---|---|---|---|---|---|---|
| atgtctcaac | ataacgagaa | aaacccacat | cagcatcaat | caccactaca | tgactcctct | 60 |
| gaagcaaagc | aggaatgga | ctccctggct | cctgaagatg | gctctcaccg | tcccgctgcc | 120 |
| gaacctacgc | cacccggcgc | acagccaact | gccccggtt | ccctaaaggc | ccctgacaca | 180 |
| agaaatgaaa | agttaaattc | tcttgaagac | gtgcgtaaag | gcagtgaaaa | ttacgctctt | 240 |
| accactaatc | aaggcgtaag | gatagctgac | gaccaaaact | ccctgcgtgc | tggctctaga | 300 |
| ggccctaccc | ttcttgagga | ttttatcctt | cgtgaaaaga | ttactcactt | cgatcacgaa | 360 |
| aggattcctg | agaggatcgt | ccatgctaga | ggttctgctg | ctcacggtta | ttttcagccc | 420 |
| tataaatccc | tttccgacat | aacgaaggca | gatttttga | gtgatcctaa | taaaataacg | 480 |
| cctgtatttg | ttagattttc | tactgtccaa | ggtggtgctg | gatcagctga | cactgttaga | 540 |
| gacatcaggg | gatttgctac | gaagttttac | actgaagagg | gcatcttcga | cttggttggt | 600 |
| aataatacac | caatattctt | tatccaagac | gcacacaaat | cccagactt | tgtgcatgct | 660 |
| gtcaaaccg | agccacattg | ggctattcca | cagggccagt | ctgcccatga | cacgttctgg | 720 |
| gattacgttt | ctctgcaacc | tgagacgctg | cacaacgtta | tgtgggcaat | gtcagatcgt | 780 |
| ggaataccta | gatcttacag | gacaatgaaa | ggctttggca | tacatacttt | caggttaata | 840 |
| aatgccgaag | gaaaggccac | attcgtcagg | tttcattgga | agcccttagc | aggtaaggcc | 900 |
| tctctagtat | gggacgaagc | tcaaaaactt | actggtagag | atccagactt | tcataggcgt | 960 |
| gaattgtggg | aagcaatcga | agccggcgac | tttcctgagt | atgagctggg | cttccagttg | 1020 |
| atcccagaag | aggacgaatt | taaatttgat | ttcgacttac | ttgatccaac | gaaactgatt | 1080 |
| cccgaggagt | tggtccctgt | ccaacgtgtc | ggtaaaatgg | tgttgaacag | gaaccctgac | 1140 |
| aatttctttg | cagaaaacga | acaagccgcc | ttccatccag | gccatatagt | accaggctta | 1200 |
| gacttcacta | atgaccccact | gctgcaaggt | agactgttta | gttacactga | tacacagata | 1260 |
| tccagactag | gtggtccaaa | cttccatgaa | atccccatca | acaggcccac | gtgccctat | 1320 |
| cacaatttcc | agcgtgatgg | catgcataga | atgggtattg | acacgaatcc | cgctaattat | 1380 |
| gagccaaaact | ctataaacga | taactggcct | agagagacgc | caccaggccc | taagcgtggt | 1440 |
| ggttttgaat | cctatcaaga | gcgtgtcgaa | ggtaataaag | taagggagag | atcaccctct | 1500 |
| ttcggcgaat | attatagtca | tccccgtttg | ttttggttat | cacagacgcc | tttcgaacaa | 1560 |
| cgtcacatag | ttgatggatt | ctcttttgag | ctttcaaaag | tggttcgtcc | ctatatcagg | 1620 |
| gaaagggttg | tcgaccagct | tgcccatatt | gatttaacac | ttgcacaagc | tgttgccaaa | 1680 |
| aacctaggaa | tagagctgac | agacgatcaa | ctaaatatca | ccccacctcc | tgatgtcaac | 1740 |
| ggcttaaaga | aggatccatc | tttaagtcta | tacgcaattc | ccgacggtga | tgttaaaggt | 1800 |
| agagtggtag | caattttgct | aaacgatgaa | gtgcgtagtg | ctgacctact | agccatctta | 1860 |
| aaggccttga | aagcaagggg | agtgcacgca | aagttactgt | acagtcgtat | gggagaggtt | 1920 |
| actgctgacg | acggtacggt | actacctatc | gccgcaacat | tgccggagc | cccaagtttg | 1980 |
| acagtcgatg | ccgttatcgt | acctgtggt | aatatcgccg | atattgccga | caacggagac | 2040 |
| gctaattact | acttaatgga | ggcctataag | cacttgaagc | ccatagcact | ggctggagac | 2100 |

```
gctcgtaaat ttaaggctac tatcaagatt gcagatcagg gcgaggaggg tattgttgag    2160
gcagacagtg cagatggatc tttcatggat gagcttctaa cactaatggc agcacataga    2220
gtatggtctc gtatccccaa gatcgacaaa atccctgcgt aa                       2262
```

<210> SEQ ID NO 66
<211> LENGTH: 753
<212> TYPE: PRT
<213> ORGANISM: Escherichia coli

<400> SEQUENCE: 66

```
Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
        275                 280                 285

Val Arg Phe His Trp Lys Pro Leu Ala Gly Lys Ala Ser Leu Val Trp
    290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Phe Asp Phe Asp
            340                 345                 350
```

```
Leu Leu Asp Pro Thr Lys Leu Ile Pro Glu Glu Leu Pro Val Gln
            355                 360                 365

Arg Val Gly Lys Met Val Leu Asn Arg Asn Pro Asp Asn Phe Phe Ala
370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
                420                 425                 430

Ile Asn Arg Pro Thr Cys Pro Tyr His Asn Phe Gln Arg Asp Gly Met
            435                 440                 445

His Arg Met Gly Ile Asp Thr Asn Pro Ala Asn Tyr Glu Pro Asn Ser
            450                 455                 460

Ile Asn Asp Asn Trp Pro Arg Glu Thr Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
            500                 505                 510

Leu Ser Gln Thr Pro Phe Glu Gln Arg His Ile Val Asp Gly Phe Ser
            515                 520                 525

Phe Glu Leu Ser Lys Val Val Arg Pro Tyr Ile Arg Glu Val Val
            530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
                565                 570                 575

Pro Asp Val Asn Gly Leu Lys Lys Asp Pro Ser Leu Ser Leu Tyr Ala
                580                 585                 590

Ile Pro Asp Gly Asp Val Lys Gly Arg Val Val Ala Ile Leu Leu Asn
            595                 600                 605

Asp Glu Val Arg Ser Ala Asp Leu Leu Ala Ile Leu Lys Ala Leu Lys
            610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
                660                 665                 670

Ala Asp Ile Ala Asp Asn Gly Asp Ala Asn Tyr Tyr Leu Met Glu Ala
                675                 680                 685

Tyr Lys His Leu Lys Pro Ile Ala Leu Ala Gly Asp Ala Arg Lys Phe
690                 695                 700

Lys Ala Thr Ile Lys Ile Ala Asp Gln Gly Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala
```

<210> SEQ ID NO 67
<211> LENGTH: 1974
<212> TYPE: DNA
<213> ORGANISM: Mus musculus

<400> SEQUENCE: 67

| | | | | | |
|---|---|---|---|---|---|
| atgtcttctt | ctaacgatca | tgttttggtt | ccaatgtctc | aaagaaacaa | caacggtttg | 60 |
| ccaagaatga | actctagagc | tgttagaact | ttggctgaag | gtgatgtttt | gtcttttcat | 120 |
| catattactt | acagagttaa | ggttaagtct | ggttttttgg | ttagaaagac | tgttgaaaag | 180 |
| gaaattttgt | ctgatattaa | cggtattatg | aagccaggtt | tgaacgctat | tttgggtcca | 240 |
| actggtggtg | gtaagtcttc | tttgttggat | gttttggctg | ctagaaagga | tccaaagggt | 300 |
| ttgtctggtg | atgttttgat | taacggtgct | ccacaaccag | ctcattttaa | gtgttgttct | 360 |
| ggttacgttt | tcaagatga | tgttgttatg | ggtactttga | ctgttagaga | aaacttgcaa | 420 |
| ttttctgctg | ctttgagatt | gccaactact | atgaagaacc | atgaaaagaa | cgaaagaatt | 480 |
| aacactatta | ttaaggaatt | gggtttggaa | aaggttgctg | attctaaggt | tggtactcaa | 540 |
| tttattagag | gtatttctgg | tggtgaaaga | agagaacttc | tattggtat | ggaattgatt | 600 |
| actgatccat | ctattttgtt | tttggatgaa | ccaactactg | gttggattc | ttctactgct | 660 |
| aacgctgttt | tgttgttgtt | gaagagaatg | tctaagcaag | gtagaactat | tatttttct | 720 |
| attcatcaac | caagatactc | tattttaag | ttgtttgatt | ctttgacttt | gttggcttct | 780 |
| ggtaagttgg | tttttcatgg | tccagctcaa | aaggctttgg | aatactttgc | ttctgctggt | 840 |
| taccattgtg | aaccatacaa | caacccagct | gattttttt | tggatgttat | taacggtgat | 900 |
| tcttctgctg | ttatgttgaa | cagagaagaa | caagataacg | aagctaacaa | gactgaagaa | 960 |
| ccatctaagg | gtgaaaagcc | agttattgaa | aacttgtctg | aatttacat | taactctgct | 1020 |
| atttacggtg | aaactaaggc | tgaattggat | caattgccag | gtgctcaaga | aaagaagggt | 1080 |
| acttctgctt | ttaaggaacc | agtttacgtt | acttctttt | gtcatcaatt | gagatggatt | 1140 |
| gctagaagat | ctttaagaa | cttgttgggt | aacccacaag | cttctgttgc | tcaattgatt | 1200 |
| gttactgtta | ttttgggttt | gattattggt | gctatttact | ttgatttgaa | gtacgatgct | 1260 |
| gctggtatgc | aaaacagagc | tggtgtttg | tttttttga | ctactaacca | atgttttct | 1320 |
| tctgtttctg | ctgttgaatt | gtttgttgtt | gaaaagaagt | tgtttattca | tgaatacatt | 1380 |
| tctggttact | acagagtttc | ttcttacttt | tttggtaagg | ttatgtctga | tttgttgcca | 1440 |
| atgagatttt | tgccatctgt | tattttact | tgtatttgt | actttatgtt | gggtttgaag | 1500 |
| aagactgttg | atgctttttt | tattatgatg | tttactttga | ttatggttgc | ttacactgct | 1560 |
| tcttctatgg | ctttggctat | tgctactggt | caatctgttg | tttctgttgc | tactttgttg | 1620 |
| atgactattg | cttttgtttt | tatgatgttg | ttttctggtt | tgttggttaa | cttgagaact | 1680 |
| attggtccat | ggttgtcttg | gttgcaatac | ttttctattc | caagatacgg | ttttactgct | 1740 |
| ttgcaataca | acgaatttt | gggtcaagaa | tttgtccag | gttttaacgt | tactgataac | 1800 |
| tctacttgtg | ttaactctta | cgctatttgt | actggtaacg | aatacttgat | taaccaaggt | 1860 |
| attgaattgt | ctccatgggg | tttgtggaag | aaccatgttg | ctttggcttg | tatgattatt | 1920 |
| atttttttga | ctattgctta | cttgaagttg | ttgtttttga | agaagtactc | ttaa | 1974 |

<210> SEQ ID NO 68
<211> LENGTH: 657
<212> TYPE: PRT
<213> ORGANISM: Mus musculus

<400> SEQUENCE: 68

```
Met Ser Ser Ser Asn Asp His Val Leu Val Pro Met Ser Gln Arg Asn
1               5                   10                  15

Asn Asn Gly Leu Pro Arg Met Asn Ser Arg Ala Val Arg Thr Leu Ala
            20                  25                  30

Glu Gly Asp Val Leu Ser Phe His Ile Thr Tyr Arg Val Lys Val
        35                  40                  45

Lys Ser Gly Phe Leu Val Arg Lys Thr Val Lys Glu Ile Leu Ser
50                  55                  60

Asp Ile Asn Gly Ile Met Lys Pro Gly Leu Asn Ala Ile Leu Gly Pro
65                  70                  75                  80

Thr Gly Gly Lys Ser Ser Leu Leu Asp Val Leu Ala Ala Arg Lys
                85                  90                  95

Asp Pro Lys Gly Leu Ser Gly Asp Val Leu Ile Asn Gly Ala Pro Gln
                100                 105                 110

Pro Ala His Phe Lys Cys Cys Ser Gly Tyr Val Val Gln Asp Asp Val
            115                 120                 125

Val Met Gly Thr Leu Thr Val Arg Glu Asn Leu Gln Phe Ser Ala Ala
130                 135                 140

Leu Arg Leu Pro Thr Thr Met Lys Asn His Glu Lys Asn Glu Arg Ile
145                 150                 155                 160

Asn Thr Ile Ile Lys Glu Leu Gly Leu Glu Lys Val Ala Asp Ser Lys
                165                 170                 175

Val Gly Thr Gln Phe Ile Arg Gly Ile Ser Gly Gly Glu Arg Lys Arg
            180                 185                 190

Thr Ser Ile Gly Met Glu Leu Ile Thr Asp Pro Ser Ile Leu Phe Leu
        195                 200                 205

Asp Glu Pro Thr Thr Gly Leu Asp Ser Ser Thr Ala Asn Ala Val Leu
    210                 215                 220

Leu Leu Leu Lys Arg Met Ser Lys Gln Gly Arg Thr Ile Ile Phe Ser
225                 230                 235                 240

Ile His Gln Pro Arg Tyr Ser Ile Phe Lys Leu Phe Asp Ser Leu Thr
                245                 250                 255

Leu Leu Ala Ser Gly Lys Leu Val Phe His Gly Pro Ala Gln Lys Ala
            260                 265                 270

Leu Glu Tyr Phe Ala Ser Ala Gly Tyr His Cys Glu Pro Tyr Asn Asn
        275                 280                 285

Pro Ala Asp Phe Phe Leu Asp Val Ile Asn Gly Asp Ser Ser Ala Val
    290                 295                 300

Met Leu Asn Arg Glu Glu Gln Asp Asn Glu Ala Asn Lys Thr Glu Glu
305                 310                 315                 320

Pro Ser Lys Gly Glu Lys Pro Val Ile Glu Asn Leu Ser Glu Phe Tyr
                325                 330                 335

Ile Asn Ser Ala Ile Tyr Gly Glu Thr Lys Ala Glu Leu Asp Gln Leu
            340                 345                 350

Pro Gly Ala Gln Glu Lys Lys Gly Thr Ser Ala Phe Lys Glu Pro Val
        355                 360                 365

Tyr Val Thr Ser Phe Cys His Gln Leu Arg Trp Ile Ala Arg Arg Ser
    370                 375                 380

Phe Lys Asn Leu Leu Gly Asn Pro Gln Ala Ser Val Ala Gln Leu Ile
385                 390                 395                 400

Val Thr Val Ile Leu Gly Leu Ile Ile Gly Ala Ile Tyr Phe Asp Leu
                405                 410                 415
```

Lys Tyr Asp Ala Ala Gly Met Gln Asn Arg Ala Gly Val Leu Phe Phe
              420                 425                 430

Leu Thr Thr Asn Gln Cys Phe Ser Ser Val Ser Ala Val Glu Leu Phe
          435                 440                 445

Val Val Glu Lys Lys Leu Phe Ile His Glu Tyr Ile Ser Gly Tyr Tyr
      450                 455                 460

Arg Val Ser Ser Tyr Phe Phe Gly Lys Val Met Ser Asp Leu Leu Pro
465                 470                 475                 480

Met Arg Phe Leu Pro Ser Val Ile Phe Thr Cys Ile Leu Tyr Phe Met
              485                 490                 495

Leu Gly Leu Lys Lys Thr Val Asp Ala Phe Phe Ile Met Met Phe Thr
          500                 505                 510

Leu Ile Met Val Ala Tyr Thr Ala Ser Ser Met Ala Leu Ala Ile Ala
      515                 520                 525

Thr Gly Gln Ser Val Val Ser Val Ala Thr Leu Leu Met Thr Ile Ala
      530                 535                 540

Phe Val Phe Met Met Leu Phe Ser Gly Leu Leu Val Asn Leu Arg Thr
545                 550                 555                 560

Ile Gly Pro Trp Leu Ser Trp Leu Gln Tyr Phe Ser Ile Pro Arg Tyr
              565                 570                 575

Gly Phe Thr Ala Leu Gln Tyr Asn Glu Phe Leu Gly Gln Glu Phe Cys
          580                 585                 590

Pro Gly Phe Asn Val Thr Asp Asn Ser Thr Cys Val Asn Ser Tyr Ala
      595                 600                 605

Ile Cys Thr Gly Asn Glu Tyr Leu Ile Asn Gln Gly Ile Glu Leu Ser
      610                 615                 620

Pro Trp Gly Leu Trp Lys Asn His Val Ala Leu Ala Cys Met Ile Ile
625                 630                 635                 640

Ile Phe Leu Thr Ile Ala Tyr Leu Lys Leu Leu Phe Leu Lys Lys Tyr
              645                 650                 655

Ser

<210> SEQ ID NO 69
<211> LENGTH: 1515
<212> TYPE: DNA
<213> ORGANISM: Mus musculus

<400> SEQUENCE: 69
atgaacttgt tttctgcttt gtctttggat actttggttt tgttggctat tattttggtt    60
ttgttgtaca gatacggtac tagaactcat ggtttgttta agaagcaagg tattccaggt   120
ccaaagccat tgccattttt gggtactgtt tgaactact acactggtat ttggaagttt   180
gatatggaat gttacgaaaa gtacggtaag acttggggtt tgtttgatgg tcaaactcca   240
ttgttggtta ttactgatcc agaaactatt aagaacgttt tggttaagga ttgtttgtct   300
gtttttacta acagaagaga atttggtcca gttggtatta tgtctaaggc tatttctatt   360
tctaaggatg aagaatggaa gagatacaga gctttgttgt ctccaacttt tacttctggt   420
agattgaagg aaatgtttcc agttattgaa caatacggtg atattttggt taagtacttg   480
agacaagaag ctgaaaaggg tatgccagtt gctatgaagg atgtttttggg tgcttactct   540 atggatgtta ttacttctac ttcttttggt gttaacgttg attctttgaa caacccagaa   600
gatccatttg ttgaagaagc taagaagttt ttgagagttg attttttttga tccattgttg   660 ttttctgttg ttttgttttcc attgttgact ccagtttacg aaatgttgaa catttgtatg   720

```
tttccaaacg attctattga atttttaag aagtttgttg atagaatgca agaatctaga    780
ttggattcta accaaaagca tagagttgat tttttgcaat tgatgatgaa ctctcataac   840
aactctaagg ataaggattc tcataaggct ttttctaaca tggaaattac tgttcaatct   900
attatttta tttctgctgg ttacgaaact acttcttcta ctttgtcttt tactttgtac    960
tgtttggcta ctcatccaga tattcaaaag aagttgcaag ctgaaattga taaggctttg  1020
ccaaacaagg ctactccaac ttgtgatact gttatggaaa tggaatactt ggatatggtt  1080
ttgaacgaaa ctttgagatt gtacccaatt gttactagat ggaaagagt ttgtaagaag   1140
gatgttgaat tgaacggtgt ttacattcca aagggttcta tggttatgat ccatcttac   1200
gctttgcatc atgatccaca acattggcca gatccagaag aatttcaacc agaaagattt  1260
tctaaggaaa acaagggttc tattgatcca tacgtttact tgccatttgg tattggtcca  1320
agaaactgta ttggtatgag atttgctttg atgaacatga agttggctgt tactaaggtt  1380
ttgcaaaact ttctttttca accatgtcaa gaaactcaaa ttccattgaa gttgtctaga  1440
caaggtattt tgcaaccaga aaagccaatt gttttgaagg ttgttccaag agatgctgtt  1500
attactggtg cttaa                                                    1515

<210> SEQ ID NO 70
<211> LENGTH: 504
<212> TYPE: PRT
<213> ORGANISM: Mus musculus

<400> SEQUENCE: 70

Met Asn Leu Phe Ser Ala Leu Ser Leu Asp Thr Leu Val Leu Leu Ala
1               5                  10                  15

Ile Ile Leu Val Leu Leu Tyr Arg Tyr Gly Thr Arg Thr His Gly Leu
            20                  25                  30

Phe Lys Lys Gln Gly Ile Pro Gly Pro Lys Pro Leu Pro Phe Leu Gly
        35                  40                  45

Thr Val Leu Asn Tyr Tyr Thr Gly Ile Trp Lys Phe Asp Met Glu Cys
    50                  55                  60

Tyr Glu Lys Tyr Gly Lys Thr Trp Gly Leu Phe Asp Gly Gln Thr Pro
65                  70                  75                  80

Leu Leu Val Ile Thr Asp Pro Glu Thr Ile Lys Asn Val Leu Val Lys
                85                  90                  95

Asp Cys Leu Ser Val Phe Thr Asn Arg Arg Glu Phe Gly Pro Val Gly
            100                 105                 110

Ile Met Ser Lys Ala Ile Ser Ile Ser Lys Asp Glu Glu Trp Lys Arg
        115                 120                 125

Tyr Arg Ala Leu Leu Ser Pro Thr Phe Thr Ser Gly Arg Leu Lys Glu
    130                 135                 140

Met Phe Pro Val Ile Glu Gln Tyr Gly Asp Ile Leu Val Lys Tyr Leu
145                 150                 155                 160

Arg Gln Glu Ala Glu Lys Gly Met Pro Val Ala Met Lys Asp Val Leu
                165                 170                 175

Gly Ala Tyr Ser Met Asp Val Ile Thr Ser Thr Ser Phe Gly Val Asn
            180                 185                 190

Val Asp Ser Leu Asn Asn Pro Glu Asp Pro Phe Val Glu Glu Ala Lys
        195                 200                 205

Lys Phe Leu Arg Val Asp Phe Phe Asp Pro Leu Leu Phe Ser Val Val
    210                 215                 220
```

```
Leu Phe Pro Leu Leu Thr Pro Val Tyr Glu Met Leu Asn Ile Cys Met
225                 230                 235                 240

Phe Pro Asn Asp Ser Ile Glu Phe Phe Lys Lys Phe Val Asp Arg Met
            245                 250                 255

Gln Glu Ser Arg Leu Asp Ser Asn Gln Lys His Arg Val Asp Phe Leu
        260                 265                 270

Gln Leu Met Met Asn Ser His Asn Asn Ser Lys Asp Lys Asp Ser His
    275                 280                 285

Lys Ala Phe Ser Asn Met Glu Ile Thr Val Gln Ser Ile Ile Phe Ile
290                 295                 300

Ser Ala Gly Tyr Glu Thr Thr Ser Ser Thr Leu Ser Phe Thr Leu Tyr
305                 310                 315                 320

Cys Leu Ala Thr His Pro Asp Ile Gln Lys Lys Leu Gln Ala Glu Ile
                325                 330                 335

Asp Lys Ala Leu Pro Asn Lys Ala Thr Pro Thr Cys Asp Thr Val Met
            340                 345                 350

Glu Met Glu Tyr Leu Asp Met Val Leu Asn Glu Thr Leu Arg Leu Tyr
        355                 360                 365

Pro Ile Val Thr Arg Leu Glu Arg Val Cys Lys Lys Asp Val Glu Leu
370                 375                 380

Asn Gly Val Tyr Ile Pro Lys Gly Ser Met Val Met Ile Pro Ser Tyr
385                 390                 395                 400

Ala Leu His His Asp Pro Gln His Trp Pro Asp Pro Glu Glu Phe Gln
                405                 410                 415

Pro Glu Arg Phe Ser Lys Glu Asn Lys Gly Ser Ile Asp Pro Tyr Val
            420                 425                 430

Tyr Leu Pro Phe Gly Ile Gly Pro Arg Asn Cys Ile Gly Met Arg Phe
        435                 440                 445

Ala Leu Met Asn Met Lys Leu Ala Val Thr Lys Val Leu Gln Asn Phe
    450                 455                 460

Ser Phe Gln Pro Cys Gln Glu Thr Gln Ile Pro Leu Lys Leu Ser Arg
465                 470                 475                 480

Gln Gly Ile Leu Gln Pro Glu Lys Pro Ile Val Leu Lys Val Val Pro
                485                 490                 495

Arg Asp Ala Val Ile Thr Gly Ala
                500

<210> SEQ ID NO 71
<211> LENGTH: 2037
<212> TYPE: DNA
<213> ORGANISM: Mus musculus

<400> SEQUENCE: 71
atgggtgatt ctcatgaaga tacttctgct actgttccag aagctgttgc tgaagaagtt      60
tctttgtttt ctactactga tattgttttg ttttctttga ttgttggtgt tttgacttac     120
tggtttattt ttaagaagaa gaaggaagaa attccagaat ttctaagat tcaaactact      180 gctccaccag ttaaggaatc ttcttttgtt gaaaagatga agaagactgg tagaaacatt     240
attgtttttt acggttctca aactggtact gctgaagaat tgctaacag attgtctaag      300 gatgctcata gatacggtat gagaggtatg tctgctgatc agaagaata cgatttggct      360 gatttgtctt ctttgccaga aattgataag tcttttggttg ttttttgtat ggctacttac     420
ggtgaaggtg atccaactga taacgctcaa gattttacg attggttgca agaaactgat      480
gttgatttga ctggtgttaa gtttgctgtt tttggtttgg gtaacaagac ttacgaacat     540
```

```
tttaacgcta tgggtaagta cgttgatcaa agattggaac aattgggtgc tcaaagaatt      600
tttgaattgg gtttgggtga tgatgatggt aacttggaag aagattttat tacttggaga      660
gaacaatttt ggccagctgt ttgtgaattt tttggtgttg aagctactgg tgaagaatct      720
tctattagac aatacgaatt ggttgttcat gaagatatgg atactgctaa ggtttacact      780
ggtgaaatgg gtagattgaa gtcttacgaa aaccaaaagc caccatttga tgctaagaac      840
ccatttttgg ctgctgttac tactaacaga agttgaacc aaggtactga aagcatttg       900 atgcatttgg aattggatat ttctgattct aagattagat acgaatctgg tgatcatgtt      960
gctgtttacc cagctaacga ttctactttg gttaaccaaa ttggtgaaat ttgggtgct     1020 gatttggatg ttattatgtc tttgaacaac ttggatgaag aatctaacaa gaagcatcca     1080
tttccatgtc caactactta cagaactgct ttgacttact acttggatat tactaaccca     1140
ccaagaacta acgttttgta cgaattggct caatacgctt ctgaaccatc tgaacaagaa     1200
catttgcata agatggcttc ttcttctggt gaaggtaagg aattgtactt gtcttgggtt     1260
gttgaagcta aagacatat tttggctatt ttgcaagatt acccatcttt gagaccacca     1320
attgatcatt tgtgtgaatt gttgccaaga ttgcaagcta gatactactc tattgcttct     1380
tcttctaagg ttcatccaaa ctctgttcat atttgtgctg ttgctgttga atacgaagct     1440
aagtctggta gagttaacaa gggtgttgct acttcttggt tgagaactaa ggaaccagct     1500
ggtgaaaacg gtagaagagc tttggttcca atgtttgtta aaagtctca atttagattg     1560 ccatttaagc caactactcc agttattatg gttggtccag gtactggtgt tgctccattt     1620 atgggttta ttcaagaaag agcttggttg agagaacaag gtaaggaagt tggtgaaact     1680
ttgttgtact acggttgtag aagatctgat gaagattact tgtacagaga agaattggct     1740
agatttcata aggatggtgc tttgactcaa ttgaacgttg cttttcttag agaacaagct     1800
cataaggttt acgttcaaca tttgttgaag agagataagg aacatttgtg gaagttgatt     1860
catgaaggtg gtgctcatat ttacgttgt ggtgatgcta gaaacatggc taaggatgtt     1920
caaaacactt tttacgatat tgttgctgaa tttggtccaa tggaacatac tcaagctgtt     1980
gattacgtta agaagttgat gactaagggt agatactctt tggatgtttg gtcttaa       2037
```

<210> SEQ ID NO 72
<211> LENGTH: 678
<212> TYPE: PRT
<213> ORGANISM: Mus musculus

<400> SEQUENCE: 72

```
Met Gly Asp Ser His Glu Asp Thr Ser Ala Thr Val Pro Glu Ala Val
1               5                   10                  15

Ala Glu Glu Val Ser Leu Phe Ser Thr Thr Asp Ile Val Leu Phe Ser
                20                  25                  30

Leu Ile Val Gly Val Leu Thr Tyr Trp Phe Ile Phe Lys Lys Lys Lys
            35                  40                  45

Glu Glu Ile Pro Glu Phe Ser Lys Ile Gln Thr Thr Ala Pro Pro Val
        50                  55                  60

Lys Glu Ser Ser Phe Val Glu Lys Met Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
                100                 105                 110
```

```
Asp Pro Glu Glu Tyr Asp Leu Ala Asp Leu Ser Ser Leu Pro Glu Ile
    115                 120                 125

Asp Lys Ser Leu Val Val Phe Cys Met Ala Thr Tyr Gly Glu Gly Asp
130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175

Thr Tyr Glu His Phe Asn Ala Met Gly Lys Tyr Val Asp Gln Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
    210                 215                 220

Pro Ala Val Cys Glu Phe Phe Gly Val Glu Ala Thr Gly Glu Glu Ser
225                 230                 235                 240

Ser Ile Arg Gln Tyr Glu Leu Val Val His Glu Asp Met Asp Thr Ala
                245                 250                 255

Lys Val Tyr Thr Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
        275                 280                 285

Asn Arg Lys Leu Asn Gln Gly Thr Glu Arg His Leu Met His Leu Glu
    290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Thr Leu Val Asn Gln Ile Gly Glu
                325                 330                 335

Ile Leu Gly Ala Asp Leu Asp Val Ile Met Ser Leu Asn Asn Leu Asp
            340                 345                 350

Glu Glu Ser Asn Lys Lys His Pro Phe Pro Cys Pro Thr Thr Tyr Arg
        355                 360                 365

Thr Ala Leu Thr Tyr Tyr Leu Asp Ile Thr Asn Pro Pro Arg Thr Asn
    370                 375                 380

Val Leu Tyr Glu Leu Ala Gln Tyr Ala Ser Glu Pro Ser Glu Gln Glu
385                 390                 395                 400

His Leu His Lys Met Ala Ser Ser Gly Glu Gly Lys Glu Leu Tyr
                405                 410                 415

Leu Ser Trp Val Val Glu Ala Arg Arg His Ile Leu Ala Ile Leu Gln
            420                 425                 430

Asp Tyr Pro Ser Leu Arg Pro Pro Ile Asp His Leu Cys Glu Leu Leu
        435                 440                 445

Pro Arg Leu Gln Ala Arg Tyr Tyr Ser Ile Ala Ser Ser Ser Lys Val
    450                 455                 460

His Pro Asn Ser Val His Ile Cys Ala Val Ala Val Glu Tyr Glu Ala
465                 470                 475                 480

Lys Ser Gly Arg Val Asn Lys Gly Val Ala Thr Ser Trp Leu Arg Thr
                485                 490                 495

Lys Glu Pro Ala Gly Glu Asn Gly Arg Arg Ala Leu Val Pro Met Phe
            500                 505                 510

Val Arg Lys Ser Gln Phe Arg Leu Pro Phe Lys Pro Thr Thr Pro Val
        515                 520                 525
```

```
Ile Met Val Gly Pro Gly Thr Gly Val Ala Pro Phe Met Gly Phe Ile
        530                 535                 540

Gln Glu Arg Ala Trp Leu Arg Glu Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Arg Phe His Lys Asp Gly Ala Leu Thr Gln Leu Asn
                580                 585                 590

Val Ala Phe Ser Arg Glu Gln Ala His Lys Val Tyr Val Gln His Leu
            595                 600                 605

Leu Lys Arg Asp Lys Glu His Leu Trp Lys Leu Ile His Glu Gly Gly
        610                 615                 620

Ala His Ile Tyr Val Cys Gly Asp Ala Arg Asn Met Ala Lys Asp Val
625                 630                 635                 640

Gln Asn Thr Phe Tyr Asp Ile Val Ala Glu Phe Gly Pro Met Glu His
                645                 650                 655

Thr Gln Ala Val Asp Tyr Val Lys Lys Leu Met Thr Lys Gly Arg Tyr
            660                 665                 670

Ser Leu Asp Val Trp Ser
            675

<210> SEQ ID NO 73
<211> LENGTH: 492
<212> TYPE: PRT
<213> ORGANISM: Arabidopsis thaliana

<400> SEQUENCE: 73

Met Asp Pro Tyr Arg Val Arg Pro Ser Ser Ala His Asp Ser Pro Phe
1               5                   10                  15

Phe Thr Thr Asn Ser Gly Ala Pro Val Trp Asn Asn Ser Ser Leu
            20                  25                  30

Thr Val Gly Thr Arg Gly Pro Ile Leu Leu Glu Asp Tyr His Leu Leu
        35                  40                  45

Glu Lys Leu Ala Asn Phe Asp Arg Glu Arg Ile Pro Glu Arg Val Val
50                  55                  60

His Ala Arg Gly Ala Ser Ala Lys Gly Phe Phe Glu Val Thr His Asp
65                  70                  75                  80

Ile Thr Gln Leu Thr Ser Ala Asp Phe Leu Arg Gly Pro Gly Val Gln
                85                  90                  95

Thr Pro Val Ile Val Arg Phe Ser Thr Val Ile His Glu Arg Gly Ser
            100                 105                 110

Pro Glu Thr Leu Arg Asp Pro Arg Gly Phe Ala Val Lys Phe Tyr Thr
        115                 120                 125

Arg Glu Gly Asn Phe Asp Leu Val Gly Asn Asn Phe Pro Val Phe Phe
    130                 135                 140

Val Arg Asp Gly Met Lys Phe Pro Asp Met Val His Ala Leu Lys Pro
145                 150                 155                 160

Asn Pro Lys Ser His Ile Gln Glu Asn Trp Arg Ile Leu Asp Phe Phe
                165                 170                 175

Ser His Pro Glu Ser Leu His Met Phe Ser Phe Leu Phe Asp Asp
            180                 185                 190

Leu Gly Ile Pro Gln Asp Tyr Arg His Met Glu Gly Ala Gly Val Asn
        195                 200                 205

Thr Tyr Met Leu Ile Asn Lys Ala Gly Lys Ala His Tyr Val Lys Phe
    210                 215                 220
```

```
His Trp Lys Pro Thr Cys Gly Ile Lys Cys Leu Ser Asp Glu Glu Ala
225                 230                 235                 240

Ile Arg Val Gly Gly Ala Asn His Ser His Ala Thr Lys Asp Leu Tyr
                245                 250                 255

Asp Ser Ile Ala Ala Gly Asn Tyr Pro Gln Trp Asn Leu Phe Val Gln
            260                 265                 270

Val Met Asp Pro Ala His Glu Asp Lys Phe Asp Phe Asp Pro Leu Asp
        275                 280                 285

Val Thr Lys Ile Trp Pro Glu Asp Ile Leu Pro Leu Gln Pro Val Gly
    290                 295                 300

Arg Leu Val Leu Asn Lys Asn Ile Asp Asn Phe Phe Asn Glu Asn Glu
305                 310                 315                 320

Gln Ile Ala Phe Cys Pro Ala Leu Val Val Pro Gly Ile His Tyr Ser
                325                 330                 335

Asp Asp Lys Leu Leu Gln Thr Arg Ile Phe Ser Tyr Ala Asp Ser Gln
            340                 345                 350

Arg His Arg Leu Gly Pro Asn Tyr Leu Gln Leu Pro Val Asn Ala Pro
        355                 360                 365

Lys Cys Ala His His Asn Asn His His Asp Gly Phe Met Asn Phe Met
    370                 375                 380

His Arg Asp Glu Glu Val Asn Tyr Phe Pro Ser Arg Leu Asp Pro Val
385                 390                 395                 400

Arg His Ala Glu Lys Tyr Pro Thr Thr Pro Ile Val Cys Ser Gly Asn
                405                 410                 415

Arg Glu Lys Cys Phe Ile Gly Lys Glu Asn Asn Phe Lys Gln Pro Gly
            420                 425                 430

Glu Arg Tyr Arg Ser Trp Asp Ser Asp Arg Gln Glu Arg Phe Val Lys
        435                 440                 445

Arg Phe Val Glu Ala Leu Ser Glu Pro Arg Val Thr His Glu Ile Arg
    450                 455                 460

Ser Ile Trp Ile Ser Tyr Trp Ser Gln Ala Asp Lys Ser Leu Gly Gln
465                 470                 475                 480

Lys Leu Ala Thr Arg Leu Asn Val Arg Pro Asn Phe
                485                 490

<210> SEQ ID NO 74
<211> LENGTH: 492
<212> TYPE: PRT
<213> ORGANISM: Arabidopsis thaliana

<400> SEQUENCE: 74

Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Asn Ser Ser Met
                20                  25                  30

Thr Val Gly Pro Arg Gly Pro Ile Leu Leu Glu Asp Tyr His Leu Val
            35                  40                  45

Glu Lys Leu Ala Asn Phe Asp Arg Glu Arg Ile Pro Glu Arg Val Val
        50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Glu Arg Gly Ser
```

```
            100                 105                 110
Pro Glu Thr Leu Arg Asp Pro Arg Gly Phe Ala Val Lys Phe Tyr Thr
            115                 120                 125
Arg Glu Gly Asn Phe Asp Leu Val Gly Asn Asn Phe Pro Val Phe Phe
            130                 135                 140
Ile Arg Asp Gly Met Lys Phe Pro Asp Met Val His Ala Leu Lys Pro
145                 150                 155                 160
Asn Pro Lys Ser His Ile Gln Glu Asn Trp Arg Ile Leu Asp Phe Phe
                165                 170                 175
Ser His His Pro Glu Ser Leu Asn Met Phe Thr Phe Leu Phe Asp Asp
            180                 185                 190
Ile Gly Ile Pro Gln Asp Tyr Arg His Met Asp Gly Ser Gly Val Asn
            195                 200                 205
Thr Tyr Met Leu Ile Asn Lys Ala Gly Lys Ala His Tyr Val Lys Phe
            210                 215                 220
His Trp Lys Pro Thr Cys Gly Val Lys Ser Leu Leu Glu Glu Asp Ala
225                 230                 235                 240
Ile Arg Val Gly Gly Thr Asn His Ser His Ala Thr Gln Asp Leu Tyr
                245                 250                 255
Asp Ser Ile Ala Ala Gly Asn Tyr Pro Glu Trp Lys Leu Phe Ile Gln
            260                 265                 270
Ile Ile Asp Pro Ala Asp Glu Asp Lys Phe Asp Phe Asp Pro Leu Asp
            275                 280                 285
Val Thr Lys Thr Trp Pro Glu Asp Ile Leu Pro Leu Gln Pro Val Gly
            290                 295                 300
Arg Met Val Leu Asn Lys Asn Ile Asp Asn Phe Phe Ala Glu Asn Glu
305                 310                 315                 320
Gln Leu Ala Phe Cys Pro Ala Ile Ile Val Pro Gly Ile His Tyr Ser
                325                 330                 335
Asp Asp Lys Leu Leu Gln Thr Arg Val Phe Ser Tyr Ala Asp Thr Gln
            340                 345                 350
Arg His Arg Leu Gly Pro Asn Tyr Leu Gln Leu Pro Val Asn Ala Pro
            355                 360                 365
Lys Cys Ala His His Asn Asn His His Glu Gly Phe Met Asn Phe Met
            370                 375                 380
His Arg Asp Glu Glu Val Asn Tyr Phe Pro Ser Arg Tyr Asp Gln Val
385                 390                 395                 400
Arg His Ala Glu Lys Tyr Pro Thr Pro Ala Val Cys Ser Gly Lys
                405                 410                 415
Arg Glu Arg Cys Ile Ile Glu Lys Glu Asn Asn Phe Lys Glu Pro Gly
            420                 425                 430
Glu Arg Tyr Arg Thr Phe Thr Pro Glu Arg Gln Glu Arg Phe Ile Gln
            435                 440                 445
Arg Trp Ile Asp Ala Leu Ser Asp Pro Arg Ile Thr His Glu Ile Arg
            450                 455                 460
Ser Ile Trp Ile Ser Tyr Trp Ser Gln Ala Asp Lys Ser Leu Gly Gln
465                 470                 475                 480
Lys Leu Ala Ser Arg Leu Asn Val Arg Pro Ser Ile
                485                 490

<210> SEQ ID NO 75
<211> LENGTH: 492
<212> TYPE: PRT
<213> ORGANISM: Arabidopsis thaliana
```

<400> SEQUENCE: 75

| | | | | | | | | | | | | | | |
|---|---|---|---|---|---|---|---|---|---|---|---|---|---|---|
Met Asp Pro Tyr Lys Tyr Arg Pro Ser Ser Ala Tyr Asn Ala Pro Phe
1               5                   10                  15

Tyr Thr Thr Asn Gly Gly Ala Pro Val Ser Asn Asn Ile Ser Ser Leu
            20                  25                  30

Thr Ile Gly Glu Arg Gly Pro Val Leu Leu Glu Asp Tyr His Leu Ile
        35                  40                  45

Glu Lys Val Ala Asn Phe Thr Arg Glu Arg Ile Pro Glu Arg Val Val
    50                  55                  60

His Ala Arg Gly Ile Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Val His Glu Arg Ala Ser
            100                 105                 110

Pro Glu Thr Met Arg Asp Ile Arg Gly Phe Ala Val Lys Phe Tyr Thr
        115                 120                 125

Arg Glu Gly Asn Phe Asp Leu Val Gly Asn Asn Thr Pro Val Phe Phe
130                 135                 140

Ile Arg Asp Gly Ile Gln Phe Pro Asp Val Val His Ala Leu Lys Pro
145                 150                 155                 160

Asn Pro Lys Thr Asn Ile Gln Glu Tyr Trp Arg Ile Leu Asp Tyr Met
                165                 170                 175

Ser His Leu Pro Glu Ser Leu Leu Thr Trp Cys Trp Met Phe Asp Asp
            180                 185                 190

Val Gly Ile Pro Gln Asp Tyr Arg His Met Glu Gly Phe Gly Val His
        195                 200                 205

Thr Tyr Thr Leu Ile Ala Lys Ser Gly Lys Val Leu Phe Val Lys Phe
    210                 215                 220

His Trp Lys Pro Thr Cys Gly Ile Lys Asn Leu Thr Asp Glu Glu Ala
225                 230                 235                 240

Lys Val Val Gly Gly Ala Asn His Ser His Ala Thr Lys Asp Leu His
                245                 250                 255

Asp Ala Ile Ala Ser Gly Asn Tyr Pro Glu Trp Lys Leu Phe Ile Gln
            260                 265                 270

Thr Met Asp Pro Ala Asp Glu Asp Lys Phe Asp Phe Asp Pro Leu Asp
        275                 280                 285

Val Thr Lys Ile Trp Pro Glu Asp Ile Leu Pro Leu Gln Pro Val Gly
    290                 295                 300

Arg Leu Val Leu Asn Arg Thr Ile Asp Asn Phe Phe Asn Glu Thr Glu
305                 310                 315                 320

Gln Leu Ala Phe Asn Pro Gly Leu Val Val Pro Gly Ile Tyr Tyr Ser
                325                 330                 335

Asp Asp Lys Leu Leu Gln Cys Arg Ile Phe Ala Tyr Gly Asp Thr Gln
            340                 345                 350

Arg His Arg Leu Gly Pro Asn Tyr Leu Gln Leu Pro Val Asn Ala Pro
        355                 360                 365

Lys Cys Ala His His Asn Asn His Glu Gly Phe Met Asn Phe Met
    370                 375                 380

His Arg Asp Glu Glu Ile Asn Tyr Tyr Pro Ser Lys Phe Asp Pro Val
385                 390                 395                 400

Arg Cys Ala Glu Lys Val Pro Thr Pro Thr Asn Ser Tyr Thr Gly Ile

```
                    405                 410                 415
Arg Thr Lys Cys Val Ile Lys Lys Glu Asn Asn Phe Lys Gln Ala Gly
            420                 425                 430

Asp Arg Tyr Arg Ser Trp Ala Pro Asp Arg Gln Asp Arg Phe Val Lys
        435                 440                 445

Arg Trp Val Glu Ile Leu Ser Glu Pro Arg Leu Thr His Glu Ile Arg
    450                 455                 460

Gly Ile Trp Ile Ser Tyr Trp Ser Gln Ala Asp Arg Ser Leu Gly Gln
465                 470                 475                 480

Lys Leu Ala Ser Arg Leu Asn Val Arg Pro Ser Ile
                485                 490
```

<210> SEQ ID NO 76
<211> LENGTH: 23
<212> TYPE: DNA
<213> ORGANISM: Artificial Sequence
<220> FEATURE:
<223> OTHER INFORMATION: Forward primer of CYP3A4

<400> SEQUENCE: 76
tgcctaataa agctcctcct act                                           23

<210> SEQ ID NO 77
<211> LENGTH: 22
<212> TYPE: DNA
<213> ORGANISM: Artificial Sequence
<220> FEATURE:
<223> OTHER INFORMATION: Reverse primer of CYP3A4

<400> SEQUENCE: 77
gctcctgaaa cagttccatc tc                                            22

<210> SEQ ID NO 78
<211> LENGTH: 22
<212> TYPE: DNA
<213> ORGANISM: Artificial Sequence
<220> FEATURE:
<223> OTHER INFORMATION: Forward primer of P450 oxidoreductase

<400> SEQUENCE: 78
ggaagagctt tggttcctat gt                                            22

<210> SEQ ID NO 79
<211> LENGTH: 23
<212> TYPE: DNA
<213> ORGANISM: Artificial Sequence
<220> FEATURE:
<223> OTHER INFORMATION: Reverse primer of P450 oxidoreductase

<400> SEQUENCE: 79
gctcccaatt cagcaacaat atc                                           23

<210> SEQ ID NO 80
<211> LENGTH: 29
<212> TYPE: DNA
<213> ORGANISM: Artificial Sequence
<220> FEATURE:
<223> OTHER INFORMATION: Forward primer of CBDA synthase

<400> SEQUENCE: 80
acatcacaat cacacaaaac taacaaaag                                     29

<210> SEQ ID NO 81

```
<211> LENGTH: 22
<212> TYPE: DNA
<213> ORGANISM: Artificial Sequence
<220> FEATURE:
<223> OTHER INFORMATION: Reverse primer of CBDA synthase

<400> SEQUENCE: 81
ggccatagtt tctcatcaat gg                                              22

<210> SEQ ID NO 82
<211> LENGTH: 28
<212> TYPE: DNA
<213> ORGANISM: Artificial Sequence
<220> FEATURE:
<223> OTHER INFORMATION: Forward primer of UGT76G1

<400> SEQUENCE: 82
gattggaaga acaagcttca ggatttcc                                        28

<210> SEQ ID NO 83
<211> LENGTH: 26
<212> TYPE: DNA
<213> ORGANISM: Artificial Sequence
<220> FEATURE:
<223> OTHER INFORMATION: Reverse primer of UGT76G1

<400> SEQUENCE: 83
ccatcctgaa tgagtccaaa aagctc                                          26

<210> SEQ ID NO 84
<211> LENGTH: 22
<212> TYPE: DNA
<213> ORGANISM: Artificial Sequence
<220> FEATURE:
<223> OTHER INFORMATION: Forward primer of ABCG2

<400> SEQUENCE: 84
ccttcaggat tgtcaggaga tg                                              22

<210> SEQ ID NO 85
<211> LENGTH: 22
<212> TYPE: DNA
<213> ORGANISM: Artificial Sequence
<220> FEATURE:
<223> OTHER INFORMATION: Reverse primer of ABCG2

<400> SEQUENCE: 85
gcaggtccat gaaacatcaa tc                                              22

<210> SEQ ID NO 86
<211> LENGTH: 27
<212> TYPE: DNA
<213> ORGANISM: Artificial Sequence
<220> FEATURE:
<223> OTHER INFORMATION: Forward primer of Trichomoe-targeted CBDAs

<400> SEQUENCE: 86
aaagatcaaa agcaagttct tcactgt                                         27

<210> SEQ ID NO 87
<211> LENGTH: 25
<212> TYPE: DNA
<213> ORGANISM: Artificial Sequence
<220> FEATURE:
<223> OTHER INFORMATION: Reverse primer of Trichome-targeted CBDAs

<400> SEQUENCE: 87
```

```
ccatgcagtt tggctatgaa catct                                        25

<210> SEQ ID NO 88
<211> LENGTH: 25
<212> TYPE: DNA
<213> ORGANISM: Artificial Sequence
<220> FEATURE:
<223> OTHER INFORMATION: Forward primer of Trichome-targeted UGT

<400> SEQUENCE: 88
agtgctcaac attctccttt tggtt                                        25

<210> SEQ ID NO 89
<211> LENGTH: 25
<212> TYPE: DNA
<213> ORGANISM: Artificial Sequence
<220> FEATURE:
<223> OTHER INFORMATION: Reverse primer of Trichome-targeted UGT

<400> SEQUENCE: 89
tctgaagcca acatcaacaa ttcca                                        25

<210> SEQ ID NO 90
<211> LENGTH: 25
<212> TYPE: DNA
<213> ORGANISM: Artificial Sequence
<220> FEATURE:
<223> OTHER INFORMATION: Forward primer of Plasma membrane-targeted UTRI

<400> SEQUENCE: 90 ttgttccta aacctcgcct ttgac                                         25

<210> SEQ ID NO 91
<211> LENGTH: 25
<212> TYPE: DNA
<213> ORGANISM: Artificial Sequence
<220> FEATURE:
<223> OTHER INFORMATION: Reverse primer of Plasma membrane-targeted UTRI

<400> SEQUENCE: 91
tcattatgga gcactccact ctctg                                        25

<210> SEQ ID NO 92
<211> LENGTH: 27
<212> TYPE: DNA
<213> ORGANISM: Artificial Sequence
<220> FEATURE:
<223> OTHER INFORMATION: Forward primer of Cytosolic-targeted CBDA
      synthase

<400> SEQUENCE: 92
aaagatcaaa agcaagttct tcactgt                                      27

<210> SEQ ID NO 93
<211> LENGTH: 25
<212> TYPE: DNA
<213> ORGANISM: Artificial Sequence
<220> FEATURE:
<223> OTHER INFORMATION: Reverse primer of Cytosolic-targeted CBDA
      synthase

<400> SEQUENCE: 93
ataaacttct ccaagggtag ctccg                                        25

<210> SEQ ID NO 94
```

```
<211> LENGTH: 25
<212> TYPE: DNA
<213> ORGANISM: Artificial Sequence
<220> FEATURE:
<223> OTHER INFORMATION: Forward primer of Cytosolic-targeted UGT

<400> SEQUENCE: 94
agaactggaa gaatccgaac tggaa                                            25

<210> SEQ ID NO 95
<211> LENGTH: 25
<212> TYPE: DNA
<213> ORGANISM: Artificial Sequence
<220> FEATURE:
<223> OTHER INFORMATION: Reverse primer of Cytosolic-targeted UGT

<400> SEQUENCE: 95
aaatcatcgg gacaccttca caaac                                            25

<210> SEQ ID NO 96
<211> LENGTH: 25
<212> TYPE: DNA
<213> ORGANISM: Artificial Sequence
<220> FEATURE:
<223> OTHER INFORMATION: Forward primer of NtGT1

<400> SEQUENCE: 96
atgaaaacaa cagaacttgt cttca                                            25

<210> SEQ ID NO 97
<211> LENGTH: 22
<212> TYPE: DNA
<213> ORGANISM: Artificial Sequence
<220> FEATURE:
<223> OTHER INFORMATION: Reverse primer of NtGT1

<400> SEQUENCE: 97
tgaagttgta ggcctagcat gg                                               22

<210> SEQ ID NO 98
<211> LENGTH: 25
<212> TYPE: DNA
<213> ORGANISM: Artificial Sequence
<220> FEATURE:
<223> OTHER INFORMATION: Forward primer of NtGT2

<400> SEQUENCE: 98
atggttcaac cacacgtctt actgg                                            25

<210> SEQ ID NO 99
<211> LENGTH: 22
<212> TYPE: DNA
<213> ORGANISM: Artificial Sequence
<220> FEATURE:
<223> OTHER INFORMATION: Reverse primer of NtGT2

<400> SEQUENCE: 99
ttgaatacac cagttggggt cg                                               22

<210> SEQ ID NO 100
<211> LENGTH: 25
<212> TYPE: DNA
<213> ORGANISM: Artificial Sequence
<220> FEATURE:
<223> OTHER INFORMATION: Forward primer of NtGT3

<400> SEQUENCE: 100
```
atgaaagaga ctaaaaaaat tgagt                                          25

<210> SEQ ID NO 101
<211> LENGTH: 23
<212> TYPE: DNA
<213> ORGANISM: Artificial Sequence
<220> FEATURE:
<223> OTHER INFORMATION: Reverse primer of NtGT3

<400> SEQUENCE: 101
catcacgcag attttgaata tgg                                            23

<210> SEQ ID NO 102
<211> LENGTH: 25
<212> TYPE: DNA
<213> ORGANISM: Artificial Sequence
<220> FEATURE:
<223> OTHER INFORMATION: Forward primer of NtGT4

<400> SEQUENCE: 102
atggctactc aggtgcataa attgc                                          25

<210> SEQ ID NO 103
<211> LENGTH: 22
<212> TYPE: DNA
<213> ORGANISM: Artificial Sequence
<220> FEATURE:
<223> OTHER INFORMATION: Reverse primer of NtGT4

<400> SEQUENCE: 103
ggccttagtt agctcgacac gg                                             22

<210> SEQ ID NO 104
<211> LENGTH: 25
<212> TYPE: DNA
<213> ORGANISM: Artificial Sequence
<220> FEATURE:
<223> OTHER INFORMATION: Forward primer of NtGT5

<400> SEQUENCE: 104
atgggctcta tcggtgcaga actaa                                          25

<210> SEQ ID NO 105
<211> LENGTH: 22
<212> TYPE: DNA
<213> ORGANISM: Artificial Sequence
<220> FEATURE:
<223> OTHER INFORMATION: Reverse primer of NtGT5

<400> SEQUENCE: 105
cggggatgaa gtccaaggtt gt                                             22

<210> SEQ ID NO 106
<211> LENGTH: 25
<212> TYPE: DNA
<213> ORGANISM: Artificial Sequence
<220> FEATURE:
<223> OTHER INFORMATION: Forward primer of Kat-E

<400> SEQUENCE: 106
atgtctcaac ataacgagaa aaacc                                          25

<210> SEQ ID NO 107
<211> LENGTH: 22
<212> TYPE: DNA

<213> ORGANISM: Artificial Sequence
<220> FEATURE:
<223> OTHER INFORMATION: Reverse primer of Kat-E

<400> SEQUENCE: 107
cgtagcaaat cccctgatgt ct								22

<210> SEQ ID NO 108
<211> LENGTH: 25
<212> TYPE: DNA
<213> ORGANISM: Artificial Sequence
<220> FEATURE:
<223> OTHER INFORMATION: Forward primer of UGT76G1

<400> SEQUENCE: 108
atggagaaca aaaccgagac aaccg							25

<210> SEQ ID NO 109
<211> LENGTH: 22
<212> TYPE: DNA
<213> ORGANISM: Artificial Sequence
<220> FEATURE:
<223> OTHER INFORMATION: Reverse primer of UGT76G1

<400> SEQUENCE: 109
cctttagcat gggaaaaccg ga							22

<210> SEQ ID NO 110
<211> LENGTH: 28
<212> TYPE: DNA
<213> ORGANISM: Artificial Sequence
<220> FEATURE:
<223> OTHER INFORMATION: Forward primer of UGT76G1 (for tobacco BY2
      cells)

<400> SEQUENCE: 110
gattggaaga acaagcttca ggatttcc						28

<210> SEQ ID NO 111
<211> LENGTH: 26
<212> TYPE: DNA
<213> ORGANISM: Artificial Sequence
<220> FEATURE:
<223> OTHER INFORMATION: Reverse primer of UGT76G1 (for tobacco BY2
      cells)

<400> SEQUENCE: 111
ccatcctgaa tgagtccaaa aagctc						26

<210> SEQ ID NO 112
<211> LENGTH: 22
<212> TYPE: DNA
<213> ORGANISM: Artificial Sequence
<220> FEATURE:
<223> OTHER INFORMATION: Forward primer of ABCG2 (for tobacco BY2 cells)

<400> SEQUENCE: 112
ccttcaggat tgtcaggaga tg							22

<210> SEQ ID NO 113
<211> LENGTH: 22
<212> TYPE: DNA
<213> ORGANISM: Artificial Sequence
<220> FEATURE:
<223> OTHER INFORMATION: Reverse primer of ABCG2 (for tobacco BY2 cells)

```
<400> SEQUENCE: 113
gcaggtccat gaaacatcaa tc                                                22
```